(12) United States Patent
Hu et al.

(10) Patent No.: US 12,343,323 B2
(45) Date of Patent: Jul. 1, 2025

(54) TAXANE-LIPID-POLYSACCHARIDE DUAL CONJUGATES, PREPARATION METHODS THEREOF AND USES THEREOF

(71) Applicant: Santolecan Pharmaceuticals LLC, Jupiter, FL (US)

(72) Inventors: Jinghua Hu, San Diego, CA (US); Xiaohai Li, Jupiter, FL (US); Yikang Shi, Jinan (CN); Si Wang, San Diego, CA (US); Hui Wang, Tiantang Town (CN); Ang Zha, Guangzhou (CN); Fengyi Cui, Tiantang Town (CN); Anny Wang, San Diego, CA (US); Daisy J. Li, Jupiter, FL (US); Taining Zhang, Zhangjiakou (CN); Haijun Cheng, Tiantang Town (CN)

(73) Assignee: Santolecan Pharmaceuticals LLC, Jupiter, FL (US)

( * ) Notice: Subject to any disclaimer, the term of this patent is extended or adjusted under 35 U.S.C. 154(b) by 489 days.

(21) Appl. No.: 17/054,706

(22) PCT Filed: Jun. 20, 2019

(86) PCT No.: PCT/CN2019/092101
§ 371 (c)(1),
(2) Date: Nov. 11, 2020

(87) PCT Pub. No.: WO2019/242691
PCT Pub. Date: Dec. 26, 2019

(65) Prior Publication Data
US 2021/0228530 A1    Jul. 29, 2021

(30) Foreign Application Priority Data
Jun. 20, 2018   (CN) .......................... 201810636499.3

(51) Int. Cl.
| | |
|---|---|
| *A61K 31/337* | (2006.01) |
| *A61K 31/07* | (2006.01) |
| *A61K 31/192* | (2006.01) |
| *A61K 31/282* | (2006.01) |
| *A61K 31/4745* | (2006.01) |
| *A61K 31/475* | (2006.01) |
| *A61K 31/506* | (2006.01) |
| *A61K 31/519* | (2006.01) |
| *A61K 31/7048* | (2006.01) |
| *A61K 38/13* | (2006.01) |
| *A61K 47/54* | (2017.01) |
| *A61K 47/61* | (2017.01) |

(52) U.S. Cl.
CPC ............ *A61K 31/337* (2013.01); *A61K 31/07* (2013.01); *A61K 31/192* (2013.01); *A61K 31/282* (2013.01); *A61K 31/4745* (2013.01); *A61K 31/475* (2013.01); *A61K 31/506* (2013.01); *A61K 31/519* (2013.01); *A61K 31/7048* (2013.01); *A61K 38/13* (2013.01); *A61K 47/543* (2017.08); *A61K 47/545* (2017.08); *A61K 47/61* (2017.08)

(58) Field of Classification Search
CPC .... A61K 31/337; A61K 47/61; A61K 47/543; A61K 47/545; A61K 31/07; A61K 31/192; A61K 31/282; A61K 31/4745; A61K 31/47; A61K 31/506; A61K 31/519; A61K 31/7048; A61K 38/13
See application file for complete search history.

(56) References Cited

FOREIGN PATENT DOCUMENTS

| | | | |
|---|---|---|---|
| WO | WO-2004035629 A2 * | 4/2004 | ............ A61K 47/61 |
| WO | 2019242691 | 12/2019 | |

OTHER PUBLICATIONS

Y. Luo et al. A hyaluronic acid-taxol antitumor bioconjugate targeted to cancer cells. Biomacromolecules. 2000 Summer;1(2):208-18. doi: 10.1021/bm000283n. PMID: 11710102. (Year: 2000).*
J. Nakamura et al. Water-soluble taxol conjugates with dextran and targets tumor cells by folic acid immobilization. Anticancer Res. Mar. 2010;30 (3): 903-9. PMID: 20393013. (Year: 2010).*
O. Matthews et al. Tumor Targeting by Covalent Conjugation of a Natural Fatty Acid to Paclitaxel. Clin Cancer Res Oct. 1, 2001; 7 (10): 3229-3238. (Year: 2001).*
Y. Luo et al. Biomacromolecules, 2000; 1(2):208-18. doi: 10.1021/bm000283n. PMID: 11710102. (Year: 2000).*
K. Liu et al. Nanoscale, 2016, 8, 16091-16156, doi.org/10.1039/C6NR04489A. (Year: 2016).*

(Continued)

*Primary Examiner* — Medhanit W Bahta
*Assistant Examiner* — Manahil Mirghani Ali Abdalhameed
(74) *Attorney, Agent, or Firm* — PROCOPIO, CORY, HARGREAVES & SAVITCH LLP; Yuefen Zhou; Brent A. Johnson

(57) ABSTRACT

The present invention pertains to a group of taxane-lipid-polysaccharide dual conjugates of the Formula I, a process for the preparation thereof, uses thereof, and pharmaceutical compositions comprising the same. The invention also relates to a series of intermediates for the preparation of taxane-lipid-polysaccharide dual conjugates, a process for their preparation, and their use as drug delivery vehicles.

Formula I

| Taxane | Linker unit | Polysaccharide | Linker unit | Lipid unit |

1 Claim, 2 Drawing Sheets

(56) References Cited

OTHER PUBLICATIONS

J. Nakamura et al. (Anticancer Res. Mar. 2010;30 (3): 903-9. PMID: 20393013. (Year: 2010).*

Y. Song et al. (Int J Nanomedicine. Mar. 15, 2018;13:1585-1600. doi: 10.2147/IJN.S155383. (Year: 2018).*

Knop et al., Poly(ethylene glycol) in drug delivery: pros and cons as well as potential alternatives, Angewandte Chemie Int Ed . 2010, 49(36):6288-308.

Kim et al., Phase II Clinical Trial of Genexol® (Paclitaxel) and Carboplatin for Patients with Advanced Non-small Cell Lung Cancer, Cancer Res. Treat., 2011:43(1), 19-23.

Xiao et al., Telodendrimer-based nanocarriers for the treatment of ovarian cancer, Ther Deliv. 2013; 4(10): 1279-1292.

Ndungu et al., Targeted Delivery of Paclitaxel to Tumor Cells: Synthesis and in Vitro Evaluation, Med. Chem. 2010, 53, 8, 3127-3132.

Roy et al., Recent progress in the development of polysaccharide conjugates of docetaxel and paclitaxel, Nanomed Nanobiotechnol, 2014: 6, 349-368.

Varshosaz, Dextran conjugates in drug delivery, Expert Opin. Drug Deliv. 2012, 9(5):509-523.

Koudelka et al., Liposomal paclitaxel formulations, Journal of Controlled Release 2012, 163, 322-334.

Irby et al., Lipid-Drug Conjugate for Enhancing Drug Delivery, Mol Pharm, 2017, 14(5):1325-1338.

Petersen et al., Meta-analysis of clinical and preclinical studies comparing the anticancer efficacy of liposomal versus conventional non-liposomal doxorubicin, Journal of Controlled Release 2016, 232, 255-264.

Bradley, Tumor Targeting by Covalent Conjugation of a Natural Fatty Acid to Paclitaxel, Clin. Cancer Res. , 2001, 7 (10), 3229-3238.

Bedikian et al., Phase 3 study of docosahexaenoic acid-paclitaxel versus dacarbazine in patients with metastatic malignant melanoma, Annals of Oncology 2011, 22: 787-793.

* cited by examiner

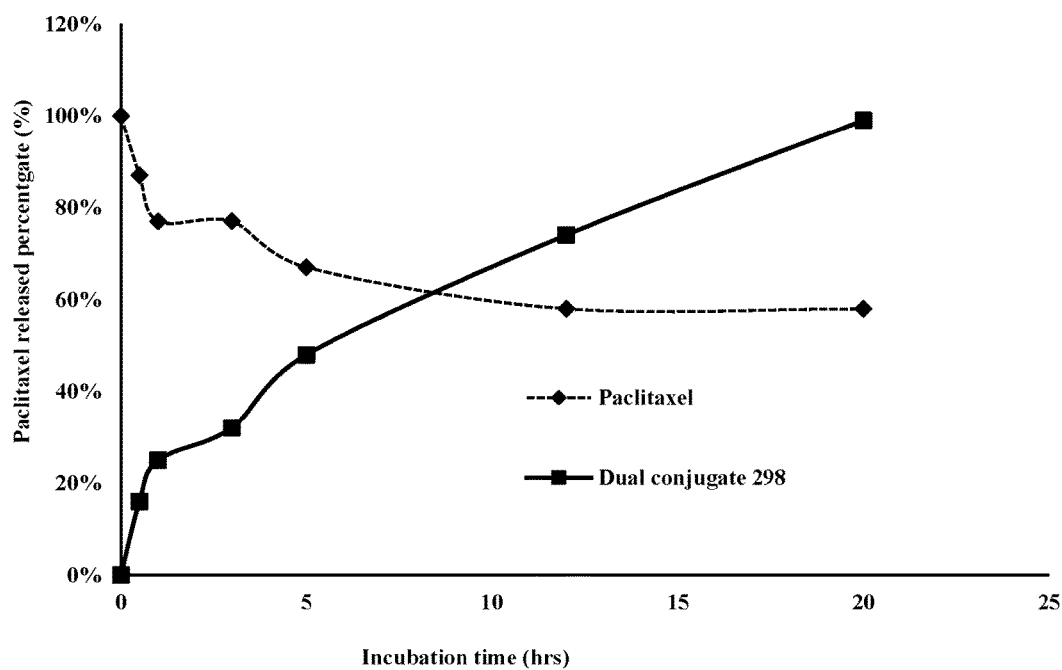
Figure 1. The percentage of paclitaxel released from dual conjugate 298 incubated in rat plasma.

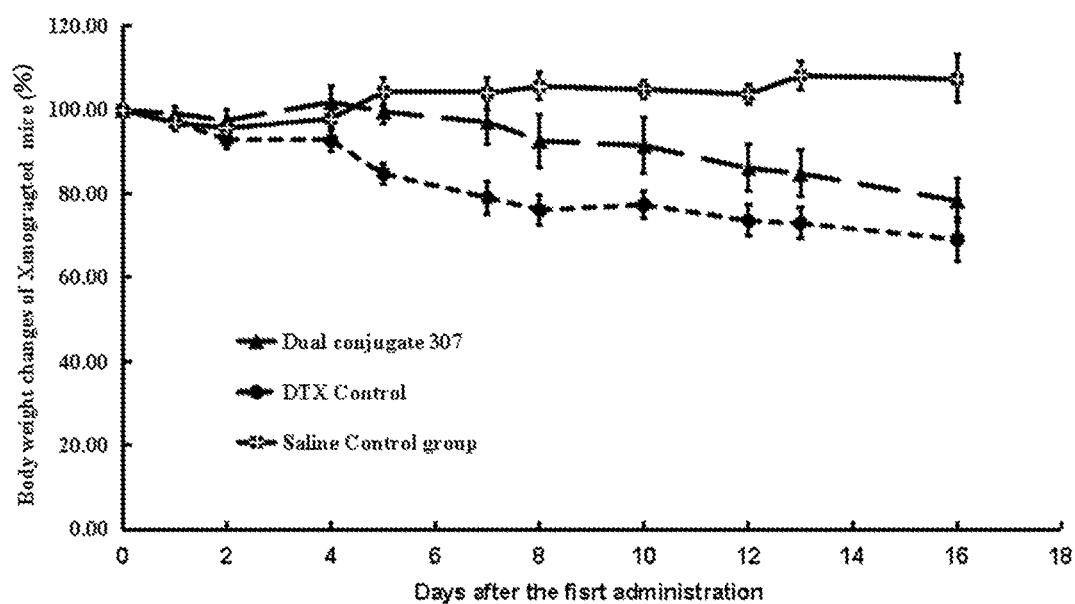
Figure 2. Body weight change of xenograft mice (%) of dual conjugate 307 group, DTX control group and saline control group.

TAXANE-LIPID-POLYSACCHARIDE DUAL CONJUGATES, PREPARATION METHODS THEREOF AND USES THEREOF

CROSS REFERENCE TO RELATED APPLICATIONS

This application is a national phase of International Patent Application No. PCT/CN2019/092101, filed Jun. 20, 2019, which claims priority to Chinese Patent Application No. 201810636499.3, filed Jun. 20, 2018, all of which are incorporated by reference herein in their entirety.

The present invention relates to a group of taxane-lipid-polysaccharide dual conjugates, a process for the preparation thereof, use thereof, and a pharmaceutical composition comprising the same. The invention also relates to a series of intermediates for the preparation of taxane-lipid-polysaccharide dual conjugates, a process for their preparation, and their use as drug delivery vehicles.

BACKGROUND OF THE INVENTION

Taxanes are a series of natural compounds and artificial semi-synthetic compounds based on taxane diterpenoids, including paclitaxel (taxol) and docetaxel (also known as docetere), cabazitaxel, and drugs in clinical trials such as milataxel (MAC-321, TL-139), tesetaxel, ortataxel, larotaxel, SB-T-1214, etc. Their chemical structures are shown in Figure-1:

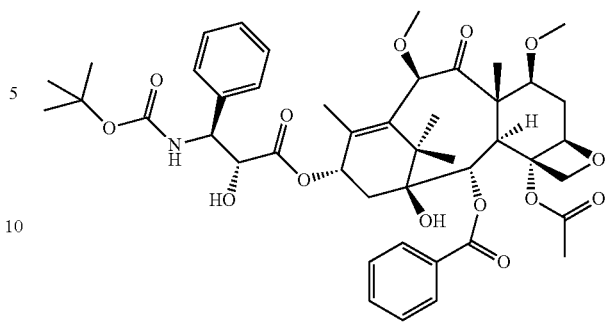

cabazitaxel

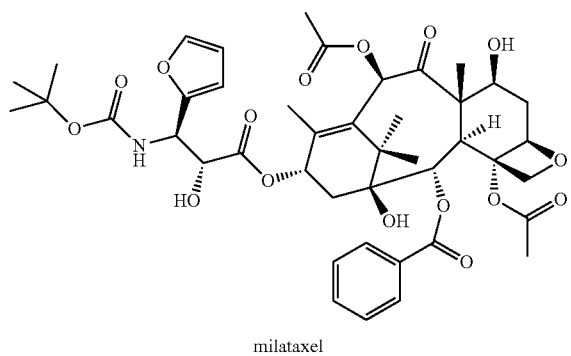

milataxel

Figure-1

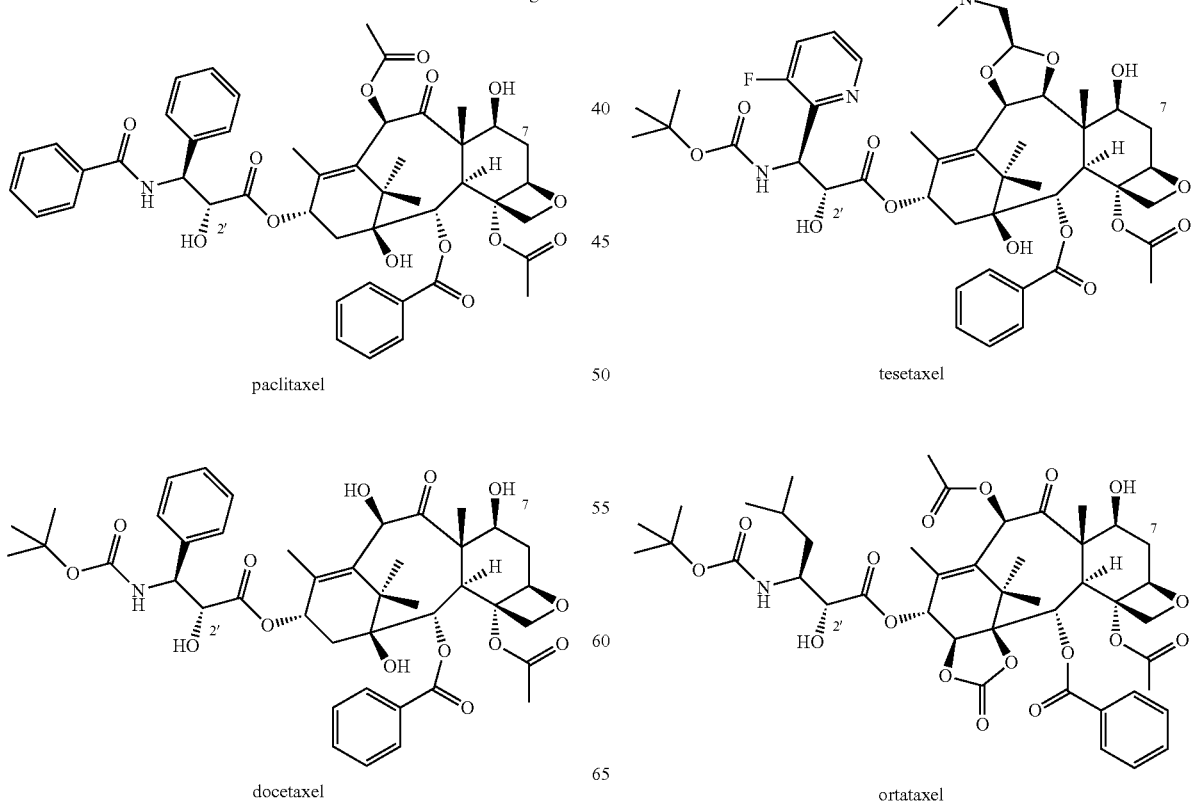

paclitaxel tesetaxel docetaxel ortataxel

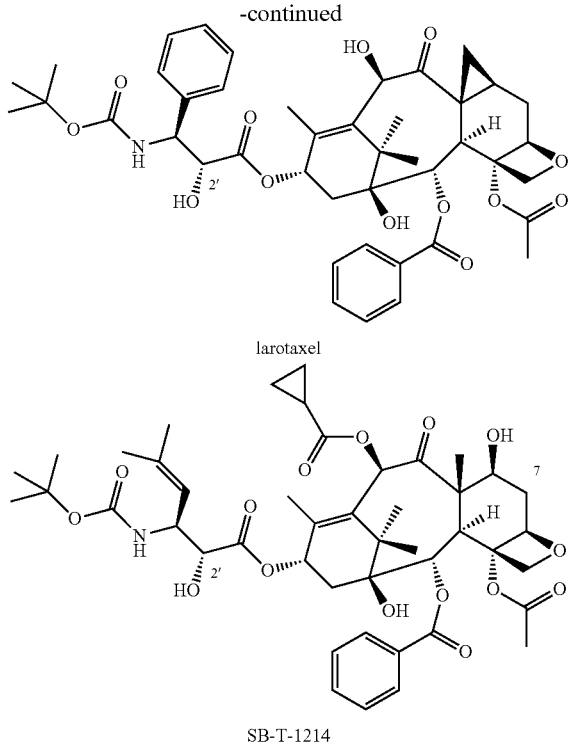

larotaxel

SB-T-1214

Taxanes inhibit cell mitosis and have significant anticancer activity for the treatment of breast cancer, ovarian cancer, lung cancer, bladder cancer, prostate cancer, melanoma, esophageal cancer and other solid tumors.

However, the taxanes are poorly water-soluble, and the clinically used paclitaxel, docetaxel, and cabazitaxel preparations require the addition of a co-solvent such as Cremophor EL (containing polyoxyethylene castor oil) or Tween-80. However, the cosolvents such as Cremophor EL and Tween-80 contain a polyethylene glycol (PEG) fragment in the chemical structure, and the polyethylene glycol fragment (PEG) can cause immune hypersensitivity and even lead to patient death. [Angew. Chem., 2010: 49(36), 6288-308.]. In addition, Cremophor EL and Tween-80 and other cosolvents can cause nephrotoxicity and neurotoxicity, as well as serious adverse reactions of immune system toxicity such as neutropenia, which seriously hurt patients.

In addition, traditional anticancer drug formulations are administered via multiple routes to achieve a certain blood concentration distributed throughout the body for optimal therapeutic effects. However, these forms of therapy and administrative methods lack specificity and selectivity for targeting cancerous tissues. While killing or inhibiting tumor cells, they also produce toxic side effects on normal tissues. Traditional taxane formulations also have such defects. Ideally, formulations of anticancer drugs like Taxane should be designed to target cancerous cells, maintaining higher concentrations in cancerous tissues as opposed to normal tissues, prolonging the duration of drug action and increasing its lethality against tumor cells while reducing the severity of its side effects.

To address the issue of Taxane insolubility to reduce co-solvent related adverse reactions, three major technologies have been developed for the preparation of water-soluble taxanes over the last few decades: 1) Small molecule modified prodrugs, including amine salts, carboxylates, sulfonates, amino acid salts, phosphates, etc.; 2) water-soluble polymers as carriers of prodrugs, water-soluble polymers including poly-ethylene glycol (PEG), poly-acrylic acid, poly-Glutamate, poly-aspartic acid, polysaccharides, etc.; 3) water-soluble drug delivery systems, including liposomes, cyclodextrin inclusions, injection emulsions, microcapsules, microspheres, nanomedicine, etc. [Practical drugs and Clinical, 2016: 19 (4), 510-517.].

To date, only the nanomedicine Abraxane (Paclitaxel-Human Albumin nano particles formulation, USA), paclitaxel liposome ("Lipusu", China) and paclitaxel microsphere (Gexenol-PM, Korea) have been marketed. Among them, Gexenol-PM preparation still contains a large amount of polyethylene glycol (PEG) components, and about 15% of patients showed hypersensitivity reactions in clinical practice [Cancer Res. Treat., 2011:43(1), 19-23.] The liposome preparation "lipushu", although it does not contain polyethylene glycol (PEG), it contains a hemolytic ionic lecithin, thus this formulation still requires desensitization and the its therapeutic effect is not improved when compared to conventional paclitaxel formulations; the nano drug Abraxane, which eliminates toxic side effects of co-solvents, has slightly improved efficacy when compared to traditional paclitaxel formulations, but nevertheless it fails to demonstrate effective tumor targeting properties and is expensive to produce. [Ther. Deliv., 2013: 4 (10), 1279-1292.].

For the aforementioned prodrug designs and for new formulations of polymer carrier-based taxane drugs, polysaccharides have been used as drug carriers due to widespread availability, low production cost, along with superior biocompatibility, biodegradability and safety. So far, although paclitaxel and docetaxel have been found to form conjugates with polysaccharides through covalent bonds, most of the polysaccharide-taxane drug conjugates reported possess weaknesses in their structural design: they are heterogeneous conjugate structures, which are resulted from the covalent bonds simultaneously linked to both the 2'-0 and 7-O— positions of the taxane anticancer drug. Studies have shown that high molecular weight polymers covalently linked to the 2'-0 position of taxane maintains effective antitumor activity. In contrast, covalent conjugation of high molecular polymers to the 7-0 position of taxane reduces the anti-tumor activity of taxane more than 10 times [J. Med. Chem., 2010: 53(8), 3127-3132.] Therefore, it is necessary for polysaccharides to be structurally designed and efficiently synthesized to only be covalently linked to the 2'-0 position of taxane; in this regard, our Chinese patent CN2013106162537 employs a position-specific synthesis technique to achieve optimal and selective attachment. Furthermore, unlike small molecule compounds, polysaccharides are macromolecular polymers with both limited choices of solvents and few reaction types to be utilized for their limited chemical structure modifications. Thus, literatures have reported a restricted number of chemical bond types for modifying the structure of polysaccharides, such as via ester bonds, amide bonds, carbamate bonds, and hydrazide bonds (Expert Opin. Drug Deliv. 2012: 9 (5)), 509-523; Nanomed Nanobiotechnol, 2014: 6, 349-368). Relevant published studies have shown that the most common conjugation structures involving polysaccharides to taxanes compounds are comprised of paclitaxel or docetaxel molecules linked to polysaccharides like carboxymethylcellulose, dextran or chitosan, heparin through simple spacers such as amino acids, adipic acid dihydrazide, butyric acid, ethylene diamine, succinic acid, and via ester or amide bonds. It should be noted that the polysaccharide polymers used in these studies tend to contain more than one functional group, such as hydroxyl and carboxyl groups (HA, CM-Dex, Hep) or amine and carboxyl groups (succinyl chitosan). The structure may be cross-linked or self-polymerized in the coupling reaction, resulting in insufficient degradation of the polysaccharide carrier, thereby hindering release of the original taxane drug.

Tumor tissues grow more rapidly than their normal counterparts, requiring more nutrients, energy, and lipid substances in the process. Particularly, lipid substances form the foundation of cellular membrane and membranous organelles, and consequently are concentrated in tumor tissues. It has been reported in literature that lipid substances are used to prepare tumor-targeted formulations. Generally, lipid substances are also used to alter both physical and chemical properties of drug molecules to improve drug dispersion status as well; thereby incorporating lipid substances in structures enhances absorption, distribution, and bioavailability of the drug in vivo, which leads to increased therapeutic effects and safety while ameliorating toxic side effects. The primary forms of lipid substances in aforementioned new pharmaceutical dosage forms and drug delivery systems are drug liposomes and drug-lipid conjugates. For example, in order to avoid toxicity and hypersensitivity caused by traditional formulations of paclitaxel, lipids have been used to prepare paclitaxel liposome formulations [J. Control Release, 2012: 163(3), 322-34.], lipids have also been covalently coupled to paclitaxel for more selective delivery to cancerous tissues [Mol. Pharm., 2017: 14(5), 1325-1338].

However, liposomes are prone to oxidation, delamination, and leakage due to decreased stability during storage. Conditions for transportation and storage must be tightly controlled. Traditional liposomes are engulfed by the reticuloendothelial system after entering the body; subcutaneous or intravenous injection of PEG-modified liposomes can cause an immune response that cause the drug to be rapidly cleared from circulation. Many studies show that there is no significant change in the anti-tumor effect of drug liposomes compared to delivering the drug alone, and the side effects caused by drug liposomes can be either reduced or enhanced [J. Control Release, 2016: 232, 255-264.].

On the other hand, lipid drug conjugates generally refer to lipid modifications by covalent bonds in the molecular structure of drugs themselves, which are often used to increase oral bioavailability, improve anticancer targeting, and reduce systemic toxicity. Normally, drugs are bound to either a fatty acid, or a steroid molecule, or a glyceride or a phospholipid via a simple linker structure, forming ester bond, amide bond or disulfide bonds so that the resulting drug lipid conjugate can achieve slowed and sustained release. However, this change inadvertently reduces the drug's overall solubility in water and increases the difficulty of the preparation of delivery via intravenous formulations. For example, the DHA and paclitaxel conjugate, Taxoprexin, has been evaluated in a variety of clinical trials for various tumors to increase tumor targeting properties and to reduce toxicity of paclitaxel [Clin. Cancer Res., 2001: 7(10), 3229-3238.]. However, a small amount of solubilizing agents such as 10% GEL (polyoxyethylene castor oil) and 10% ethanol are needed in intravenous preparations in order to disperse and dissolve the drug. Hence patients must undergo premedication with hormones or antihistamines to reduce hypersensitivity reactions to the solubilizing agents. Recent studies have shown no significant differences in final survival rates between the DHA-paclitaxel and dacarbazine groups in the treatment of patients with metastatic malignant melanoma cancer. Similarly, there is no significant change in response rate, duration of response, time to progression, and time to treatment failure between the two drugs [. Ann. Oncol., 2011: 22(4), 787-93.].

Taxoprexin failed to achieve expected results because the simple and direct chemical bond could not fully release the free paclitaxel drug and allow it to exert its full anticancer effects. For lipid-drug covalent conjugates of this type, the in vivo release of parent drug by degradation of linkage bonds is key to ensuring optimal therapeutic effects. However, due to the inability of linker bonds to degrade effectively, these conjugates drugs tend to demonstrate lower anticancer activity than their parent drugs. [Mol. Pharm., 2017: 14 (5, 1325-1338.]

To address aforementioned technical problems, defects, and limitations, the present invention presents a series of novel structures of taxane-lipid-polysaccharides dual conjugates and their related intermediates through extensive and intensive experimental research in order to improve antitumor activity of taxanes and to further reduce their toxic side effects. Taxane-lipid-polysaccharide dual conjugates and their related intermediates are defined by the following statement, wherein the taxanes and lipid components are covalently linked to polysaccharides via spacers and/or linker s. The dual conjugates in this invention are specifically designed and optimized, are different from prior inventions with significant differences in terms of the structural construction of the conjugates, the composition of the carriers, the in vivo optimized release mechanism, and the capability to target cancerous tissues. Particularly, the dual conjugates prepared in this way not only resolves the issue of solubility of taxane compounds, but also optimizes the release mechanism of taxane from the conjugates in vivo. The introduction of lipids in conjugate form greatly enhances tumor targeting feature of drug conjugates, therefore synergistically improving the anticancer therapeutic properties of taxane drugs. It is important to note that the potential lipophilic interactions between taxanes and lipid components can not only stabilize the nanoparticles formed by the dual conjugates when dissolved in solution, but also protect hydrolytic sites in conjugate form, so the majority of taxane-lipid-polysaccharides dual conjugates can be delivered to tumor sites prior to the release of taxane drugs.

As mentioned above, there are many challenges of available methods for chemically modifying the structures of polysaccharides, such as very limited choices in available solvents, utilizable reaction types, and linker groups. In addition, conjugation of two or more complex pharmaceutical components to polysaccharides demands the consideration of compatibilities of chemical reactions which ensure not only the stability of taxanes or other conjugated drugs, but also efficient, targeted release drug molecules in vivo. Thus, the preparation of taxane-lipid-polysaccharides drug conjugate presents a number of challenges. So far, a successful and systematic design of using polysaccharides as carriers to covalently conjugate with two or more functional pharmaceutical components has yet not been reported in literature.

SUMMARY OF THE INVENTION

In the present invention, a taxane compound and a lipid compound are simultaneously linked to polysaccharides in covalent bonds to form a dual conjugates. The structure of the dual conjugates is relatively uniform in term of the conjugation sites. This innovative design of conjugation not only solves the solubility issue with the taxane drugs, but also maintains their good biological activities, and improves the bioavailability and tumor targeting of the taxane drugs.

Particularly, for dual conjugates with polysaccharides (MW more than 250 k Da), they are expected to have better cancer targeting properties, which make them the more potential drug candidates for the treatment of diseases such as cancers that are sensitive to taxane compounds.

The first aspect of the present invention provides a taxane-lipid-polysaccharide dual conjugates or a pharmaceutically acceptable salt or solvate thereof, as shown by Formula I:

Formula I

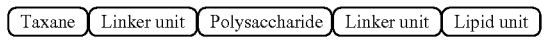

within their structures:
the linker unit(s) may be selected from

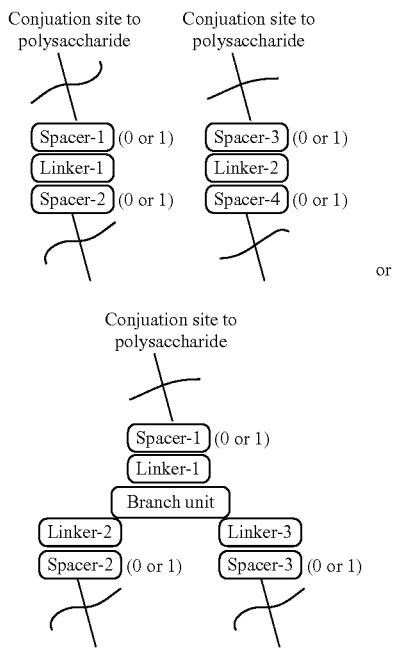

the polysaccharide is covalently linked to the linker unit(s) through one or more conjugation sites thereof,
the linker unit is covalently linked to a taxane compound or a lipid compound unit;
the polysaccharide conjugation site refers to a hydroxyl group, a carboxyl group, an amino group, a phosphate group or a sulfonic acid group inherent to the polysaccharide;
the molecular molar ratio of the taxane compounds to the lipid compounds unit is an arbitrary ratio, preferably 0.1 to 99.9%, more preferably 0.1 to 60%, and far more preferably the following ratio range: 0.1 to 50, 0.1 to 20, 0.1 to 10, 0.1~5, 0.1~1, 1~50, 1-20, 1~10 or 1-5, such as 0.9, 0.8, 0.7, 0.6, 0.5, 0.4, 0.3, 0.2 or 0.1, or 9, 8, 7, 6, 5, 4, 3, 2 or 1;
the polysaccharide is selected from phyto-polysaccharides, animal polysaccharides, microbial polysaccharides or synthetic polysaccharides and derivatives thereof,
the taxane compound is selected from a natural or artificial semi-synthetic compound and derivatives thereof, which contains the core structure of taxane diterpenes;
the lipid compound unit is a single molecular lipid compound or a structural unit composed of a plurality of the same or different single molecular lipid compounds;

the linker1-3, the spacer 1-4, and the branch unit are all connected to each other by a covalent bond, and are also covalently bonded to the polysaccharide and the taxane compound; The covalent bond is selected from the group type of bonds consisting of an amide bond, an amino-carbamate bond, an aminothio carbamate bond, an ester bond, an isourea bond, a thiourea bond, a urea bond, a disulfide bond, a carbonate bond, a phosphate ester bond, phosphamide bond, sulfonamide bond, alpha or beta glycosylic bond, covalent bond containing triazole, and covalent bond containing thiomaleimide;

preferably, the polysaccharides are selected from the group consisting of homopolysaccharides or heteropolysaccharides, and may be linear, branched, or cyclic in structure, such as dextran, levosaccharide, hyaluronic acid, cyclodextrin ($\alpha$, $\beta$, And $\gamma$ etc.), hydroxyethyl starch, xylan, water-soluble starch, water-soluble cellulose, carboxymethyl cellulose, galactose, polysialic acid, rhamnose, *Ganoderma lucidum* polysaccharides, lentinan, chitin (Chitin), chitosan, alginate, carrageenan, gellan gum, pullulan, scleroglucan, xanthan, xyloglucan, Amylose, etc.; the glycosylic bonds between the sugar units of the homopolysaccharide or heteropolysaccharide may be $\alpha$ or $\beta$ or $\alpha,\beta$-mixed type; the sugar unit of the homopolysaccharides is selected from the group consisting of a three-carbon sugar, a four-carbon sugar, a five-carbon sugar, a six-carbon sugar, a seven-carbon sugar, and an eight-carbon sugar or a deoxy sugar unit, which are structurally composed of a plurality of a single sugar unit composition, such as dextran, xylan, polysialic acid, etc.; the heteropolysaccharides, their sugar units are or a mixture of two or more types of saccharide units, such as hyaluronic acid, heparin, etc.; the polysaccharide may be by nature bearing or structurally modified with one or more substituents selected from the group consisting of: a carboxylic acid group, a carboxylate group, an amino group, a sulfonic acid group, a sulfonate group, a phosphoric acid group, a phosphate group, a hydroxyethyl group, a hydroxypropyl group, a methyl group, an acyl group or acyl, carboxymethyl, natural amino acid groups, unnatural amino acid groups, or the like;

more preferably, the polysaccharide is selected from the dextran, hyaluronic acid, hydroxyethyl starch, carboxymethyl cellulose, poly-galactosamine, poly-sialic acid, polysaccharide of *Ganoderma lucidum*, lentinan (polysaccharide of *Lentinula edodes*); the polysaccharide may have a molecular weight ranging from 300 to 3,000,000.

preferably, the taxane compound is selected from the group list used in clinics or clinical trials consisting of paclitaxel (taxol), docetaxel (also known as docetere), cabazitaxel, and in clinical trials such as milataxel. (MAC-321, TL-139), tesetaxel, ortataxel, larotaxel, SB-T-1214, etc.; more preferably, the taxane compound is selected from the group consisting of paclitaxel, docetaxel, cabazitaxel and milataxel.

preferably, the polysaccharide is linked to the taxane by a linker and/or a spacer, optionally linked to 2'-O position, 7-O position, 10-O position of the taxane core structure or the side chain of the altered structure; more preferably, 2'-O position of the taxane or the side chain of the altered structure.

preferably, as for the lipid compound unit, the single molecular lipid compound is selected from the group consisting of saturated or unsaturated fatty acids and derivatives thereof, saturated or unsaturated cyclic alkyl acids and derivatives thereof, aryl or heterocyclic aryl acids and derivatives thereof, glycerides, glycerol phosphates, sphingolipids, sterols and derivatives thereof, prenol lipids and derivatives thereof, glycolipids and derivatives thereof, lipid-soluble vitamins and derivatives thereof; these lipid compounds are optionally substituted by one or more substituents which may be the same or different, the substituents are independently selected from the group consisting of $C_{1-20}$ alkyl, $C_{2-10}$ alkenyl, $C_{2-10}$ alkyne, $C_{3-15}$ cycloalkyl, $C_{5-20}$ aryl, $C_{7-20}$ arylalkyl, heteroaryl, heterocycloalkyl, ester group, keto group, hydroxyl group, phenolic hydroxyl group, $C_{1-18}$ alkoxy group, $C_{3-15}$ monocyclic or polycyclic alkoxy group, amino group, $C_{1-10}$ alkyl group, mono or disubstituted amino group, amide group, sulfonic acid group, sulfonamide group, halogen (fluorine, chlorine, bromine, iodine), trifluoromethyl group; wherein group R may be selected from the group consisting of an alkyl group, a cycloalkyl group, an aryl group, an aryl alkyl group, a cycloalkyl alkyl group and the like.

more preferably, the saturated or unsaturated fatty acid of the single molecular lipid compound and its derivative are selected from the group consisting of stearic acid, palmitic acid, octanoic acid, tannic acid, lauric acid, myristic acid, arachidonic acid, behenic acid, and twenty lignoceric acid, lignoceric acid, hexadecanoic acid, myristic acid, palmitoleic acid, sapienic acid, oleic acid, anti-oleic acid, 11-octadecene acid, linoelaidic acid, alpha-linolenic acid (ALA), gamma-linoleic acid (GLA), arachidonic acid, eicosapentaic acid (EPA), erucic acid, docosahexaenoic acid (DHA) and its corresponding alcohol, amine, azide compound and isocyanate; such as docosahexaenoic acid (DHA) derived corresponding alcohols, amines, sufurhydryl-containing compounds, azide compounds and isocyanates, see Figure-2. more preferably, the saturated or unsaturated fatty acid is selected from the group consisting of docosahexaenoic acid (DHA), alpha-linolenic acid (ALA), gamma-linoleic acid (GLA), eicosapentaenoic acid (EPA)), stearic acid. Figure-2 illustrates DHA and its derivatives:

preferably, the saturated cycloalkyl acid of the single molecular lipid compound is selected from the group consisting of $C_{3-10}$ saturated cyclic hydrocarbon acids, 3-12 membered saturated heterocyclic hydrocarbon acids containing at least one N, O or S hetero atom, wherein $C_{3-10}$ The saturated cyclic alkyl group is preferably a $C_{3-10}$ cycloalkyl group such as a cyclopropyl group, a cyclobutyl group, a cyclopentyl group or a cyclohexyl group, wherein the saturated 3-12 membered heterocycloalkyl group is preferably selected from the group consisting of tetrahydrofuran, tetrahydrothiophene, azetidine, acridine, tetrahydropyrrole, 1,3-dihydrothiazole, 1,3-dihydrooxazole, piperidine, piperazine, morpholine, thiomorpholine or tetrahydrothiazide; the unsaturated cyclic alkyl acid group is selected from the group consisting of $C_{5-10}$ cycloalkenylalkyl, $C_{5-10}$ cycloalkynyl acid, $C_{5-10}$ cycloalkenyloxyalkyl acid, $C_{5-10}$ cycloalkynyloxyalkyl acid; 5-10 membered heterocycloalkenyl allyl acid which containing at least one N, O or S hetero-atom, a 5-10 membered heterocycloalkenyloxyalkyl acid having at least one N, O or S hetero atom, 5-10 membered heterocyclic alkynyl hydrocarbamic acid, containing at least one N, O or S hetero atom; a 5-10 membered heterocycloalkynyloxyalkyl acid having at least one N, O or S heteroatom, wherein the $C_{5-10}$ cycloalkenyl group is preferably a cyclopentenyl group, a cyclohexenyl group, cycloheptenyl; $C_{5-10}$ cycloalkynyl is preferably selected as a cyclo-octynyl group, and the 5-10 membered heterocycloalkynyl group is preferably selected as a cyclo-octynyl group containing at least one N, O or S hetero atom; and the corresponding alcohol, amine, sulfhydryl, an azide compound and an isocyanate of the above mentioned saturated or unsaturated cyclic hydrocarbon acid;

more preferably, the saturated or unsaturated cyclic alkyl acid is selected from the following structures and derivatives thereof, shown in the following Figure-3:

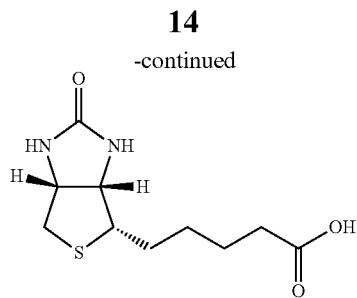

more preferably, the aryl acid or heterocyclic aryl acid of the single molecular lipid compound and its derivative are selected from an aryl alkyl group($C_{0-8}$) acid, an aryl alkenyl group ($C_{0-8}$) acid, and two or more aryl alkyl ($C_{0-10}$) acids, two or more aromatic ring fused alkyl ($C_{0-10}$) acids, heterocyclic aryl alkyl groups containing at least one N, O or S hetero atom ($C_{0-10}$) acid, whose structure is as shown in Figure-4:

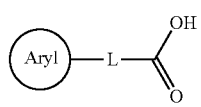

Figure-4 wherein the aromatic group (Aryl) is selected from the group consisting of:
1) a five-membered heteroaryl, six-membered aryl, six-membered heteroaryl group, preferably phenyl, pyridyl, pyrrolyl, imidazolyl; optionally substituted by the substituents defined above for a single molecular lipid compound;
2) double ring, double fused ring and triple fused ring, selected from the structure shown in Figure-5; it is optionally substituted with the substituents defined above for a single molecular lipid compound;

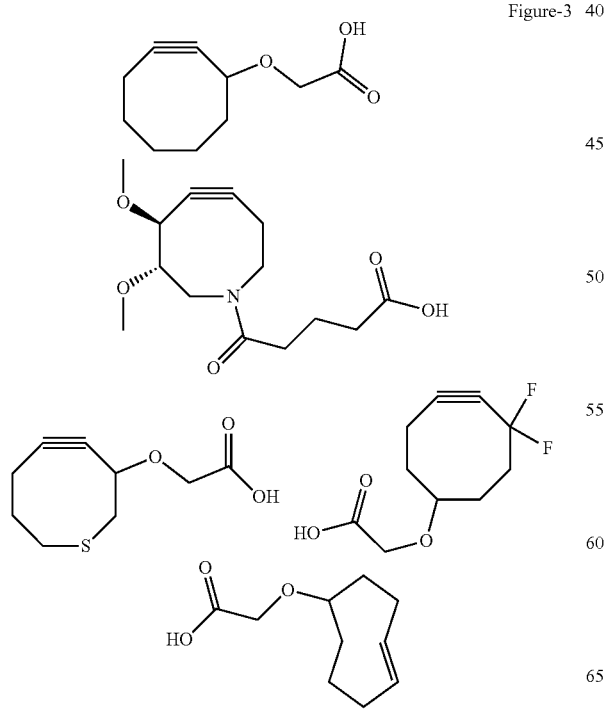

Figure-3

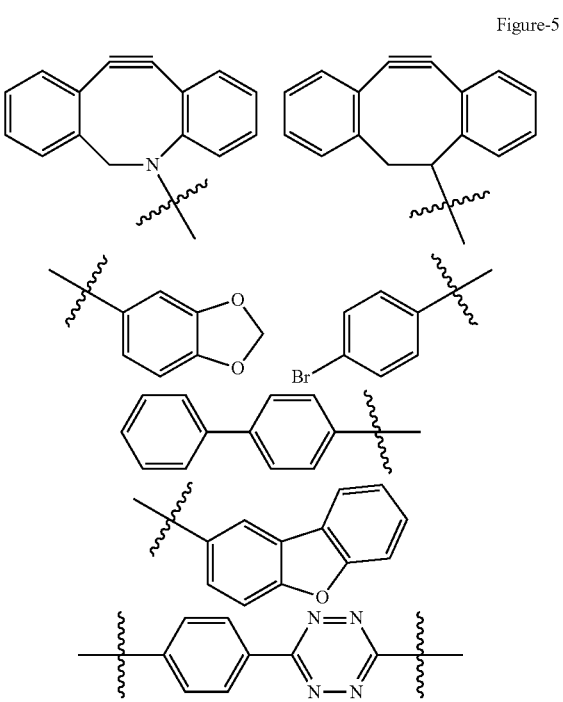

Figure-5

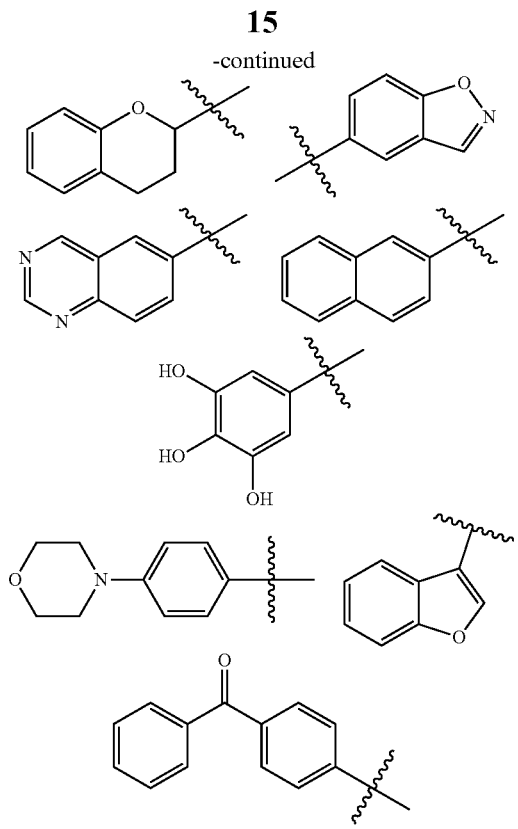

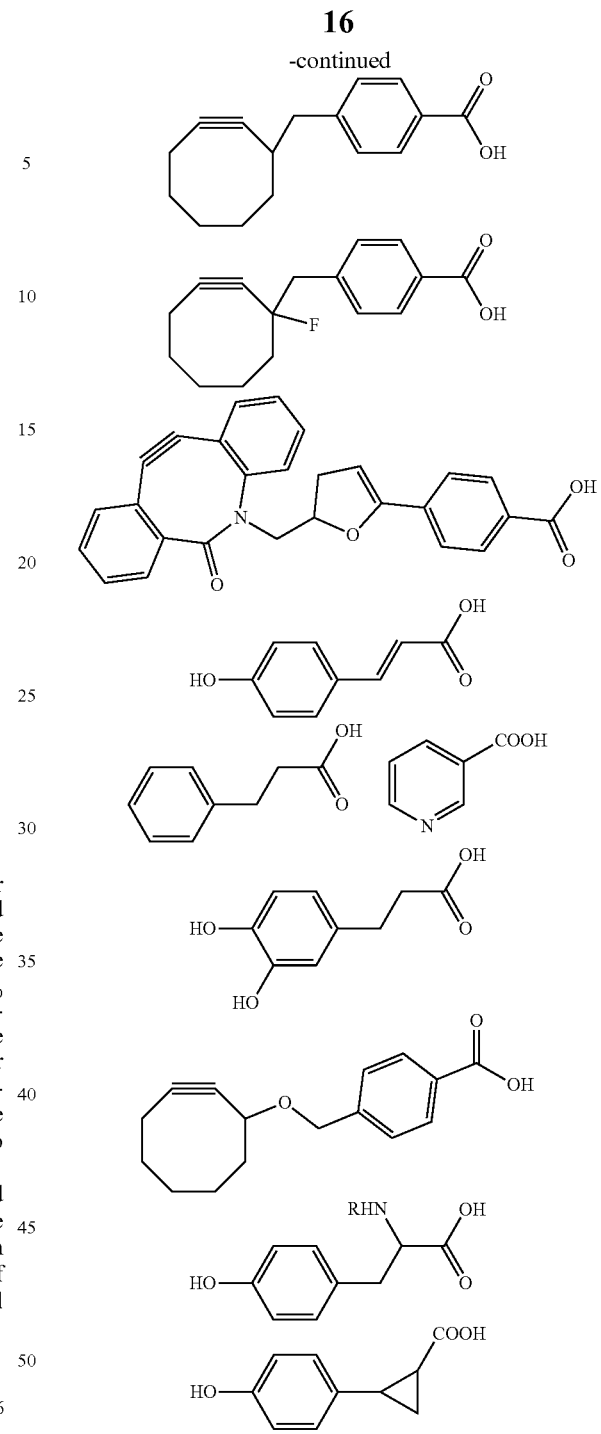

3) L is selected from a disubstituted saturated linear or branched or cyclic $C_{0-15}$ alkyl group, a disubstituted $C_{2-10}$ alkenyl group containing one or more double bonds, and a disubstituted $C_{2-12}$ containing one or more triple bonds; an alkyne group, a disubstituted $C_{3-10}$ heterocycloalkyl group, a disubstituted $C_{3-12}$ heterocycloalkyl group containing one or more double or triple bonds, a keto group; and a disubstituted straight or branched $C_{0-15}$ alkyl group which is optionally substituted with a substituent as defined above for a single molecular lipid compound wherein at least one hetero atom selected from N, O or S;

more preferably, the aromatic acid or heteroaromatic acid of the single molecular lipid compound is selected from the structures and derivatives and isomers thereof, shown in Figure-6., wherein R is selected from the group consisting of an alkyl group, a cycloalkyl group, an aryl group, an aryl alkyl group, and a cycloalkyl alkyl group, etc.;

Figure-6

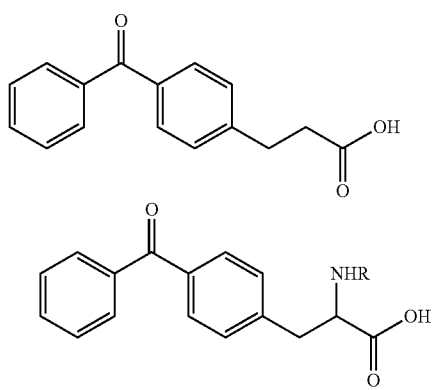

preferably, the glyceride of the single molecular lipid compound is selected from the group consisting of a saturated or unsaturated fatty acid, a saturated or unsaturated cyclic alkyl acid, or a monocarboxylic acid ester or a biscarboxylic acid ester, or a tri-ester of an aromatic carboxylic acid or a heteroaryl acid with glycerol; more preferably a monoester and a biscarboxylic acid ester of a unsaturated fatty acid and glycerol and a derivative thereof, preferably, the glycerol phosphate of the single molecular lipid compound is selected from the group consisting of cephalin, lecithin, phosphatidylethanolamine, phospholipid serine, phosphatidylinositol, etc.; more preferably cephalin, lecithin, phosphatidylethanolamine and derivatives thereof;

preferably, the sphingolipid compound of the single molecular lipid compound is selected from the group consisting of sphingomyelin, ceramide, glycosphingolipid; more preferably sphingomyelin or ceramide and derivatives thereof;

preferably, the sterols of the single molecular lipid compound and derivatives thereof are selected from the group consisting of 1) cholesterol and derivatives thereof, as shown in figure-7. 2) free bile acids and conjugated bile acids and their derivatives, such as cholic acid, deoxycholic acid, chenodeoxycholic acid, lithocholic acid, deoxycholic acid, glycocholic acid, taurocholic acid; 3) $C_{18}$ sterols and their derivatives such as estrogen; 4) $C_{19}$ sterols and their derivatives, including androgens such as testosterone and androstenone; 5) $C_{21}$ sterols, including progesterone, glucocorticoids and mineralocorticoids; 6) phytosterols and derivatives thereof such as β-sitosterol, sterol and Brassicasterol; more preferably bile acids, β-sitosterol and derivatives thereof;

Figure-7 illustrates cholesterol and its derivatives:

trisaccharides), the monoester and the polyester formed thereof, more preferably, a poly-carboxylic acid ester or amide formed by a saturated fatty acid or an unsaturated fatty acid and a sugar, and a derivative thereof;

preferably, the fat-soluble vitamins and derivatives thereof of the single molecular lipid compound are selected from the group consisting of vitamin A, vitamin D (including vitamins $D_1$, $D_2$, $D_3$, $D_4$ and $D_5$), and vitamin E (including α, β, γ and δ tocopherol and α, β, γ and δ tocotrienol). vitamin K (including vitamin $K_1$ and $K_2$), vitamin P and their derivatives; more preferably vitamin A, vitamin D, vitamin E and its derivatives;

preferably, the structural unit consisting of a plurality of identical or different single molecular lipid compounds comprises two types: a grafted lipid compound unit and a dendritic lipid compound unit, shown in the following Figure-8:

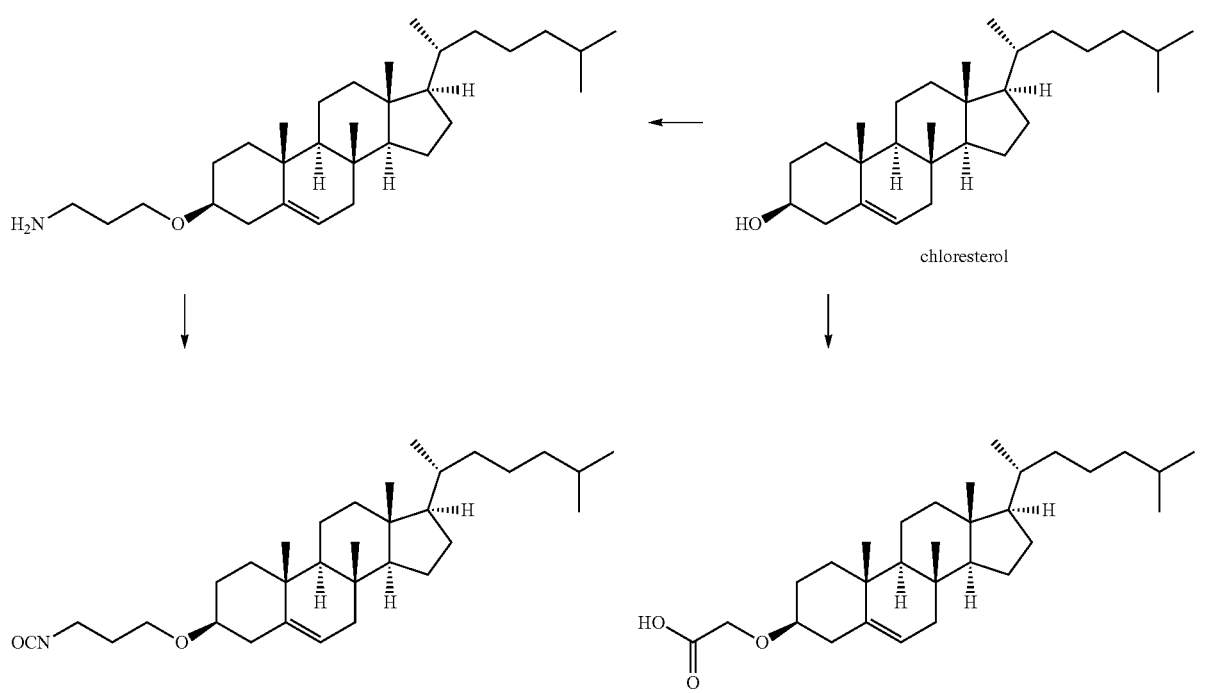

Figure-7

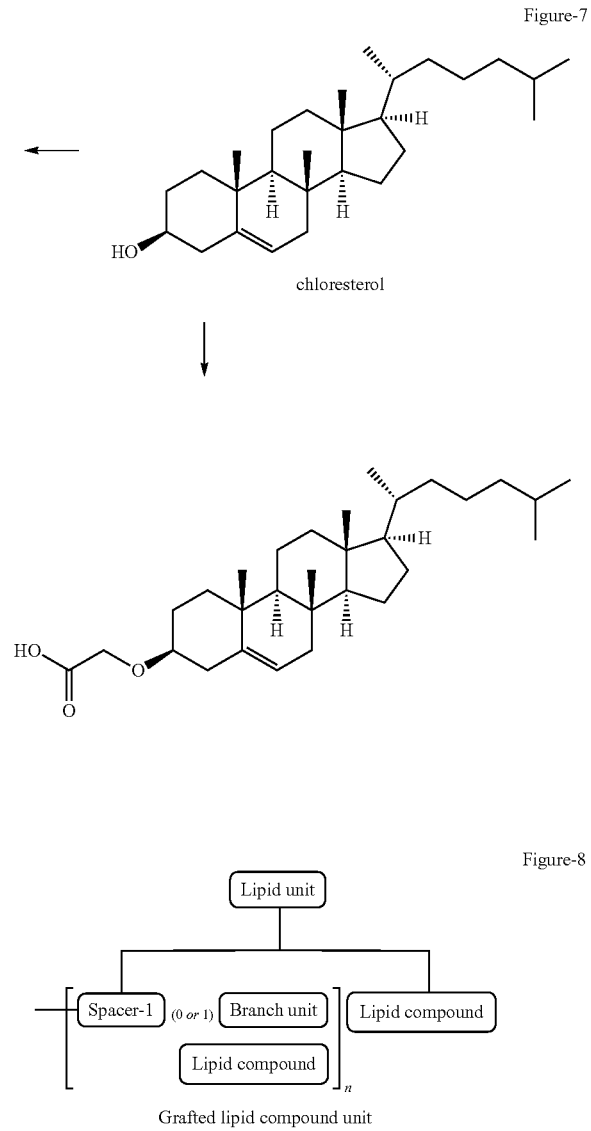

Figure-8

Grafted lipid compound unit preferably, the prenol lipids and derivatives thereof of the single molecular lipid compound are selected from the group consisting of isoprene monomers, diploids or/and polyploids and derived alcohols, amines, acids, phospholipids and derivatives thereof, more preferred are isoprene diploids and polyploid-derived alcohols, amines, acids, phospholipids and derivatives thereof;

preferably, the glycolipid of the single molecular lipid compound is selected from the group consisting of saturated fatty acids, unsaturated fatty acids, cyclic alkyl acids, unsaturated cyclic alkyl acids, and aromatic carboxylic acids and sugars (including monosaccharides, disaccharides, and

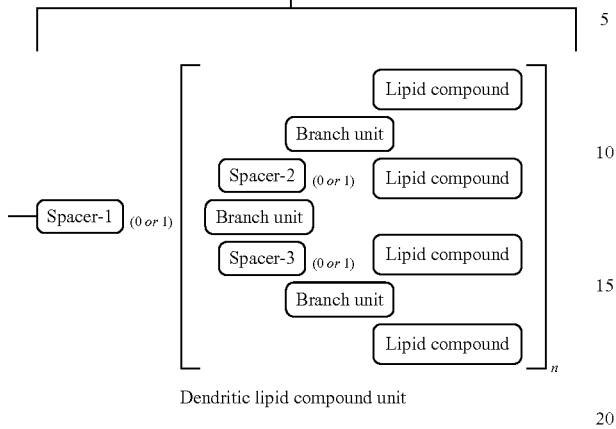

Dendritic lipid compound unit wherein n is selected from an integer of 0 to 10, preferably an integer of 2 to 5;

wherein the lipid compound is selected from the aforementioned general or preferred definitions for a single molecular lipid compound; more preferably, the structural unit composed of the lipid compound with so called plurality of identical or different single molecules is selected from the following structures, derivatives and isomers thereof, shown in the following Figure-9:

Figure-9

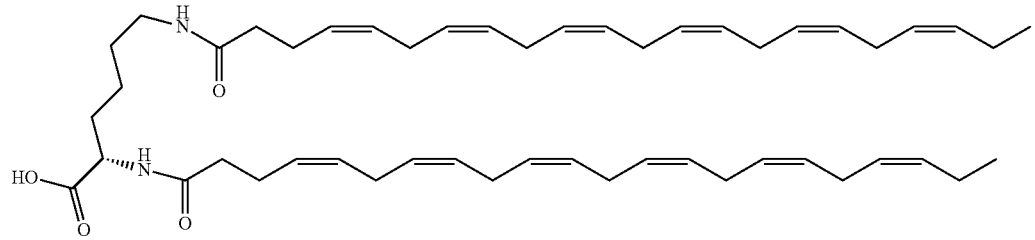

185

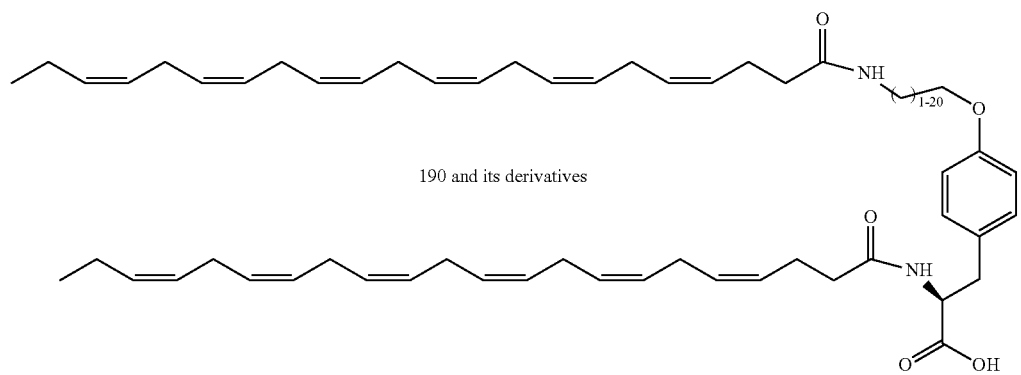

190 and its derivatives

-continued
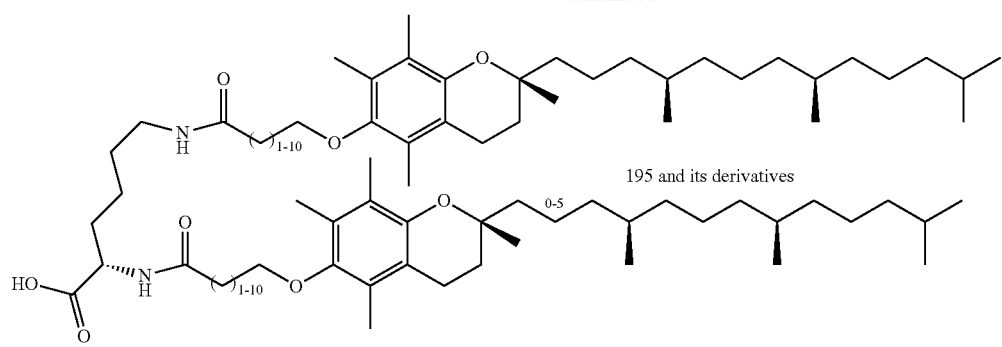
195 and its derivatives
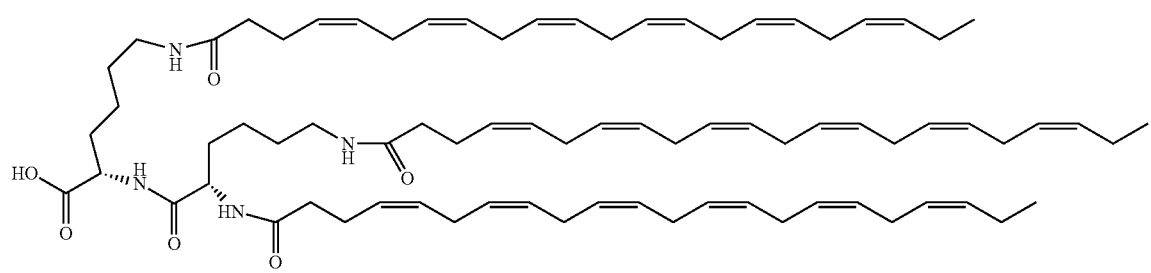
197
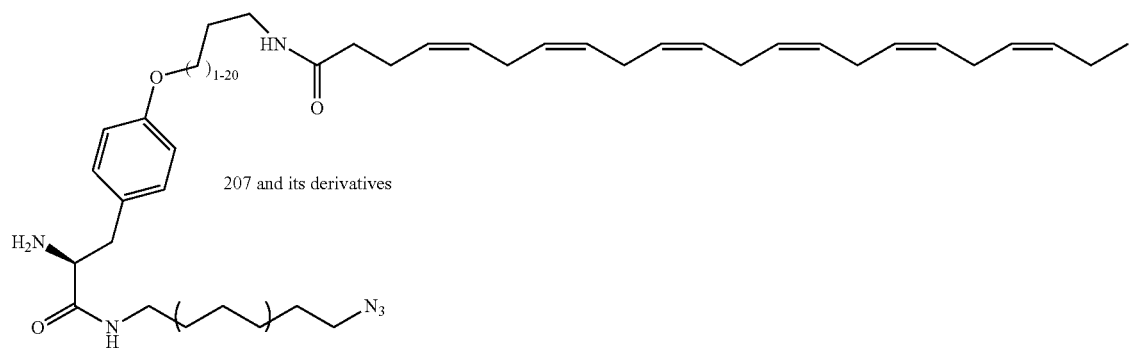
207 and its derivatives
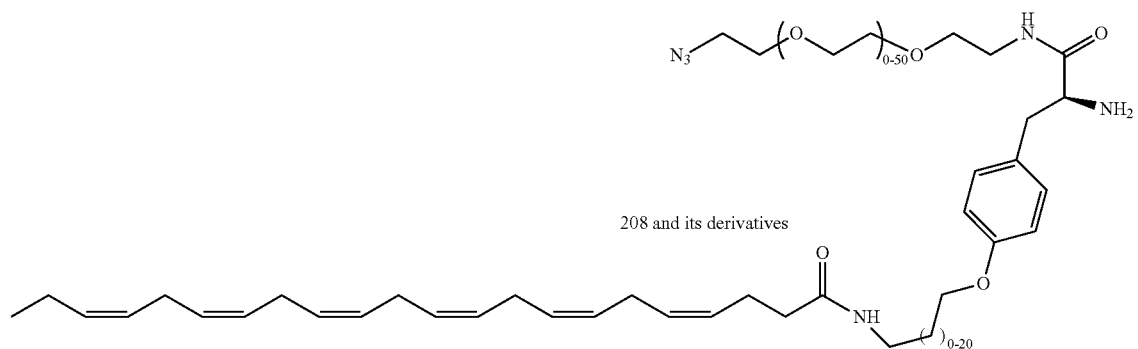
208 and its derivatives

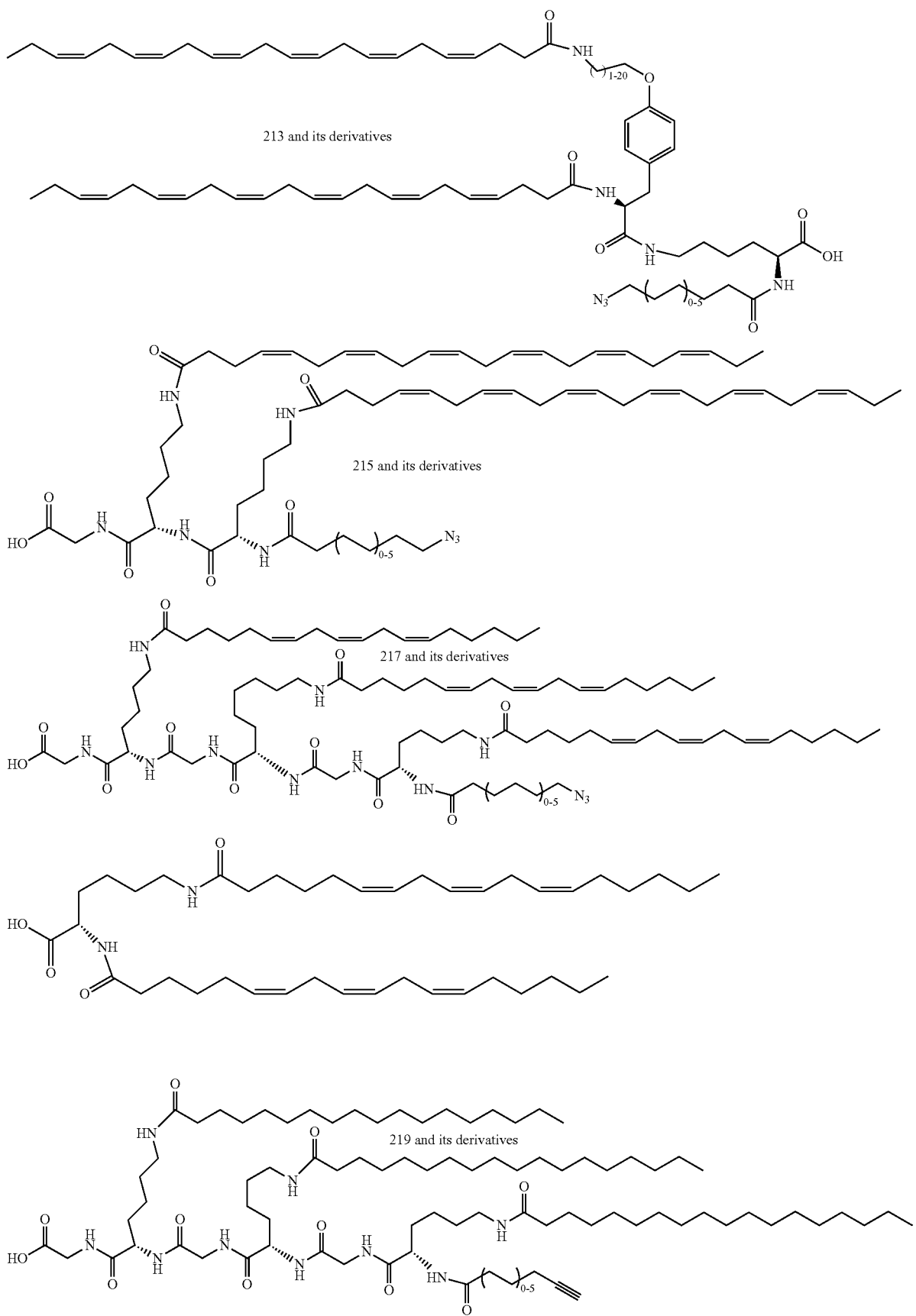

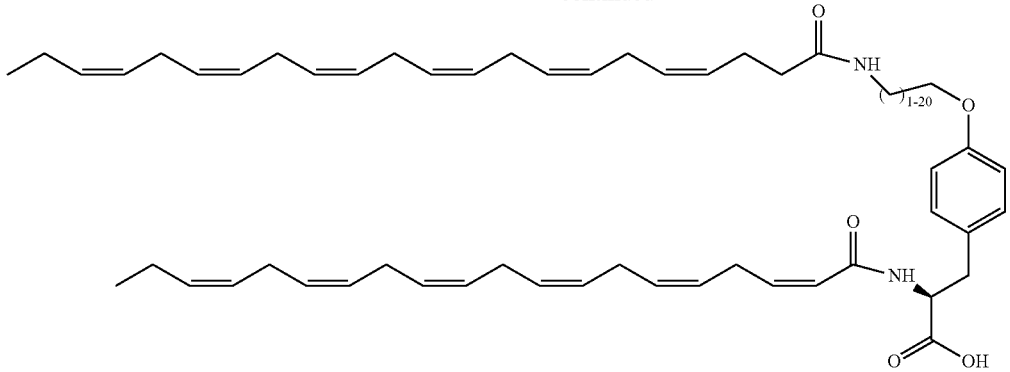

preferably, the linkers-1, 2, 3, they may be the same or each independently different from each other, having the following formula shown by Figure-10:

Figure-10

| Linker-1 | Convalently connected unit | Linker-2 | the linker-i and the linker-2 can be the same or different and are independently selected from the following structures:
1) natural amino acids, unnatural amino acids, such as D-amino acids, β-aminopropionic acid, γ-aminobutyric acid or ε-aminocaproic acid, or derivatives thereof, or 2 to 100 oligopeptides composed of these amino acids or a polypeptide fragment;
2) —[X1]$_0$ or 1-[disubstituted alkyl-1]$_0$ or 1-[X2]$_0$ or 1-[disubstituted aryl]$_0$ or 1-[X3]$_0$ or 1-[disubstituted a structural moiety of alkyl-2]$_0$ or 1-[X4]$_0$ or 1-;
wherein X1, X2, X3 and X4 can be the same or different and are selected from O, S, NH or NR, CO, CONH, CONHR, S—S, COO, OCOO, SO$_2$NH, SO$_2$NR, NHCOO, NRCOO, NHCONH, NRCONH, NR$_1$CONR$_2$, OPO$_3$, OPO$_2$NH, OPO$_2$NR, a covalent bond containing a triazole; wherein R, R$_1$, R$_2$ are independently selected from the group consisting of an alkyl group, a cycloalkyl group, an aryl group, an aryl alkyl group, a cycloalkyl alkyl group or the like;

the disubstitutedalkyl-1 fragment and the disubstitutedalkyl-2 fragment are the same or different and are selected from a linear or branched or cyclic (including fused ring or spiro-ring) C$_{1-20}$ alkyl group (preferably a C$_{1-12}$ alkyl group). a linear or branched cyclic (including fused ring or spiro-ring) C$_{1-20}$ alkyl group (preferably a C$_{1-12}$ alkyl group) containing at least one heteroatom selected from N, O or S; a linear or branched C$_{2-15}$ alkyl group containing one or more double bonds (preferably a C$_{2-10}$ alkyl group having a double bond), a linear or branched C$_{2-10}$ alkyl group having one or more triple bonds (preferably a C$_{2-8}$ alkyl group having a triple bond), a C$_{3-10}$ cycloalkyl group containing one or more double bonds (including a fused ring or a spiro ring, preferably a 3-8 membered cyclic alkyl group containing a double bond), a cyclic C$_{2-12}$ alkyl group containing one or more triple bonds (including fused ring or spiro ring, preferably a 3-8 membered cycloalkyl group containing a triple bond, a 3-10 membered heterocycloalkyl group containing at least one heteroatom selected from N, O or S (including a fused ring or a spiro-ring, preferably 3-6 membered heterocycloalkyl group); a heterocyclic alkyl group having at least one 3-10 membered heterocycloalkyl group and a hetero atom selected from N, O or S and one or more double bonds (a fused ring or spiro ring, preferably a 3-8 membered heterocycloalkyl group containing a double bond), and a 5-12 membered heterocycloalkyl group containing at least one heteroatom selected from N, O or S and one or more triple bonds (including a fused ring or a spiro-ring, preferably a 6-9 membered heterocycloalkyl group containing a triple bond);

the disubstituted aryl group is selected from a single aryl group or a fused ring aryl group, a single heteroaryl group or a fused ring heteroaryl group;

the disubstitutedalkyl-1 fragment, the disubstitutedalkyl-2 fragment and the disubstituted aryl fragment are optionally substituted by a mono- or poly-substituent as defined for a single molecular lipid compound.

3) polymer fragments such as polyethylene glycol (PEG) having a molecular weight of 100 to 50,000, [CH$_2$SCH$_2$]$_{1-100000}$, [CH$_2$CH$_2$OCH$_2$CH$_2$]$_{1-10000}$, polyamide, polylactic acid (PGA), poly(lactic-glycolic acid) copolymer (PLGA);

4) covalently linked (C$_{3-8}$) structural fragments consisting of 1-100 saccharide units and derivatives thereof, such as glycerol, mannitol, glucosamine and their derivatives;

wherein the covalent structural linking unit is the structural fragment formed by reacting a functional group of a functionalized polysaccharide with a functional group of a functionalized taxane or a functional group of a functionalized lipid, it is selected from the group consisting of consisting of a 1,2,3-triazole fragment, a 1,2,3-triazole fragment with a fused ring with a substituent, a cyclooctyl[d]hydropyridazine fragment, 2-hydrocarbylthiosuccinate lactam fragment, 3-alkylthiomaleimide fragment, 2-hydrocarbylethylsulfone fragment, amide fragment, disulfide bond fragment, disulfide-substituted aryl moiety, urea bond fragment, substituted 3-(alkylthio)-a 3-phenylacrylonitrile fragment, a substituted cyclooctane[d]hydropyridazine fragment, a substituted 1,2,4-triazolidine-3,5-dione fragment, 1,6a-dihydropyrrolo[3 a 4-triazol-4,6(5aH, 5H)-dione fragment; The so-called substituents being as defined for a substituent of a single molecular lipid compound;

for example, the covalently connected unit is selected from, but not limited to, the following fragments:
1) a fragment formed by an addition reaction or a substitution reaction of a thiol, as shown in Figure-11:

Figure-11

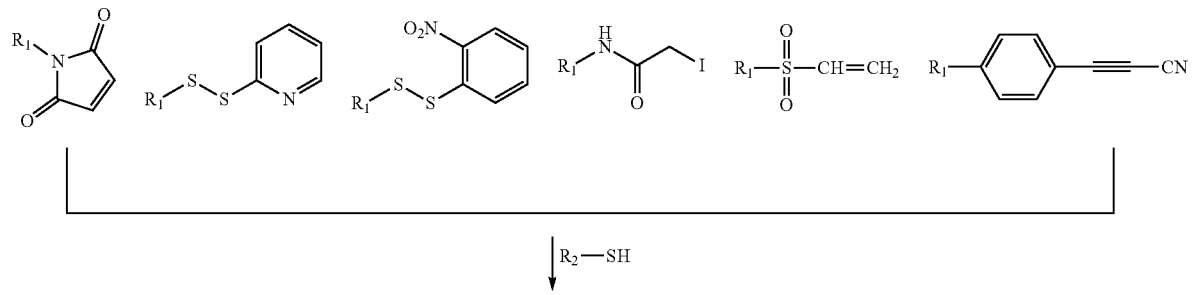

wherein $R_1$, $R_2$ are independently selected from the group consisting of an alkyl group, a cycloalkyl group, an aryl group, an aryl alkyl group, a cycloalkyl alkyl group, and the like; 2) fragments of derivatives produced by di-sulfane substitution as shown in Figure-12:

Figure-12

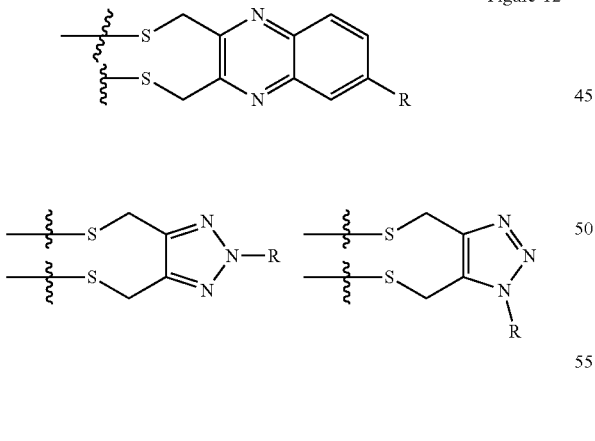

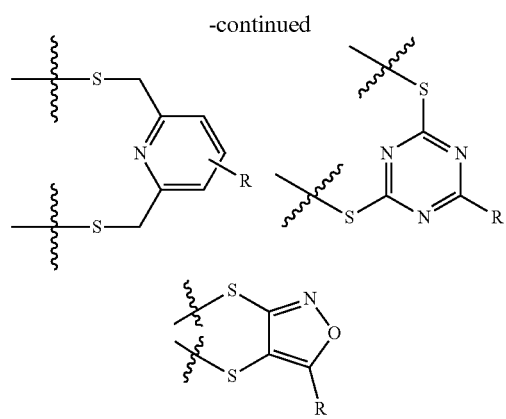

-continued

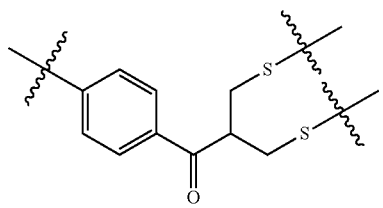

wherein R is selected from the group consisting of an alkyl group, a cycloalkyl group, an aryl group, an aryl alkyl group, a cycloalkyl alkyl group, and the like;

3) a triazole fragment produced by click chemistry under the catalysis of copper (Cu(I)) or a fused-ring triazole fragment produced by a click chemistry catalyzed without a copper salt as shown in Figure-13.

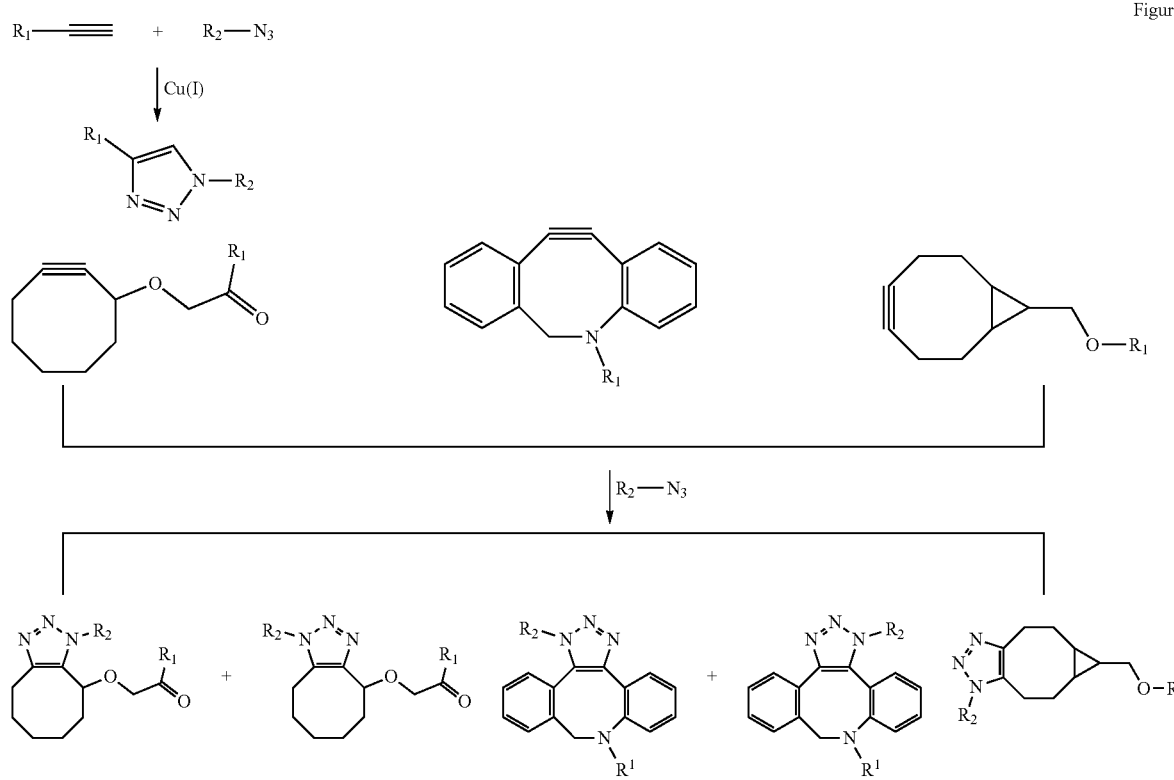

Figure-13 wherein $R_1$, $R_2$ are independently selected from the group consisting of an alkyl group, a cycloalkyl group, an aryl group, an aryl alkyl group, a cycloalkyl alkyl group, and the like;

4) an amide fragment (—CONH—, or —CONR—) produced by a coupling reagent based-catalyzed reaction of a substituted carboxyl group and a substituted amino group, or an amide fragment (—CONH—) formed by a staudinger ligation reaction, as shown in Figure-14:

Figure-14

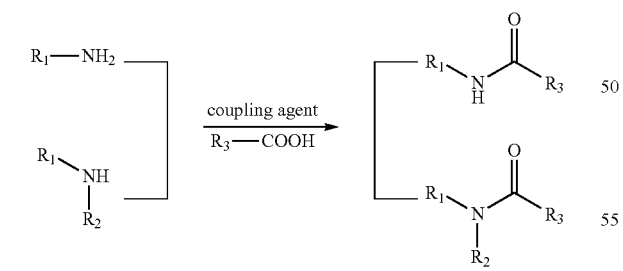

-continued wherein R, $R_1$, $R_2$, $R_3$ are independently selected from the group consisting of an alkyl group, a cycloalkyl group, an aryl group, an aryl alkyl group, a cycloalkyl alkyl group, and the like;

5) cycloocta [d]hydropyridazine fragment formed by Diels-Alder reaction and 1,6a-dihydropyrrolo[3,4-d]triazole-4,6(5aH, 5H)-dione, etc. as in Figure-15:

Figure-15

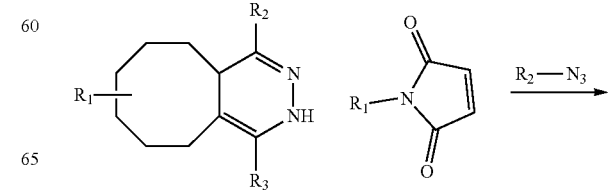

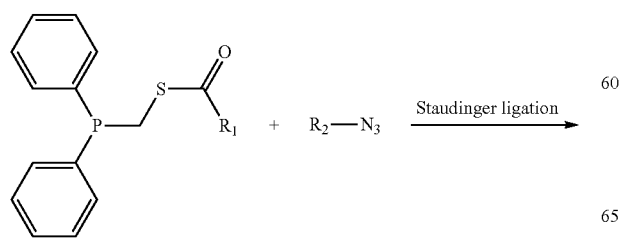

31
-continued

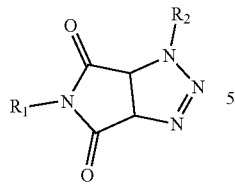

32
-continued

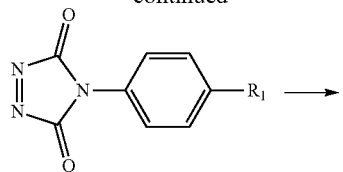

wherein the $R_1$, $R_2$, $R_3$ are independently selected from the group consisting of an alkyl group, a cycloalkyl group, an aryl group, an aryl alkyl group, a cycloalkyl alkyl group, and the like;

6) 1,2,4-triazolidine-3,5-dione derivatives formed by the reaction of phenolic compounds and phenol derivatives with 4-phenyl-3H-1,2,4-triazoline-3,5(4H)-dione (PTAD), as shown in Figure-16:

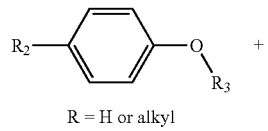

Figure-16

R = H or alkyl

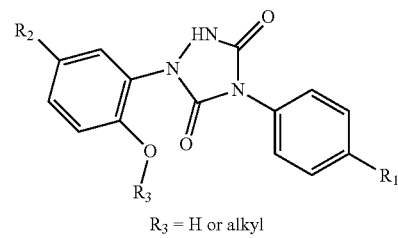

$R_3$ = H or alkyl more preferably, the linkers are preferably the following structures and derivatives and isomers thereof as shown in Figure-17:

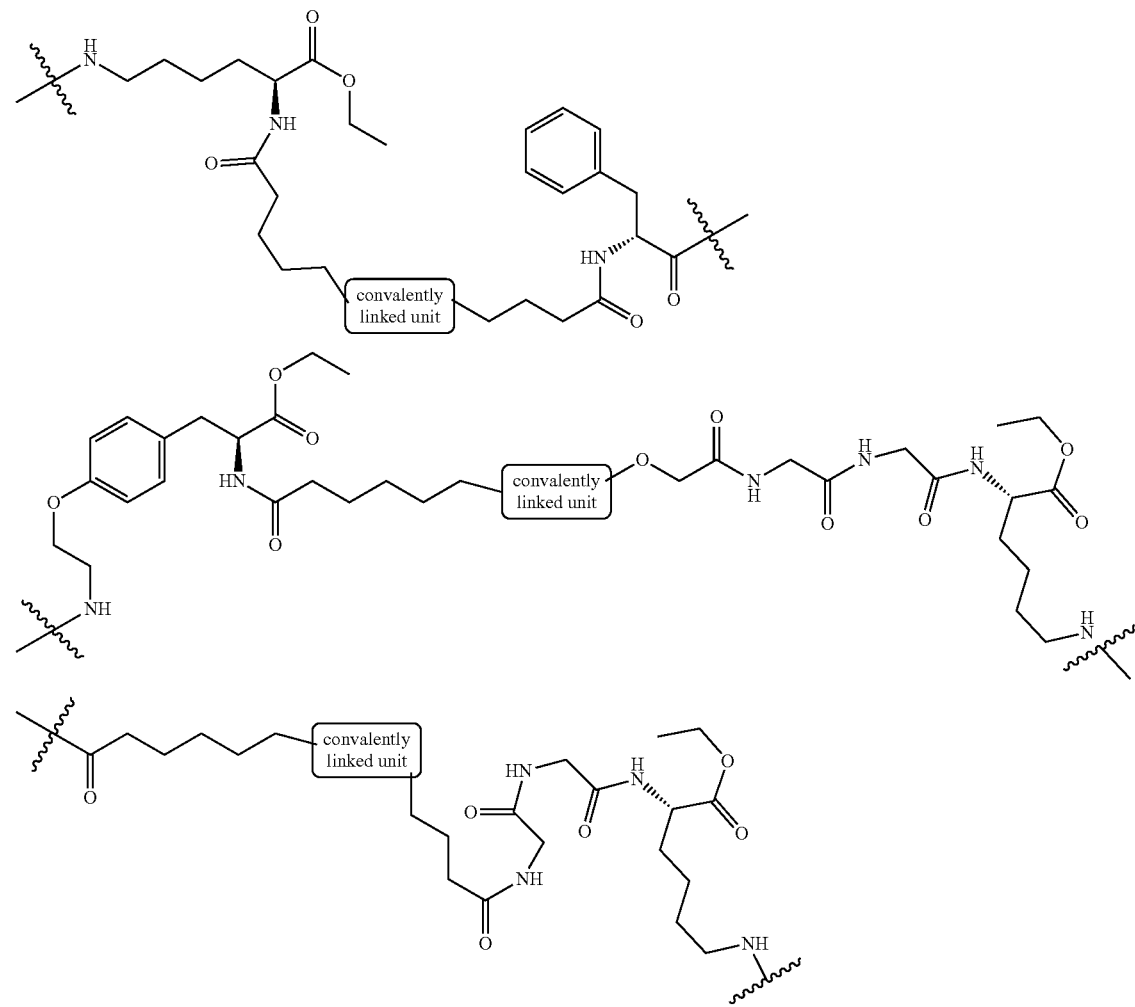

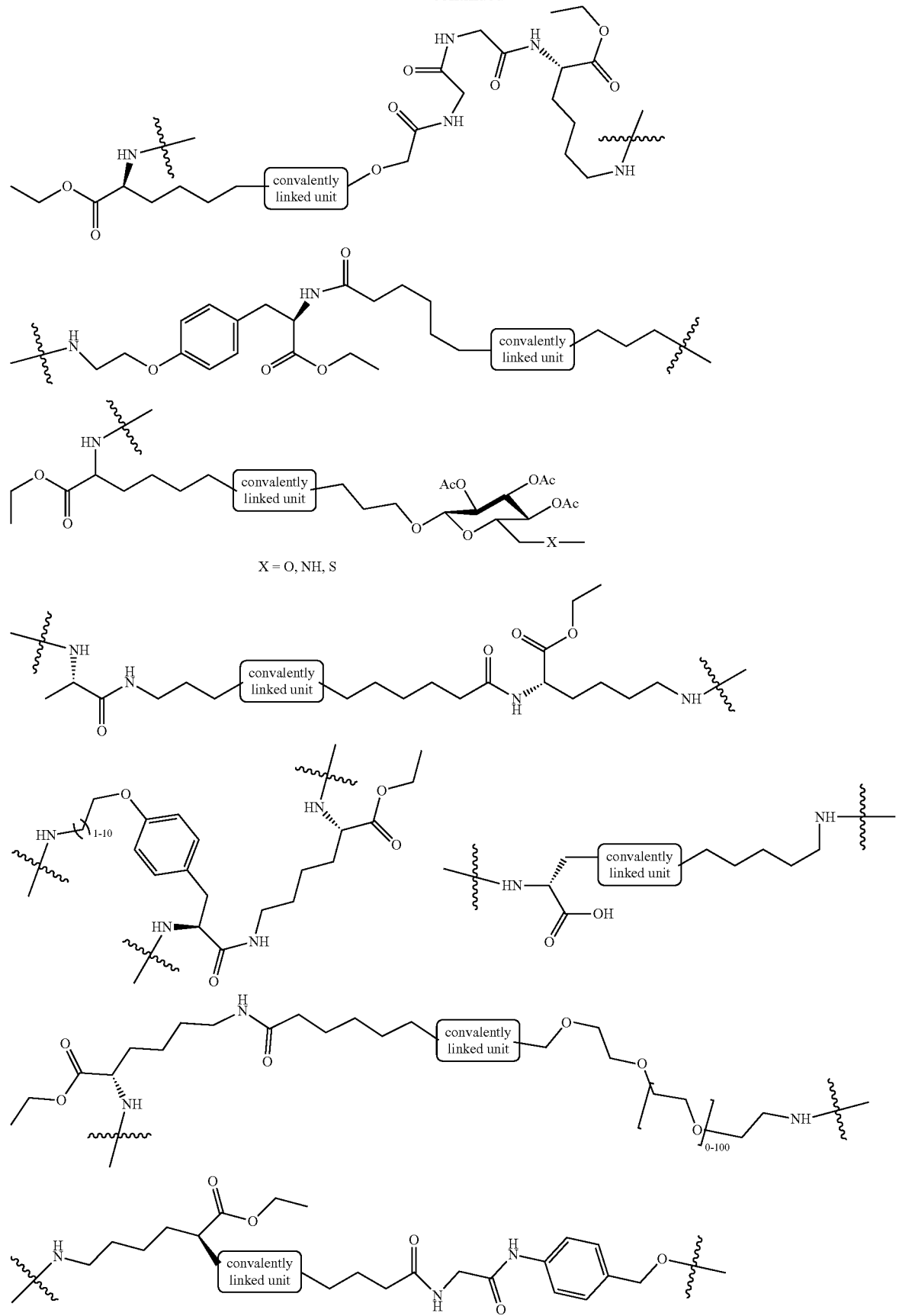

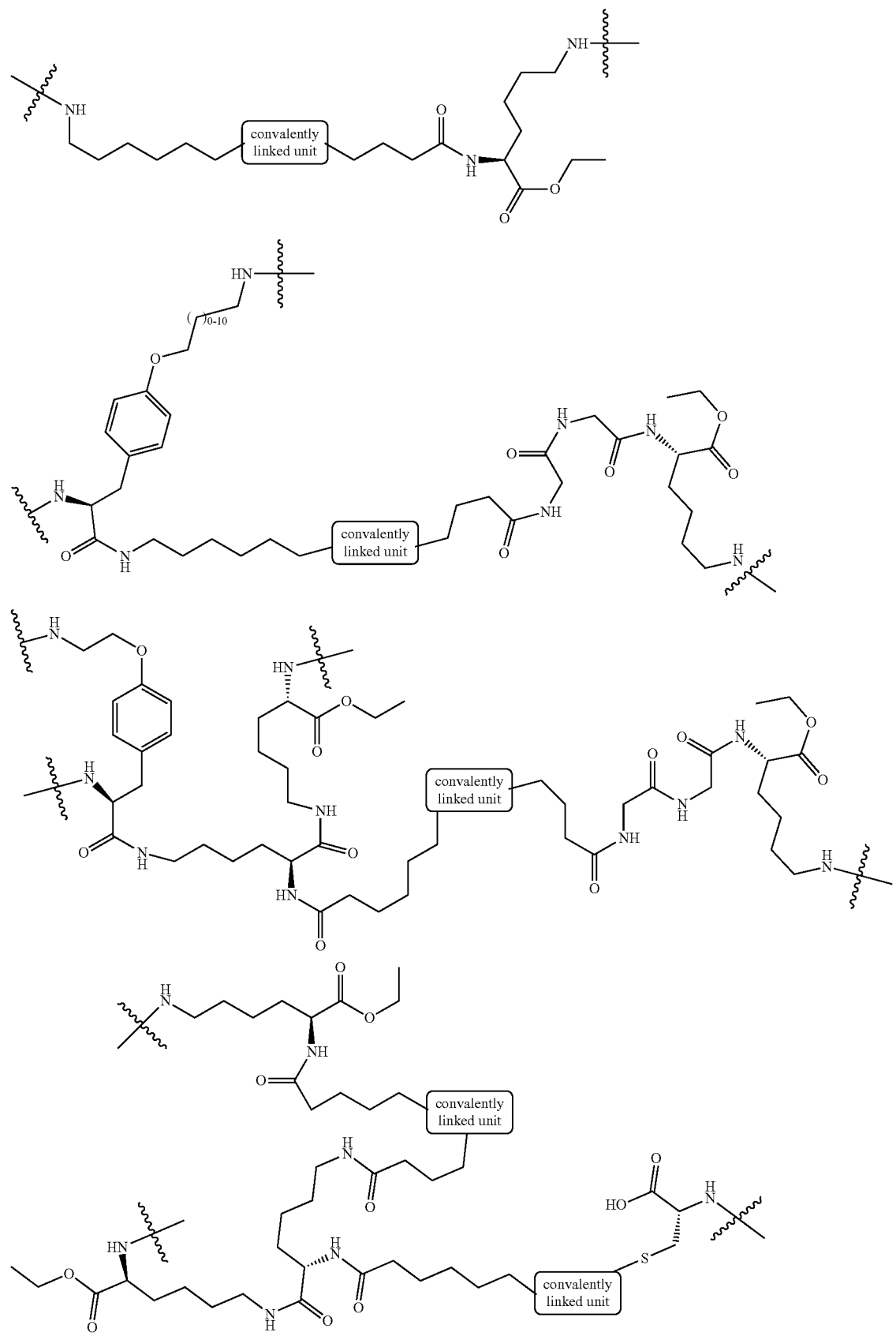

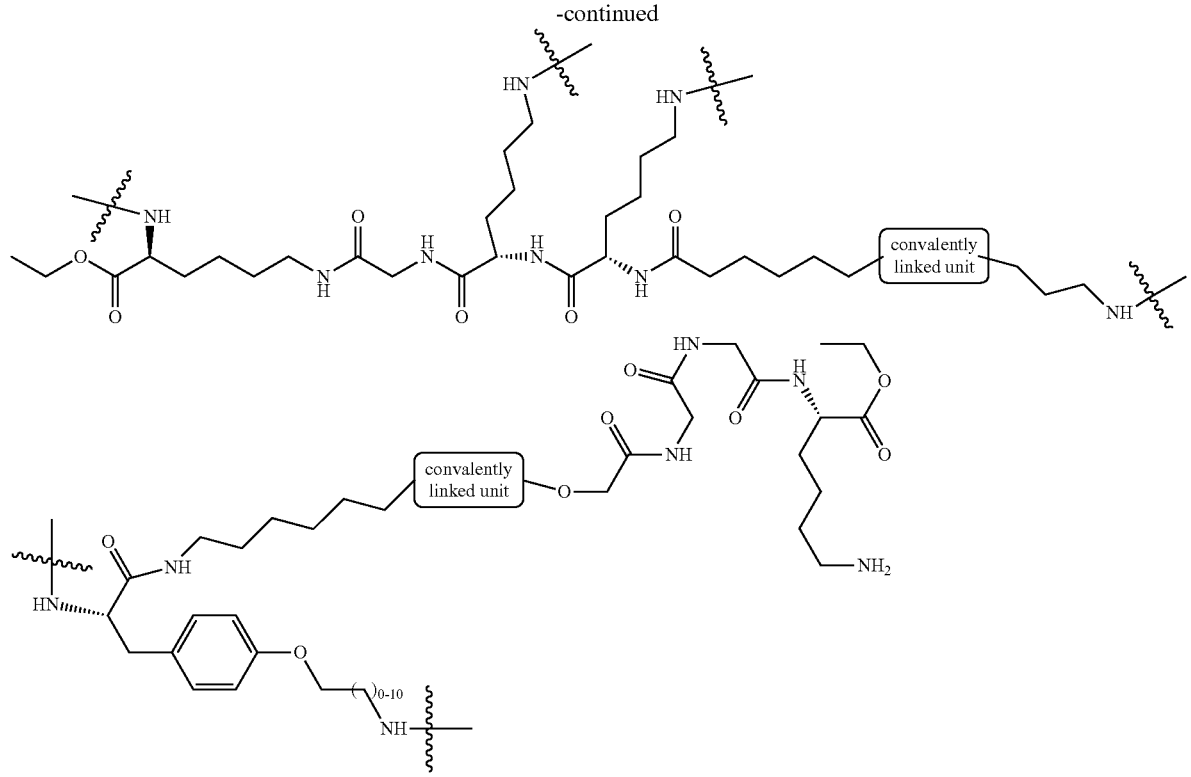
among the structure, the covalently linked unit(s) are selected from the followings:
Figure-17
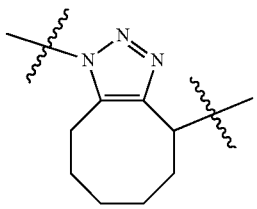 or 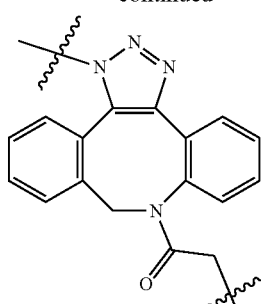 or
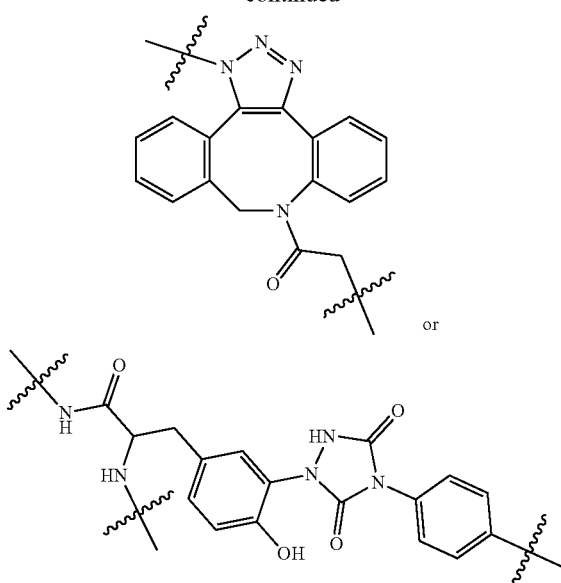
-continued
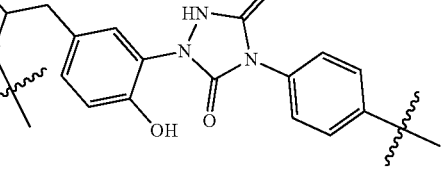 or
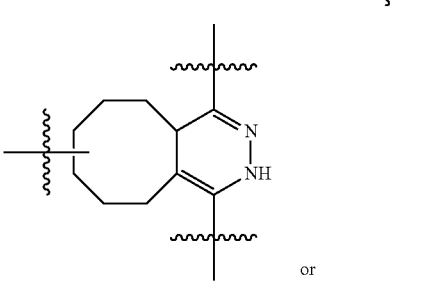 or

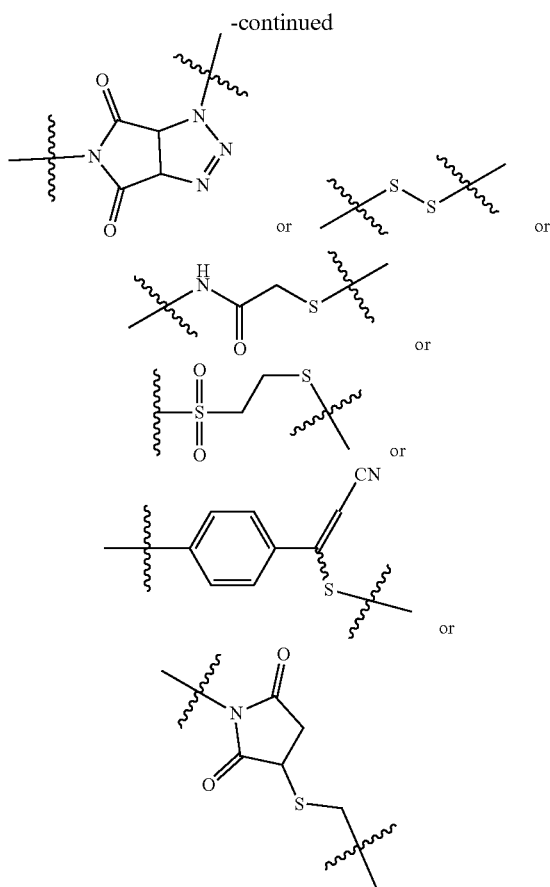

preferably, the number of the spacers 1-4 is selected from 0 or 1; the same or each independently different from each other, selected from the following structures:

1) a natural amino acid, a non-natural amino acid (such as a D-amino acid, β-aminopropionic acid, γ-aminobutyric acid or ε-aminocaproic acid) or a derivative thereof or a short peptide fragment comprised of 2 to 20 of these amino acids;

2) —[X1]$_{0\ or\ 1}$-[disubstitutedalkyl-1]$_{0\ or\ 1}$—[X2]$_{0\ or\ 1}$-[disubstituted aryl]$_{0\ or\ 1}$—[X3]$_{0\ or\ 1}$-[disubstituted a structural moiety of aalkyl-2]$_{0\ or\ 1}$—[X4]$_{0\ or\ 1}$;

wherein X1, X2, X3 and X4 are the same or different and are selected from O, S, NH or NR, CO, CONH, CONHR, S—S, COO, OCOO, $SO_2NH$, $SO_2NR$, NHCOO, NRCOO, NHCONH, NRCONH, $NR_1CONR_2$, $OPO_3$, $OPO_2NH$, $OPO_2NR$, a covalent bond containing a triazole; wherein R, $R_1$, $R_2$ are independently selected from the group consisting of an alkyl group, a cycloalkyl group, an aryl group, an aryl alkyl group, a cycloalkyl alkyl group;

the disubstitutedalkyl-1 fragment and the disubstitutedalkyl-2 fragment are the same or different and are selected from a linear or branched or cyclic (including fused ring or spiro-ring) $C_{1-20}$ alkyl group (preferably a $C_{1-12}$ alkyl group). a linear or branched cyclic (including fused ring or spiro-ring) $C_{1-20}$ alkyl group (preferably a $C_{1-12}$ alkyl group) containing at least one heteroatom selected from N, O or S; a linear or branched $C_{2-15}$ alkyl group containing one or more double bonds (preferably a $C_{2-10}$ alkyl group having a double bond), a linear or branched $C_{2-10}$ alkyl group having one or more triple bonds (preferably a $C_{2-8}$ alkyl group having a triple bond), a $C_{3-10}$ cycloalkyl group containing one or more double bonds (including a fused ring or a spiro ring, preferably a 3-8 membered cyclic alkyl group containing a double bond), a cyclic $C_{2-12}$ alkyl group containing one or more triple bonds (including fused ring or spiro-ring, preferably a 3-8 membered cycloalkyl group containing a triple bond, a 3-10 membered heterocycloalkyl group containing at least one heteroatom selected from N, O or S (including a fused ring or a spiro ring, preferably 3-6 membered heterocycloalkyl group); a heterocyclic alkyl group having at least one 3-10 membered heterocycloalkyl group and a hetero atom selected from N, O or S and one or more double bonds (a fused ring or spiro-ring, preferably a 3-8 membered heterocycloalkyl group containing a double bond), and a 5-12 membered heterocycloalkyl group containing at least one heteroatom selected from N, O or S and one or more triple bonds (including a fused ring or a spiro-ring, preferably a 6-9 membered heterocycloalkyl group containing a triple bond);

The disubstituted aromatic group is selected from a single aryl or fused ring aryl group, a single heteroaryl group or a fused ring heteroaryl group;

the disubstitutedalkyl-1 fragment, the disubstitutedalkyl-2 fragment, and the disubstituted aryl fragment are optionally mono- or polysubstituted, and the substituents for a single molecular lipid compound are independently selected from the group consisting of $C_{1-20}$ hydrocarbyl, $C_{2-10}$ alkenyl, $C_{2-10}$ alkyne, $C_{3-15}$ cycloalkyl, $C_{5-20}$ aryl, $C_{7-20}$ arylalkyl, heteroaryl, heterocycloalkyl, ester group, keto group, hydroxyl group, phenolic hydroxyl group, $C_{1-18}$ alkoxy group, $C_{3-15}$ monocyclic or polycyclic alkoxy group, amino group, $C_{1-10}$ alkyl group, mono or disubstituted amino group, amide group, sulfonic acid group, sulfonamide group, halogen (fluorine, chlorine, bromine, iodine), and trifluoromethyl group;

3) short polymer fragments, such as polyethylene glycol (PEG), polyamide, polylactic acid (PGA), poly(lactic-co-glycolic acid) copolymer (PLGA) having a molecular weight of 100-2000;

4) covalently linked structural fragments consisting of 1-10 sugar units and derivatives thereof such as glycerol, mannitol, glucosamine and their derivatives;

preferably, the spacer is selected from the following structures and derivatives and isomers thereof as shown in Figure-18:

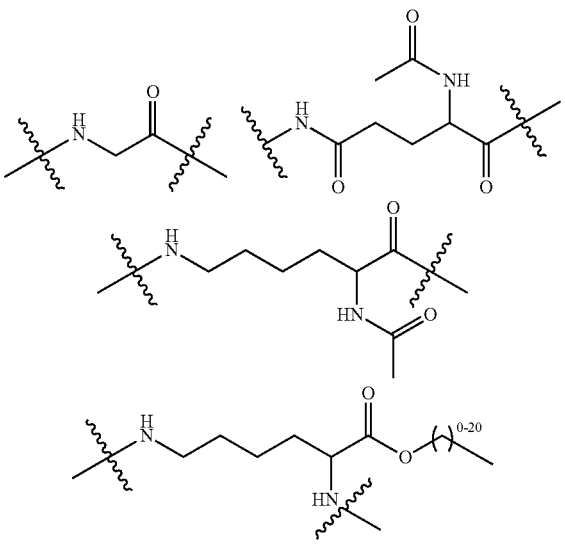

Figure-18

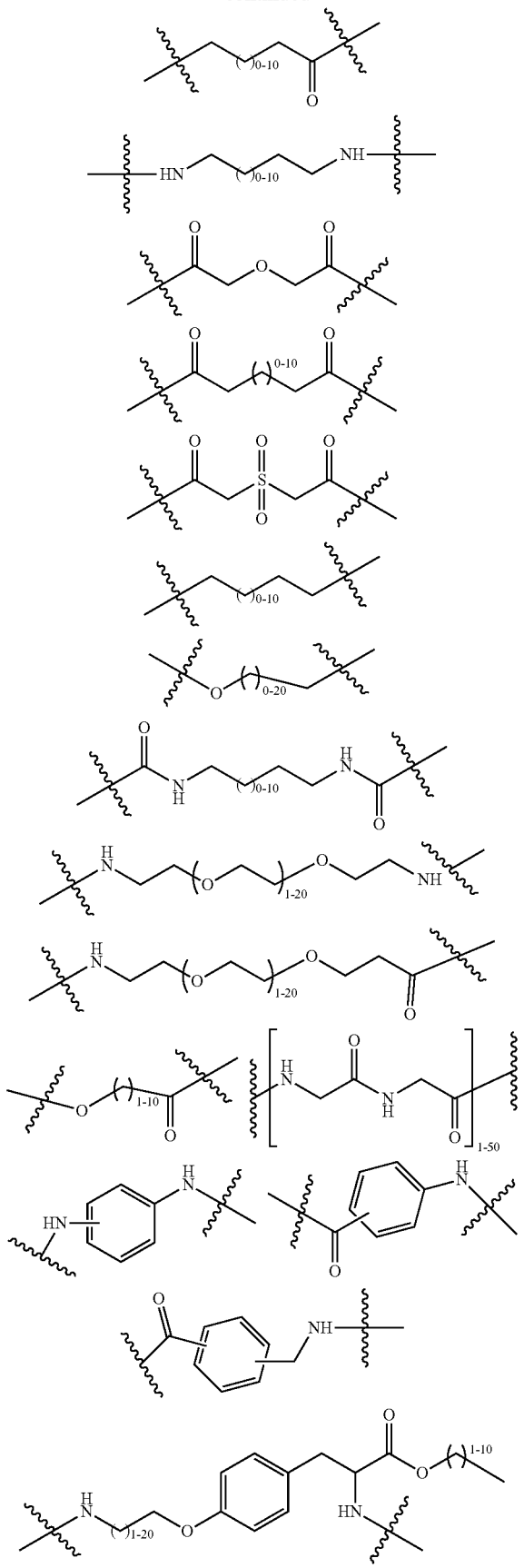
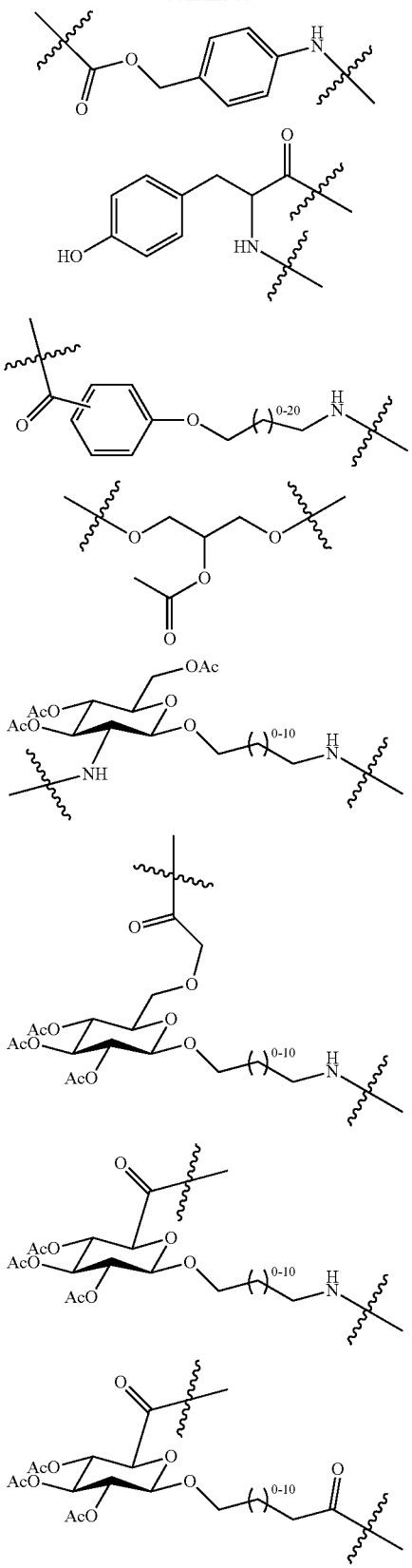
It should be noted that the definitions for preferably, more preferably and exemplary spacers herein apply equally to the spacers 1-3 in the above structural units (Figure.18) composed of a plurality of identical or different single molecular lipid compounds.

preferably, the branch unit is defined as one parent structural unit in which three or more identical or different functional groups are attached on. more preferably the branch unit is selected from the group consisting of amino acids (including natural amino acids and unnatural amino acids) and derivatives thereof, saccharide units and derivatives thereof, aryl substituted compounds and derivatives thereof, substituted hydrocarbons and derivatives thereof, derivatives containing triazole, substituted by di-sulfane compound;

preferably, the branch unit is selected from the following structures and derivatives and isomers thereof as shown in Figure-19:

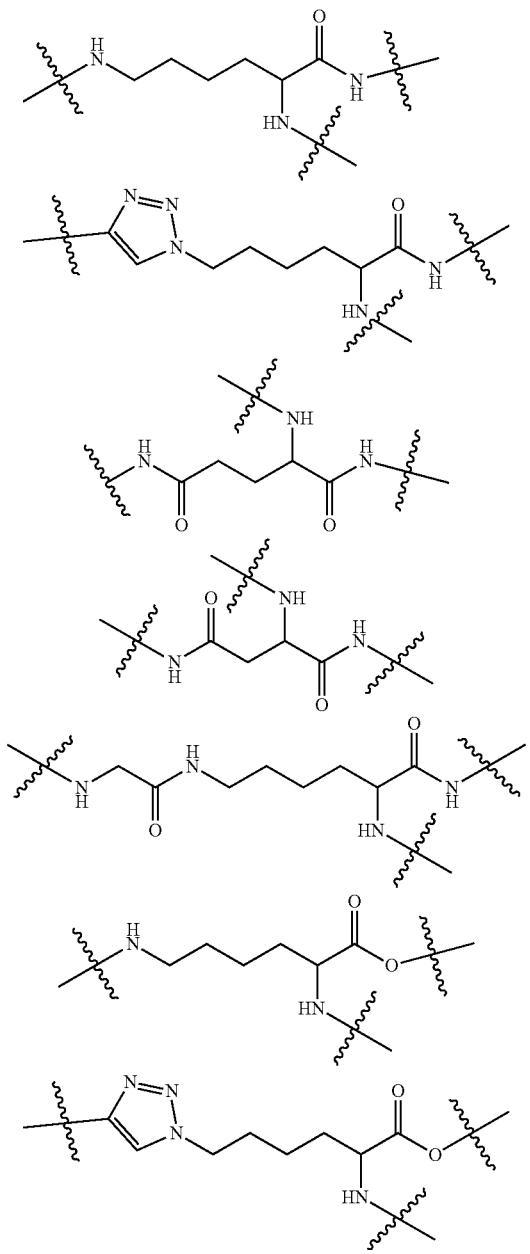

Figure-19

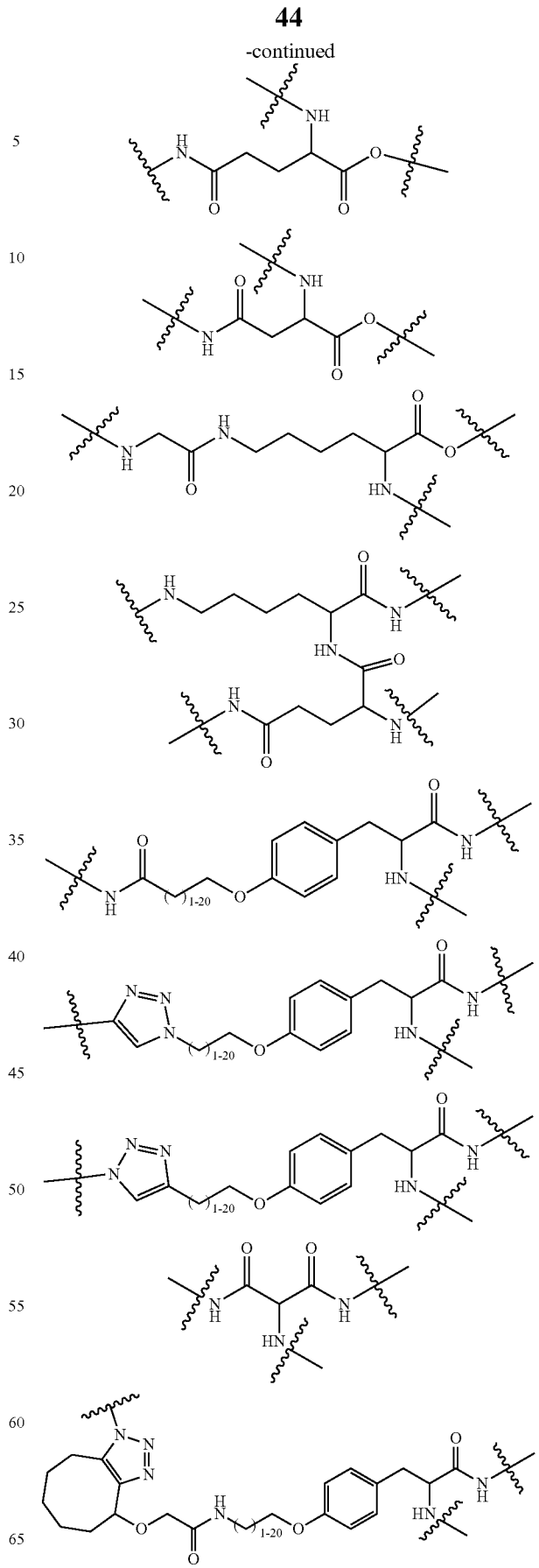

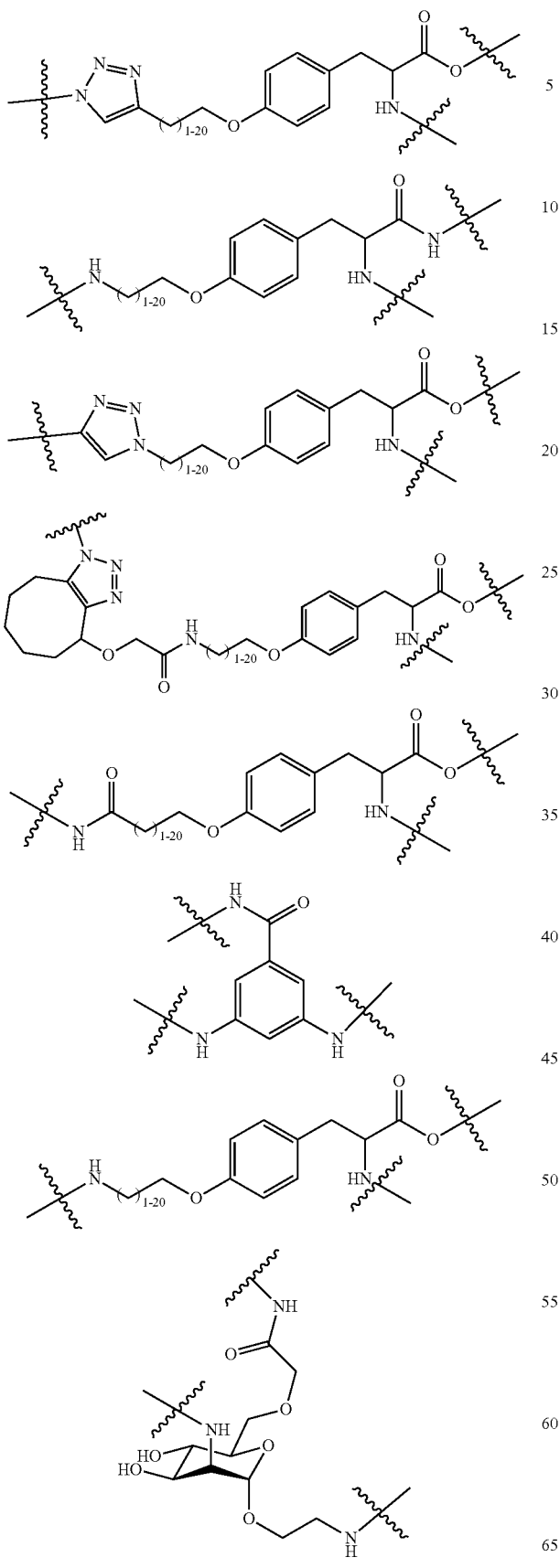
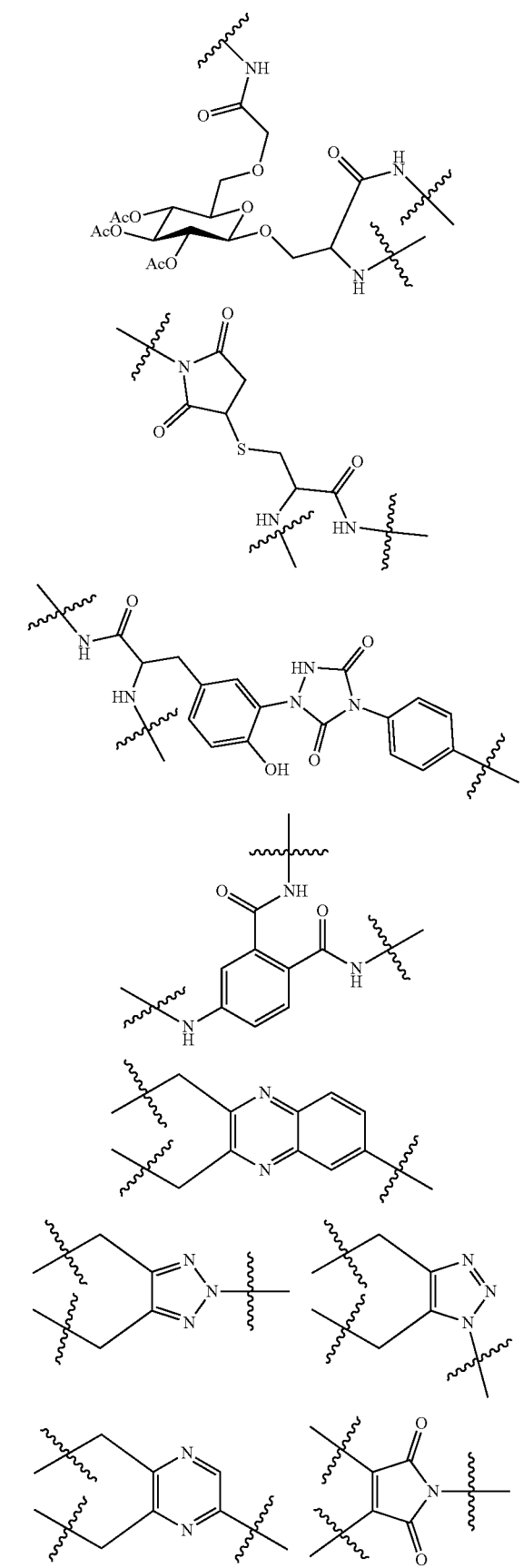

-continued
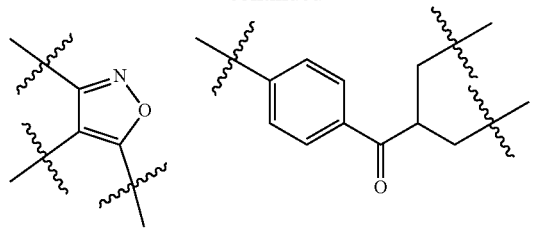
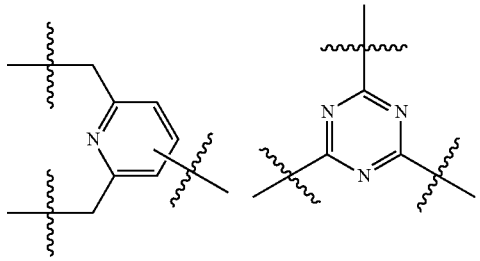
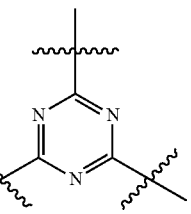
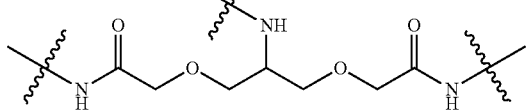
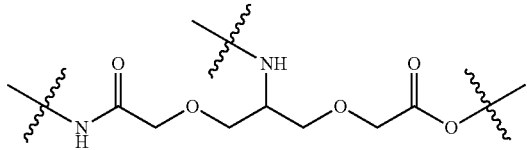
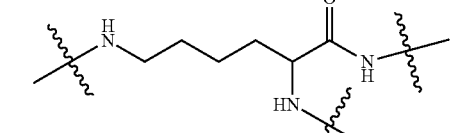
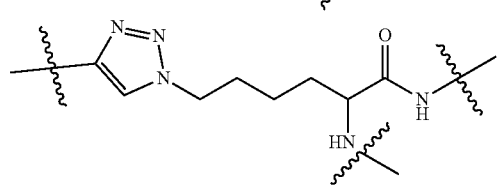
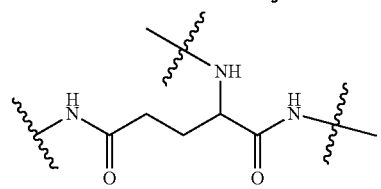
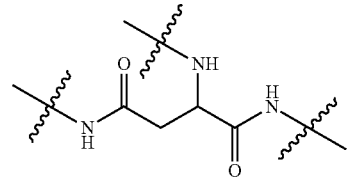
-continued
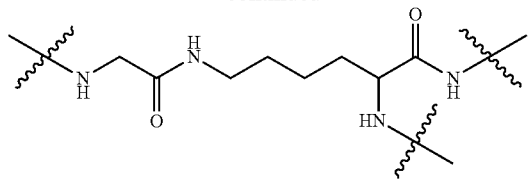
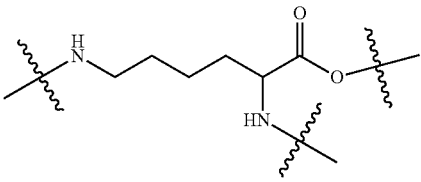
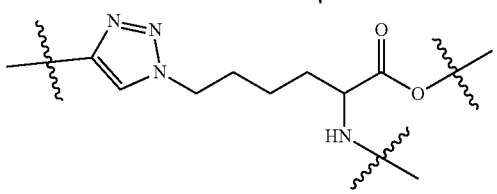
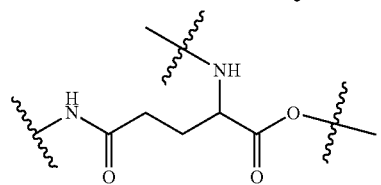
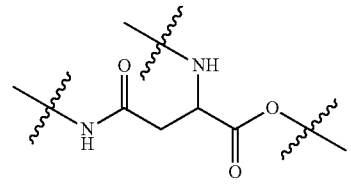
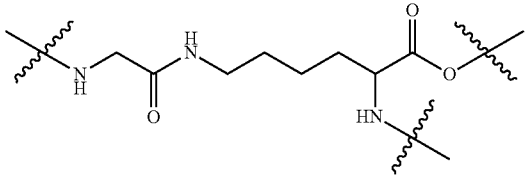
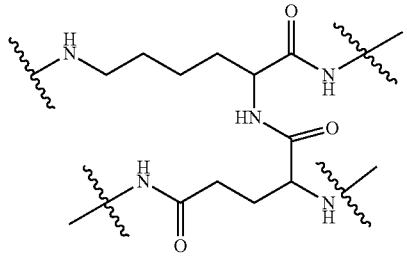
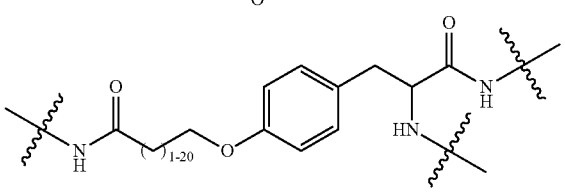
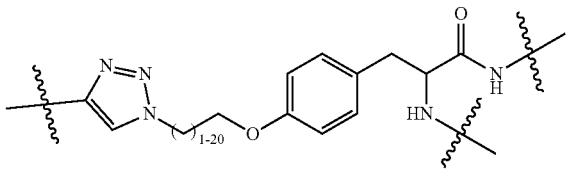

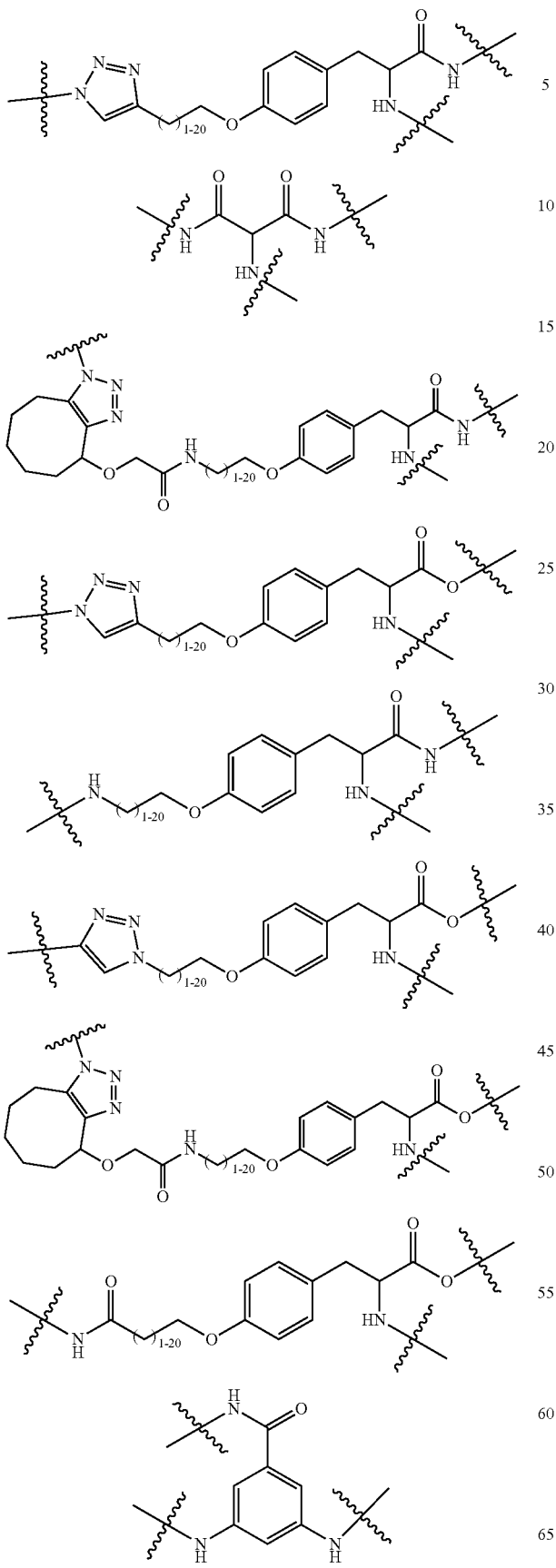
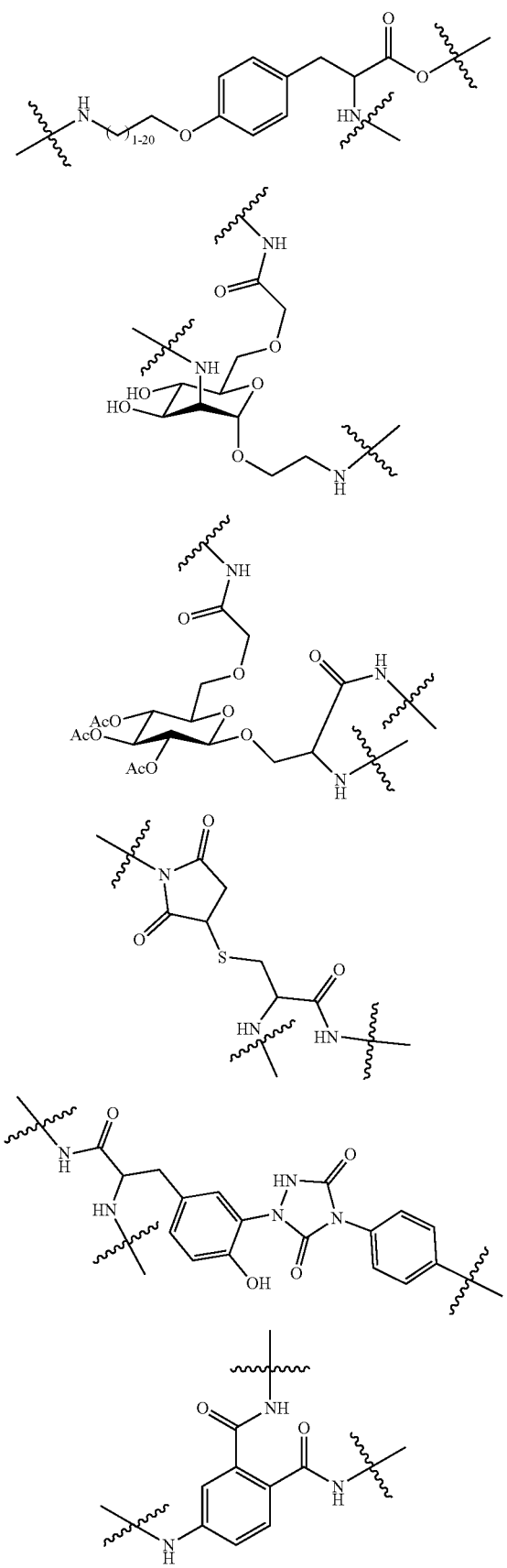

-continued

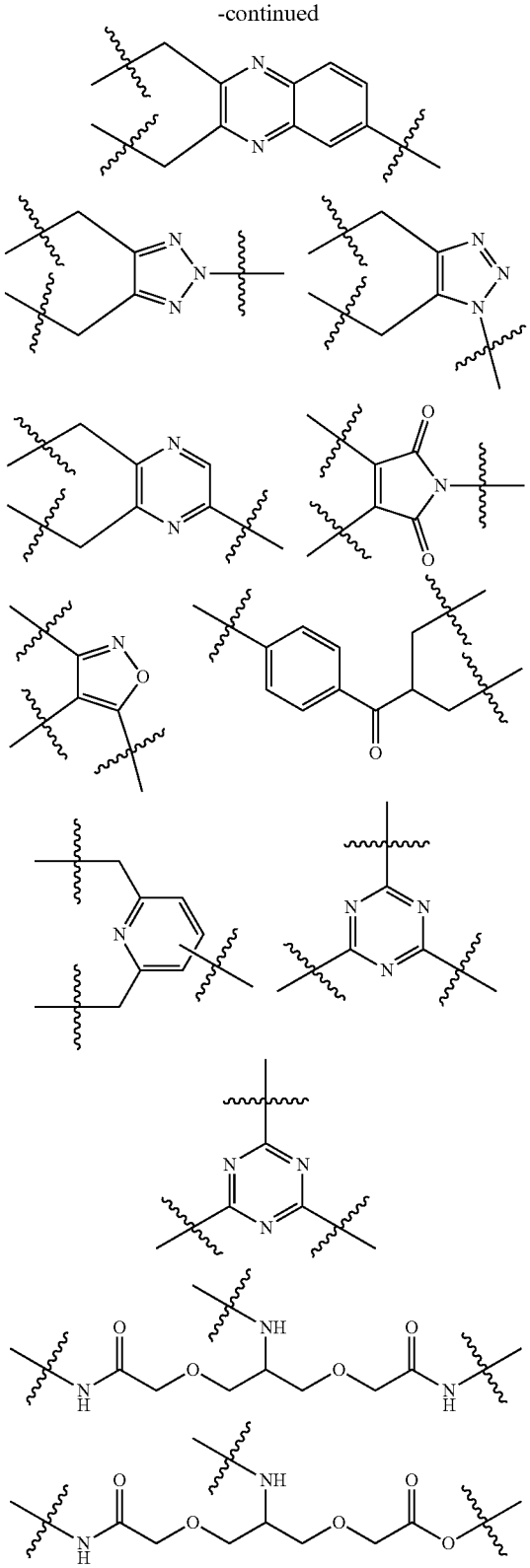

It is to be noted that the definitions of preferred, more preferred and further preferred branch units herein apply equally to the structural units consisting of a plurality of identical or different single molecular lipid compounds (FIG. 8). A forked structural unit in the middle.

According to the first aspect of present invention, there is preferably provided a taxane-lipid-polysaccharide dual conjugate of the above Formula I: or a pharmaceutically acceptable salt or solvate thereof, wherein the linker unit is selected from the structures of A or B as described above;

the polysaccharide is covalently linked to the linker unit(s) through one or more conjugation sites thereof;

the linker unit is covalently linked to a taxane compound or a lipid compound unit;

the polysaccharide conjugation site refers to a hydroxyl group, a carboxyl group, an amino group, a phosphate group or a sulfonic acid group inherent to the polysaccharide;

the molecular molar ratio of the taxane compounds to the lipid compounds unit is an arbitrary ratio, preferably 0.1 to 99.9%, more preferably 0.1 to 60%, and far more preferably the following ratio ranges: 0.1 to 50, 0.1 to 20, 0.1 to 10, 0.1~5, 0.1~1, 1~50, 1-20, 1~10 or 1-5, such as 0.9, 0.8, 0.7, 0.6, 0.5, 0.4, 0.3, 0.2 or 0.1, or 9, 8, 7, 6, 5, 4, 3, 2 or 1;

the polysaccharides is selected from the group consisting of dextran, hyaluronic acid, hydroxyethyl starch, carboxymethyl cellulose, polygalactosamine, polysialic acid, *Ganoderma lucidum* polysaccharide, and lentinan;

the taxane compound is selected from the group consisting of paclitaxel, docetaxel, cabazitaxel and milataxel or a derivative thereof; the polysaccharides is linked to 2'-O position of the taxane compound or the side chain of the altered the structure via a linker or spacer;

the single molecular lipid compound in the lipid compound unit is selected from the group consisting of saturated or unsaturated fatty acids and derivatives thereof, or from fat-soluble vitamins and derivatives thereof; the lipid compound unit is a single molecular lipid compound or a structural unit composed of a plurality of the same or different single molecular lipid compounds selected from the structures shown in Figure-9 above and the derivatives and isomers thereof;

the linkers1-3 are each independently selected from the structures shown in Figure-17 above and their derivatives and isomers thereof;

the spacers 1-4 are each independently selected from the structures shown in Figure-18 above and their derivatives and isomers thereof;

the branch unit is selected from the structure shown in Figure-19 above and its derivatives and isomers thereof;

the linker1-3, the spacer 1-4, and the branch unit are all connected to each other by a covalent bond, and are also covalently bonded to the polysaccharide and the taxane compound; the covalent bond is selected from the group type of bonds consisting of an amide bond, an aminocarbamate bond, an aminothiocarbamate bond, an ester bond, an isourea bond, a thiourea bond, a urea bond, a disulfide bond, a carbonate bond, a phosphate ester bond, Phosphamide bond, sulfonamide bond, alpha or beta glycosylic bond, covalent bond containing triazole.

according to the first aspect of present invention, the taxane-lipid-polysaccharide dual conjugate as shown by Formula I is selected from the structures, or its derivatives or isomers, or a pharmaceutically acceptable salt or solvate thereof, in Figure-20 as follows, Figure-20
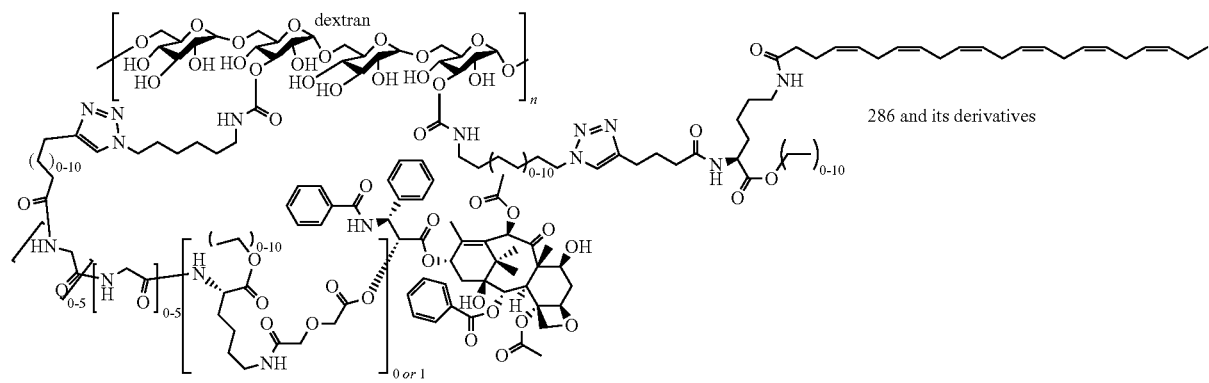
286 and its derivatives
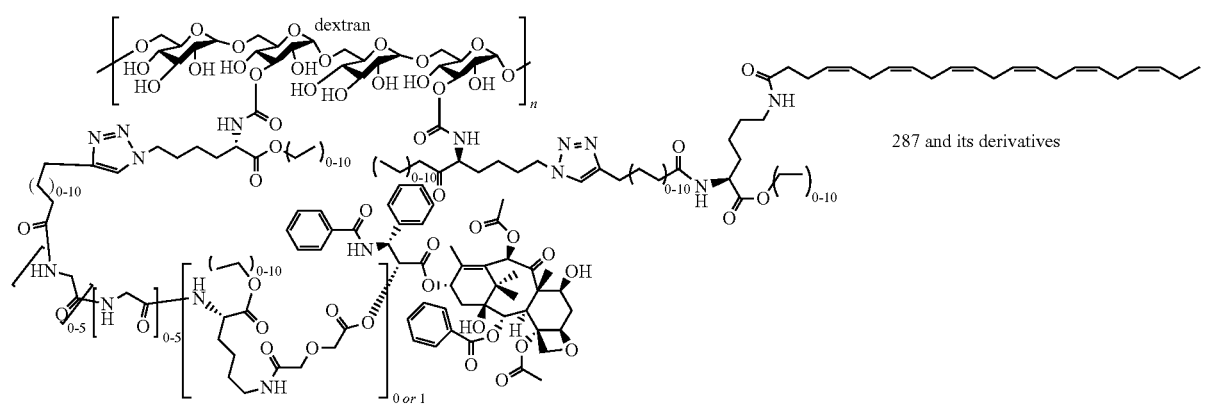
287 and its derivatives
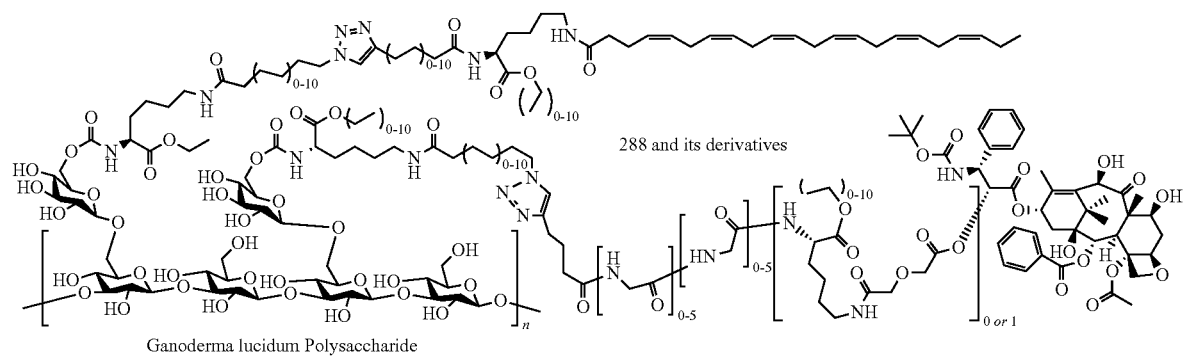
288 and its derivatives
Ganoderma lucidum Polysaccharide
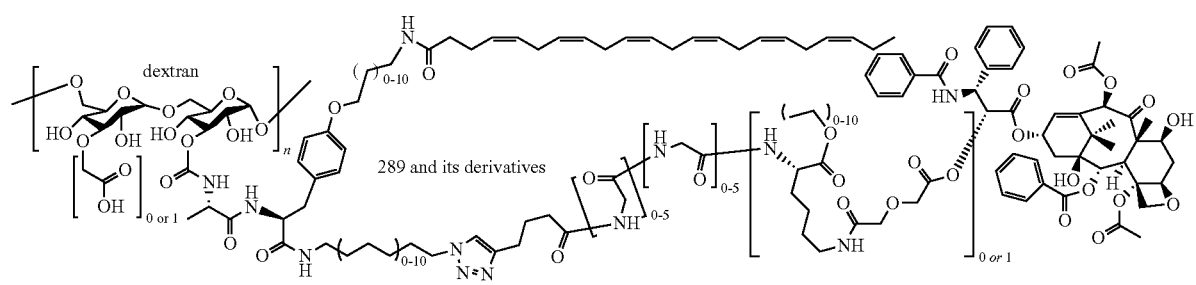
289 and its derivatives -continued
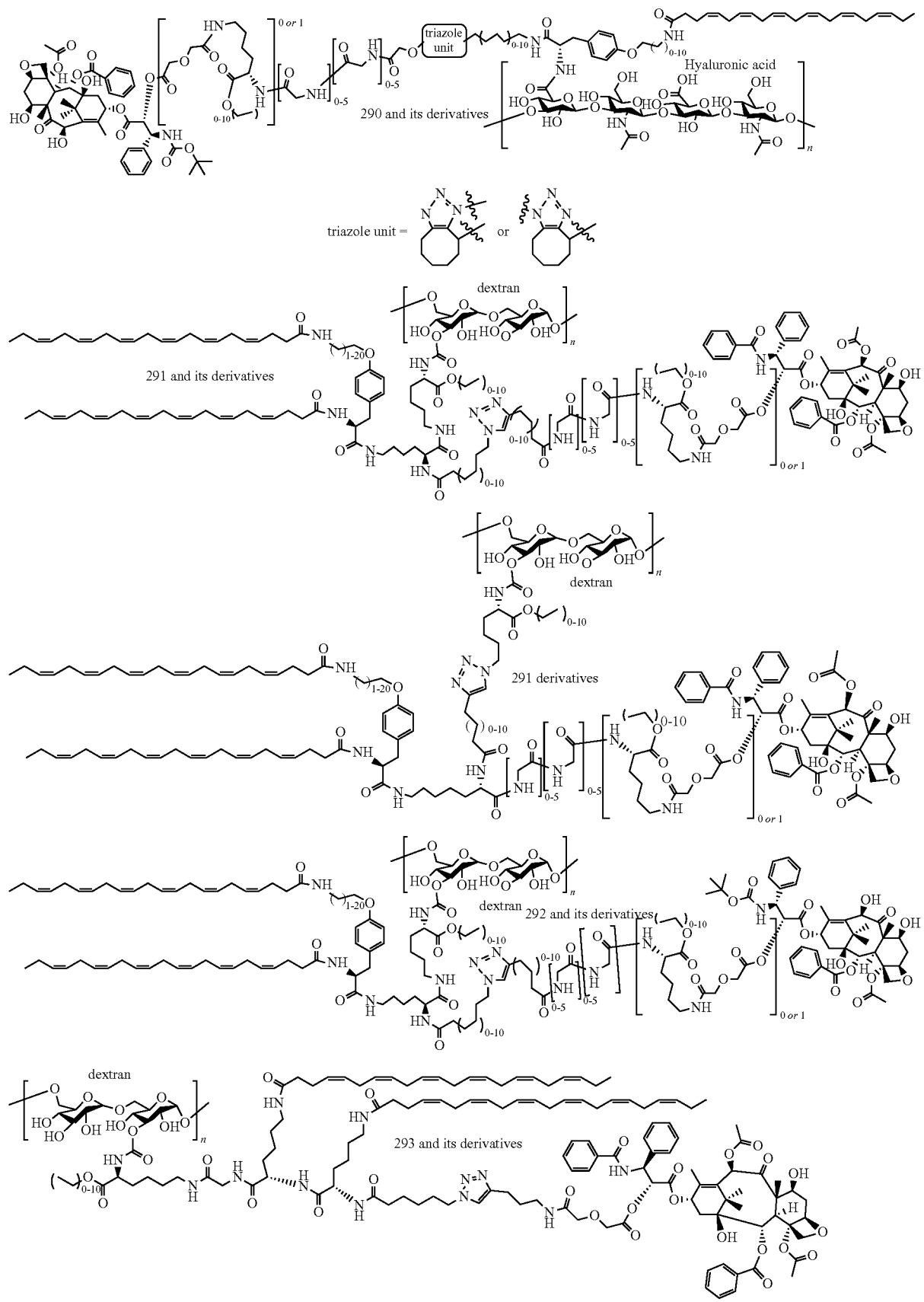

-continued
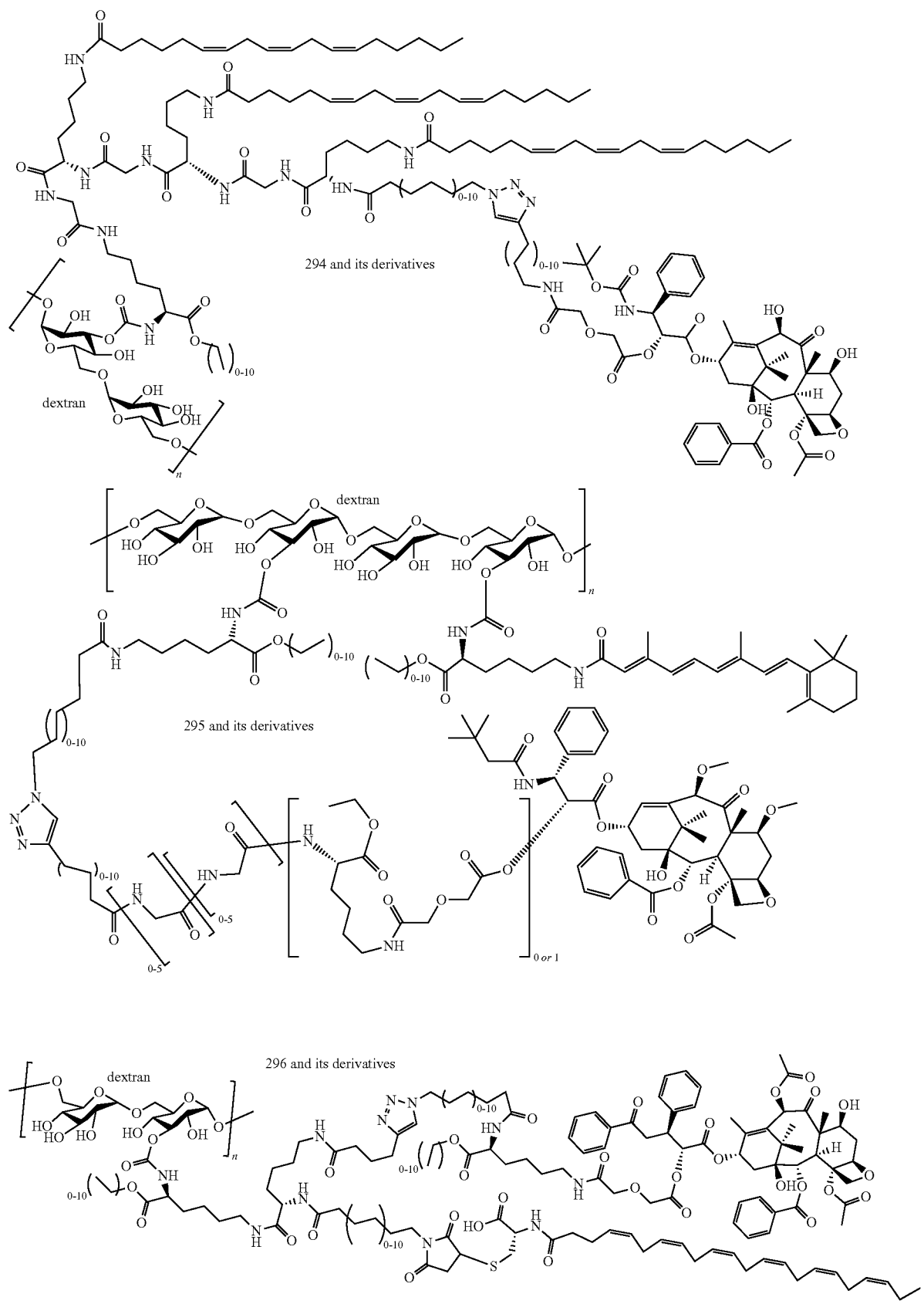
294 and its derivatives
295 and its derivatives
296 and its derivatives -continued
297 and its derivatives 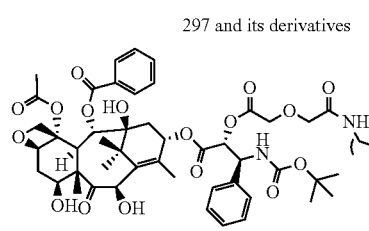 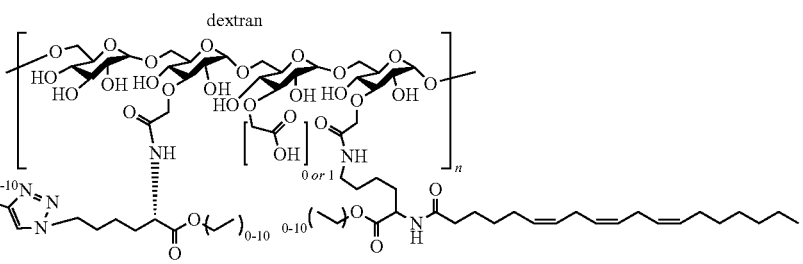
298 and its derivatives 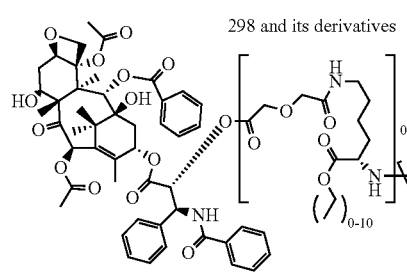 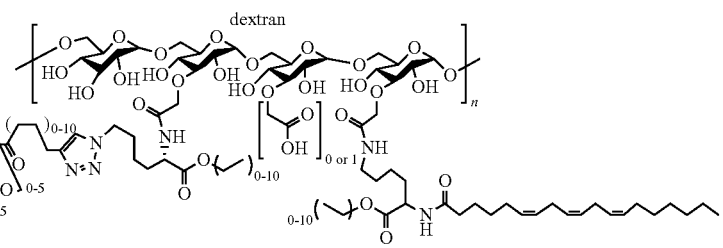
299 and its derivatives 
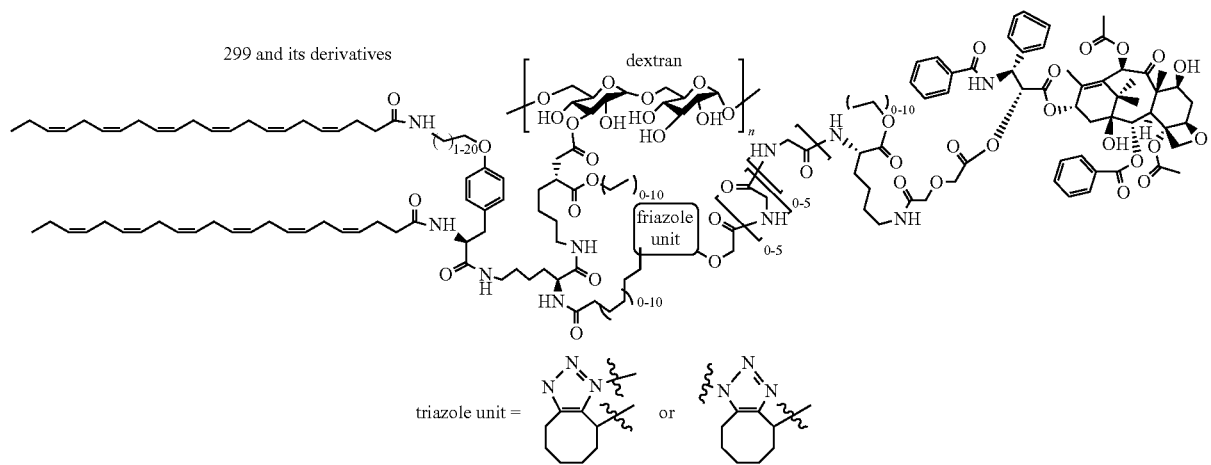
triazole unit =
300 and its derivatives 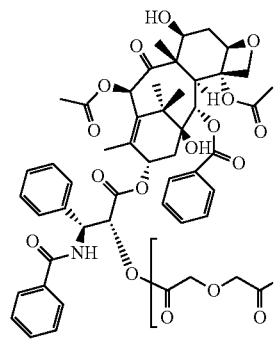  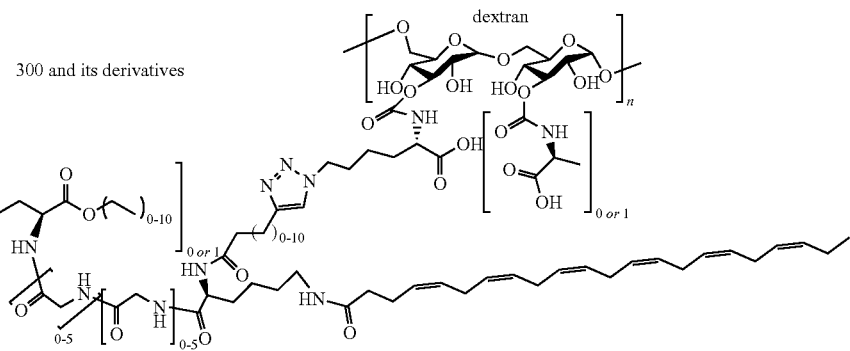

-continued
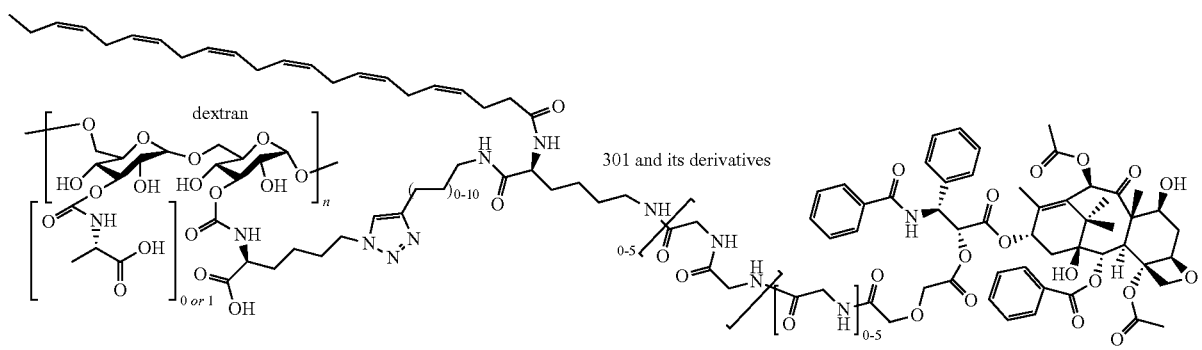
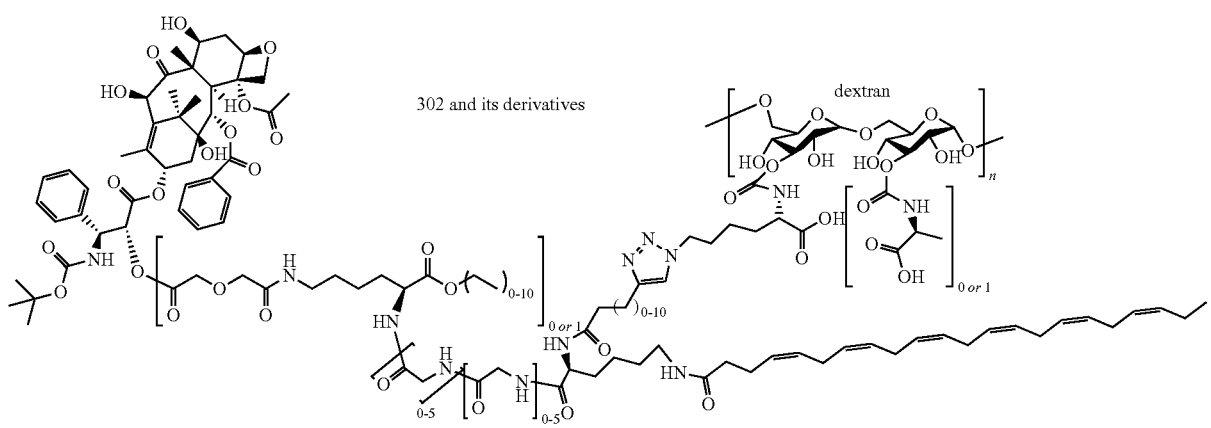
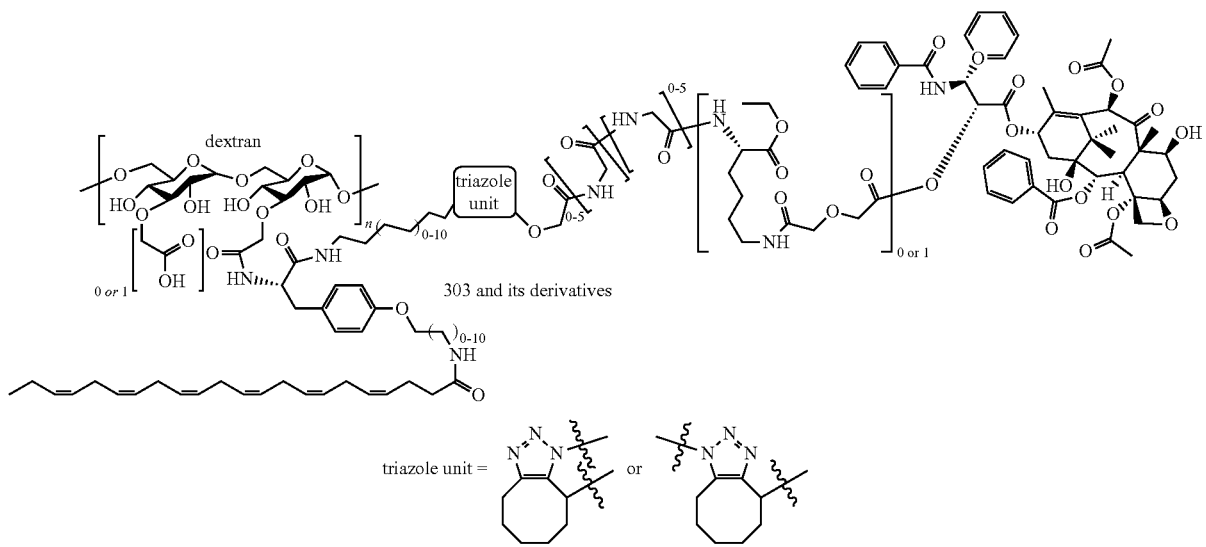

-continued
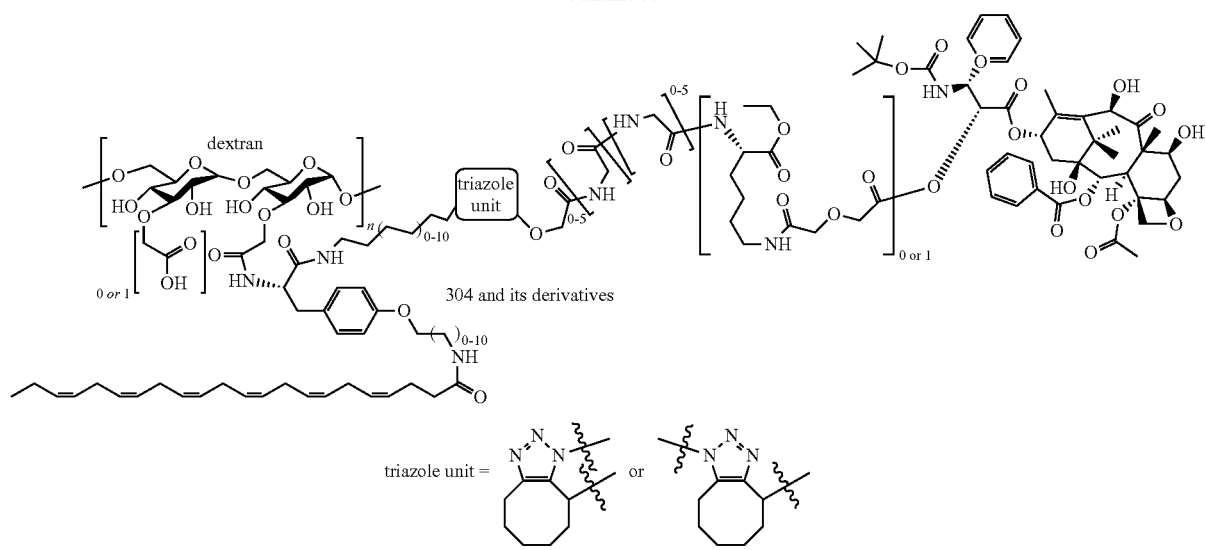
304 and its derivatives
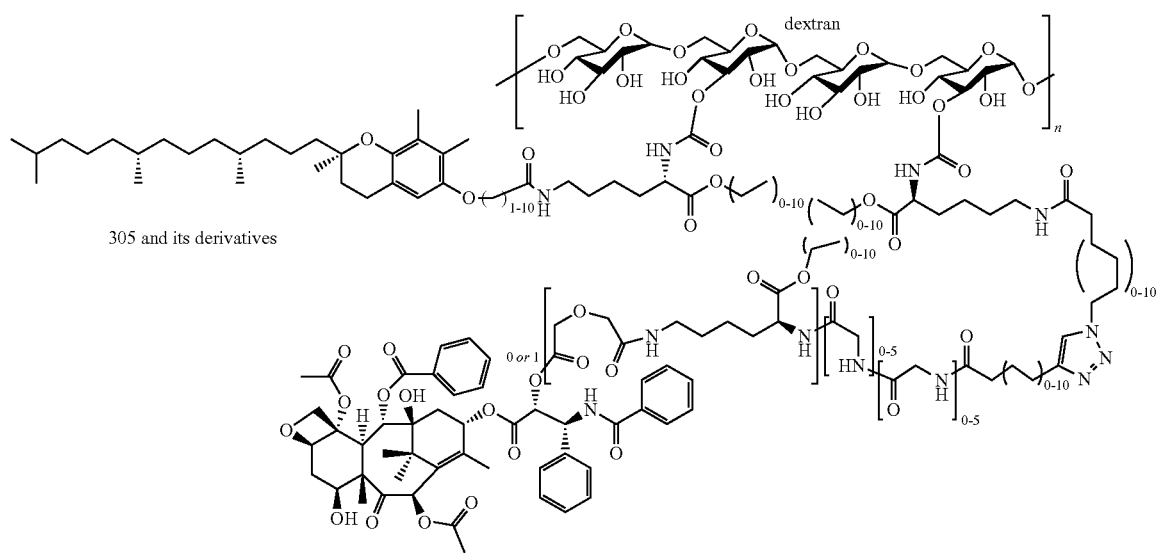
305 and its derivatives
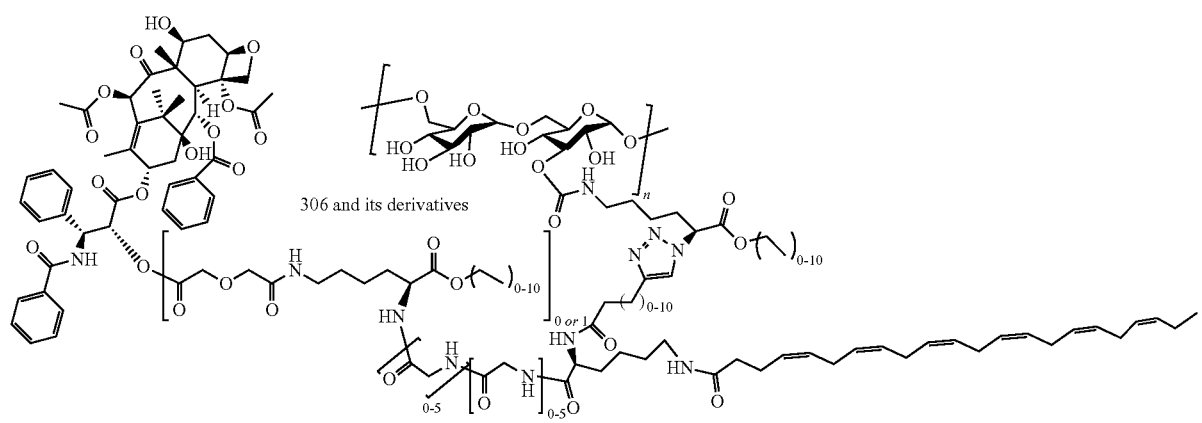
306 and its derivatives

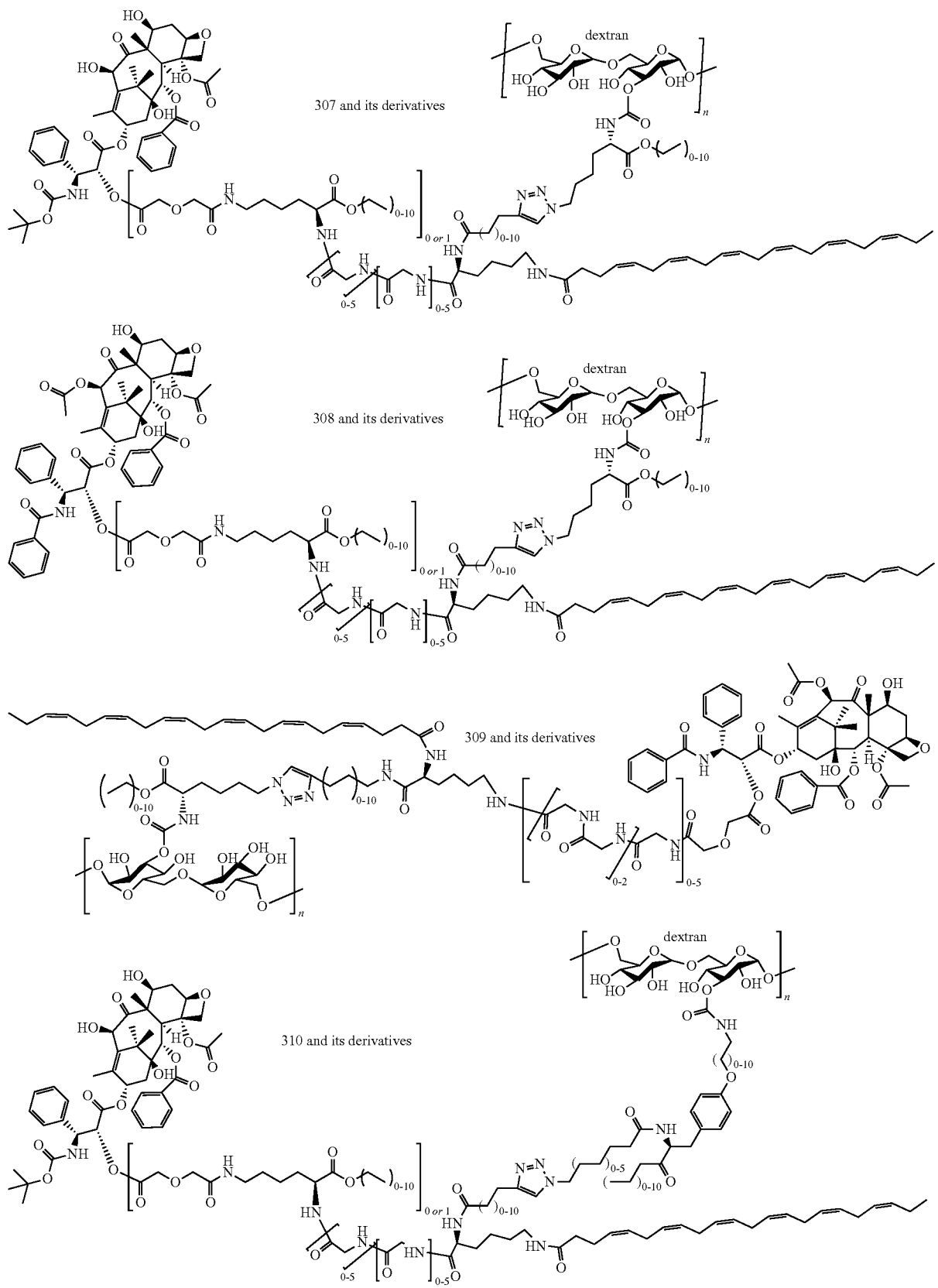

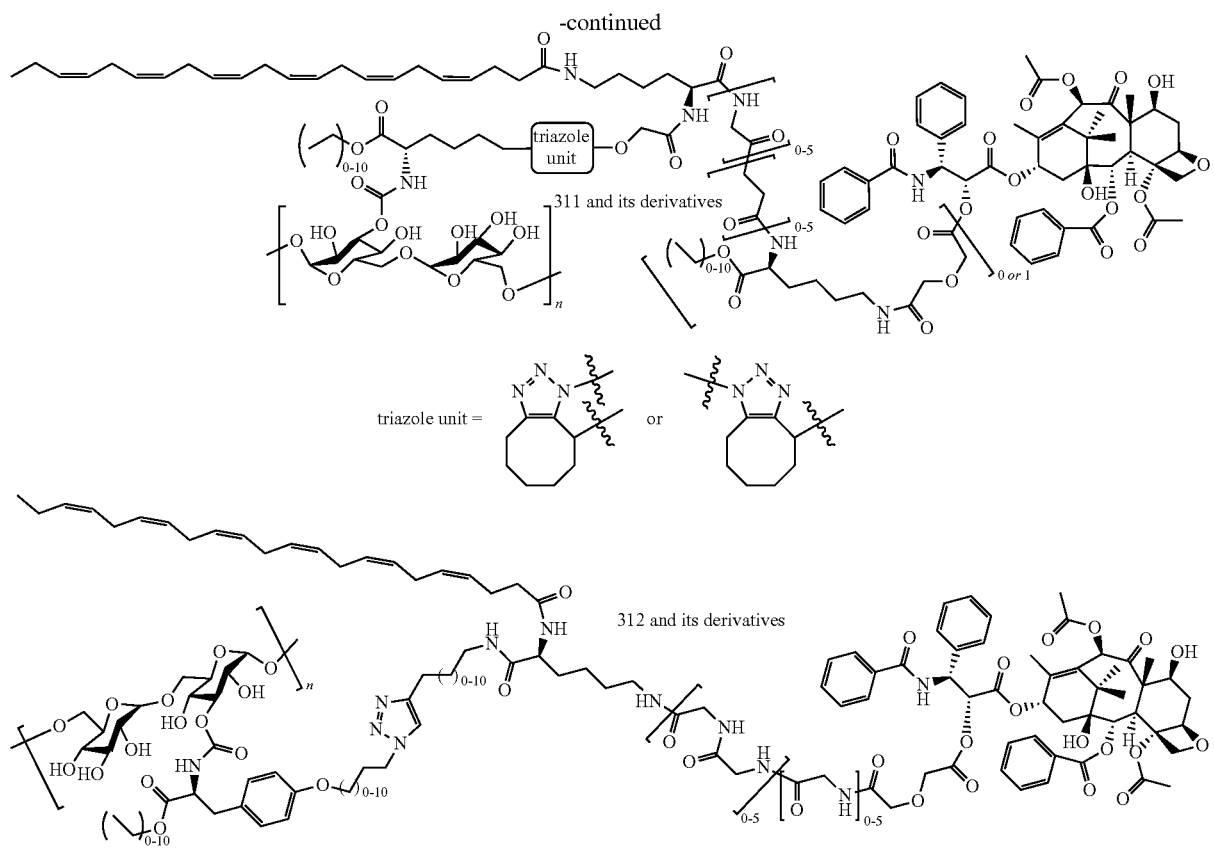

According to the first aspect of the present invention, as shown by Formula I, the taxane-lipid-polysaccharides dual conjugate or its derivatives or isomers, or a pharmaceutically acceptable salt or solvate thereof, improve the solubility of taxane drugs thereby improving bioavailability of taxanes. These compounds also maintain good biological activities of taxanes by increasing tumor targeting and enhancing the anti-tumor effect of taxanes in vivo, thus potentially improving therapeutic effects of these compounds for the treatment of sensitive diseases.

Accordingly, the present invention relates to taxane-lipid-polysaccharide dual conjugates or a pharmaceutically acceptable salt or solvate thereof, as shown by Formula I, for the treatment of the diseases susceptible to taxane compounds.

According to the second aspect of the invention, a functionalized taxane of Formula II, or its derivatives or isomers, or a pharmaceutically acceptable salt or solvate thereof, is provided:

Formula II

| Taxane | Spacer-1 (0 or 1) | Linker-1 | Spacer-2 (0 or 1) | Functional group | wherein the taxane compound, spacer-1, spacer-2 and linker-1 are as defined either in general or preferably, as described above in the first aspect of the present invention; the number of spacers is optionally 0 or 1;

wherein the covalent bond of the taxane compound linking to spacer-1 is selected from the group consisting of a urethane bond, an amino thiocarboxylate bond, an ester bond, a carbonate bond, a phosphate bond, an alpha or beta glycosylic bond;

wherein the functional group is selected from:

1) simple substituents such as Amino (—$NH_2$), substituted amino (—NHR), carboxyl (—COOH), azide (—$N_3$), sulfhydryl (—SH), sulfonic acid (—$SO_3H$), sulfonylamino (—$SO_2NH$—, —$SO_2NHR$), phosphate group (—$PO_4H$), phosphate ester group (—$PO_3R$), phosphoramido group (—$PO_3NH$—, —$PO_3NR$—), isothiocyano group, iso-oxycyano group, phenolic hydroxyl group; among them, the substituent R group is selected from an alkyl group, a cycloalkyl group, an aryl group, an aryl alkyl group, a cycloalkyl alkyl group and the like;

2) an alkynyl compound capable of coupling with an azide compound, a monocyclic derivative containing an acetylenic bond, a fused ring derivative containing an acetylenic bond, any of above compounds is selected from Biarylazacyclooctynone (BARAC) Dibenzoazacyclooctyne (DIBAC), Bicyclononyne (BCN), Dibenzocyclooctyne (DIBO), Difluorocyclooctyne (DIFO)), Monofluororinated cyclooctyne (MOFO), cyclooctyne (OCT), Dimethoxy azacyclooctyne (DIMAC), Nonfluoroocyclooctyne (NOFO), Arylless cyclooctyne (ALO), Thiocyclooctyne (thioOCT), Tetramethoxy dibenzocyclooctyne (TMDIBO); preferably as the structures shown in Figure-21:

Figure-21

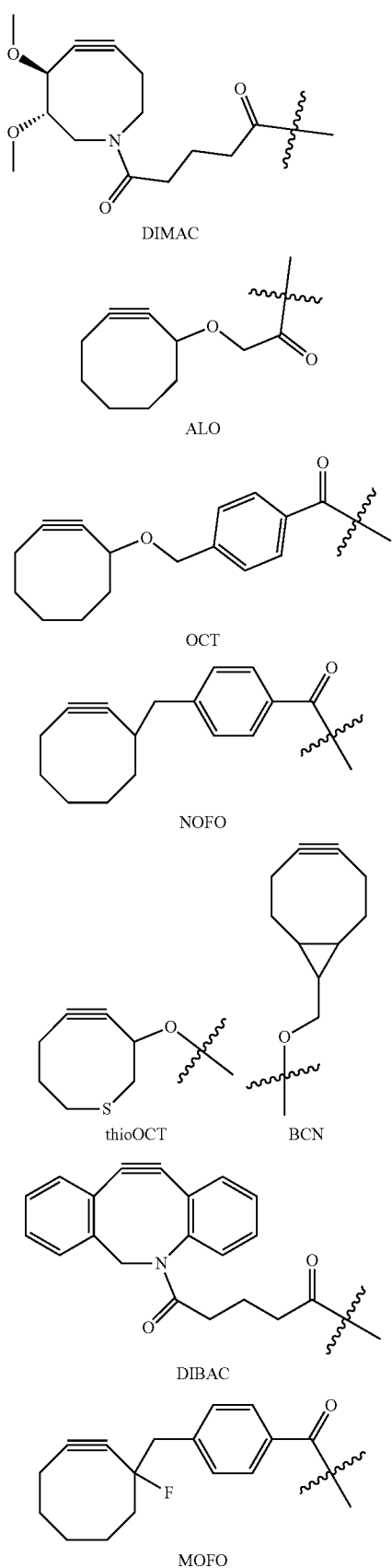

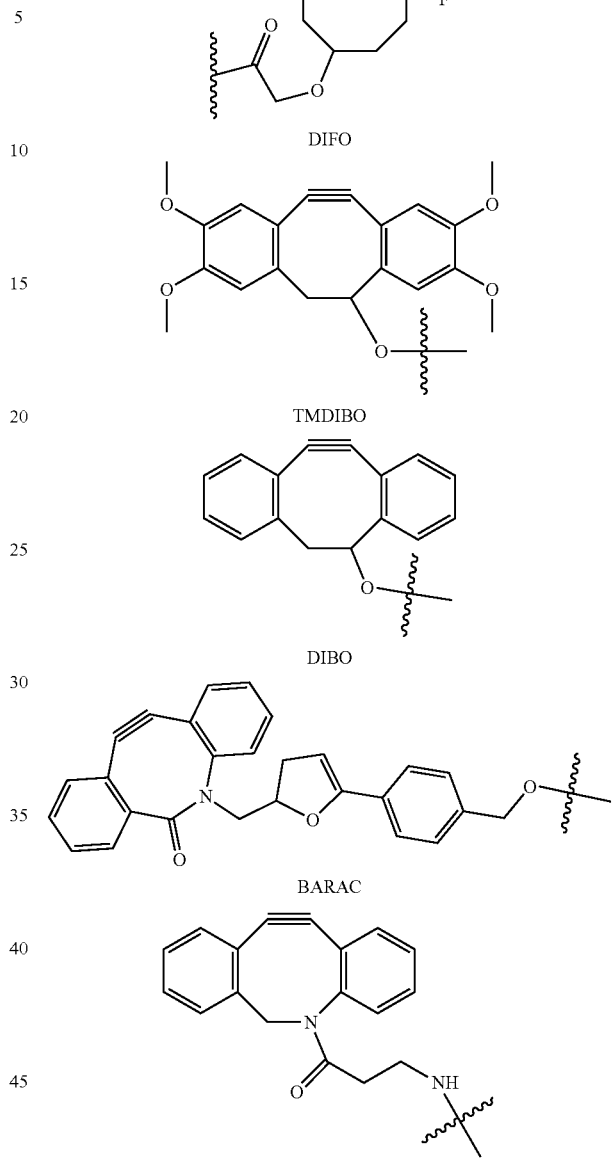

3) any one of the following groups which is capable of coupling with sulfhydryl group: maleimide group, substituted propynyl nitrile group, halogen (chlorine, bromine, or iodine) substituted acetamide group, acryl group, substituted vinyl sulfone group, 2-pyridine disulfide group; a 3-nitro-2-pyridine dithio group, reactive with a bi-sulfhydryl group; preferably any group with the structure shown in Figure-22:

Figure-22

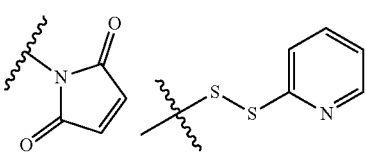

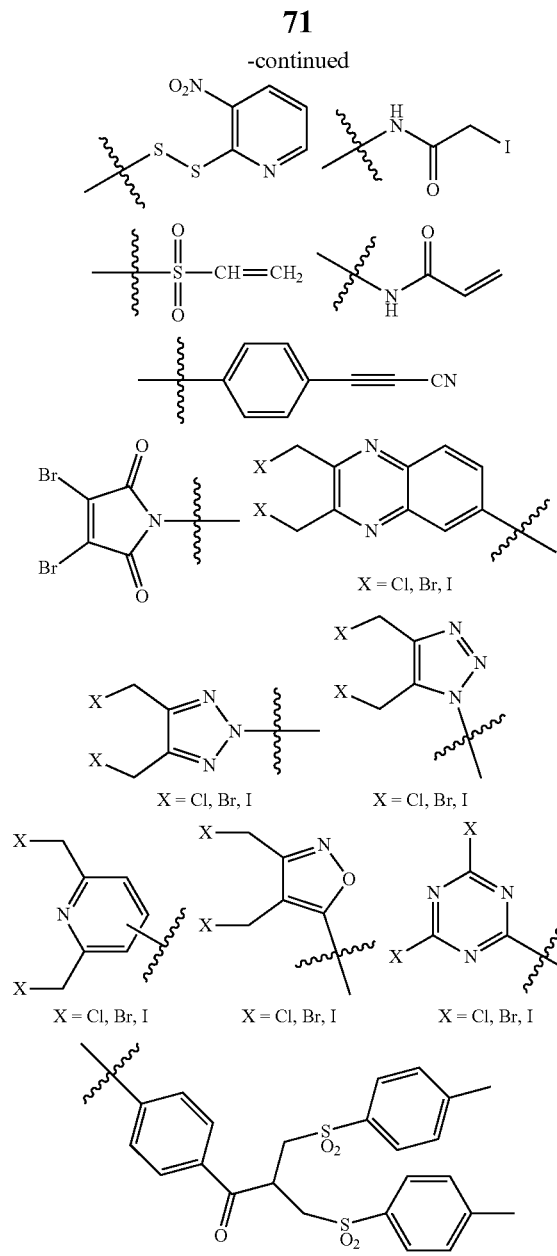

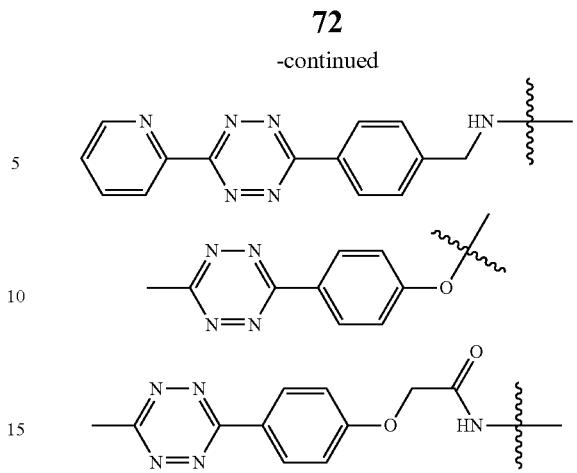

5) phenolic compounds and derivatives thereof, and substituted derivatives of 4-phenyl-3H-1,2,4-triazoline-3,5 (4H)-dione (PTAD), preferably the compound with structure as shown in figure-24:

Figure-24

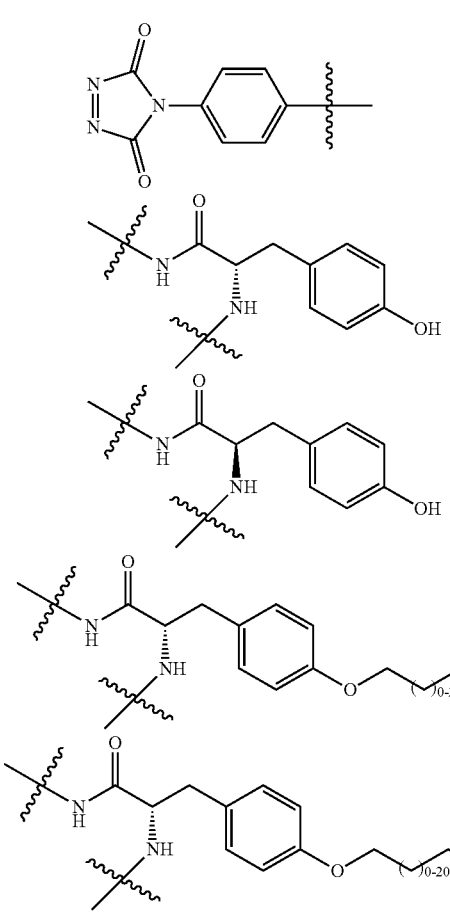

4) a substituted tetrazinyl group capable of undergoing coupling reaction, a monocyclic derivative group containing a trans-olefinic bond, preferably a group with the structure as shown in Figure-23:

Figure-23

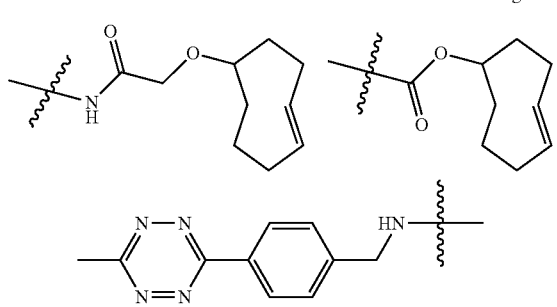

wherein the "substitution" is as defined in the first aspect of the present invention for a substituent of a single molecular lipid compound;

according to the second aspect of the invention, the spacer attached to the taxane in Formula II is preferably selected from the structural fragments as shown in Figure-25:

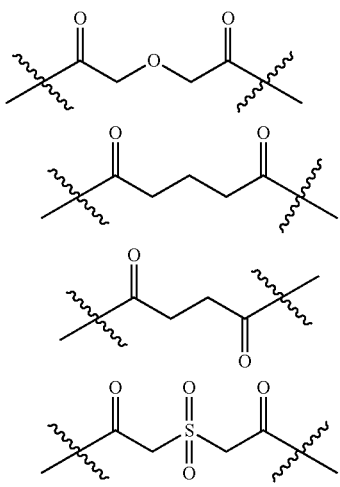

Figure-25

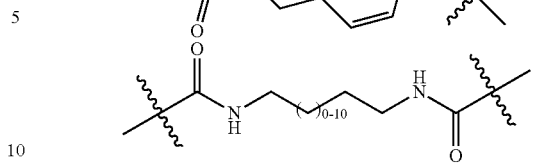

according to the second aspect of the present invention, the functional group in Formula II is preferably selected from the group consisting of amino, carboxyl, azido, sulfhydryl, phenolic hydroxyl, alkynyl, maleimide, cycloheptynyl, tetrazinyl;

according to the second aspect of the present invention, the functionalized taxane in Formula II is preferably selected from the group consisting of the following compounds, or its derivatives or isomers, or a pharmaceutically acceptable salt or solvate thereof:

Firgure-26

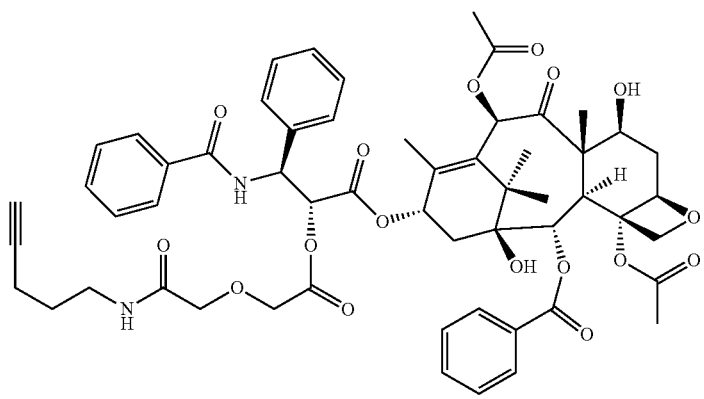

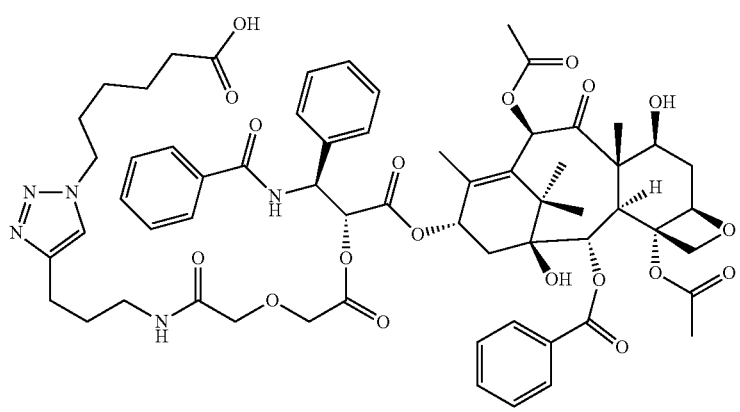

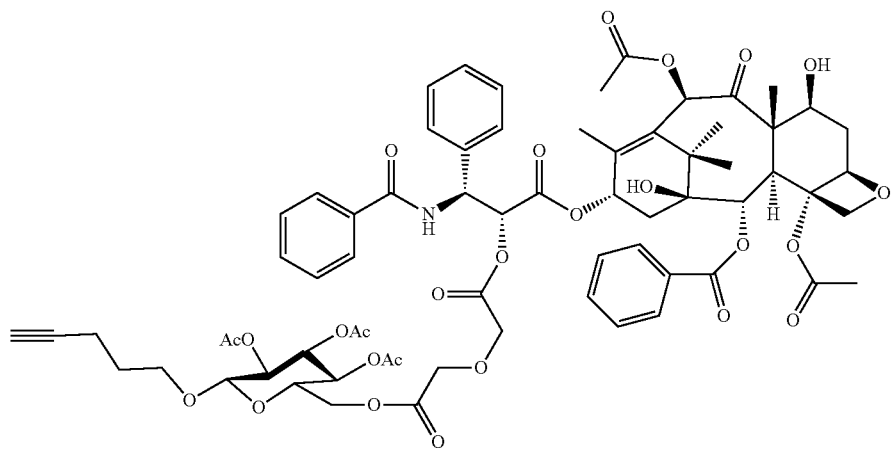
15
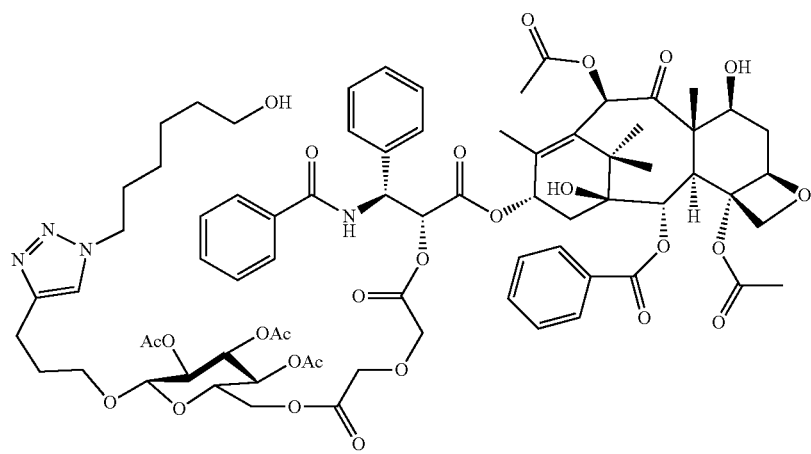
16
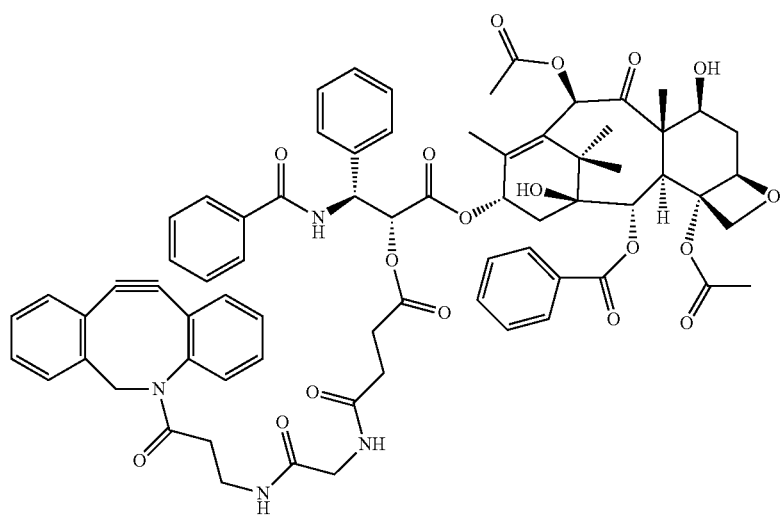
21

-continued
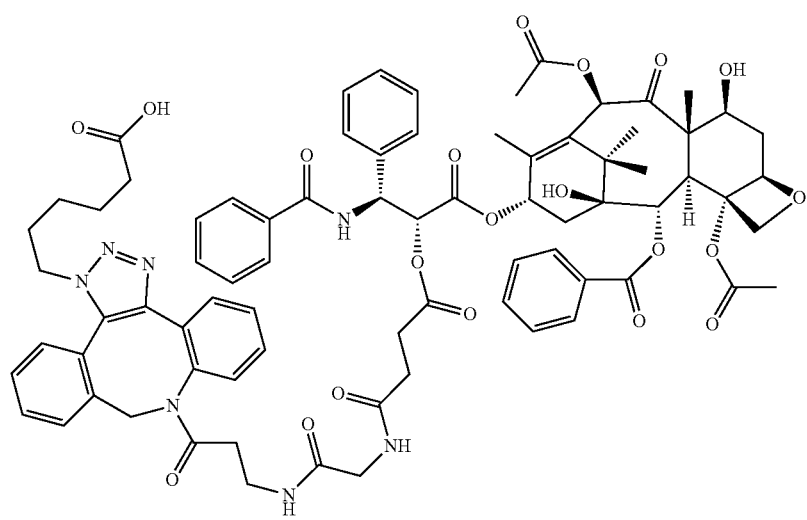
22a
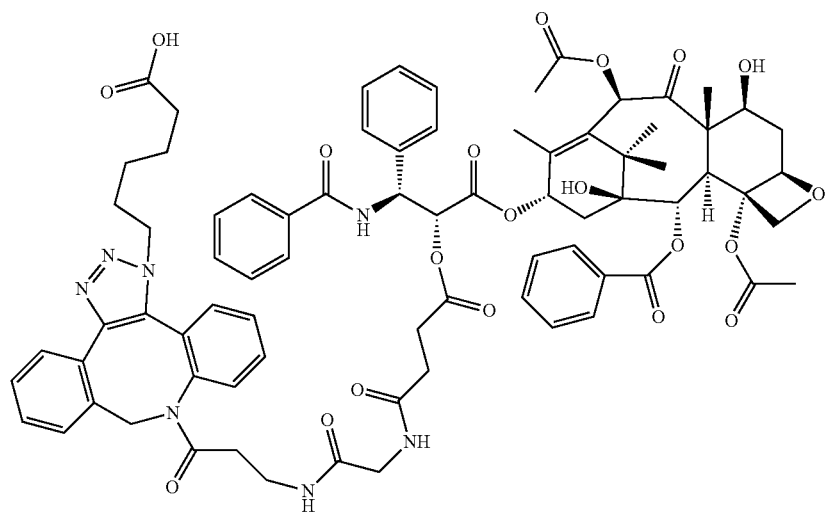
22b
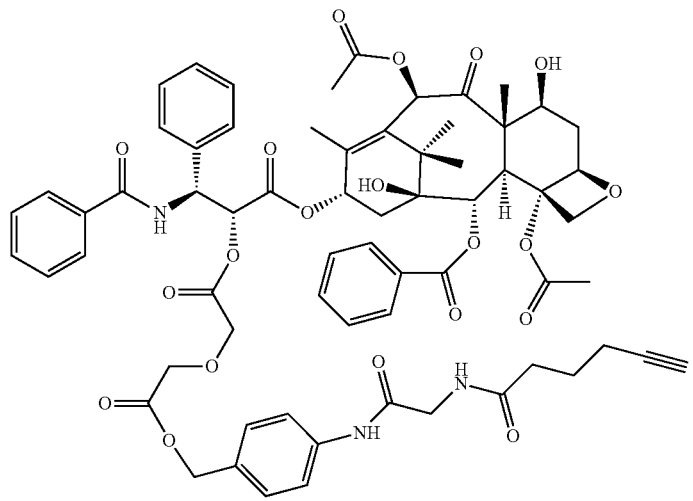
27

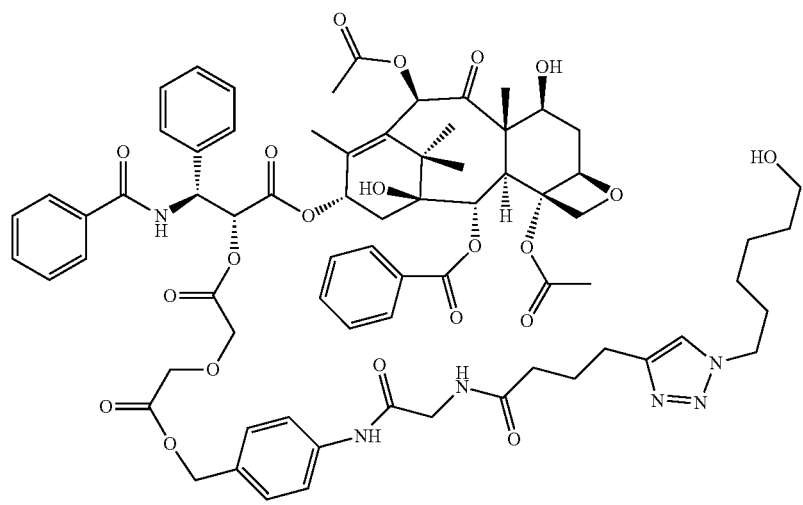
28
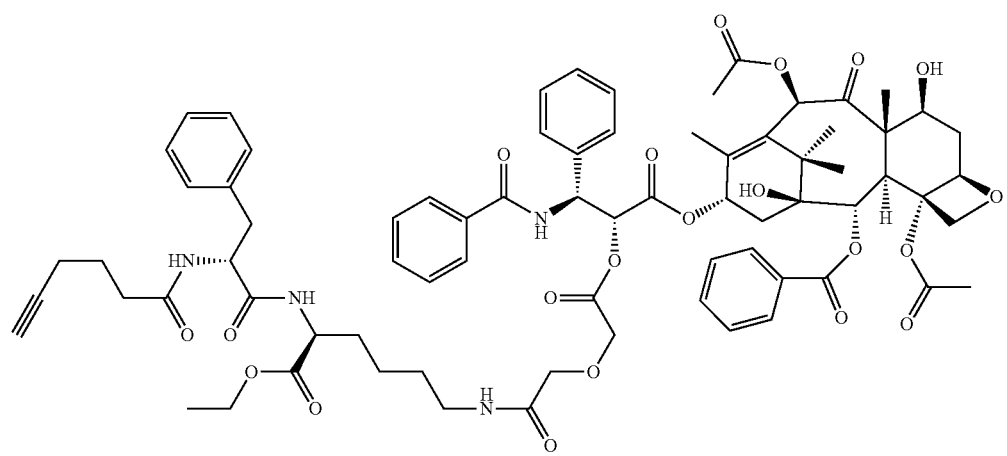
32
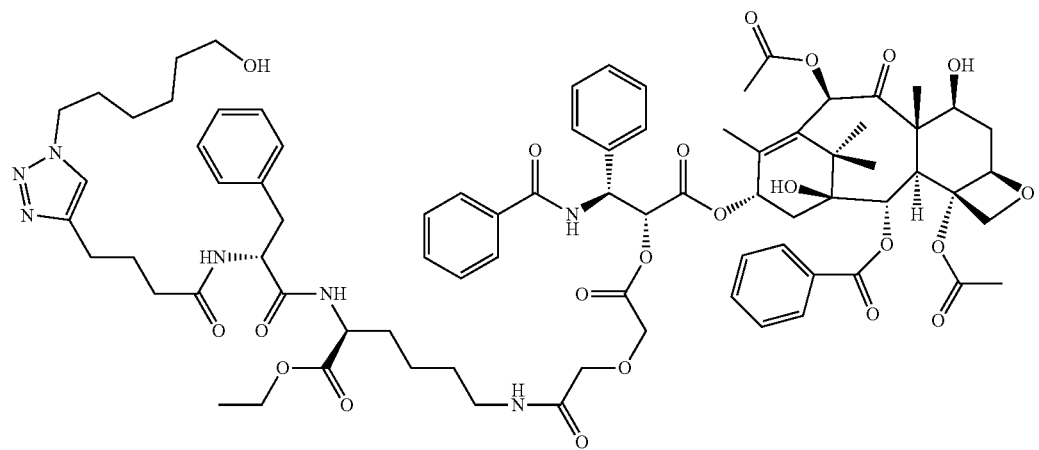
33

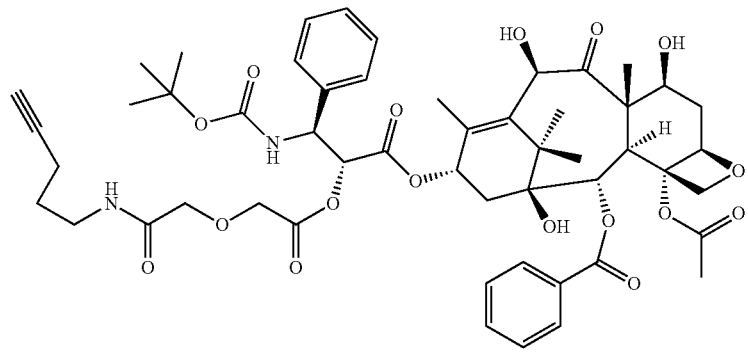
39
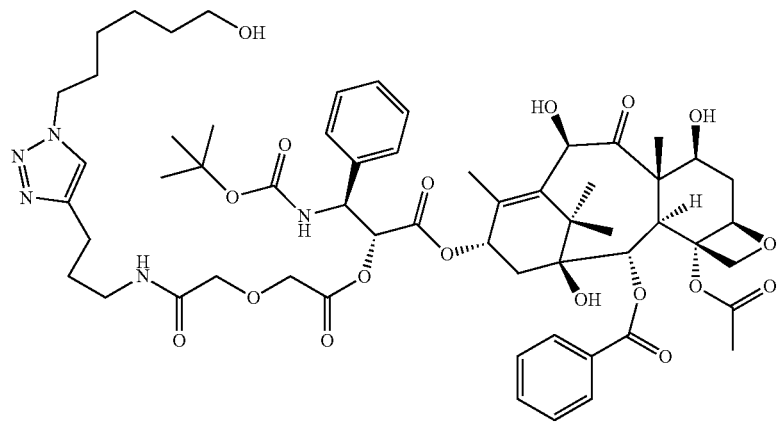
40
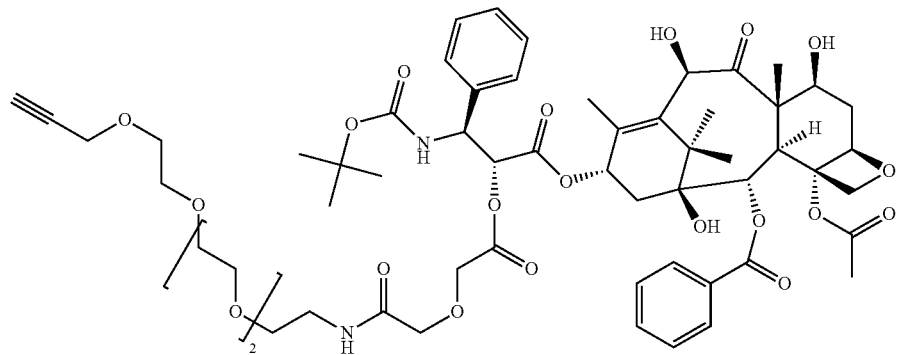
50

Figure-26
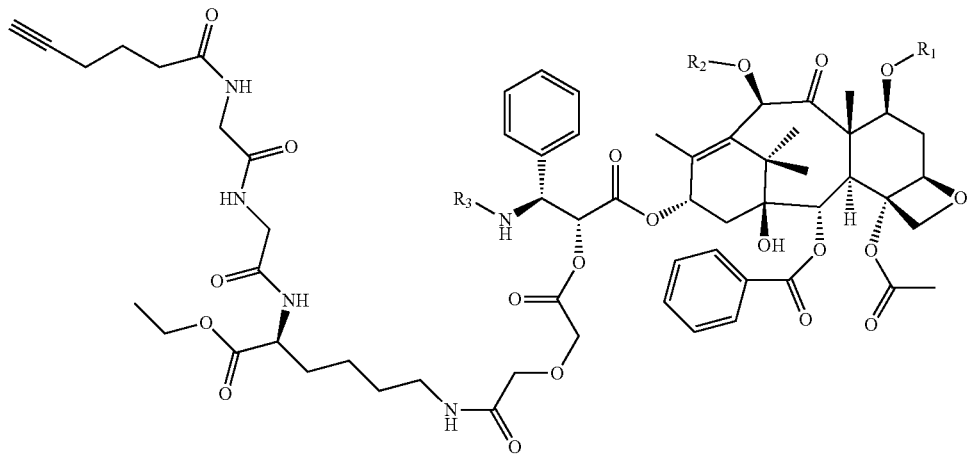
56 R₁ = Alloc, R₂ = Acetyl, R₃ = Bz
57 R₁ = Alloc, R₂ = Alloc, R₃ = Boc
58 R₁ = CH₃, R₂ = CH₃, R₃ = Boc
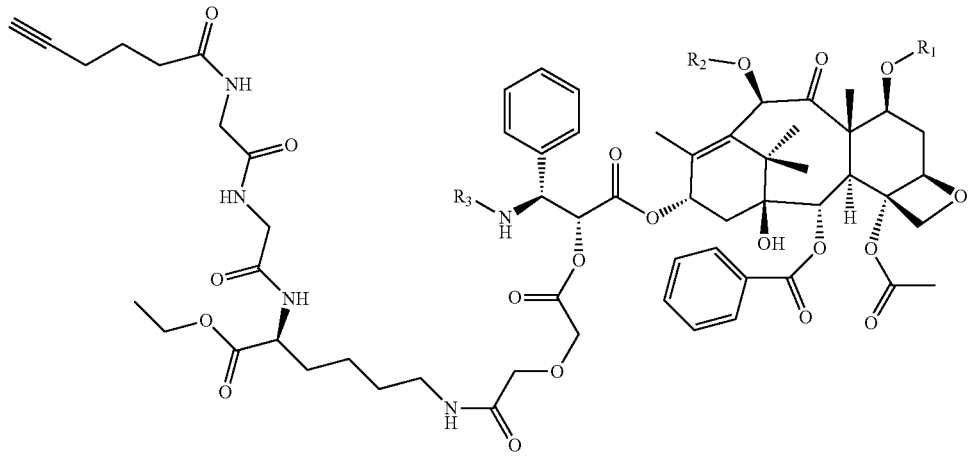
59 R₁ = H, R₂ = Acetyl, R₃ = Bz
60 R₁ = H, R₂ = H, R₃ = Boc
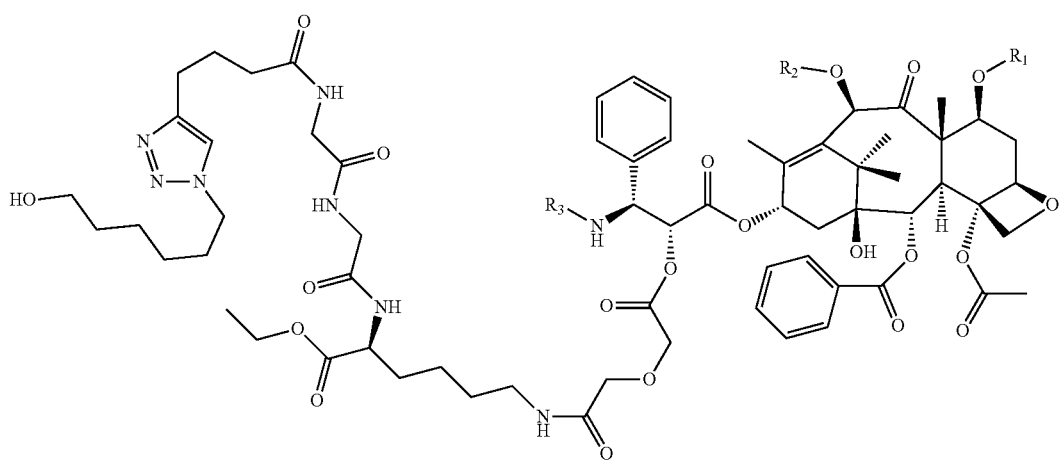
61 R₁ = H, R₂ = Acetyl, R₃ = Bz
62 R₁ = H, R₂ = H, R₃ = Boc
63 R₁ = CH₃, R₂ = CH₃, R₃ = Boc

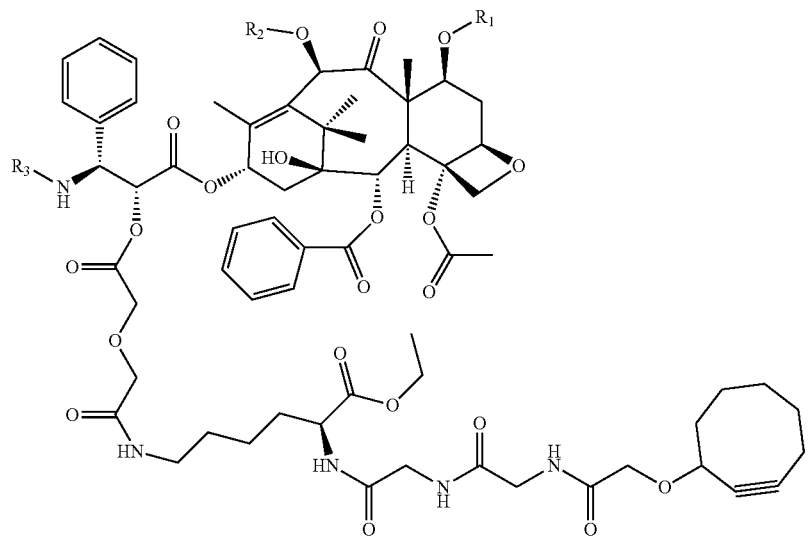
71 R₁ = Alloc, R₂ = Acetyl, R₃ = Bz
72 R1 = Alloc, R2 = Alloc, R₃ = Boc
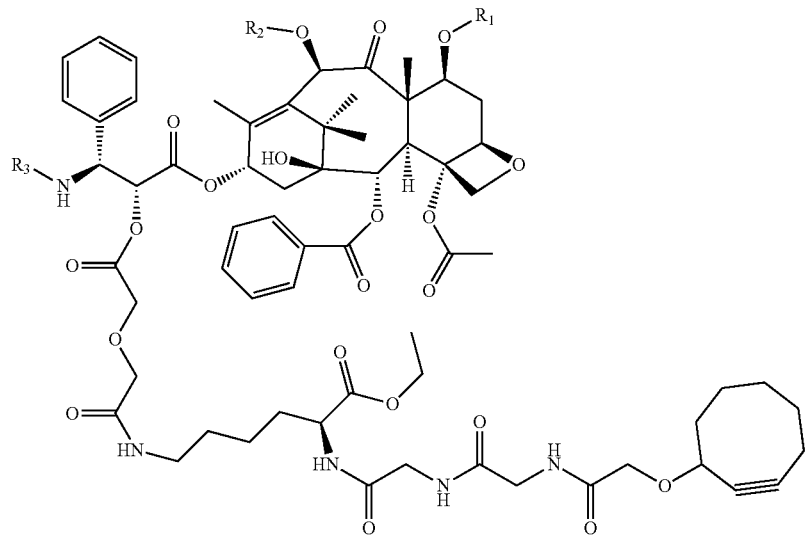
73 R₁ = H, R₂ = Acetyl, R₃ = Bz
74 R₁ = H, R₂ = H, R₃ = Boc

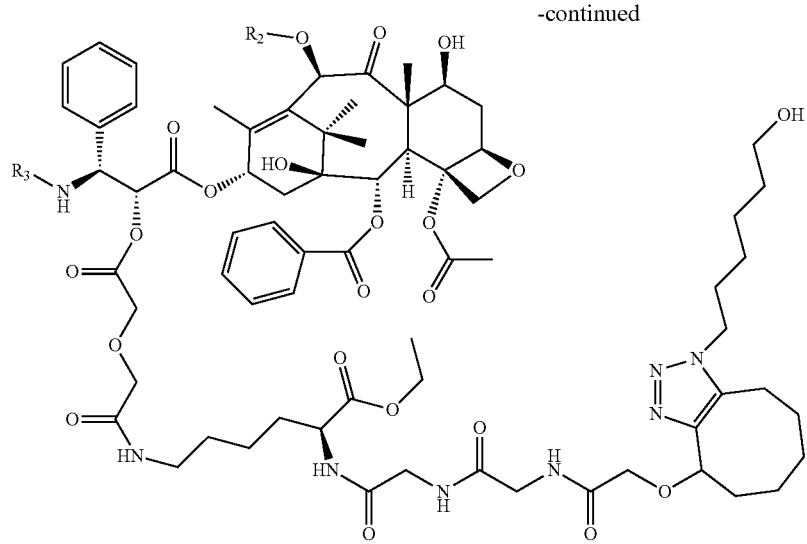

75a R$_2$ = Acetyl, R$_3$ = Bz
76a R$_2$ = H, R$_3$ = Boc

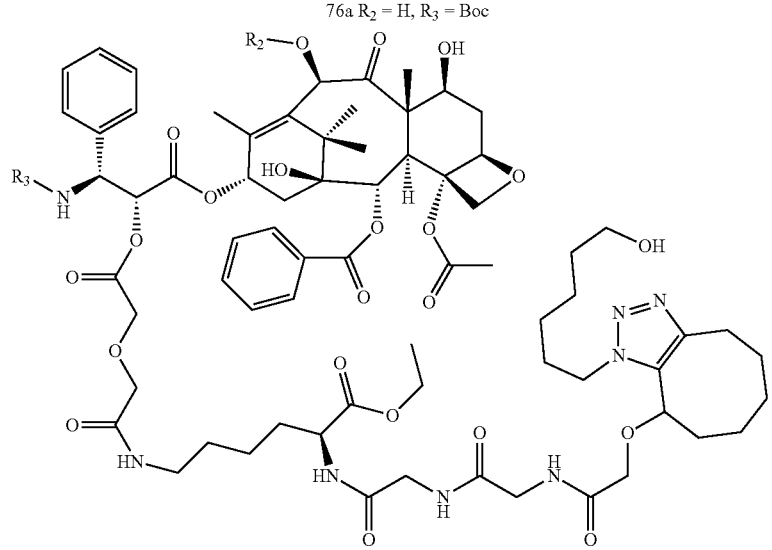

75b R$_2$ = Acetyl, R$_3$ = Bz
76b R$_2$ = H, R$_3$ = Boc

80

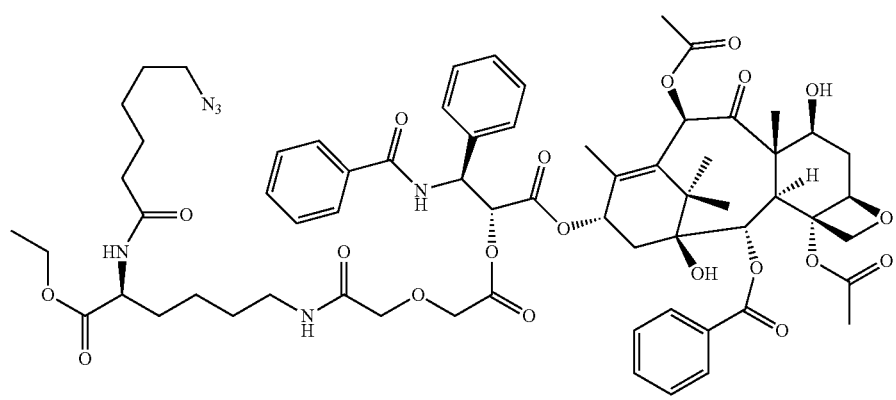

(Note: Alloc: Allyloxycarbonyl; Bz: Benzoyl; Boc: Tert-butoxycarbonyl)

According to the second aspect of the present invention, as shown in Formula II, the functionalized taxane compound, or the pharmaceutically acceptable salt, solvate or isomer thereof, can be used directly in the preparation of a taxane pharmaceutical composition or a pharmaceutical formulation, also used for the treatment of diseases which are susceptible to taxanes; on the other hand, the aforementioned compounds provide the necessary intermediates, which can be used for the preparation of a taxane-polysaccharide conjugate (as shown in Formula V), a functionalized taxane-lipid conjugate (as shown in Formula VIII) or the taxane-lipid-polysaccharide dual conjugate (as shown in Formula I);

accordingly, the present invention relates to a functionalized taxane as in Formula II or a pharmaceutically acceptable salt or solvate thereof, which can be used for the treatment of taxane-susceptible diseases; it also relates to the group of intermediates as shown in Formula II, the functionalized taxanes, the pharmaceutically acceptable salts or solvates thereof, which can be used for the preparation of a taxane-polysaccharide conjugate (Formula V), a functionalized taxane-lipid conjugate (Formula VIII) or a taxane-lipid-polysaccharide dual conjugate (Formula I).

According to the third aspect of present invention, the present invention provides a functionalized polysaccharide derivative as shown in Formula III, or a pharmaceutically acceptable salt or solvate thereof, including isomers thereof.

Formula III

| Polysaccharide | Spacer-1 (0 or 1) | Linker-1 | Spacer-2 (0 or 1) | Functional group | wherein the polysaccharide, spacer-1, spacer-2 and linker-1 are as defined generally or preferably in accordance with first aspect of present invention described above; wherein the number of spacers is optionally 0 or 1;

wherein the covalent bond of the polysaccharide to spacer-1 is selected from the group consisting of an amide bond, a carbamate bond, a urethane bond, an amino-thiocarbamate bond, an ester bond, an isourea bond, a thiourea bond, a urea bond, a disulfide a bond, a carbonate bond, a phosphate bond, a phosphate ester bond, a sulfonamide bond, an alpha or beta glycosylic bond, a triazole-containing covalent bond;

wherein the functional groups are as defined generally or preferably in accordance with the second aspect of the present invention described above;

according to the third aspect of present invention, the polysaccharides derivative as of the Formula III is preferably selected from the group of compounds and or its derivatives or isomers, or a pharmaceutically acceptable salt or solvate thereof, which is shown as following in Figure-27:

Figure-27

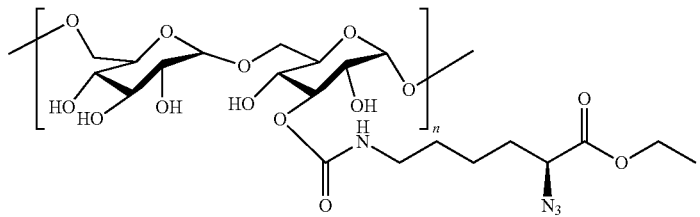

85

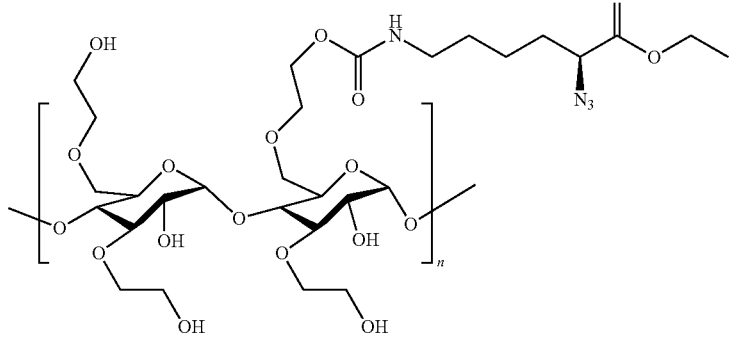

86

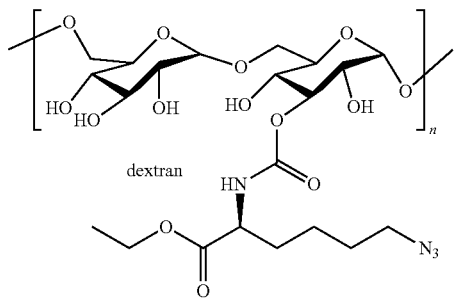

91

-continued
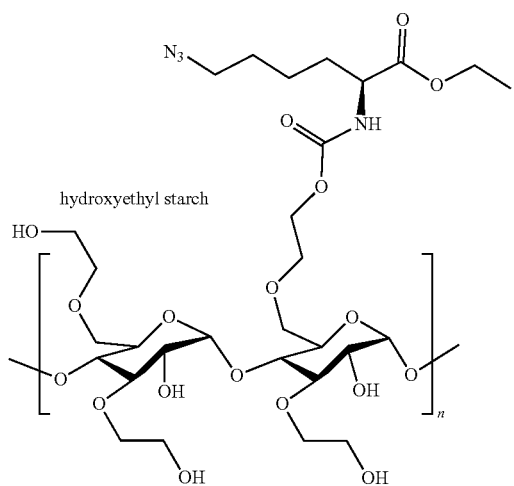
hydroxyethyl starch
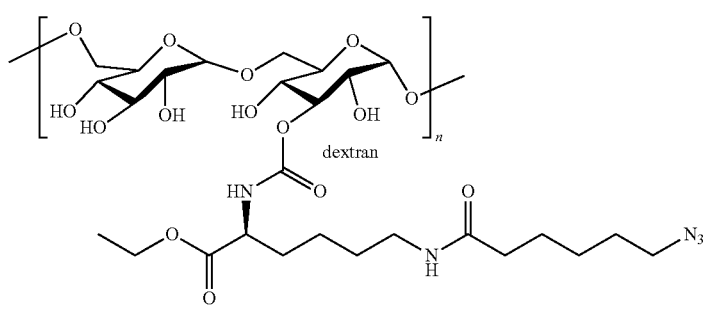
dextran
92
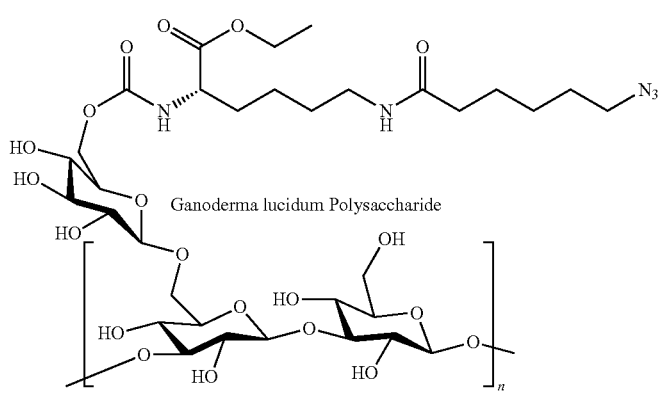
Ganoderma lucidum Polysaccharide
97
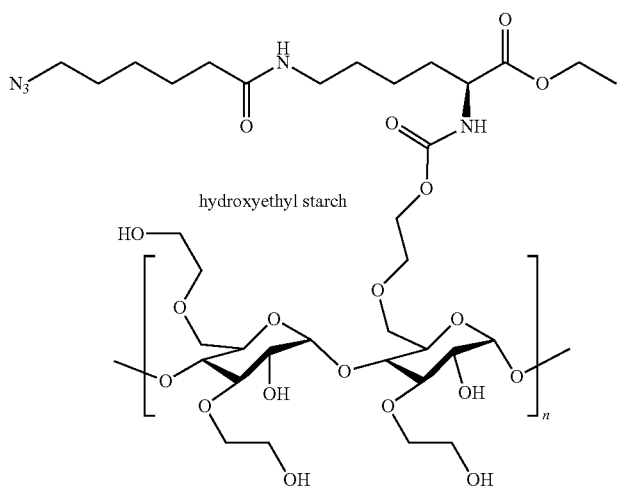
hydroxyethyl starch
98
99

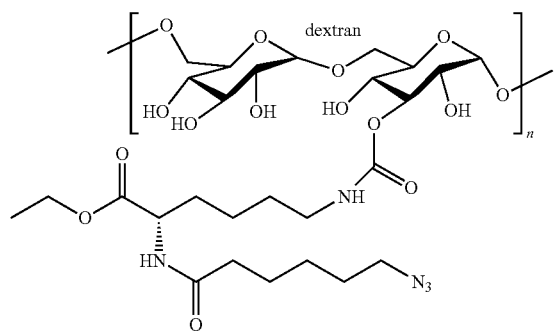
101
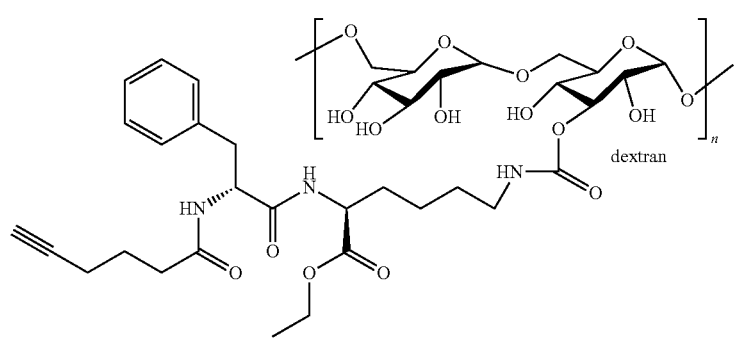
103
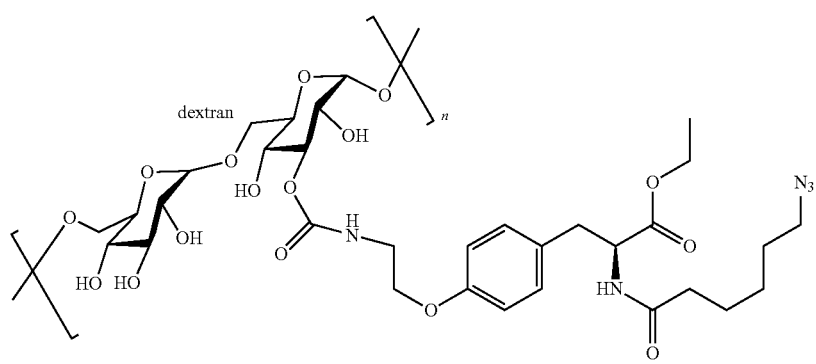
108
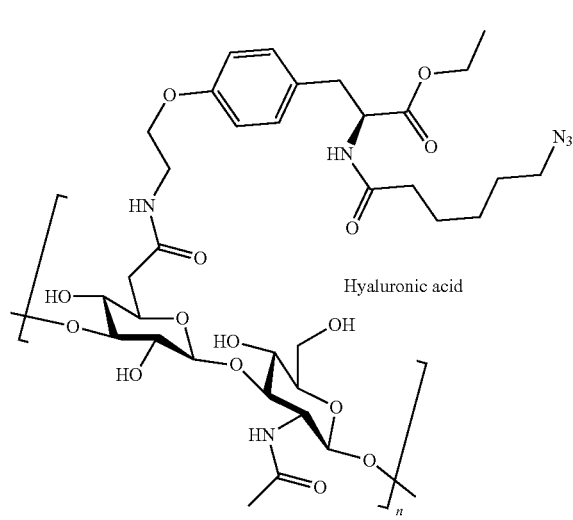
109

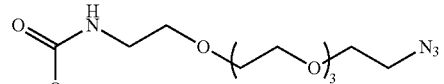
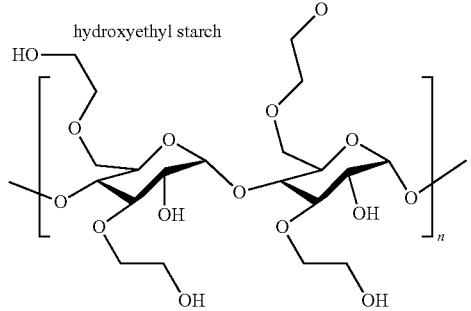
113
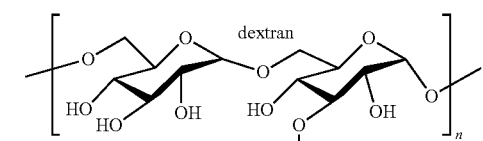
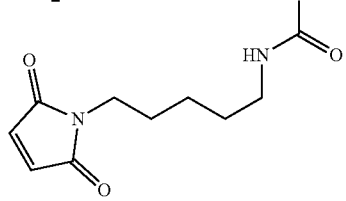
115
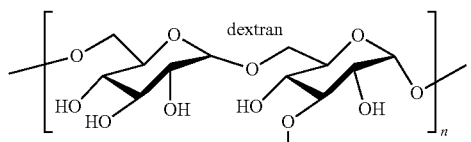
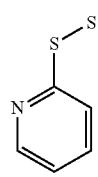
118
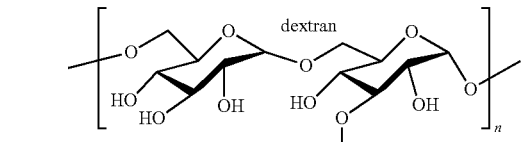
120

-continued
122
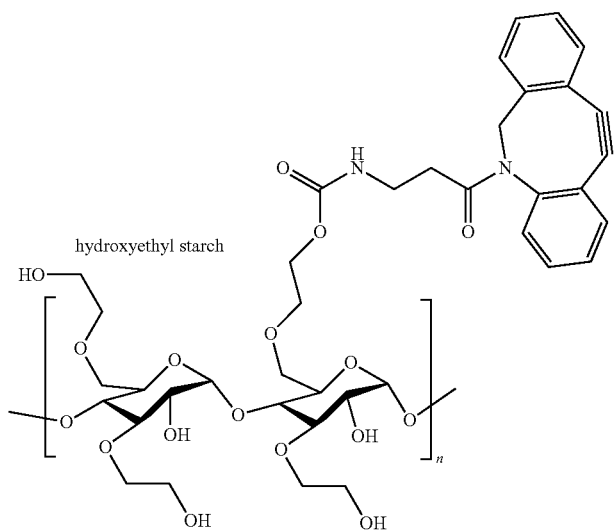
125
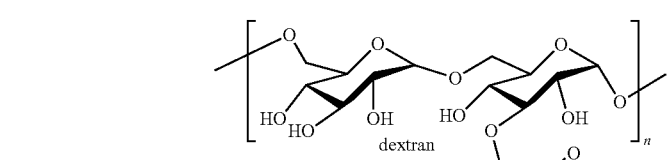
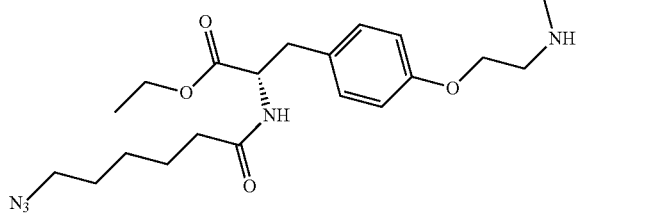
130
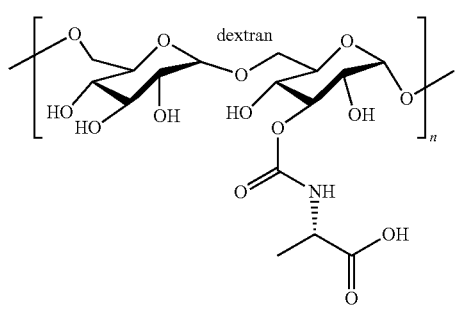
139
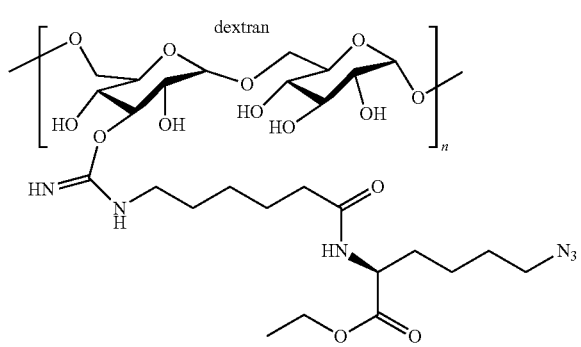

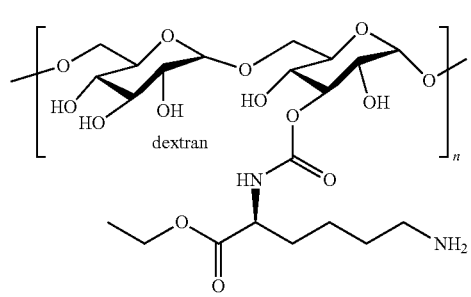

142

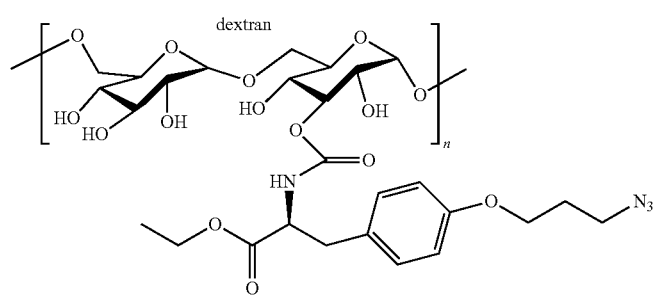

151

According to the third aspect of the present invention, as shown in Formula III, the functionalized polysaccharides, along with pharmaceutically acceptable salts, solvates or isomers thereof, can be used as a delivery vehicle for drugs, preferably drugs with low solubility such as taxanes. The present invention can be covalently linked to poorly soluble drug, or physically mixed with the poorly soluble drugs and other components in a pharmaceutical composition or formulation for increasing its solubility, thus improving bioavailability; on the other hand, those compounds provide the necessary intermediates for the preparation of taxane-polysaccharide conjugates (Formula V), polysaccharide-lipid conjugates (Formula VI) and functionalized form thereof (Formula VII), or taxane-lipid-polysaccharide dual conjugates (Formula I).

Accordingly, the present invention also relates to a functionalized polysaccharide as shown in general by Formula III, as a pharmaceutical carrier which can be either covalently linked to or physically mixed with the subject drug for improving the solubility and bioavailability of a drug. a drug is preferably a taxane compound, or pharmaceutically acceptable salts, solvates or isomers thereof, wherein the other drugs which may be covalently linked are preferably, but not limited to, vinblastine, vincristine, Lipitor, SN-38, capecitabine, gemcitabine, etc.; it also relates to the group of intermediates as shown in Formula III, the functionalized polyssacharides and the pharmaceutical acceptable salts or solvates, or isomers thereof, which can be used for the preparations of a taxane-polysaccharide conjugate (Formula V), a polysaccharide-lipid conjugate (Formula VI) and a functionalized form thereof (Formula VII), or a taxane-lipid-polysaccharide dual conjugate (Formula I).

According to the fourth aspect of the present invention, the present invention provides bifunctional or multifunctional polysaccharides or its derivatives or isomers, or a pharmaceutically acceptable salt or solvate thereof, shown by Formula IV, Formula IV

[Functional group-1]—[Linker unit]—[Polysaccharide]—[Linker unit]—[Functional group-2]

wherein the polysaccharide and the linker units are as defined in general or preferably as in the first aspect of this present invention. The covalent bond connecting the polysaccharides to the linking unit is selected from the group consisting of an amide bond, a carbamate bond, an urethane bond, an amino-thiocarbamate bond, an ester bond, an iso-urea bond, a thiourea bond, an urea bond, a disulfide bond, a carbonate bond, a phosphate bond, a phosphoric acid amide bond, a sulfonamide bond, an alpha or beta glycosylic bond, a covalent bond containing a triazole moiety;

the functional groups-1 and -2 are as defined above for the general or preferred functional groups in accordance with the second aspect of this invention.

according to the fourth aspect of the present invention, the bifunctional or multifunctional polysaccharide derivatives, are preferably selected from the compounds, as shown in Figure-28, or derivatives or isomers thereof, or their pharmaceutically acceptable salts or solvates thereof as shown in Figure-28.

Figure-28
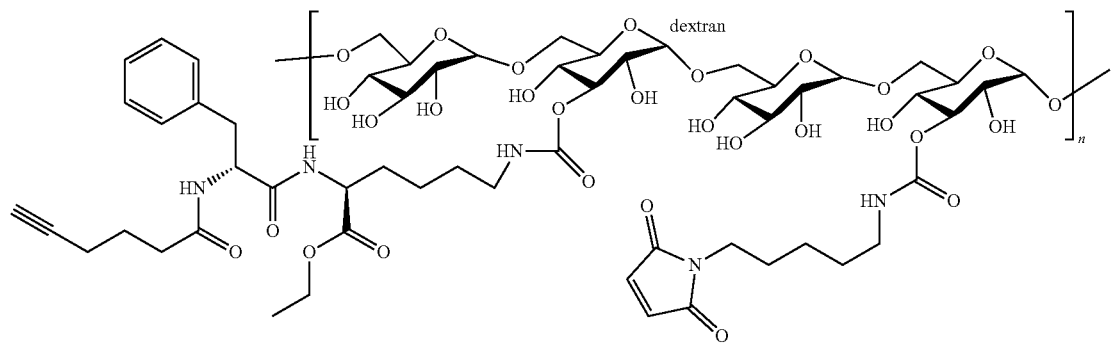
116
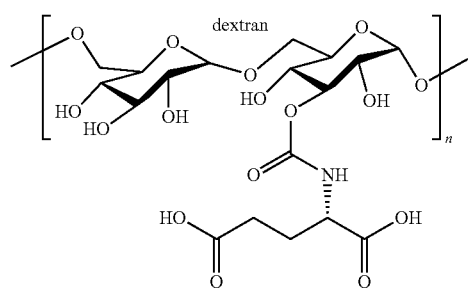
136
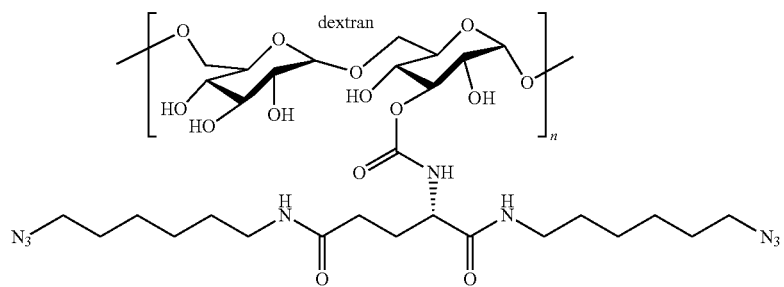
137
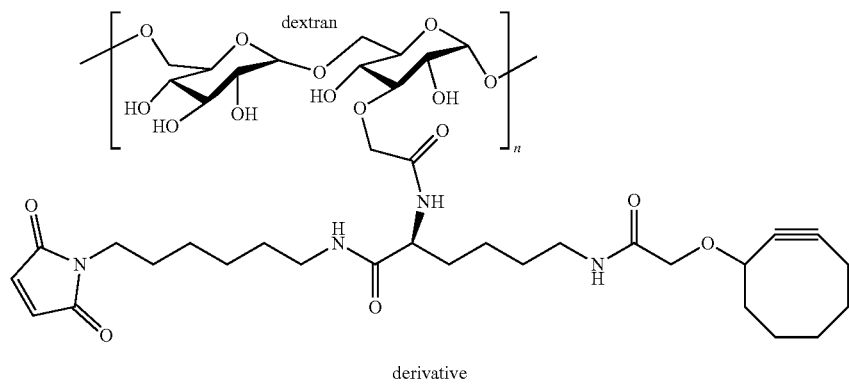
derivative
123

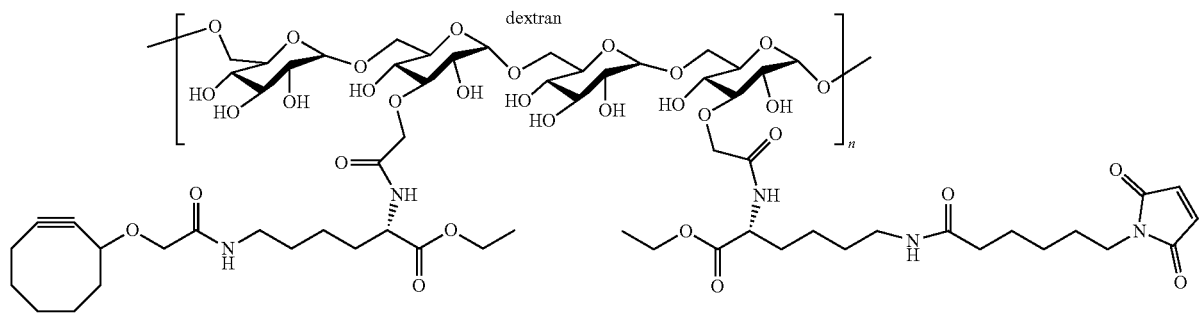
123
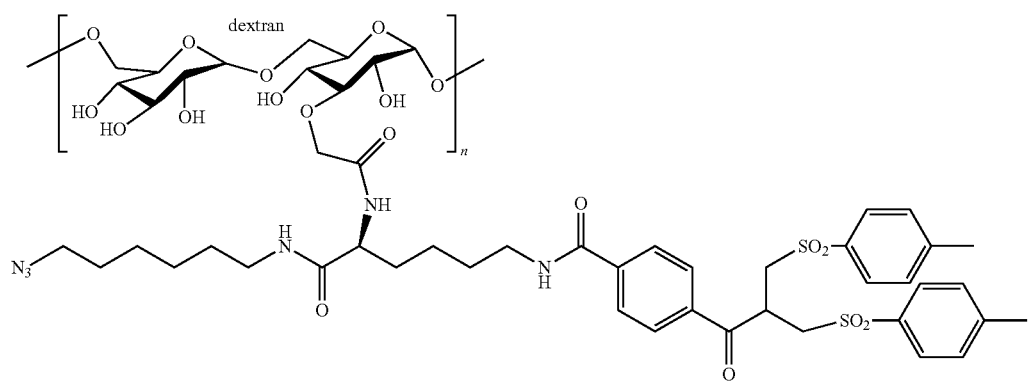
123 derivative
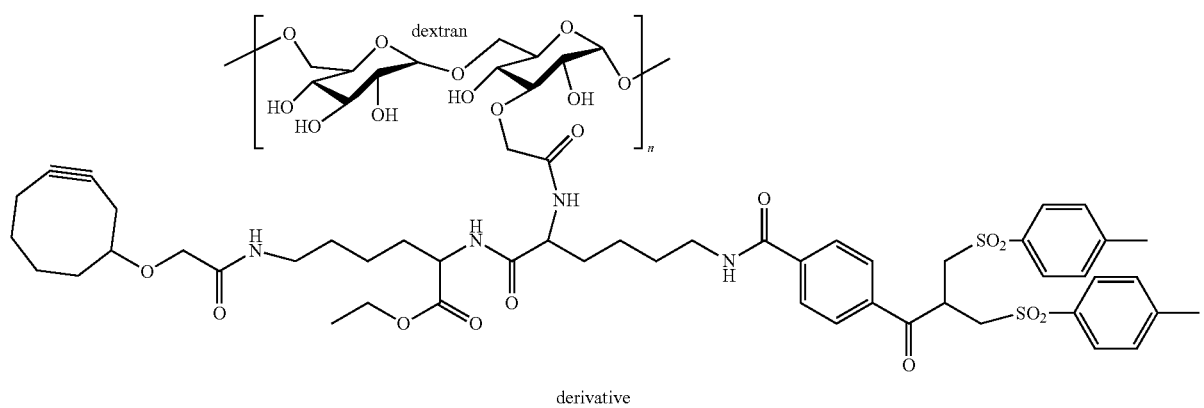
123 derivative
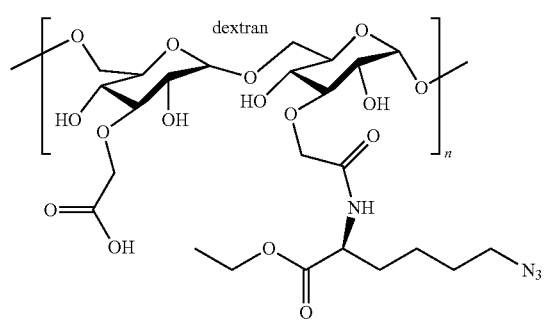
124

-continued
126
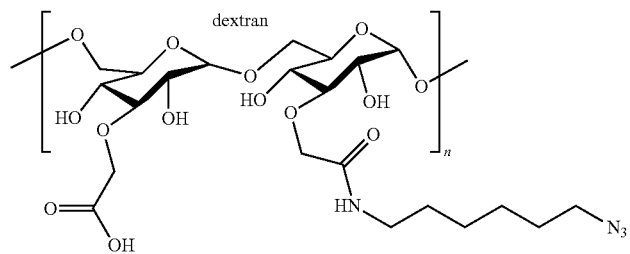
127
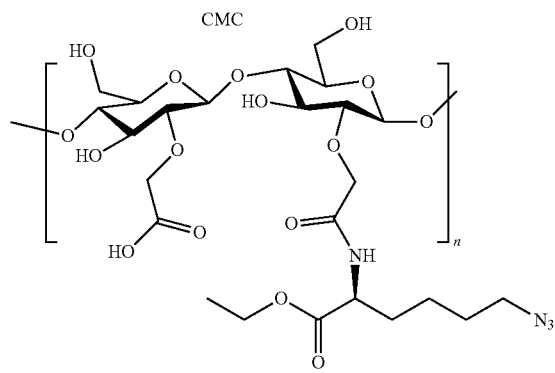
131
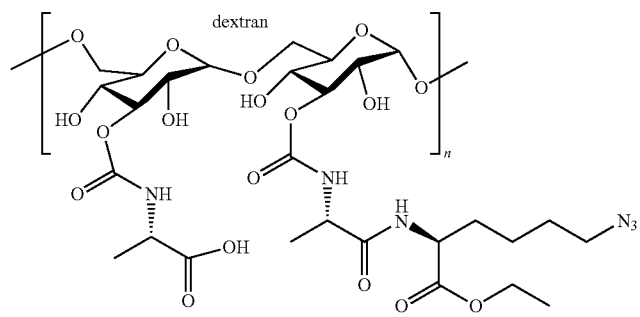
132
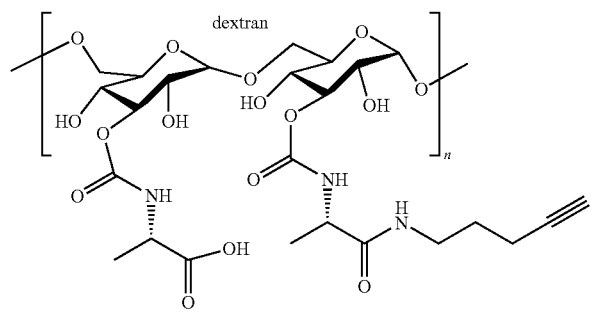

-continued
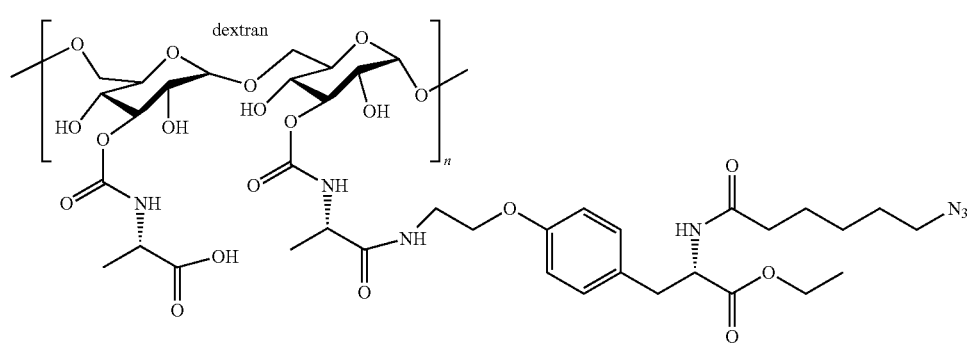
133
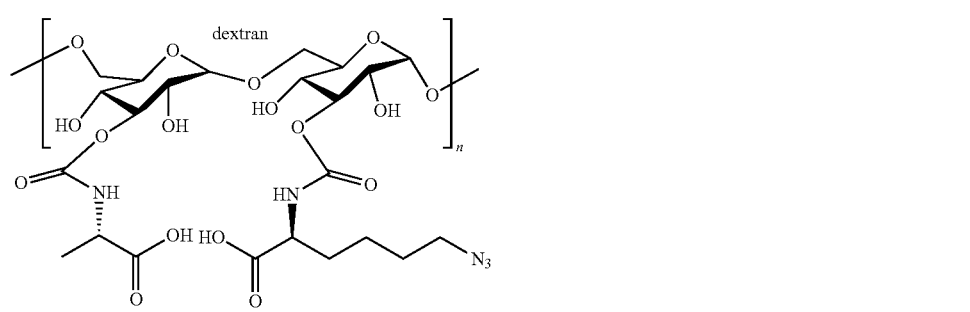
140
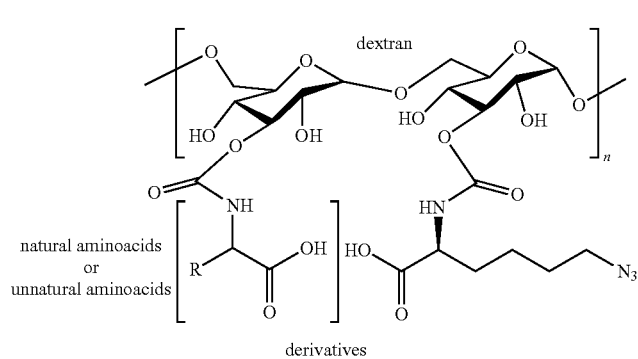
140
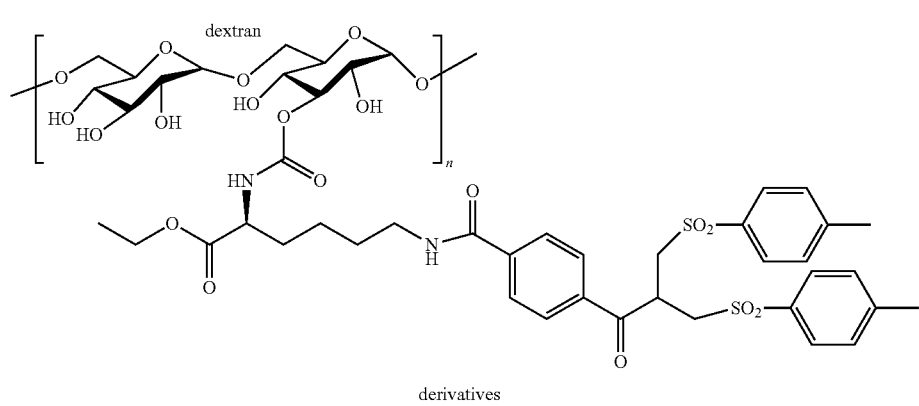
142

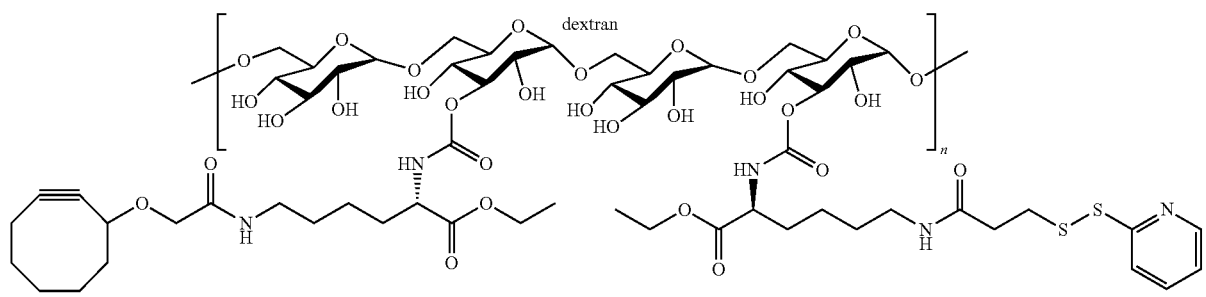

143

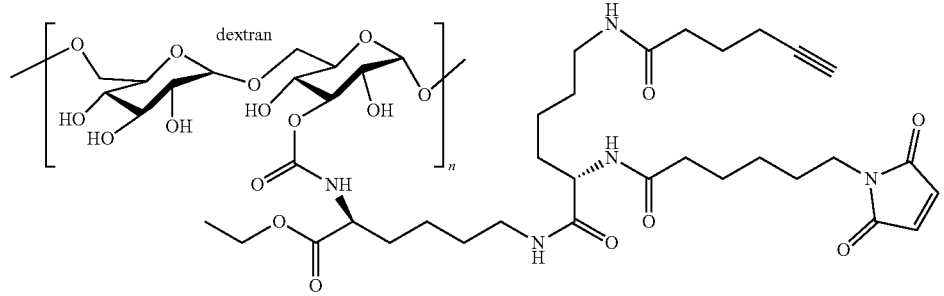

147

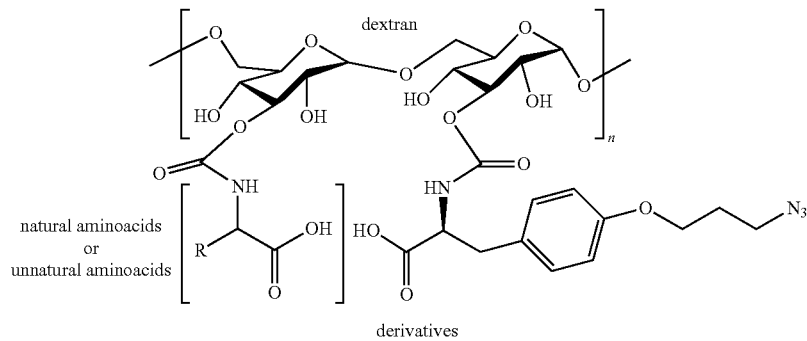

151

According to the fourth aspect of the present invention, as shown in Formula IV, the bifunctional or multifunctional polysaccharide derivatives, or the pharmaceutically acceptable salts, solvates and isomers thereof, can be used as a delivery vehicle for a drug, preferably a poorly soluble drug such as taxane. The present invention can covalently be linked to poorly soluble drugs, or physically mixed with the poorly soluble drugs and other components in a pharmaceutical composition or formulation for increasing the solubility of the drug, improving bioavailability; and on the other hand, those compounds provide the necessary intermediates for preparations of functionalized polysaccharides-lipid conjugates (Formula VII) along with taxane-lipid-polysaccharides dual conjugates (Formula I).

Accordingly, the present invention also relates to the bifunctional or multifunctional polysaccharides derivatives, the pharmaceutically acceptable salts, solvates, and isomers thereof, as shown generally by Formula IV, that work as a pharmaceutical carrier which can be either covalently linked to or physically mixed with the subject drug for improving the solubility and bioavailability of a drug. The drug is preferably a taxane compound, or wherein the other drugs which may be covalently linked are preferably, but not limited to, vinblastine, vincristine, lipitor, SN-38, capecitabine, gemcitabine, etc.; It also relates to the bifunctional or multifunctional polysaccharide derivatives, the pharmaceutically acceptable salts, solvates or isomers thereof, as shown in Formula IV, which can be used for the preparations of intermeidates for making taxane-lipid-polysaccharide conjugates (as in Formula I).

According to the fifth aspect of the present invention, the present invention provides the polysaccharide-taxane conjugates, or its derivatives or isomers, or a pharmaceutically acceptable salt or solvate thereof, shown by Formula V.

Formula V

wherein polysaccharide, taxane compound, spacer-1, -2, linker-1 are as defined in general or preferably, as above in accordance with the first aspect of the present invention; The number of spacers is optionally 0 or 1.

according to a fifth aspect of the present invention, the polysaccharide-taxane conjugate, or its derivatives or isomers, or a pharmaceutically acceptable salt or solvate thereof, shown in Formula V, is preferably selected from the structures as shown in Figure-29 below:

Figure-29
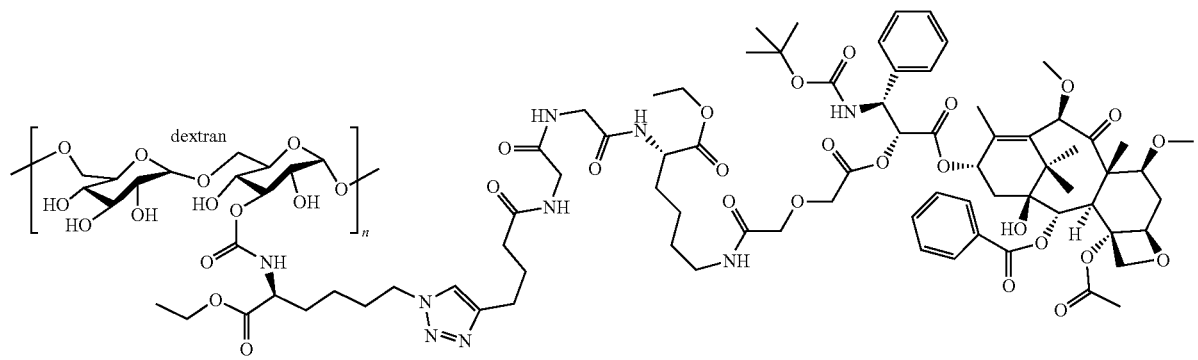
229
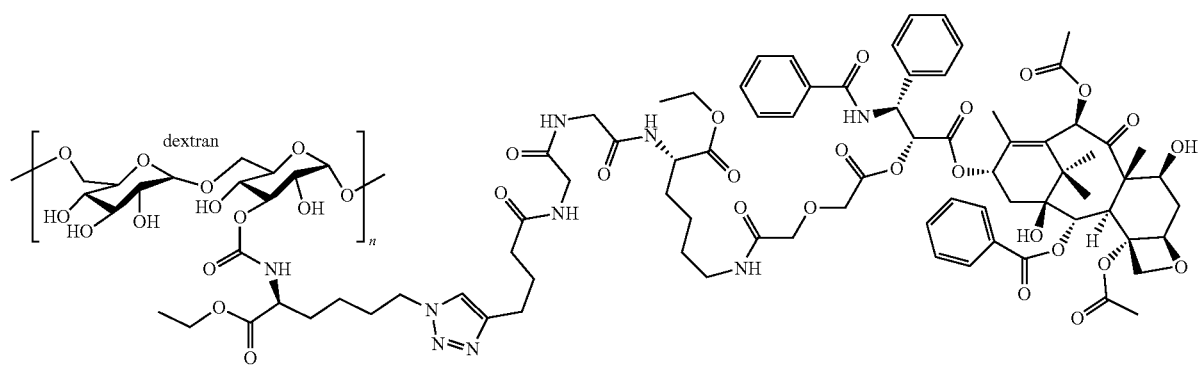
230
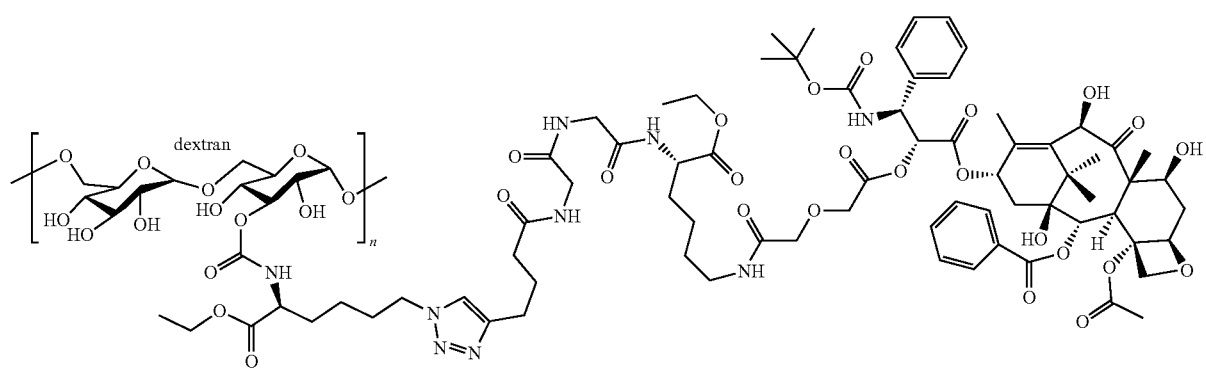
231
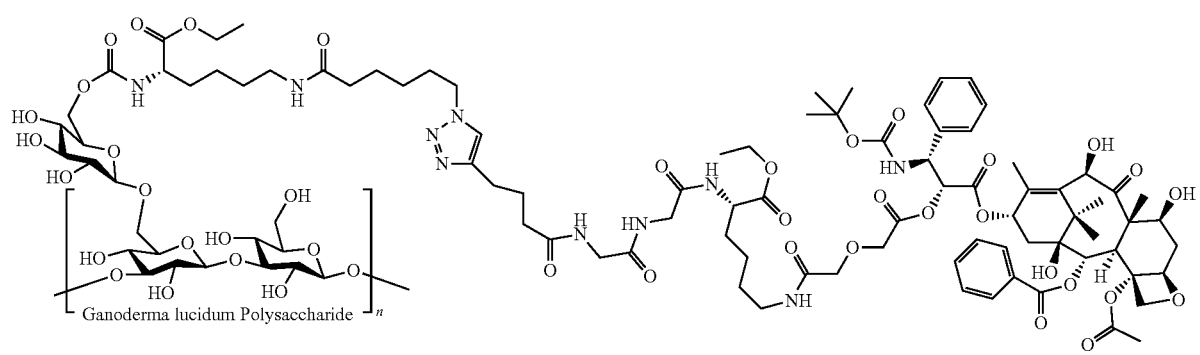
232

233
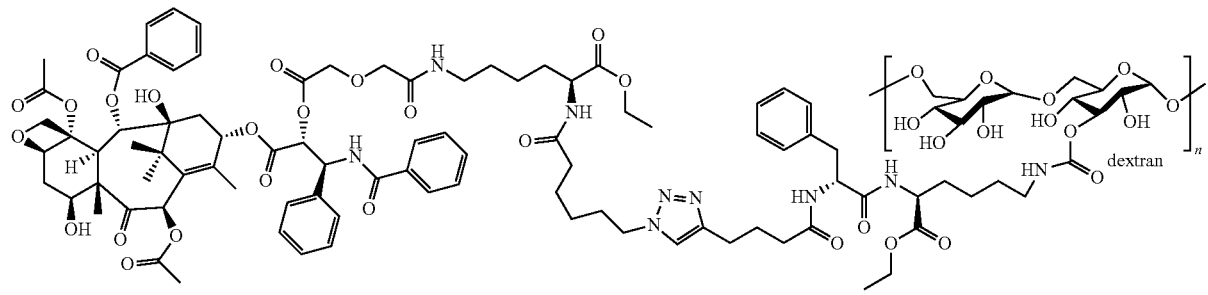
234
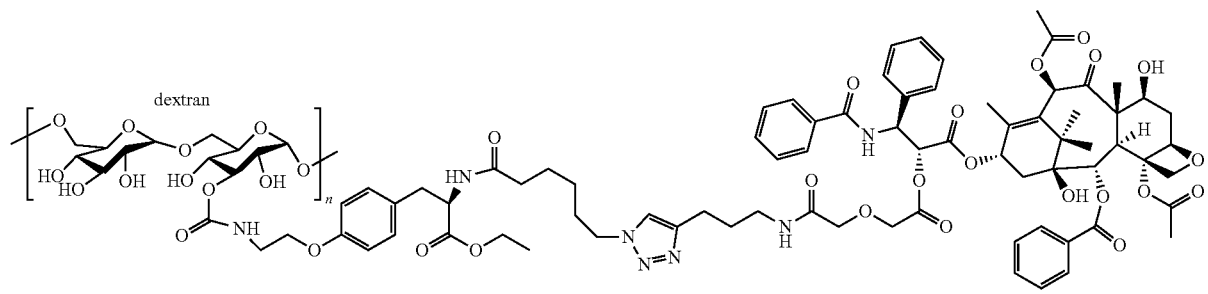
235
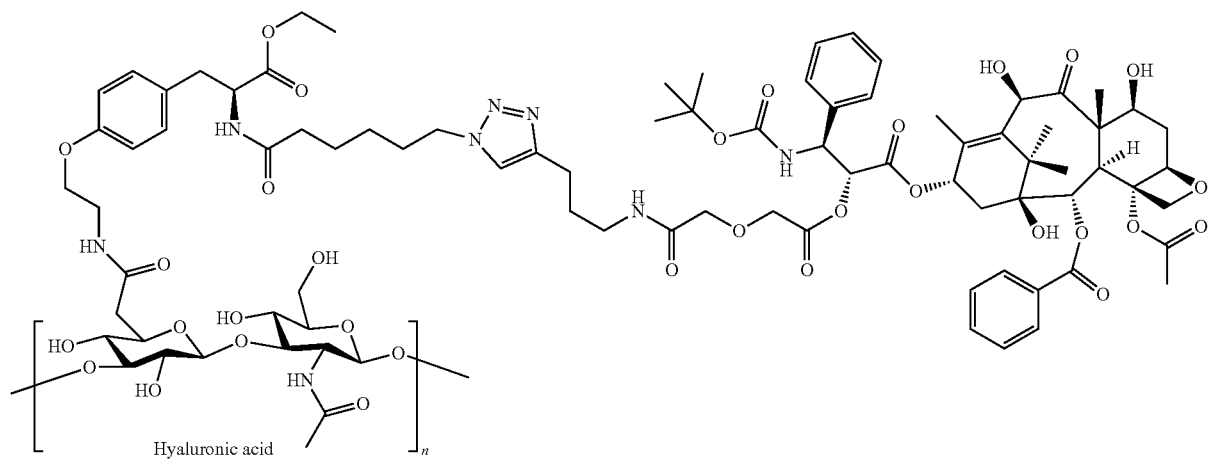
236
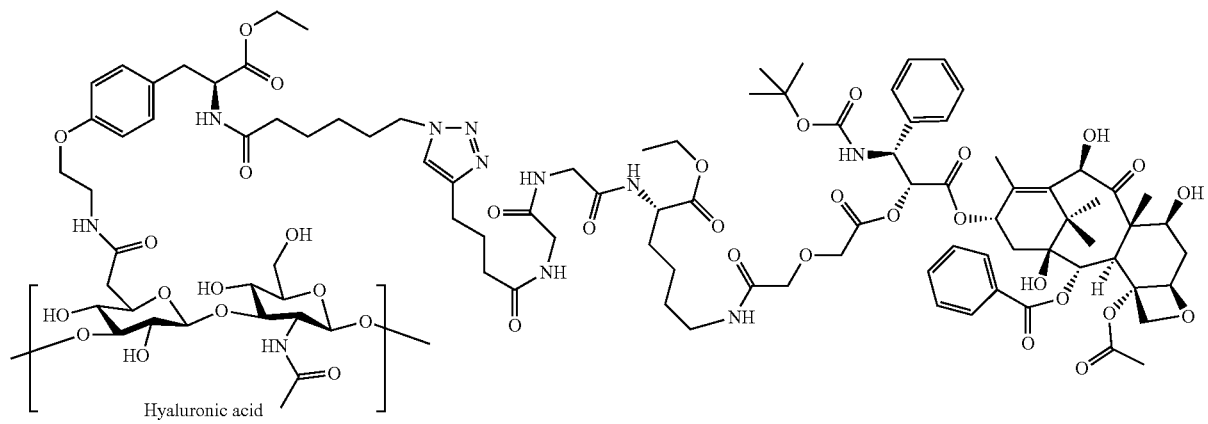

237
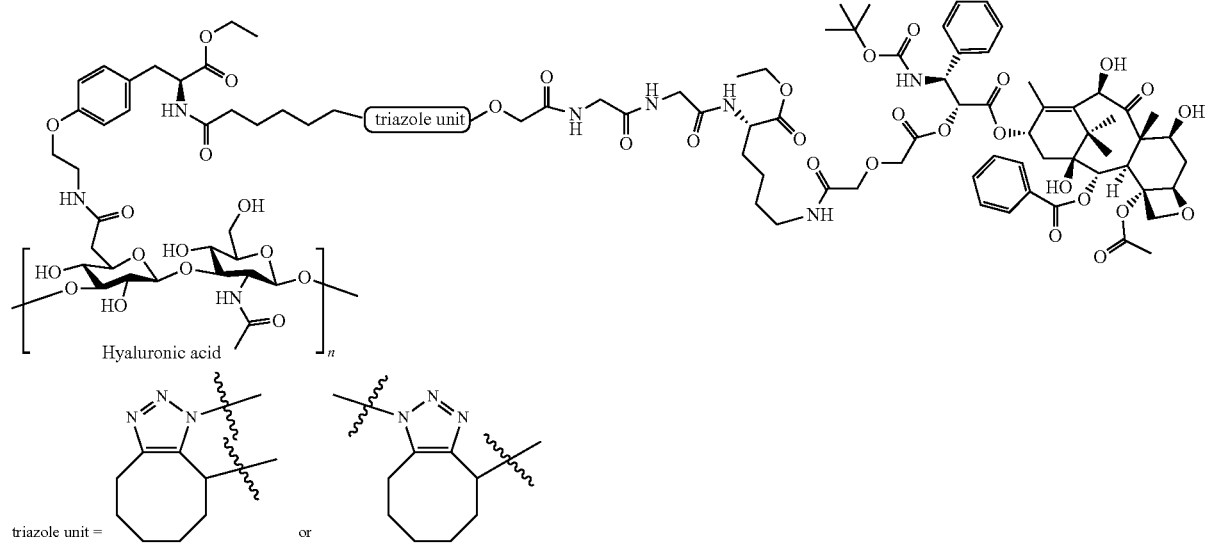
238
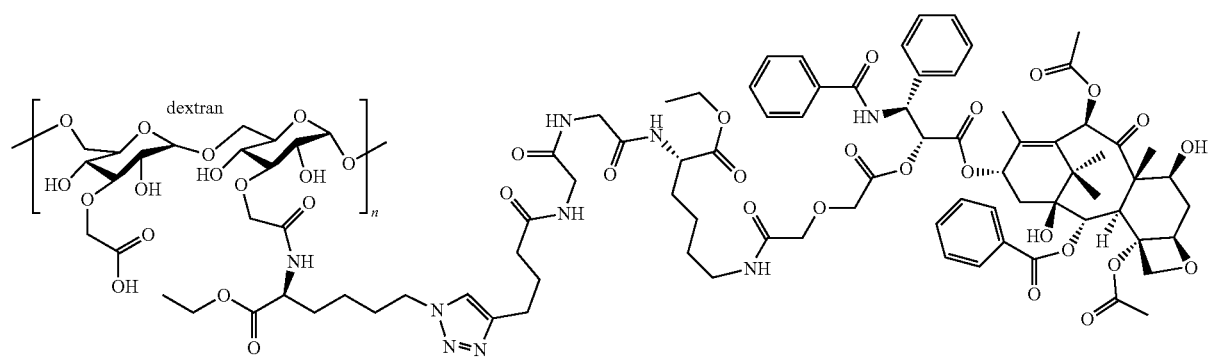
239
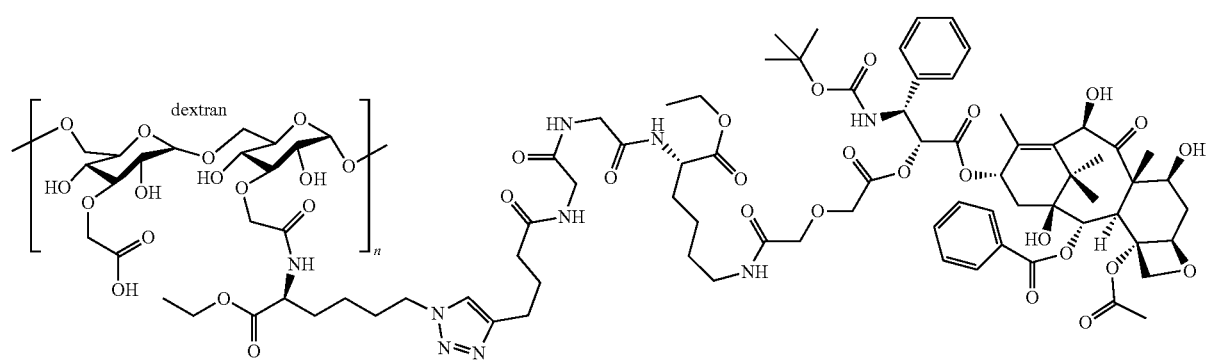
240
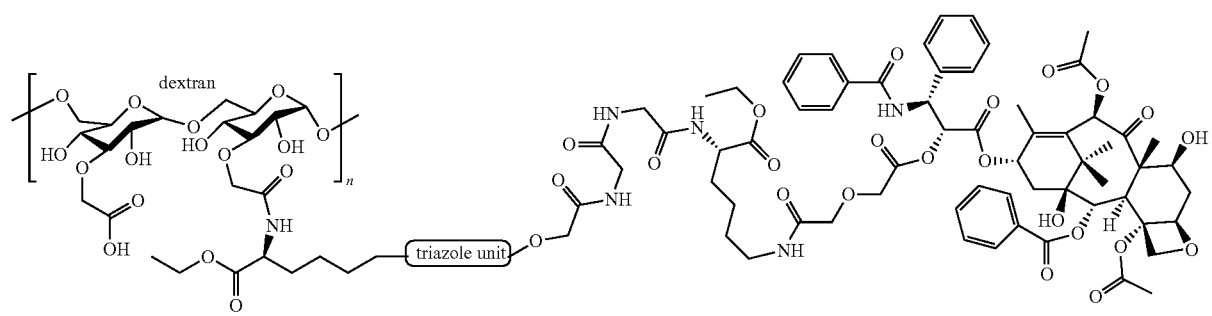

-continued
triazole unit = 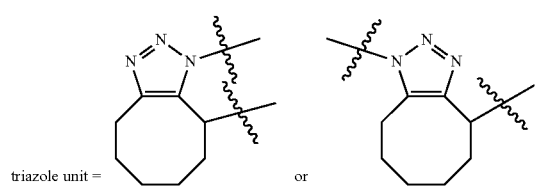 or
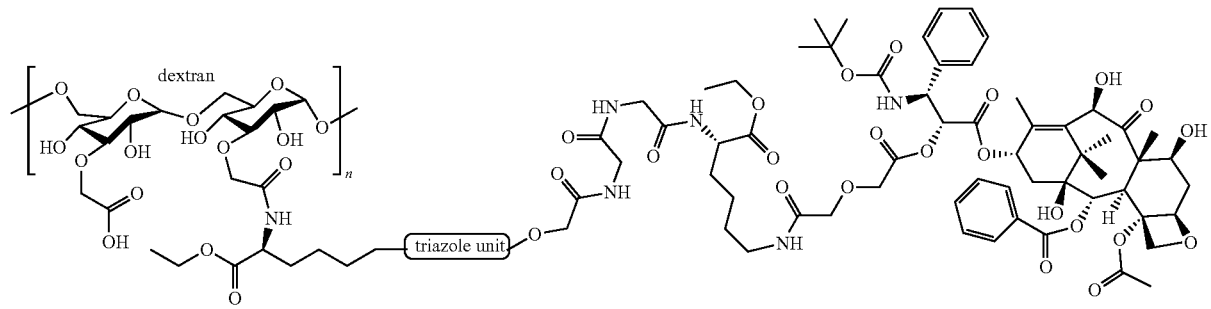
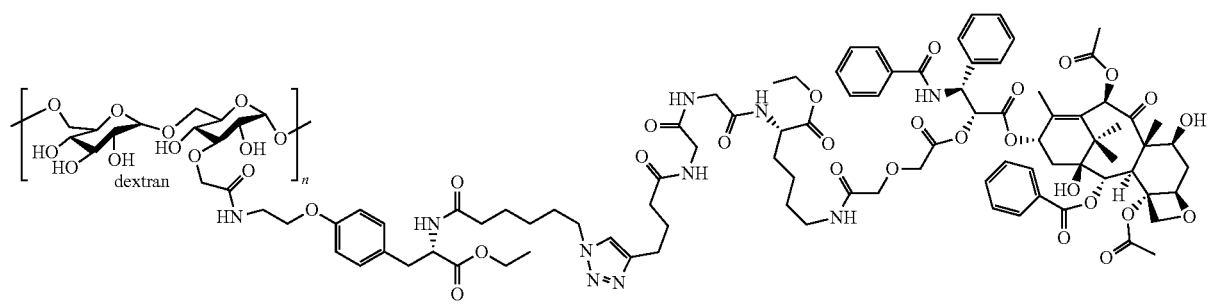
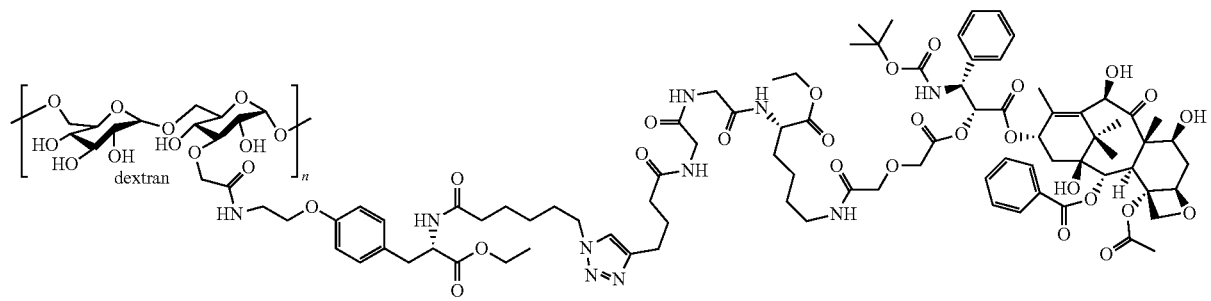
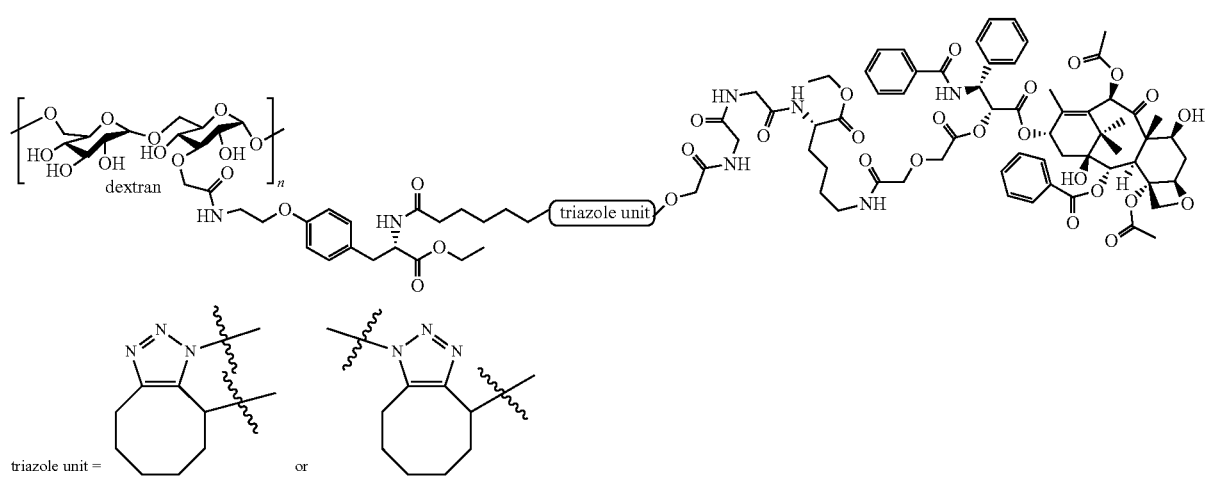
triazole unit = or

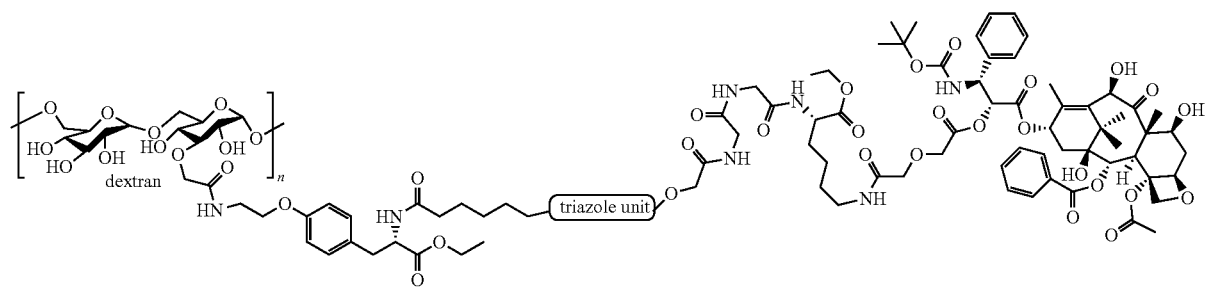
245
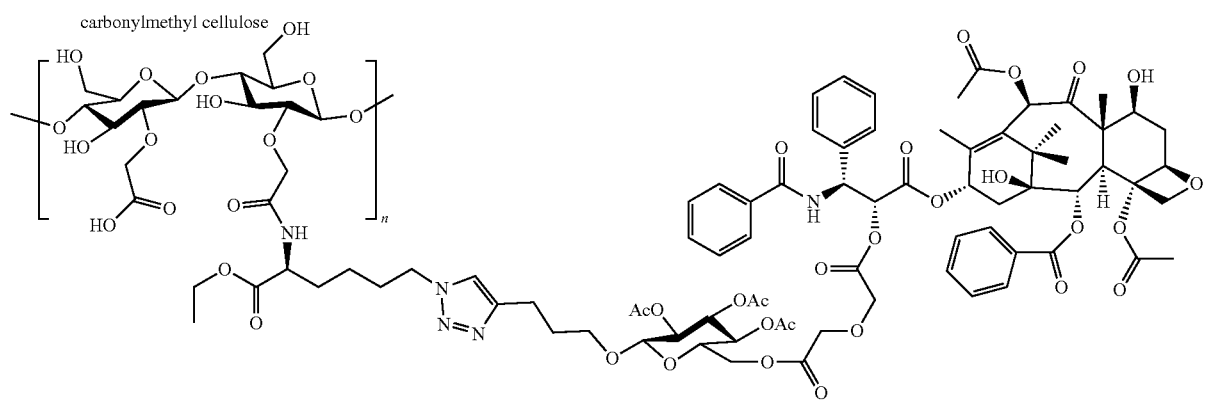
246
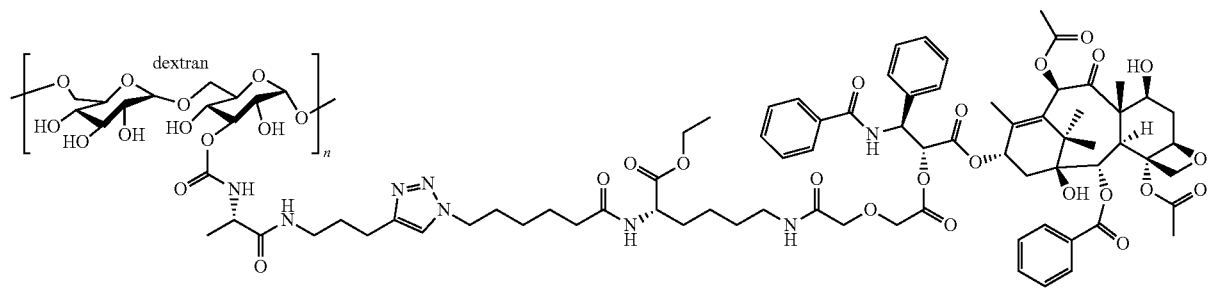
247
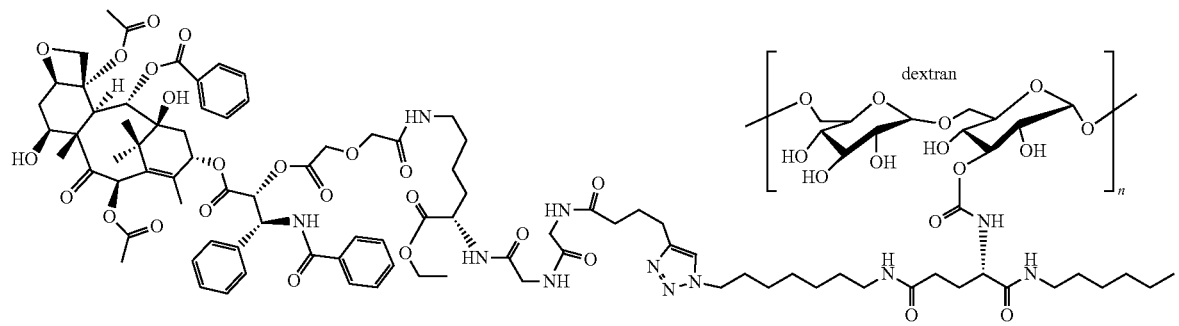
248

-continued
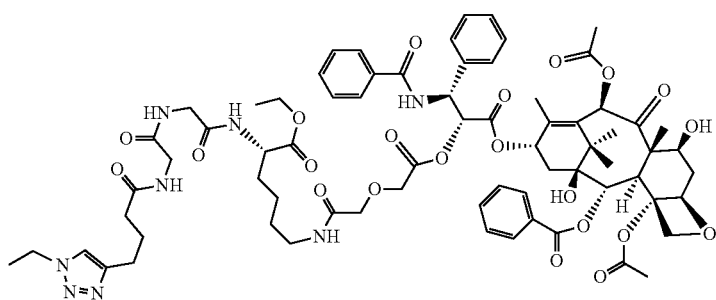
249
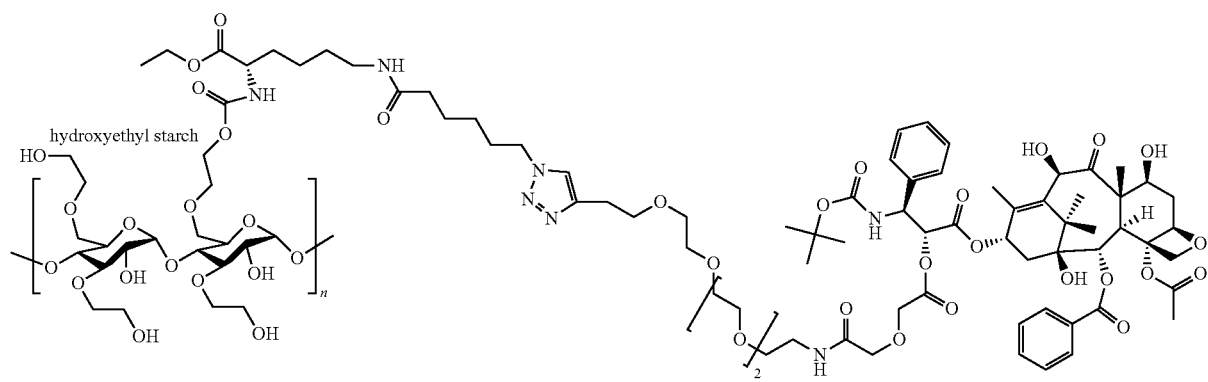
250
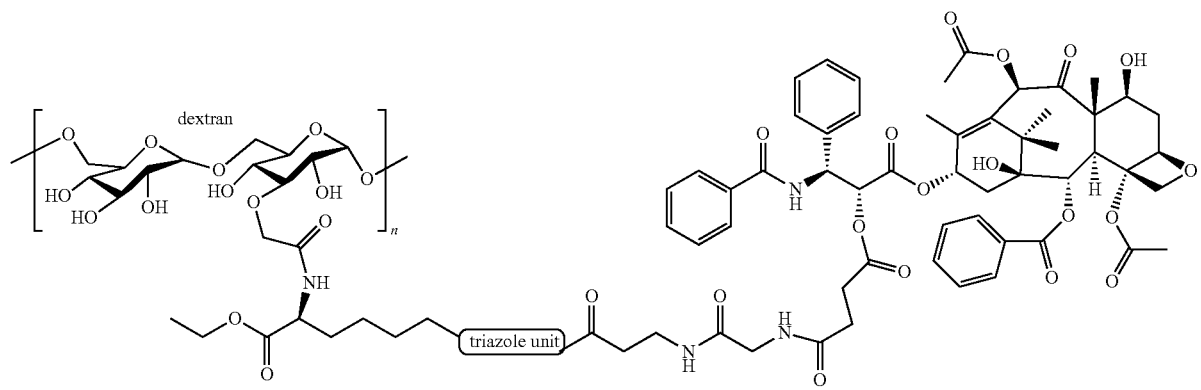
triazole unit
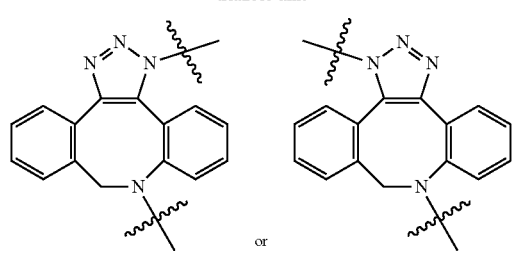
or

251

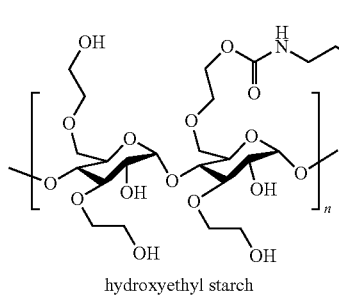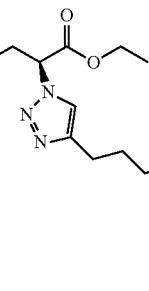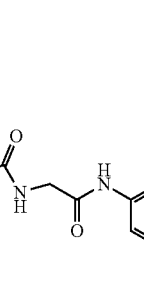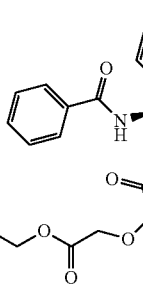

hydroxyethyl starch

According to the fifth aspect of the present invention, shown in Formula V, the polysaccharides-taxane conjugates or a pharmaceutically acceptable salt or solvate thereof, improve the solubility of the taxane drug, thereby improving the bioavailability of the taxanes while maintaining good biological activity of taxanes, and providing an improved treatment effects for taxane-susceptible diseases.

Accordingly, the present invention relates to a polysaccharide-taxane conjugate, or a pharmaceutically acceptable salt or solvate thereof, shown by Formula V, for the treatment of taxanes-susceptible diseases; These conjugates improve drug solubility, bioavailability, and in vivo release property therefore provides the enhanced anti-tumor effects in vivo.

According to the sixth aspect of the present invention, the present invention provides the polysaccharides-lipid conjugates, or its derivatives or isomers, or a pharmaceutically acceptable salt or solvate thereof, shown by Formula VI.

Formula VI

| Polysaccharide | Spacer-1 $_{(0\ or\ 1)}$ | Linker-1 | Spacer-2 $_{(0\ or\ 1)}$ | Lipid unit | wherein polysaccharide, spacer-1, -2, linker-1 and a lipid unit are as generally defined above or preferably according to the first aspect of the invention; The number of spacers is optionally 0 or 1.

according to the sixth aspect of the present invention, the polysaccharide-lipid conjugates, or its derivatives or isomers, or a pharmaceutically acceptable salt or solvate thereof, shown by Formula VI, are preferably from the following structures in Figure-30:

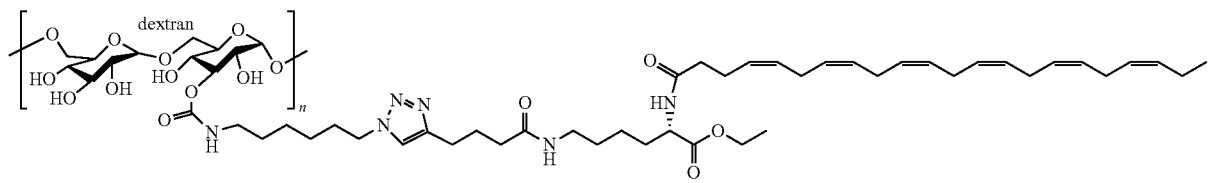

161

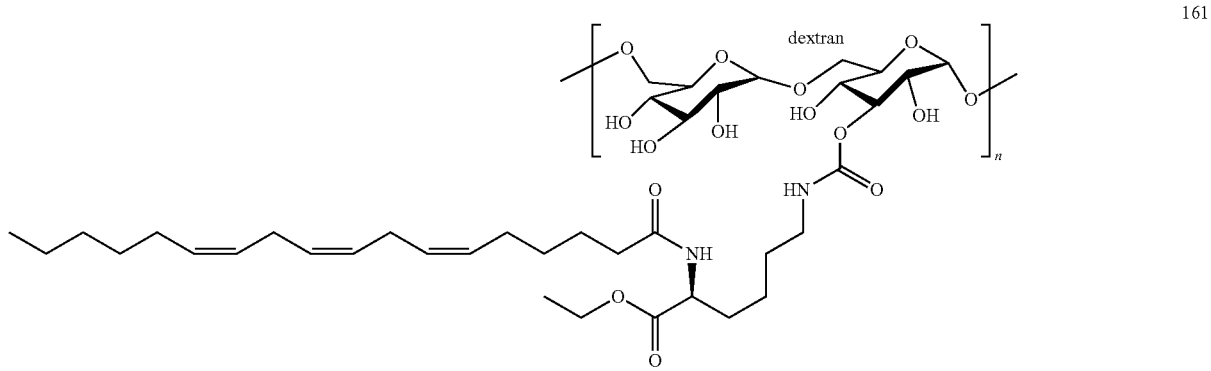

-continued
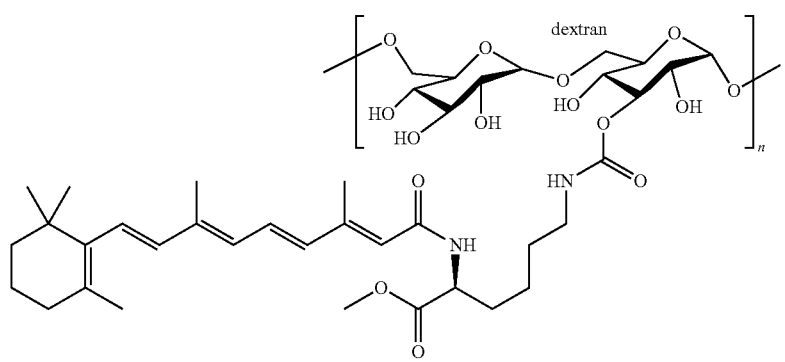
165
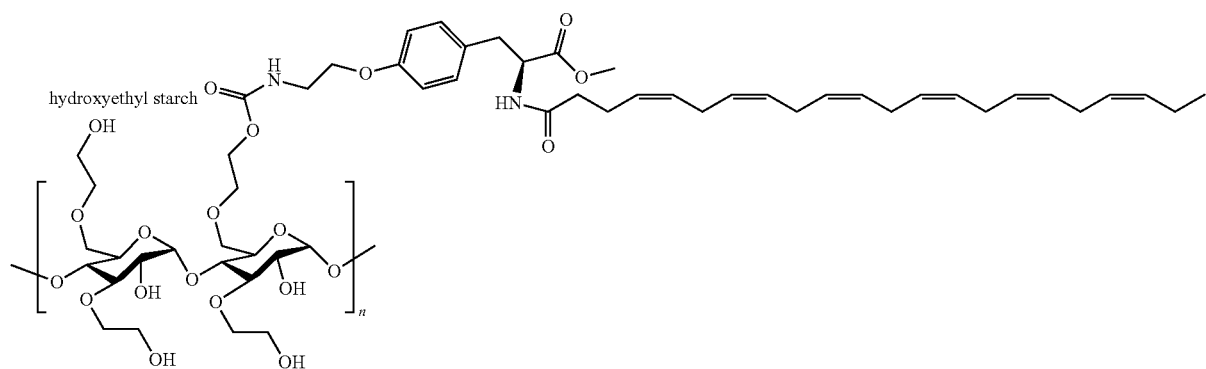
171
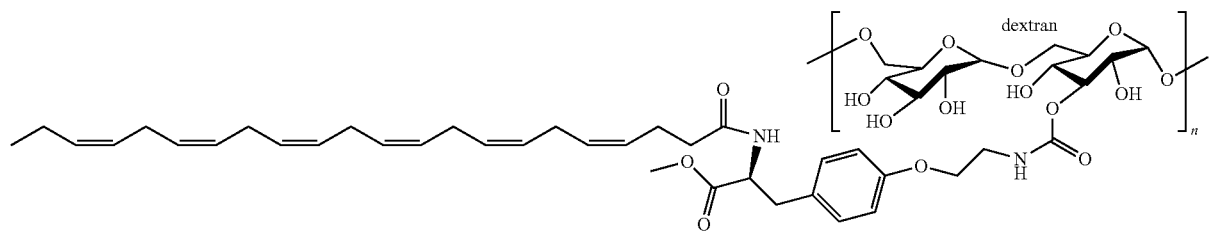
170
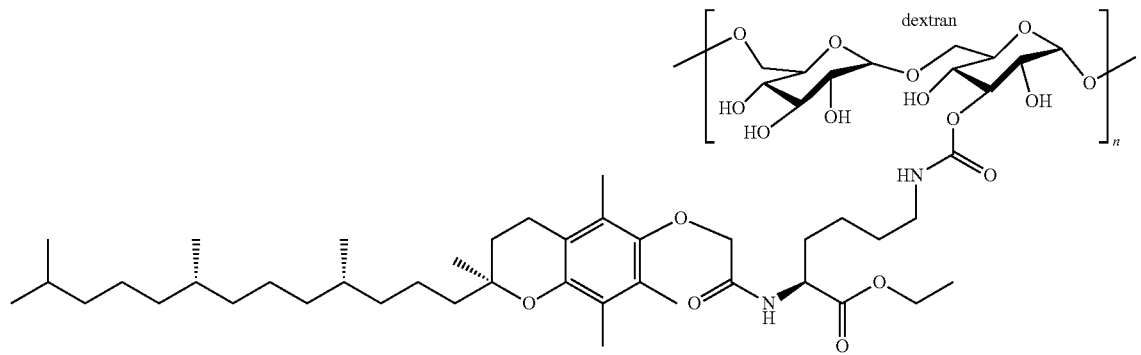
179

181
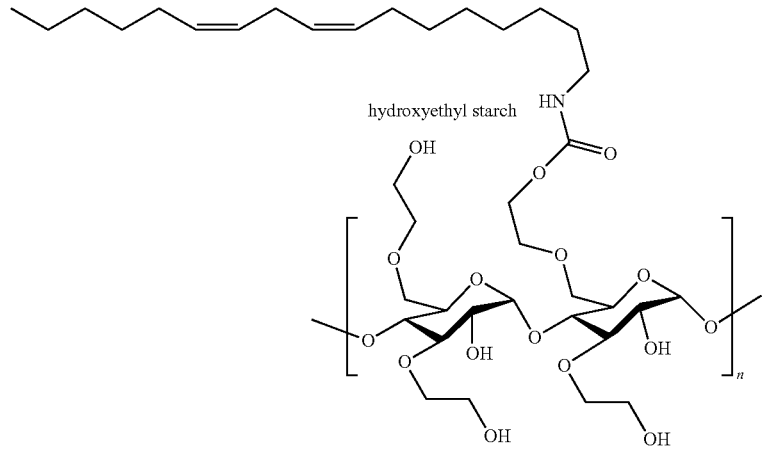
183
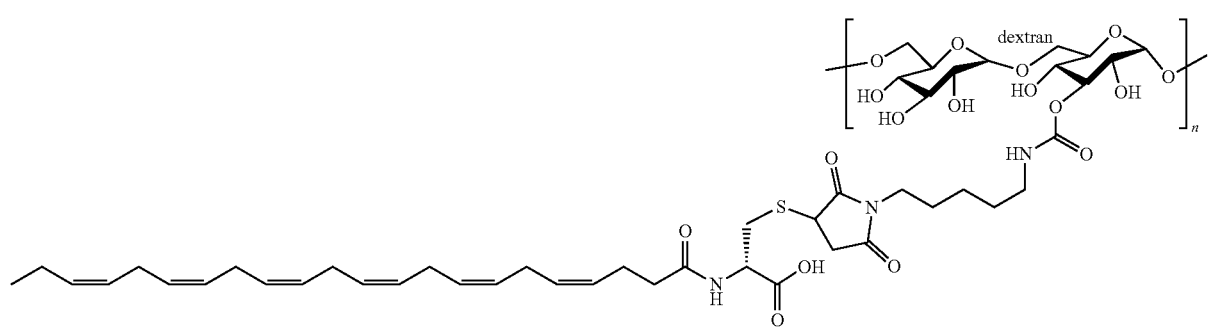
186
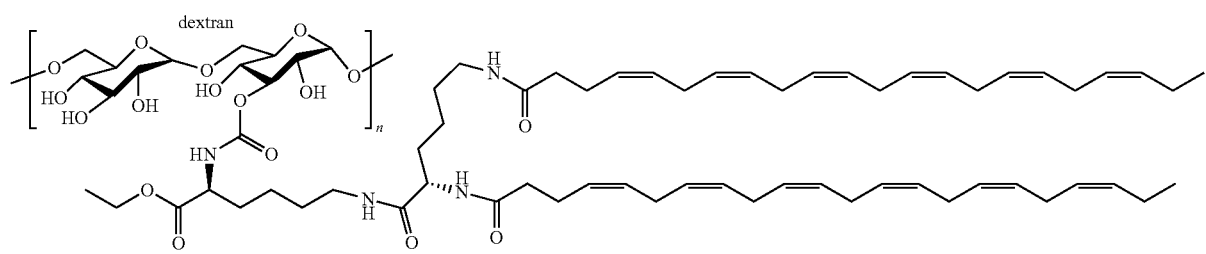
191
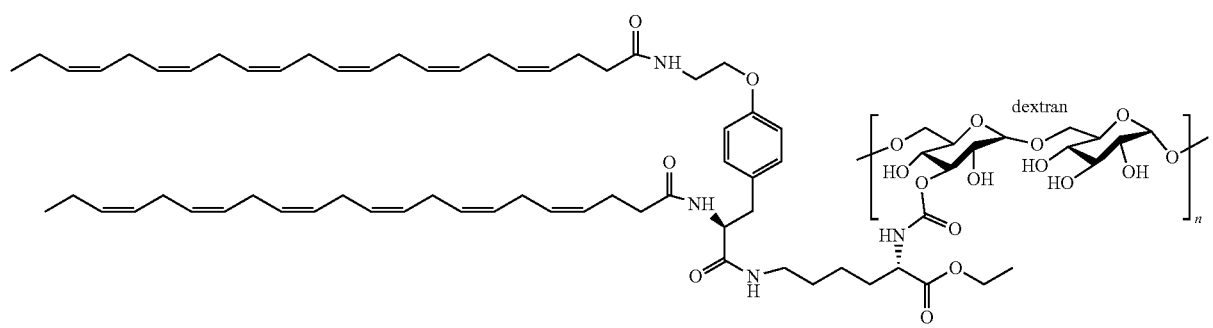

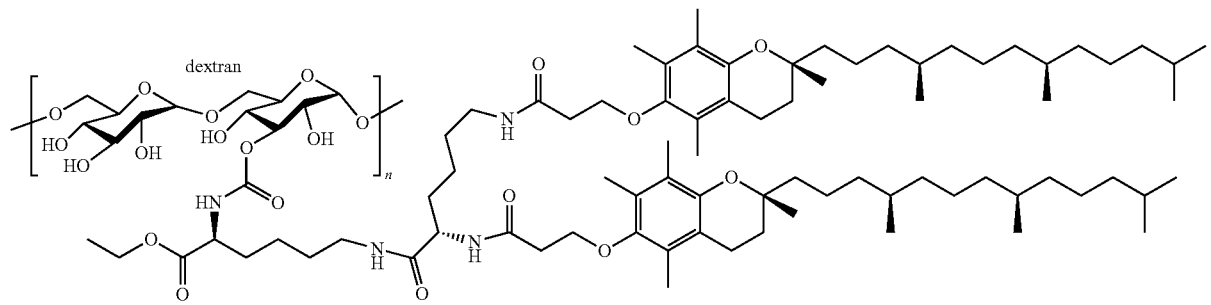

196

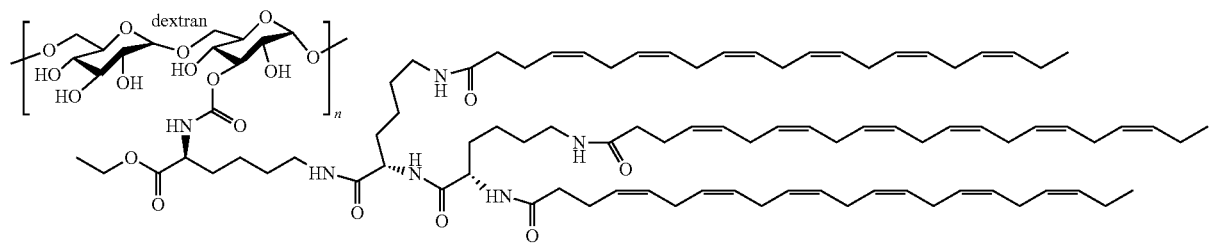

198

According to the sixth aspect of the present invention, as shown in Formula VI, the polysaccharides-lipid conjugates or the pharmaceutically acceptable salts, solvates or isomers thereof, can be used as a delivery vehicle for a drug, preferably a poorly soluble drug such as a taxane compound. Those compounds can be mixed with poorly soluble drugs and other components in a pharmaceutical composition or formulation for increasing the solubility of the drug, improving bioavailability; and on the other hand, those compounds provide the necessary intermediates for the preparation of functionalized polysaccharides-lipid conjugates (Formula VII), and taxane-lipid-polysaccharides dual conjugates (Formula I).

Accordingly, the present invention also relates to the polysaccharides-lipid conjugates, or the pharmaceutically acceptable salts or solvents thereof, shown by Formula VI, for improving the solubility of a poorly soluble drug, preferably a taxane compound, and also improving their bioavailability and drug release, and enhancing the tumor targeting. It also relates to the polysaccharides-lipid conjugates, the pharmaceutically acceptable salts, solvates or isomers thereof, as shown in Formula VI, which can be used for the drug delivery carriers for poorly soluble drugs, preferably the taxane compounds;

According to the seventh aspect of the invention, the present invention provides a functionalized polysaccharides-lipid conjugate, or its derivatives or isomers, or a pharmaceutically acceptable salt or solvate thereof, as shown by the Formula VII:

Formula VII

[Functional group]—[Linker unit]—[Polysaccharide]—[Linker unit]—[Lipid unit]

wherein the linker unit, the polysaccharide and the lipid unit are as defined in general or preferably as above in accordance with the first aspect of the present invention; wherein the functional group is as described above in general or preferred for the functional group according to the second aspect of the invention.

according to the seventh aspect of the invention, the functionalized polysaccharide-lipid conjugates, the derivatives and isomers thereof, or a pharmaceutically acceptable salt or solvate thereof, shown in Formula VII, preferably from the structures shown below in Figure-31:

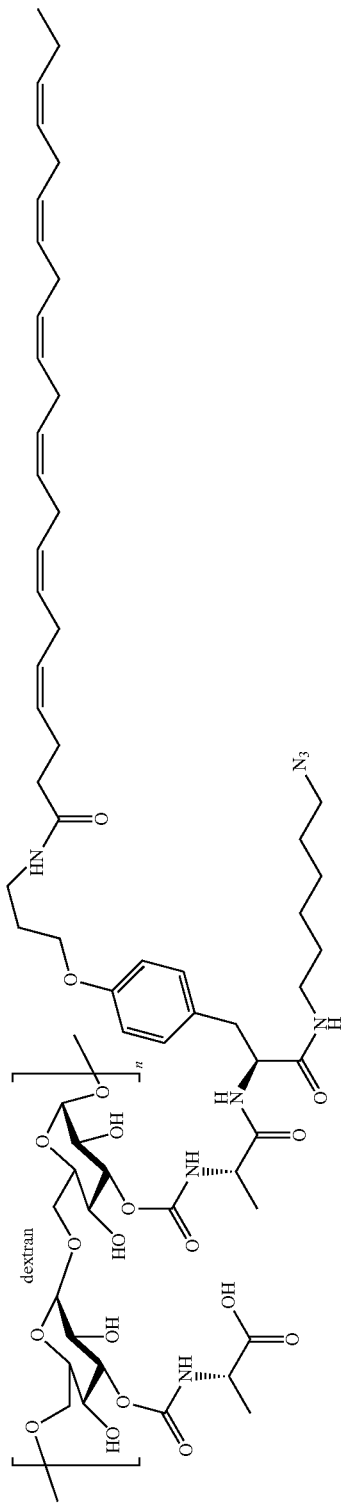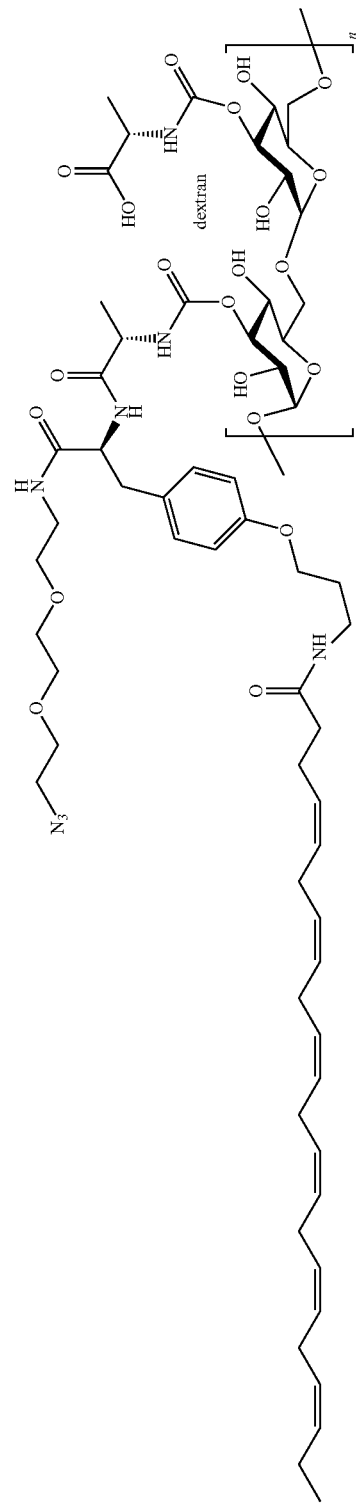
Figure-31

-continued
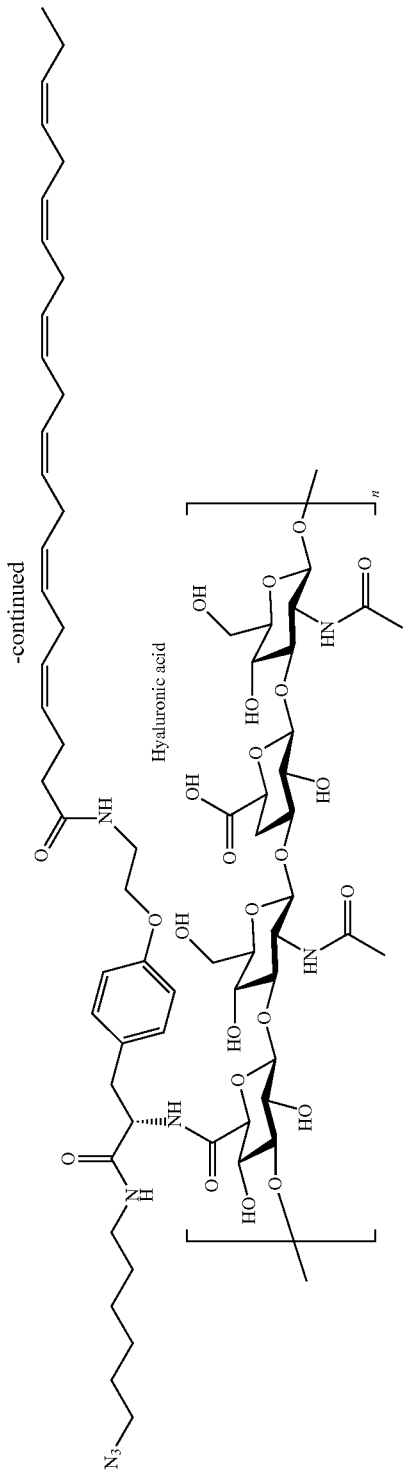
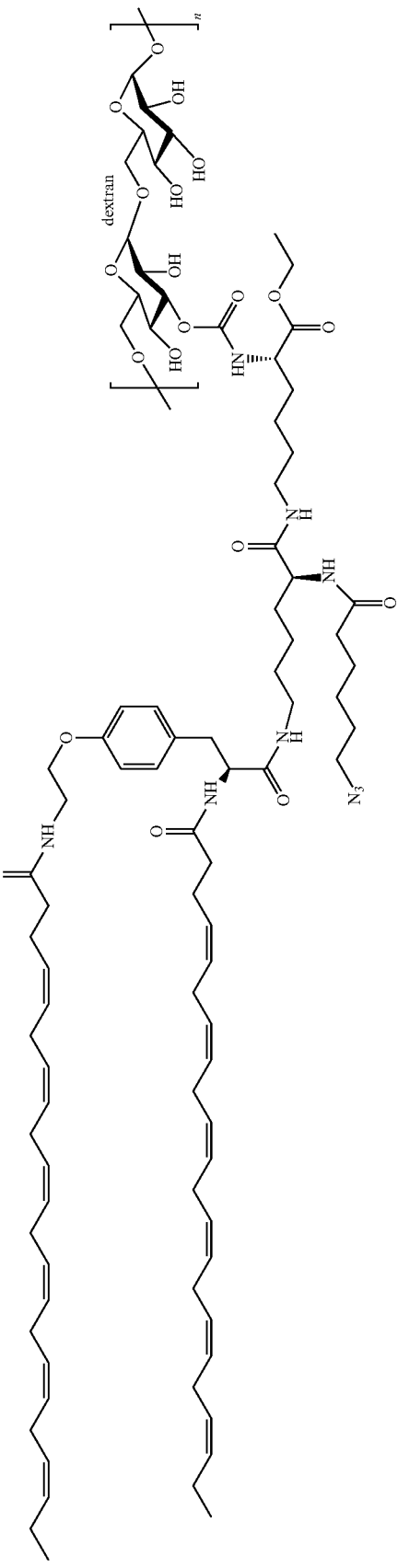

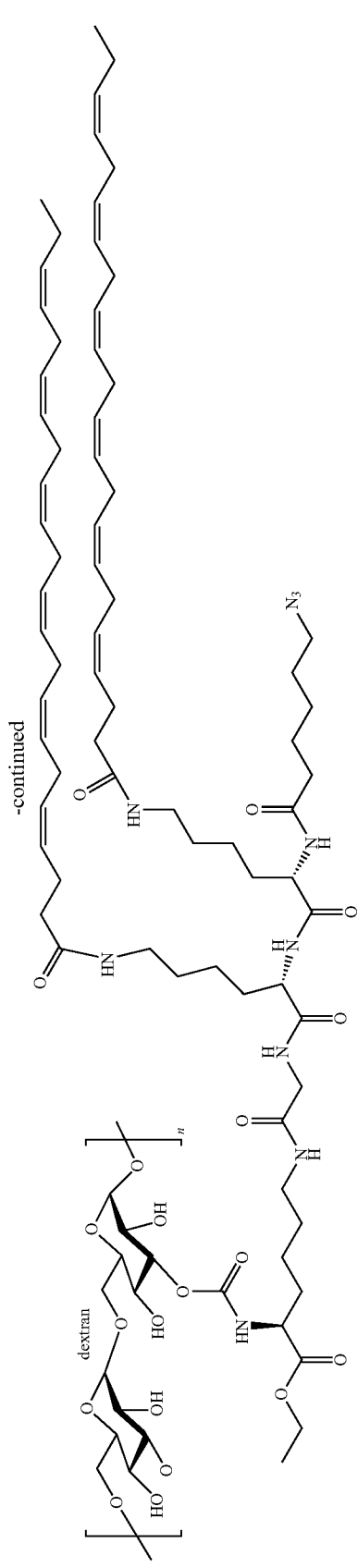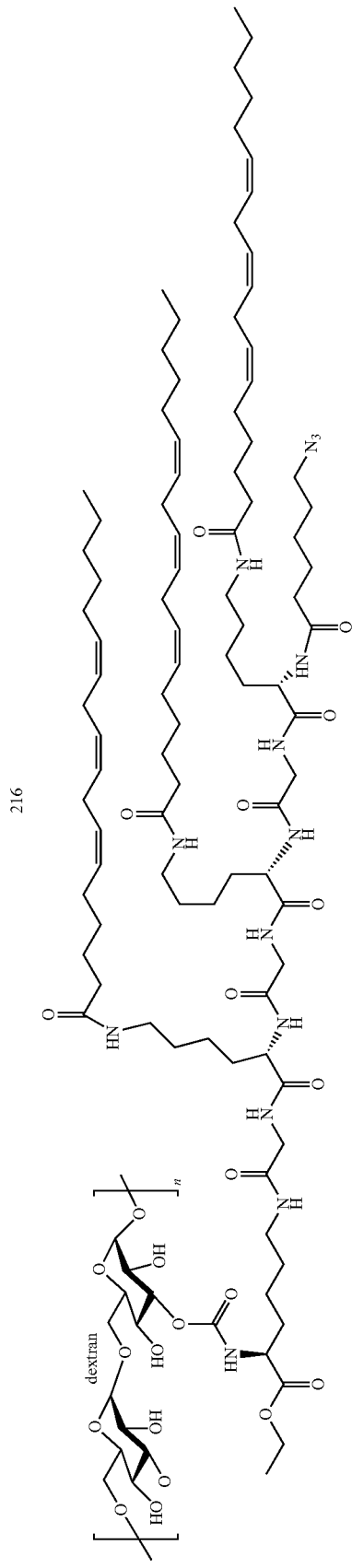

137
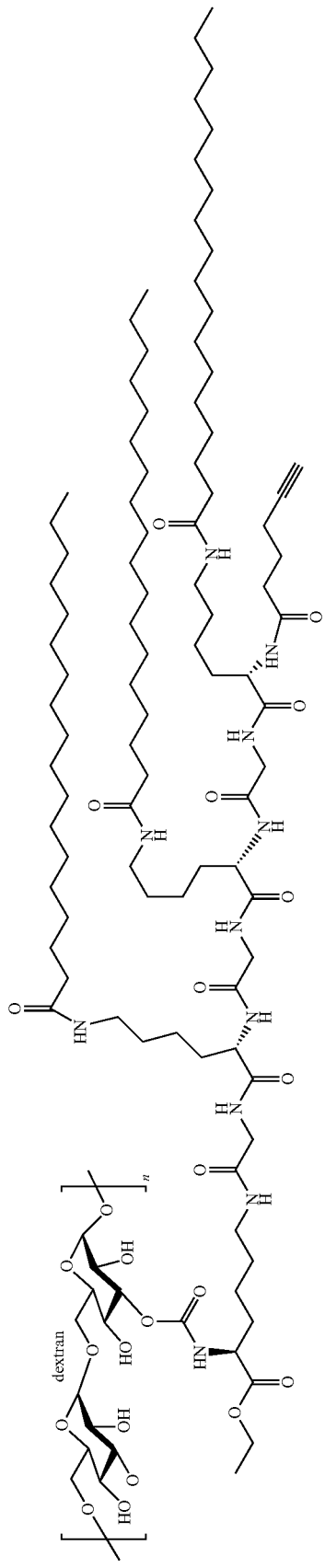
138
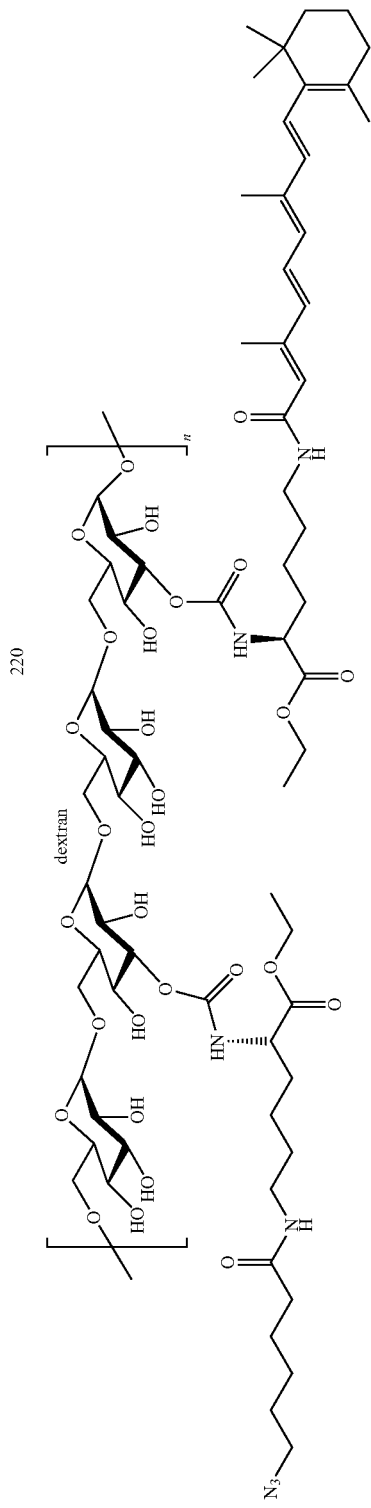

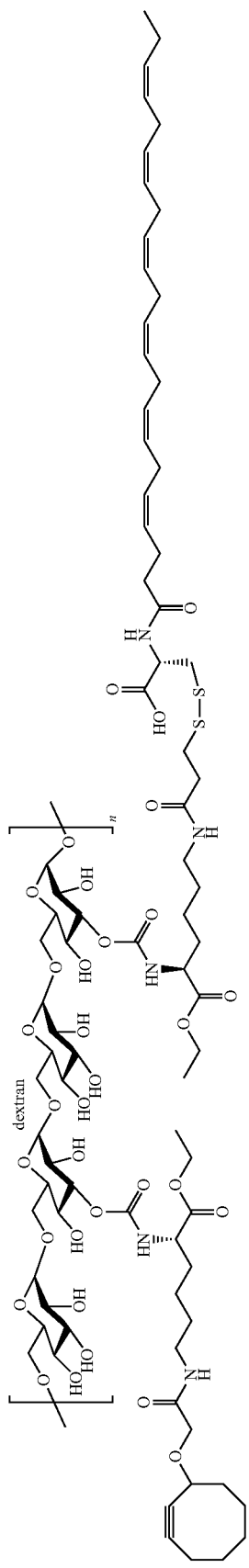
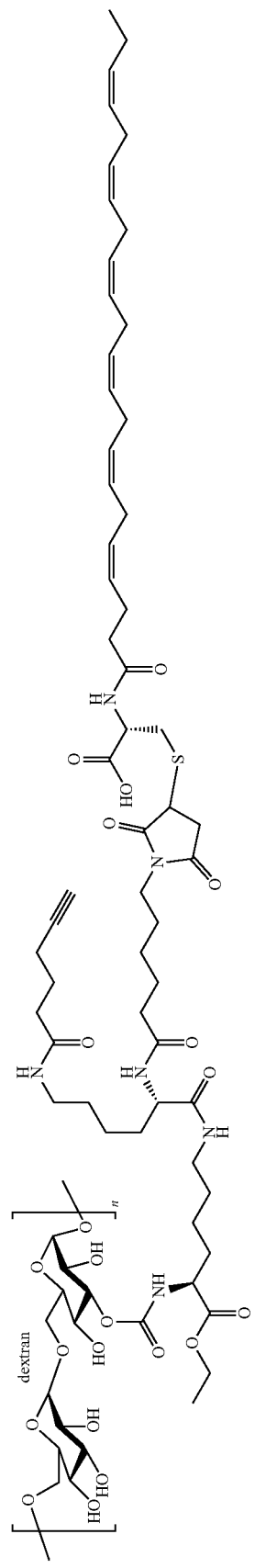
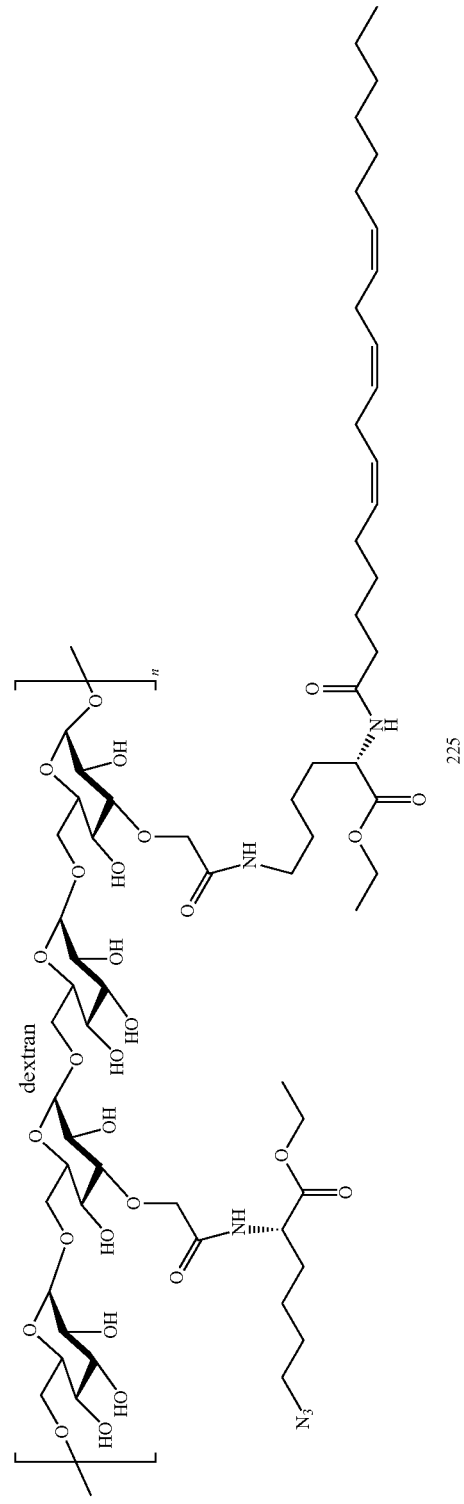

141
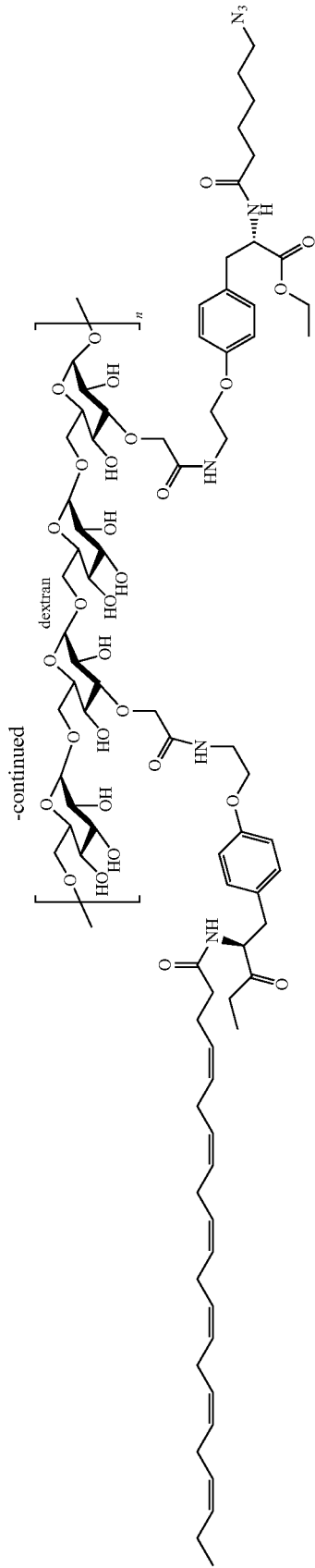
226
142
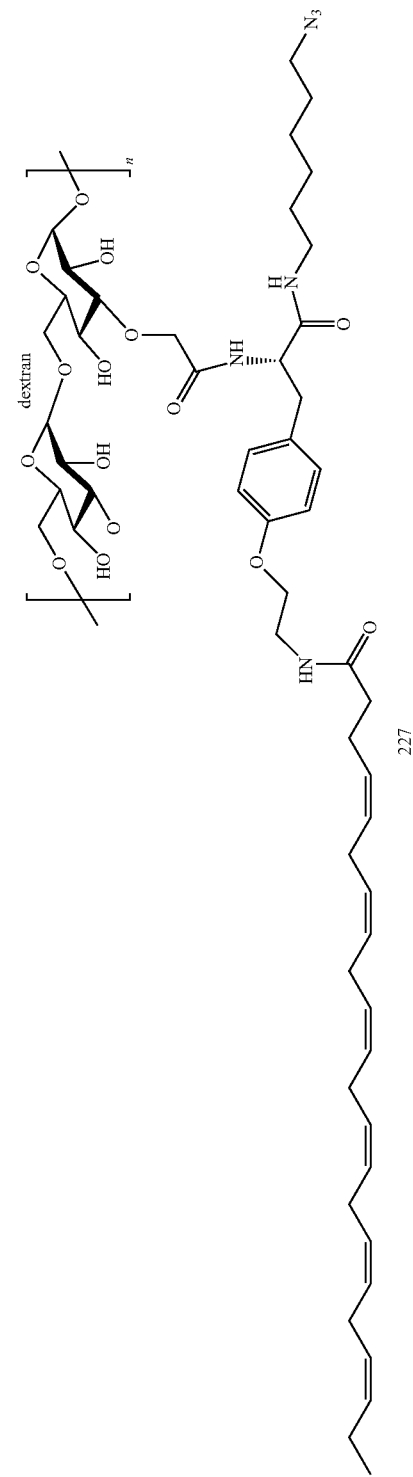
227
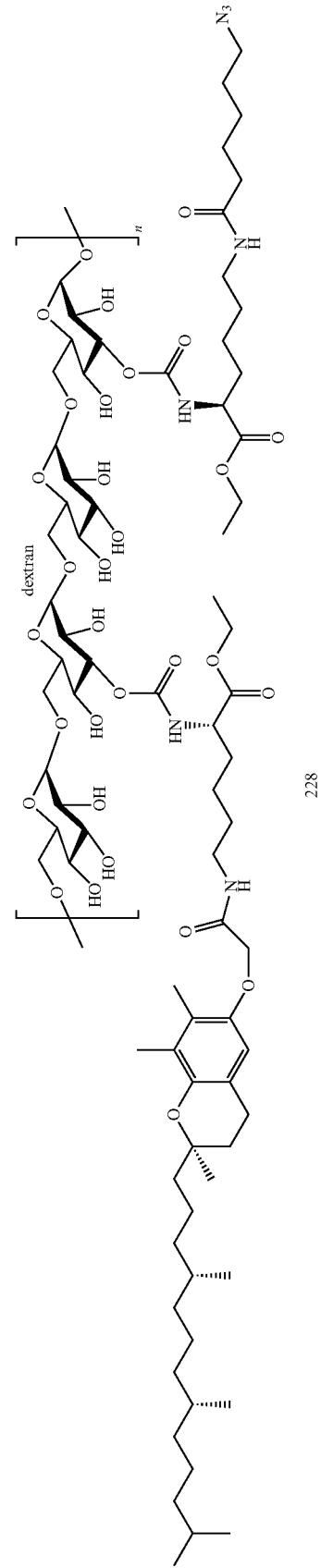
228

According to the seventh aspect of the present invention, as shown in Formula VII, the polysaccharides-lipid conjugates or the pharmaceutically acceptable salts, solvates or isomers thereof, can be used as a delivery vehicle for a drug, preferably a poorly soluble drug such as a taxane compound. Those compounds can covalently be linked to poorly soluble drug, or physically mixed with the poorly soluble drugs and other components in a pharmaceutical composition or pharmaceutical formulation for improving the solubility of a poorly soluble drug, preferably a taxane compound, and also improving their bioavailability and drug release, and enhancing the tumor targeting. On the other hand, those compounds provide the necessary intermediates for the preparations of taxane-lipid-polysaccharides dual conjugates (Formula I).

Accordingly, the present invention also relates to the functionalized polysaccharides-lipid conjugates, the pharmaceutically acceptable salts, solvates or isomers thereof, as shown generally by Formula VII, as a pharmaceutical carrier which can be either covalently linked to or physically mixed with the subject drug for improving the solubility and bioavailability of a poorly-soluble drug. The drug is preferably a taxane compound, or wherein the other drugs which may be covalently linked with, but not limited to, vinblastine, vincristine, Lipitor, SN-38, capecitabine, gemcitabine, etc.; It also relates to the functionalized polysaccharides-lipid conjugates, the pharmaceutically acceptable salts, solvates or isomers thereof, as shown in Formula VII, which can be used for the preparations of intermediates for making the taxane-lipid-polysaccharide dual conjugates (as in Formula I).

According to the eighth aspect of the present invention, the present invention provides a functionalized taxane-lipid conjugate or its derivatives or isomers, or a pharmaceutically acceptable salt or solvate thereof, as shown by Formula VIII:

Formula VIII

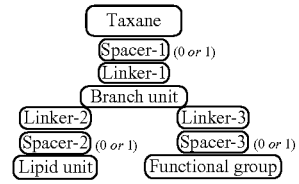

wherein the taxane compound, spacer-1, -2, -3, linker-1, -2, -3, branched unit, or lipid unit are as defined in general or preferably as above in accordance with the first aspect of the present invention; The functional groups are as defined in general or preferably as above for the functional groups according to the second aspect of the present invention.

According to the eighth aspect of the present invention, the functionalized taxane-lipid conjugates, and its derivatives and isomers thereof, and their pharmaceutically acceptable salt or solvate thereof, are preferably from the structures shown below in Figure-32:

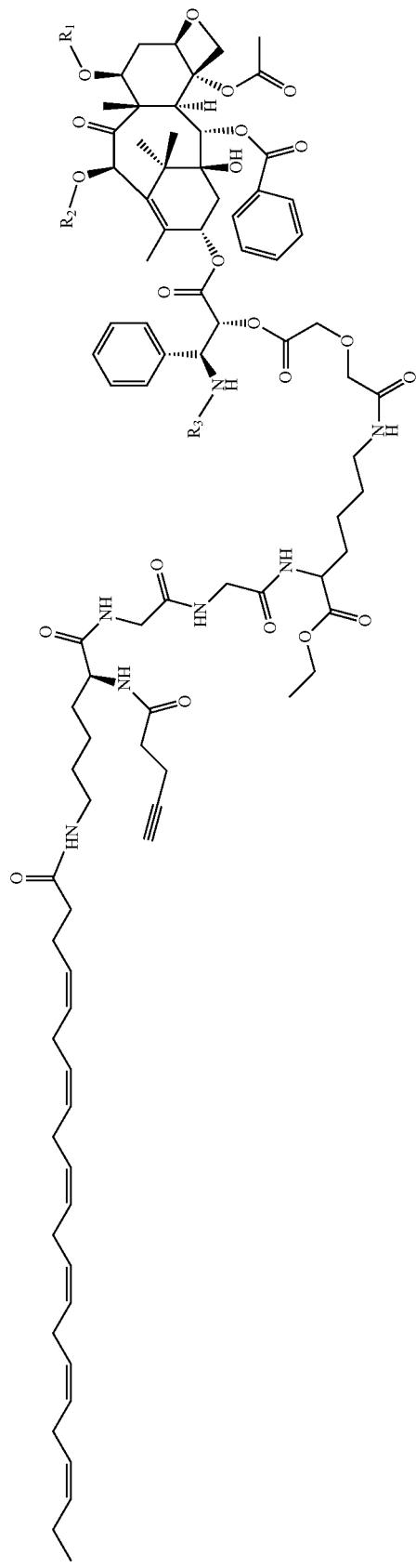
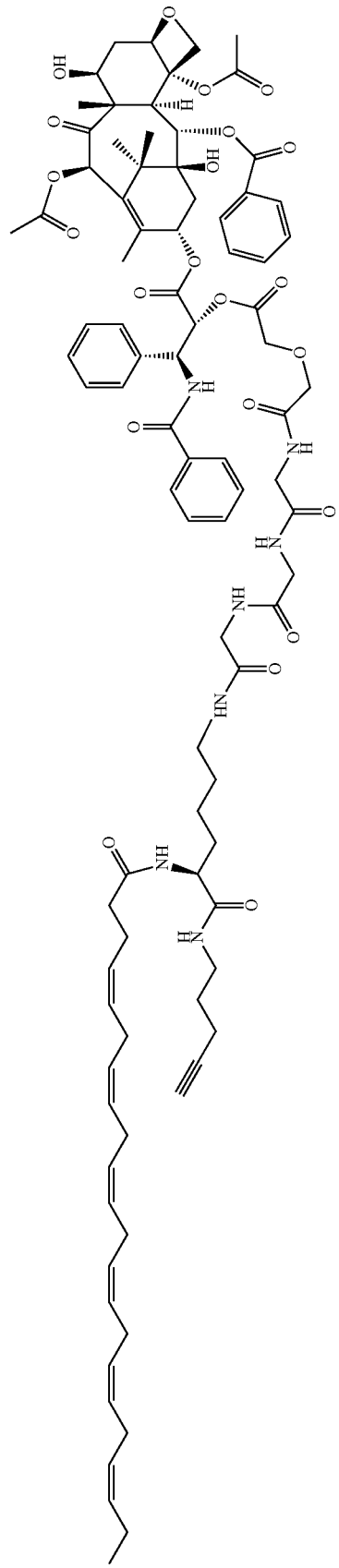
266 R₁ = H, R₂ = H, R₃ = Boc
267 R₁ = H, R₂ = Acetyl, R₃ = Bz
266 and 267 derivatives
275 and its derivatives
Figure-32

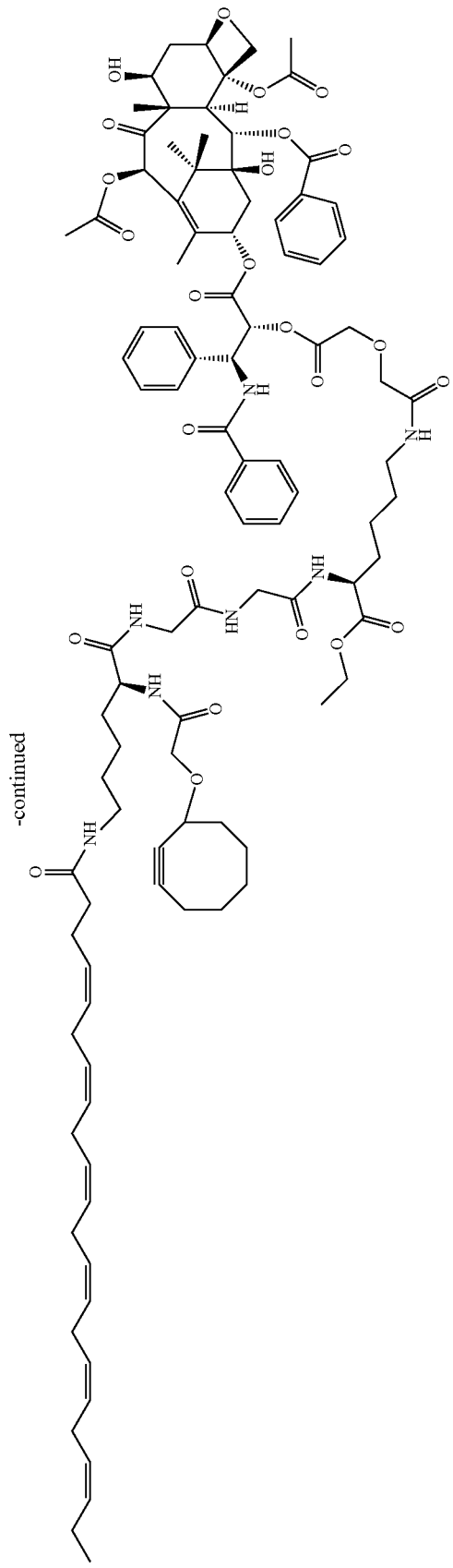
285 and its derivates

According to the eighth aspect of the present invention, as shown in Formula VIII, the functionalized taxane lipid conjugates or the pharmaceutically acceptable salts, solvates thereof, can improve the tumor targeting of taxane drugs, maintain or further synergically fortify the biological activities of taxane drugs. This provides an improved treatment for taxane susceptible diseases. On the other hand, those compounds provide the necessary intermediates for the preparations of taxane-lipid-polysaccharides dual conjugates (Formula I).

Accordingly, the present invention also relates to a functionalized taxane-lipid conjugate, or a pharmaceutical acceptable salt or solvate thereof; As shown by Formula VIII, these compounds are designed for improving the solubility, bioavailability, drug release properties, and tumor targeting of taxanes. The present invention also relates to a functionalized taxane-lipid conjugates, or a pharmaceutically acceptable salt or solvate thereof, as shown by Formula VIII, which are the intermediates for the preparation of a taxane-lipid-polysaccharide dual conjugate, as depicted by Formula I.

According to the ninth aspect of the present invention, the invention provides a process for the preparations of compounds as depicted by the Formula I, II, III, IV, V, VI, VII or VIII, which are defined above. The preparation process of the general formulas II, III and V is shown in the following Figure-33

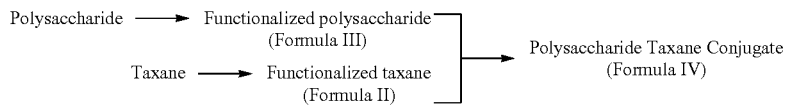

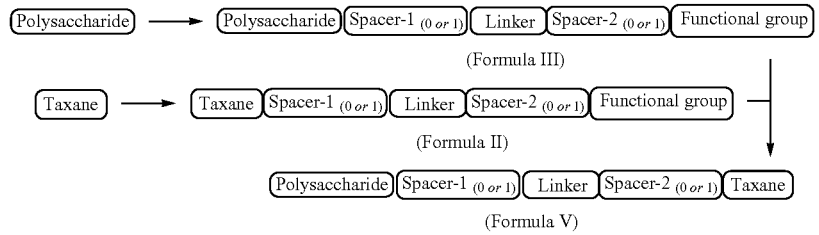

Figure-34 shows the preparation process for compounds as depicted by Formula VI

Described in details

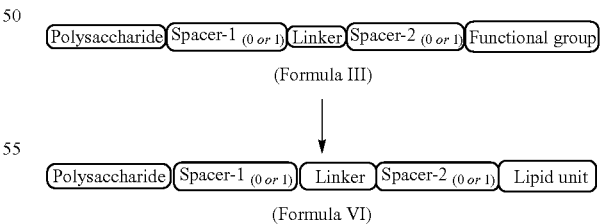

Methods for preparing a functionalized polysaccharide, a functionalized taxane, and a covalent conjugate of the polysaccharides and a taxane are disclosed in our Chinese patent CN201310616253.7, the entire disclosure of which is incorporated herein by reference.

In a particular embodiment of the preparation of the compound depicted by Formula I, the compound of Formula I is prepared in the scheme as shown in Figure-35

Figure-35

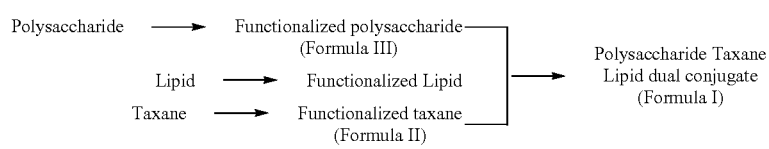

It includes the following steps:
1) Polysaccharides are reacted with a functional group containing lipid or aromatic isocyanate in suitable solvent, in the presence of a base, optionally with a coupling reagent to form a functionalized polysaccharides (Formula III);
2) A lipid compound is reacted with a compound having a functional group and linker or spacer to form a functionalized lipid compound with the functional group;
3) The linker and/or spacer which contains functional group is covalently linked to a side chain position of the taxane compound to form a functionalized taxane compound (Formula II) by employing the combination strategy of position-specific synthesis approach with selectively protecting/deprotecting the hydroxyl group of the taxane compound.
4) The functionalized taxanes and functionalized lipids are covalently coupled to the functionalized polysaccharides through the reaction in the presence of a coupling reagent or an optional catalyst, respectively, to form Taxane-lipid-polysaccharide dual conjugates (Formula I) which contain variable proportions of taxanes and lipids in conjugate form;

Step 1), step 2) and step 3) can be carried out separately in any order.

In a preferred embodiment of the scheme in Figure-35, in step 1), the polysaccharides and the functional group containing fatty or aromatic isocyanate are dissolved in a anhydrous or hydrous conventional solvents such as DMSO, DMF, or, dioxane, tetrahydrofuran, dichloromethane, chloroform, methanol or ethanol, preferably in DMSO and DMF, and then reacted in the presence of a base and an optional coupling agent to form a functionalized polysaccharides (Formula III).

In step (1) for the preparation of the functionalized polysaccharides, the reaction temperature is between 5 to 100° C., preferably between 10° C. to 30° C.; the base is selected from an organic base such as a tertiary amine (triethylamine, trimethylamine, diisopropyl-Ethylethylamine) or dimethylaminopyridine (DMAP), 1,8-diazabicyclo [5.4.0]undec-7-ene (DBU), or an inorganic base such as sodium hydroxide or potassium hydroxide, sodium carbonate, potassium carbonate, sodium hydrogencarbonate, or potassium hydrogencarbonate; the coupling agent is preferably, but not limited to, carbodiimide (DCC, EDC, DIPC) or N,N'-carbonyldiimidazole; the group is as defined above for the functional group according to the second aspect of the present invention, preferably an amino group, a carboxyl group, an azide group, a sulfurhydryl group, a phenolic hydroxyl group, an alkynyl group, a maleic acid lactam group, a cyclo-octynyl group or a tetrazinyl group.

In this regard, the present invention also generally relates to a process for the preparation of a functionalized polysaccharide (Formula III) which comprises the preferred embodiment step (1) as described above.

In another preferred embodiment of the scheme shown in Figure-35, in step (2) the lipid compound is reacted with the compound bearing a functional group and a linker or spacer, optionally in the presence of the base and/or coupling agent. The reaction is carried out to form a functionalized lipid compound with a functional group, wherein the reaction solvents, the reaction temperature, the base, the coupling agent, and the functional group are similar to or the same as the preparation of the functionalized polysaccharides in step (1) in the above preferred embodiment. The linkers and spacers are as defined above in accordance with the first aspect of the invention.

In this regard, the present invention also generally relates to a process for the preparation of a functionalized lipid compound which comprises the preferred embodiment step (2) as described above.

In another preferred embodiment of the process shown in the Figure-35, in step (3), a linking group and/or a spacer with a functional group is covalently attached to a side chain position of the taxane compound, preferably at 2'-O position of the side chain, to form a functionalized taxane compound (Formula II). In the reaction, the hydroxyl group of the taxane compound is selectively protected/deprotected by a position-specific synthesis method, optionally in the presence of a base and/or a coupling reagent, wherein the reaction solvents, the reaction temperature, the base, the coupling agent, and the functional group are like or the same as the preparation of the functionalized lipid in the step (2) in the above preferred embodiment. The linker s, spacers are defined above as the same for the linkers and spacers in accordance with the first aspect of the invention.

In this regard, the present invention also generally relates to a process for the preparation of a functionalized taxane compound (Formula II) which comprises the preferred embodiment step (3) as described above.

In another preferred embodiment of the process as shown in Figure-35, the functionalized taxanes and functionalized lipids are covalently coupled to the functionalized polysaccharides through the reaction in the presence of a coupling reagent or an optional catalyst, respectively, to form taxane-lipid-polysaccharide dual conjugate (shown by Formula I) containing variable proportions of taxanes and lipids in conjugate form, wherein the molar ratios of the functionalized polysaccharides, the functionalized taxane compound, the functionalized lipid compound are optionally set about 10:5:0.1 to 10:0.1:5; the preparation reaction temperature is between −10° C. to −50° C., preferably between 5° C.-30° C.; the coupling reagent is selected from carbodiimides (DCC, EDC, DIPC) or N,N'-carbonyldiimidazole; the preparation solvent is anhydrous or aqueous conventional solvent such as DMSO, DMF, dioxane, tetrahydrofuran, methanol or ethanol, preferably DMSO or DMF; the catalyst is selected from the group consisting of a click chemistry copper salt catalyst, such as a cuprous halide (cuprous chloride, cuprous iodide), a vitamin C sodium salt or a cuprous salt or ligand containing valent (I) copper salt produced from gallic acid and cupric sulfate salt. When coupling is carried out without using a catalyst, the coupling reaction is selected from a copper-free click chemistry reaction and an addition reaction with maleic acid lactam and thiol group.

In a particularly preferred embodiment of the process of Figure-35, the method of preparation comprises the following steps:

1) The polysaccharides and the functional group containing lipid or aromatic isocyanate are dissolved in a anhydrous or hydrous conventional solvents such as DMSO, DMF, dioxane, tetrahydrofuran, dichloromethane, chloroform, methanol or ethanol, preferably in DMSO and DMF, and then reacted in the presence of a base and an optionally coupling agent to form a functionalized polysaccharides (Formula III). wherein the reaction temperature is between 5 to 100° C., between 10° C. to 30° C.; the base is selected from an organic base such as a tertiary amine (triethylamine, trimethylamine, diisopropyl-ethylamine) or dimethylaminopyridine (DMAP), 1,8-diazabicyclo [5.4.0]undec-7-ene (DBU), or an inorganic base such as sodium hydroxide or potassium hydroxide, sodium carbonate, potassium carbonate, sodium hydrogencarbonate, potassium hydrogencarbonate; the coupling agent is preferably, but not limited to, carbodiimide (DCC, EDC, DIPC) or N,N'-carbonyldiimidazole; The group is as defined above for the functional group according to the second aspect of the present invention;

2) The lipid compound is reacted with the compound having the functional group and a linker unit and/or spacer, optionally in the presence of a base and/or a coupling agent, to form a functionalized lipid compound, wherein the reaction solvent is selected from anhydrous or aqueous conventional solvents such as DMSO, DMF, dioxane, tetrahydrofuran, dichloromethane, chloroform, methanol or ethanol, preferably DMSO or DMF; the preparation reaction temperature, base, coupling agent are the same or similar to the preparation of the functionalized polysaccharides as defined in general or preferably as in the second aspect of the present invention;

3) In the presence of a base and/or a coupling reagent, the linker and/or spacer which contains functional group is covalently linked to a side chain position of the taxane compound, preferably at 2'-O position of the side chain to form a functionalized taxane compound (according to Formula II) by employing the combination strategy of position-specific synthesis approach with selectively protecting/deprotecting the hydroxyl group of the taxane compound.

wherein the solvent used for the preparation, the reaction temperature, the base, The coupling agent is as defined or approximated in the preparation of the functionalized lipid compound as in 2) above; the functional group is generally or preferably defined above in accordance with the second aspect of the invention;

4) The functionalized taxanes and functionalized lipids are covalently coupled to the functionalized polysaccharides through the reaction in the presence of a coupling reagent or an optional catalyst, respectively, to form taxane-lipid-polysaccharide dual conjugate (Formula I) containing variable proportions of taxanes and lipids in conjugate form, wherein the molar ratios of the functionalized polysaccharides, the functionalized taxane compound, the functionalized lipid compound are optionally set about 10:5:0.1 to 10:0.1:5; the preparation reaction temperature is between −10° C. to −50° C., preferably between 5° C.-30° C.; the coupling reagent is selected from carbodiimides (DCC, EDC, DIPC) or N,N'-carbonyldiimidazole; the preparation solvent is anhydrous or aqueous conventional solvent such as DMSO, DMF, dioxane, tetrahydrofuran, methanol or ethanol, preferably DMSO or DMF; the catalyst is selected from the group consisting of a click chemistry copper salt catalyst, such as a cuprous halide (Cuprous chloride, cuprous iodide), a vitamin C sodium salt or a cuprous salt or ligand containing valent (I) copper salt produced from gallic acid and cupric sulfate salt. When coupling is carried out without aid of a catalyst, the coupling reaction is selected from a copper-free click chemistry reaction and an addition reaction with maleic acid lactam and thiol group.

Step 1), step 2) and step 3) can be carried out in any order.

In another embodiment of the preparation of the compound of Formula I, the compound of formula (I) is prepared as shown in the scheme of Figure-36.

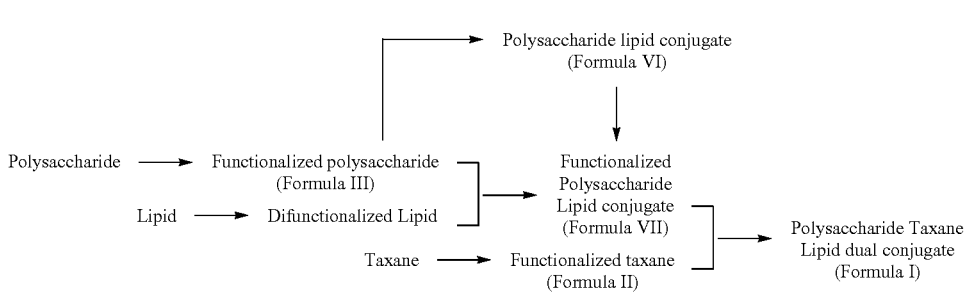

Figure-36

It includes the following steps:
1) The polysaccharides are reacted with a functional group containing lipid or aromatic isocyanate in the presence of a base, optionally in the presence of a coupling agent, to form a functionalized polysaccharides (Formula III);
2) A lipid compound is derivatized by a coupling reaction to have at least two identical or different functional groups in order to form a functionalized lipid compound with bifunctional or multifunctional groups;
3) A functionalized group of a bifunctional or multifunctional lipid compound is coupled with a functionalized polysaccharide under the reaction in the presence of a coupling agent or an optional catalyst, therefore to form a functionalized lipid polysaccharide conjugate in which it itself still has a free functional group (as Formula VII); or a functionalized polysaccharide is converted into a polysaccharides-lipid conjugate (as Formula VI), which is further converted into a functionalized polysaccharides-lipid conjugate (as Formula VII);
4) In the presence of a base and/or a coupling reagent, the linker and/or spacer which contains functional group is covalently linked to a side chain position of the taxane compound, preferably at the 2'-O position of the side chain to form a functionalized taxane compound (according to Formula II) by employing the combination strategy of position-specific synthesis approach with selectively protecting/deprotecting the hydroxyl group of the taxane compound;
5) The functionalized taxane compound is covalently coupled to the functionalized polysaccharides-lipid conjugate with certain ratio through the reaction in the presence of a coupling reagent or an optional catalyst, respectively, to form taxane-lipid-polysaccharide dual conjugate (by Formula I) containing variable proportions of taxanes and lipids in conjugate form; In a preferred embodiment of the process as indicated by Figure-36, The preparation includes the following steps:
1) The polysaccharide is reacted with a functional group containing lipid or aromatic isocyanate in the presence of a base, optionally in the presence of a coupling reagent, to form a functionalized polysaccharides (Formula III); The reaction temperature, reagent, base, coupling reagent and functional group are as defined as in above mentioned process of preferred embodiment of Figure-35 in step (1) for the preparation of the functionalized polysaccharides;
2) A lipid compound is derivatized by a coupling reaction to have at least two identical or different functional groups, in the presence of optionally a base and/or a coupling agent, to form a bifunctionalized or multifunctionalized lipid compound; The reaction temperature, the reagent, the base, the coupling reagent and the functional group are defined in above process flowchart of Figure-35 as the step (2) in the preferred embodiment for the preparation of the functionalized lipid compound;
3) A functionalized group of a bifunctional or multifunctional lipid compound is coupled with a functionalized polysaccharide under the reaction in the presence of a coupling agent or an optional catalyst, therefore to form a functionalized lipid polysaccharides conjugate in which itself still bearing a free functional group (as Formula VII); or a functionalized polysaccharides is converted into a polysaccharides-lipid conjugate (as Formula VI), which is further converted into functionalized polysaccharides-lipid conjugate (as Formula VII); the reaction temperature, reagents, catalysts, coupling agents and functional groups are as defined in step (4) of the preferred embodiment described above in scheme shown in Figure-35;

In the presence of a base and/or a coupling reagent, the linker and/or spacer which contains functional group is covalently linked to a side chain position of the taxane compound, preferably at the 2'-O position of the side chain to form a functionalized taxane compound (according to Formula II) by employing the combination strategy of position-specific synthesis approach with selectively protecting/deprotecting the hydroxyl group of the taxane compound. The reaction temperature, reagents, bases, coupling reagents, the linker s, spacers and functional groups are as defined in step (3) of the preferred embodiment described above as shown in Figure-35;

The functionalized taxane compound is covalently coupled to the functionalized polysaccharides-lipid conjugate (Formula VII) with certain ratio through the reaction in the presence of a coupling reagent or an optional catalyst, respectively, to form Taxane-lipid-polysaccharide dual conjugate (Formula I) containing variable proportions of taxanes and lipids in conjugate, wherein the molar ratios of the functionalized taxane compound, the functionalized polysaccharides-lipid conjugate are optionally set about 1:99~90:10, for example as 1: 99~80:20, 1: 99~70:30, 1: 99~60:40, preferably as 1: 99~50:50; The reaction temperature, reagents, catalysts, coupling agents, and functional groups are as defined in step (4) of the preferred embodiment described in the scheme of Figure-35 above.

Based on a particular embodiment of the preparation of the compound of Formula I, the present invention also generally relates to a process for the preparation of a bifunctionalized or multifunctionalized lipid compound including the step (2) as described in the preferred embodiment of the scheme of Figure-36 above.

Based on a particular embodiment of the preparation of the compound of Formula I, the invention also generally relates to a process for the preparation of a functionalized polysaccharides-lipid conjugates (Formula VII) comprising of step (1), step (2) and step (3) in the preferred embodiment of the scheme of Figure-36 above.

In another embodiment of the preparation of the compound of formula (I), the compound of formula (I) is prepared as shown in scheme of Figure-37:

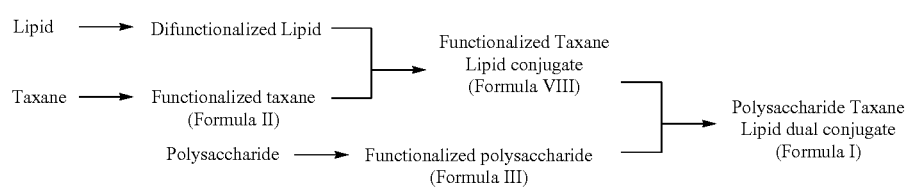

Figure-37

It includes the following steps:
1) The polysaccharides are reacted with a functional group containing lipid or aromatic isocyanate in the presence of a base, optionally in the presence of a coupling agent, to form a functionalized polysaccharides (Formula III);
2) A lipid compound is derivatized by a coupling reaction to have at least two identical or different functional groups to form a bifunctionalized or multifunctionalized lipid compound;
3) The linker and/or spacer which contains functional group is covalently linked to a side chain position of the taxane compound to form a functionalized taxane compound (Formula II) by employing the combination strategy of position-specific synthesis approach with selectively protecting/deprotecting the hydroxyl group of the taxane compound.

4) The one functional group of dual-functionalized lipid compound is covalently coupled to the functionalized taxane compound with certain ratio through the reaction in the presence of a coupling reagent or an optional catalyst, respectively, to form the functionalized taxane-lipid conjugate (by Formula VIII) which still contains free functional group.

5) The functionalized polysaccharides are covalently coupled to free functional group of the functionalized taxane lipid conjugate in the presence of a coupling reagent or an optional catalyst, respectively, to form taxane-lipid-polysaccharide dual conjugate (Formula I).

In a preferred embodiment of the process of Figure-37, the method of preparation comprises the steps of:

1) The polysaccharide is reacted with a functional group containing fatty or aromatic isocyanate in the presence of a base, optionally in the presence of a coupling reagent, to form a functionalized polysaccharide (Formula III); The reaction temperature, reagent, base, coupling reagent and functional group are as defined above in step (1) of the preferred embodiment described in the scheme of Figure-35;

2) A lipid compound is derivatized by a coupling reaction to have at least two same or different functional groups, in the presence of optionally a base and/or a coupling agent, to form a bifunctional or multifunctional lipid compound; The reaction temperature, the reagent, the base, the coupling reagent and the functional group are defined in the preparation of the functionalized lipid compound in step (2) of the preferred embodiment described above in the scheme of Figure-35;

3) In the presence of a base and/or a coupling reagent, the linker and/or spacer which contains functional group is covalently linked to a side chain position of the taxane compound, preferably at the 2'-O position of the side chain to form a functionalized taxane compound (Formula II) by employing the combination strategy of position-specific synthesis approach with selectively protecting/deprotecting the hydroxyl group of the taxane compound, wherein the reaction temperature, base, coupling agent and the functional group are as defined in step (3) of the preferred embodiment described in the scheme of Figure-35 above;

4) The one functional group of dual-functionalized lipid compound is covalently coupled to the functionalized taxane compound with certain ratio through the reaction in the presence of a coupling reagent or an optional catalyst, respectively, to form the functionalized taxane-lipid conjugate (by Formula VIII) which still contains free functional group. The reaction temperature, reagents, catalysts, coupling agents, and functional groups are defined in step (4) of the preferred embodiment of scheme of Figure-35 above;

5) The functionalized polysaccharides is covalently coupled to free functional group of the functionalized taxane compound lipid conjugate in the presence of a coupling reagent or an optional catalyst, respectively, to form taxane-lipid-polysaccharide dual conjugate (Formula I), wherein the molar ratios of the functionalized taxane lipid conjugate and the functionalized polysaccharides are optionally set about 1:99~90:10, for example as 1:99~80:20, 1:99~70:30, 1:99~60:40, preferably as 1:99~50:50; The reaction temperature, reagent, catalyst, coupling agent and functional group are defined in step (4) of the preferred embodiment of the scheme of Figure-35 above.

Based on a particular embodiment of the preparation of the compound of formula (I), the present invention also generally relates to a process for the preparation of a functionalized taxane lipid conjugate (Formula VIII) comprising the above step 2), step 3) and step 4) as state in the preferred embodiment of the scheme of Figure-37;

The various types of taxane-containing conjugates prepared based on the above methods as stated in the present invention have not only improved solubility, but also increased potential of tumor-targeting property of taxane compounds. When incubated with animal plasma, the conjugates can be enzymatically hydrolyzed by plasma enzymes which leads to effective release of parent taxane compound in in vitro release studies (see supplement FIG. 1).

The conventional solvents used in the above method embodiments are all commercially available.

The starting materials used in the above method embodiments are either commercially available or can be obtained by conventional modification of commercially available starting materials by methods well known to those skilled in the art.

The coupling reactions involved in the above method embodiments can be carried out through the conventional methods well known to those skilled in the art; non-limiting examples of suitable coupling agents include carbodiimide coupling agents such as DCC (N,N'-Dicyclohexylcarbodiimide), EDC (1-ethyl-(3-dimethylaminopropyl) carbodiimide), DIPC (1,3-diisopropylcarbodiimide), or N,N'-carbonyldiimidazole, or a combination thereof, preferably using EDC and N,N'-carbonyldiimidazole.

The "position-specific synthesis method" referred to in the above method embodiments is employed for preparations of the functionalized taxane compounds. This position-specific synthesis method can be carried out using a protecting group and further protecting/deprotecting method which is well known in the art. For example, see CN201310616253.7. It can be carried out by protecting the 2'-position alcoholic hydroxyl group of the taxane compound with a hydroxy protecting group; then protecting the 7- and/or 10-position alcoholic hydroxyl groups of the taxane compound with a hydroxy protecting group; then selectively removing the protecting group on 2'-position of taxane compound, coupling a linker and/or a spacer which bearing a functional group to the 2' position in the presence of a coupling agent and an organic base; optionally removing the protecting group on the hydroxyl group of the 7- and/or the 10-position to obtain a functionalized taxane compound.

Alternatively, for example, the following localization synthesis method is also feasible: protecting the 2'-position alcoholic hydroxyl group of the taxane compound with a hydroxy protecting group; and connecting the functional group-bearing linker and/or spacer to the 7- and/or 10-position alcoholic hydroxyl group of the taxane compound in the presence of a coupling agent and an organic base; then the 2'-OH protecting group of the taxane compound can be removed to obtain a functionalized taxane compound.

Wherein, the hydroxyl protecting group used for the 2' position hydroxyl group is selected from the group consisting of: tert-butyldimethylsilyl (TBS), triisopropylsilyl (TIP), triethylsilyl (TES), trimethylsilyl or tert-butyldiphenylsilyl (TBDPS); the hydroxyl protecting group used for the hydroxyl group at the 7-position and/or the 10-position is selected from the group consisting of allyloxycarbonyl (Aloc), benzyloxycarbonyl (Z), trihydrocarbyl silicon ($R_3Si$) and the like.

The "spacer" and "linker" referred to in the above method embodiments have the above general or preferred definitions according to the first aspect of the invention, the "functional group" involved having the above general or preferred definition according to the second aspect of the present invention;

According to the tenth aspect of the present invention, the present invention provides a pharmaceutical composition comprising one or more compounds (in any ratio), or the pharmaceutically acceptable salts thereof, or the solvates thereof, which are schematically defined as in Formula I according to the first aspect of the present invention, in Formula II according to the second aspect of the present invention, in the Formula V according to the fifth aspect of the invention or of the Formula VIII according to the eighth aspect of the invention, the composition also optionally comprises a pharmaceutically acceptable conventional excipient or an adjuvant such as a carrier, a diluent, a filler, a disintegrant, a lubricant, a binder, a colorant, a pigment, a stabilizer, a preservative or an antioxidant, which contains 0.1 to 99.9%, preferably 0.1 to 60% of taxanes by weight.

The pharmaceutical composition comprises a taxane-lipid-polysaccharide dual conjugates (Formula I), a functionalized taxane (Formula II), a taxane-polysaccharides conjugate (Formula V) and/or functionalized taxane-lipid conjugates (Formula VIII), all above modifications on taxanes lead to their improved water solubility, pharmacokinetics, in vivo drug release and/or tumor targeting properties; Therefore, aforementioned pharmaceutical compositions provide an improved therapeutic effect in the treatment or prevention of diseases that are sensitive to taxanes.

In a preferred embodiment, the pharmaceutical composition comprises the compound of Formula I according to the first aspect of the invention, or a pharmaceutically acceptable salt thereof, or a solvate thereof, optionally a pharmaceutically acceptable conventional excipient or an adjuvant. The pharmaceutical composition as aforementioned contains 0.1 to 60% taxane compound by weight.

The pharmaceutical composition comprises a taxane-lipid-polysaccharides dual conjugates (Formula I), of which water solubility, pharmacokinetics, and/or tumor targeting properties are improved due to the above conjugation modification of the taxane compound. Within their structures, the specific linker unit (linker s and spacers and their structures) can be effectively degraded in vivo, thereby effectively regulating the release rate and the percentage of release of the taxane compound, thereby enhancing the anti-tumor therapeutic effect in the treatment or prevention of diseases which are sensitive to taxanes.

In a preferred embodiment, the above pharmaceutical composition further comprises one or more compounds as defined by Formula III according to the third aspect of the invention, Formula IV according to the fourth aspect of the invention, Formula VI according to the sixth aspect of the invention, Formula VII according to the seventh aspect of the invention, wherein the pharmaceutical composition comprises any one or more compounds as defined by the Formula I, II, V and VIII and any one or more combinations of compounds defined by Formula III, Formula IV, Formula VI, and Formula VII.

The aforementioned pharmaceutical composition also comprises one or more compounds as defined as functionalized polysaccharides (Formula III), bifunctionalized or multifunctionalized polysaccharides (Formula IV), polysaccharides-lipid conjugates (Formula VI) and functionalized polysaccharides-lipid conjugates (Formula VII), those compounds not only have the advantages of much improved water solubility, biocompatibility and biodegradability and the like due to their conjugation with polysaccharides, but also have the tumor targeting properties due to conjugated lipids in their structure. All these beneficial properties of these compounds work together and help to further improve the delivery of the taxane compound in the pharmaceutical composition and therefore enhance its therapeutic effect.

The pharmaceutical compositions of this present invention may be formulated by techniques known to those skilled in the art, such as those techniques disclosed in Remington's Pharmaceutical Sciences, 20th Edition. The compounds according to the present invention or the above-described pharmaceutical compositions comprising the same can be administered to a subject by any convenient route of administration, whether system/peripheral or at the desired site of action. For the administration system, the pharmaceutical composition of the present invention can be prepared into a general preparation, a sustained release preparation, a controlled release preparation, a targeted preparation or various microparticle delivery systems and the like. In addition, the pharmaceutical composition of the present invention may be formulated into a liquid dosage form or a solid dosage form or an aerosol, and the liquid dosage form may be a colloidal type, a nanoparticles dosage form, a microparticulate form, a suspension form, an emulsion, a micelle dosage form, a liposome dosage form and the like; the solid dosage form may be a tablet, a capsule, a dropping pill, a pill, a lyophilized powder injection, a granule, etc., for oral administration, parenteral administration, rectal administration, nasal administration, topical application or aerosol agent. Dosage forms for oral administration include coated and uncoated tablets, soft gelatin capsules, hard gelatin capsules, lozenges, lozenges, solutions, emulsions, suspensions, syrups, elixirs, Powders and granules for reconstitution, dispersible powders and granules, pharmaceutical gums, chewable tablets and effervescent tablets. Dosage forms for parenteral administration include solutions, emulsions, suspensions, dispersions, and powders for reconstitution, as well as granules. Emulsions are a preferred dosage form for parenteral administration. Dosage forms for rectal and vaginal administration include suppositories and ovules. Dosage forms for nasal administration can be administered by inhalation and insufflation, such as by a metered dose inhaler. Dosage forms for topical administration include creams, gels, ointments, salves, patches, and transdermal delivery systems. Particularly preferred are intravenous pharmaceutical compositions.

In order to prepare a suitable pharmaceutical dosage form, various carriers, various types of excipients, and various types of additives known in the pharmaceutical field can be widely used in the present invention. Diluents and absorbents, such as starch, dextrin, calcium sulfate, lactose, mannitol, sucrose, sodium chloride, urea, calcium carbonate, kaolin, microcrystalline cellulose, aluminum silicate, etc.; wetting agents and bonding agents such as water, glycerin, polyethylene glycol, ethanol, propanol, starch syrup, dextrin, syrup, honey, glucose solution, gum arabic, gelatin syrup, sodium carboxymethylcellulose, shellac, methylcellulose, potassium phosphate, polyvinylpyrrolidone, etc.; disintegrating agents, such as dry starch, sodium alginate, agar powder, sodium hydrogencarbonate and sodium citrate, calcium carbonate, polyoxyethylene sorbitan fatty acid ester, dodecyl sulfonic acid Sodium, methyl cellulose, ethyl cellulose, etc.; disintegration inhibitors such as sucrose, triglyceride, cocoa butter, hydrogenated oil, etc.; absorption enhancers such as quaternary ammonium salts; lubricants such as talc Powder, silica, corn starch, stearate, boric acid, liquid paraffin, polyethylene glycol, etc.; diluent is selected from the group consisting of water, ethanol, polyethylene glycol, ethoxylated isostearic alcohol, and polyoxidized stearic acid alcohol, polyoxyethylene sorbitol stearic acid, etc.; lyophilized support agents such as small molecule polysaccharides, small molecule amino acids and polyols, etc., one or more of them are compounded; small molecule polysaccharides refer to sucrose, lactose, maltose, etc., one or more of them are compounded; small molecule amino acids refer to one or more of 20 natural amino acids, polyols refer to one or more of mannitol or sorbitol; pH adjusters such as sodium dihydrogen phosphate, disodium hydrogen phosphate, potassium dihydrogen phosphate, dipotassium hydrogen phosphate, boric acid, borax, sodium acetate, citric acid, sodium citrate, tartaric acid, sodium tartrate, sodium carbonate, potassium carbonate, sodium hydrogencarbonate, potassium hydrogencarbonate, sodium hydroxide, potassium hydroxide, hydrochloric acid, phosphoric acid, one or more compounding agents, etc.; stabilizers such as sodium sulfite, sodium hydrogen sulfite, sodium metabisulfite, sodium nitrite, sodium thiosulfate, ascorbic acid (vitamin C), thiourea, ascorbyl stearate, dibutyl cresol, cysteine, disodium edetate (EDTA-2Na, disodium edetate), sodium calcium edetate, dimercaptopropanol, glycerol, mannitol, etc.; antioxidants such as vitamin C, vitamin E, sulfites, EDTA or a combination thereof and one or more of cysteine hydrochloride or N-acetylcysteine; isotonic reagents, such as sodium chloride, potassium chloride, boric acid, sodium sulfate, sodium nitrate, potassium nitrate, sodium acetate, mannitol, glycerin, propylene glycol, glucose, etc., one or more of them, etc.; thickeners, such as sodium hyaluronate, chondroitin sulfate, methyl cellulose, hydroxypropyl Methylcellulose, hydroxypropylmethylcellulose, hydroxypropylethylcellulose, povidone, polyvinylpyrrolidone, polyvinyl alcohol, carbomer, etc., one or more of which are compounded; solubilizing agents, such as Ethanol, Tween, glycerin, propylene glycol, polyethylene glycol, etc., one or more of them, etc.; preservatives, such as benzalkonium bromide, benzoic acid, etc.; if necessary, colorants, flavors or other materials can also be added to pharmaceutical preparations.

Therefore, in a preferred embodiment, the above pharmaceutical composition of the present invention is in the form of a pharmaceutical formulation comprising a liquid dosage form or a solid dosage form selected from the group consisting of a true solution, a colloid type, a microparticle dosage form, a nanoparticles preparation, and a suspension dosage form, and an eye drop; the solid dosage form is selected from the group consisting of an implant, a tablet, a capsule, a dropping pill, an aerosol, a pill, a powder, an emulsion, a granule, a suppository, and a lyophilized powder. More preferred forms of pharmaceutical preparations are lyophilized powders, nanoparticles formulations, and solutions.

Accordingly, in a preferred embodiment, the pharmaceutical preparation of the above pharmaceutical composition of the present invention may be in the form of a general preparation, a sustained release preparation, a controlled release preparation, a targeted preparation or a nanoparticles drug delivery system To achieve an enhanced therapeutic effect, the physician will determine the actual dosage that is most suitable for the individual patient. The particular dosage level and dosage frequency for any particular individual subject can vary and depend on various factors, such as the nature and severity of the diseases to be prevented or treated, sex, age, weight, personality of the patient or animal, individual response, the route of administration and the purpose of treatment. Thus, the dose of the substance of the present invention may vary widely, for example, the dose of the taxane may be 0.1-1000 mg/kg body weight, preferably 0.1-500 mg/kg, more preferably, it is 10 to 300 mg/kg, and furthermore preferably from 20 to 200 mg/kg. The total dose required for each treatment can be divided into multiple or single dose administrations. In addition, the dosage of the compound of the present invention may be adjusted as appropriate in combination with other therapeutic agents, depending on the needs of the combination.

According to an eleventh aspect of the present invention, the present invention further provides a combination of a compound defined as Formula I, Formula II, Formula V and/or Formula VIII of the invention with one or more additional therapeutic agents.

The compounds of the Formula I, Formula II, Formula V and/or Formula VIII of the present invention may be administered in a monotherapy, and they may also be administered in combination with one or more additional therapeutic agents, as appropriate, to provide enhanced or synergistically strengthened therapeutic effect for treating the disease. When a compound of the Formula I, Formula II, Formula V and/or Formula VIII of the present invention is used in combination with a second therapeutically active agent for the treatment or prevention of a disease susceptible to a taxane, the dosage of each compound may be different from the dosage when the corresponding compound is used alone; including in a single pharmaceutical preparation or in a separate pharmaceutical preparation, simultaneously/concomitantly administering compounds of Formula I, Formula II, Formula V and/or Formula VIII of the present invention with one or more additional therapeutic agents, or a compound of Formula I, Formula II, Formula V and/or Formula VIII of the invention and one or more additional therapeutic agents are administered sequentially or separately. The combination therapy can improve the therapeutic effect of a disease sensitive to taxane compounds while improving additional therapeutic effects on the disease to which the additional therapeutic agent is administered for, or even providing a synergistic therapeutic effect.

Further, according to the present invention, the compounds of Formula I to Formula VIII includes polysaccharides as hydrophilic moiety, a lipophilic moiety lipid compound and/or a hydrophobic moiety taxane compound in a structural composition, and thus can be directly and physically mixed with low solubility drugs or used as excipients, adjuvants, additives, cosolvents or carrier materials, etc., thereby increasing their solubility in water, for the treatment of related diseases that solubilized drugs purposed for; The advantages include improved solubility, biocompatibility, biodegradability due to conjugation with polysaccharides and/or tumor targeting property imparted by the conjugation with lipid compounds can effectively improve the delivery of poorly soluble drugs in the pharmaceutical composition, and achieve improved therapeutic effects of related diseases. The compound may be formulated with one or more solubilized drugs according to the method, material and amount of the above-described tenth aspect of this invention, in the forms of tablets, capsules, powders, lyophilized powders, nanoparticles formulation, suspension or sustained release preparation, and the like.

Accordingly, in this aspect, the present invention also provides a combination therapeutic preparation comprising a combination of one or more poorly water-soluble drugs and a pharmaceutical carrier, and optionally a pharmaceutically acceptable conventional pharmaceutical excipient or adjuvant wherein the carrier material is selected from any one or more of the compounds of Formula I, II, III, IV, V, VI, VII, VIII, or a pharmaceutically acceptable salt thereof, or a solvate thereof, as defined in the preceeding claims, wherein the poorly water-soluble drug is selected from the group consisting of: paclitaxel, docetaxel, cabazitaxel, vinblastine, vincristine, Lipitor, artemisinin, dihydroartemisinin, indomethacin, Capecitabine, Oxalipril, gefitinib, doxorubicin, irinotecan, gemcitabine, pemetrexed, temozolomide, imatinib, vinorelbine, letrozole, teniposide, etoposide, ghost white toxin, camptothecin, 10-hydroxycamptothecin, 9-hydroxycamptothecin, 7-ethyl-10-hydroxycamptothecin, SN-38, topotecan, irinotecan, vindesine, vinflunine, vinpocetine, desmethylcantharidin, silybin, propofol, florfenicol, mitiglinide, sirolimus, buprofol, nitrendipine, nicardipine, nimodipine, gliclazide, cisapride, nifedipine, felodipine, glibenclamide, acyclovir, oleanolic acid, breviscapine, ferulic acid, paracetamol, palmitoylmycin, Auf DER buckwheat, vitamin A, vitamin D, tamoxifen, noviben, valproic acid, tacrolimus, cyclosporine A, amphotericin B, ketoconazole, Domperidone, sulpiride, fenofibrate, bezafibrate, azithromycin, itraconazole, miconazole, propofol, brimonidine, latanoprost, silybin, erythromycin, Erythromycin, rifathiamine, cisapride, cyclosporin, diclofenac, felodipine, ibuprofen, nicardipine, nifedipine, terfenadine, theophylline, ketoprofen, furosemide, spironolactone, dipyridamole, piroxicam, mefenamic acid, trichlorothiazide, Pindolol, saturated or not Saturated fatty acids (such as stearic acid, palmitic acid, oleic acid, linoleic acid, DHA, etc.) or combinations thereof.

According to the twelfth aspect of the present invention, this invention provides a pharmaceutical carrier selected from one or more compounds of Formula III according to the third aspect of the present invention, Formula IV according to the fourth aspect of the present invention, and Formula VII according to the seventh aspect the present invention.

The above compounds of the present invention contain hydrophilic polysaccharides and/or a lipophilic compound with tumor-targeting properties, along with a free functional group; therefore, apart from conjugating covalently with taxane compounds, the conjugate structure can also be covalently linked to many other types of drugs, preferably but not limited to vinblastine, vincristine, Lipitor, SN-38, capecitabine, gemcitabine, other important drugs? etc., to improve the drug solubility and in vivo delivery, enhancing tumor targeting properties and fortifying efficacy of carried drug.

According to the thirteenth aspect of the present invention, the present invention provides a compound of the Formula I, Formula II, Formula V or Formula VIII of the present invention or a pharmaceutically acceptable salt or solvate thereof, for the treatment or prevention of a tumor or related diseases.

Alternatively, the invention provides a method for treating or preventing tumors or related diseases via administering an effective amount of compound, or a pharmaceutically acceptable salt or solvate thereof, of Formula I, Formula II, Formula V or Formula VIII of the invention to a subject or patient in need.

Alternatively, the present invention provides a compound or a pharmaceutically acceptable salt or solvate thereof, of the Formula I, Formula II, Formula V or Formula VIII of the present invention, for the preparations of a medication for the treatment or prevention of a tumor or related diseases.

The tumor involved in the above use is preferably a tumor sensitive to a taxane compound, preferably but not limited to lung cancer, breast cancer, oral cancer, liver cancer, intestinal cancer, stomach cancer, blood cancer, bladder cancer, pancreatic cancer, uterine cancer, skin cancer, etc. The compound of the present invention is to be used in a dose equivalent to a therapeutic dose of the taxane compound from 0.1 to 500 mg/kg, from 10 to 300 mg/kg, more preferably 20 to 200 mg/kg.

A subject in need of treatment according to the present invention may be an animal (eg, a non-human animal), a vertebrate, a mammal, a rodent (eg, a guinea pig, a hamster, a rat, a mouse), a murine (eg, a mouse)., canines (such as dogs), felines (such as cats), equines (such as horses), primates, apes (such as monkeys and baboons), monkeys (such as macaques, marmosets, baboons), baboons (eg gorillas, chimpanzees, orangutans, gibbons) or human. preferably, the subject/patient is a mammal; more preferably, the subject/patient is human.

Based on the above, the present invention also relates to the use of a compound or a pharmaceutically acceptable salt or solvate thereof, of the Formula I to VIII of the present invention, as a drug delivery vehicle (physically mixed or covalently linked); wherein the drug is preferably difficultly soluble drugs, more preferably poorly soluble antitumor drugs, such as taxanes, vinblastine, vincristine, Lipitor, SN-38, capecitabine, gemcitabine.

Definitions

The following words, phrases and symbols used in the present application have definitions as listed below, unless otherwise stated in the context of the present invention.

Unless specifically stated otherwise, terms such as "a" are used to mean one or more.

The term "hydrocarbyl" or "alkanyl" as used herein, unless otherwise specifically defined, means having from 1 to 20 carbon atoms, for example from 1 to 18 carbon atoms, from 1 to 12 carbon atoms, for example from 1 to 6 carbons, and further for example, a linear or branched saturated alkyl group of from 1 to 4 carbon atoms. Examples of alkyl groups include, but are not limited to, methyl ("Me"), ethyl ("Et"), n-propyl ("n-Pr"), isopropyl ("i-Pr"), n-butyl ("n-Bu"), isobutyl ("i-Bu"), sec-butyl ("s-Bu") and tert-butyl ("t-Bu").

The term "alkenyl" as used herein, refers to aalkyl group containing from 2 to 10 carbon atoms, for example 2 to 6 carbon atoms, containing one or more, for example 1, 2 or 3 carbon-carbon double bonds (C=C). Further, for example, a linear or branchedalkyl group of 2 to 4 carbon atoms. Examples of olefinic groups include, but are not limited to, vinyl, 2-propenyl, and 2-butenyl.

The term "alkynyl" as used herein, refers to aalkyl group containing from 2 to 10 carbon atoms, for example 2 to 6 carbon atoms, containing one or more, for example 1, 2 or 3, carbon-carbon triple bonds (C≡C). Further, for example, a linear or branched alkyl group of 2 to 4 carbon atoms. Examples of alkyne groups include, but are not limited to, ethynyl, 2-propynyl, and 2-butynyl.

The term "halogen" as used herein means fluoro, chloro, bromo and iodo.

The term "hydrocarbyloxyl" as used herein refers to a group-o-hydrocarbyl, wherein thealkyl group is as defined as above. Examples of alkoxy groups include, but are not limited to, methoxy, ethoxy, n-propoxy, isopropoxy, n-butoxy, isobutoxy, tert-butoxy, pentyloxy and hexyloxy, including their isomers.

The term "cycloalkyl" as used herein, means a saturated or partially unsaturated cyclic alkyl group having 3 to 15 ring carbon atoms, for example 3 to 12 ring carbon atoms, 3 to 10 ring carbon atoms, 3 to 8 ring carbon atoms, and further, for example, 3 to 6 ring carbon atoms, which may have one or more rings, for example having 1 or 2 rings; it may contain one or more, for example 1, 2 or 3 carbon-carbon double bonds or carbon-carbon triple bonds, in which case "cycloalkyl" refers to "cycloalkenyl" or "cycloalkynyl", respectively. For example, "C3-8 cycloalkyl" means the above described cyclic alkyl group having 3 to 8 ring carbon atoms. Examples of cycloalkyl groups include, but are not limited to, cyclopropyl, cyclobutyl, cyclopentyl, cyclohexyl, cycloheptyl, cyclooctyl, cyclopentenyl, cyclohexenyl, cycloheptynyl, and the like. The cycloalkyl group is optionally substituted with the substituents described above for the individual lipid compound molecules.

The term "cycloalkoxy" as used herein refers to a group-O-cycloalkyl, wherein the cycloalkyl is as defined above. Examples of cycloalkoxy groups include, but are not limited to, cyclopropyloxy, cyclobutyloxy, cyclopentyloxy, cyclohexyloxy, cycloheptyloxy, cyclooctyloxy, cyclopentenyloxy, cyclohexenyloxy group, a cycloheptynyloxy group, or the like.

The term "aryl", "aryl", "aromatic" as used herein, refers to a fused of one or more rings containing from 5 to 20 ring carbon atoms, for example from 6 to 14 ring carbon atoms, for example, a carbocyclic alkyl group of 6 to 12 ring carbon atoms, wherein at least one ring is an aromatic ring and the other ring is not a heteroaryl group as defined below, and the point of attachment may be on the aromatic ring or on other rings. Examples of aryl groups include, but are not limited to, phenyl, naphthyl, 1,2,3,4-tetrahydronaphthyl, indenyl, indanyl, Benzimidazolyl, preferably phenyl and naphthyl. The aryl group is optionally substituted with the substituents described above for the individual lipid compound molecules.

The term "heterocycloalkyl" as used herein, refers to a monocyclic, bicyclic or tricyclic, saturated and partially unsaturated ring selected from 3 to 12 members, such as 5 to 10 members, 3 to 8 members; It including at least one, for example 1-4, further such as 1-3 or further, for example 1 or 2 heteroatoms selected from O, S and N, and comprising at least one carbon atom. The point of attachment of the heterocycloalkyl group can be on a hetero atom or on carbon atom. Examples of heterocycloalkyl groups include, but are not limited to, tetrahydrofuran, tetrahydrothiophene, azetidine, acridine, tetrahydropyrrole, 1,3-dihydrothiazole, 1,3-dihydrooxazole, piperidine, piperazine, morpholine, thiomorpholine, thiazine, and the like. The heterocycloalkyl group is optionally substituted with the substituents described above for the individual lipid compound molecules.

The term "aryl", "heteroaryl" or "heteroaryl alkyl" as used herein, refers to an aromatic cyclic group, including monocyclic aryl groups and bridged and/or fused ring systems containing at least one aromatic ring. (eg a ring system consisting of two or three fused rings, wherein at least one of these fused rings is aromatic; or a bridged ring system consisting of two or three rings, wherein at least one of these bridged rings is aromatic; A aryl group comprising one or more (eg 1, 2, 3 or 4) ring heteroatoms independently selected from O, S and N, and the remaining ring atoms are carbon atoms, one or a plurality of S ring atoms (if present) and/or one or more N ring atoms (if present) may optionally be oxidized; preferably comprising one or more, for example 1, 2 or 3, in the ring, for example 1 or 2 ring heteroatoms independently selected from N, O and S having 5, 6 or 7 ring atoms, for example a monocyclic aryl group having 6 ring atoms, or having 8 to 12 ring atoms, for example a bicyclic aryl group having 9 or 10 ring atoms.

Examples of heteroaryl groups include, but are not limited to, pyridyl, N-oxypyridyl; pyrazinyl; pyrimidinyl; pyrazolyl; imidazolyl; oxazolyl; isoxazolyl; thiazolyl; isothiazolyl; thiadiazolyl; tetrazolyl; triazolyl; thienyl; furyl; pyranyl; pyrrolyl; pyridazinyl; benzo[d]thiazolyl; benzodioxolyl, such as benzo[d[1,3]dioxolyl; benzoxazolyl, such as benzo[d]oxazolyl; imidazopyridyl, such as imidazo[1,2-a]pyridinyl; triazole Pyridyl, for example, [1,2,4]triazolo[4,3-a]pyridinyl and [1,2,4]triazolo[1,5-a]pyridinyl; oxazolyl; 2H-A pyrazolopyryl group, such as pyrrolo[3,4-d]pyrimidinyl, 7H-pyrrolo[2,3-d]pyrimidinyl; pyrazolopyrimidinyl, eg pyrazolo[1,5-a]pyrimidinyl; tetrazolopyridinyl, such as tetrazolo[1,5-a]pyridinyl; benzothienyl; benzofuranyl; benzimidazolyl; indenyl; porphyrin Mercapto group, for example, 9H-fluorenyl and 7H-fluorenyl; quinolyl; isoquinolinyl; 1,2,3,4-tetrahydroquinolinyl and 5,6,7,8-tetrahydroisoquino Alkyl group.

The term "hydroxy" as used herein refers to a-OH group.

The term "mercapto or sulfurhydryl" as used herein refers to a —SH group.

The term "oxo" as used herein refers to a =O group.

The term "carboxy" as used herein refers to a —C(O)—OH group.

The term "cyano" as used herein refers to a —CN group.

The term "phosphoric acid" as used herein refers to —PO$_3$H.

The term "amino" as used herein, refers to a —NH$_2$ group, including the —NHR1, —NR1, —R2 groups.

The term "sulfonic acid group" as used herein refers to a —HSO$_3$ group.

The term "amide bond" as used herein means —CO—NH—, including —CO—NR—, wherein R means an alkyl group, a cycloalkyl group, an aryl group, an aryl alkyl group, a cycloalkyl alkyl group or the like.

The term "aminocarbamate" as used herein refers to —NHCOO—.

The term "aminothiocarbamate linkage" as used herein refers to —OC(S)—NH—, —OC(S)—NR—, wherein R refers to an alkyl group, a cycloalkyl group, an aryl group, an aryl alkyl group, A cycloalkyl alkyl group or the like.

The term "ester bond" as used herein refers to —C(O)O—.

The term "isourea bond" as used herein refers to —O—C=NH—NH$_2$.

The term "urea linkage" as used herein, refers to —NH—(CO)—NH—, including —NR$_1$—(CO)—NH—, —NR$_1$—(CO)—NR$_2$—, wherein R$_1$ and R$_2$ are each independently an alkyl, a cyclic alkyl group, an aryl group, an aryl alkyl group, a cycloalkyl alkyl group or the like.

The term "disulfide bond" as used herein refers to —S—S—.

The term "carbonate linkage" as used herein refers to —O—C(O)—O—.

The term "phosphoramide linkage" as used herein refers to —P(O)NHR$_1$, P(O)NR$_1$R$_2$, wherein R$_1$ and R$_2$ are each independently an alkyl group, a cycloalkyl group, an aryl group, an aryl alkyl group, a cycloalkyl alkyl group, and the like.

The term "sulfonamide bond" as used herein means —SONH—, —SO$_2$NR—, wherein R means an alkyl group, a cycloalkyl group, an aryl group, an aryl alkyl group, a cycloalkyl alkyl group or the like.

The term "alpha Glycosidic bond" as used herein refers to a condensation between monosaccharide units at the alpha position.

The term "beta glycosidic bond" as used herein refers to a condensation between monosaccharide units at the beta position.

The term "triazole-containing covalent bond" as used herein refers to a structural unit of a five-membered ring containing 1,2,3-triazole.

As used herein, the term "click chemistry" is the reaction of a pair of functional groups to each other rapidly and selectively under certain conditions. For a common type of "click chemistry" reaction, see H. C. Kolb; M. G. Finn; K. B. Sharpless (2001). "Click Chemistry: Diverse Chemical Function from a Few Good Reactions". Angewandte Chemie International Edition. 40 (11): 2004-2021; also https://en.wikipedia.org/wiki/Click_chemistry.

The term "amino acid" or "amino acid residue" as used herein refers to any of the 20 standard protein-derived alpha amino acids (ie, Ala, Arg, Asn, Asp, Cys, Glu, Gln, Gly, His, Ile, Leu, Lys, Met, Phe, Pro, Ser, Thr, Trp, Tyr and Val), but also non-proteinaceous and/or non-standard alpha amino acids (eg ornithine, citrulline, homolysine, pyrrole lysine, 4 hydroxyproline, norvaline, norleucine, tertiary leucine (tert leucine) or alanine or glycine substituted by a cyclic group on the side chain, such as cyclopenta Acid, cyclohexylalanine, phenylalanine, naphthylalanine, pyridylalanine, thienylalanine, cyclohexylglycine or phenylglycine) and beta-amino acids (eg beta alanine), γ-amino acids (such as γ-aminobutyric acid) and δ-amino acids. Unless otherwise defined, it is preferred that the "amino acid" is selected from the group consisting of an alpha-amino acid, more preferably an alpha-amino acid selected from the source of 20 standard protein-derived alpha amino acids (which may exist as the L-isomer or the D-isomer, and preferably as L—the isomer).

As used herein, the term "side chain of a modified structure" means while the taxane core structure remains the same, the structure of the taxane 13-O position side chain may be of various types and can have a functional group which can participate in the reaction.

The term "substituted" as used herein, unless specifically defined, refers to a substituent substituted by a substituent defined for a monomolecular lipid compound according to the first aspect of the invention.

As used herein, "spacer" or "linker" refers to a linker or linker component that joins two moieties by covalent attachment but decomposes under physiologically relevant conditions so covalent linkages between the moieties can be cleaved, and the group can thus be degraded. Typically, the degradable group is cleaved in a more rapid manner in the intracellular environment than outside the cell, resulting in a loaded drug preferentially released inside the target cell. Lysis can be enzymatic or non-enzymatic. The cleavage may leave some fragments of spacer or linker component on the loaded drug or may release the loaded drug without any linker residues.

According to the present invention, the term "pharmaceutically acceptable salt" refers to a salt of a free acid or base of the invention which is non-toxic, biologically tolerable or otherwise biologically suitable for administration to a subject to be treated, generally see for example: S M Berge et al., "*Pharmaceutical Salts*", J. Pharm. Sci., 1977, 66:1-19, and *Handbook of Pharmaceutical Salts, Properties, Selection, and Use*, Stahl and Wermuth, Wiley-VCH and VHCA, Zurich, 2002. The compounds of the present invention are capable of forming salts of acids and/or bases due to the presence or by the derivatization of groups containing amino groups and/or carboxyl groups or similar. A pharmaceutically acceptable acid addition salt can be formed from a mineral acid and an organic acid. Inorganic acids from which salts can be derived include, for example, hydrochloric acid, sulfuric acid, phosphoric acid, hydrobromic acid, nitric acid, and the like. The organic acids from which salts can be derived include, for example, formic acid, acetic acid, propionic acid, maleic acid, malonic acid, succinic acid, fumaric acid, tartaric acid, citric acid, glycolic acid, pyruvic acid, oxalic acid, benzoic acid, p-toluenesulfonic acid., cinnamic acid, mandelic acid, methanesulfonic acid, ethanesulfonic acid, salicylic acid, and the like. Pharmaceutically acceptable base addition salts can be formed with inorganic and organic bases. The inorganic base from which the salt can be derived includes sodium, potassium, calcium, magnesium, lithium, ammonium, iron, copper, manganese, zinc, aluminum, etc.; sodium, potassium, calcium, ammonium, magnesium salts and the like are preferred. The organic base from which the salt can be derived includes primary amines, secondary amines, tertiary amines, substituted amines, and the like, and also includes naturally occurring substituted amines, cyclic amines, basic ion exchange resins, and the like, particularly trimethylamine, diethylamine, isopropylamine, Triethylamine, tripropylamine, ethanolamine, and the like. Those skilled in the art can determine various synthetic methods which can be used to prepare non-toxic pharmaceutically acceptable salts without many experimentations.

The term "isomer" as used herein includes all possible isomers, including configurational isomers or conformational isomers (mixture forms or pure or substantially pure forms) of the compounds of the invention.

The term "solvate" as used herein, means a solvent addition form comprising a stoichiometric or non-stoichiometric amount of a solvent, including any solvated forms of the compounds of the invention, including, for example, solvates with water, such as hydrates, or a solvate with an organic solvent, such as methanol, ethanol or acetonitrile, ie as a methanolate, an ethanolate or an acetonitrile, respectively; or in the form of any polymorphyism. It will be understood that such solvates of the compound also include solvates of pharmaceutically acceptable salts.

The term "tumor" or "cancer" as used herein refers to neoplastic cell growth and proliferation, whether malignant or benign, and all pre-cancerous cells and cancer cells and tissues. For the compound, pharmaceutical composition and use of the present invention, the tumor is preferably, but not limited to, lung cancer, breast cancer, oral cancer, liver cancer, intestinal cancer, gastric cancer, blood cancer, bladder cancer, pancreatic cancer, uterine cancer, skin cancer, and the like.

The term "treating or treatment" as used herein refers to the administration of one or more drug substances, particularly to an individual, such as a human, having the disease, or having symptoms of the disease, or having a situation predisposed to the disease. As mentioned in this present invention, the compounds and/or a pharmaceutically acceptable salt or solvate thereof, for curing, healing, alleviating, altering, treating, ameliorating, or affecting the disease, the symptoms or predisposition of the disease. In some embodiments, the disease or disorder is a tumor or cancer.

The term "prevention" as used herein is well known in the art, for example, a patient/subject suspected of having or susceptible to a disease as defined herein may particularly benefit from the "prevention", such that the risk of getting the defined disease is in reduction. The term "prevention" encompasses the use of a compound of the invention prior to the diagnosis or determination of any clinical and/or pathological condition.

The term "effective dosage" as used herein refers to an amount or dose that is generally enough to produce a beneficial therapeutic effect on a tumor patient in need of treatment. One skilled in the art can determine the effective amount or dosage of the active ingredient of the present invention by conventional methods in conjunction with estimating conventional influencing factors.

In general, the term "about" is used herein to adjust the value given to be greater than or less than 20% of the value.

The technical and scientific terms not specifically defined herein have the meanings as commonly understood by one of ordinary skill in the art to which this invention belongs.

The use of any and all embodiments or exemplary language, such as "a or for example", is just for giving examples to the best in the present invention, but the scope of the invention, which is otherwise claimed, is not limited.

The general or preferred definitions of the specified features in the various enumerated embodiments of the invention may be combined with other specified features in a general or preferred combination to yield additional embodiments of the invention.

In this specification, several prior publications are cited. These publications are not to be considered as relating to the patentability of the present invention, but the entire contents thereof are hereby incorporated for reference. References in this specification to any prior publication (or information derived therefrom) are not, and should not be construed as affirming or recognizing or any form of revelation, ie the corresponding prior publication (or information derived from it) constitutes common knowledge in the technical field related to the present specification.

DESCRIPTION OF THE DRAWINGS

The present invention is also described by the following exemplary figures. The attached figures show:

FIG. 1 shows the percentage of paclitaxel released from dual conjugate 298 incubated in rat plasma.

DETAILED DESCRIPTION

Figure 2:
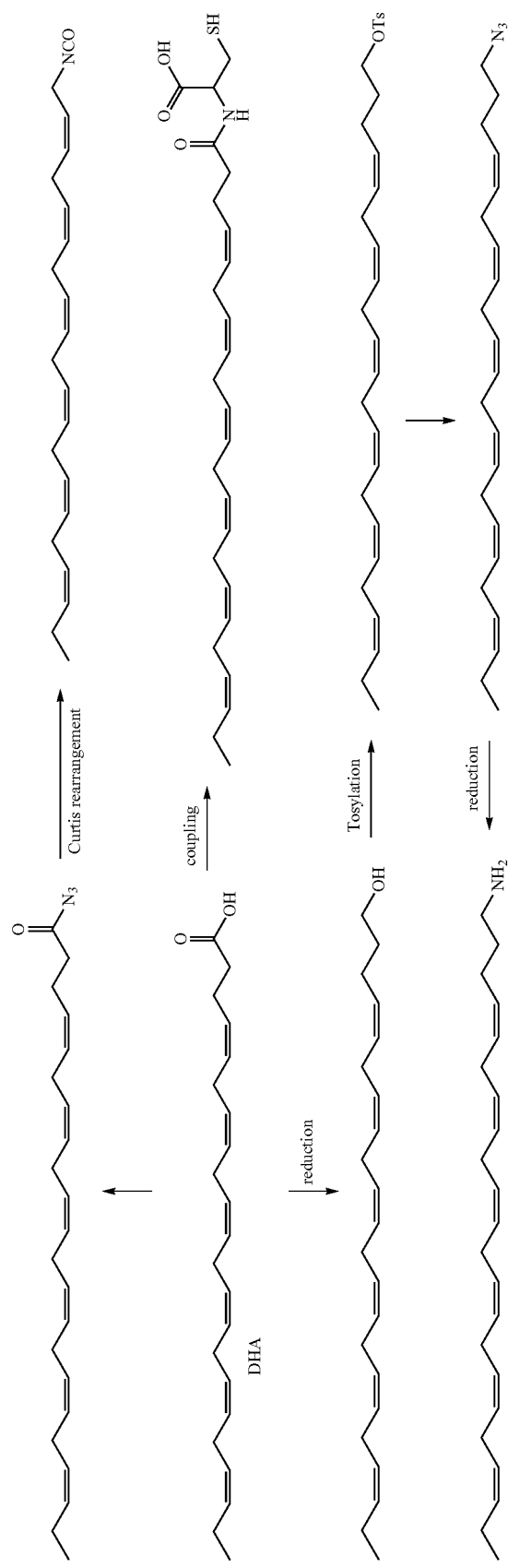
FIG. 2 shows the body weight change of xenograft mice (%) of dual conjugate 307 group, DTX control group and saline control group.

In the following, the present invention will be further described in the embodiments. It should be noted that the following embodiments are not intended to limit the protection scope of the present invention, and any improvement made on the basis of the present invention does not violate the spirit of the present invention.

Synthesis Examples

Each abbreviation in the following synthesis examples has the meaning commonly understood by those skilled in the art.

Part 1. Preparation of Functionalized Taxanes

Synthetic Scheme 1

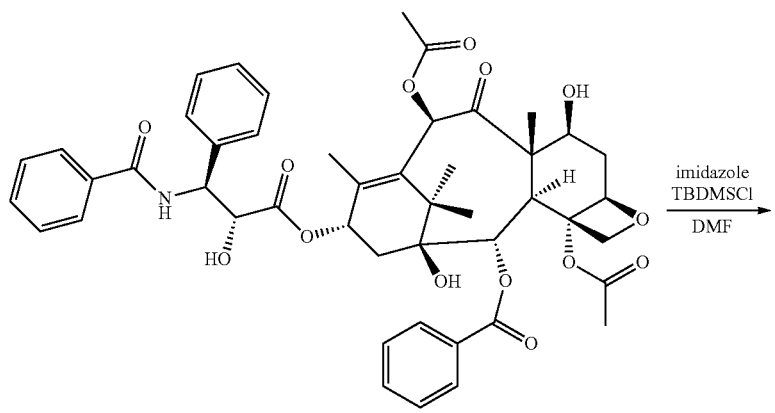

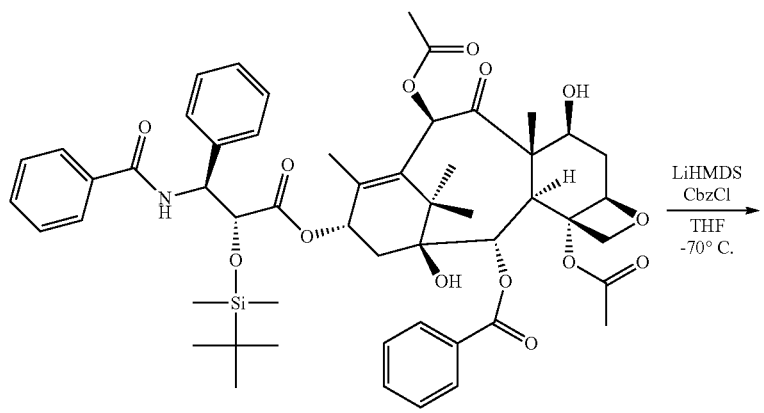

-continued
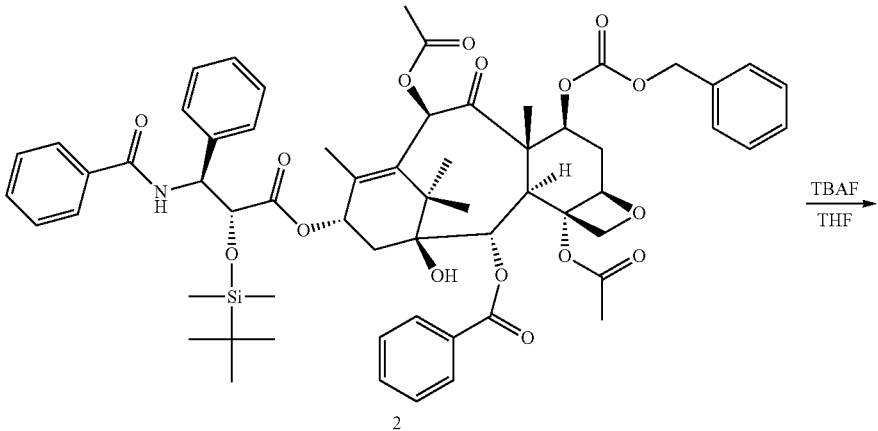
2
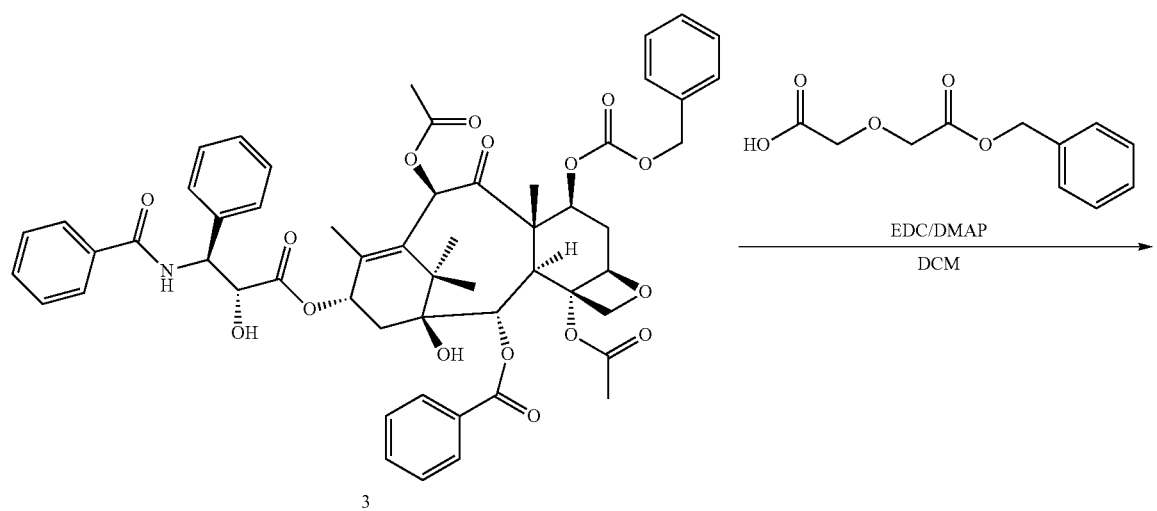
3
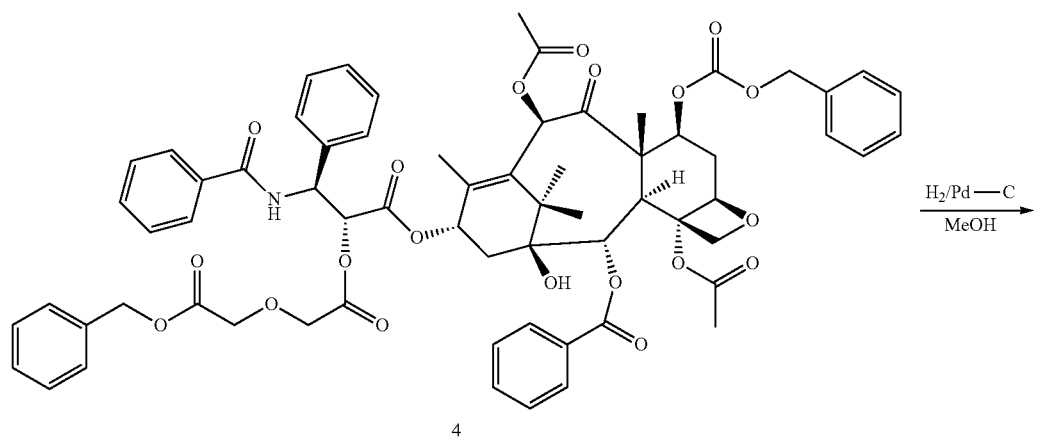
4

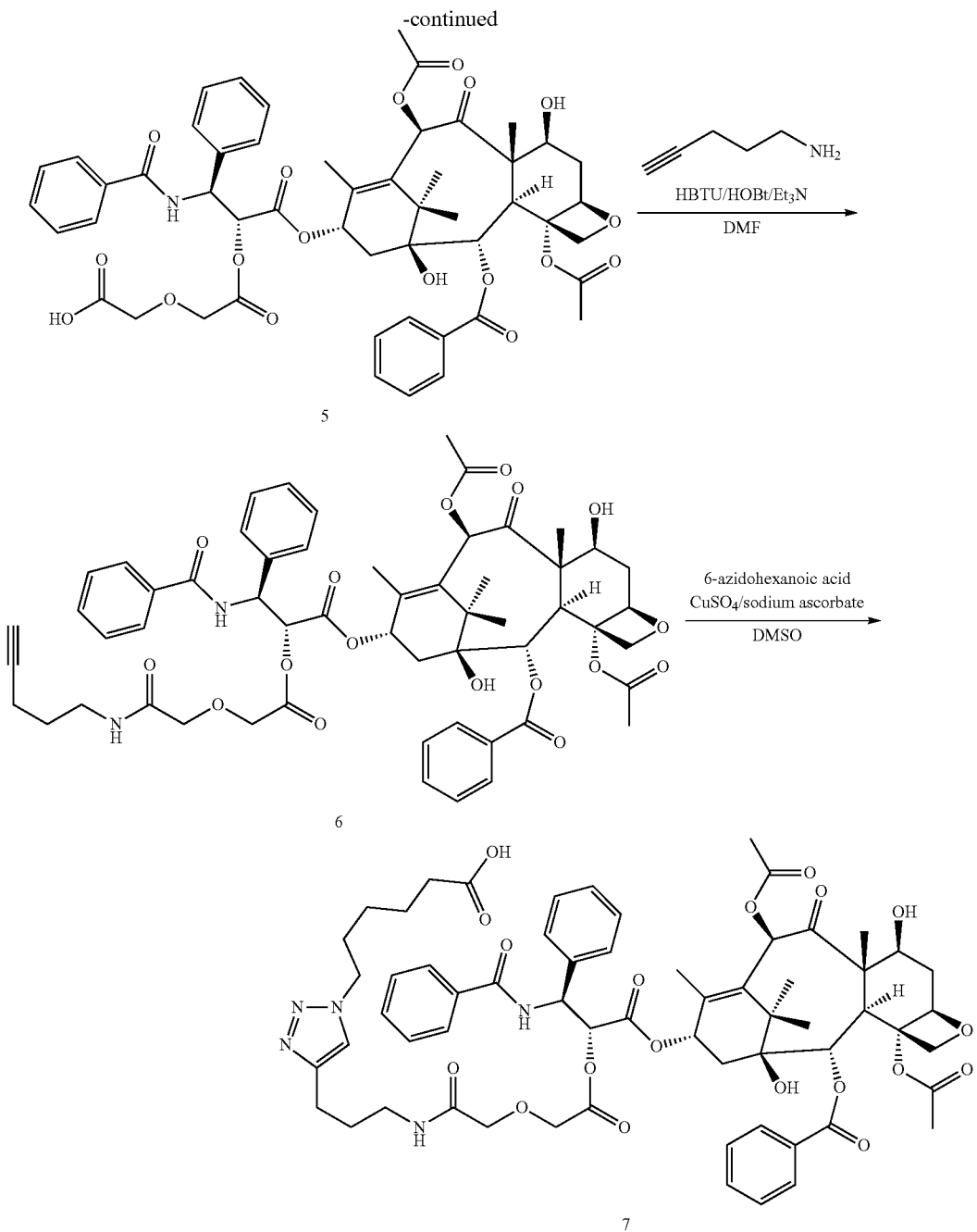

Sample 1: Preparation of Compound 1

To a 1000 mL round-bottom flask charged with 86.0 g (100.6 mmol) of paclitaxel and 23.8 g (350.21 mmol) of imidazole, 300 mL of anhydrous dimethylformamide (DMF) was added, followed by addition of 52.7 g (350.21 mmol) of tert-butyldimethylchloride, and the reaction mixture was stirred at room temperature for 12 h. Upon completion of the reaction, the mixture was partitioned between ethyl acetate (800 mL) and brine (800 mL). The organic phase was further washed with brine (600 mL×2), dried over anhydrous $MgSO_4$, filtered, concentrated, and purified on a silica gel column and eluted with ethyl acetate in petroleum (10-70%) to provide 91.9 g of compound 1. Yield: 95%.

$^1$H NMR (500 MHz, $CDCl_3$, ppm): δ 8.13 (d, J=7.2 Hz, 2H), 7.75 (d, J=7.2 Hz, 2H), 7.63 (t, J=7.2 Hz, 2H), 7.52 (m, 3H), 7.40 (m, 4H), 7.32 (m, 3H), 7.07 (d, J=9.0 Hz, 1H), 6.28 (m, 2H), 5.75 (d, J=9.0 Hz, 1H), 5.72 (d, J=9.0 Hz, 1H), 4.98 (d, J=9.0 Hz, 1H), 4.68 (s, 1H), 4.47 (brs, 1H), 4.36 (d, J=9.0 Hz, 1H), 4.21 (d, J=9.0 Hz, 1H), 3.86 (d, J=7.2 Hz, 1H), 2.57 (m, 4H), 2.52 (s, 1H), 2.43 (m, 1H), 2.23 (s, 3H), 2.16 (m, 1H), 1.87 (s, 3H), 1.83 (m, 1H), 1.71 (s, 3H), 1.25 (s, 3H), 1.15 (s, 3H), 0.81 (s, 9H), −0.03 (s, 3H), −0.26 (s, 3H); ESI-MS (m/z): calcd for $C_{53}H_{65}N_3O_{14}Si$ $[M+H]^+$: 968.4; found: 968.3.

Sample 2: Preparation of Compound 2

In a 500 mL round-bottom flask, 30.0 g (31.02 mmol) of compound 1 was dissolved in 150 mL of anhydrous THF under nitrogen protection and cooled down to −70° C.; 34.2 mL (1.0M) of lithium bis(trimethylsilyl) amide (LHMDS) in THF was then added and stirred for 1 h. To the above solution, 5.86 g (34.2 mmol) of benzyl chloroformate was dropwise added and stirred at −70° C. for 1 h, and then the reaction mixture was allowed to warm up to room temperature and quenched with 5.0 ml of acetic acid. After removal of volatiles, the residue was partitioned between ethyl acetate (500 mL) and brine (500 mL), the organic phase was further washed with brine twice (500 mL×2), dried over anhydrous $MgSO_4$, filtered, concentrated, and purified on a silica gel column and eluted with ethyl acetate in petroleum (10-60%) to provide 30.7 g of compound 2. Yield: 89%.

$^1$H NMR (500 MHz, $CDCl_3$, ppm): δ 8.13 (d, J=7.8 Hz, 2H), 7.77 (d, J=7.8 Hz, 2H), 7.62 (t, J=7.8 Hz, 1H), 7.54 (m, 3H), 7.31-7.45 (m, 12H), 7.10 (d, J=7.8 Hz, 1H), 6.45 (s, 1H), 6.29 (t, J=8.4 Hz, 1H), 5.76 (d, J=7.8 Hz, 1H), 5.72 (d, J=7.8 Hz, 1H), 5.57 (t, J=7.8 Hz, 1H), 5.27 (d, J=12.0 Hz, 1H), 5.20 (d, J=12.0 Hz, 1H), 5.00 (d, J=9.0 Hz, 1H), 4.69 (s, 1H), 4.36 (d, J=7.8 Hz, 1H), 4.22 (d, J=8.4 Hz, 1H), 4.13 (d, J=6.6 Hz, 1H), 4.00 (d, J=6.6 Hz, 1H), 2.57 (m, 1H), 2.56 (s, 3H), 2.43 (m, 1H), 2.19 (s, 3H), 2.18 (m, 1H), 2.04 (s, 3H), 1.98 (s, 3H), 1.97 (t, J=12.0 Hz, 1H), 1.83 (s, 3H), 1.24 (s, 3H), 1.19 (s, 3H), 0.82 (s, 9H), −0.01 (s, 3H), −0.28 (s, 3H);

ESI-MS (m/z): calcd for $C_{61}H_{72}NO_{16}Si$ $[M+H]^+$: 1102.4; found: 1102.5.

Sample 3: Preparation of Compound 3

In a 250 mL round-bottom flask, 25.0 g (21.78 mmol) of compound 2 was dissolved in anhydrous THF (100 mL), and 43.6 mL of tetrabutylammonium fluoride (TBAF, 1.0M) in THF was added and stirred for 5 h at room temperature. Upon completion of the reaction, the resulting reaction mixture was concentrated and purified on a silica gel column and eluted with ethyl acetate in petroleum (10-70%) to provide 19.1 g of compound 3. Yield: 88%.

$^1$H NMR (500 MHz, $CDCl_3$, ppm): δ 8.12 (d, J=7.8 Hz, 2H), 7.77 (d, J=7.8 Hz, 2H), 7.62 (t, J=7.8 Hz, 1H), 7.51 (m, 5H), 7.42 (m, 6H), 7.35 (m, 4H), 7.13 (d, J=7.8 Hz, 1H), 6.41 (s, 1H), 6.21 (t, J=8.4 Hz, 1H), 5.82 (t, J=8.4 Hz, 1H), 5.70 (d, J=6.6 Hz, 1H), 5.51 (m, 1H), 5.26 (d, 1H, J=12.0 Hz, 1H), 5.19 (d, J=12.0 Hz, 1H), 4.96 (d, J=9.0 Hz, 1H), 4.83 (s, 1H), 4.32 (d, J=8.4 Hz, 1H), 4.20 (d, J=8.4 Hz, 1H), 3.95 (d, J=9.6 Hz, 1H), 2.61 (m, 1H), 2.39 (s, 3H), 2.34 (m, 1H), 2.20 (s, 3H), 2.05 (s, 3H), 1.98 (t, J=12.0 Hz, 1H), 1.89 (s, 3H), 1.82 (s, 3H), 1.23 (s, 3H), 1.19 (s, 3H); ESI-MS (m/z): calcd for $C_{55}H_{58}NO_{16}$ $[M+H]^+$: 988.4; found: 988.5.

Sample 4: Preparation of Compound 4

To a 250 mL round-bottom flask charged with 3.41 g (15.18 mmol) of benzyl diglycolic acid monoester and 2.90 g (15.18 mmol) of 1-ethyl-3-(3-dimethylaminopropyl) carbodiimide (EDC), 100 mL of anhydrous chloroform was added and stirred at room temperature for 30 min. To the above solution, 10.0 g (10.11 mmol) of compound 3 and 1.85 g (15.18 mmol) of 4-dimethylaminopyridine (DMAP) were added and stirred for 12 h. Upon completion of the reaction, the reaction mixture was washed with brine three times (150 mL×3), dried over anhydrous $MgSO_4$, filtered, concentrated, and purified on a silica gel column and eluted with ethyl acetate in petroleum (10-60%) to provide 10.3 g of compound 4. Yield: 86%.

$^1$H NMR (500 MHz, $CDCl_3$, ppm): δ 8.15 (d, J=7.8 Hz, 2H), 7.79 (d, J=7.8 Hz, 2H), 7.63 (t, J=7.8 Hz, 1H), 7.53 (m, 3H), 7.38-7.44 (m, 14H), 7.11 (d, J=7.8 Hz, 1H), 6.44 (s, 1H), 6.28 (t, J=9.6 Hz, 1H), 6.06 (d, J=9.6 Hz, 1H), 5.26 (m, 1H), 5.19 (m, 2H), 5.09 (m, 2H), 4.98 (d, J=9.6 Hz, 1H), 4.36 (m, 3H), 4.21 (s, 2H), 3.98 (d, J=6.0 Hz, 1H), 2.61 (m, 1H), 2.49 (s, 3H), 2.41 (m, 2H), 2.29 (m, 1H), 2.19 (s, 3H), 2.06 (s, 3H), 1.98 (t, J=12.0 Hz, 1H), 1.82 (s, 3H), 1.24 (s, 3H), 1.19 (s, 3H); ESI-MS (m/z): calcd for $C_{66}H_{68}NO_{20}$ $[M+H]^+$: 1194.3; found: 1194.5.

Sample 5: Preparation of Compound 5

In a 250 mL hydrogenation glass bottle, 7.0 g (5.86 mmol) of compound 4 was dissolved in 80 mL of methanol, and was treated with 500 mg of 10% Pd—C under hydrogen gas of 1.2 atm for 12 h. Solid material was filtered off, and the filtrate was concentrated and purified on a RP-C18 column and eluted with methanol in water (5-80%) to give 4.62 g of compound 5. Yield: 81%.

$^1$H NMR (500 MHz, $CD_3OD$, ppm): δ 8.15 (d, J=7.2 Hz, 2H), 7.82 (d, J=7.2 Hz, 2H), 7.68 (t, J=7.2 Hz, 1H), 7.60 (d, J=7.2 Hz, 2H), 7.41-7.51 (m, 9H), 7.30 (t, J=7.2 Hz, 1H), 6.46 (s, 1H), 6.11 (m, 1H), 5.91 (d, J=6.6 Hz, 1H), 5.67 (d, J=6.6 Hz, 1H), 5.61 (d, J=6.6 Hz, 1H), 5.02 (d, J=9.6 Hz, 2H), 4.44 (m, 2H), 4.62 (m, 5H), 3.84 (d, J=6.6 Hz, 1H), 2.51 (m, 1H), 2.47 (s, 3H), 2.28 (m, 1H), 2.18 (s, 3H), 1.98 (m, 3H), 1.92 (m, 1H), 1.82 (t, J=12.0 Hz, 1H), 1.67 (s, 3H), 1.16 (s, 3H), 1.15 (s, 3H); ESI-MS (m/z): calcd for $C_{51}H_{56}NO_{18}$ $[M+H]^+$: 970.3; found: 970.3.

Sample 6: Preparation of Compound 6

In a 100 mL round-bottom flask, 3.0 g (3.09 mmol) of compound 5 and 1.41 g (3.71 mmol) of benzotriazole-N, N, N', N'-tetramethyluronium hexafluorophosphate (HBTU) and 502 mg (3.71 mmol) of 1-hydroxybenzotriazole (HOBt) were dissolved in 15.0 mL of dry DMF, and followed by addition of 309 mg (3.71 mmol) 4-pentyn-1-amine and 0.85 mL (6.18 mmol) of triethylamine, and stirred at room temperature for 3 h. Upon completion of the reaction, the reaction mixture was partitioned between ethyl acetate (300 mL) and brine (300 mL). The organic phase was further washed with brine twice (300 mL×2), dried over anhydrous $MgSO_4$, filtered, concentrated, and purified on a silica gel column and eluted with methanol in chloroform (1-10%) to provide 2.43 g of compound 6. Yield: 76%.

$^1$H NMR (500 MHz, DMSO-$d_6$, ppm): δ 8.11 (d, J=7.2 Hz, 2H), 7.63 (d, J=7.2 Hz, 2H), 7.53 (t, J=7.2 Hz, 1H), 7.20-7.45 (m, 10H), 6.76 (m, 2H), 6.21 (s, 1H), 6.18 (t, J=9.0 Hz, 1H), 5.96 (d, J=6.0 Hz, 1H), 5.87 (d, J=7.2 Hz, 1H), 5.50 (s, 1H), 5.43 (t, J=9.0 Hz, 1H), 4.87 (d, J=12.0 Hz, 1H), 4.37 (t, J=7.2 Hz, 1H), 4.22 (m, 1H), 4.12 (m, 1H), 4.05 (dd, J=12.0, 7.2 Hz, 1H), 3.90 (m, 2H), 3.71 (d, J=7.2 Hz, 1H), 3.27 (dd, J=12.0, 7.2 Hz, 2H), 2.47 (m, 1H), 2.37 (s, 3H), 2.29 (m, 1H), 2.06 (s, 3H), 1.93 (m, 3H), 1.85 (m, 3H), 1.81 (t, J=12.0 Hz, 1H), 1.70 (m, 3H), 1.63 (s, 3H), 1.17 (s, 3H), 1.06 (s, 3H); ESI-MS (m/z): calcd for $C_{56}H_{63}N_2O_{17}$ $[M+H]^+$: 1035.4; found: 1035.5.

Sample 7: Preparation of Compound 7

To a 10 mL round-bottom flask charged with 300 mg (0.29 mmol) of compound 6 and 60 mg (0.38 mmol) of 6-azido-hexanoic acid, 5.0 mL of DMSO was added. 100 μL of copper sulfate (1.0M) in water and 100 μL of sodium ascorbate (1.0M) in water were mixed together and added to the above solution. After stirring for 2 days at room temperature, the reaction mixture was partitioned between ethyl acetate (50 mL) and brine (50 mL). The organic phase was further washed with brine twice (50 mL×2), dried over anhydrous $MgSO_4$, filtered, concentrated, and purified on a silica gel column and eluted with methanol in chloroform (1-10%) to give 275 mg of compound 7. Yield: 87%.

$^1$H NMR (500 MHZ, DMSO-$d_6$, ppm): δ 8.11 (d, J=7.2 Hz, 2H), 7.50-7.78 (m, 6H), 7.25-7.45 (m, 9H), 6.43 (s, 1H), 6.03 (t, J=7.8 Hz, 1H), 5.86 (d, J=6.0 Hz, 1H), 5.60 (d, J=7.2 Hz, 1H), 5.58 (d, J=7.2 Hz, 1H), 5.23 (d, J=9.0 Hz, 1H), 4.94 (d, J=9.0 Hz, 1H), 4.63 (s, 1H), 4.46 (s, 1H), 4.35 (m, 4H), 4.18 (m, 2H), 4.13 (m, 2H), 4.02 (m, 3H), 3.77 (d, J=7.2 Hz, 1H), 3.22 (t, J=7.2 Hz, 2H), 2.67 (t, J=7.2 Hz, 2H), 2.43 (m, 2H), 2.37 (s, 3H), 2.25 (m, 3H), 2.16 (m, 1H), 2.15 (s, 3H), 1.97 (s, 3H), 1.81 (m, 3H), 1.73 (t, J=12.0 Hz, 1H), 1.61 (s, 3H), 1.58 (m, 4H), 1.26 (m, 2H), 1.12 (s, 3H), 1.07 (s, 3H); ESI-MS (m/z): calcd for $C_{62}H_{74}N_5O_{19}$ [M+H]$^+$: 1092.5; found: 1092.7.

Synthetic Scheme 2

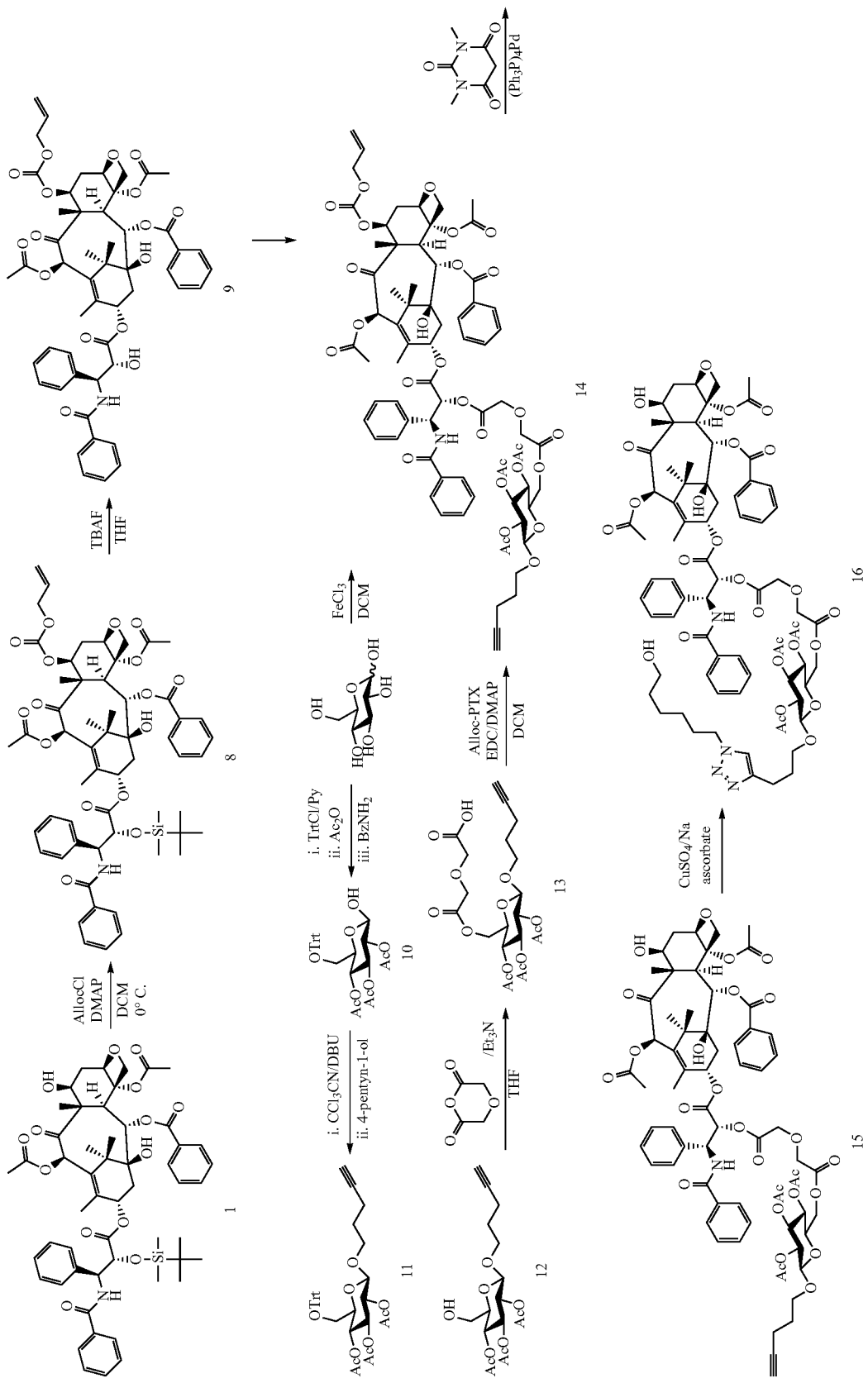

Sample 8: Preparation of Compound 8

To a 250 mL round-bottom flask charged with 30.0 g (30.98 mmol) of compound 1, 120 mL of anhydrous chloroform was added under nitrogen protection and cooled down to 0° C., and followed by 22.71 g (185.9 mmol) of DMAP and 22.71 g (185.9 mmol) of allyl chloroformate Upon completion of addition, the cooled batch was removed, and the reaction mixture was stirred at room temperature for 12 h. After removal of volatiles, the residue was purified on a silica gel column and eluted with ethyl acetate in petroleum (5-60%) to provide 31.5 g of compound 8. Yield: 96%.

$^1$H NMR (300 MHz, CDCl$_3$, ppm): δ 8.12 (d, J=7.2 Hz, 2H), 7.76 (d, J=7.2 Hz, 2H), 7.60 (t, J=7.2 Hz, 2H), 7.51 (m, 3H), 7.42 (m, 4H), 7.33 (m, 3H), 7.15 (d, J=9.0 Hz, 1H), 6.37 (s, 1H), 6.25 (t, J=9.0 Hz, 1H), 5.97 (m, 1H), 5.75 (d, J=9.0 Hz, 1H), 5.71 (d, J=7.2 Hz, 1H), 5.38 (dd, J=10.2, 7.8 Hz, 1H), 5.31 (d, J=15.6 Hz, 1H), 5.23 (d, J=15.6 Hz, 1H), 4.98 (d, J=9.6 Hz, 1H), 4.75 (m, 1H), 4.69 (s, 1H), 4.63 (m, 1H), 4.35 (d, J=9.0 Hz, 1H), 4.20 (d, J=9.0 Hz, 1H), 3.97 (d, J=6.6 Hz, 1H), 2.61 (m, 1H), 2.57 (s, 3H), 2.43 (dd, J=15.0, 9.0 Hz, 1H), 2.21 (dd, J=15.0, 9.0 Hz, 1H), 2.17 (s, 3H), 2.03 (s, 3H), 1.97 (m, 1H), 1.81 (s, 3H), 1.26 (s, 3H), 1.16 (s, 3H), 0.83 (s, 9H), −0.03 (s, 3H), −0.27 (s, 3H); ESI-MS (m/z): calcd for C$_{57}$H$_{70}$NO$_{16}$Si [M+H]$^+$: 1052.4; found: 1052.5.

Sample 9: Preparation of Compound 9

In a 100 mL round-bottom flask, 16.0 g (15.21 mmol) of compound 8 was dissolved in anhydrous THF (50 mL), and 30.5 mL of tetrabutylammonium fluoride (TBAF, 1.0M) in THF was added and stirred for 2 h at room temperature. Upon completion of the reaction, the resulting reaction mixture was concentrated and purified on a silica gel column and eluted with ethyl acetate in petroleum (10-60%) to provide 12.1 g of compound 9. Yield: 85%.

$^1$H NMR (500 MHz, CDCl$_3$, ppm): δ 8.12 (d, J=7.2 Hz, 2H), 7.75 (d, J=7.2 Hz, 2H), 7.60 (t, J=7.2 Hz, 2H), 7.30-7.51 (m, 10H), 7.11 (d, J=9.0 Hz, 1H), 6.37 (s, 1H), 6.17 (t, J=9.0 Hz, 1H), 5.96 (m, 1H), 5.83 (d, J=9.0 Hz, 1H), 5.67 (d, J=7.2 Hz, 1H), 5.43 (m, 1H), 5.32 (d, J=12.0 Hz, 1H), 5.21 (d, J=12.0 Hz, 1H), 4.93 (d, J=9.0 Hz, 1H), 4.77 (s, 1H), 4.70 (m, 1H), 4.63 (m, 1H), 4.31 (d, J=8.4 Hz, 1H), 4.16 (d, J=8.4 Hz, 1H), 4.08 (dd, J=15.0, 7.2 Hz, 1H), 3.90 (d, J=7.2 Hz, 1H), 2.61 (m, 1H), 2.37 (s, 3H), 2.35 (m, 1H), 2.13 (m, 4H), 1.97 (t, J=12.0 Hz, 1H), 1.84 (s, 3H), 1.81 (m, 1H), 1.80 (s, 3H), 1.19 (s, 3H), 1.15 (s, 3H); ESI-MS (m/z): calcd for C$_{51}$H$_{56}$NO$_{16}$ [M+H]$^+$: 938.3; found: 938.6.

Sample 10: Preparation of Compound 10

In a 500 mL round bottom flask, 20.0 g (111.1 mmol) of anhydrous glucose and 32.0 g (114.8 mmol) of triphenylchloromethane were combined in 160 mL of anhydrous pyridine, heated to 50° C., and stirred for 12 h; then 50 mL of acetic anhydride was added and stirred for another 8 h. Upon completion of the reaction, the reaction mixture was poured into ice water upon which a white precipitate formed; the resulting precipitate was filtered, dried under high vacuum, redissolved in anhydrous ether (200 mL), and cooled down to 0° C.; 35.7 g (333.3 mmol) of benzylamine was added to the above ether solution and stirred overnight. The final reaction mixture was washed with water (100 mL×2), dried over anhydrous MgSO$_4$, filtered, concentrated, and purified on a silica gel column and eluted ethyl acetate in petroleum (10-70%) to give 37.8 g of compound 10. Yield: 62%.

$^1$H NMR (300 MHz, CDCl$_3$, ppm): δ 7.20-7.60 (m, 15H), 5.51 (d, J=3.6 Hz, 1H), 5.46 (t, J=10.0 Hz, 1H), 5.21 (t, J=10.0 Hz, 1H), 4.95 (dd, J=3.6, 10.0 Hz, 1H), 4.17 (m, 1H), 3.27 (d, J=10.0 Hz, 1H), 3.11 (m, 1H), 2.08 (s, 3H), 2.00 (s, 3H), 1.74 (s, 3H); ESI-MS (m/z): calcd for C$_{31}$H$_{33}$O$_9$ [M+H]$^+$: 549.2; found: 549.3.

Sample 11: Preparation of Compound 11

To a 250 mL round-bottom flask charged with 20.0 g (36.42 mmol) of compound 10, 100 mL of anhydrous chloroform was added, followed by addition of 4.38 mL (185.9 mmol) of trichloroacetonitrile and 0.5 mL (3.65 mmol) of 1,8-diazabicyclo (5,4,0) undec-7-ene under the protection of nitrogen, and stirred at room temperature overnight. After removal of volatiles and the residue was purified by flash chromatography on silica gel (ethyl acetate:petroleum/10-70%) to provide an intermediate as an oil; The intermediate was dissolved in 120 mL of anhydrous chloroform and cooled down to −70° C. under nitrogen protection, and then 5.9 mL (40.06 mmol) of trimethylsilyl trifluoromethanesulfonate was added and stirred for 2 h, and followed by addition of 6.13 g (72.85 mmol) of 4-pentyn-1-ol. After stirring for another 5 h, the reaction was stopped by slowly adding 5.9 mL of triethylamine. The reaction mixture was filtered, and the filtrate was concentrated and purified on a silica gel column and eluted ethyl acetate in petroleum (10-70%) to give 12.5 g of compound 11. Yield: 56%.

$^1$H NMR (300 MHz, CDCl$_3$, ppm): δ 7.27-7.60 (m, 15H), 5.31 (d, J=3.6 Hz, 1H), 5.05 (t, J=10.0 Hz, 1H)), 4.53 (d, J=10.0 Hz, 1H), 4.17 (m, 1H), 4.05 (m, 1H), 3.78 (m, 1H), 3.57 (m, 1H), 3.27 (d, J=10.0 Hz, 1H), 3.11 (m, 1H), 2.31 (t, J=7.0 Hz, 2H), 2.08 (s, 3H), 1.95 (s, 1H), 2.00 (s, 3H), 1.74 (s, 3H), 1.67 (m, 2H); ESI-MS (m/z): calcd for C$_{31}$H$_{33}$O$_9$ [M+H]$^+$: 615.2; found: 615.3.

Sample 12: Preparation of Compound 12

In a 250 mL round-bottom flask, 10.0 g (16.25 mmol) of compound 11 was dissolved 100 mL of dichloromethane, and followed by addition of 7.89 g (48.75 mmol) of ferric chloride, and stirred at room temperature overnight. Upon completion of the reaction, the reaction mixture was washed with distilled water (100 mL×3), dried over anhydrous MgSO$_4$, filtered, concentrated, and purified on a silica gel column and eluted ethyl acetate in petroleum (10-80%) to give 4.52 g of compound 12. Yield: 75%.

$^1$H NMR (300 MHz, CDCl$_3$, ppm): δ 5.18 (d, J=3.6 Hz, 1H), 4.97 (t, J=10.0 Hz, 1H), 4.90 (d, J=10.0 Hz, 1H), 4.49 (m, 1H), 3.91 (m, 1H), 3.78 (m, 1H), 3.50-3.70 (m, 4H), 2.21 (t, J=7.0 Hz, 2H), 1.93-2.10 (m, 10H), 1.70 (m, 2H); ESI-MS (m/z): calcd for C$_{17}$H$_{25}$O$_9$ [M+H]$^+$: 373.1; found: 373.2.

Sample 13: Preparation of Compound 13

In a 250 mL round-bottom flask, 3.6 g (9.65 mmol) of compound 12 was dissolved in 50 mL of anhydrous dichloromethane, followed by addition of 3.36 g (28.95 mmol) of diglycolic acid anhydride and 3.0 mL of triethylamine, and stirred at room temperature overnight. After removal of volatiles, the residue was partitioned between ethyl acetate (100 mL) and saturated citric acid (100 mL); the aqueous phase was extracted with ethyl acetate (60 mL×2), and the organic phases were pooled, dried over anhydrous MgSO$_4$, filtered, concentrated, and purified on a silica gel column and eluted with methanol in chloroform (0-10%) to give 3.39 g of compound 13. Yield: 72%.

$^1$H NMR (300 MHz, CDCl$_3$, ppm): δ 5.21 (d, J=3.6 Hz, 1H), 5.09 (t, J=10.0 Hz, 1H), 4.93 (d, J=10.0 Hz, 1H), 4.50 (d, J=10.0 Hz, 1H), 4.41 (d, J=10.0 Hz, 1H), 4.27 (m, 5H), 4.12 (m, 1H), 3.92 (m, 1H), 3.72 (m, 1H), 3.60 (m, 1H), 2.20 (t, J=7.0 Hz, 2H), 1.92-2.07 (m, 10H), 1.70-1.75 (m, 2H); ESI-MS (m/z): calcd for C$_{21}$H$_{29}$O$_{13}$ [M+H]$^+$: 489.1; found: 489.2.

Sample 14: Preparation of Compound 14

To a 250 mL round-bottom flask charged with 2.5 g (5.12 mmol) of compound 13 and 978 mg (5.12 mmol) of 1-ethyl-3-(3-dimethylaminopropyl) carbodiimide (EDC), 30 mL of anhydrous dichloromethane was added, and stirred at room temperature for 30 min; and then 2.39 g (2.56 mmol) of compound 3 and 629 mg (5.12 mmol) of DMAP were added. The reaction was continuously stirred for 12 h. After removal of volatiles, the residue was partitioned between ethyl acetate (100 mL) and brine (100 mL); the aqueous phase was extracted with ethyl acetate (60 mL×2), and the organic phases were pooled, dried over anhydrous $MgSO_4$, filtered, concentrated, and purified on a silica gel column and eluted with ethyl acetate in petroleum (10-80%) to provide 3.09 g of compound 14. Yield: 86%.

$^1$H NMR (500 MHz, $CDCl_3$, ppm): δ 8.15 (d, J=7.2 Hz, 2H), 7.73 (d, J=7.2 Hz, 2H), 7.60 (t, J=7.2 Hz, 1H), 7.15-7.51 (m, 10H), 6.97 (d, J=9.0 Hz, 1H), 6.31 (m, 2H), 6.05 (m, 1H), 5.71 (d, J=9.0 Hz, 1H), 5.62 (d, J=7.2 Hz, 1H), 5.46 (m, 1H), 4.90-5.36 (m, 6H), 4.00-4.60 (m, 14H), 3.95 (d, J=7.2 Hz, 1H), 3.82 (m, 1H), 3.60 (m, 1H), 2.58 (m, 1H), 2.37 (s, 3H), 2.33 (m, 1H), 2.20 (m, 6H), 1.92-2.05 (m, 11H), 1.84 (s, 3H), 1.82 (m, 4H), 1.70-1.81 (m, 5H), 1.20 (s, 3H), 1.15 (s, 3H); ESI-MS (m/z): calcd for $C_{72}H_{82}NO_{28}$ [M+H]$^+$: 1408.5; found: 1408.7.

Sample 15: Preparation of Compound 15

To a 250 mL round-bottom flask charged with 2.0 g (1.42 mmol) of compound 14, 165 mg (0.142 mmol) of tetrakis(triphenylphosphine) palladium (0), and 266 mg (1.70 mmol) of 1,3-dimethylbarbituric acid under nitrogen protection, 20.0 mL of anhydrous THF was added and the reaction mixture was stirred at room temperature for 5 h. After removal of volatiles and the residue was purified on a silica gel column and eluted with methanol in chloroform (0-8%) to give 1.57 g of compound 15. Yield: 83%.

$^1$H NMR (500 MHz, $CDCl_3$, ppm): δ 8.13 (d, J=7.2 Hz, 2H), 7.74 (d, J=7.2 Hz, 2H), 7.58 (t, J=7.2 Hz, 1H), 7.15-7.51 (m, 10H), 6.95 (d, J=9.0 Hz, 1H), 6.30 (m, 2H), 6.03 (m, 1H), 5.72 (d, J=9.0 Hz, 1H), 5.60 (d, J=7.2 Hz, 1H), 4.90-5.36 (m, 3H), 4.00-4.60 (m, 14H), 3.96 (d, J=7.2 Hz, 1H), 3.81 (m, 1H), 3.61 (m, 1H), 2.61 (m, 1H), 2.36 (s, 3H), 2.35 (m, 1H), 2.21 (m, 6H), 1.92-2.05 (m, 11H), 1.85 (s, 3H), 1.81 (m, 4H), 1.70-1.80 (m, 5H), 1.21 (s, 3H), 1.15 (s, 3H); ESI-MS (m/z): calcd for $C_{68}H_{78}NO_{26}$ [M+H]$^+$: 1324.4; found: 1324.3.

Sample 16: Preparation of Compound 16

To a 25 mL round-bottom flask charged with 500 mg (0.38 mmol) of compound 15 and 108 mg (0.76 mmol) of 6-azido-hexanoic acid, 5.0 mL of DMSO was added. 100 μL of copper sulfate (1.0M) in water and 100 μL of sodium ascorbate (1.0M) in water were mixed together and added to the above solution. After stirring for 2 days at room temperature, the reaction mixture was partitioned between ethyl acetate (50 mL) and brine (50 mL), the organic phase was further washed with brine twice (50 mL×2), dried over anhydrous $MgSO_4$, filtered, concentrated, and purified on a silica gel column and eluted with methanol in chloroform (1-10%) to provide 496 mg of compound 16. Yield: 91%.

$^1$H NMR (500 MHz, $CD_3OD$, ppm): δ 8.15 (d, J=7.2 Hz, 2H), 7.73 (d, J=7.2 Hz, 2H), 7.60 (t, J=7.2 Hz, 1H), 7.15-7.51 (m, 11H), 6.97 (d, J=9.0 Hz, 1H), 6.32 (m, 2H), 6.03 (m, 1H), 5.73 (d, J=9.0 Hz, 1H), 5.62 (d, J=7.2 Hz, 1H), 4.90-5.36 (m, 3H), 4.00-4.60 (m, 14H), 3.96 (d, J=7.2 Hz, 1H), 3.81 (m, 1H), 3.61 (m, 3H), 2.721 (m, 2H), 2.53 (m, 1H), 2.33-2.37 (m, 4H), 2.21 (m, 6H), 1.92-2.05 (m, 11H), 1.85 (s, 3H), 1.81 (m, 4H), 1.70-1.80 (m, 7H), 1.42 (m, 2H), 1.25 (m, 4H), 1.22 (s, 3H), 1.13 (s, 3H); ESI-MS (m/z): calcd for $C_{74}H_{91}N_4O_{27}$ [M+H]$^+$: 1467.6; found: 1467.9.

Synthetic Scheme 3

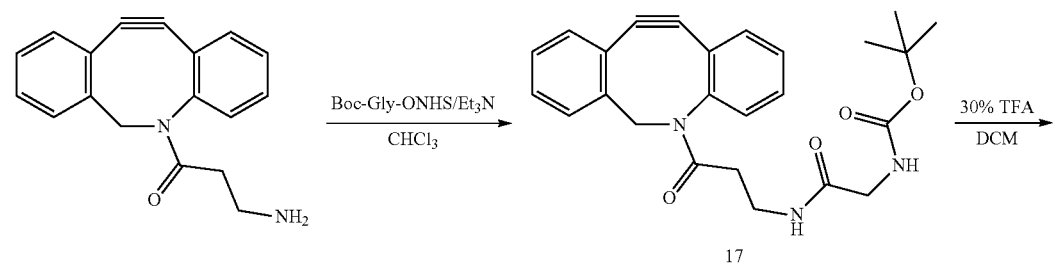

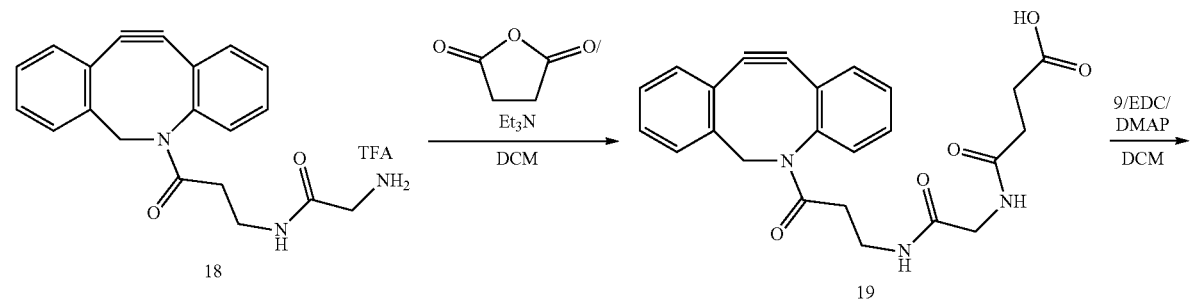

-continued
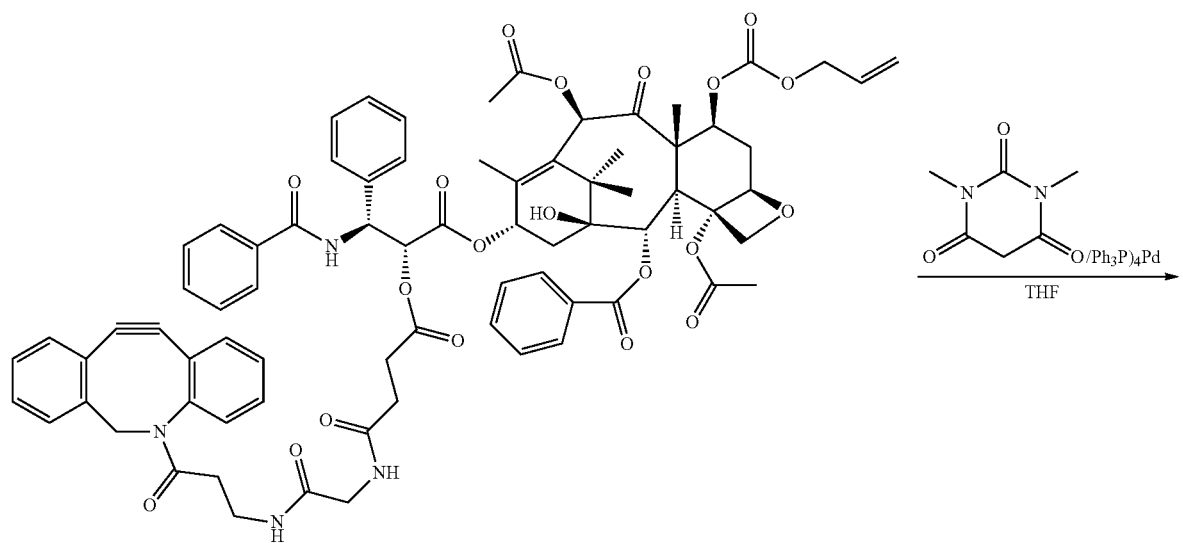
20
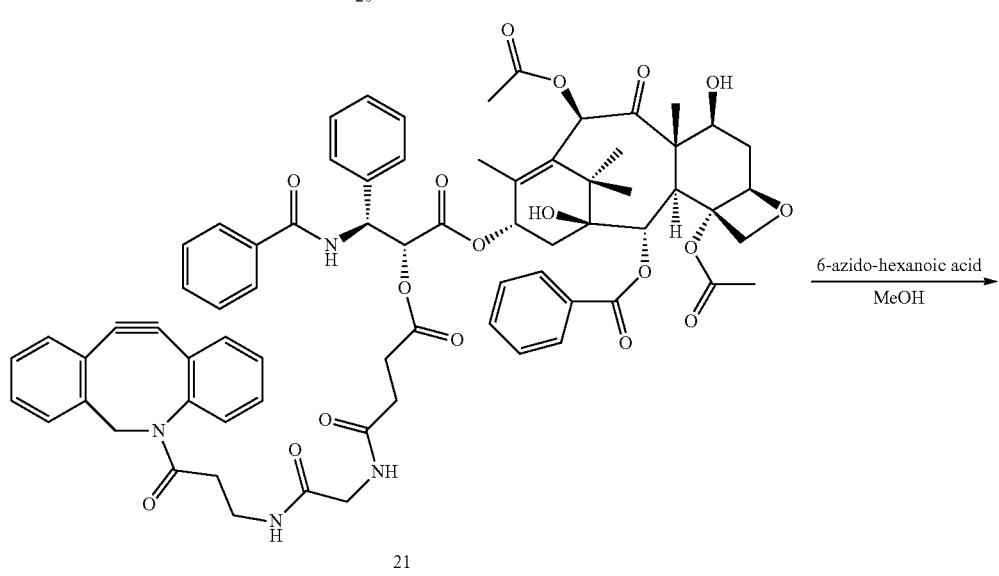
21
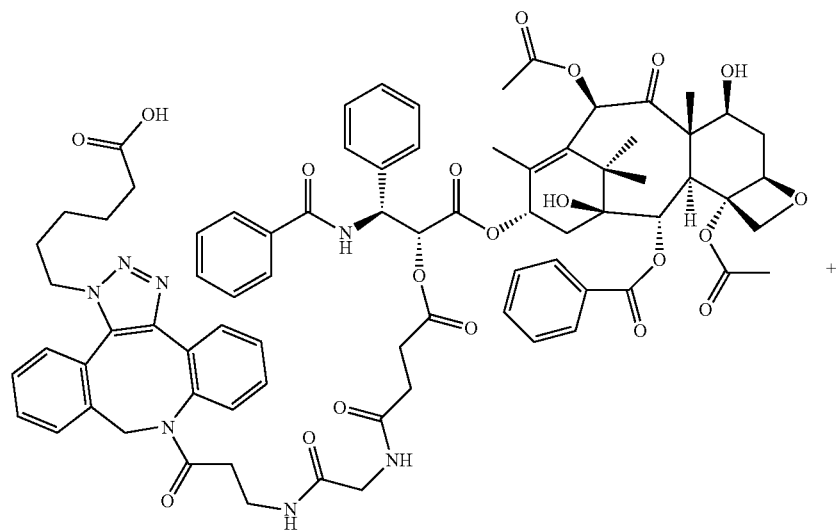
22a
+

-continued

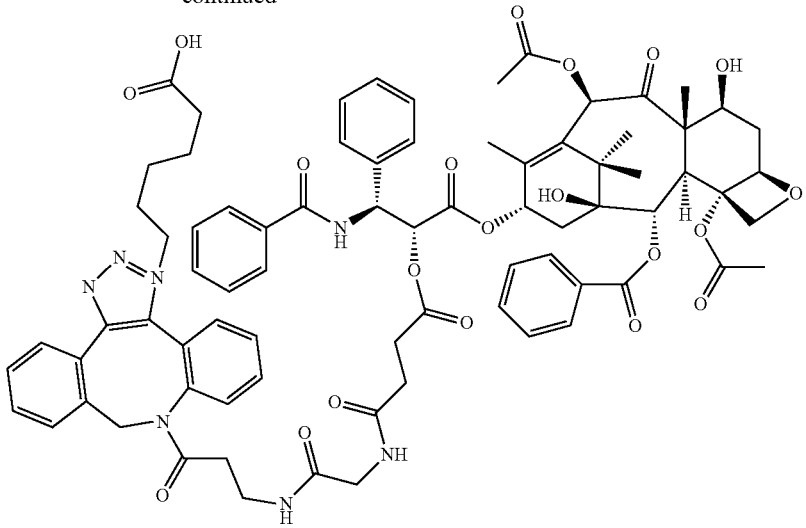

22b

Sample 17: Preparation of Compound 17

In a 250 mL round-bottom flask, 5.0 g (18.09 mmol) of 3-amniopropanoyl dibenzocyclooctyne amide was dissolved in 100 mL of anhydrous chloroform, followed by addition of 5.0 mL of triethylamine and 5.35 g (19.91 mmol) of Boc-glycine N-hydroxyl succinimide ester, and stirred at room temperature overnight. The reaction mixture was washed with brine twice (100 mL×2), dried over anhydrous $MgSO_4$, filtered, concentrated, and purified on a silica gel column and eluted with acetone in chloroform (0-50%) to give 6.73 g of compound 17. Yield: 85%.

$^1$H NMR (300 MHz, $CDCl_3$, ppm): δ 7.73 (m, 1H), 7.13-7.16 (m, 7H), 6.50 (s, 1H), 5.10 (d, J=15.0 Hz, 1H), 3.80 (m, 2H), 3.68 (d, J=15.0 Hz, 1H), 2.57 (m, 1H), 2.05 (m, 1H), 1.46 (s, 9H); ESI-MS (m/z): calcd for $C_{25}H_{28}N_3O_4$ $[M+H]^+$: 434.2; found: 434.3.

Sample 18: Preparation of Compound 18

To a 100 mL round-bottom flask charged with 6.0 g (12.82 mmol) of compound 17, 30 mL of dichloromethane and 10.0 mL of trifluoracetic acid were successively added at 0° C., and stirred overnight. After removal of volatiles, the residue was purified on a reverse phase C-18 column and eluted with acetonitrile in water (5-70%) to provide 1.62 g of compound 18. Yield: 38%.

$^1$H NMR (300 MHz, $CD_3OD$, ppm): δ 7.68 (m, 1H), 7.13-7.16 (m, 7H), 5.13 (d, J=15.0 Hz, 1H), 3.86 (m, 2H), 3.73 (d, J=15.0 Hz, 1H), 3.33 (m, 2H), 2.52 (m, 1H), 2.07 (m, 1H); ESI-MS (m/z): calcd for $C_{20}H_{20}N_3O_2$ $[M+H]^+$: 334.1; found: 334.1.

Sample 19: Preparation of Compound 19

To a 100 mL round-bottom flask charged with 1.7 g (3.62 mmol) of compound 18, 20 mL of chloroform, 5.0 mL of triethylamine, and 905 mg (9.05 mmol) of diglycolic acid anhydride were successively added at 0° C., and stirred overnight. After removal of volatiles, the residue was partitioned between chloroform (20 mL) and aqueous HCl (1.0 N, 20 mL); the organic phase was evaporated, and the residue was purified on a reverse phase C-18 column and eluted with acetonitrile in water (10-80%) to provide 1.52 g of compound 19. Yield: 96%.

$^1$H NMR (300 MHz, DMSO-$d_6$, ppm): δ 7.70-7.93 (m, 3H), 7.29-7.61 (m, 4H), 5.34 (d, J=15.0 Hz, 1H), 4.02 (m, 2H), 3.65 (d, J=15.0 Hz, 1H), 3.23 (m, 2H), 2.25-2.52 (m, 6H); ESI-MS (m/z): calcd for $C_{24}H_{24}N_3O_5$ $[M+H]^+$: 434.1; found: 434.2.

Sample 20: Preparation of Compound 20

To a 100 mL round-bottom flask charged with 1.0 g (2.31 mmol) of compound 19 and 440 mg (2.31 mmol) of 1-ethyl-3-(3-dimethylaminopropyl) carbodiimide (EDC), 30 mL of anhydrous dichloromethane was added, and stirred at room temperature for 30 min; and then 1.11 g (1.16 mmol) of compound 9 and 282 mg (2.31 mmol) of DMAP were added. The reaction was continuously stirred for 12 h. After removal of volatiles, the residue was partitioned between ethyl acetate (50 mL) and brine (50 mL); the aqueous phase was extracted with ethyl acetate (30 mL×2), and the organic phases were pooled, dried over anhydrous $MgSO_4$, filtered, concentrated, and purified on a silica gel column and eluted with methanol in dichloromethane (0-10%) to provide 1.31 g of compound 20. Yield: 83%.

$^1$H NMR (500 MHz, $CDCl_3$, ppm): δ 8.11 (d, J=7.2 Hz, 2H), 7.17-7.77 (m, 23H), 6.37 (s, 1H), 6.20 (t, J=9.0 Hz, 1H), 5.95 (m, 1H), 5.82 (d, J=9.0 Hz, 1H), 5.68 (d, J=7.2 Hz, 1H), 5.46 (m, 1H), 5.35 (d, J=12.0 Hz, 1H), 5.26 (m, 2H), 4.97 (d, J=9.0 Hz, 1H), 4.72 (m, 1H), 4.41 (m, 2H), 4.29 (m, 1H), 4.21 (m, 1H), 4.02 (m, 2H), 3.52-3.76 (m, 5H), 3.21 (m, 2H), 2.75 (m, 4H), 2.57 (m, 2H), 2.42 (s, 3H), 2.33 (m, 1H), 2.15 (m, 3H), 1.98 (m, 2H), 1.86 (s, 3H), 1.82 (m, 1H), 1.80 (s, 3H), 1.19 (s, 3H), 1.17 (s, 3H); ESI-MS (m/z): calcd for $C_{75}H_{77}N_4O_{20}$ $[M+H]^+$: 1353.5; found: 1353.3.

Sample 21: Preparation of Compound 21

To a 25 mL round-bottom flask charged with 900 mg (0.663 mmol) of compound 20, 60 mg (0.051 mmol) of tetrakis (triphenylphosphine) palladium (0), and 115 mg (0.769 mmol) of 1,3-dimethylbarbituric acid under nitrogen protection, 10.0 mL of anhydrous THF was added; the reaction mixture was stirred at room temperature for 2 h. After removal of volatiles and the residue was purified on a silica gel column and eluted with methanol in chloroform (0-10%) to give 691 mg of compound 21. Yield: 82%.

$^1$H NMR (500 MHz, $CDCl_3$, ppm): δ 8.12 (d, J=7.2 Hz, 2H), 7.17-7.77 (m, 23H), 6.52 (m, 2H), 6.20 (t, J=9.0 Hz, 1H), 5.99 (m, 1H), 5.75 (d, J=9.0 Hz, 1H), 5.68 (d, J=7.2 Hz, 1H), 5.21 (m, 2H), 4.99 (d, J=9.0 Hz, 1H), 4.72 (m, 1H), 4.41 (m, 2H), 4.29 (m, 1H), 4.21 (m, 1H), 4.01 (m, 2H), 3.52-3.76 (m, 5H), 3.20 (m, 2H), 2.73 (m, 4H), 2.55 (m, 2H), 2.42 (s, 3H), 2.33 (m, 1H), 2.15 (m, 3H), 1.98 (m, 2H), 1.87 (s, 3H), 1.83 (m, 1H), 1.81 (s, 3H), 1.19 (s, 3H), 1.18 (s, 3H); ESI-MS (m/z): calcd for $C_{71}H_{73}N_4O_{18}$ [M+H]$^+$: 1269.5; found: 1269.6.

Sample 22: Preparation of Compound 22

To a 25 mL round-bottom flask charged with 250 mg (0.196 mmol) of compound 21 and 46 mg (0.196 mmol) of 6-azido-hexanoic acid, 5.0 mL of methanol was added. 100 µL of copper sulfate (1.0M) in water and 100 µL of sodium ascorbate (1.0M) in water were mixed together, and then added to the above solution. After stirring overnight at room temperature, the reaction mixture was concentrated, and purified on a reverse phase column and eluted with acetonitrile in water (1-10%) to provide 201 mg of compound 22a and 22b. Yield: 72%.

$^1$H NMR (500 MHz, CDCl$_3$, ppm): δ 8.11 (d, J=7.2 Hz, 2H), 7.17-7.77 (m, 24H), 6.51 (m, 2H), 6.22 (t, J=9.0 Hz, 1H), 5.97 (m, 1H), 5.73 (d, J=9.0 Hz, 1H), 5.67 (d, J=7.2 Hz, 1H), 5.20 (m, 2H), 4.97 (d, J=9.0 Hz, 1H), 4.72 (m, 1H), 4.42 (m, 2H), 4.27 (m, 1H), 4.22 (m, 1H), 4.03 (m, 2H), 3.52-3.76 (m, 5H), 3.23 (m, 4H), 2.73 (m, 4H), 2.53 (m, 4H), 2.42 (s, 3H), 2.33 (m, 1H), 2.15 (m, 3H), 1.98 (m, 2H), 1.87 (s, 3H), 1.83 (m, 1H), 1.75-1.81 (m, 5H), 1.45 (m, 2H), 1.29 (m, 2H), 1.17 (s, 3H), 1.13 (s, 3H); ESI-MS (m/z): calcd for $C_{77}H_{84}N_7O_{20}$ [M+H]$^+$: 1426.5; found: 1426.7.

Synthetic Scheme 4

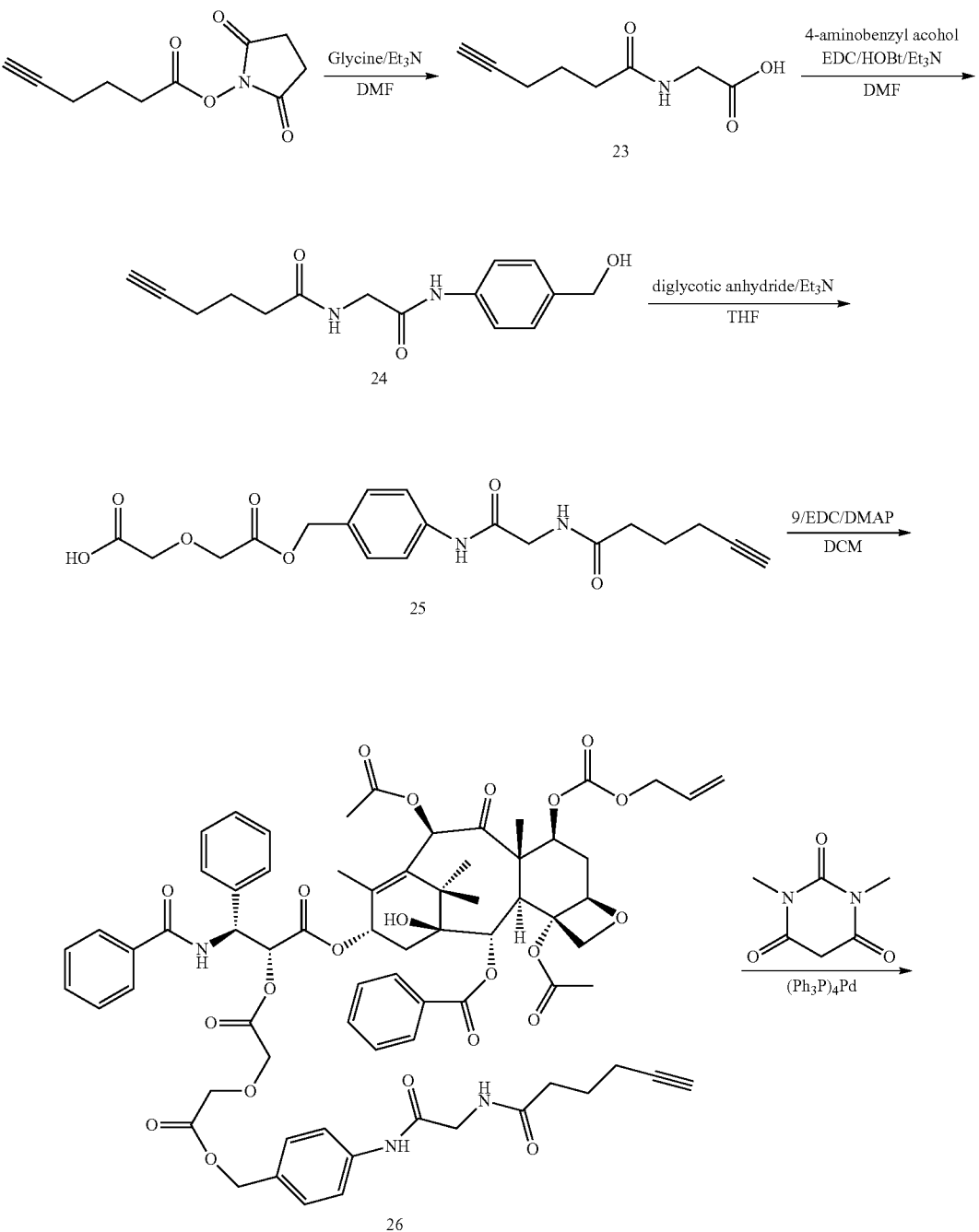

-continued

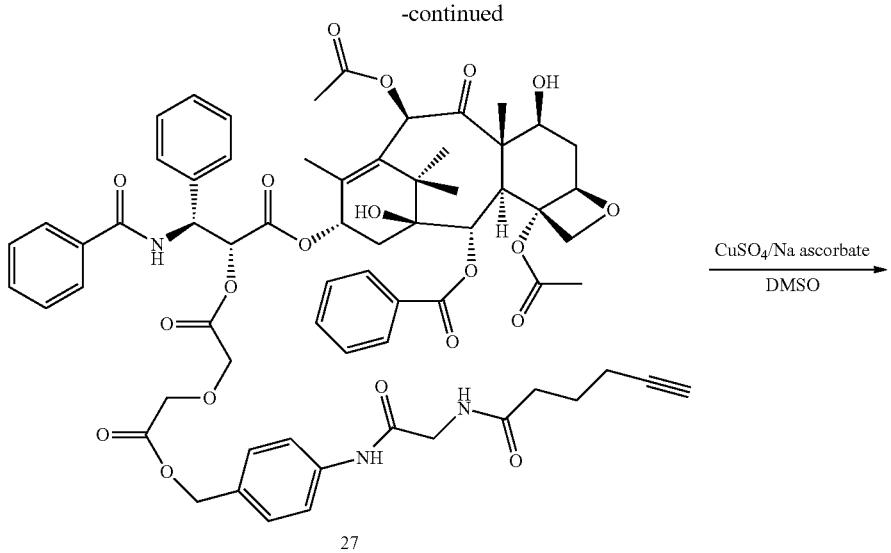

27

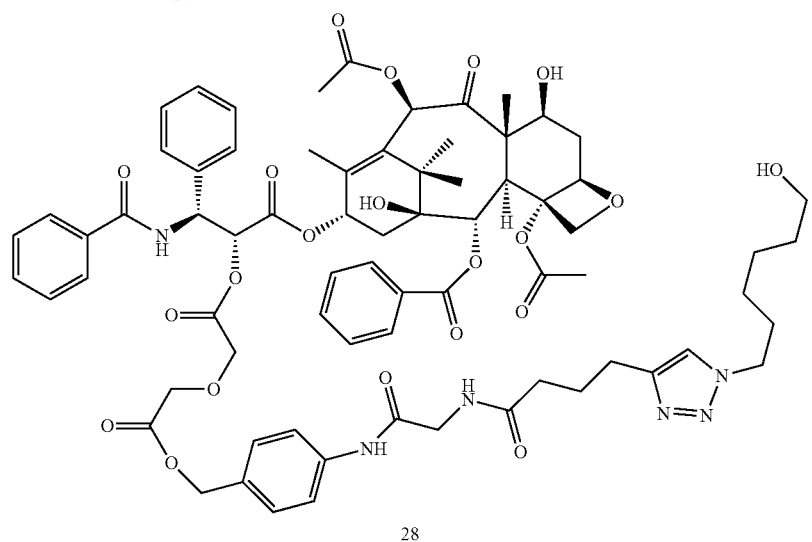

28

Sample 23: Preparation of Compound 23

To a 250 mL round bottom flask charged with 3.0 g (39.97 mmol) of glycine and 5.0 mL (36.17 mmol) of triethylamine in 15.0 mL of DMF, 5.57 g (26.64 mmol) of 4-alkynoic acid N-hydroxysuccinimide ester in dry DMF was dropwise added, and stirred at room temperature overnight. After removal of volatiles, the residue was acidified with concentrated HCl solution, and extracted with ethyl acetate twice (250 mL×2); the organic phases were pooled, dried over anhydrous MgSO$_4$, filtered, concentrated, and purified on a reverse phase C-18 column and eluted with acetonitrile in water (10-70%) to provide 3.38 g of compound 23. Yield: 75%.

$^1$H NMR (300 MHz, D$_2$O, ppm): δ 3.95 (s, 2H), 2.43 (t, J=7.2 Hz, 2H), 2.33 (t, J=3.0 Hz, 1H), 2.23 (m, 2H), 1.79 (m, 2H); ESI-MS (m/z): calcd for C$_8$H$_{12}$NO$_3$ [M+H]$^+$: 170.1; found: 170.1.

Sample 24: Preparation of Compound 24

To a 100 mL round-bottom flask charged with 2.5 g (14.78 mmol) of compound 23, 3.39 g (17.75 mmol) of 1-ethyl-3-(3-dimethylaminopropyl) carbodiimide (EDC), and 2.40 g (17.75 mmol) of 1-hydroxybenzotriazole (HOBt) in 100 mL of anhydrous DMF, 2.73 g (22.17 mmol) of 4-aminobenzyl alcohol, and 3.0 mL of triethylamine were added; and stirred at room temperature for 3 h. Upon completion of the reaction, the reaction mixture was partitioned between ethyl acetate (300 mL) and brine (300 mL), and the organic phase was further washed with brine twice (300 mL×2), dried over anhydrous MgSO$_4$, filtered, concentrated, and purified on a silica gel column and eluted with methanol in chloroform (1-10%) to provide 3.48 g of compound 24. Yield: 86%.

$^1$H NMR (300 MHz, DMSO-d$_6$, ppm): δ 9.81 (s, 1H), 8.08 (s, 1H), 7.42 (d, J=7.8 Hz, 2H), 7.13 (d, J=7.8 Hz, 2H), 4.99 (brs, 1H), 4.31 (s, 2H), 3.74 (s 2H), 1.96-2.15 (m, 5H), 1.57 (t, J=7.2 Hz, 2H); ESI-MS (m/z): calcd for C$_{15}$H$_{19}$N$_2$O$_3$ [M+H]$^+$: 275.1; found: 275.1.

Sample 25: Preparation of Compound 25

To a 250 mL round-bottom flask charged with 2.3 g (8.39 mmol) of compound 24, 20 mL of chloroform, 5.0 mL of triethylamine, and 2.92 g (25.17 mmol) of diglycolic acid anhydride were successively added and stirred at room temperature overnight. After removal of volatiles, the residue was partitioned between ethylacetate (150 mL) and saturated citric acid (150 mL); the aqueous phase was further extracted with ethyl acetate (100 mL×2), and the organic phases were combined together, dried over anhydrous MgSO$_4$, filtered, concentrated, and purified on a silica gel column and eluted with methanol in chloroform (0-15%) to provide 2.52 g of compound 25. Yield: 77%.

$^1$H NMR (500 MHz, DMSO-d$_6$, ppm): δ 10.0 (s, 1H), 8.12 (s, 1H), 7.42 (d, J=7.8 Hz, 2H), 7.19 (d, J=7.8 Hz, 2H), 4.99 (s, 2H), 4.11 (s, 2H), 3.92 (s, 2H), 3.75 (s, 2H), 2.05-2.15 (m, 5H), 1.57 (t, J=7.2 Hz, 2H); ESI-MS (m/z): calcd for C$_{19}$H$_{23}$N$_2$O$_7$ [M+H]$^+$: 391.1; found: 391.1.

Sample 26: Preparation of Compound 26

To a 100 mL round-bottom flask charged with 1.5 g (3.85 mmol) of compound 25 and 736 mg (3.85 mmol) of 1-ethyl-3-(3-dimethylaminopropyl) carbodiimide (EDC), 50 mL of anhydrous dichloromethane were added, and stirred at room temperature for 30 min; and then 1.8 g (1.93 mmol) of compound 9 and 470 mg (3.85 mmol) of DMAP were added. The reaction was continuously stirred for another 12 h. After removal of volatiles, the residue was partitioned between ethyl acetate (100 mL) and brine (100 mL); the aqueous phase was extracted with ethyl acetate (50 mL×3), and the organic phases were pooled, dried over anhydrous MgSO$_4$, filtered, concentrated, and purified on a silica gel column and eluted with methanol in dichloromethane (0-10%) to provide 2.33 g of compound 26. Yield: 92%.

$^1$H NMR (500 MHz, CDCl$_3$, ppm): δ 8.85 (s, 1H), 8.03 (d, J=7.2 Hz, 2H), 7.62 (t, J=7.2 Hz, 1H), 749 (t, J=7.2 Hz, 1H), 7.30-7.42 (m, 6H), 7.20-7.30 (m, 7H), 7.13 (m, 1H), 7.10 (m, 2H), 6.57 (s, 1H), 6.27 (s, 1H), 6.15 (t, J=9.0 Hz, 1H), 5.92 (m, 1H), 5.85 (m, 1H), 5.60 (d, J=7.2 Hz, 1H), 5.52 (d, J=7.2 Hz, 1H), 5.41 (m, 1H), 5.29 (m, 1H), 5.11 (m, 1H), 4.92 (m, 2H), 4.61 (m, 1H), 4.53 (m, 1H), 4.22 (m, 2H), 4.10 (m, 4H), 4.03 (dd, J=14.7, 8.4 Hz, 1H), 3.83 (d, J=7.0 Hz, 1H), 2.52 (m, 2H), 2.39 (s, 5H), 2.28 (m, 3H), 2.07-2.14 (m, 4H), 1.94 (s, 3H), 1.84 (m, 5H), 1.75 (m, 2H), 1.72 (s, 3H), 1.67 (m, 4H), 1.10 (s, 3H), 1.06 (s, 3H); ESI-MS (m/z): calcd for C$_{19}$H$_{23}$N$_2$O$_7$ [M+H]$^+$: 1310.4; found: 1310.5.

Sample 27: Preparation of Compound 27

To a 100 mL round-bottom flask charged with 1.30 g (1.00 mmol) of compound 26, 116 mg (0.10 mmol) of tetrakis (triphenylphosphine) palladium (0), and 188 mg (1.20 mmol) of 1,3-dimethylbarbituric acid under nitrogen protection, 20.0 mL of anhydrous THF was added, and stirred at room temperature for 2 h. After removal of volatiles, and the residue was purified on a silica gel column and eluted with methanol in chloroform (2-10%) to give 1.11 g of compound 27. Yield: 91%.

$^1$H NMR (500 MHz, CDCl$_3$, ppm): δ 8.95 (s, 1H), 8.05 (d, J=7.2 Hz, 2H), 7.62 (t, J=7.2 Hz, 1H), 7.49 (t, J=7.2 Hz, 1H), 7.30-7.42 (m, 6H), 7.20-7.30 (m, 7H), 7.13 (m, 1H), 7.10 (m, 2H), 6.78 (s, 1H), 6.27 (s, 1H), 6.18 (t, J=9.0 Hz, 1H), 5.93 (m, 1H), 5.58 (d, J=7.2 Hz, 1H), 5.49 (d, J=7.2 Hz, 1H), 4.97 (m, 2H), 4.87 (m, 1H), 4.34 (m, 1H), 4.25 (m, 3H), 4.15 (m, 4H), 4.03 (dd, J=14.7, 8.4 Hz, 1H), 3.89 (m, 2H), 3.73 (d, J=7.0 Hz, 1H), 2.52 (m, 2H), 2.36 (s, 5H), 2.28 (m, 3H), 2.02-2.18 (m, 8H), 1.94 (s, 3H), 1.84 (m, 2H), 1.82 (s, 3H), 1.75 (m, 5H), 1.58 (s, 3H), 1.12 (s, 3H), 1.04 (s, 3H); ESI-MS (m/z): calcd for C$_{66}$H$_{72}$N$_3$O$_2$ [M+H]$^+$: 1266.4; found: 1226.5.

Sample 28: Preparation of Compound 28

To a 25 mL round-bottom flask charged with 300 mg (0.25 mmol) of compound 27 and 72 mg (0.50 mmol) of 6-azido-hexanoic acid, 5.0 mL of DMSO was added. 150 µL of copper sulfate (1.0M) in water and 150 µL of sodium ascorbate (1.0M) in water were mixed together, and then added to the above solution. After stirring overnight at room temperature for 2 days, the reaction mixture was partitioned between ethyl acetate (50 mL) and brine (50 mL); the organic phase was washed with ethyl acetate (30 mL×2), dried over anhydrous MgSO$_4$, filtered, concentrated, and purified on a silica gel column and eluted with methanol in chloroform (1-10%) to provide 328 mg of compound 28. Yield: 95%.

$^1$H NMR (500 MHz, CD$_3$OD, ppm): δ 8.02 (d, J=7.2 Hz, 2H), 7.70 (t, J=7.2 Hz, 1H), 7.67 (s, 1H), 7.55 (t, J=7.2 Hz, 1H), 7.47 (m, 4H), 7.39 (m, 3H), 7.31 (m, 5H), 7.15 (m, 3H), 6.38 (s, 1H), 5.99 (t, J=9.0 Hz, 1H), 5.78 (d, J=7.2 Hz, 1H), 5.54 (d, J=7.2 Hz, 1H), 5.48 (d, J=7.2 Hz, 1H), 5.38 (s, 2H), 4.98 (m, 2H), 4.89 (m, 1H), 4.25 (m, 6H), 4.10 (m, 4H), 3.90 (s, 2H), 3.73 (d, J=7.0 Hz, 1H), 3.41 (d, J=7.0 Hz, 1H), 2.65 (t, J=7.0 Hz, 2H), 2.38 (m, 1H), 2.32 (s, 3H), 2.23 (t, J=7.0 Hz, 2H), 2.10 (m, 1H), 2.05 (s, 3H), 1.83-1.89 (m, 7H), 1.82 (s, 3H), 1.81 (m, 2H), 1.53 (s, 3H), 1.41 (m, 2H), 1.27 (m, 2H), 1.19 (m, 2H), 1.03 (s, 3H), 1.02 (s, 3H); ESI-MS (m/z): calcd for C$_{72}$H$_{85}$N$_6$O$_{21}$ [M+H]$^+$: 1369.5; found: 1369.3.

Synthetic Scheme 5

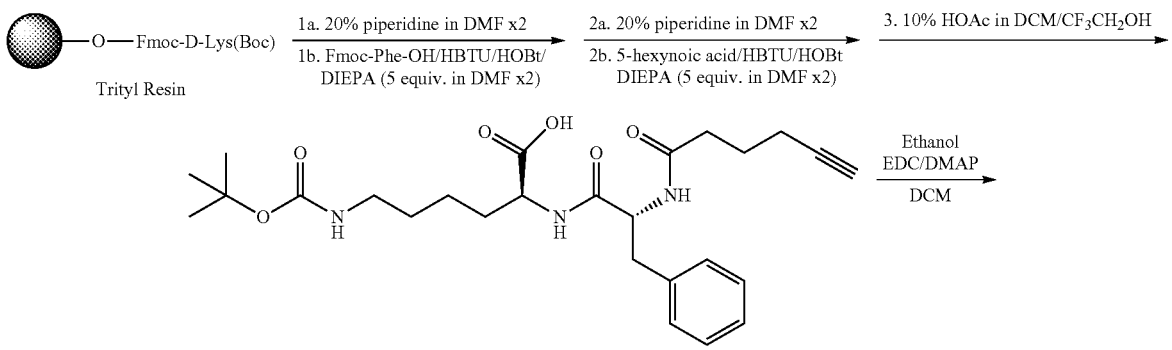

-continued
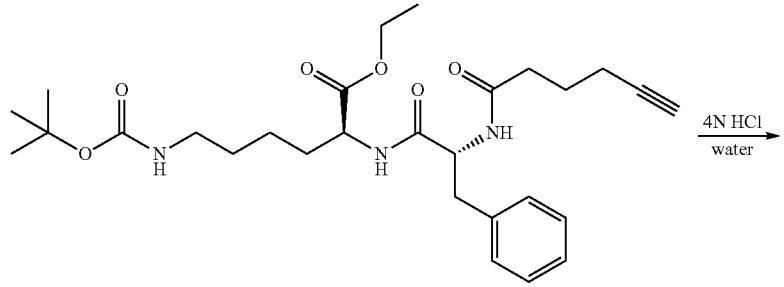
30
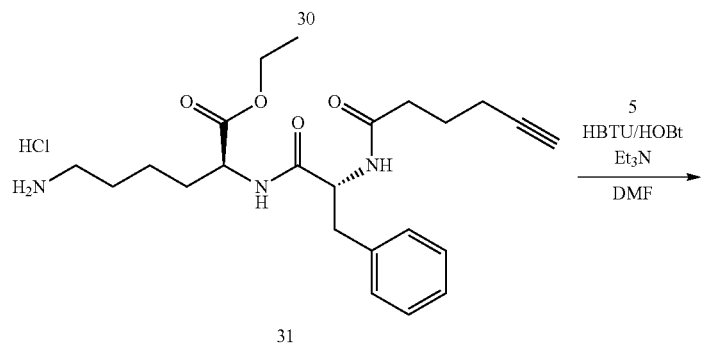
31
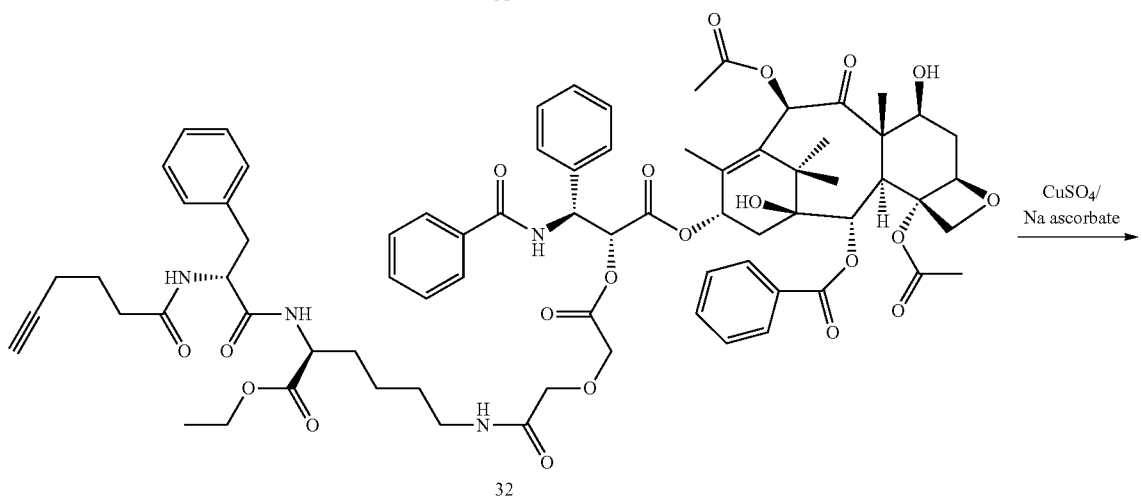
32
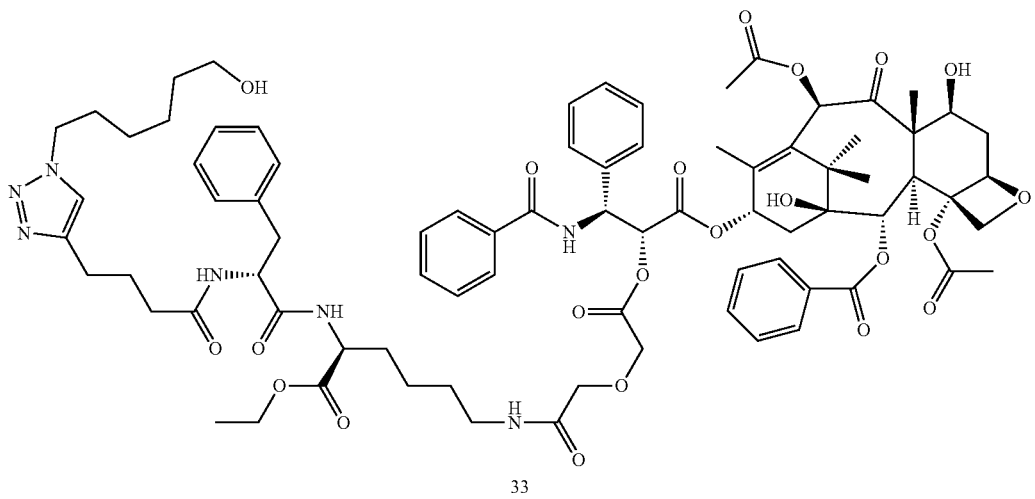
33

Sample 29: Preparation of Compound 29

Compound 29 was prepared by standard Fmoc solid-phase peptide synthesis method. 20.0 g of pre-loaded Fmoc-L-Lys (Boc)-Trityl resin (substitution: 0.51 mmol/g) was swollen in DMF for 30 min, drained, and followed by initial Fmoc deprotection (20% piperidine in DMF) twice. After DMF wash twice, sequential coupling of the remaining residues began: elongating amino acid sequence involved adding the appropriate Fmoc amino acid (5-fold excess) precombined with HBTU (5-fold excess) and HOBt (5-fold excess) in DMF to the resin; After mixing for 5 min, diisopropyl ethylamine (DIPEA, 5-fold excess) was added and allowed to react for 45 min; After DMF washing the previous piperidine deprotection conditions were used; These steps were repeated for each added amino acid. Finally, the crude desired product was cleaved from the resin with the cocktail (dichloromethane: acetic acid, trifluoro-ethanol/8:1:1); after filtering off solid resin, the filtrate was concentrated and purified on a reverse phase column and eluted with acetonitrile in water to provide 3.67 g of compound 29. Yield: 72%.

$^1$H NMR (300 MHz, CDCl$_3$, ppm): δ 7.20-7.50 (m, 5H), 6.71 (brs, 1H), 5.98 (brs, 1H), 4.72 (m, 1H), 4.51 (m, 1H), 2.98-3.25 (m, 4H), 2.35 (t, J=7.2 Hz, 2H), 2.16 (m, 2H), 1.98 (t, J=3.0 Hz, 1H), 1.89 (m, 2H), 1.35-1.52 (m, 13H); ESI-MS (m/z): calcd for C$_{26}$H$_{38}$N$_3$O$_6$ [M+H]$^+$: 488.2; found: 488.3.

Sample 30: Preparation of Compound 30

To a 100 mL round-bottom flask charged with 3.3 g (6.76 mmol) of compound 29 and 1.94 g (10.51 mmol) of 1-ethyl-3-(3-dimethylaminopropyl) carbodiimide (EDC) in 50 mL of anhydrous chloroformate, 3.0 mL of absolute ethanol and 1.25 g (10.51 mmol) of DMAP were added and stirred at room temperature overnight. After removal of volatiles, the residue was partitioned between ethyl acetate (100 mL) and brine (100 mL); the aqueous phase was extracted with ethyl acetate (50 mL×2), and the organic phases were pooled, dried over anhydrous MgSO$_4$, filtered, concentrated, and purified on a silica gel column and eluted with ethyl acetate in petroleum (10-70%) to give 3.02 g of compound 30. Yield: 86%.

$^1$H NMR (300 MHz, CDCl$_3$, ppm): δ 7.20-7.50 (m, 5H), 4.76 (m, 1H), 4.51 (m, 1H), 4.22 (q, J=7.2 Hz, 2H), 2.98-3.25 (m, 4H), 2.35 (t, J=7.2 Hz, 2H), 2.16 (m, 2H), 1.97 (t, J=3.0 Hz, 1H), 1.83 (m, 2H), 1.35-1.52 (m, 13H), 1.25 (t, J=7.2 Hz, 3H); ESI-MS (m/z): calcd for C$_{28}$H$_{42}$N$_3$O$_6$ [M+H]$^+$: 516.3; found: 516.3.

Sample 31: Preparation of Compound 31

To a 100 mL round-bottom flask charged with 3.50 g (6.78 mmol) of compound 30, 20 mL of hydrochloride ethanol solution (4.0N) was added, and stirred at room temperature overnight. After removal of volatiles, the residue was purified on a reverse phase C-18 column and eluted with acetonitrile in water (10-80%) to provide 2.85 g of compound 31. Yield: 93%.

$^1$H NMR (300 MHz, CDCl$_3$, ppm): δ 7.10-7.30 (m, 5H), 4.66 (m, 1H), 4.31 (m, 1H), 4.12 (q, J=7.2 Hz, 2H), 3.11 (m, 1H), 2.89-3.05 (m, 3H), 2.21 (t, J=7.2 Hz, 2H), 2.12 (m, 2H), 1.95 (t, J=3.0 Hz, 1H), 1.79 (m, 2H), 1.50-1.70 (m, 6H), 1.35 (m, 2H), 1.25 (t, J=7.2 Hz, 3H); ESI-MS (m/z): calcd for C$_{23}$H$_{34}$N$_3$O$_4$ [M+H]$^+$: 416.2; found: 416.2.

Sample 32: Preparation of Compound 32

In a 100 mL round-bottom flask, 1.5 g (1.54 mmol) of compound 5 and 0.72 g (1.86 mmol) of benzotriazole-N, N, N', N'-tetramethyluronium hexafluorophosphate (HBTU) and 251 mg (1.86 mmol) of 1-hydroxybenzotriazole (HOBt) were dissolved in 10.0 mL of dry DMF followed by addition of 835 mg (1.85 mmol) compound 31 and 0.43 mL (3.14 mmol) of triethylamine, and stirred at room temperature for 3 h. Upon completion, the reaction mixture was partitioned between ethyl acetate (150 mL) and brine (150 mL), the organic phase was further washed with brine twice (100 mL×2), dried over anhydrous MgSO$_4$, filtered, concentrated, and purified on a silica gel column and eluted with methanol in chloroform (1-10%) to provide 1.51 g of compound 32. Yield: 71%.

$^1$H NMR (500 MHz, CDCl$_3$, ppm): δ 8.12 (d, J=7.2 Hz, 2H), 7.65 (d, J=7.2 Hz, 2H), 7.10-7.50 (m, 16H), 6.76 (m, 2H), 6.20 (s, 1H), 6.17 (t, J=9.0 Hz, 1H), 5.86 (d, J=7.2 Hz, 1H), 5.45 (t, J=9.0 Hz, 1H), 4.86 (m 1H), 4.67 (m, 1H), 4.35 (m, 2H), 4.25 (m, 1H), 4.08 (m, 3H), 3.92 (m, 2H), 3.68 (m, 1H), 2.90-3.20 (m, 4H), 2.45 (m, 1H), 2.37 (s, 3H), 2.00-2.30 (m, 8H), 1.95 (m, 4H), 1.85 (m, 3H), 1.79 (m, 3H), 1.50-1.70 (m, 12H), 1.35 (m, 2H), 1.25 (t, J=7.2 Hz, 3H), 1.19 (s, 3H), 1.07 (s, 3H); ESI-MS (m/z): calcd for C$_{74}$H$_{87}$N$_4$O$_{21}$ [M+H]$^+$: 1376.5; found: 1367.5.

Sample 33: Preparation of Compound 33

To a 10 mL round-bottom flask charged with 200 mg (0.15 mmol) of compound 32 and 45 mg (0.31 mmol) of 6-azido-hexan-1-ol, 5.0 mL of DMSO was added. 100 μL of copper sulfate (1.0M) in water and 200 μL of sodium ascorbate (1.0M) in water were mixed together, and then added to the above solution. After stirring overnight at room temperature for 2 days, the reaction mixture was partitioned between ethyl acetate (50 mL) and brine (50 mL); the organic phase was washed with ethyl acetate (50 mL×2), dried over anhydrous MgSO$_4$, filtered, concentrated, and purified on a silica gel column and eluted with methanol in chloroform (1-10%) to provide 185 mg of compound 33. Yield: 82%.

$^1$H NMR (500 MHz, CDCl$_3$, ppm): δ 8.13 (d, J=7.2 Hz, 2H), 7.65 (d, J=7.2 Hz, 2H), 7.10-7.50 (m, 17H), 6.75 (m, 2H), 6.21 (s, 1H), 6.19 (t, J=9.0 Hz, 1H), 5.88 (d, J=7.2 Hz, 1H), 5.43 (t, J=9.0 Hz, 1H), 4.85 (m 1H), 4.66 (m, 1H), 4.35 (m, 2H), 4.25 (m, 1H), 4.10 (m, 3H), 3.92 (m, 2H), 3.59 (m, 2H), 3.27 (m, 2H), 2.90-3.23 (m, 4H), 2.47 (m, 1H), 2.35 (s, 3H), 2.00-2.30 (m, 7H), 1.93 (m, 4H), 1.83 (m, 3H), 1.76 (m, 3H), 1.50-1.70 (m, 13H), 1.35 (m, 4H), 1.29 (m, 4H), 1.25 (t, J=7.2 Hz, 3H), 1.15 (s, 3H), 1.05 (s, 3H); ESI-MS (m/z): calcd for C$_{80}$H$_{100}$N$_7$O$_{22}$ [M+H]$^+$: 1510.7; found: 1510.9.

Synthetic Scheme 6
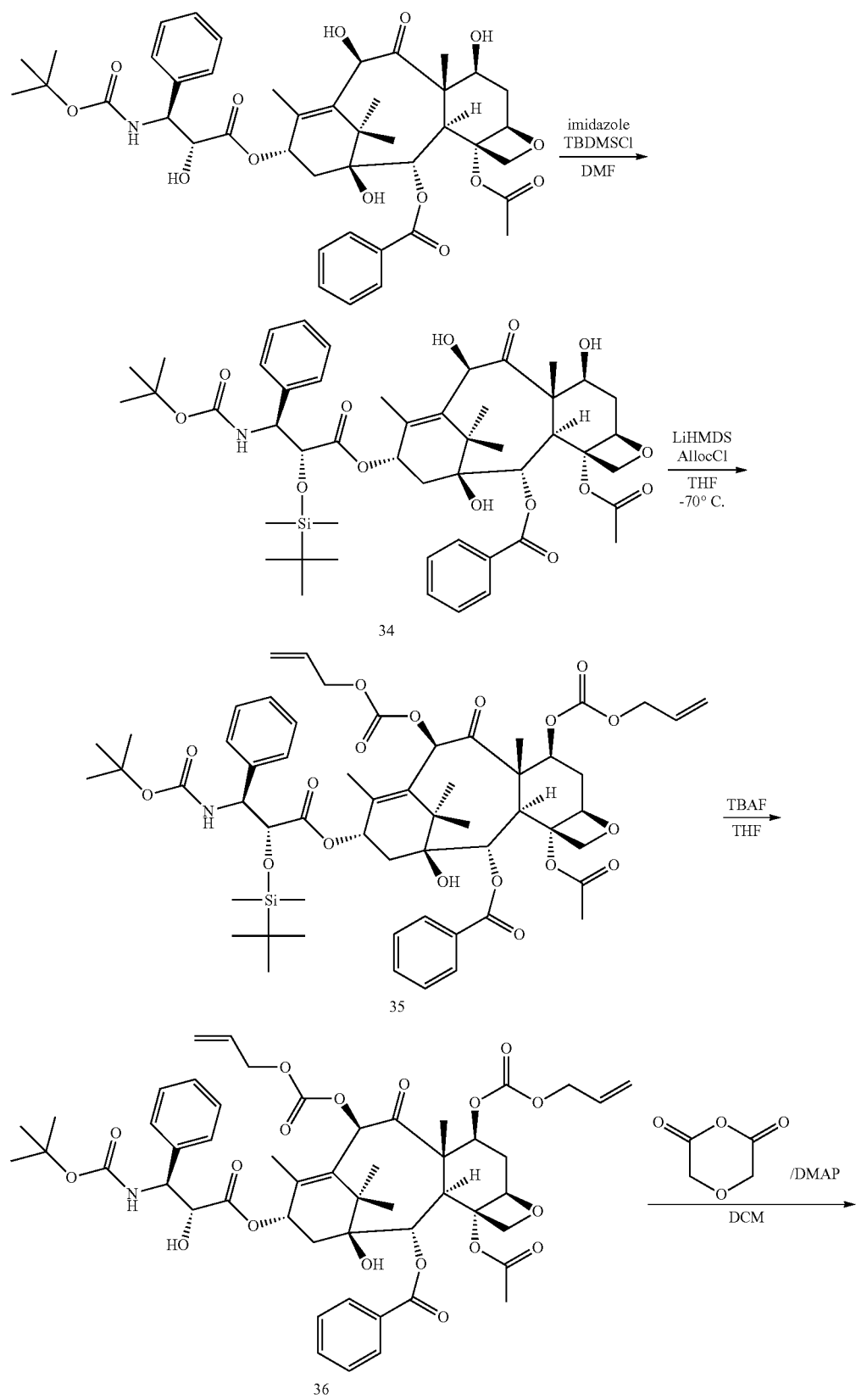

-continued
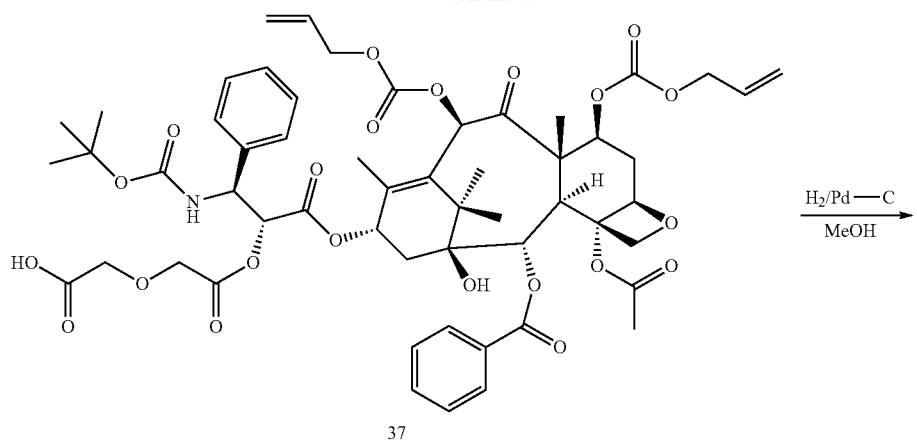
37
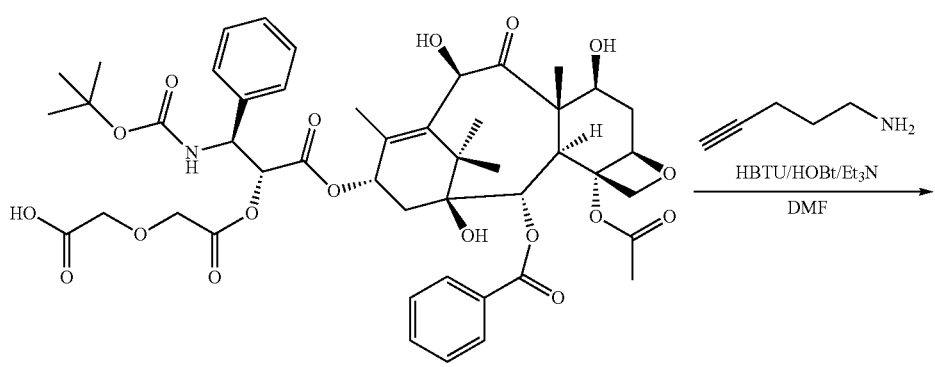
38
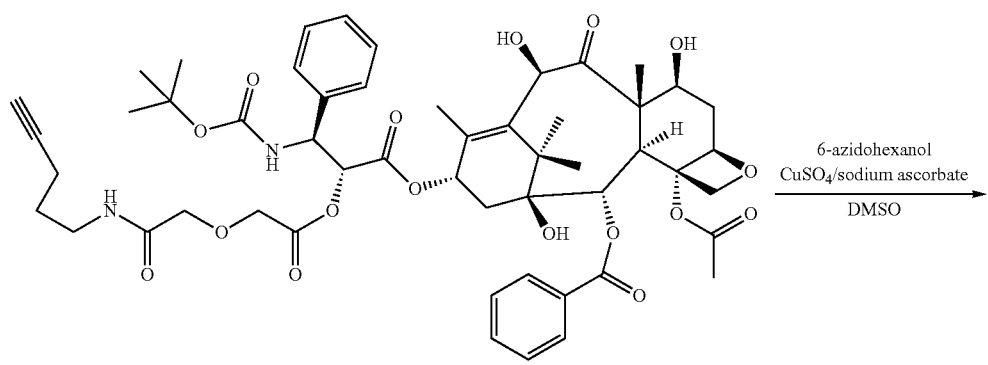
39
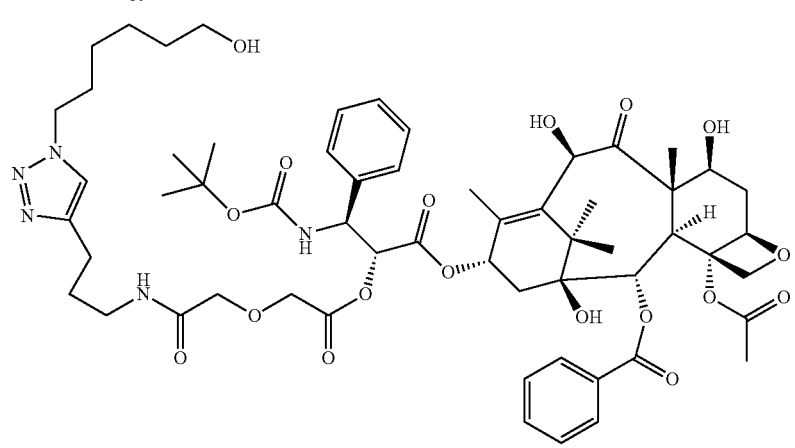
40

Sample 34: Preparation of Compound 34

To a 500 mL round-bottom flask charged with 50.0 g (60.8 mmol) of docetaxel and 32.6 g (216.3 mmol) of imidazole, 150 mL of anhydrous dimethylformamide (DMF) was added, and followed by addition of 14.3 g (216.3 mmol) of tert-butyldimethylchloride. The reaction mixture was stirred at room temperature for 12 h. Upon completion of the reaction, the reaction mixture was partitioned between ethyl acetate (500 mL) and brine (500 mL). The organic phase was further washed with brine (500 mL×2), dried over anhydrous $MgSO_4$, filtered, concentrated, and purified on a silica gel column and eluted with ethyl acetate in petroleum (10-70%) to provide 53.6 g of compound 34. Yield: 95%.

$^1$H NMR (500 MHz, DMSO-$d_6$, ppm): δ 7.97 (d, J=7.2 Hz, 2H), 7.73 (t, J=7.2 Hz, 1H), 7.61 (t, J=7.2 Hz, 2H), 7.57 (d, J=9.0 Hz, 1H), 7.35 (m, 4H), 7.17 (brs, 1H), 5.78 (t, J=9.0 Hz, 1H), 5.37 (d, J=7.2 Hz, 1H), 5.07 (s, 1H), 5.01 (d, J=7.2 Hz, 1H), 4.97 (s, 1H), 4.92 (m, 2H), 4.41 (m, 2H), 4.07 (m, 3H), 3.62 (d, J=6.6 Hz, 1H), 2.31 (s, 3H), 2.25 (m, 1H), 1.85 (m, 1H), 1.67 (m, 1H), 1.63 (m, 3H), 1.53 (m, 4H), 1.37 (s, 9H), 0.97 (s, 3H), 0.83 (s, 12H), 0.08 (s, 3H), 0.03 (s, 3H); ESI-MS (m/z): calcd for $C_{49}H_{68}NO_{14}Si$ [M+H]$^+$: 922.1; found: 922.3.

Sample 35: Preparation of Compound 35

To a 500 mL round-bottom flask charged with 20.0 g (21.71 mmol) of compound 34, 120 mL of absolute THF was added under nitrogen protection and cooled down to −70° C., followed by addition of 54.9 mL of lithium bis(trimethylsilyl) amide THF solution (1.0M) and stirred for 1 h, and then 54.9 g (45.9 mmol) of allyl chloroformate was added to the above solution. After stirring for another 1 h, the cooled batch was removed and the reaction mixture allowed to warm up to room temperature, and the reaction was stopped by addition of 15.0 mL of acetic acid. After removal of volatiles, the residue was partitioned between ethyl acetate (500 mL) and brine (500 mL). The organic phase was further washed with brine (500 mL×2), dried over anhydrous $MgSO_4$, filtered, concentrated, and purified on a silica gel column and eluted with ethyl acetate in petroleum (5-50%) to provide 21.56 g of compound 35. Yield: 91%.

$^1$H NMR (500 MHz, DMSO-$d_6$, ppm): δ 7.98 (d, J=7.2 Hz, 2H), 7.83 (t, J=7.2 Hz, 1H), 7.63 (m, 3H), 7.38 (m, 4H), 7.15 (t, J=7.2 Hz, 1H), 6.01 (s, 1H), 5.95 (m, 2H), 5.77 (t, J=9.0 Hz, 1H), 5.41 (d, J=7.2 Hz, 1H), 5.23-5.37 (m, 5H), 5.02 (d, J=8.4 Hz, 1H), 4.91 (t, J=8.4 Hz, 1H), 4.77 (s, 1H), 4.63 (m, 2H), 4.57 (m, 2H), 4.41 (d, J=7.8 Hz, 1H), 4.07 (s, 2H), 3.69 (d, J=7.2 Hz, 1H), 2.45 (m, 3H), 2.35 (s, 3H), 1.85 (m, 1H), 1.77 (t, J=12.0 Hz, 1H), 1.75 (s, 3H), 1.66 (s, 3H), 1.61 (m, 1H), 1.37 (s, 9H), 0.97 (s, 3H), 0.91 (s, 9H), 0.12 (s, 3H), 0.05 (s, 3H); ESI-MS (m/z): calcd for: $C_{57}H_{75}NO_{18}Si$ [M+H]$^+$: 1090.4; found: 1090.5.

Sample 36: Preparation of Compound 36

In a 250 mL round-bottom flask, 21.5 g (22.95 mmol) of compound 35 was dissolved 50.0 mL of tetrabutylammonium fluoride solution (TBAF, 1.0M) was added and stirred for 3 h at room temperature. Upon completion of the reaction, the reaction mixture was concentrated and purified on a silica gel column and eluted with ethyl acetate in petroleum (10-70%) to provide 21.5 g of compound 36. Yield: 96%.

$^1$H NMR (500 MHz, DMSO-$d_6$, ppm): δ 7.97 (d, J=7.2 Hz, 2H), 7.73 (t, J=7.2 Hz, 1H), 7.61 (d, J=7.2 Hz, 2H), 7.47 (d, J=9.0 Hz, 1H), 7.35 (t, J=7.8 Hz, 1H), 7.30 (d, J=7.2 Hz, 2H), 7.22 (t, J=7.2 Hz, 1H), 6.09 (s, 1H), 5.87-5.98 (m, 2H), 5.47 (d, J=7.2 Hz, 1H), 5.21-5.38 (m, 5H), 4.97 (d, J=9.0 Hz, 1H), 4.92 (t, J=9.0 Hz, 1H), 4.81 (s, 1H), 4.61 (m, 2H), 4.59 (d, J=6.0 Hz, 2H), 4.37 (d, J=6.0 Hz, 1H), 4.07 (m, 2H), 3.67 (d, J=7.2 Hz, 1H), 2.45 (m, 1H), 2.25 (s, 3H), 1.95 (m, 1H), 1.83 (m, 1H), 1.81 (s, 3H), 1.75 (t, J=12.0 Hz, 1H), 1.67 (s, 3H), 1.36 (s, 9H), 1.05 (s, 3H), 0.97 (s, 3H); ESI-MS (m/z): calcd for: $C_{51}H_{62}NO_{18}$ [M+H]$^+$: 976.4; found: 976.5.

Sample 37: Preparation of Compound 37

To a 250 mL round-bottom flask charged with 12.0 g (12.30 mmol) of compound 36, 4.27 g (36.84 mmol) of diglycolic acid anhydride, and 4.50 g (38.84 mmol) of 4-dimethylaminopyridine (DMAP), 70.0 mL of anhydrous dichloromethane was added and stirred at room temperature for 12 h. After removal of volatiles, the residue was partitioned between ethyl acetate (200 mL) and 10% citric acid solution (200 mL); the aqueous phase was extracted with ethyl acetate (150 mL×2), and the organic phases were pooled, dried over anhydrous $MgSO_4$, filtered, concentrated, and purified on a silica gel column and eluted with methanol in chloroform (0-10%) to give 11.1 g of compound 37. Yield: 83%.

$^1$H NMR (500 MHz, CDCl$_3$, ppm): δ 8.12 (d, J=7.8 Hz, 2H), 7.63 (t, J=7.8 Hz, 1H), 7.52 (t, J=7.8 Hz, 2H), 7.33 (m, 5H), 6.20 (s, 2H), 6.01 (m, 2H), 5.65 (s, 1H), 5.21-5.51 (m, 6H), 4.97 (d, J=7.2 Hz, 1H), 4.69 (m, 6H), 4.31 (m, 1H), 4.15 (m, 2H), 4.12 (m, 2H), 3.90 (m, 4H), 2.63 (m, 1H), 2.49 (s, 3H), 2.33 (m, 1H), 2.11 (m, 1H), 1.98 (s, 3H), 1.82 (s, 3H), 1.28 (s, 9H), 1.18 (s, 3H), 1.16 (s, 3H); ESI-MS (m/z): calcd for: $C_{55}H_{66}NO_{22}$ [M+H]$^+$: 1092.4; found: 1092.5.

Sample 38: Preparation of Compound 38

In a 250 mL round-bottom flask, 25.0 g (22.91 mmol) of compound 37 was dissolved in 100 mL of methanol, and bubbled with hydrogen gas in the presence of 1.2 g of 10% Pd—C for 6 h. Solid material was filtered off, and the filtrate was concentrated and purified on a reverse phase C-18 column and eluted with acetonitrile in water (10-80%) to give 17.55 g of compound 38. Yield: 83%.

$^1$H NMR (500 MHz, CD$_3$OD, ppm): δ 8.11 (d, J=7.8 Hz, 2H), 7.63 (t, J=7.8 Hz, 1H), 7.55 (t, J=7.8 Hz, 2H), 7.38 (m, 4H), 7.21 (m, 1H), 6.07 (s, 2H), 5.61 (t, J=7.2 Hz, 1H), 5.30 (t, J=9.0 Hz, 1H), 5.27 (s, 1H), 4.97 (d, J=9.0 Hz, 1H), 4.86 (m, 2H), 4.55 (m, 2H), 4.28 (m, 2H), 4.15 (m, 1H), 4.14 (s, 2H), 3.86 (s, 2H), 3.83 (m, 2H), 2.45 (m, 1H), 2.36 (s, 3H), 1.98 (m, 1H), 1.86 (s, 3H), 1.78 (t, J=12.1 Hz, 1H), 1.46 (s, 3H), 1.38 (s, 9H), 1.14 (s, 3H), 1.09 (s, 3H); ESI-MS (m/z): calcd for: $C_{47}H_{58}NO_{18}$ [M+H]$^+$: 924.3; found: 924.4.

Sample 39: Preparation of Compound 39

In a 100 mL round-bottom flask, 2.0 g (1.08 mmol) of compound 38 and 608 mg (1.60 mmol) of benzotriazole-N,N,N',N'-tetramethyluronium hexafluorophosphate (HBTU) and 216 mg (1.60 mmol) of 1-hydroxybenzotriazole (HOBt) were dissolved in 7.0 mL of dry DMF, and followed by addition of 208 mg (3.71 mmol) 4-pentyn-1-amine and 0.30 mL (2.16 mmol) of triethylamine, and stirred at room temperature for 5 h. Upon completion of the reaction, the reaction mixture was partitioned between ethyl acetate (80 mL) and brine (80 mL), the organic phase was further washed with brine twice (60 mL×2), dried over anhydrous $MgSO_4$, filtered, concentrated, and purified on a silica gel column and eluted with methanol in chloroform (1-10%) to provide 1.52 g of compound 39. Yield: 77%.

$^1$H NMR (300 MHz, CDCl$_3$+CD$_3$OD, ppm): δ 8.11 (d, J=7.2 Hz, 2H), 7.20-7.85 (m, 8H), 6.15 (s, 2H), 5.89 (m, 2H), 5.59 (d, J=7.2 Hz, 1H), 5.42 (m, 2H), 5.12-5.29 (m, 6H), 4.87 (d, J=9.8 Hz, 1H), 4.56 (m, 3H), 4.33 (s, 2H), 4.23 (m, 3H), 4.08 (d, J=8.4 Hz, 1H), 3.85 (d, J=7.2 Hz, 1H), 3.64 (s, 1H), 3.23 (m, 2H), 2.54 (m, 1H), 2.43 (m, 4H), 2.23 (m, 1H), 2.13 (m, 3H), 1.95 (s, 1H), 1.92 (s, 3H), 1.69 (m, 2H), 1.59 (m, 2H), 1.25 (s, 9H), 1.16 (s, 3H), 1.08 (s, 3H); ESI-MS (m/z): calcd for: $C_{52}H_{65}N_2O_{17}$ [M+H]$^+$: 989.4; found: 989.6.

Sample 40: Preparation of Compound 40

To a 25 mL round-bottom flask charged with 300 mg (0.303 mmol) of compound 39 and 76 mg (0.607 mmol) of 6-azido-hexan-1-ol, 5.0 mL of DMSO was added. 100 μL of copper sulfate (1.0M) in water and 200 μL of sodium ascorbate (1.0M) in water were mixed together, and then added to the above solution. After stirring overnight at room temperature for 2 days, the reaction mixture was partitioned between ethyl acetate (50 mL) and brine (50 mL); the organic phase was washed with brine (50 mL×2), dried over anhydrous MgSO$_4$, filtered, concentrated, and purified on a silica gel column and eluted with methanol in chloroform (1-10%) to provide 296 mg of compound 40. Yield: 86%.

$^1$H NMR (300 MHz, CDCl$_3$, ppm): δ 8.12 (d, J=7.2 Hz, 2H), 7.20-7.85 (m, 9H), 6.13 (s, 2H), 5.87 (m, 2H), 5.57 (d, J=7.2 Hz, 1H), 5.40 (m, 2H), 5.12-5.29 (m, 6H), 4.85 (d, J=9.8 Hz, 1H), 4.52 (m, 3H), 4.29 (s, 2H), 4.21 (m, 3H), 4.05 (d, J=8.4 Hz, 1H), 3.83 (d, J=7.2 Hz, 1H), 3.57 (m, 3H), 3.21 (m, 4H), 2.52 (m, 1H), 2.41 (m, 4H), 2.19 (m, 1H), 2.11 (m, 3H), 1.93 (s, 1H), 1.89 (s, 3H), 1.50-1.80 (m, 8H), 1.26-1.45 (m, 4H), 1.26 (s, 9H), 1.15 (s, 3H), 1.06 (s, 3H); ESI-MS (m/z): calcd for: $C_{58}H_{78}N_5O_{18}$ [M+H]$^+$: 1132.5; found: 1132.8.

Synthetic Scheme 7

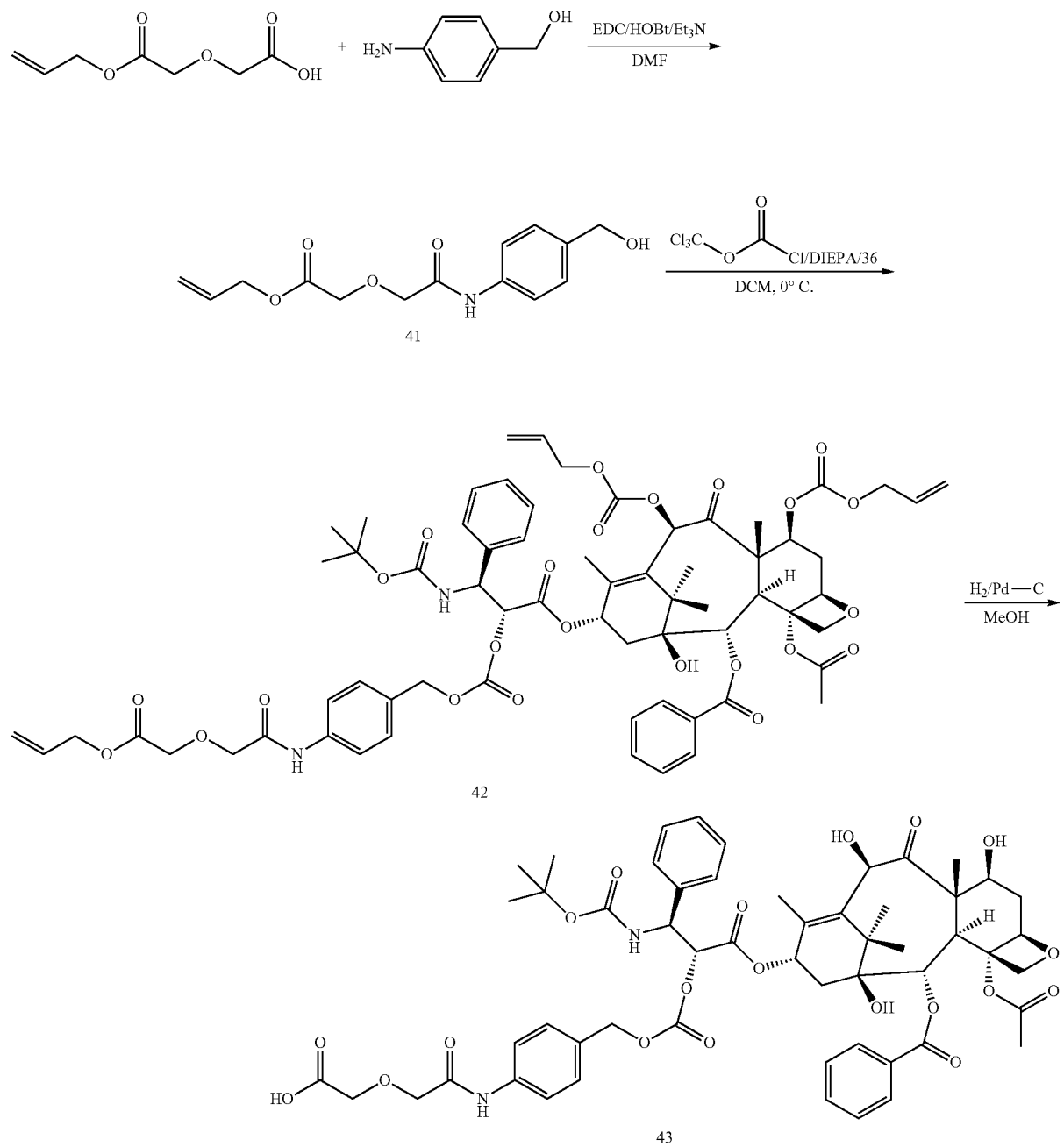

Sample 41: Preparation of Compound 41

To a 250 mL round-bottom flask charged with 5.0 g (28.71 mmol) of diglycolic acid anhydride allyl monoester, 2.90 g (15.18 mmol) of 1-ethyl-3-(3-dimethylaminopropyl) carbodiimide (EDC), and 4.65 g (34.50 mmol) of 1-hydroxybenzotriazole (HOBt), 30.0 mL of dry DMF was added and stirred for 30 min, followed by 4-aminobenzyl alcohol and 5.0 ml of triethylamine, and stirred at room temperature for another 6 h. Upon completion, the reaction mixture was partitioned between ethyl acetate (200 mL) and brine (200 mL), the organic phase was further washed with brine twice (100 mL×2), dried over anhydrous MgSO$_4$, filtered, concentrated, and purified on a silica gel column and eluted with methanol in chloroform (1-10%) to provide 3.92 g of compound 41. Yield: 54%.

$^1$H NMR (300 MHz, CDCl$_3$, ppm): δ 8.25 (s, 1H), 7.53 (d, J=7.8 Hz, 2H), 7.21 (d, J=7.8 Hz, 2H), 5.86 (m, 1H), 5.25 (d, J=16.8 Hz, 1H), 5.21 (d, J=9.8 Hz, 1H), 4.62 (d, J=7.0 Hz, 2H), 4.55 (s, 2H), 4.17 (s, 1H), 4.11 (s, 2H); ESI-MS (m/z): calcd for: $C_{14}H_{18}NO_5$ [M+H]$^+$: 280.1; found: 280.1.

Sample 42: Preparation of Compound 42

In a 250 mL round-bottom flask, 2.0 g (7.16 mmol) of compound 41 was dissolved in anhydrous chloroform and cooled down to 0° C. under argon protection, and 600 uL (5.02 mmol) of diphosgene and 5.0 mL (28.3 mmol) of N,N-diisopropyl ethylamine were successively added and stirred for 1 h. After removal of volatiles, the residue was redissolved in 50.0 mL of anhydrous chloroform under argon protection; 4.0 g (4.10 mmol) of compound 36 and 5.0 mL (28.3 mmol) of N,N-diisopropylethylamine were added to the above solution, and stirred at room temperature for 12 h. After removal of volatiles, the residue was partitioned between ethyl acetate (50 mL) and brine (50 mL), the organic phase was further washed with brine twice (100 mL×2), dried over anhydrous MgSO$_4$, filtered, concentrated, and purified on a silica gel column and eluted with ethyl acetate in petroleum (20-80%) to provide 2.32 g of compound 42. Yield: 58%.

$^1$H NMR (300 MHz, CDCl$_3$, ppm): δ 8.85 (s, 1H), 8.09 (d, J=7.2 Hz, 2H), 7.20-7.85 (m, 12H), 6.14 (s, 1H), 5.82 (m, 3H), 5.61 (d, J=7.0 Hz, 1H), 5.41 (m, 1H), 5.10-5.35 (m, 6H), 5.01 (m, 2H), 4.85 (d, J=9.0 Hz, 1H), 4.60 (d, J=7.0 Hz, 1H), 4.52 (m, 4H), 4.26 (d, J=8.4 Hz, 1H), 4.21 (s, 2H), 4.08 (s, 2H), 4.05 (m, 1H), 2.57 (m, 1H), 2.36 (s, 3H), 2.27 (m, 1H), 2.13 (m, 1H), 1.97 (s, 3H), 1.91 (t, J=12.6 Hz, 1H), 1.67 (s, 3H), 1.25 (s, 9H), 1.19 (s, 3H), 1.16 (s, 3H); ESI-MS (m/z): calcd for: $C_{66}H_{77}N_2O_{24}$ [M+H]$^+$: 1281.4; found: 1281.5.

Sample 43: Preparation of Compound 43

In a 100 mL round-bottom flask, 1.0 g (0.78 mmol) of compound 42 was dissolved in 20 mL of methanol, and bubbled with hydrogen gas in the presence of 300 mg of 10% Pd—C at room temperature for 5 h. Solid material was filtered off, and the filtrate was concentrated and purified on a reverse phase C-18 column and eluted with methanol in water (20-80%) to give 537 mg of compound 43. Yield: 69%.

$^1$H NMR (300 MHz, CD$_3$OD, ppm): δ 8.11 (d, J=7.2 Hz, 2H), 7.10-7.85 (m, 9H), 5.98 (t, J=6.0 Hz, 1H), 5.53 (d, J=7.0 Hz, 1H), 5.18 (m, 2H), 5.13 (d, J=6.0 Hz, 1H), 5.04 (m, 2H), 4.90 (d, J=9.8 Hz, 1H), 4.15 (m, 1H), 4.07 (s, 2H), 4.03 (s, 2H), 3.95 (s, 2H), 3.73 (d, J=7.0 Hz, 1H), 2.37 (m, 1H), 2.32 (s, 3H), 2.07 (m, 1H), 1.85 (m, 1H), 1.97 (s, 3H), 1.57 (s, 3H), 1.31 (s, 9H), 1.05 (s, 3H), 1.03 (s, 3H); ESI-MS (m/z): calcd for: $C_{55}H_{65}N_2O_{20}$ [M+H]$^+$: 1073.4; found: 1073.5.

Synthetic Scheme 8

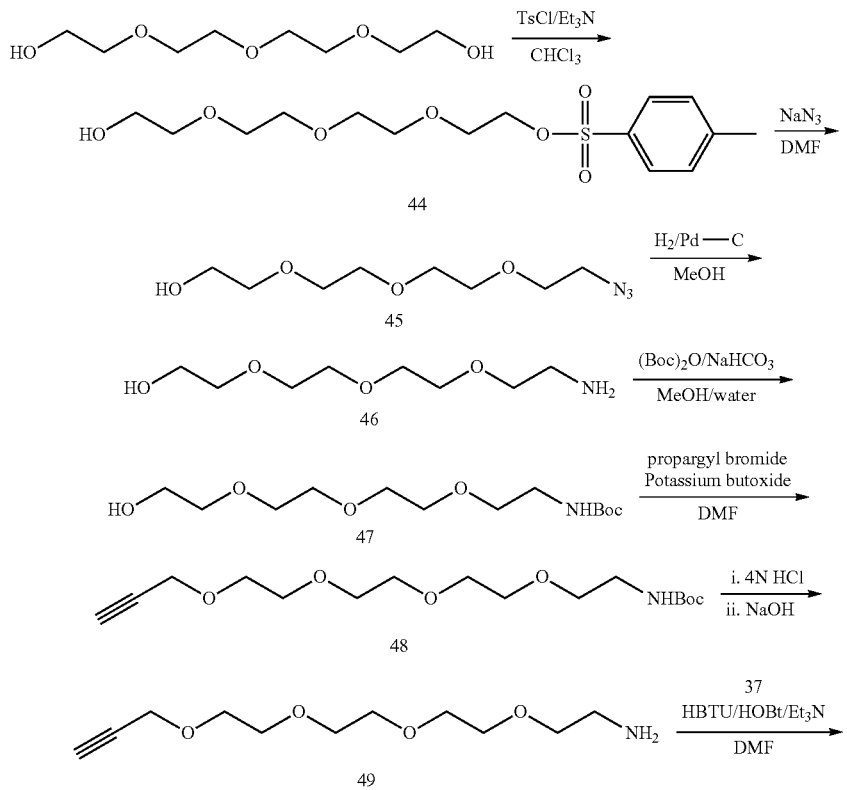

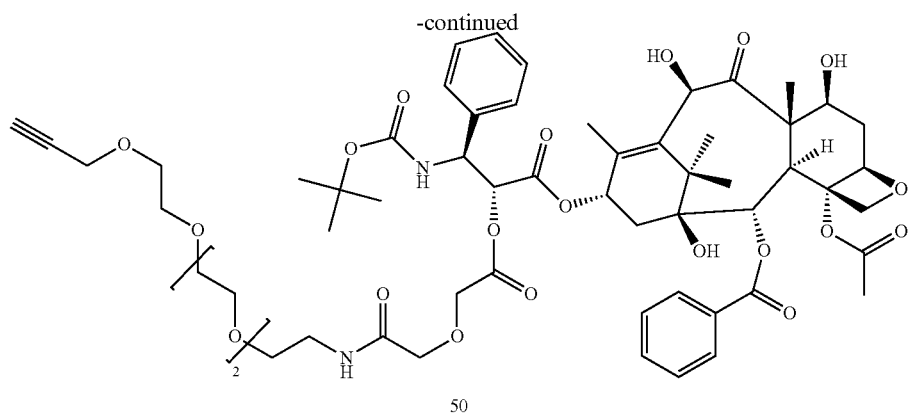

50

Sample 44: Preparation of Compound 44

To a 500 mL round-bottom flask charged with 60 g (308.9 mmol) of polyethylene glycol (PEG$_4$), 150 ml of anhydrous chloroform and 47 mL (339.8) of triethyl amine were added and cooled down to 0° C., followed by slow addition of 64.78 g (339.8 mmol) of 4-toluenesulfonyl chloride in anhydrous chloroform and stirred for 12 h. Upon completion of the reaction, the reaction mixture was washed with brine twice (200 mL×2), dried over anhydrous MgSO$_4$, filtered, concentrated, and purified on a silica gel column and eluted with acetone in chloroform (0-30%) to provide 47.3 g of compound 44. Yield: 43%.

$^1$H NMR (300 MHz, CDCl$_3$, ppm): δ 7.81 (d, J=7.2 Hz, 2H), 7.41 (d, J=7.2 Hz, 2H), 4.21 (d, J=7.0 Hz, 2H), 3.50-3.80 (m, 14H), 2.48 (s, 3H); ESI-MS (m/z): calcd for: C$_{15}$H$_{25}$O$_7$S [M+H]$^+$: 349.1; found: 349.1.

Sample 45: Preparation of Compound 45

To a 500 mL round-bottom flask charged with 30.0 g (86.11 mmol) of compound 44, 100 ml of anhydrous DMF and 16.8 g (258.3 mmol) of sodium azide were added and heated to 90° C., and stirred for 12 h. Upon completion of the reaction, the reaction mixture was evaporated under reduced vacuum, and the residue was partitioned between chloroform (500 mL) and brine (500 mL), the organic phase was further washed with brine twice (500 mL×2), dried over anhydrous MgSO$_4$, filtered, concentrated, and purified on a silica gel column and eluted with acetone in chloroform (0-30%) to provide 13.1 g of compound 45. Yield: 76%.

$^1$H NMR (300 MHz, CDCl$_3$, ppm): δ 3.67 (d, J=7.0 Hz, 2H), 3.50-3.75 (m, 10H), 3.28 (d, J=7.2 Hz, 2H); ESI-MS (m/z): calcd for: C$_8$H$_{18}$N$_3$O$_4$ [M+H]$^+$: 220.1; found: 220.1.

Sample 46: Preparation of Compound 46

In a 250 mL round-bottom flask, 25.0 g (114.0 mmol) of compound 45 was dissolved in 100 mL of methanol, and bubbled with hydrogen gas in the presence of 3.0 g of 10% Pd—C at room temperature for 6 h. Solid material was filtered off, and the filtrate was concentrated and purified on a reverse phase C-18 column and eluted with acetonitrile in water (10-50%) to provide 19.1 g of compound 46. Yield: 86%.

$^1$H NMR (300 MHz, CDCl$_3$, ppm): δ 3.67 (m, 4H), 3.65 (m, 8H), 3.53 (d, J=7.0 Hz, 2H), 3.02 (brs, 2H), 2.80 (t, J=7.0 Hz, 2H); ESI-MS (m/z): calcd for: C$_8$H$_{20}$NO$_4$ [M+H]$^+$: 194.1; found: 194.1.

Sample 47: Preparation of Compound 47

To a 500 mL round-bottom flask charged with 20.0 g (103.5 mmol) of compound 46 and 17.1 g (203.5 mmol) of sodium bicarbonate in 150 ml of methanol-water (7:3) 44.2 g (203.5 mmol) of ditert-butyl decarbonate in anhydrous THF was added and stirred at room temperature overnight. Upon completion of the reaction, the reaction mixture was concentrated and extracted with chloroform three times (300 mL×3); the organic phases were combined together, dried over anhydrous MgSO$_4$, filtered, concentrated, and purified on a silica gel column and eluted with acetone in chloroform (0-20%) to provide 17.6 g of compound 47. Yield: 58%.

$^1$H NMR (300 MHz, CDCl$_3$, ppm): δ 3.67 (d, J=7.0 Hz, 2H), 3.65 (m, 8H), 3.57 (d, J=7.0 Hz, 2H), 3.26 (t, J=7.2 Hz, 2H), 1.47 (s, 9H); ESI-MS (m/z): calcd for: C$_{13}$H$_{28}$NO$_6$ [M+H]$^+$: 294.1; found: 294.1.

Sample 48: Preparation of Compound 48

To a 500 mL round-bottom flask charged with 12.0 g (40.96 mmol) of compound 47, 150 ml of anhydrous DMF and 61.35 mL (1.0M) of potassium tert-butoxide in THF were added under nitrogen protection, cooled down to 0° C., and followed by slow addition of 7.30 g (61.35 mmol) of propargyl bromide; Upon completion of addition, the cooled bath was removed. After stirring at room temperature for 12 h, After removal of volatiles, the residue was partitioned between chloroform (300 mL) and brine (300 mL); the organic phase was washed with brine twice (200 mL×2), dried over anhydrous MgSO$_4$, filtered, concentrated, and purified on a silica gel column and eluted with ethyl acetate in chloroform (0-70%) to provide 11.2 g of compound 48. Yield: 76%.

$^1$H NMR (300 MHz, CDCl$_3$, ppm): δ 4.20 (s, 2H), 4.00 (t, J=7.0 Hz, 2H), 3.60-3.73 (m, 14H), 2.42 (s, 1H), 1.47 (s, 9H); ESI-MS (m/z): calcd for: C$_{16}$H$_{30}$NO$_6$ [M+H]$^+$: 332.1; found: 332.1.

Sample 49: Preparation of Compound 49

In a 250 mL round-bottom flask, 8.2 g (24.73 mmol) of compound 48 was dissolved in 70 mL of hydrochloride (4.0N) at 0° C., and stirred overnight. The reaction mixture was washed with chloroform twice (70 mL×2); the aqueous phase was basified with sodium hydroxide (2.0N) to pH=11.0, concentrated, and extracted with chloroform three times (50 mL×3); The organic phases were combined together, dried over anhydrous MgSO$_4$, filtered, and evaporated to dryness to provide 4.75 g of compound 49. Yield: 83%.

$^1$H NMR (300 MHz, CDCl$_3$, ppm): δ 4.21 (s, 2H), 3.65 (m, 14H), 3.51 (t, J=7.0 Hz, 2H), 2.87 (t, J=7.0 Hz, 2H), 2.43 (s, 1H); ESI-MS (m/z): calcd for: C$_{11}$H$_{22}$NO$_4$ [M+H]$^+$: 232.1; found: 232.1.

Sample 50: Preparation of Compound 50

In a 100 mL round-bottom flask, 3.0 g (3.25 mmol) of compound 38 and 1.48 g (3.89 mmol) of benzotriazole-N, N, N', N'-tetramethyluronium hexafluorophosphate (HBTU) and 526 mg (3.89 mmol) of 1-hydroxybenzotriazole (HOBt) were dissolved in 15.0 mL of dry DMF, followed by addition of 899 mg (3.89 mmol) compound 49 and 900 uL (6.50 mmol) of triethylamine, and stirred at room temperature for 5 h. Upon completion of the reaction, the reaction mixture was partitioned between ethyl acetate (80 mL) and brine (80 mL), the organic phase was further washed with brine twice (60 mL×2), dried over anhydrous MgSO₄, filtered, concentrated, and purified on a silica gel column and eluted with methanol in chloroform (1-10%) to provide 2.66 g of compound 50. Yield: 71%.

$^1$H NMR (300 MHz, CDCl₃, ppm): δ 8.13 (d, J=7.2 Hz, 2H), 7.20-7.85 (m, 10H), 6.13 (s, 2H), 5.68 (t, J=7.2 Hz, 1H), 5.29 (m, 3H), 4.96 (d, J=9.0 Hz, 1H), 4.83 (m, 2H), 4.55 (m, 2H), 4.10-4.30 (m, 7H), 3.85 (s, 2H), 3.81 (m, 2H), 3.50-3.75 (m, 14H), 2.46 (m, 1H), 2.35 (m, 3H), 2.03 (s, 3H), 1.97 (m, 1H), 1.60-1.85 (m, 4H), 1.39 (s, 9H), 1.17 (s, 3H), 1.13 (s, 3H); ESI-MS (m/z):

calcd for: $C_{58}H_{77}N_2O_{21}$ [M+H]⁺: 1137.5; found: 1137.6.

Synthetic Scheme 9

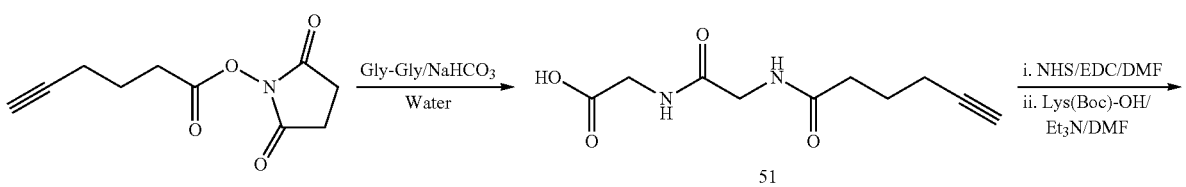

51

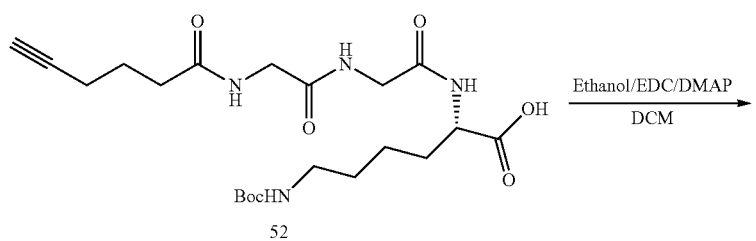

52

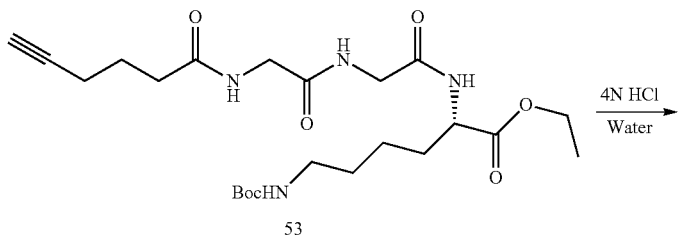

53

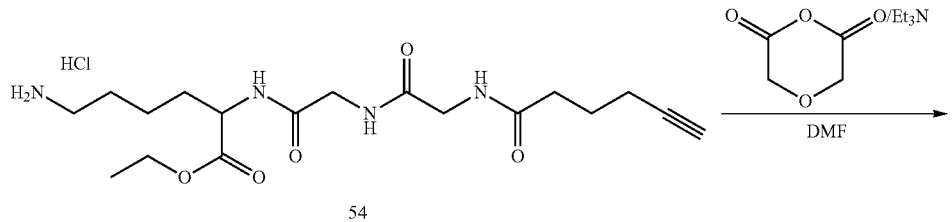

54

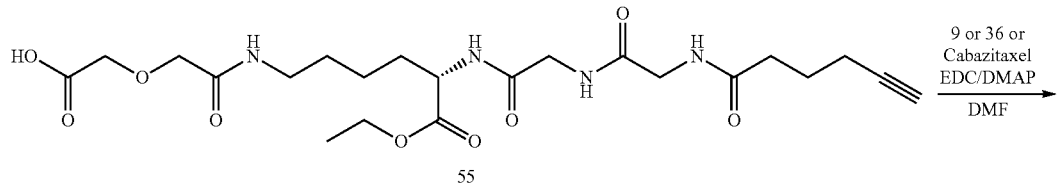

55

-continued
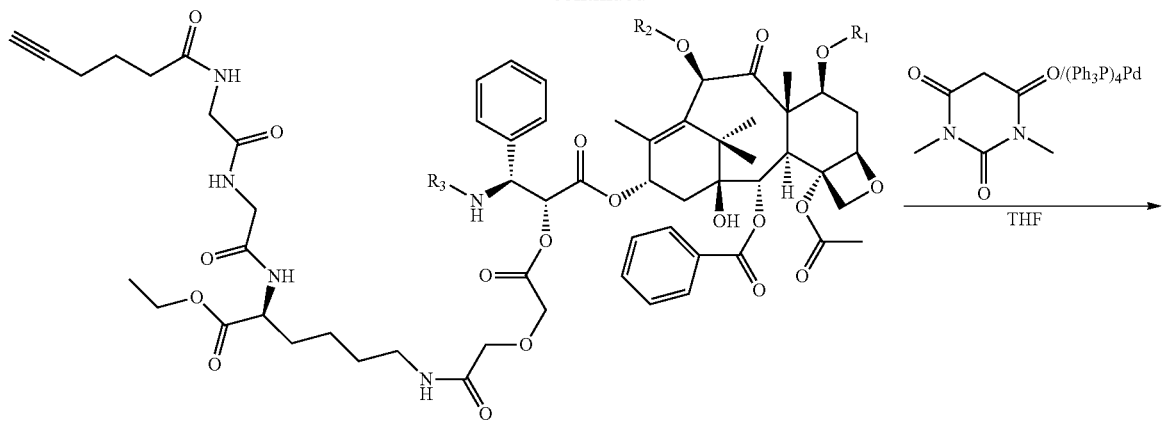
56 R₁ = Alloc, R₂ = Acetyl, R₃ = Bz
57 R₁ = Alloc, R₂ = Alloc, R₃ = Boc
58 R₁ = CH₃, R₂ = CH₃, R₃ = Boc
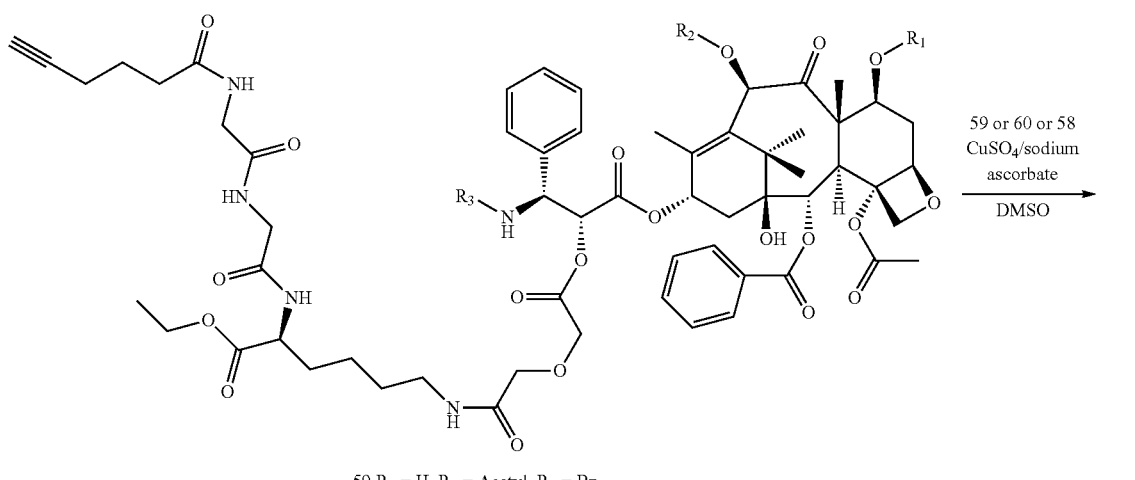
59 R₁ = H, R₂ = Acetyl, R₃ = Bz
60 = R₁ = H, R₂ = H, R₃ = Boc
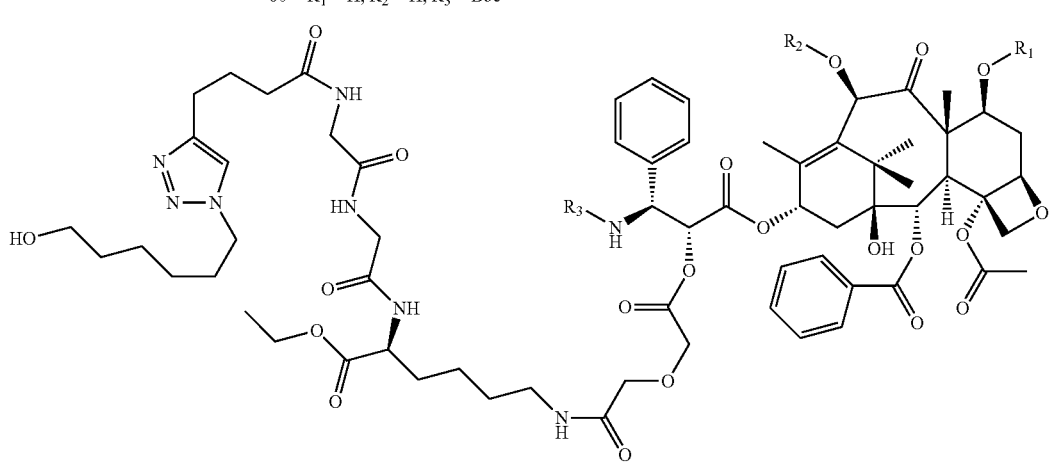
61 R₁ = H, R₂ = Acetyl, R₃ = Bz
62 R₁ = H, R₂ = H, R₃ = Boc
63 R₁ = CH₃, R₂ = CH₃, R₃ = Boc Sample 51: Preparation of Compound 51

To a 500 mL round-bottom flask charged with 21.1 g (159.7 mmol) of Gly-Gly and 26.9 g (320.0 g) of sodium carbonate in 150 mL of distilled water, 17.0 g (81.3 mmol) of 5-pentynoic acid N-hydroxy-succinimide ester in THF was dropwise added and stirred at room temperature for 5 h; and then was acidified with hydrochloride solution (2.0N) to pH=1.0. After removal of volatiles, the residue was purified on a reverse phase column and eluted with acetonitrile in water (0-30%) to provide 10.1 g of compound 51. Yield: 66%.

$^1$H NMR (300 MHz, DMSO-$d_6$, ppm): δ 3.75 (d, J=6.0 Hz, 2H), 3.65 (d, J=6.0 Hz, 2H), 2.76 (t, J=3.0 Hz, 1H), 2.25 (t, J=7.2 Hz, 2H), 2.19 (m, 2H), 1.65 (m, 2H); ESI-MS (m/z): calcd for: $C_{10}H_{15}N_2O_4$ [M+H]$^+$: 227.1; found: 227.1.

Sample 52: Preparation of Compound 52

To a 500 mL round-bottom flask charged with 10.0 g (44.0 mmol) of compound 51, 6.1 g (52.9 mmol) of N-hydroxysuccinimide, and 9.3 g (48.7 mmol) of 1-ethyl-3-(3-dimethylaminopropyl) carbodiimide (EDC), 60.0 mL of dry DMF was added and stirred at room temperature for 12 h. The above solution was drop wise added to the solution of 10.9 g (44.7 mmol) of N6-Boc-L-Lysine and 12.3 mL (88.0 mmol) of triethyl amine in dry DMF, and the reaction mixture was further stirred at room temperature overnight. After removal of volatiles, and the residue was partitioned between ethyl acetate (300 mL) and 30% citric acid solution (300 ml); the aqueous phase was further extracted with ethyl acetate (200 mL×2), and the organic phases were combined together, dried over anhydrous MgSO$_4$, filtered, concentrated, and purified on a silica gel column and eluted with methanol in chloroform (0-25%) to provide 13.0 g of compound 52. Yield: 55%.

$^1$H NMR (300 MHz, DMSO-$d_6$, ppm): δ 8.15 (t, J=7.2 Hz, 1H), 8.09 (t, J=7.2 Hz, 1H), 8.03 (d, J=7.2 Hz, 1H), 6.76 (t, J=7.2 Hz, 1H), 4.13 (m, 1H), 3.76 (d, J=7.2 Hz, 1H), 3.68 (d, J=7.2 Hz, 1H), 2.87 (m, 2H), 2.72 (t, J=3.0 Hz, 1H), 2.23 (t, J=7.2 Hz, 2H), 2.08 (m, 2H), 1.66 (m, 3H), 1.54 (m, 1H), 1.36 (m, 11H), 1.25 (m, 1H); ESI-MS (m/z): calcd for: $C_{21}H_{35}N_4O_7$ [M+H]$^+$: 455.3; found: 455.3.

Sample 53: Preparation of Compound 53

To a 250 mL round-bottom flask charged with 13.0 g (28.63 mmol) of compound 52 and 10.6 g (55.48 mmol) of 1-ethyl-3-(3-dimethylaminopropyl) carbodiimide (EDC), 150 mL of anhydrous dichloromethane was added, and stirred at room temperature for 30 min; and then 2.0 mL of absolute ethanol and 6.8 g (55.7 mmol) of DMAP were added. The reaction was continuously stirred overnight. After removal of volatiles, the residue was partitioned between ethyl acetate (200 mL) and brine (200 mL); the aqueous phase was extracted with ethyl acetate (200 mL×2), and the organic phases were pooled, dried over anhydrous MgSO$_4$, filtered, concentrated, and purified on a silica gel column and eluted with methanol in dichloromethane (0-15%) to provide 10.2 g of compound 53. Yield: 74%.

$^1$H NMR (300 MHz, DMSO-$d_6$, ppm): δ 8.16 (t, J=7.2 Hz, 1H), 8.07 (d, J=7.2 Hz, 1H), 8.02 (t, J=7.2 Hz, 1H), 6.73 (t, J=7.2 Hz, 1H), 4.12 (m, 1H), 4.08 (q, J=7.2 Hz, 2H), 3.73 (d, J=7.2 Hz, 1H), 3.60 (d, J=7.2 Hz, 1H), 2.81 (m, 2H), 2.72 (t, J=3.0 Hz, 1H), 2.20 (t, J=7.2 Hz, 2H), 1.95 (m, 2H), 1.63 (m, 3H), 1.52 (m, 1H), 1.36 (m, 11H), 1.23 (m, 1H); ESI-MS (m/z): calcd for $C_{23}H_{39}N_4O_7$ [M+H]$^+$: 483.3; found: 483.4.

Sample 54: Preparation of Compound 54

In a 250 mL round-bottom flask, 10.2 g (21.15 mmol) of compound 53 was dissolved in 100 mL of hydrochloride ethanol solution (4.0N) at 0° C., and stirred overnight. The reaction mixture was evaporated to dryness to provide 8.8 g of compound 54, which was directly used in next step without purification. Yield: 100%.

$^1$H NMR (300 MHz, CD$_3$OD, ppm): δ 4.36 (m, 1H), 4.12 (q, J=7.2 Hz, 2H), 3.81 (s, 1H), 3.78 (s, 2H), 2.81 (t, J=7.2 Hz, 2H), 2.32 (t, J=7.2 Hz, 2H), 2.11 (m, 3H), 1.60-1.82 (m, 4H), 1.56 (m, 2H), 1.32 (m, 2H), 1.13 (t, J=7.2 Hz, 2H); ESI-MS (m/z): calcd for $C_{18}H_{31}N_4O_5$ [M+H]$^+$: 383.2; found: 383.3.

Sample 55: Preparation of Compound 55

To a 250 mL round-bottom flask charged with 8.8 g (22.96 mmol) of compound 54 and 14.8 mL (107.0 mmol) of triethyl amine in 100 mL of anhydrous DMF, 12.3 g (106.0 mmol) of diglycolic acid anhydride was added and stirred at room temperature overnight. After removal of volatiles, the residue was acidified with hydrochloride solution (2.0N) to pH=1.0, concentrated, and purified on a reverse phase column C-18 eluted with acetonitrile in water (5-60%) to provide 4.0 g of compound 55. Yield: 37%.

$^1$H NMR (300 MHz, D$_2$O, ppm): δ 4.31 (m, 1H), 4.21 (s, 2H), 4.13 (q, J=7.2 Hz, 2H), 4.06 (s, 2H), 3.90 (s, 2H), 3.88 (s, 2H), 3.18 (t, J=7.2 Hz, 2H), 2.37 (t, J=7.2 Hz, 2H), 2.35 (t, J=3.0 Hz, 2H), 2.15 (m, 2H), 1.60-1.85 (m, 4H), 1.45 (m, 2H), 1.31 (m, 2H), 1.15 (t, J=7.2 Hz, 3H); ESI-MS (m/z): calcd for $C_{22}H_{35}N_4O_9$ [M+H]$^+$: 499.2; found: 499.3.

Sample 56: Preparation of Compound 56

To a 100 mL round-bottom flask charged with 1.27 g (2.56 mmol) of compound 55 and 813 mg (4.26 mmol) of 1-ethyl-3-(3-dimethylaminopropyl) carbodiimide (EDC), 15 mL of dry DMF was added, and stirred at room temperature for 30 min; and then 2.0 g (2.13 mmol) of compound 9 and 520 mg (4.26 mmol) of DMAP were added. The reaction was continuously stirred for 24 h. Upon completion of the reaction, the reaction mixture was partitioned between ethyl acetate (100 mL) and brine (100 mL); the aqueous phase was further extracted with ethyl acetate (50 mL×2), and the organic phases were pooled, dried over anhydrous MgSO$_4$, filtered, concentrated, and purified on a silica gel column and eluted with methanol in chloroform (0-10%) to provide 2.15 g of compound 56. Yield: 71%.

$^1$H NMR (300 MHz, CDCl$_3$, ppm): δ 8.12 (d, J=7.2 Hz, 2H), 8.09 (t, J=7.2 Hz, 1H), 7.20-7.80 (m, 16H), 6.39 (s, 1H), 6.10 (m, 1H), 5.97 (m, 1H), 5.62 (m, 2H), 5.51 (m, 1H), 4.97 (d, J=9.7 Hz, 1H), 4.63 (m, 2H), 4.39 (m, 3H), 4.00-4.25 (m, 6H), 3.96 (s, 2H), 3.70-3.97 (m, 5H), 3.23 (t, J=7.2 Hz, 2H), 2.45 (m, 1H), 2.43 (m, 1H), 2.41 (m, 4H), 2.36 (s, 3H), 2.25 (m, 4H), 2.17 (m, 1H), 1.95-2.05 (m, 6H), 1.83 (s, 3H), 1.60-1.85 (m, 4H), 1.45 (m, 2H), 1.31 (m, 2H), 1.17 (t, J=7.2 Hz, 3H), 1.15 (s, 3H), 1.12 (s, 3H); ESI-MS (m/z): calcd for $C_{73}H_{88}N_5O_{24}$ [M+H]$^+$: 1418.6; found: 1418.7.

Sample 57: Preparation of Compound 57

To a 100 mL round-bottom flask charged with 1.23 g (2.56 mmol) of compound 55 and 783 mg (4.10 mmol) of 1-ethyl-3-(3-dimethylaminopropyl) carbodiimide (EDC), 15 mL of dry DMF was added, and stirred at room temperature for 30 min; and then 2.0 g (2.05 mmol) of compound 36 and 500 mg (4.10 mmol) of DMAP were added. The reaction was continuously stirred for 24 h. Upon completion of the reaction, the reaction mixture was partitioned between ethyl acetate (100 mL) and brine (100 mL); the aqueous phase was extracted with ethyl acetate (50 mL×2), and the organic phases were pooled, dried over anhydrous MgSO$_4$, filtered, concentrated, and purified on a silica gel column and eluted with methanol in chloroform (0-10%) to provide 2.06 g of compound 57. Yield: 69%.

$^1$H NMR (300 MHz, CDCl$_3$, ppm): δ 8.13 (d, J=7.2 Hz, 2H), 7.20-7.85 (m, 10H), 6.15 (s, 1H), 5.98 (m, 2H), 5.65 (t, J=7.2 Hz, 1H), 5.43 (m, 2H), 5.25 (s, 1H), 4.97 (d, J=9.6 Hz, 1H), 4.63 (m, 4H), 4.37 (m, 6H), 4.15 (m, 4H), 4.01 (s, 2H), 3.70-4.00 (m, 5H), 3.21 (t, J=7.2 Hz, 2H), 2.46 (m, 1H), 2.00-2.35 (m, 9H), 1.96 (m, 1H), 1.60-1.80 (m, 9H), 1.37 (s, 9H), 1.23 (t, J=7.2 Hz, 3H), 1.16 (s 3H), 1.13 (s, 3H); ESI-MS (m/z): calcd for $C_{73}H_{93}N_5O_{26}$ [M+H]$^+$: 1455.6; found: 1455.7.

Sample 58: Preparation of Compound 58

To a 50 mL round-bottom flask charged with 639 mg (1.28 mmol) of compound 55 and 410 mg (2.15 mmol) of 1-ethyl-3-(3-dimethylaminopropyl) carbodiimide (EDC), 15 mL of dry DMF was added, and stirred at room temperature for 30 min; and then 900 mg (1.07 mmol) of cabazitaxel and 263 mg (2.15 mmol) of DMAP were added. The reaction was continuously stirred for 24 h. Upon completion of the reaction, the reaction mixture was partitioned between ethyl acetate (100 mL) and brine (100 mL); the aqueous phase was extracted with ethyl acetate (50 mL×2), and the organic phases were pooled, dried over anhydrous MgSO$_4$, filtered, concentrated, and purified on a silica gel column and eluted with methanol in chloroform (0-10%) to provide 1.17 g of compound 58. Yield: 75%.

$^1$H NMR (300 MHz, CDCl$_3$, ppm): δ 8.10 (d, J=7.8 Hz, 2H), 7.20-7.80 (m, 10H), 6.23 (m, 1H), 5.62 (t, J=7.2 Hz, 1H), 5.50 (m, 1H), 5.42 (m, 2H), 5.01 (d, J=9.6 Hz, 1H), 4.80 (s, 1H), 4.53 (m, 1H), 4.10-4.40 (m, 5H), 4.17 (s, 2H), 3.80-4.05 (m, 6H), 3.48 (m, 3H), 3.28 (m, 4H), 2.47 (m, 1H), 2.30-2.40 (m, 4H), 2.07 (s, 3H), 2.05 (m, 2H), 1.96 (m, 1H), 1.65-1.80 (m, 9H), 1.37 (s, 9H), 1.25 (t, J=7.2 Hz, 3H), 1.18 (s 3H), 1.16 (s, 3H); ESI-MS (m/z): calcd for $C_{67}H_{90}N_5O_{22}$ [M+H]$^+$: 1455.6; found: 1455.8.

Sample 59: Preparation of Compound 59

To a 50 mL round-bottom flask charged with 1.5 g (1.06 mmol) of compound 56, 73 mg (0.063 mmol) of tetrakis (triphenylphosphine) palladium (0), and 198 mg (1.27 mmol) of 1,3-dimethylbarbituric acid under nitrogen protection, 20.0 mL of anhydrous THF was added and the reaction mixture was stirred at room temperature for 5 h. After removal of volatiles and the residue was purified on a silica gel column and eluted with methanol in chloroform (0-15%) to give 1.17 g of compound 59. Yield: 79%.

$^1$H NMR (300 MHz, CDCl$_3$, ppm): δ 8.10 (d, J=7.2 Hz, 2H), 7.20-7.85 (m, 14H), 6.38 (s, 1H), 6.10 (m, 1H), 5.93 (m, 1H), 5.63 (m, 2H), 4.97 (d, J=9.7 Hz, 1H), 4.38 (m, 3H), 4.00-4.25 (m, 6H), 3.96 (s, 2H), 3.82 (s, 2H), 3.75 (m, 3H), 3.65 (m, 1H), 3.17 (t, J=7.2 Hz, 2H), 2.45 (m, 1H), 2.42 (m, 1H), 2.37 (s, 3H), 2.35 (m, 4H), 2.17 (m, 1H), 2.15 (m, 2H), 2.13 (m, 2H), 1.99 (m, 2H), 1.84 (s, 3H), 1.60-1.80 (m, 4H), 1.45 (m, 2H), 1.31 (m, 2H), 1.18 (t, J=7.2 Hz, 3H), 1.12 (s, 3H), 1.10 (s, 3H); ESI-MS (m/z): calcd for $C_{69}H_{84}N_5O_{22}$ [M+H]$^+$: 1334.5; found: 1334.7.

Sample 60: Preparation of Compound 60

To a 50 mL round-bottom flask charged with 1.7 g (1.17 mmol) of compound 57, 135 mg (0.117 mmol) of tetrakis (triphenylphosphine) palladium (0), and 401 mg (2.57 mmol) of 1,3-dimethylbarbituric acid under nitrogen protection, 20.0 mL of anhydrous THF was added and the reaction mixture was stirred at room temperature for 5 h. After removal of volatiles and the residue was purified on a silica gel column and eluted with methanol in chloroform (0-15%) to give 1.29 g of compound 60. Yield: 85%.

$^1$H NMR (300 MHz, CDCl$_3$, ppm): δ 8.12 (d, J=7.8 Hz, 2H), 7.20-7.85 (m, 10H), 6.13 (m, 1H), 5.68 (t, J=7.2 Hz, 1H), 5.43 (m, 2H), 5.26 (s, 1H), 4.97 (d, J=9.6 Hz, 1H), 4.48 (m, 1H), 4.38 (m, 5H), 4.17 (s, 2H), 4.12 (q, J=7.2 Hz, 2H), 4.01 (s, 2H), 3.70-4.00 (m, 5H), 3.59 (s, 3H), 3.18 (t, J=7.2 Hz, 2H), 2.46 (m, 1H), 2.37 (t, J=7.2 Hz, 2H), 2.35 (m, 2H), 2.06 (s, 3H), 2.05 (m, 2H), 1.95 (m, 1H), 1.60-1.80 (m, 9H), 1.38 (s, 9H), 1.20 (t, J=7.2 Hz, 3H), 1.18 (s 3H), 1.15 (s, 3H); ESI-MS (m/z): calcd for $C_{65}H_{86}N_5O_{22}$ [M+H]$^+$: 1288.6; found: 1288.9.

Sample 61: Preparation of Compound 61

To a 25 mL round-bottom flask charged with 200 mg (0.15 mmol) of compound 59 and 42 mg (0.30 mmol) of 6-azido-hexanoic acid, 5.0 mL of DMSO was added. 100 μL of copper sulfate (1.0M) in water and 100 μL of sodium ascorbate (1.0M) in water were mixed together and added to the above solution. After stirring for 2 days at room temperature, the reaction mixture was partitioned between ethyl acetate (50 mL) and brine (50 mL), the organic phase was further washed with brine twice (30 mL×2), dried over anhydrous MgSO$_4$, filtered, concentrated, and purified on a silica gel column and eluted with methanol in chloroform (1-15%) to provide 166 mg of compound 61. Yield: 76%.

$^1$H NMR (300 MHz, CDCl$_3$, ppm): δ 8.12 (d, J=7.2 Hz, 2H), 7.20-7.85 (m, 15H), 6.36 (s, 1H), 6.11 (m, 1H), 5.92 (m, 1H), 5.65 (m, 2H), 4.96 (d, J=9.7 Hz, 1H), 4.37 (m, 3H), 4.00-4.25 (m, 6H), 3.97 (s, 2H), 3.81 (s, 2H), 3.77 (m, 3H), 3.50-3.80 (m, 8H), 3.18 (t, J=7.2 Hz, 2H), 2.46 (m, 1H), 2.41 (m, 1H), 2.38 (s, 3H), 2.36 (m, 4H), 2.16 (m, 1H), 2.15 (m, 2H), 2.13 (m, 2H), 1.99 (m, 2H), 1.83 (s, 3H), 1.60-1.80 (m, 6H), 1.48 (m, 4H), 1.31 (m, 6H), 1.19 (t, J=7.2 Hz, 3H), 1.13 (s, 3H), 1.09 (s, 3H); ESI-MS (m/z): calcd for $C_{75}H_{96}N_8O_{23}$ [M+H]$^+$: 1459.7; found: 1459.9.

Sample 62: Preparation of Compound 62

To a 25 mL round-bottom flask charged with 200 mg (0.155 mmol) of compound 60 and 45 mg (0.31 mmol) of 6-azido-hexanoic acid, 5.0 mL of DMSO was added. 100 μL of copper sulfate (1.0M) in water and 100 μL of sodium ascorbate (1.0M) in water were mixed together and added to the above solution. After stirring for 2 days at room temperature, the reaction mixture was partitioned between ethyl acetate (50 mL) and brine (50 mL), the organic phase was further washed with brine twice (30 mL×2), dried over anhydrous MgSO$_4$, filtered, concentrated, and purified on a reverse phase C-18 column and eluted with methanol in chloroform (10-70%) to provide 195 mg of compound 62. Yield: 89%.

$^1$H NMR (300 MHz, CDCl$_3$, ppm): δ 8.11 (d, J=7.8 Hz, 2H), 7.20-7.85 (m, 11H), 6.15 (m, 1H), 5.69 (t, J=7.2 Hz, 1H), 5.42 (m, 2H), 5.28 (s, 1H), 4.96 (d, J=9.5 Hz, 1H), 4.41 (m, 5H), 4.18 (s, 2H), 4.15 (q, J=7.2 Hz, 2H), 4.02 (s, 2H), 3.70-4.00 (m, 5H), 3.50-3.85 (m, 5H), 3.18 (t, J-7.2 Hz, 2H), 2.45 (m, 1H), 2.36 (t, J=7.2 Hz, 2H), 2.33 (m, 2H), 2.05 (s, 3H), 2.04 (m, 2H), 1.97 (m, 1H), 1.60-1.80 (m, 11H), 1.45 (m, 2H), 1.38 (s, 9H), 1.20-1.30 (m, 5H), 1.18 (s 3H), 1.15 (s, 3H); ESI-MS (m/z): calcd for: $C_{71}H_{98}N_8O_{23}$ [M+H]$^+$: 1430.7; found: 1430.8.

Sample 63: Preparation of Compound 63

To a 25 mL round-bottom flask charged with 200 mg (0.137 mmol) of compound 58 and 39 mg (0.275 mmol) of 6-azido-hexanoic acid, 5.0 mL of DMSO was added. 100 μL of copper sulfate (1.0M) in water and 100 μL of sodium ascorbate (1.0M) in water were mixed together and added to the above solution. After stirring for 2 days at room temperature, the reaction mixture was partitioned between ethyl acetate (50 mL) and brine (50 mL), the organic phase was further washed with brine twice (30 mL×2), dried over anhydrous MgSO$_4$, filtered, concentrated, and purified on a silica gel column and eluted with methanol in chloroform (1-15%) to provide 186 mg of compound 63. Yield: 93%.

$^1$H NMR (300 MHz, CDCl$_3$, ppm): δ 8.09 (d, J=7.8 Hz, 2H), 7.20-7.80 (m, 11H), 6.23 (m, 1H), 5.63 (t, J=7.2 Hz, 1H), 5.48 (m, 1H), 5.45 (m, 2H), 4.97 (d, J=9.6 Hz, 1H), 4.81 (s, 1H), 4.52 (m, 1H), 4.10-4.40 (m, 5H), 4.17 (s, 2H), 3.70-4.05 (m, 8H), 3.51 (m, 5H), 3.26 (m, 4H), 2.45 (m, 1H), 2.30-2.40 (m, 4H), 2.06 (s, 3H), 2.05 (m, 2H), 1.96 (m, 1H), 1.65-1.80 (m, 11H), 1.47 (m, 2H), 1.37 (s, 9H), 1.29 (m, 4H), 1.25 (t, J=7.2 Hz, 3H), 1.18 (s 3H), 1.16 (s, 3H); ESI-MS (m/z): calcd for: $C_{73}H_{103}N_8O_{23}$ [M+H]$^+$: 1459.7; found: 1460.0.
Synthetic Scheme 10
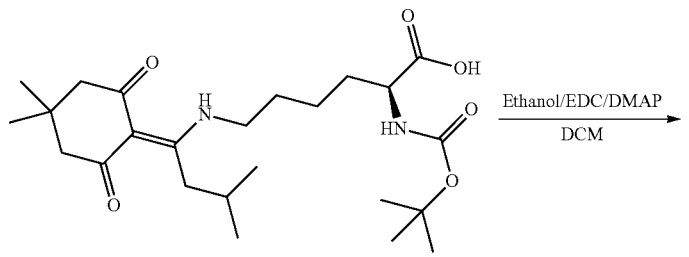
64
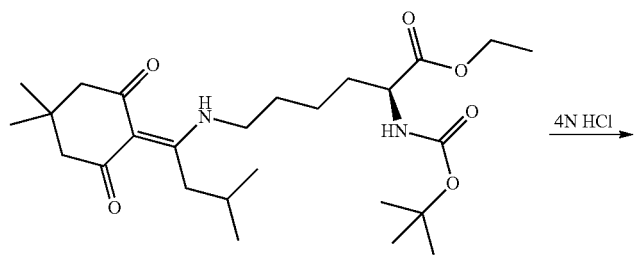
65
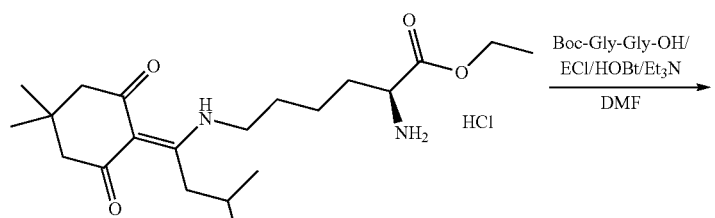
66
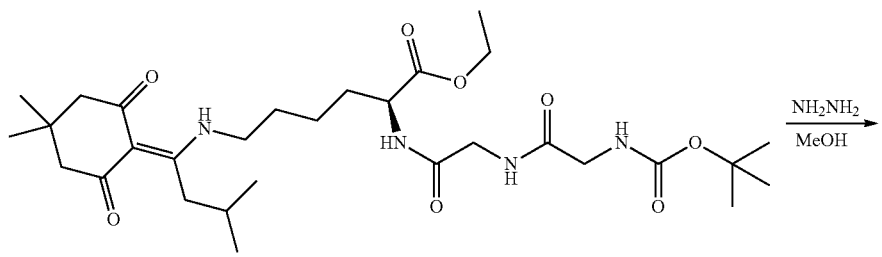
67
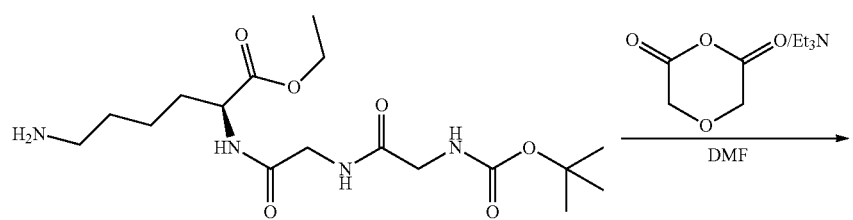

-continued
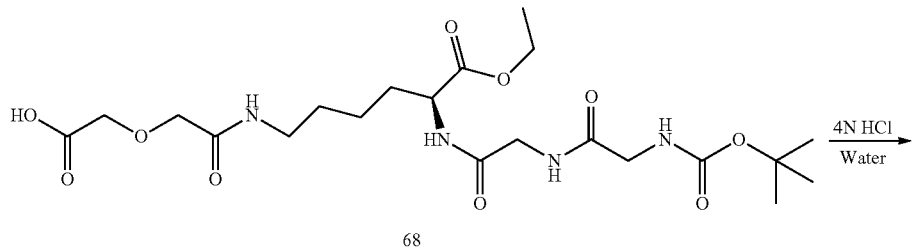
68
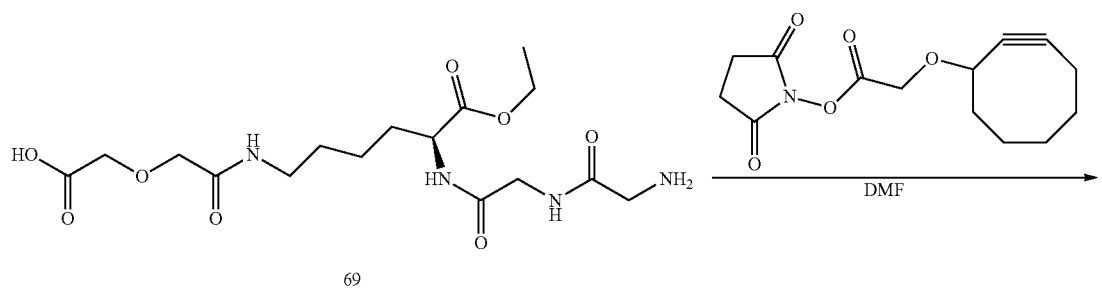
69
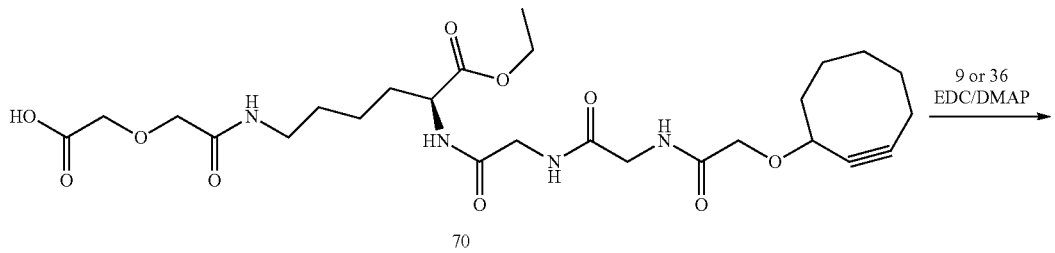
70
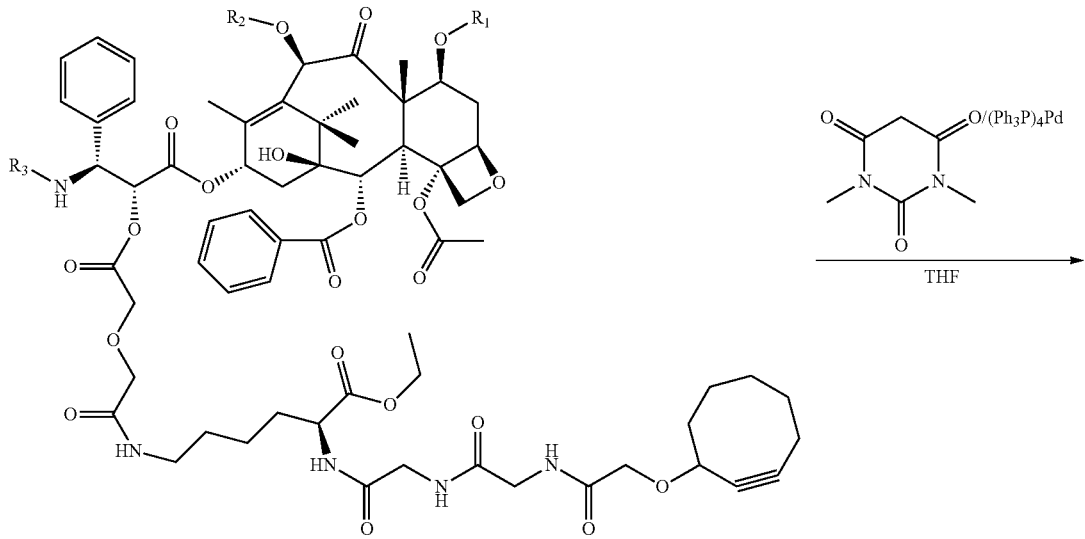
71 R₁ = Alloc, R₂ = Acetyl, R₃ = Bz
72 R₁ = Alloc, R₂ = Alloc, R₃ = Boc -continued
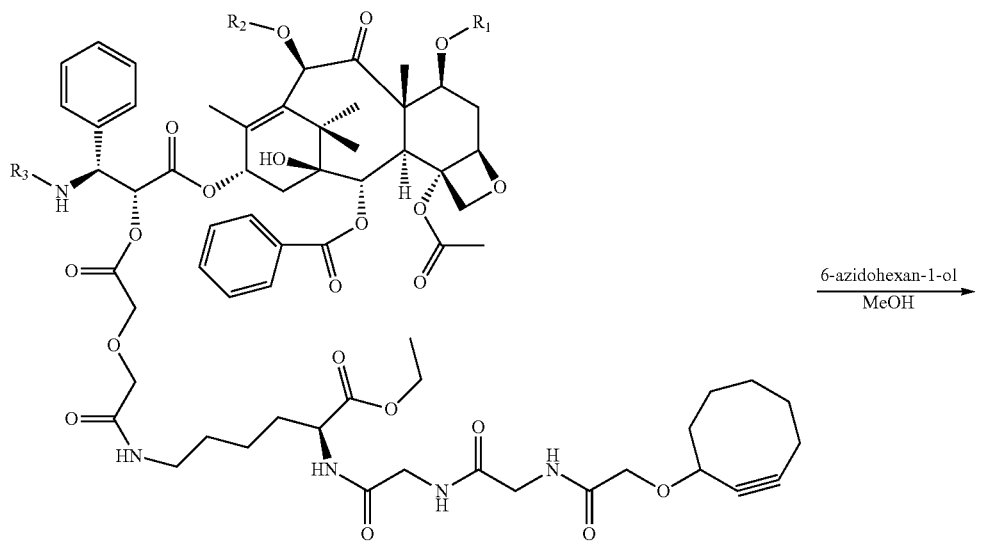
73 R₁ = H, R₂ = Acetyl, R₃ = Bz
74 R₁ = H, R₂ = H, R₃ = Boc
$\xrightarrow{\text{6-azidohexan-1-ol}}{\text{MeOH}}$
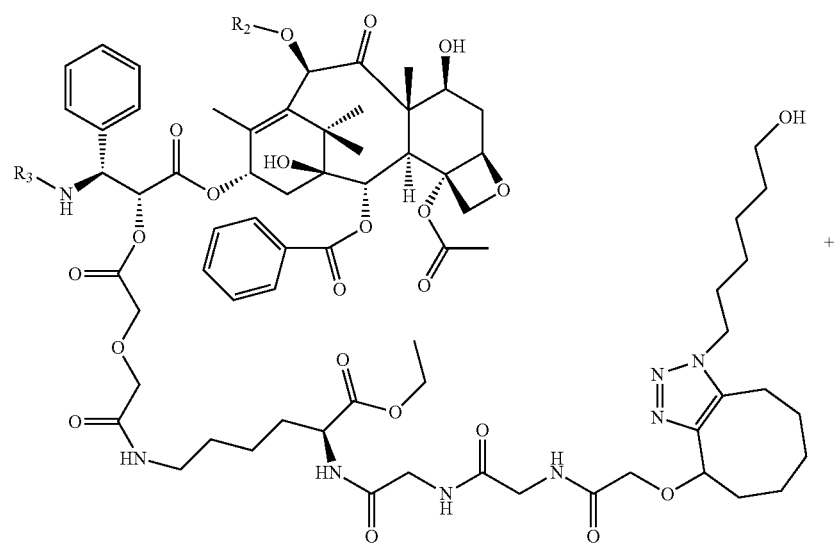
75a R₂ = Acetyl, R₃ = Bz
76a R₂ = H, R₃ = Boc -continued

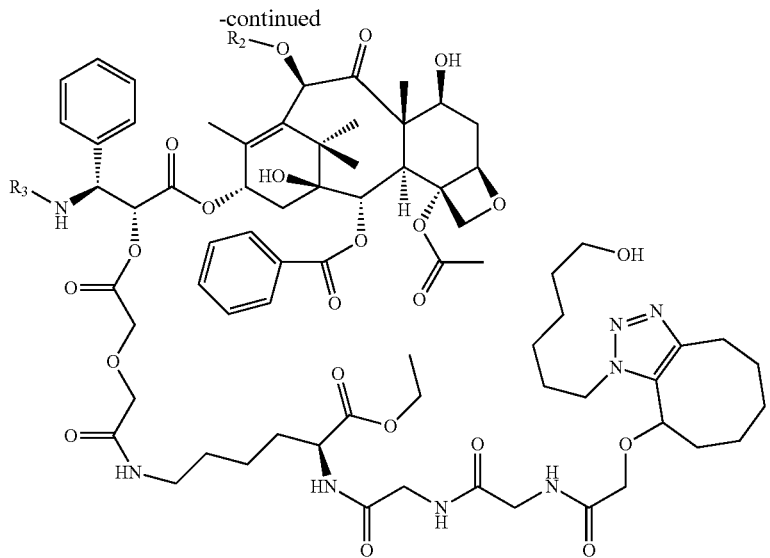

75b R₂ = Acetyl, R₃ = Bz
76b R₂ = H, R₃ = Boc

Sample 64: Preparation of Compound 64

In a 250 mL round-bottom flask, 3.38 g (6.0 mmol) of Nα-Boc-Nε-ivDde-L-lysine, 1.73 g (9.0 mmol) of 1-ethyl-3-(3-dimethylaminopropyl) carbodiimide (EDC), and 1.1 g (9.0 mmol) of DMAP were combined in 20 mL of anhydrous DCM and stirred at room temperature for 30 min; and then 5.0 mL of absolute ethanol was added and continued stirring overnight. After removal of volatiles, the residue was partitioned between ethyl acetate (50 mL) and brine (50 mL), the organic phase was further washed with brine twice (30 mL×2), dried over anhydrous MgSO₄, filtered, concentrated, and purified on a silica gel column and eluted with ethyl acetate in petroleum (10-70%) to provide 2.95 g of compound 64. Yield: 83%.

$^1$H NMR (300 MHz, CDCl₃, ppm): δ 5.09 (s, 1H), 4.27 (m, 1H), 4.18 (q, J=7.0 Hz, 2H), 3.41 (m, 2H), 2.96 (m, 2H), 2.46 (s, 4H), 2.16 (m, 2H), 1.96 (m, 1H), 1.79 (m, 2H), 1.63 (m, 3H), 1.51 (m, 1H), 1.43 (s, 9H), 1.25 (t, J=7.0 Hz, 3H), 1.03 (s, 6H), 0.98 (s, J=7.0 Hz, 6H); ESI-MS (m/z): calcd for C₂₆H₄₅N₂O₆ [M+H]⁺: 481.3; found: 481.3.

Sample 65: Preparation of Compound 65

To a 250 mL round-bottom flask charged with 3.0 g (5.08 mmol) of compound 64, 50 mL of hydrochloride ethanol solution (4.0N) was added and stirred at room temperature overnight. After removal of volatiles, the residue was purified on a reverse phase C-18 column and eluted with acetonitrile in water (10-70%) to provide 1.43 g of compound 65. Yield: 57%.

$^1$H NMR (300 MHZ, CDCl₃, ppm): δ 8.89 (s, 3H), 4.26 (q, J=7.0 Hz, 2H), 4.10 (m, 1H), 3.51 (m, 2H), 2.97 (m, 2H), 2.35 (s, 4H), 2.16 (m, 2H), 1.97 (m, 1H), 1.78 (m, 2H), 1.56 (m, 2H), 1.23 (t, J=7.0 Hz, 3H), 1.03 (s, 6H), 0.98 (s, J=7.0 Hz, 6H); ESI-MS (m/z): calcd for C₂₁H₃₇N₂O₄ [M+H]⁺: 381.2; found: 381.2.

Sample 66: Preparation of Compound 66

To a 100 mL round-bottom flask charged with 710 mg (3.06 mmol) of Boc-Gly-Gly-OH, 584 mg (3.06 mmol) of 1-ethyl-3-(3-dimethylaminopropyl) carbodiimide (EDC) and 413 mg (3.06 mmol) of 1-hydroxybenzotriazole (HOBt), 6.0 mL of dry DMF was added and stirred for 30 min, and followed by addition of 1.0 g (2.02 mmol) of compound 66 and 0.56 mL of triethylamine and stirred at room temperature for another 3 h. Upon completion of the reaction, the reaction mixture was partitioned between ethyl acetate (50 mL) and brine (50 mL), the organic phase was further washed with brine twice (30 mL×2), dried over anhydrous MgSO₄, filtered, concentrated, and purified on a silica gel column and eluted with methanol in chloroform (1-10%) to provide 1.12 g of compound 66. Yield: 62%.

$^1$H NMR (300 MHz, CDCl₃, ppm): δ 7.51 (d, J=5.0 Hz, 1H), 7.02 (d, J=5.0 Hz, 1H), 5.47 (d, J=5.0 Hz, 1H), 4.53 (m, 1H), 4.17 (q, J=7.0 Hz, 2H), 3.82 (d, J=6.0 Hz, 2H), 3.81 (d, J=6.0 Hz, 2H), 3.42 (m, 2H), 2.97 (m, 2H), 2.34 (s, 4H), 1.93 (m, 1H), 1.72 (m, 4H), 1.63 (m, 2H), 1.42 (s, 9H), 1.21 (t, J=7.0 Hz, 3H), 1.03 (s, 6H), 0.96 (s, J=7.0 Hz, 6H); ESI-MS (m/z): calcd for C₃₀H₅₁N₄O₈ [M+H]⁺: 595.4; found: 595.5.

Sample 67: Preparation of Compound 67

To a stirred solution of 1.40 g (2.35 mmol) of compound 66 in 50 mL of methanol, 154 uL (23.50 mmol) of hydrazine hydrate was added and stirred at room temperature overnight. Upon completion of the reaction, the white solid was filtered off, and the filtrate was concentrated, and purified on a reverse phase C-18 column and eluted with acetonitrile in water (10-80%) to provide 796 mg of compound 67. Yield: 87%.

$^1$H NMR (300 MHz, DMSO-d₆, ppm): δ 8.39 (s, 1H), 8.06 (s, 1H), 7.08 (s, 1H), 4.27 (m, 1H), 4.12 (q, J=7.0 Hz, 2H), 3.78 (d, J=6.0 Hz, 2H), 3.65 (d, J=6.0 Hz, 2H), 2.75 (d, J=7.0 Hz, 2H), 1.68 (m, 1H), 1.51 (m, 4H), 1.47 (s, 9H), 1.38 (m, 1H); ESI-MS (m/z): calcd for C₁₇H₃₃N₄O₆ [M+H]⁺: 389.2; found: 389.2.

Sample 68: Preparation of Compound 68

To a 100 mL round-bottom flask charged with 1.8 g (4.63 mmol) of compound 67 and 1.61 g (13.90 mmol) of diglycolic acid anhydride, 10 mL of anhydrous DMF and 1.92 mL (13.90 mmol) of triethylamine were successively added and stirred at room temperature overnight. After removal of volatiles, the residue was acidified to pH=1.0 with 2.0 N hydrochloride solution; the aqueous solution was further concentrated, and purified on a reverse phase C-18 column and eluted with acetonitrile in water (5-70%) to provide 1.92 g of compound 68. Yield: 82%.

$^1$H NMR (300 MHZ, D$_2$O, ppm): δ 4.36 (m, 1H), 4.27 (s, 2H), 4.15 (q, J=7.0 Hz, 2H), 4.17 (s, 2H), 4.01 (s, 2H), 3.87 (s, 2H), 3.23 (d, J=7.0 Hz, 2H), 1.86 (m, 1H), 1.75 (m, 1H), 1.56 (m, 2H), 1.43 (s, 9H), 1.35 (m, 2H); ESI-MS (m/z): calcd for C$_{21}$H$_{37}$N$_4$O$_{10}$ [M+H]$^+$: 505.2; found: 505.2.

Sample 69: Preparation of Compound 69

To a 250 mL round-bottom flask charged with 2.0 g (3.67 mmol) of compound 68, 50 mL of hydrochloride ethanol solution (4.0N) was added and stirred at room temperature overnight. After removal of volatiles, the residue was purified on a reverse phase C-18 column and eluted with acetonitrile in water (10-70%) to provide 848 mg of compound 69. Yield: 57%.

$^1$H NMR (300 MHZ, D$_2$O, ppm): δ 4.39 (m, 1H), 4.28 (s, 2H), 4.23 (q, J=7.0 Hz, 2H), 4.20 (s, 2H), 4.04 (s, 2H), 3.90 (s, 2H), 3.26 (d, J=7.0 Hz, 2H), 1.92 (m, 2H), 1.89 (m, 1H), 1.56 (m, 2H), 1.39 (s, 2H), 1.25 (t, J=7.0 Hz, 3H); ESI-MS (m/z): calcd for C$_{16}$H$_{29}$N$_4$O$_8$ [M+H]$^+$: 405.2; found: 405.2.

Sample 70: Preparation of Compound 70

To a 50 mL round-bottom flask charged with 603 mg (1.50 mmol) of compound 69 in 3.0 mL of anhydrous DMF, 829 uL (6.0 mmol) of triethylamine, and 502 mg (1.08 mmol) of 2-(cyclohept-2-yn-1-yloxy) acetic acid-(N-hydroxysuccinyl lactam) ester were successively added and stirred at room temperature overnight. After removal of volatiles, the residue was acidified to pH=1.0 with 2.0 N hydrochloride solution; the aqueous solution was further concentrated, and purified on a reverse phase C-18 column and eluted with acetonitrile in water (10-70%) to provide 621 mg of compound 70. Yield: 72%.

$^1$H NMR (300 MHZ, D$_2$O, ppm): δ 4.00-4.50 (m, 12H), 3.88 (d, J=6.0 Hz, 2H), 3.25 (t, J=7.0 Hz, 2H); 2.00-2.30 (m, 4H), 1.70-2.00 (m, 5H), 1.55 (m, 5H), 1.25-1.55 (m, 3H), 1.23 (t, J=7.0 Hz, 3H); ESI-MS (m/z): calcd for C$_{26}$H$_{41}$N$_4$O$_{10}$ [M+H]$^+$: 569.3; found: 569.3.

Sample 71: Preparation of Compound 71

To a 50 mL round-bottom flask charged with 333 mg (0.587 mmol) of compound 70 and 153 mg (0.789 mmol) of 1-ethyl-3-(3-dimethylaminopropyl) carbodiimide (EDC), 3.0 mL of dry DMF was added and stirred at room temperature for 30 min; and then 500 mg (0.533 mmol) of compound 9 and 98 mg (0.798 mmol) of DMAP were added. The reaction was continuously stirred for 24 h. Upon completion of the reaction, the reaction mixture was partitioned between ethyl acetate (50 mL) and brine (50 mL); the aqueous phase was extracted with ethyl acetate (30 mL×2), and the organic phases were pooled, dried over anhydrous MgSO$_4$, filtered, concentrated, and purified on a silica gel column and eluted with methanol in chloroform (0-12%) to provide 657 mg of compound 71. Yield: 82%.

$^1$H NMR (300 MHz, CDCl$_3$, ppm): δ 8.11 (d, J=7.2 Hz, 2H), 7.00-7.80 (m, 15H), 6.35 (s, 1H), 6.17 (t, J=9.0 Hz, 1H), 5.93 (m, 2H), 5.85 (d, J=9.0 Hz, 1H), 5.65 (d, J=7.2 Hz, 1H), 5.23 (m, 2H), 4.97 (d, J=9.0 Hz, 1H), 4.81 (m, 3H), 4.00-4.50 (m, 14H), 3.75-4.00 (m, 4H), 3.25 (t, J=7.0 Hz, 2H), 2.51 (m, 1H), 2.37 (s, 3H), 2.00-2.35 (m, 9H), 1.70-2.00 (m, 13H), 1.25-1.55 (m, 3H), 1.25 (t, J=7.0 Hz, 3H), 1.25 (s, 3H), 1.16 (s, 3H), 1.13 (s, 3H); ESI-MS (m/z): calcd for C$_{77}$H$_{94}$N$_5$O$_{25}$ [M+H]$^+$: 1488.6; found: 1488.8.

Sample 72: Preparation of Compound 72

To a 50 mL round-bottom flask charged with 192 mg (0.338 mmol) of compound 70 and 90 mg (0.462 mmol) of 1-ethyl-3-(3-dimethylaminopropyl) carbodiimide (EDC), 3.0 mL of dry DMF was added and stirred at room temperature for 30 min; and then 300 mg (0.308 mmol) of compound 6 and 58 mg (0.462 mmol) of DMAP were added. The reaction mixture was continuously stirred for 24 h. Upon completion of the reaction, the reaction mixture was partitioned between ethyl acetate (50 mL) and brine (50 mL); the aqueous phase was extracted with ethyl acetate (30 mL×2), and the organic phases were pooled, dried over anhydrous MgSO$_4$, filtered, concentrated, and purified on a silica gel column and eluted with methanol in chloroform (0-12%) to provide 399 mg of compound 72. Yield: 85%.

$^1$H NMR (300 MHz, CDCl$_3$, ppm): δ 8.10 (d, J=7.2 Hz, 2H), 7.20-7.80 (m, 10H), 6.15 (s, 1H), 5.91 (m, 1H), 5.63 (s, 1H), 5.25-5.50 (m, 5H), 4.98 (d, J=9.8 Hz, 1H), 4.00-4.80 (m, 19H), 3.50-4.00 (m, 6H), 3.26 (t, J=7.2 Hz, 2H), 2.45 (m, 1H), 2.00-2.35 (m, 9H), 1.98 (m, 1H), 1.50-1.90 (m, 12H), 1.37 (s, 9H), 1.25 (m, 3H), 1.22 (t, J=7.2 Hz, 3H), 1.16 (s, 3H), 1.11 (s, 3H); ESI-MS (m/z): calcd for C$_{77}$H$_{100}$N$_5$O$_{27}$ [M+H]$^+$: 1526.7; found: 1526.9

Sample 73: Preparation of Compound 73

To a 50 mL round-bottom flask charged with 600 mg (0.402 mmol) of compound 71, 39 mg (0.033 mmol) of tetrakis (triphenylphosphine) palladium (0), and 75 mg (0.483 mmol) of 1,3-dimethylbarbituric acid under nitrogen protection, 20.0 mL of anhydrous THF was added; the reaction mixture was stirred at room temperature for 5 h. After removal of volatiles, the residue was purified on a silica gel column and eluted with methanol in chloroform (0-8%) to give 451 mg of compound 73. Yield: 80%.

$^1$H NMR (300 MHz, CDCl$_3$, ppm): δ 8.12 (d, J=7.2 Hz, 2H), 7.00-7.80 (m, 15H), 6.32 (s, 1H), 6.18 (t, J=9.0 Hz, 1H), 5.96 (m, 1H), 5.82 (d, J=9.0 Hz, 1H), 5.68 (d, J=7.2 Hz, 1H), 4.99 (d, J=9.0 Hz, 1H), 4.78 (s, 1H), 4.00-4.50 (m, 14H), 3.75-4.00 (m, 4H), 3.23 (t, J=7.0 Hz, 2H), 2.56 (m, 1H), 2.35 (s, 3H), 2.00-2.35 (m, 9H), 1.70-2.00 (m, 13H), 1.25-1.55 (m, 3H), 1.23 (t, J=7.0 Hz, 3H), 1.20 (s, 3H), 1.17 (s, 3H), 1.15 (s, 3H); ESI-MS (m/z): calcd for C$_{73}$H$_{90}$N$_5$O$_{23}$ [M+H]$^+$: 1404.6; found: 1404.5.

Sample 74: Preparation of Compound 74

To a 50 mL round-bottom flask charged with 450 mg (0.294 mmol) of compound 72, 41 mg (0.035 mmol) of tetrakis (triphenylphosphine) palladium (0), and 105 mg (0.672 mmol) of 1,3-dimethylbarbituric acid under nitrogen protection, 20.0 mL of anhydrous THF was added; the reaction mixture was stirred at room temperature for 5 h. After removal of the volatiles, the residue was purified on a silica gel column and eluted with methanol in chloroform (0-8%) to give 291 mg of compound 74. Yield: 73%.

$^1$H NMR (300 MHz, CDCl$_3$, ppm): δ 8.13 (d, J=7.2 Hz, 2H), 7.20-7.80 (m, 10H), 6.18 (s, 1H), 5.65 (s, 1H), 5.25-5.50 (m, 3H), 4.98 (d, J=9.8 Hz, 1H), 4.00-4.60 (m, 17H), 3.50-4.00 (m, 6H), 3.25 (t, J=7.2 Hz, 2H), 2.47 (m, 1H), 2.00-2.35 (m, 9H), 1.97 (m, 1H), 1.50-1.90 (m, 12H), 1.39 (s, 9H), 1.27 (m, 3H), 1.23 (t, J=7.2 Hz, 3H), 1.15 (s, 3H), 1.12 (s, 3H); ESI-MS (m/z): calcd for C$_{69}$H$_{92}$N$_5$O$_{23}$ [M+H]$^+$: 1358.6; found: 1358.7.

Sample 75: Preparation of Compound 75a (75b)

In a 25 mL round-bottom flask, 100 mg (0.071 mmol) of compound 73 and 20 mg (0.142 mmol) of 6-azidohexan-1-ol were combined in 1.0 mL of methanol and stirred at room temperature overnight, and directly and purified on a reverse phase C-18 column and eluted with acetonitrile in water (10-70%) to provide 101 mg of compounds 75a (75b). Yield: 91%.

$^1$H NMR (300 MHz, CDCl$_3$, ppm): δ 8.10 (d, J=7.2 Hz, 2H), 7.00-7.80 (m, 15H), 6.35 (s, 1H), 6.17 (t, J=9.0 Hz, 1H), 5.95 (m, 1H), 5.83 (d, J=9.0 Hz, 1H), 5.66 (d, J=7.2 Hz, 1H), 4.95 (d, J=9.0 Hz, 1H), 4.76 (s, 1H), 4.00-4.50 (m, 14H), 3.50-4.00 (m, 8H), 3.25 (t, J=7.0 Hz, 2H), 2.56 (m, 1H), 2.35 (s, 3H), 2.00-2.35 (m, 9H), 1.70-2.00 (m, 15H), 1.25-1.55 (m, 9H), 1.23 (t, J=7.0 Hz, 3H), 1.21 (s, 3H), 1.13 (s, 3H), 1.10 (s, 3H); ESI-MS (m/z): calcd for $C_{79}H_{103}N_8O_{24}$ [M+H]$^+$: 1547.7; found: 1547.6.

Sample 76: Preparation of Compound 76a (76b)

In a 25 mL round-bottom flask, 100 mg (0.073 mmol) of compound 73 and 21 mg (0.147 mmol) of 6-azidohexan-1-ol were combined in 1.0 mL of methanol and stirred at room temperature overnight, and directly and purified on a reverse phase C-18 column and eluted with acetonitrile in water (10-70%) to provide 92 mg of compounds 76a (76b). Yield: 84%.

$^1$H NMR (300 MHz, CDCl$_3$, ppm): δ 8.12 (d, J=7.2 Hz, 2H), 7.20-7.80 (m, 10H), 6.15 (s, 1H), 5.67 (s, 1H), 5.25-5.50 (m, 3H), 4.95 (d, J=9.8 Hz, 1H), 4.00-4.60 (m, 17H), 3.50-4.00 (m, 10H), 3.23 (t, J=7.2 Hz, 2H), 2.45 (m, 1H), 2.00-2.35 (m, 9H), 1.95 (m, 1H), 1.50-1.90 (m, 16H), 1.38 (s, 9H), 1.28 (m, 7H), 1.25 (t, J=7.2 Hz, 3H), 1.13 (s, 3H), 1.10 (s, 3H); ESI-MS (m/z): calcd for $C_{75}H_{105}N_8O_{24}$ [M+H]$^+$: 1501.7; found: 1501.8.

Synthetic Scheme 11 of sodium carbonate, 70 mL of DMF and 30 mL of distilled water were added, followed by 9.3 g (36.56 mmol) of 6-azido-hexanoic acid-(N-hydroxysuccinyl lactam) ester, and stirred at room temperature overnight. Upon completion of the reaction, the reaction mixture was acidified with hydrochloride solution (2.0N) to pH=1.0, and extracted with ethyl acetate three times (300 mL×3); the organic phases were combined together, dried over anhydrous MgSO$_4$, filtered, concentrated, and purified on a silica gel column and eluted with methanol in chloroform (2-10%) to provide 8.91 g of compound 77. Yield: 57%.

$^1$H NMR (300 MHz, CDCl$_3$, ppm): δ 6.21 (s, 1H), 4.55 (m, 1H), 3.23 (t, J=7.2 Hz, 2H), 2.25 (t, J=7.2 Hz, 2H), 1.82 (m, 2H), 1.52-1.75 (m, 4H), 1.45 (m, 2H), 1.42 (s, 9H), 1.26-1.41 (m, 4H); ESI-MS (m/z): calcd for $C_{17}H_{32}N_5O_5$ [M+H]$^+$: 386.2; found: 386.2.

Sample 78: Preparation of Compound 78

To a 100 mL round-bottom flask charged with 8.0 g (20.76 mmol) of compound 77 and 5.95 g (31.15 mmol) of 1-ethyl-3-(3-dimethylaminopropyl) carbodiimide (EDC), 100 mL of anhydrous dichloromethane was added and stirred at room

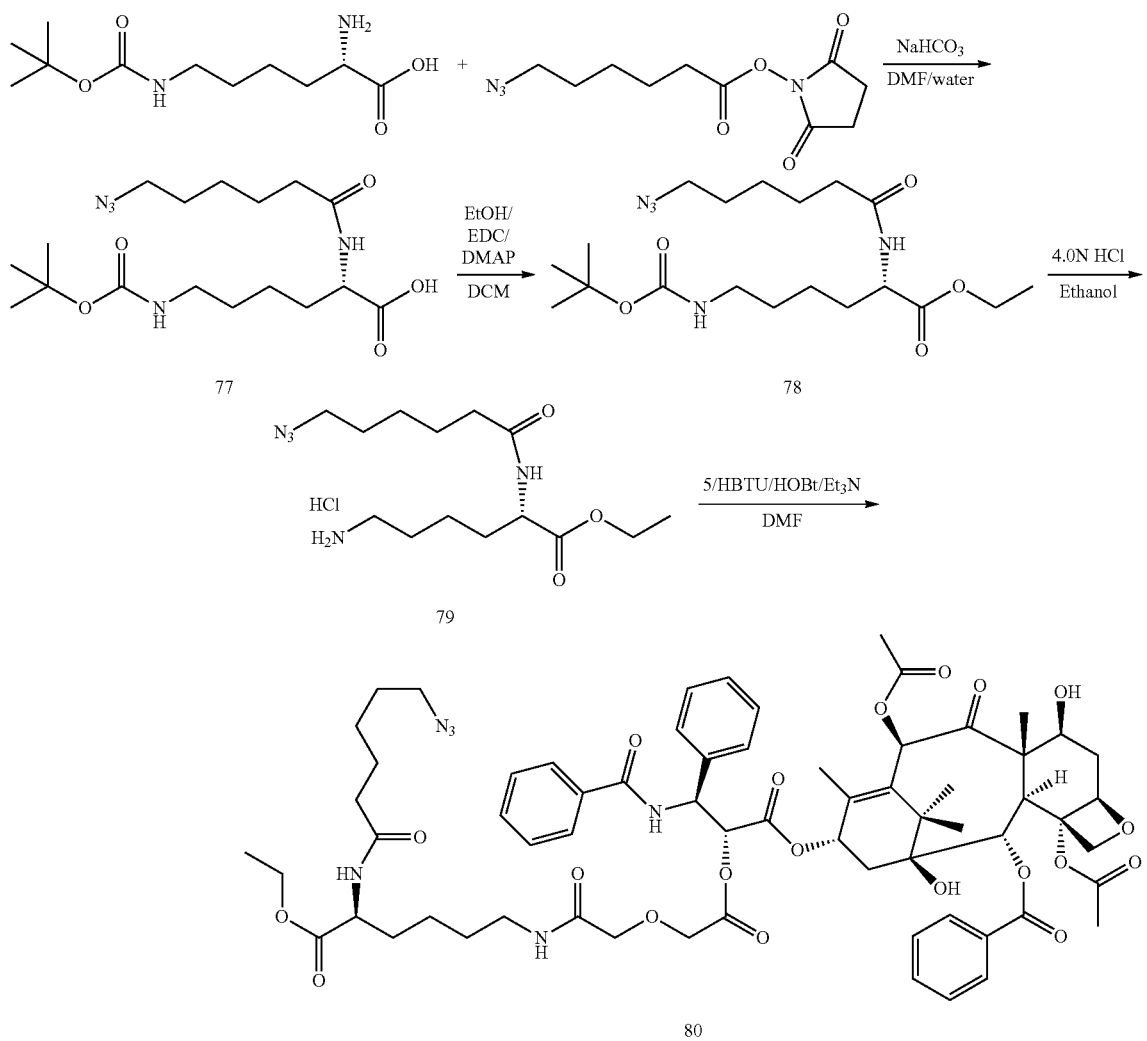

Sample 77: Preparation of Compound 77

To a 250 mL round-bottom flask charged with 10.0 g (40.62 mmol) of N6-Boc-L-lysine and 6.28 g (81.24 mmol)

temperature for 30 min; and then 6.0 mL of absolute ethanol and 38.27 g (31.15 mmol) of DMAP were added. The reaction mixture was continuously stirred overnight. Upon completion of the reaction, the reaction mixture was washed with brine (100 mL×2), dried over anhydrous MgSO$_4$, filtered, concentrated, and purified on a silica gel column and eluted with ethyl acetate in petroleum (10-80%) to provide 6.26 g of compound 78. Yield: 73%.

$^1$H NMR (300 MHz, CDCl$_3$, ppm): δ 6.11 (s, 1H), 4.52 (m, 1H), 4.12 (q, J=7.2 Hz, 2H), 3.25 (t, J=7.2 Hz, 2H), 2.24 (t, J=7.2 Hz, 2H), 1.83 (m, 2H), 1.52-1.75 (m, 4H), 1.45 (m, 2H), 1.42 (s, 9H), 1.26-1.41 (m, 4H), 1.25 (t, J=7.2 Hz, 3H); ESI-MS (m/z): calcd for C$_{19}$H$_{36}$N$_5$O$_5$ [M+H]$^+$: 414.2; found: 414.3.

Sample 79: Preparation of Compound 79

In a 250 mL round-bottom flask, 5.0 g (12.09 mmol) of compound 78 was dissolved in 50 mL of hydrochloride ethanol solution (4.0N) at room temperature, and stirred overnight. The reaction mixture was concentrated, and purified on a reverse phase C-18 column and eluted with acetonitrile in water (10-70%) to provide 3.85 g of compounds 79. Yield: 91%.

$^1$H NMR (300 MHz, CDCl$_3$, ppm): δ 6.21 (s, 1H), 4.57 (m, 1H), 4.18 (q, J=7.2 Hz, 2H), 3.25 (t, J=7.2 Hz, 2H), 2.69 (s, 3H), 2.28 (t, J=7.2 Hz, 2H), 1.82 (m, 2H), 1.52-1.75 (m, 4H), 1.45 (m, 2H), 1.26-1.41 (m, 4H), 1.25 (t, J=7.2 Hz, 3H); ESI-MS (m/z): calcd for C$_{14}$H$_{28}$N$_5$O$_3$ [M+H]$^+$: 314.2; found: 314.2.

Sample 80: Preparation of Compound 80

In a 100 mL round-bottom flask, 2.0 g (2.06 mmol) of compound 5 and 1.17 g (3.09 mmol) of benzotriazole-N, N, N', N'-tetramethyluronium hexafluorophosphate (HBTU) and 418 mg (3.09 mmol) of 1-hydroxybenzotriazole (HOBt) were dissolved in 10.0 mL of dry DMF, followed by addition of 1.07 mg (3.09 mmol) of compound 79 and 0.57 mL (4.12 mmol) of triethylamine, and stirred at room temperature for 3 h. Upon completion of the reaction, the reaction mixture was partitioned between ethyl acetate (200 mL) and brine (200 mL), the organic phase was further washed with brine twice (200 mL×2), dried over anhydrous MgSO$_4$, filtered, concentrated, and purified on a silica gel column and eluted with methanol in chloroform (2-10%) to provide 1.79 g of compound 80. Yield: 67%.

$^1$H NMR (300 MHz, CDCl$_3$, ppm): δ 8.11 (d, J=7.2 Hz, 2H), 7.20-7.80 (m, 13H), 7.10 (d, J=7.0 Hz, 1H), 6.23 (s, 1H), 6.21 (m, 2H), 5.79 (m, 1H), 5.68 (d, J=9.6 Hz, 1H), 4.96 (d, J=9.6 Hz, 1H), 4.79 (m, 1H), 4.57 (m, 1H), 4.00-4.50 (m, 9H), 3.81 (m, 1H), 3.25 (m, 4H), 2.56 (m, 1H), 2.47 (m, 1H), 2.38 (s, 3H), 2.30-2.37 (m, 6H), 2.23 (s, 3H), 1.82 (m, 2H), 1.79 (m, 4H), 1.68 (s, 3H), 1.57 (m, 7H), 1.23-1.46 (m, 6H), 1.22 (s, 3H), 1.21 (t, J=7.2 Hz, 3H), 1.15 (s, 3H); ESI-MS (m/z): calcd for C$_{65}$H$_{81}$N$_6$O$_{20}$ [M+H]$^+$: 1265.6; found: 1265.7.

Part 2. Preparation of Functionalized Polysaccharides

Synthetic Scheme 12

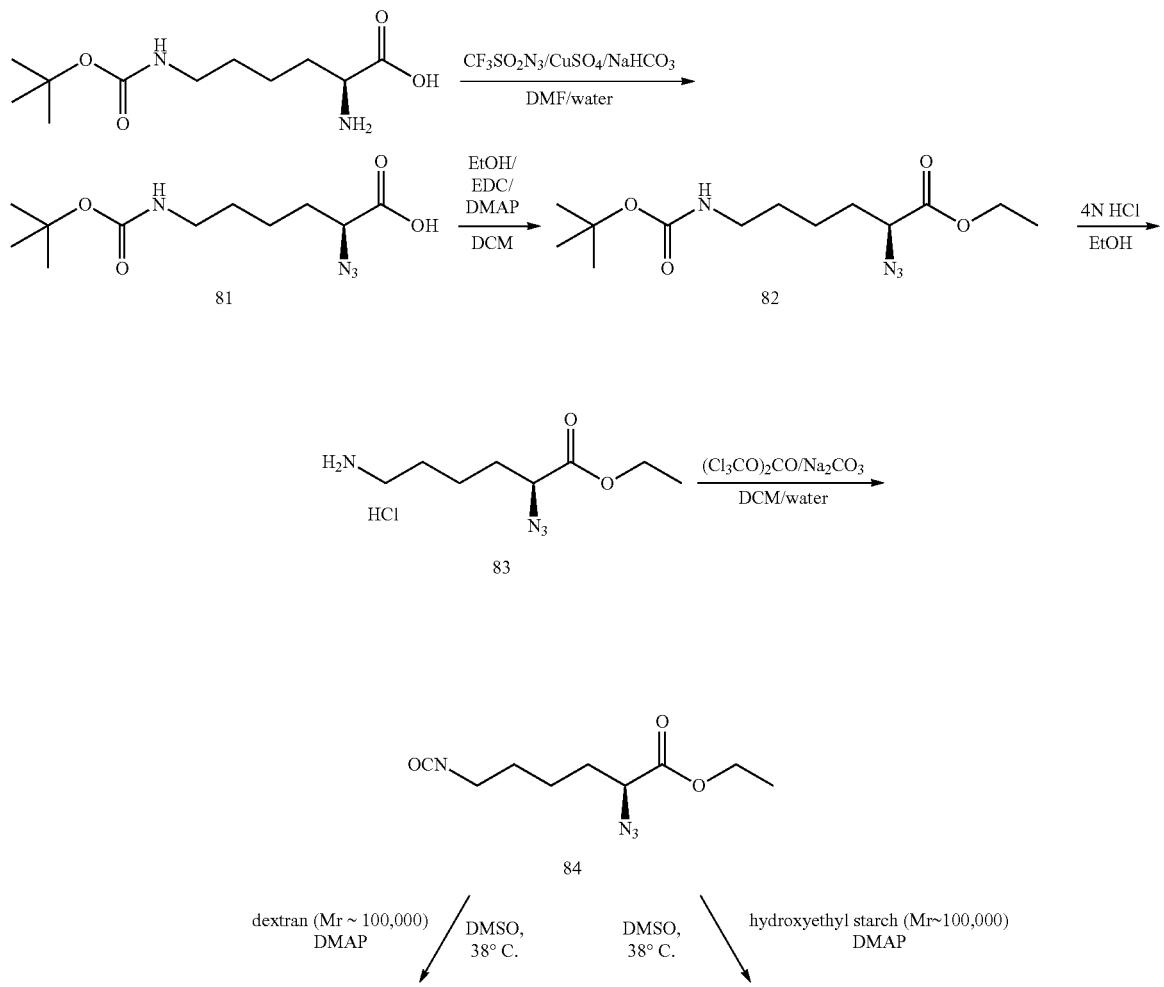

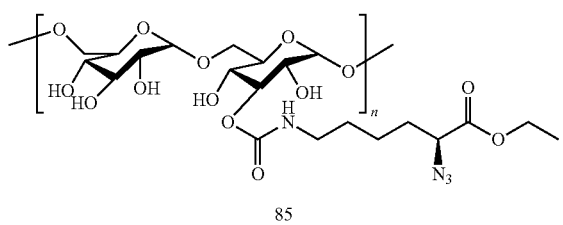

85

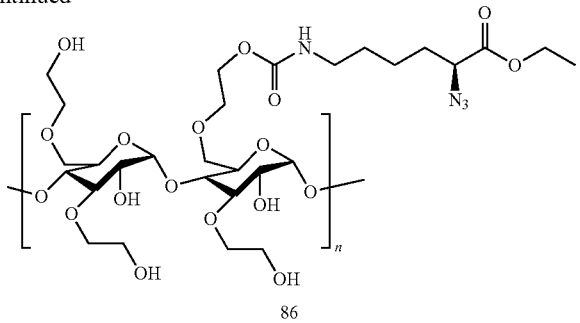

86

Sample 81: Preparation of Compound 81

In a 250 mL round bottom flask, 5.46 g (65.12 mmol) of sodium bicarbonate and 105 mg (0.66 mmol) of copper sulfate were dissolved in 90 mL of water-methanol (2:1), followed by addition of 8.0 g (32.56 mmol) N6-Boc-L-lysine and stirred for 20 min. To the above solution 6.85 g (39.07 mmol) of trifluoromethanesulfonic azide in THF was dropwise added and stirred at room temperature overnight. Upon completion of the reaction, the reaction mixture was concentrated, acidified with hydrochloride solution (2.0N) to pH=1.0, and extracted with ethyl acetate three times (50 mL×3); the organic phases were combined together, dried over anhydrous MgSO$_4$, filtered, concentrated, and purified on a silica gel column and eluted with acetone in chloroform (5-30%) to provide 4.97 g of compound 81. Yield: 56%.

$^1$H NMR (300 MHz, CDCl$_3$, ppm): δ 3.92 (m, 1H), 3.12 (t, J=7.2 Hz, 2H), 1.87 (m, 2H), 1.81 (m, 2H), 1.55 (m, 2H), 1.45 (s, 9H); ESI-MS (m/z): calcd for CH$_{21}$N$_4$O$_4$ [M+H]$^+$: 273.1; found: 273.1.

Sample 82: Preparation of Compound 82

To a 250 mL round-bottom flask charged with 4.0 g (14.71 mmol) of compound 81 and 4.20 g (22.04 mmol) of 1-ethyl-3-(3-dimethylaminopropyl) carbodiimide (EDC), 50 mL of anhydrous dichloromethane was added, and stirred at room temperature for 30 min; and then 3.0 mL of absolute ethanol and 2.69 g (22.04 mmol) of DMAP were added. The reaction was continuously stirred overnight. Upon completion of the reaction, the reaction mixture was washed with brine (50 mL×2), dried over anhydrous MgSO$_4$, filtered, concentrated, and purified on a silica gel column and eluted with ethyl acetate in petroleum (5-60%) to provide 3.67 g of compound 82. Yield: 83%.

$^1$H NMR (300 MHz, CDCl$_3$, ppm): δ 4.24 (q, J=7.2 Hz, 2H), 3.81 (m, 1H), 3.11 (t, J=7.2 Hz, 2H), 1.83 (m, 2H), 1.77 (m, 2H), 1.52 (m, 2H), 1.46 (m, 2H), 1.46 (s, 9H), 1.31 (t, J=7.2 Hz, 3H); ESI-MS (m/z): calcd for C$_{13}$H$_{25}$N$_4$O$_4$ [M+H]$^+$: 301.2; found: 301.2.

Sample 83: Preparation of Compound 83

In a 250 mL round-bottom flask, 4.5 g (14.98 mmol) of compound 82 was dissolved in 50 mL of hydrochloride ethanol solution (4.0N), and stirred overnight. The reaction mixture was concentrated, and purified on a reverse phase C-18 column and eluted with acetonitrile in water (10-70%) to provide 3.35 g of compounds 83. Yield: 95%.

$^1$H NMR (300 MHz, CDCl$_3$, ppm): δ 4.27 (q, J=7.2 Hz, 2H), 3.92 (m, 1H), 3.02 (s, 3H), 1.85 (m, 4H), 1.52 (m, 2H), 1.27 (t, J=7.2 Hz, 3H); ESI-MS (m/z): calcd for C$_8$H$_{17}$N$_4$O$_2$ [M+H]$^+$: 201.1; found: 201.1.

Sample 84: Preparation of Compound 84

In a 250 mL round bottom flask, 2.5 g (8.23 mmol) of diphosgene was dissolved in 60.0 mL of dichloromethane and cooled to 0° C., followed by addition of 60 mL of saturated sodium carbonate solution and 2.0 g (8.23 mmol) of compound 83 in dichloromethane and stirred for 3 h. Upon completion of the reaction, the organic phase was separated, dried over anhydrous MgSO$_4$, filtered, concentrated, and purified on a silica gel column and eluted with ethyl acetate in petroleum (5-60%) to provide 1.07 g of compound 84. Yield: 85%.

$^1$H NMR (300 MHz, CDCl$_3$, ppm): δ 4.27 (q, J=7.2 Hz, 2H), 3.91 (m, 1H), 3.35 (t, J=7.2 Hz, 2H), 1.85 (m, 2H), 1.65 (m, 2H), 1.52 (m, 2H), 1.31 (t, J=7.2 Hz, 3H); ESI-MS (m/z): calcd for C$_9$H$_{15}$N$_4$O$_3$ [M+H]$^+$: 227.1; found: 227.1.

Sample 85: Preparation of Functionalized Dextran 85

In a 100 mL round bottom flask, 20.0 mL of anhydrous DMSO was added and heated to 60° C., followed by addition of 2.0 g of dextran (average molecular weight~100,000) and stirred until completely dissolved. After the solution was cooled down to 38° C., 200 mg (0.88 mmol) of compound 84 and 107 mg (0.88 mmol) of 4-dimethylaminopyridine (DMAP) were added and stirred for 12 hours. Upon completion of the reaction, the reaction mixture was precipitated in methanol, dialyzed against distilled water, and lyophilized to provide 1.52 g of functionalized dextran 85. Yield. 76%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.50-1.90 (m, CH$_2$), 1.23 (t, CH$_3$).

Sample 86: Preparation of Functionalized Dextran 86

In a 100 mL round bottom flask, 20.0 mL of anhydrous DMSO was added and heated to 60° C., followed by addition of 2.0 g of hydroxyethyl starch (average molecular weight~100,000) and stirred until completely dissolved. After the solution was cooled down to 38° C., 200 mg (0.88 mmol) of compound 84 and 107 mg (0.88 mmol) of 4-dimethylaminopyridine (DMAP) were added and stirred for 12 hours Upon completion of the reaction, the reaction mixture was precipitated in methanol, dialyzed against distilled water, and lyophilized to provide 1.41 g of functionalized dextran 86. Yield: 70%.

$^1$H NMR (selected characteristic signals, 500 MHz, DMSO-d$_6$, ppm): major signals: 4.50-5.00 (m, CHOH, CHOH, CH$_2$OH), 3.30-4.20 (m, CHOH, CH$_2$OH, CH$_2$O); minor signals: 1.50-1.90 (m, CH$_2$), 1.24 (t, CH$_3$).

Synthetic Scheme 13

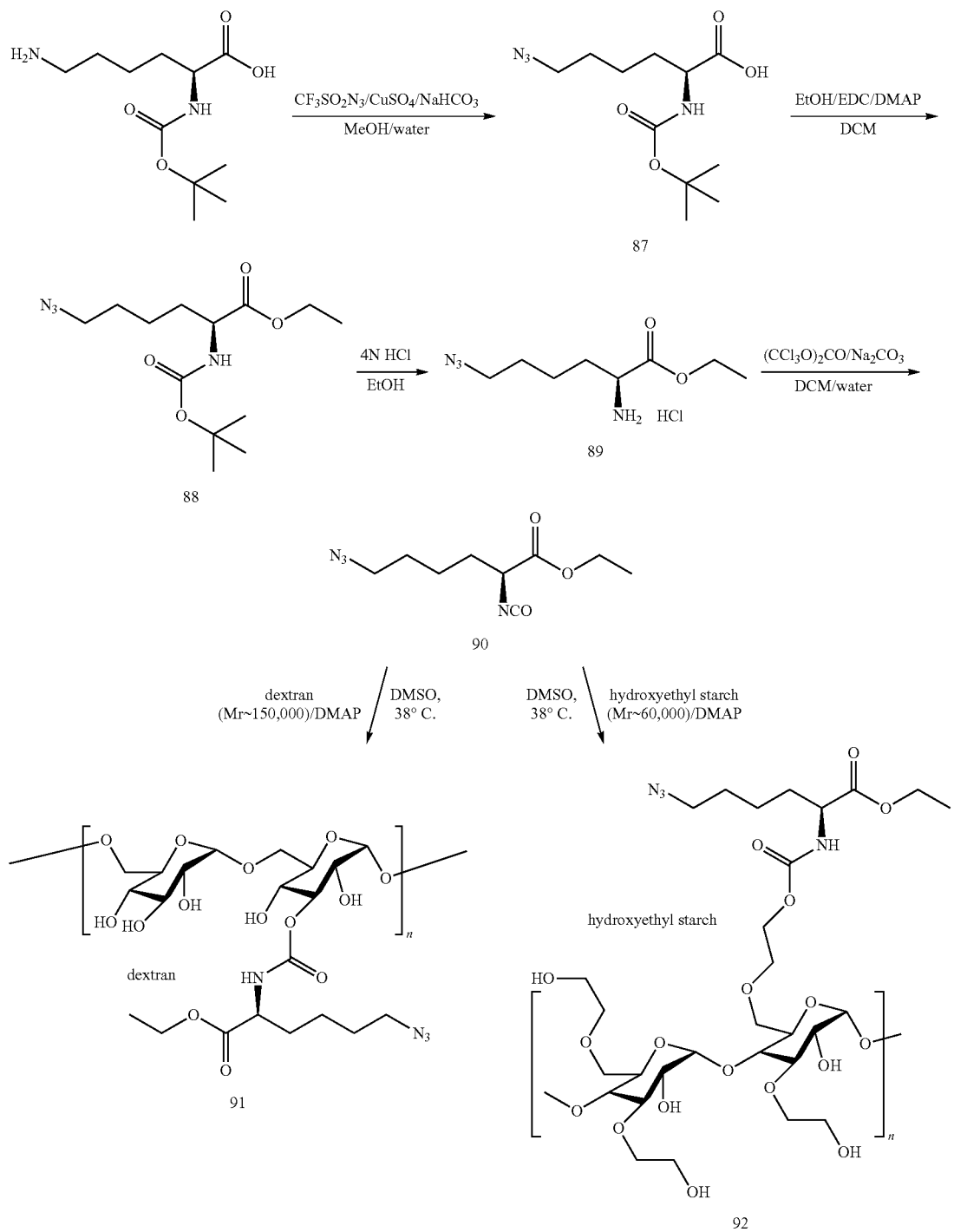

Sample 87: Preparation of Compound 87

In a 500 mL round bottom flask, 8.20 g (97.56 mmol) of sodium bicarbonate and 156 mg (0.98 mmol) of copper sulfate were dissolved in 300 mL of water-methanol (2:1), followed by addition of 12.0 g (48.78 mmol) of Boc-L-lysine and stirred for 30 min. To the above solution 10.3 g (58.53 mmol) of trifluoromethanesulfonic azide in THF was dropwise added and stirred at room temperature overnight. Upon completion of the reaction, the reaction mixture was concentrated, acidified with hydrochloride solution (2.0N) to pH-1.0, and extracted with ethyl acetate three times (100 mL×3); the organic phases were combined together, dried over anhydrous MgSO$_4$, filtered, concentrated, and purified on a silica gel column and eluted with acetone in chloroform (5-30%) to provide 5.18 g of compound 87. Yield: 39%.

$^1$H NMR (300 MHz, CDCl$_3$, ppm): δ 5.07 (d, J=6.0 Hz, 1H), 4.32 (m, 1H), 3.28 (t, J=7.2 Hz, 2H), 1.87 (m, 1H), 1.72

(m, 1H), 1.61 (m, 3H), 1.47 (m, 1H), 1.44 (s, 9H); ESI-MS (m/z): calcd for $C_1H_{21}N_4O_4$ [M+H]$^+$: 273.1; found: 273.1.

Sample 88: Preparation of Compound 88

A 250 mL round-bottom flask charged with 5.0 g (18.38 mmol) of compound 87 and 5.27 g (27.57 mmol) of 1-ethyl-3-(3-dimethylaminopropyl) carbodiimide (EDC), 50 mL of anhydrous dichloromethane was added, and stirred at room temperature for 30 min; and then 3.0 mL of absolute ethanol and 3.36 g (27.57 mmol) of DMAP were added. The reaction was continuously stirred overnight. Upon completion of reaction, the reaction mixture was washed with brine (50 mL×2), dried over anhydrous $MgSO_4$, filtered, concentrated, and purified on a silica gel column and eluted with ethyl acetate in petroleum (5-60%) to provide 3.79 g of compound 88. Yield: 76%.

$^1$H NMR (300 MHz, $CDCl_3$, ppm): δ 5.05 (d, J=6.0 Hz, 1H), 4.28 (m, 1H), 4.19 (q, J-7.2 Hz, 2H), 3.26 (t, J=7.2 Hz, 2H), 1.82 (m, 1H), 1.75 (m, 1H), 1.61 (m, 3H), 1.47 (m, 1H), 1.45 (s, 9H), 1.23 (t, J=7.2 Hz, 3H); ESI-MS (m/z): calcd for $C_{13}H_{25}N_4O_4$ [M+H]$^+$: 301.2; found: 301.2.

Sample 89: Preparation of Compound 89

In a 250 mL round-bottom flask, 3.5 g (11.65 mmol) of compound 88 was dissolved in 30 mL of hydrochloride ethanol solution (4.0N), and stirred overnight. The reaction mixture was concentrated, and purified on a reverse phase C-18 column and eluted with acetonitrile in water (10-70%) to provide 2.61 g of compounds 89. Yield: 95%.

$^1$H NMR (300 MHz, $CDCl_3$, ppm): δ 4.26 (q, J-7.2 Hz, 2H), 3.98 (s, 1H), 3.27 (t, J=7.2 Hz, 2H), 1.95 (m, 2H), 1.63 (m, 2H), 1.52 (m, 2H), 1.27 (t, J=7.2 Hz, 3H); ESI-MS (m/z): calcd for $C_8H_{17}N_4O_2$ [M+H]$^+$: 201.1; found: 201.1.

Sample 90: Preparation of Compound 90

In a 250 mL round bottom flask, 3.13 g (10.56 mmol) of diphosgene was dissolved in 60.0 mL of dichloromethane and cooled to 0° C., followed by addition of 60 mL of saturated sodium carbonate solution and 2.50 g (10.56 mmol) of compound 89 in dichloromethane and stirred for 3 h. Upon completion of reaction, the organic phase was separated, dried over anhydrous $MgSO_4$, filtered, concentrated, and purified on a silica gel column and eluted with ethyl acetate in petroleum (5-60%) to provide 1.72 g of compound 90. Yield: 72%.

$^1$H NMR (300 MHz, $CDCl_3$, ppm): δ 4.27 (q, J=7.2H), 4.02 (m, 1H), 3.29 (t, J=7.2 Hz), 1.85 (m, 2H), 1.62 (m, 2H), 1.51 (m, 2H), 1.25 (t, J=7.2 Hz, 3H); ESI-MS (m/z): calcd for $C_9H_{15}N_4O_3$ [M+H]$^+$: 227.1; found: 227.1.

Sample 91: preparation of functionalized dextran 91

In a 500 mL round bottom flask, 200 mL of anhydrous DMSO was added and heated to 60° C., followed by addition of 20.0 g of dextran (average molecular weight~150,000) and stirred until completely dissolved. After the solution was cooled down to 38° C., 1.0 g (4.42 mmol) of compound 90 and 539 mg (0.88 mmol) of 4-dimethylaminopyridine (DMAP) were added and stirred for 12 hours. Upon completion of the reaction, the reaction mixture was precipitated in methanol, dialyzed against distilled water, and lyophilized to provide 16.3 g of functionalized dextran 91. Yield: 81%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 1.50-1.90 (m, $CH_2$), 1.24 (t, $CH_3$).

Sample 92: Preparation of Functionalized Hydroxyethyl Starch 92

In a 100 mL round bottom flask, 20 mL of anhydrous DMSO was added and heated to 60° C., followed by addition of 2.0 g of hydroxyethyl starch (average molecular weight ~60,000) and stirred until completely dissolved. After the solution was cooled down to 38° C., 200 mg (0.88 mmol) of compound 90 and 107 mg (0.88 mmol) of 4-dimethylaminopyridine (DMAP) were added and stirred for 12 hours. Upon completion of the reaction, the reaction mixture was precipitated in methanol, dialyzed against distilled water, and lyophilized to provide 1.06 g of functionalized hydroxyethyl starch 92. Yield: 51%.

$^1$H NMR (selected characteristic signals, 500 MHz, DMSO-$d_6$, ppm): major signals: 4.50-5.00 (m, CHOH, CHOH, $CH_2OH$), 3.30-4.20 (m, CHOH, $CH_2OH$, $CH_2O$); minor signals: 1.50-1.90 (m, $CH_2$), 1.23 (t, $CH_3$).

Synthetic Scheme 14

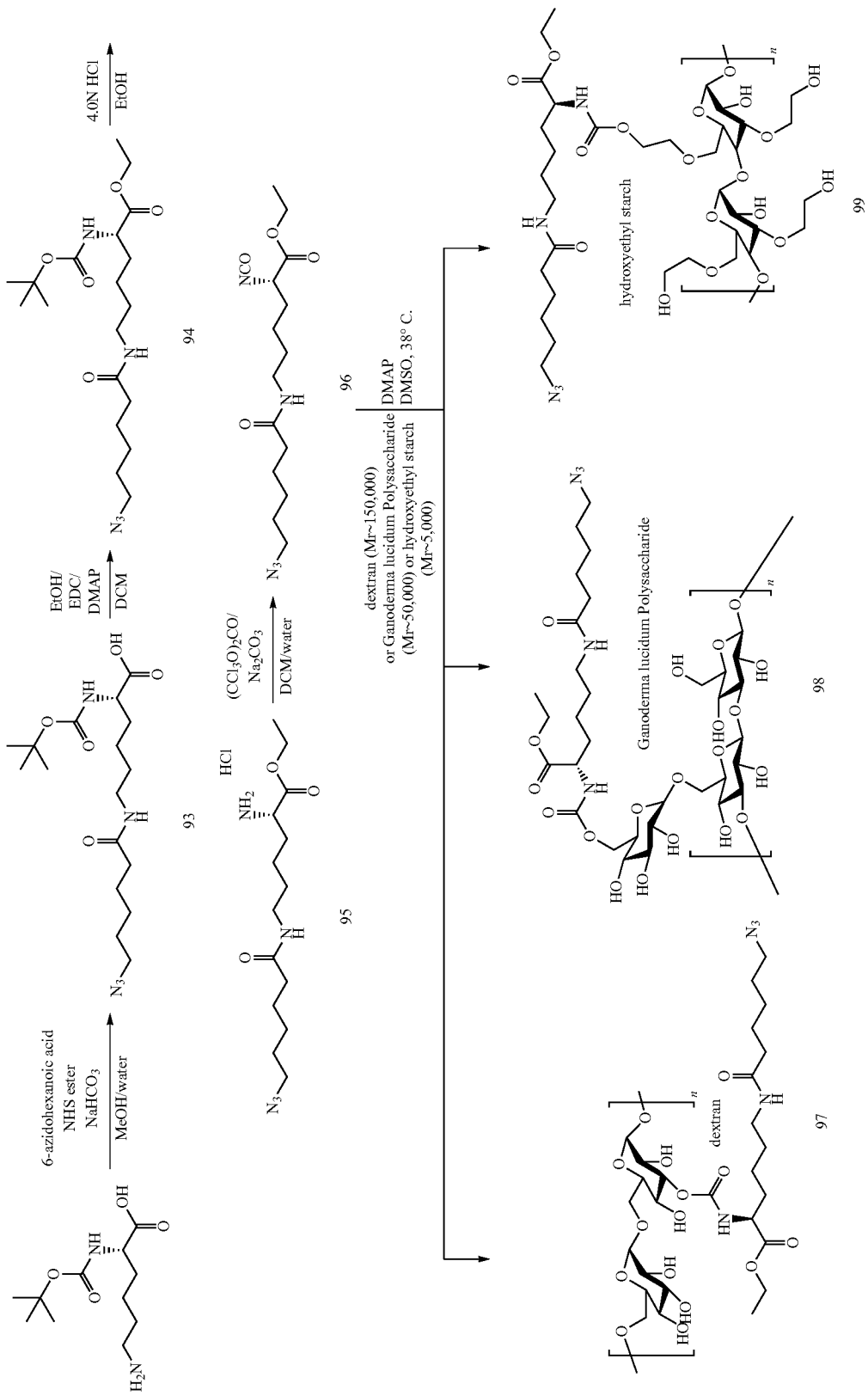

Sample 93: Preparation of Compound 93

In a 250 mL round bottom flask, 12.0 g (48.78 mmol) of compound Boc-L-lysine and 8.20 g (97.56 mmol) of sodium bicarbonate were dissolved in 200.0 mL of methanol-water (2:1), followed by addition of 13.6 g (53.46 mmol) of 6-azido-n-hexanoic acid-(N-hydroxysuccinyl lactam) ester and stirred overnight. Upon completion of the reaction, the reaction mixture was neutralized with 2.0N HCl to pH=1.0, extracted with ethyl acetate (100 mL×3); the organic phases were combined, dried over MgSO$_4$, concentrated, and purified on a reverse phase C-18 column and eluted with acetonitrile in water (10-80%) to provide 11.9 g of compound 93. Yield: 63%.

$^1$H NMR (300 MHz, CDCl$_3$, ppm): δ 6.69 (s, 1H), 5.28 (s, 1H), 4.28 (m, 1H), 3.28 (m, 4H), 2.23 (t, J=7.2 Hz, 2H), 1.81 (m, 1H), 1.69 (m, 2H), 1.63 (m, 3H), 1.53 (m, 2H), 1.42 (s, 9H), 1.38 (m, 4H); ESI-MS (m/z): calcd for C$_{17}$H$_{32}$N$_5$O$_5$ [M+H]$^+$: 386.2; found: 386.2.

Sample 94: Preparation of Compound 94

To a 250 mL round-bottom flask charged with 10.0 g (25.95 mmol) of compound 93 and 7.43 g (38.93 mmol) of 1-ethyl-3-(3-dimethylaminopropyl) carbodiimide (EDC), 100 mL of anhydrous dichloromethane was added and stirred at room temperature for 30 min; and then 5.0 mL of absolute ethanol and 4.75 g (38.93 mmol) of DMAP were added. The reaction was continuously stirred overnight. Upon completion of the reaction, the reaction mixture was washed with brine (80 mL×2), dried over anhydrous MgSO$_4$, filtered, concentrated, and purified on a silica gel column and eluted with ethyl acetate in petroleum ether (10-70%) to provide 3.79 g of compound 94. Yield: 75%.

$^1$H NMR (300 MHz, CDCl$_3$, ppm): δ 5.19 (s, 1H), 4.25 (q, J=7.2 Hz, 2H), 4.15 (m, 1H), 3.23 (m, 4H), 2.17 (t, J=7.2 Hz, 2H), 1.81 (m, 1H), 1.69 (m, 2H), 1.63 (m, 3H), 1.53 (m, 2H), 1.42 (s, 9H), 1.38 (m, 4H), 1.23 (t, J=7.2 Hz, 3H); ESI-MS (m/z): calcd for C$_{19}$H$_{36}$N$_5$O$_5$ [M+H]$^+$: 414.2; found: 414.3.

Sample 95: Preparation of Compound 95

To a 250 mL round-bottom flask charged with 7.0 g (16.93 mmol) of compound 94, 50 mL of hydrochloride ethanol solution (4.0N) was added and stirred at room temperature overnight. After removal of volatiles, the residue was purified on a reverse phase C-18 column and eluted with acetonitrile in water (10-70%) to provide 5.46 g of compound 95. Yield: 92%.

$^1$H NMR (300 MHz, CDCl$_3$, ppm): δ 7.16 (s, 1H), 4.24 (q, J=7.2 Hz, 2H), 3.97 (m, 1H), 3.24 (m, 4H), 2.25 (t, J=7.2 Hz, 2H), 1.98 (m, 2H), 1.56 (m, 6H), 1.48 (m, 2H), 1.36 (m, 2 h), 1.26 (t, J=7.2 Hz, 3H); ESI-MS (m/z): calcd for C$_{14}$H$_{28}$N$_5$O$_3$ [M+H]$^+$: 314.2; found: 314.2.

Sample 96: Preparation of Compound 96

In a 250 mL round bottom flask, 2.54 g (8.57 mmol) of diphosgene was dissolved in 50.0 mL of dichloromethane and cooled to 0° C., followed by addition of 50 mL of saturated sodium carbonate solution and 3.0 g (8.57 mmol) of compound 89 in dichloromethane and stirred for 3 h. Upon completion of the reaction, the organic phase was separated, dried over anhydrous MgSO$_4$, filtered, concentrated, and purified on a silica gel column and eluted with ethyl acetate in petroleum (5-60%) to provide 1.89 g of compound 96. Yield: 65%.

$^1$H NMR (300 MHz, CDCl$_3$, ppm): δ 7.13 (s, 1H), 4.29 (q, J=7.2 Hz, 2H), 4.11 (m, 1H), 3.27 (m, 4H), 2.25 (t, J=7.2 Hz, 2H), 1.87 (m, 2H), 1.63 (m, 2H), 1.56 (m, 4H), 1.46 (m, 2H), 1.35 (m, 2 h), 1.28 (t, J=7.2 Hz, 3H); ESI-MS (m/z): calcd for C$_{15}$H$_{26}$N$_5$O$_4$ [M+H]$^+$: 340.2; found: 340.2.

Sample 97: Preparation of Compound 97

In a 100 mL round bottom flask, 20 mL of anhydrous DMSO was added and heated to 60° C., followed by addition of 2.0 g of dextran (average molecular weight ~150,000) and stirred until completely dissolved. After the solution was cooled down to 38° C., 250 mg (0.73 mmol) of compound 96 and 89 mg (0.73 mmol) of 4-dimethylaminopyridine (DMAP) were added and stirred for 12 hours. Upon completion of the reaction, the reaction mixture was precipitated in methanol, dialyzed against distilled water, and lyophilized to provide 1.72 g of functionalized dextran 97. Yield. 86%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.35-1.90 (m, CH$_2$), 1.23 (t, CH$_3$).

Sample 98: preparation of functionalized polysaccharide 98

In a 500 mL round bottom flask, 5.0 mL of anhydrous DMSO was added and heated to 60° C., followed by addition of 500 mg of *Ganoderma Lucidum* polysaccharide (average molecular weight ~50,000) and stirred until completely dissolved. After the solution was cooled down to 38° C., 100 mg (0.29 mmol) of compound 96 and 35 mg (0.29 mmol) of 4-dimethylaminopyridine (DMAP) were added and stirred for 12 hours Upon completion of the reaction, the reaction mixture was precipitated in methanol, dialyzed against distilled water, and lyophilized to provide 436 mg of functionalized polysaccharide 98. Yield: 87%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.35-1.90 (m, CH$_2$), 1.25 (t, CH$_3$).

Sample 99: Preparation of Functionalized Hydroxyethyl Starch 99

In a 100 mL round bottom flask, 20 mL of anhydrous DMSO was added and heated to 60° C., followed by addition of 2.0 g of hydroxyethyl starch (average molecular weight ~5,000) and stirred until completely dissolved. After the solution was cooled down to 38° C., 260 mg (0.76 mmol) of compound 96 and 93 mg (0.76 mmol) of 4-dimethylaminopyridine (DMAP) were added and stirred for 12 hours. Upon completion of the reaction, the reaction mixture was precipitated in methanol, dialyzed against distilled water, and lyophilized to provide 1.86 g of functionalized hydroxyethyl starch 99. Yield: 93%.

$^1$H NMR (selected characteristic signals, 500 MHz, DMSO-d$_6$, ppm): major signals: 4.50-5.00 (m, CHOH, CHOH, CH$_2$OH), 3.30-4.20 (m, CHOH, CH$_2$OH, CH$_2$O); minor signals: 1.35-1.90 (m, CH$_2$), 1.24 (t, CH$_3$).

Synthetic Scheme 15

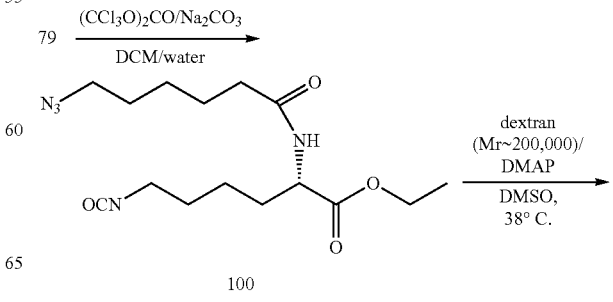

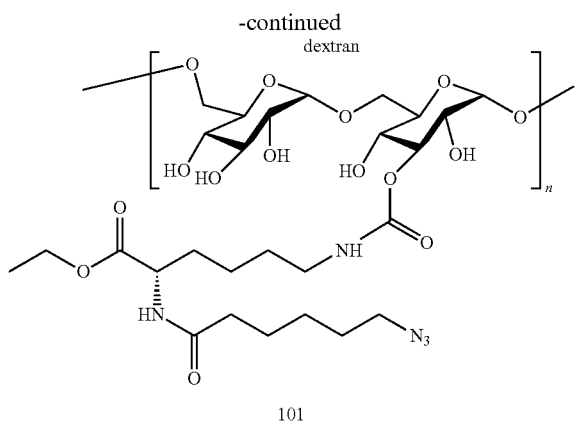

101

Sample 100: Preparation of Compound 100

In a 250 mL round bottom flask, 2.54 g (8.57 mmol) of diphosgene was dissolved in 50.0 mL of dichloromethane and cooled to 0° C., followed by addition of 50 mL of saturated sodium carbonate solution and 3.0 g (8.57 mmol) of compound 79 in dichloromethane and stirred for 6 h. Upon completion of the reaction, the organic phase was separated, dried over anhydrous $MgSO_4$, filtered, concentrated, and purified on a silica gel column and eluted with ethyl acetate in petroleum (5-60%) to provide 1.83 g of compound 100. Yield: 63%.

$^1$H NMR (300 MHz, $CDCl_3$, ppm): § 6.22 (s, 1H), 4.56 (m, 1H), 4.21 (q, J=7.2 Hz, 2H), 3.25-3.40 (m, 4H), 2.25 (t, J=7.2 Hz, 2H), 1.82 (m, 2H), 1.52-1.75 (m, 6H), 1.45 (m, 2H), 1.26-1.44 (m, 4H), 1.25 (t, J=7.2 Hz, 3H); ESI-MS: calcd for $C_{15}H_{26}N_5O_4$ [M+H]$^+$: 340.2; found: 340.2.

Sample 101: Preparation of Functionalized Dextran 101

In a 100 mL round bottom flask, 20.0 mL of anhydrous DMSO was added and heated to 60° C., followed by addition of 3.0 g of dextran (average molecular weight ~200,000) and stirred until completely dissolved. After the solution was cooled down to 38° C., 270 mg (0.76 mmol) of compound 100 and 93 mg (0.76 mmol) of 4-dimethylaminopyridine (DMAP) were added and stirred for 12 hours. Upon completion of the reaction, the reaction mixture was precipitated in methanol, dialyzed against distilled water, and lyophilized to provide 2.75 g of functionalized dextran 101. Yield: 92%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 1.35-1.90 (m, $CH_2$), 1.23 (t, $CH_3$).

Synthetic Scheme 16

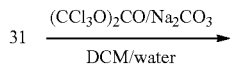

$$31 \xrightarrow[\text{DCM/water}]{(CCl_3O)_2CO/Na_2CO_3}$$

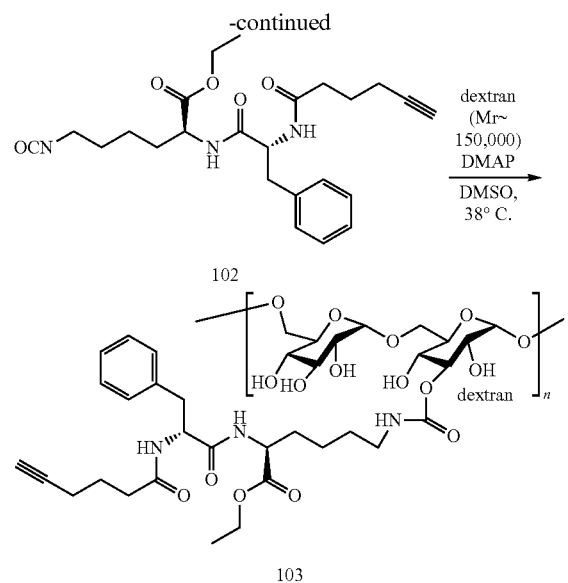

Sample 102: Preparation of Compound 102

In a 250 mL round bottom flask, 1.65 g (5.53 mmol) of diphosgene was dissolved in 30.0 mL of dichloromethane and cooled to 0° C., followed by addition of 30 mL of saturated sodium carbonate solution and 2.5 g (5.53 mmol) of compound 31 in dichloromethane and stirred for 6 h. Upon completion of the reaction, the organic phase was separated, dried over anhydrous $MgSO_4$, filtered, concentrated, and purified on a silica gel column and eluted with ethyl acetate in petroleum (5-50%) to provide 1.76 g of compound 102. Yield: 72%.

$^1$H NMR (500 MHz, $CDCl_3$, ppm): δ 7.10-7.35 (m, 5H), 4.71 (m, 1H), 4.46 (m, 1H), 4.15 (q, J=7.2 Hz, 2H), 3.25 (t, J=7.2 Hz, 2H), 3.11 (m, 1H), 2.98 (m, 1H), 2.31 (t, J=7.2 Hz, 2H), 2.05 (m, 2H), 1.96 (t, J=3.0 Hz, 1H), 1.81 (m, 2H), 1.50-1.70 (m, 6H), 1.35 (m, 2H), 1.25 (t, J=7.2 Hz, 3H); ESI-MS: calcd for $C_{24}H_{32}N_3O_5$ [M+H]$^+$: 442.2; found: 442.3.

Sample 103: Preparation of Compound 103

In a 100 mL round bottom flask, 20.0 mL of anhydrous DMSO was added and heated to 60° C., followed by addition of 3.0 g of dextran (average molecular weight ~150,000) and stirred until completely dissolved. After the solution was cooled down to 38° C., 270 mg (0.76 mmol) of compound 102 and 93 mg (0.76 mmol) of 4-dimethylaminopyridine (DMAP) were added and stirred for 12 hours. Upon completion of the reaction, the reaction mixture was precipitated in methanol, dialyzed against distilled water, and lyophilized to provide 2.75 g of functionalized dextran 103. Yield: 92%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.10-8.50 (m, CONH, ArH), 1.23 (t, $CH_3$).

Synthetic Scheme 17

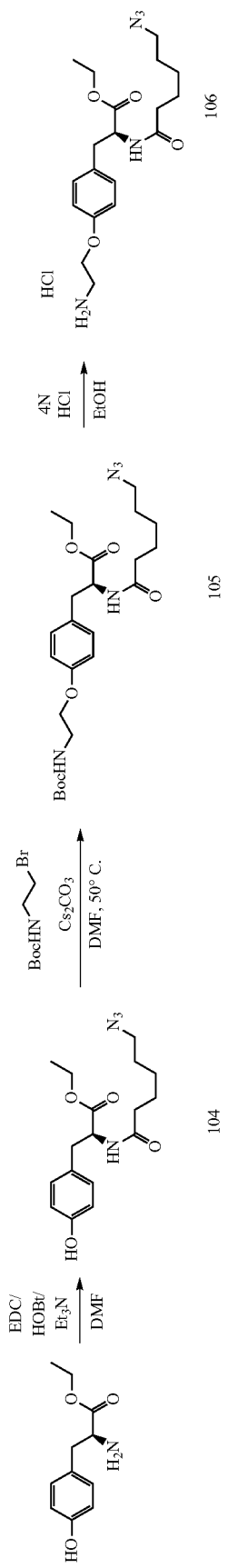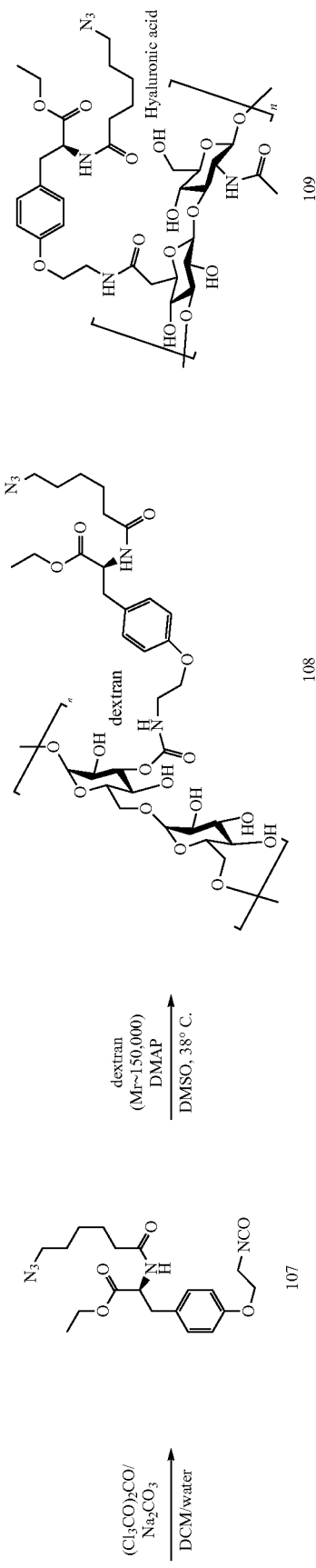

Sample 104: Preparation of Compound 104

To a 250 mL round-bottom flask charged with 8.99 g (57.31 mmol) of 6-azidohexanoic acid, 11.0 g (57.31 mmol) of 1-ethyl-3-(3-dimethylaminopropyl) carbodiimide (EDC), and 7.75 g (57.31 mmol) of 1-hydroxybenzotriazole (HOBt), 50.0 mL of dry DMF was added and stirred for 30 min, followed by addition of 10.0 g (47.79 mmol) of L-tyrosine methyl ester and 13.0 mL (95.60 mmol) of triethylamine and stirred at room temperature for another 5 h. Upon completion of the reaction, the reaction mixture was partitioned between ethyl acetate (200 mL) and brine (200 mL), the organic phase was further washed with brine twice (100 mL×2), dried over anhydrous $MgSO_4$, filtered, concentrated, and purified on a silica gel column and eluted with ethyl acetate in petroleum ether (20-80%) to provide 15.92 g of compound 104. Yield: 95%.

$^1$H NMR (500 MHz, $CDCl_3$, ppm): δ 6.95 (d, J=7.0 Hz, 2H), 6.71 (d, J=7.0 Hz, 2H), 6.05 (d, J=7.0 Hz, 2H), 4.86 (m, 1H), 4.21 (q, J=7.2 Hz, 2H), 3.24 (t, J=7.2 Hz, 2H), 3.05 (m, 1H), 2.99 (m, 1H), 2.19 (t, J=7.2 Hz, 2H), 1.53 (m, 4H), 1.34 (m, 2H), 1.25 (t, J=7.2 Hz, 2H); ESI-MS: calcd for $C_{17}H_{25}NO_4$ $[M+H]^+$: 349.2; found: 349.2.

Sample 105: Preparation of Compound 105

In a 250 mL round bottom flask, 7.0 g (30.17 mmol) of Boc-2-bromoethylamine and 6.76 g (20.11 mmol) of compound 104 were dissolved in 30.0 mL of anhydrous dimethylformamide, followed by addition of 9.83 g (30.17 mmol) of cesium carbonate, heated at 50° C. overnight. Upon completion of the reaction, the reaction mixture was partitioned between ethyl acetate (150 mL) and brine (150 mL); the organic phase was further washed with brine (60 mL×2), dried over anhydrous $MgSO_4$, filtered, concentrated, and purified on a silica gel column and eluted with ethyl acetate in petroleum ether (10-70%) to give 7.61 g of compound 105. Yield: 77%.

$^1$H NMR (500 MHz, $CDCl_3$, ppm): δ 7.01 (d, J=7.0 Hz, 2H), 6.79 (d, J=7.0 Hz, 2H), 5.89 (d, J=7.0 Hz, 2H), 4.81 (m, 1H), 4.19 (q, J=7.2 Hz, 2H), 3.97 (t, J=7.2 Hz, 2H), 3.50 (t, J=7.2 Hz, 2H), 3.23 (t, J=7.2 Hz, 2H), 3.02 (m, 1H), 2.99 (m, 1H), 2.17 (t, J=7.2 Hz, 2H), 1.62 (m, 4H), 1.45 (s, 9H), 1.36 (m, 2H), 1.24 (t, J=7.2 Hz, 2H); ESI-MS: calcd for $C_{24}H_{38}N_5O_6[M+H]^+$: 492.3; found: 492.3.

Sample 106: Preparation of Compound 106

To a 200 mL round-bottom flask charged with 7.0 g (16.93 mmol) of compound 105, 50 mL of hydrochloride ethanol solution (4.0N) was added and stirred at room temperature overnight. After removal of volatiles, the residue was purified on a reverse phase C-18 column and eluted with acetonitrile in water (10-70%) to provide 5.85 g of compound 106. Yield: 96%.

$^1$H NMR (500 MHz, $CDCl_3$, ppm): δ 6.99 (d, J=7.0 Hz, 2H), 6.72 (d, J=7.0 Hz, 2H), 5.92 (d, J=7.0 Hz, 2H), 4.82 (m, 1H), 4.19 (q, J=7.2 Hz, 2H), 3.94 (t, J=7.2 Hz, 2H), 3.23 (t, J=7.2 Hz, 2H), 2.99-3.06 (m, 4H), 2.18 (t, J=7.2 Hz, 2H), 1.63 (m, 4H), 1.34 (m, 2H), 1.23 (t, J=7.2 Hz, 2H); ESI-MS: calcd for $C_{19}H_{30}N_5O_4$ $[M+H]^+$: 392.2; found: 392.3.

Sample 107: Preparation of Compound 107

In a 250 mL round bottom flask, 3.50 g (5.53 mmol) of diphosgene was dissolved in 30.0 mL of dichloromethane and cooled to 0° C., followed by addition of 50 mL of saturated sodium carbonate solution and 5.0 g (11.68 mmol) of compound 106 in dichloromethane and stirred for 5 h. Upon completion of the reaction, the organic phase was separated, dried over anhydrous $MgSO_4$, filtered, concentrated, and purified on a silica gel column and eluted with ethyl acetate in chloroform (5-70%) to provide 3.31 g of compound 107. Yield: 68%.

$^1$H NMR (500 MHz, $CDCl_3$, ppm): δ 7.01 (d, J=7.0 Hz, 2H), 6.82 (d, J=7.0 Hz, 2H), 5.92 (d, J=7.0 Hz, 2H), 4.81 (m, 1H), 4.16 (q, J-7.2 Hz, 2H), 4.07 (t, J=7.2 Hz, 2H), 3.62 (t, J=7.2 Hz, 2H), 3.04 (m, 1H), 2.99 (m, 1H), 2.18 (t, J=7.2 Hz, 2H), 1.63 (m, 4H), 1.35 (m, 2H), 1.26 (t, J=7.2 Hz, 2H); ESI-MS: calcd for $C_{20}H_{28}N_5O_5$ $[M+H]^+$: 418.2; found: 418.3.

Sample 108: Preparation of Functionalized Dextran 108

In a 100 mL round bottom flask, 20.0 mL of anhydrous DMSO was added and heated to 60° C., followed by addition of 3.0 g of dextran (average molecular weight ~150,000) and stirred until completely dissolved After the solution was cooled down to 38° C., 300 mg (0.72 mmol) of compound 107 and 87 mg (0.72 mmol) of 4-dimethylaminopyridine (DMAP) were added and stirred for 12 hours. Upon completion of the reaction, the reaction mixture was precipitated in methanol, dialyzed against distilled water, and lyophilized to provide 2.51 g of functionalized dextran 108. Yield: 83%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 6.75-7.20 (m, ArH), 1.23 (t, $CH_3$).

Sample 109: Preparation of Functionalized Dextran 109

To a 250 mL round-bottom flask charged with 500 mg of hyaluronic acid (average molecular weight ~10,000), 10.0 mL of anhydrous DMSO was added and heated at 60° C. completely dissolved, and then cooled down to room temperature. To the above solution, 35 mg (0.18 mmol) of 1-ethyl-3-(3-dimethylaminopropyl) carbodiimide (EDC), and 25 mg (0.18 mmol) of 1-hydroxybenzotriazole (HOBt), and 50 mg (0.12 mmol) of compound 106 were added and stirred at room temperature for 2 days. Upon completion of the reaction, the reaction mixture was precipitated in methanol, dialyzed against distilled water, and lyophilized to provide 312 mg of functionalized dextran 109. Yield: 62%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 6.75-7.20 (m, ArH), 2.05 (s, $CH_3CO$), 1.23 (t, $CH_3$).

Synthetic Scheme 18

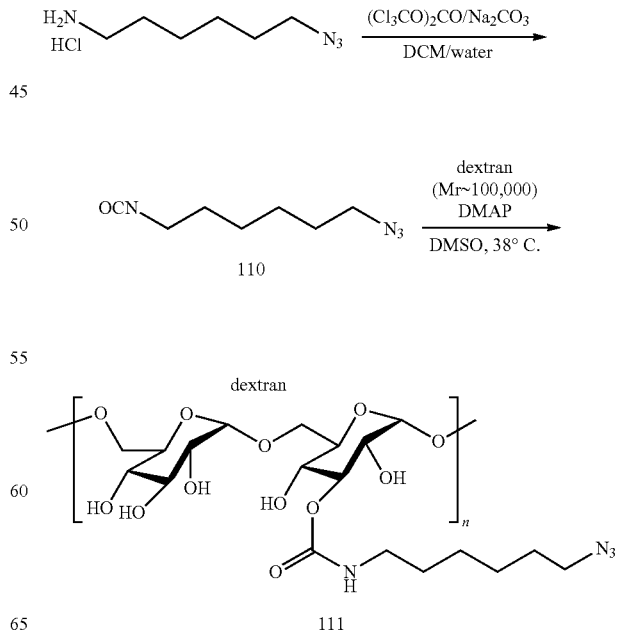

Sample 110: Preparation of Compound 110

In a well ventilation hood, 60.0 g (202.13 mmol) of diphosgene was dissolved in 300 mL of dichloromethane in a 1000 mL round bottom flask and cooled to 0° C., followed by addition of 300 mL of saturated sodium carbonate solution and 36.0 g (202.13 mmol) of 6-azido-hexylamine hydrochloride in dichloromethane and stirred for 3 h. Upon completion of the reaction, the organic phase was separated, dried over anhydrous MgSO$_4$, filtered, concentrated, and purified by fractional distillation to provide 10.5 g of compound 110. Yield: 31%.

$^1$H NMR (500 MHz, CDCl$_3$, ppm): δ 3.20-3.45 (m, 4H), 1.35-1.85 (m, 8H); ESI-MS: calcd for C$_7$H$_{12}$N$_4$O [M+H]$^+$: 168.1; found: 168.1.

Sample 111: Preparation of Functionalized Dextran 111

In a 100 mL round bottom flask, 20.0 mL of anhydrous DMSO was added and heated to 60° C., followed by addition of 3.0 g of dextran (average molecular weight ~100,000) and stirred until completely dissolved. After the solution was cooled down to 38° C., 600 mg (3.57 mmol) of compound 110 and 436 mg (3.57 mmol) of 4-dimethylaminopyridine (DMAP) were added and stirred for 12 hours. Upon completion of the reaction, the reaction mixture was precipitated in methanol, dialyzed against distilled water, and lyophilized to provide 2.89 g of functionalized dextran 111 Yield: 96%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.35-1.90 (m, CH$_2$).

Synthetic Scheme 19

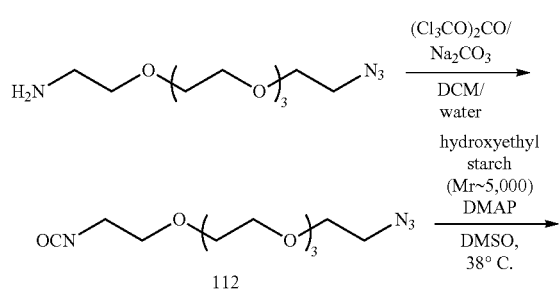

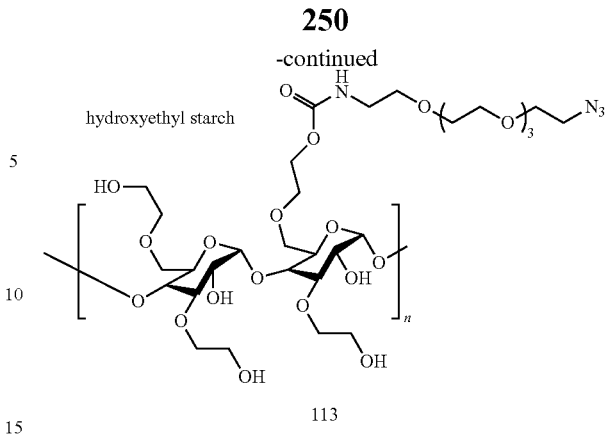

113

Sample 112: Preparation of Compound 112

In a 250 mL round bottom flask, 4.95 g (16.68 mmol) of diphosgene was dissolved in 50.0 mL of dichloromethane and cooled to 0° C., followed by addition of 70 mL of saturated sodium carbonate solution and 6.0 g (16.68 mmol) of azido-tetra-ethylene glycol amine in dichloromethane and stirred for 5 h. Upon completion of the reaction, the organic phase was separated, dried over anhydrous MgSO$_4$, filtered, concentrated, and purified on a silica gel column and eluted with acetone in chloroform (10-70%) to provide 3.16 g of compound 112. Yield: 57%.

$^1$H NMR (300 MHz, CDCl$_3$, ppm): δ 3.61 (m, 20H), 3.31 (m, 4H); ESI-MS: calcd for C$_{13}$H$_{25}$N$_4$O$_6$ [M+H]$^+$: 333.1; found: 333.1.

Sample 113: Preparation of Functionalized Hydroxyethyl Starch 113

In a 100 mL round bottom flask, 20 mL of anhydrous DMSO was added and heated to 60° C., followed by addition of 2.0 g of hydroxyethyl starch (average molecular weight ~5,000) and stirred until completely dissolved. After the solution was cooled down to 38° C., 600 mg (1.81 mmol) of compound 112 and 220 mg (1.81 mmol) of 4-dimethylaminopyridine (DMAP) were added and stirred for 24 hours. Upon completion of the reaction, the reaction mixture was precipitated in methanol, dialyzed against distilled water, and lyophilized to provide 1.32 g of functionalized hydroxyethyl starch 113. Yield: 66%.

$^1$H NMR (selected characteristic signals, 500 MHz, DMSO-d$_6$, ppm): major signals: 4.50-5.00 (m, CHOH, CHOH, CH$_2$OH), 3.20-4.20 (m, CHOH, CH$_2$OH, CH$_2$O, CH$_2$N).

Synthetic Scheme 20

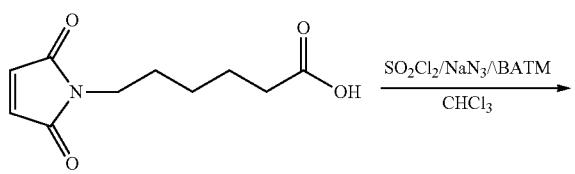

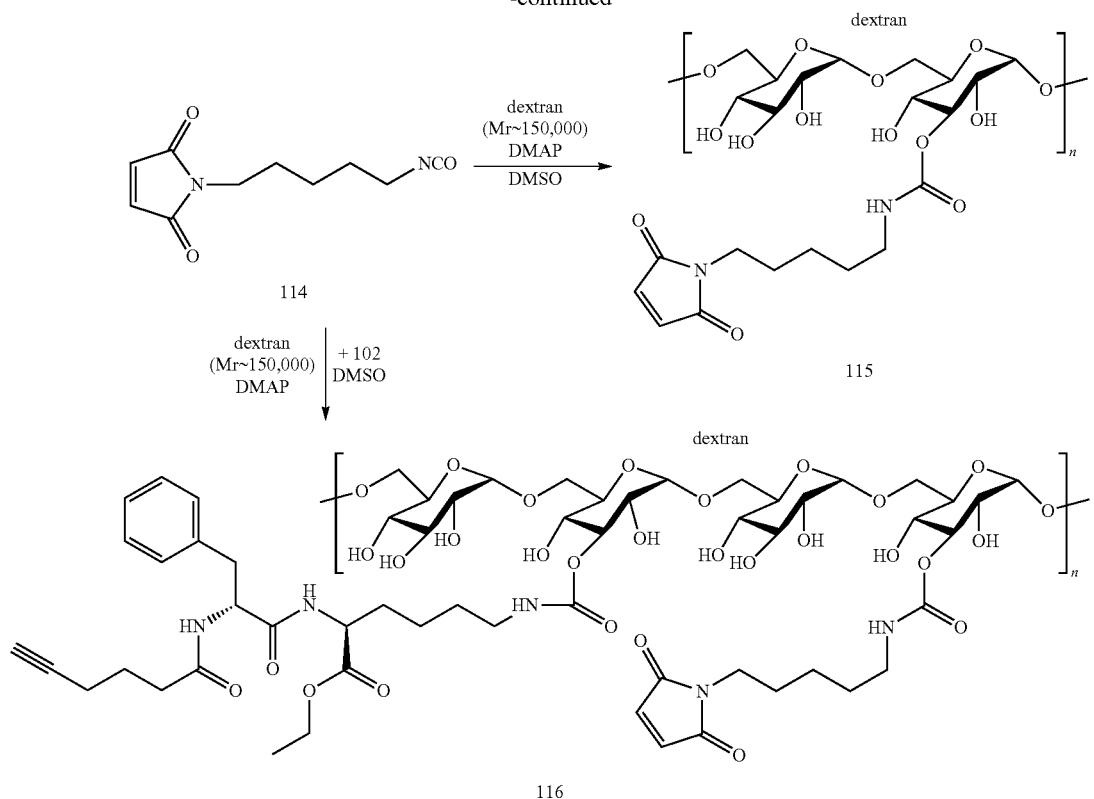

Sample 114: Preparation of Compound 114

In a 250 mL round bottom flask, 20.0 g (94.7 mmol) of 6-(N-maleimide) hexanoic acid was suspended in 78 mL (284.1 mmol) of sulfonyl chloride and heated at 50° C. for 3 hours. After removal of volatiles, the residue was dissolved in 250 mL of chloroform and cooled to 0° C., then 12.3 g (189.4 mmol) sodium azide in water (200 mL) and 2.16 g (9.46 mmol) of phenyltrimethylammonium fluoride were added and stirred for 2 hours. The organic phase was washed with 5% sodium bicarbonate (250 mL×2), dried over anhydrous $MgSO_4$ and filtered, and the filtrate was refluxed until there were no bubbles, and the solvent was evaporated, and the residue was purified by fractional distillation under vacuum to provide 7.92 g of compound 114. Yield: 41%.

$^1$H NMR (300 MHz, $CDCl_3$, ppm): δ 6.73 (s, 2H), 3.53 (t, J=7.0 Hz, 2H), 3.31 (t, J=7.0 Hz, 2H), 1.50-1.70 (m, 4H), 1.30-1.45 (m, 2H); ESI-MS: calcd for $C_{10}H_{13}N_2O_3$ $[M+H]^+$: 209.1; found: 209.1.

Sample 115: Preparation of Functionalized Dextran 115

In a 100 mL round bottom flask, 20.0 mL of anhydrous DMSO was added and heated to 60° C., followed by addition of 3.0 g of dextran (average molecular weight ~150,000) and stirred until completely dissolved. After the solution was cooled down to room temperature, 210 mg (1.0 mmol) of compound 114 and 122 mg (1.0 mmol) of 4-dimethylaminopyridine (DMAP) were added and stirred for 36 hours. Upon completion of the reaction, the reaction mixture was precipitated in methanol, dialyzed against distilled water, and lyophilized to provide 2.11 g of functionalized dextran 115. Yield: 70%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.05 (s, CH), 1.30-1.70 (m, $CH_2$).

Sample 116: Preparation of Functionalized Dextran 116

In a 100 mL round bottom flask, 20.0 mL of anhydrous DMSO was added and heated to 60° C., followed by addition of 3.0 g of dextran (average molecular weight ~150,000) and stirred until completely dissolved. After the solution was cooled down to room temperature, 100 mg (0.48 mmol) of compound 114, 211 mg (0.48 mmol) of compound 102, and 117 mg (1.0 mmol) of 4-dimethylaminopyridine (DMAP) were added and stirred for 36 hours. Upon completion of the reaction, the reaction mixture was precipitated in methanol, dialyzed against distilled water, and lyophilized to provide 2.32 g of functionalized dextran 116. Yield: 77%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.00-8.50 (m, CONH, ArH, CH), 1.23 (t, $CH_3$).

Synthetic Scheme 21

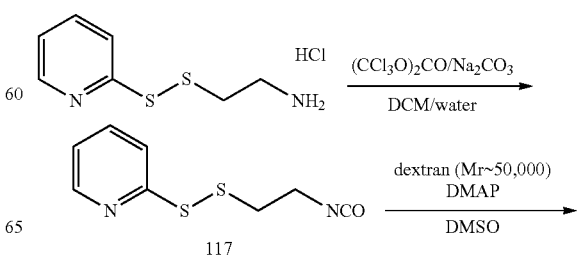

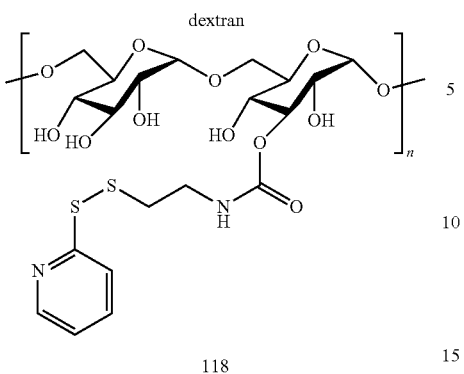

118

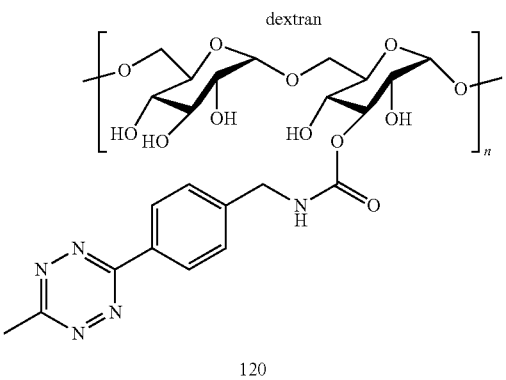

120

Sample 117: Preparation of Compound 117

In a 250 mL round bottom flask, 2.67 g (8.98 mmol) of diphosgene was dissolved in 30.0 mL of dichloromethane and cooled to 0° C., followed by addition of 30 mL of saturated sodium carbonate solution and 2.0 g (8.98 mmol) of 2-(pyridyldithio) ethylamine hydrochloride in dichloromethane and stirred for 5 h. Upon completion of the reaction, the organic phase was separated, dried over anhydrous $MgSO_4$, filtered, concentrated, and purified on a silica gel column and eluted with ethyl acetate in chloroform (5-60%) to provide 1.39 g of compound 117. Yield: 73%.

$^1$H NMR (300 MHz, $CDCl_3$, ppm): δ 8.52 (m, 1H), 7.68 (m, 2H), 7.15 (m, 1H), 3.60 (t, J=7.0 Hz, 2H), 2.97 (t, J=7.0 Hz, 2H); ESI-MS: calcd for $C_{10}H_{13}N_2O_3$ [M+H]$^+$: 213.0; found: 213.0.

Sample 118: Preparation of Functionalized Dextran 118

In a 100 mL round bottom flask, 20.0 mL of anhydrous DMSO was added and heated to 60° C., followed by addition of 2.0 g of dextran (average molecular weight ~50,000) and stirred until completely dissolved. After the solution was cooled down to room temperature, 160 mg (0.75 mmol) of compound 117 and 92 mg (0.72 mmol) of 4-dimethylaminopyridine (DMAP) were added and stirred for 36 hours Upon completion of the reaction, the reaction mixture was precipitated in methanol, dialyzed against distilled water, and lyophilized to provide 1.32 g of functionalized dextran 118. Yield. 66%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.20-8.50 (m, ArH)

Synthetic Scheme 22

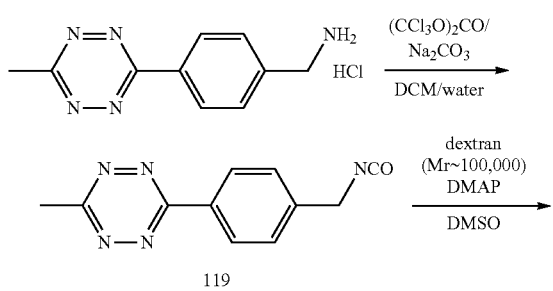

119

Sample 119: Preparation of Compound 119

In a 100 mL round bottom flask, 250 mg (0.842 mmol) of diphosgene was dissolved in 10.0 mL of dichloromethane and cooled to 0° C., followed by addition of 10 mL of saturated sodium carbonate solution and 200 mg (0.842 mmol) of 3-(4-aminophenyl)-4-methyl-1,2,4,5-tetrazole hydrochloride in dichloromethane and stirred for 3 h. Upon completion of the reaction, the organic phase was separated, dried over anhydrous $MgSO_4$, filtered, concentrated, and purified on a silica gel column and eluted with ethyl acetate in petroleum ether (5-60%) to provide 151 mg of compound 119. Yield: 79%.

$^1$H NMR (500 MHZ, $CDCl_3$, ppm): δ 8.60 (d, J=7.0 Hz, 2H), 7.51 (d, J=7.0 Hz, 2H), 4.65 (s, 2H), 3.10 (s, 3H); ESI-MS: calcd for $C_{11}H_{10}N_5O$ [M+H]$^+$: 228.1; found: 228.1.

Sample 120: Preparation of Compound 120

In a 50 mL round bottom flask, 6.0 mL of anhydrous DMSO was added and heated to 60° C., followed by addition of 1.0 g of dextran (average molecular weight ~100,000) and stirred until completely dissolved. After the solution was cooled down to room temperature, 80 mg (0.35 mmol) of compound 119 and 86 mg (0.70 mmol) of 4-dimethylaminopyridine (DMAP) were added and stirred for 36 hours. Upon completion of the reaction, the reaction mixture was precipitated in methanol, dialyzed against distilled water, and lyophilized to provide 0.78 g of functionalized dextran 120 Yield: 78%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.30-8.60 (m, ArH).

Synthetic Scheme 23

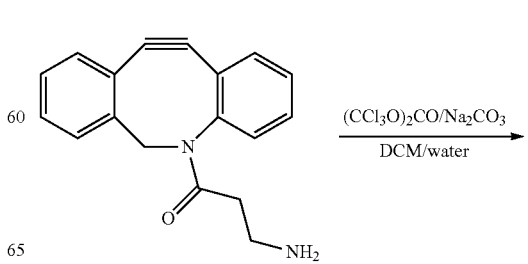

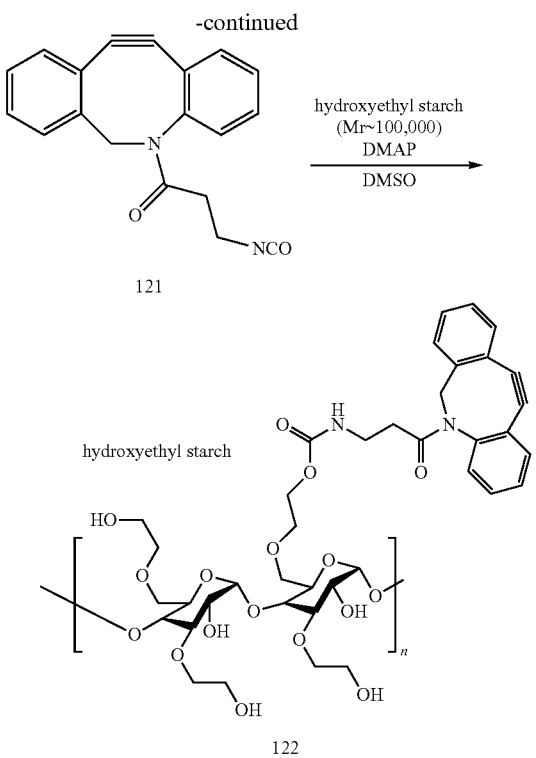

Sample 121: Preparation of Compound 121 In a 250 mL round bottom flask, 2.69 g (9.05 mmol) of diphosgene was dissolved in 50.0 mL of dichloromethane and cooled to 0° C., followed by addition of 50 mL of saturated sodium carbonate solution and 2.5 g (9.05 mmol) of 3-aminopropionyl-diphenylazetidine (DBCO)) in dichloromethane and stirred for 5 h. Upon completion of the reaction, the organic phase was separated, dried over anhydrous MgSO$_4$, filtered, concentrated, and purified on a silica gel column and eluted with ethyl acetate in chloroform (5-60%) to provide 2.36 g of compound 121. Yield: 86%.

$^1$H NMR (300 MHz, CDCl$_3$, ppm): δ 7.75 (m, 1H), 7.23-7.50 (m, 7H), 5.11 (d, J=15.0 Hz, 1H), 3.72 (d, J=15.0 Hz, 1H), 3.27 (m, 2H), 2.53 (m, 1H), 2.05 (m, 1H); ESI-MS: calcd for C$_{19}$H$_{15}$N$_2$O$_2$ [M+H]$^+$: 303.1; found: 303.1.

Sample 122: Preparation of Functionalized Hydroxyethyl Starch 122

In a 100 mL round bottom flask, 20.0 mL of anhydrous DMSO was added and heated to 60° C., followed by addition of 2.0 g of hydroxyethyl starch (average molecular weight ~100,000) and stirred until completely dissolved. After the solution was cooled down to room temperature, 200 mg (0.66 mmol) of compound 121 and 81 mg (1.81 mmol) of 4-dimethylaminopyridine (DMAP) were added and stirred for 24 hours. Upon completion of the reaction, the reaction mixture was precipitated in methanol, dialyzed against distilled water, and lyophilized to provide 1.62 g of functionalized hydroxyethyl starch 122. Yield: 81%.

$^1$H NMR (selected characteristic signals, 500 MHz, DMSO-d$_6$, ppm): major signals: 4.50-5.00 (m, CHOH, CHOH, CH$_2$OH), 3.30-4.20 (m, CHOH, CH$_2$OH); minor signals: 7.20-7.90 (m, ArH).

Synthetic Scheme 24

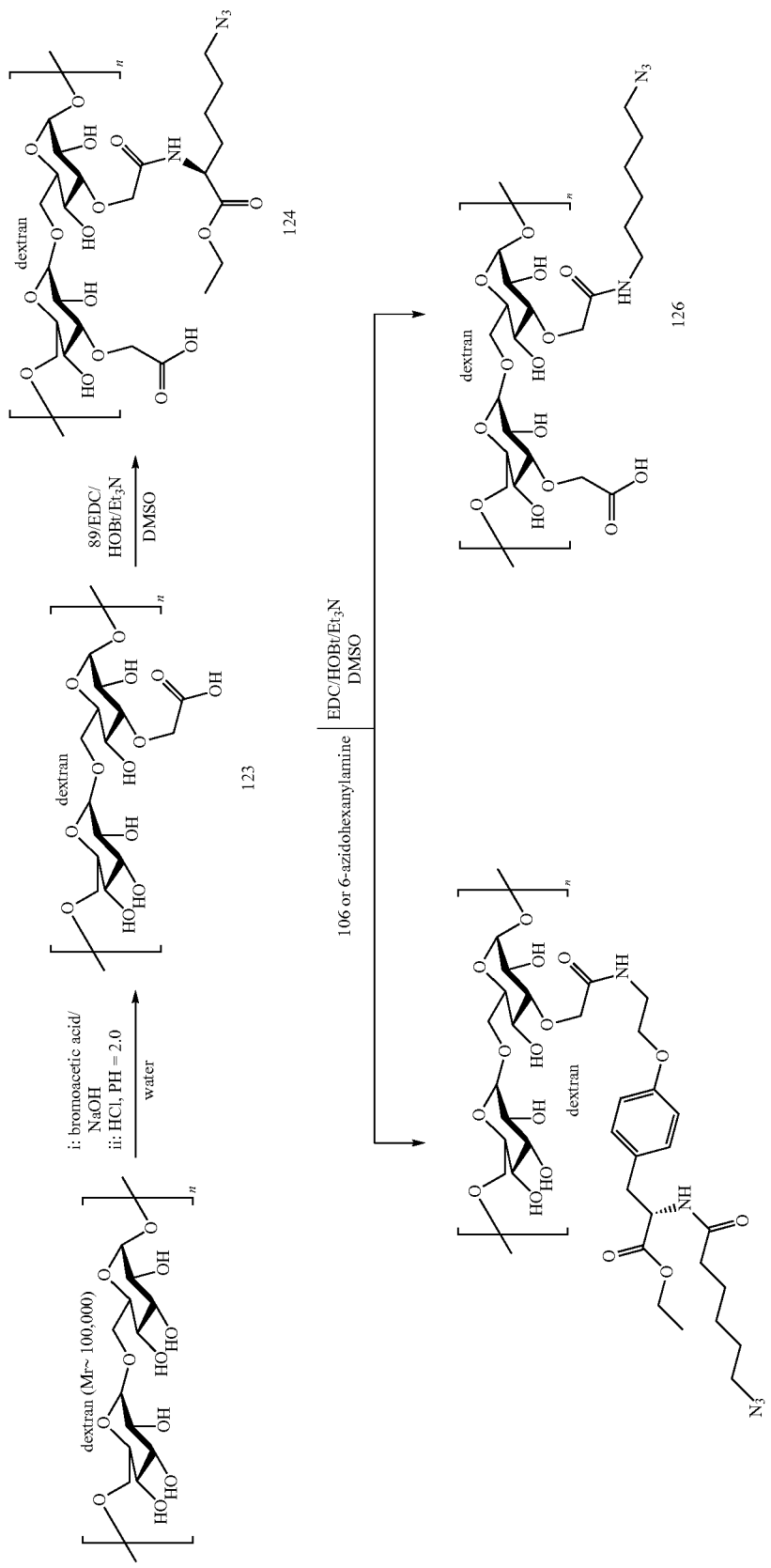

Sample 123: Preparation of Functionalized Dextran 123

To a stirred solution of 10.0 g of dextran (average molecular weight ~100,000), 10% sodium hydroxide aqueous solution was added, and flowed by 1.5 g (10.8 mmol) of bromoacetic acid in tert-butanol (50 mL), and then heated to 60° C., stirred for 3 hours. After cooling, the reaction mixture was poured into 100 mL of acetone to precipitate, and the supernatant was decanted. The precipitate was further washed with methanol three times, and then dissolved in 100 mL of distilled water, adjusted to pH=2.0 with 5% hydrochloric acid, dialyzed against distilled water, and lyophilized to give 8.6 g of functionalized dextran 123. Yield: 86%.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH).

Sample 124: Preparation of Functionalized Dextran 124

To a 100 mL round-bottom flask charged with 2.0 g of functionalized dextran 123, 20.0 mL of anhydrous DMSO was added and heated at 60° C. till completely dissolved, and then cooled down to room temperature. To the above solution, 398 mg (2.08 mmol) of 1-ethyl-3-(3-dimethylaminopropyl) carbodiimide (EDC), and 281 mg (2.08 mmol) of 1-hydroxybenzotriazole (HOBt), and 430 uL (3.12 mmol) of triethylamine were added and stirred for 1 hour, and then 350 mg (1.04 mmol) of compound 89 was added and stirred at room temperature for 2 days. Upon completion of the reaction, the reaction mixture was precipitated in methanol, dialyzed against distilled water, and lyophilized to provide 1.52 g of functionalized dextran 124. Yield: 71%.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 1.45-1.90 (m, CH$_2$), 1.23 (t, CH$_3$).

Sample 125: Preparation of Functionalized Dextran 125

To a 100 mL round-bottom flask charged with 2.0 g of functionalized dextran 123, 20.0 mL of anhydrous DMSO was added and heated at 60° C. till completely dissolved, and then cooled down to room temperature. To the above solution, 398 mg (2.08 mmol) of 1-ethyl-3-(3-dimethylaminopropyl) carbodiimide (EDC), and 281 mg (2.08 mmol) of 1-hydroxybenzotriazole (HOBt), and 430 uL (3.12 mmol) of triethylamine were added and stirred for 1 hour, and then 429 mg (1.00 mmol) of compound 106 was added and stirred at room temperature for 2 days. Upon completion of the reaction, the reaction mixture was precipitated in methanol, dialyzed against distilled water, and lyophilized to provide 1.77 g of functionalized dextran 125. Yield: 88%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 6.75-7.20 (m, ArH), 1.23 (t, CH$_3$).

Sample 126: Preparation of Functionalized Dextran 126

To a 100 mL round-bottom flask charged with 2.0 g of functionalized dextran 123, 20.0 mL of anhydrous DMSO was added and heated at 60° C. till completely dissolved, and then cooled down to room temperature. To the above solution, 398 mg (2.08 mmol) of 1-ethyl-3-(3-dimethylaminopropyl) carbodiimide (EDC), and 281 mg (2.08 mmol) of 1-hydroxybenzotriazole (HOBt), and 430 uL (3.12 mmol) of triethylamine were added and stirred for 1 hour, and then 179 mg (1.00 mmol) of 6-azido-hexanylamine was added and stirred at room temperature for 2 days. Upon completion of the reaction, the reaction mixture was precipitated in methanol, dialyzed against distilled water, and lyophilized to provide 1.65 g of functionalized dextran 126. Yield: 73%.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 1.35-1.80 (m, CH$_2$).

Synthetic Scheme 25

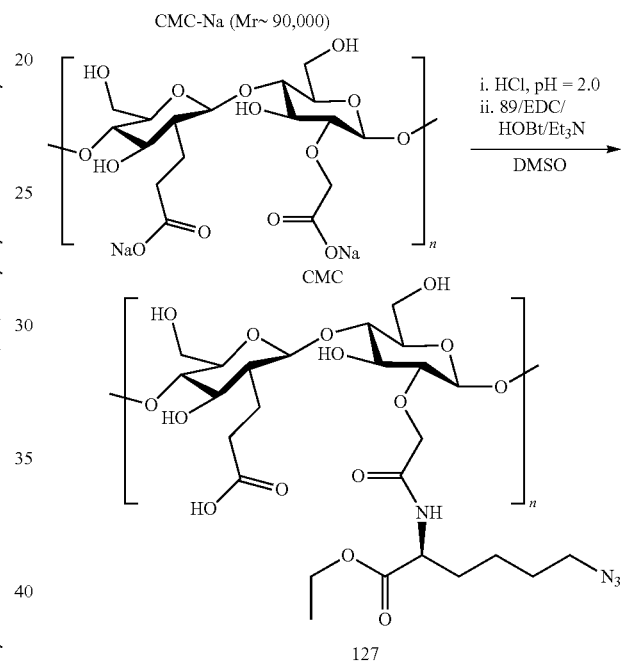

127

Sample 127: Preparation of Functionalized Cellulose 127

10.0 g of sodium carboxymethylcellulose (average molecular weight ~90,000) was dissolved in 100 mL of distilled water, adjusted to pH=2.0 with 5% hydrochloric acid, dialyzed against distilled water three times, and lyophilized to obtain 7.2 g of carboxymethylcellulose. In a 100 mL round bottom flask, 1.0 g of carboxymethyl cellulose was suspended in 20 mL of DMSO solution containing 10% tetrabutylammonium fluoride, heated at 60° C., stirred for 30 minutes, and then cooled down to room temperature. To the above solution, 192 mg (1.00 mmol) N-(3-dimethylaminopropyl)-N'-ethyl-carbodiimide hydrochloride (EDC), 136 mg (1.00 mmol) 1-hydroxybenzotriazole (HOBt) and 300 uL (2.17 mmol) of triethylamine were added and stirred for 1 hour, and then 120 mg (0.50 mmol) of compound 89 was added and stirred for 48 hours. Upon completion of the reaction, the reaction mixture was precipitated in methanol, dialyzed against distilled water, and lyophilized to give 0.53 g of functionalized cellulose 127. Yield: 53%.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 1.40-1.90 (m, CH$_2$), 1.23 (t, CH$_3$).

Synthetic Scheme 26

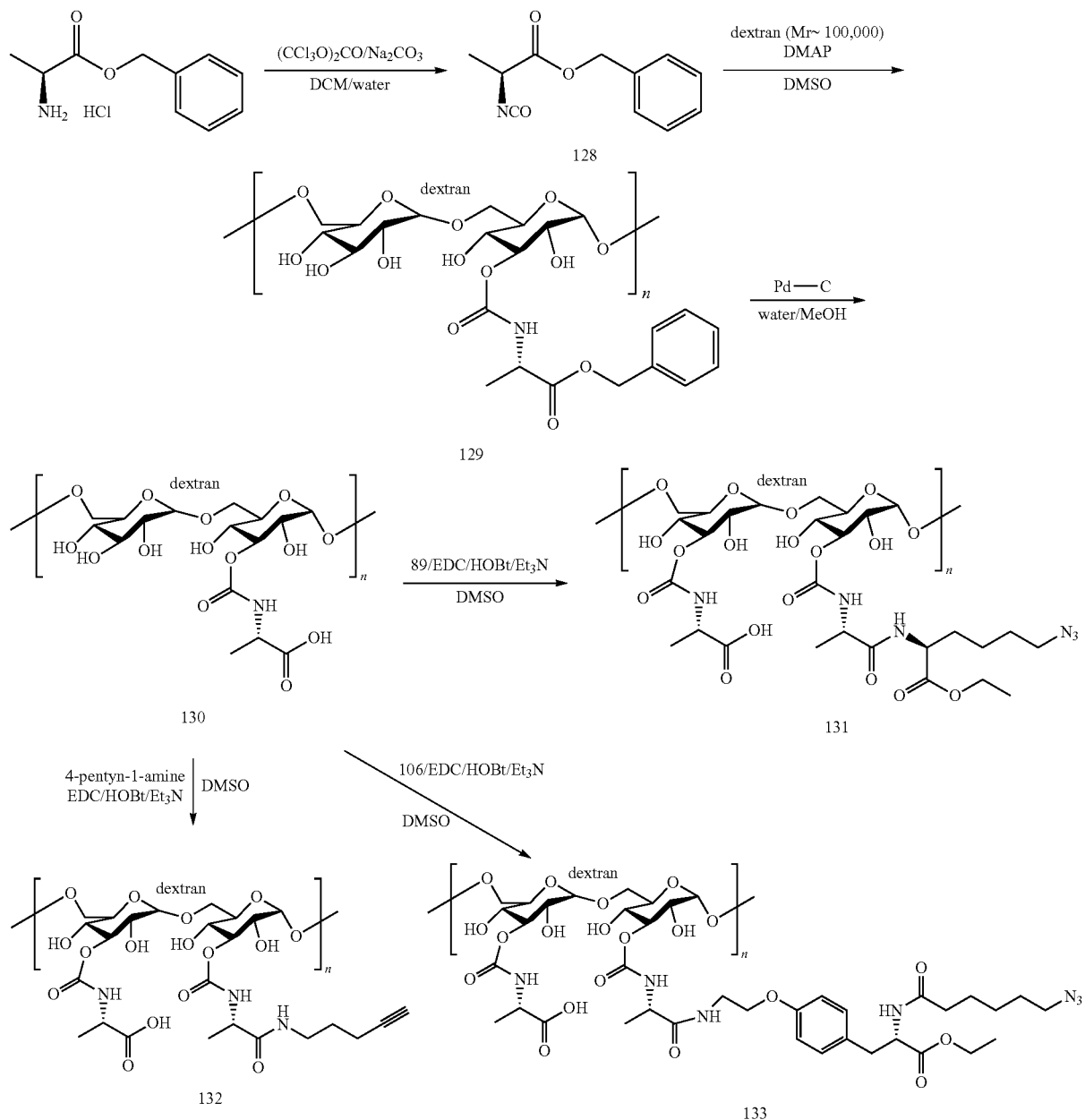

Sample 128: Preparation of Compound 128

In a 250 mL round bottom flask, 5.50 g (18.54 mmol) of diphosgene was dissolved in 100.0 mL of dichloromethane and cooled to 0° C., followed by addition of 100 mL of saturated sodium carbonate solution and 4.0 g (18.54 mmol) of L-alanine benzyl ester hydrochloride in dichloromethane and stirred for 5 h. Upon completion of the reaction, the organic phase was separated, dried over anhydrous $MgSO_4$, filtered, concentrated, and purified on a silica gel column and eluted with ethyl acetate in petroleum ether (5-60%) to provide 2.51 g of compound 128. Yield: 66%.

$^1$H NMR (500 MHz, $CDCl_3$, ppm): δ 7.38 (m, 5H), 5.23 (s, 2H), 4.12 (m, 1H), 1.50 (d, J=7.2 Hz, 3H); ESI-MS: calcd for $C_{11}H_{12}NO_3$ [M+H]$^+$: 206.1, found: 206.1.

Sample 129: Preparation of Compound 129

In a 250 mL round bottom flask, 120 mL of anhydrous DMSO was added and heated to 60° C., and followed by addition of 20.0 g of dextran (average molecular weight ~100,000) and stirred until completely dissolved. After the solution was cooled down to room temperature, 2.0 g (9.73 mmol) of compound 128 and 1.18 g (9.73 mmol) of 4-dimethylaminopyridine (DMAP) were added and stirred for 24 hours. Upon completion of the reaction, the reaction mixture was precipitated in methanol, dialyzed against distilled water, and lyophilized to provide 17.9 g of functionalized dextran 129. Yield: 89%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-7.50 (m, ArH), 1.26 (d, CH$_3$).

Sample 130: Preparation of Functionalized Dextran 130

In a 300 mL hydrogenation flask, 10.0 g of functionalized dextran 129 was dissolved in 100 mL of methanol-water (9.1), and followed by addition of 700 mg of Pd—C and shaken for 12 hours under 1.2 atmospheres of hydrogen gas. Upon completion of the reaction, solid material was filtered off, washed with ethyl acetate three times (60 mL×3), and the aqueous phase was lyophilized to give 8.73 g of functionalized dextran 130. Yield: 87%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.23 (d, CH$_3$).

Sample 131: Preparation of Functionalized Dextran 131

To a 100 mL round-bottom flask charged with 2.0 g of functionalized dextran 130, 20.0 mL of anhydrous DMSO was added and heated at 60° C. till completely dissolved, and then cooled down to room temperature. To the above solution, 383 mg (2.00 mmol) of 1-ethyl-3-(3-dimethylaminopropyl) carbodiimide (EDC), 271 mg (2.00 mmol) of 1-hydroxybenzotriazole (HOBt), and 500 uL (3.61 mmol) of triethylamine were added and stirred for 1 hour, and then 238 mg (1.00 mmol) of compound 89 was added and stirred at room temperature for 2 days. Upon completion of the reaction, the reaction mixture was precipitated in methanol, dialyzed against distilled water, and lyophilized to provide 1.56 g of functionalized dextran 131. Yield: 78%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.45-1.90 (m, CH$_2$), 1.23 (m, CH$_3$).

Sample 132: Preparation of Functionalized Dextran 132

To a 100 mL round-bottom flask charged with 2.0 g of functionalized dextran 130, 20.0 mL of anhydrous DMSO was added and heated at 60° C. till completely dissolved, and then cooled down to room temperature. To the above solution, 383 mg (2.00 mmol) of 1-ethyl-3-(3-dimethylaminopropyl) carbodiimide (EDC), 271 mg (2.00 mmol) of 1-hydroxybenzotriazole (HOBt), and 500 uL (3.61 mmol) of triethylamine were added and stirred for 1 hour, and then 83 mg (1.00 mmol) of 4-pentyn-1-amine was added and stirred at room temperature for 2 days. Upon completion of the reaction, the reaction mixture was precipitated in methanol, dialyzed against distilled water, and lyophilized to provide 1.23 g of functionalized dextran 132. Yield: 61%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.70-2.00 (m, CH$_2$, CH), 1.23 (d, CH$_3$).

Sample 133: Preparation of Functionalized Dextran 133

To a 100 mL round-bottom flask charged with 3.0 g of functionalized dextran 130, 30.0 mL of anhydrous DMSO was added and heated at 60° C. till completely dissolved, and then cooled down to room temperature. To the above solution, 573 mg (3.00 mmol) of 1-ethyl-3-(3-dimethylaminopropyl) carbodiimide (EDC), 367 mg (2.00 mmol) of 1-hydroxybenzotriazole (HOBt), and 700 uL (5.06 mmol) of triethylamine were added and stirred for 1 hour, and then 642 mg (1.50 mmol) of compound 106 was added and stirred at room temperature for 2 days. Upon completion of the reaction, the reaction mixture was precipitated in methanol, dialyzed against distilled water, and lyophilized to provide 2.35 g of functionalized dextran 133. Yield: 78%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 6.75-7.20 (m, ArH), 1.25 (m, CH$_3$).

Synthetic Scheme 27

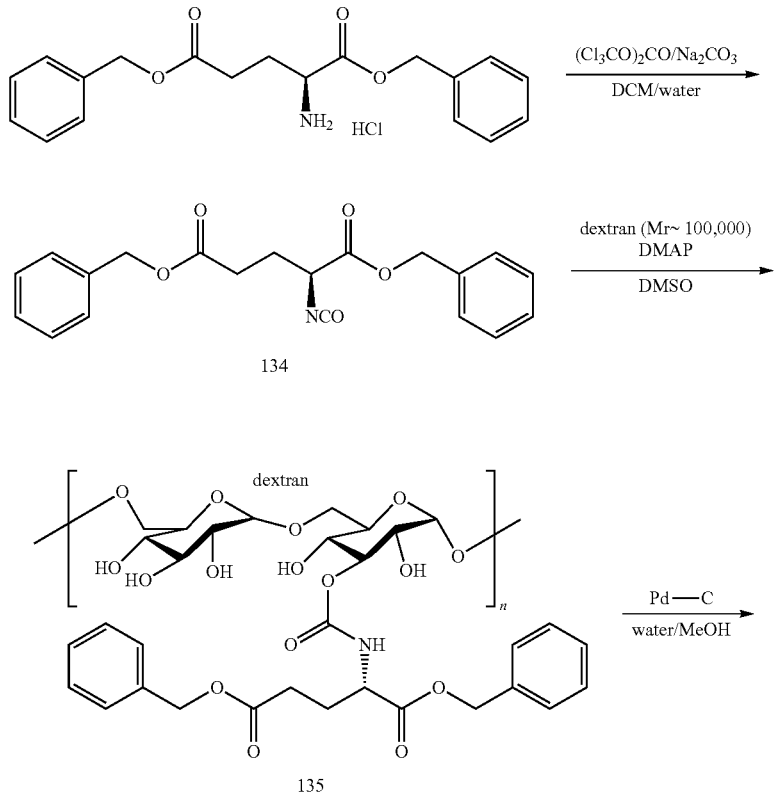

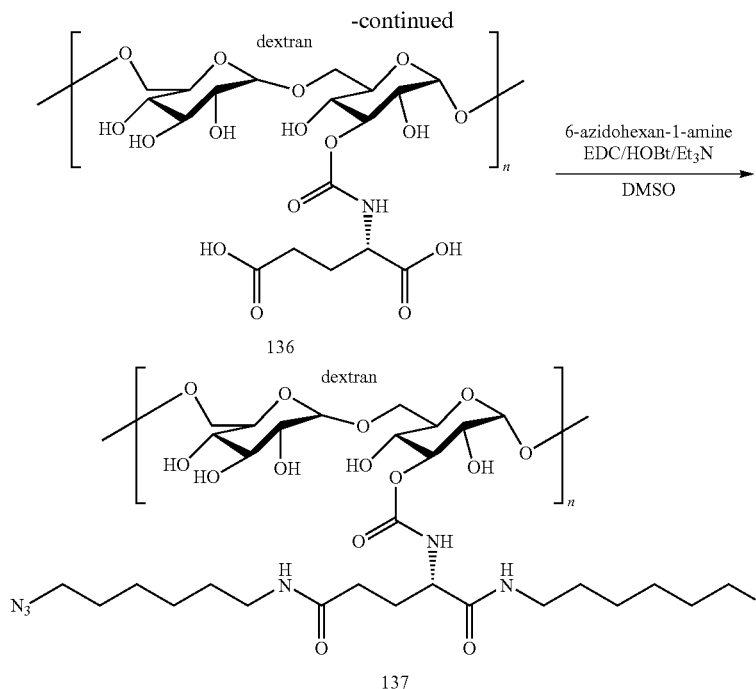

Sample 134: Preparation of Compound 134

In a 500 mL round bottom flask, 9.16 g (27.51 mmol) of diphosgene was dissolved in 150 mL of dichloromethane and cooled to 0° C., followed by addition of 100 mL of saturated sodium carbonate solution and 10.0 g (27.51 mmol) of L-glutamic acid dibenzyl ester hydrochloride in dichloromethane and stirred overnight. Upon completion of the reaction, the organic phase was separated, dried over anhydrous MgSO$_4$, filtered, concentrated, and purified on a silica gel column and eluted with ethyl acetate in chloroform (5-60%) to provide 8.32 g of compound 134. Yield: 85%.

$^1$H NMR (300 MHz, CDCl$_3$, ppm): δ 7.35 (m, 10H), 5.15 (s, 2H), 5.10 (s, 2H), 4.19 (m, 1H), 2.50 (m, 2H), 2.06 (m, 1H), 2.02 (m, 1H); ESI-MS: calcd for C$_{20}$H$_{20}$NO$_5$ [M+H]$^+$: 354.1; found: 354.2.

Sample 135: Preparation of Functionalized Dextran 135

In a 250 mL round bottom flask, 50.0 mL of anhydrous DMSO was added and heated to 60° C., followed by addition of 5.0 g of dextran (average molecular weight ~100,000) and stirred until completely dissolved. After the solution was cooled down to room temperature, 708 mg (2.00 mmol) of compound 134 and 245 mg (2.00 mmol) of 4-dimethylaminopyridine (DMAP) were added and stirred for 24 hours. Upon completion of the reaction, the reaction mixture was precipitated in methanol, dialyzed against distilled water, and lyophilized to provide 3 95 g of functionalized hydroxyethyl starch 135. Yield: 79%.

$^1$H NMR (selected characteristic signals, 500 MHz, DMSO-d$_6$, ppm): major signals: 4.50-5.20 (m, CHOH, CHOH, CH$_2$OH), 3.30-4.00 (m, CHOH, CH$_2$OH); minor signals: 7.20-7.50 (m, ArH).

Sample 136: Preparation of Functionalized Dextran 136

In a 200 mL hydrogenation flask, 3.6 g of functionalized dextran 135 was dissolved in 60 mL of methanol-water (9:1), followed by addition of 300 mg of Pd—C and shaken for 12 hours with 1.2 atmospheres of hydrogen. Upon completion of the reaction, solid material was filtered off, washed with ethyl acetate three times (30 mL×3), and the aqueous phase was lyophilized to give 2.755 g of functionalized dextran 136. Yield: 76%.

$^1$H NMR (selected characteristic signals, 500 MHz, DMSO-d$_6$, ppm): major signals: 4.50-5.20 (m, CHOH, CHOH, CH$_2$OH), 3.30-4.00 (m, CHOH, CH$_2$OH); minor signals: 2.00-2.50 (m, CH$_2$).

Sample 137: Preparation of Functionalized Dextran 137

To a 100 mL round-bottom flask charged with 2.0 g of functionalized dextran 136, 20.0 mL of anhydrous DMSO was added and heated at 60° C. till completely dissolved, and then cooled down to room temperature. To the above solution, 955 mg (5.00 mmol) of 1-ethyl-3-(3-dimethylaminopropyl) carbodiimide (EDC), 610 mg (5.00 mmol) of 1-hydroxybenzotriazole (HOBt), and 830 uL (3.61 mmol) of triethylamine were added and stirred for 1 hour, and then 445 mg (2.50 mmol) of compound 106 was added and stirred at room temperature for 2 days. Upon completion of the reaction, the reaction mixture was precipitated in methanol, dialyzed against distilled water, and lyophilized to provide 1.53 g of functionalized dextran 137. Yield: 76%.

$^1$H NMR (selected characteristic signals, 500 MHz, DMSO-d$_6$, ppm): major signals: 4.50-5.20 (m, CHOH, CHOH, CH$_2$OH), 3.30-4.00 (m, CHOH, CH$_2$OH); minor signals: 1.35-1.85 (m, CH$_2$).

Synthetic Scheme 28

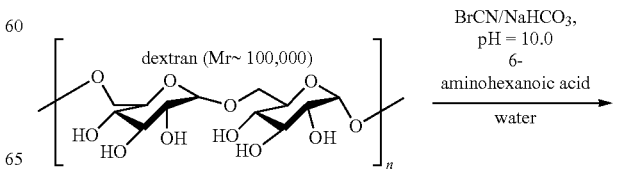

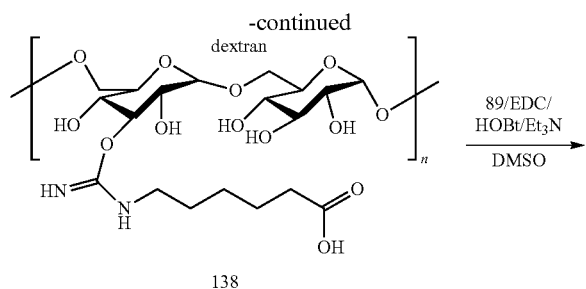

138

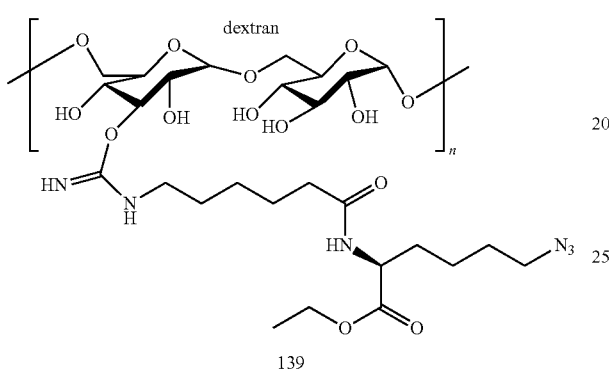

139

Sample 138: Preparation of Functionalized Dextran 138

In a 250 mL round bottom flask, 5.0 g of dextran (average molecular weight ~7,000) was dissolved in 50 mL of distilled water, then 2.0 g of cyanogen bromide was added, and pH was adjusted to 10 with sodium bicarbonate. To the above solution, 2.0 g of 6-amino-hexanoic acid was added and stirred at room temperature for 48 hours. Upon completion of the reaction, the reaction mixture was adjusted to pH=2.0 with 1.0 N hydrochloric acid, filtered, dialyzed against distilled water, and lyophilized to give 3.23 g of functionalized dextran 138. Yield: 65%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 1.45-2.30 (m, CH$_2$).

Sample 139: Preparation of Functionalized Dextran 139

To a 100 mL round-bottom flask charged with 2.6 g of functionalized dextran 138, 26.0 mL of anhydrous DMSO was added and heated at 60° C. till completely dissolved, and then cooled down to room temperature. To the above solution, 402 mg (2.10 mmol) of 1-ethyl-3-(3-dimethylaminopropyl) carbodiimide (EDC), 256 mg (2.10 mmol) of 1-hydroxybenzotriazole (HOBt), and 600 uL (4.35 mmol) of triethylamine were added and stirred for 1 hour, and then 250 mg (1.05 mmol) of compound 89 was added and stirred at room temperature for 2 days. Upon completion of the reaction, the reaction mixture was precipitated in methanol, dialyzed against distilled water, and lyophilized to provide 1.23 g of functionalized dextran 139. Yield: 47%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 1.45-2.30 (m, CH$_2$), 1.23 (t, CH$_3$).

Synthetic Scheme 29

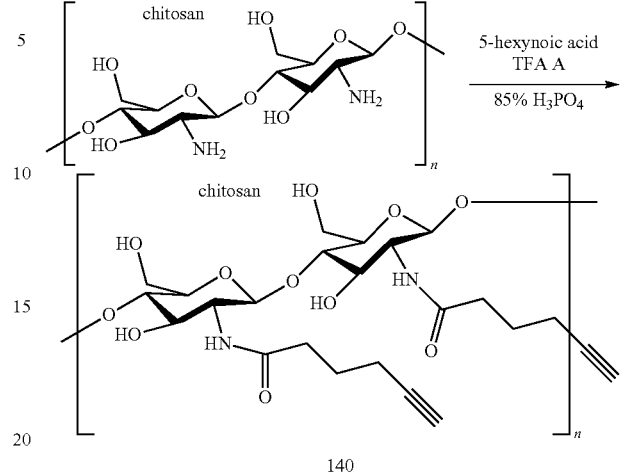

140

In a 250 mL round-bottom flask, 5.0 g (23.78 mmol) trifluoroacetic anhydride and 1.0 g (8.91 mmol) 5-hexynoic acid were combined together, heated to 40° C., and stirred for 1 hour, and then cooled to room temperature. To the stirred mixture 0.3 g of 85% phosphoric acid and 1.0 g of chitosan (Mr~5000) were added, heated to 50° C., and stirred for 24 hours. Upon completion of reaction, the reaction mixture was cooled down to room temperature and precipitated with ether. The precipitate was filtered and washed 5 times with ether. The solid powder was collected, dialyzed against distilled water, and lyophilized to provide 1.12 g of functionalized dextran 140. Yield: 100%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 1.45-2.35 (m, CH$_2$, CH).

Synthetic Scheme 29-1

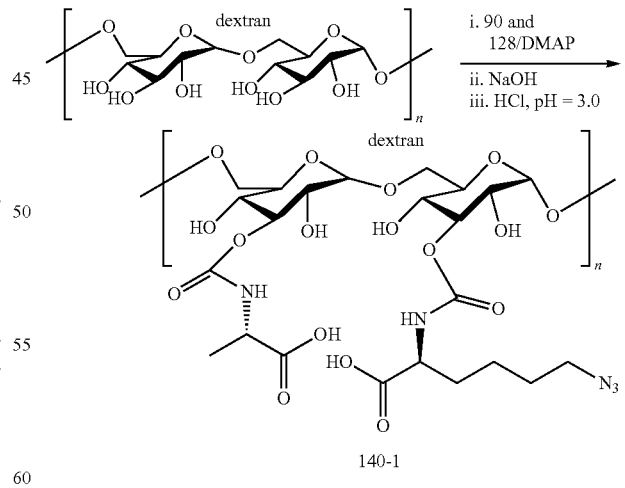

140-1

Sample 140-1: Preparation of Functionalized Dextran 140-1

In a 100 mL round bottom flask, 20.0 mL of anhydrous DMSO was added and heated to 60° C., followed by addition of 3.0 g of dextran (average molecular weight ~100,000) and stirred until completely dissolved. After the solution was cooled down to room temperature, 678 mg (3.0 mmol) of compound 90, 205 mg (1.0 mmol) of compound 128, and 489 mg (4.0 mmol) of 4-dimethylaminopyridine (DMAP) were added and stirred for 24 hours. Upon completion of the reaction, the reaction mixture is precipitated in methanol, and the precipitate is dissolved in 20 mL of 1.0 N sodium hydroxide solution, stirred for 6 hours, and then acidified to pH=3.0 with 1.0N hydrochloric acid, finally the reaction solution is concentrated, dialyzed against distilled water, and lyophilized to provide 2.76 g of functionalized dextran 140-1. Yield: 92%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.00-1.75 (m, CH$_2$, CH$_3$).

Synthetic Scheme 30

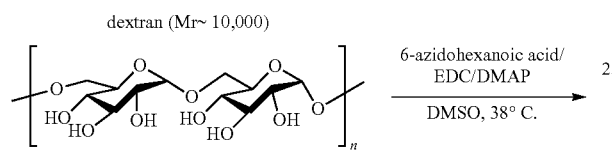

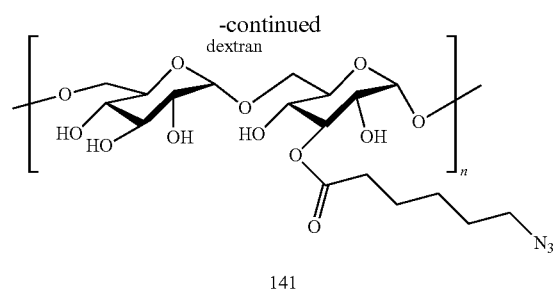

141

Sample 141: Preparation of Functionalized Dextran 141

To a 100 mL round-bottom flask charged with 3.0 g of dextran (average molecular weight ~ 100,000), 30.0 mL of anhydrous DMSO was added and heated at 60° C. till completely dissolved, and then cooled down to room temperature. To the above solution, 300 mg (1.91 mmol) of 6-azidohexanoic acid, 730 mg (3.82 mmol) of 1-ethyl-3-(3-dimethylaminopropyl) carbodiimide (EDC), and 466 mg (3.82 mmol) of 4-dimethylaminopyridine (DMAP) were added and stirred at room temperature for 2 days. Upon completion of the reaction, the reaction mixture was precipitated in methanol, dialyzed against distilled water, and lyophilized to provide 2.12 g of functionalized dextran 141. Yield: 70%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 1.35-2.35 (m, CH$_2$).

Synthetic Scheme 31

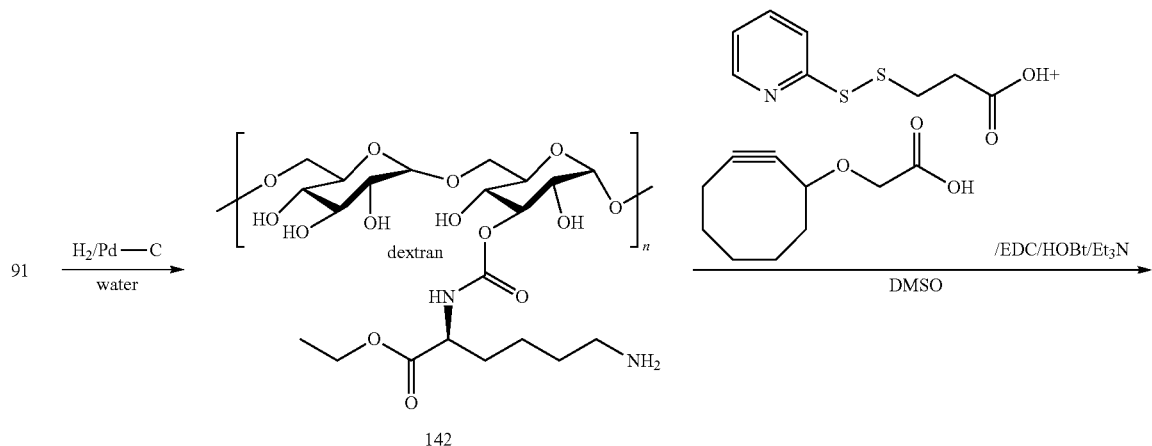

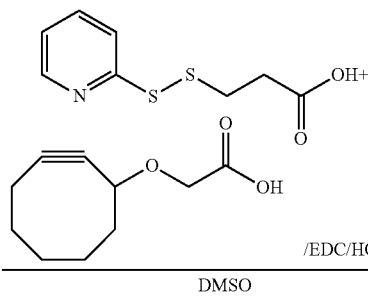

142

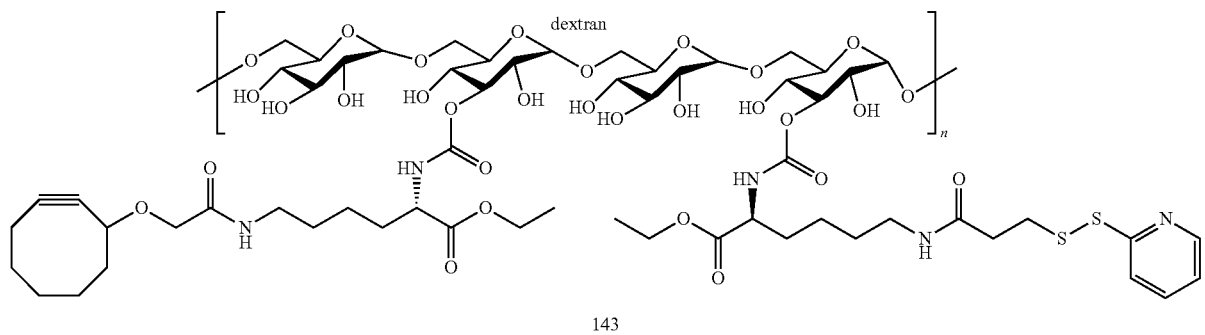

143

Sample 142: Preparation of Functionalized Dextran 142

In a 500 mL hydrogenation flask, 20.0 g of functionalized dextran 91 was dissolved in 150 mL of distilled water and shaken under 1.5 atmospheres of hydrogen gas in the presence of 1.0 g of 10% Pd—C. After shaking for 12 hours, the solid PD-C was filtered off, and filtrate was precipitated in methanol, dialyzed against distilled water, and lyophilized to provide 17.3 g of functionalized dextran 142. Yield: 86%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 1.45-2.20 (m, CH$_2$), 1.25 (t, CH$_3$).

Sample 143: Preparation of Functionalized Dextran 143

To a 100 mL round-bottom flask charged with 3.0 g of functionalized dextran 142, 30.0 mL of anhydrous DMSO was added and stirred till completely dissolved. To the above solution, of 113 mg (0.5 mmol) of 3-(2-Pyridyldithio) propionic 91 mg (0.5 mmol) acid, 2-(cyclooct-2-ynyloxy) acetic acid 383 mg (2.0 mmol) of 1-ethyl-3-(3-dimethylaminopropyl) carbodiimide (EDC), 271 mg (2.00 mmol) of 1-hydroxybenzotriazole (HOBt), and 415 uL (3.00 mmol) of triethylamine were added and stirred at room temperature for 2 days. Upon completion of the reaction, the reaction mixture was precipitated in methanol, dialyzed against distilled water, and lyophilized to provide 2.33 g of functionalized dextran 143. Yield: 77%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.60 (m, CONH, ArH), 1.35-2.00 (m, CH$_2$), 1.22 (t, CH$_3$).

Synthetic Scheme 32

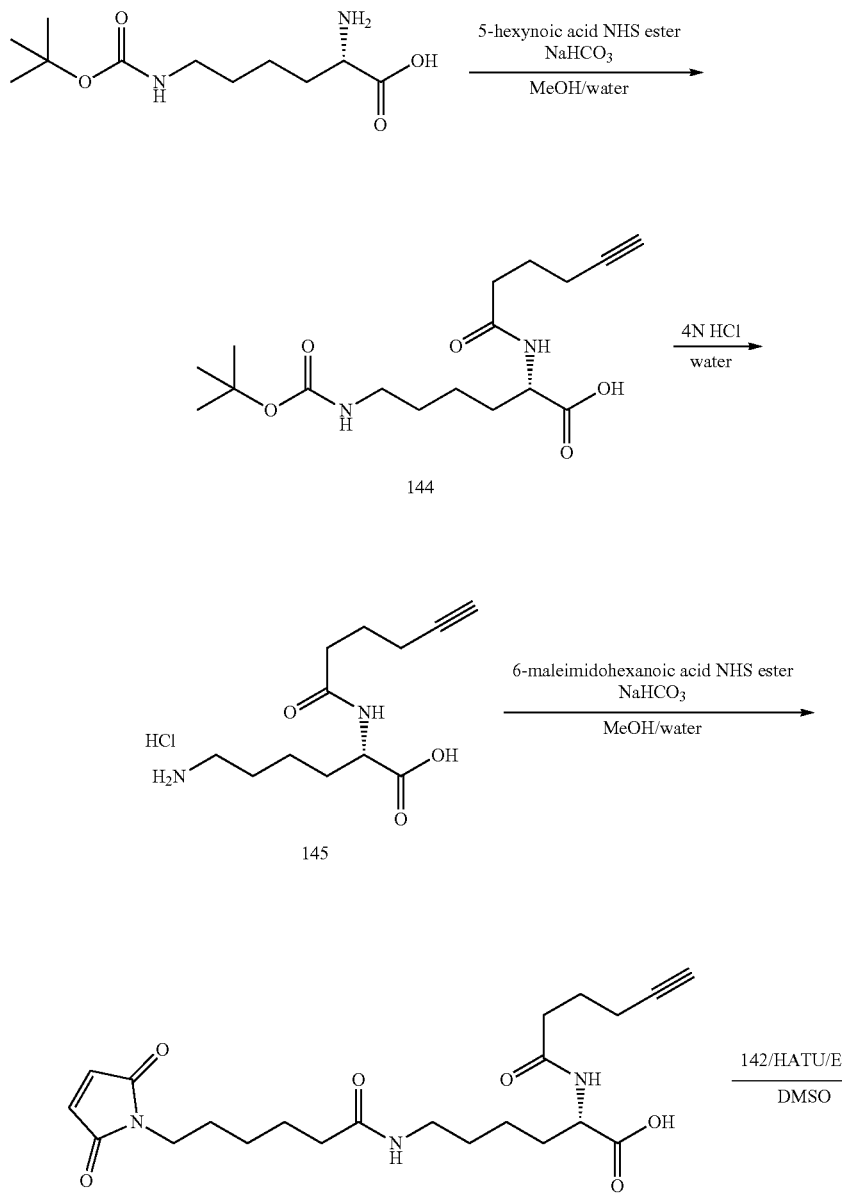

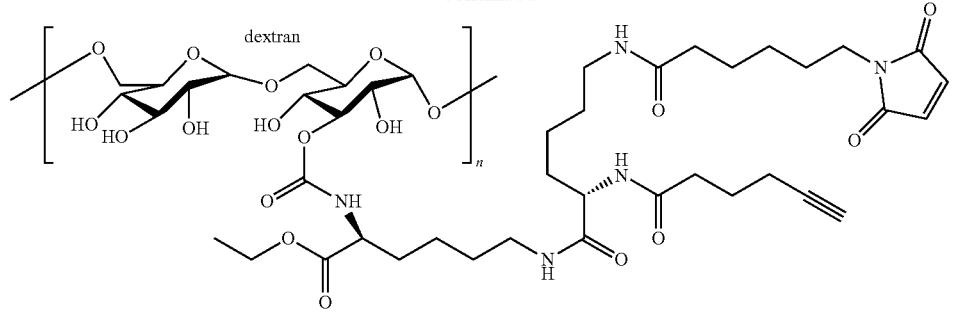

147

Sample 144: Preparation of Compound 144

In a 250 mL round bottom flask, 10.0 g (40.62 mmol) of Nε-Boc-lysine and 6.28 g (81.24 mmol) of $NaHCO_3$ were dissolved in 100.0 mL of methanol-water (2:1), followed by slow addition of 7.6 g (36.56 mmol) of 5-hexynoic acid-(N-hydroxysuccinyl lactam) ester and stirred overnight. Upon completion of the reaction, the reaction mixture was acidified to pH=1.0 with 2.0N HCl, extracted with ethyl acetate three times (300 mL×3), and the organic phases were pooled, dried over $MgSO_4$, filtered, concentrated, and purified on a silica gel column and eluted with methanol in chloroform (2-10%) to give 6.35 g of compound 144 Yield: 51%.

$^1$H NMR (300 MHz, $CDCl_3$, ppm): δ 6.81 (s, 1H), 4.55 (m, 1H), 3.12 (t, J=7.2 Hz, 2H), 2.38 (t, J=7.2 Hz, 2H), 2.38 (m, 2H), 1.97 (t, J=2.1 Hz, 1H), 1.75 (m, 4H), 1.35-1.50 (m, 9H); ESI-MS (m/z): calcd for $C_{17}H_{29}N_2O_5$ $[M+H]^+$: 341.2; found: 341.2.

Sample 145: Preparation of Compound 145

To a 250 mL round-bottom flask charged with 6.0 g (18.21 mmol) of compound 144, 50 mL of hydrochloride ethanol solution (4.0N) was added and stirred at room temperature overnight. After removal of volatiles, the residue was purified on a reverse phase C-18 column and eluted with acetonitrile in water (10-70%) to provide 3.35 g of compound 145. Yield: 92%.

$^1$H NMR (300 MHz, $D_2O$, ppm): δ 4.27 (m, 1H), 3.87 (t, J=7.2 Hz, 2H), 2.35 (t, J=7.2 Hz, 2H), 2.25 (t, J=2.1 Hz, 1H), 2.35 (m, 2H), 1.75 (m, 4H), 1.63 (m, 2H), 1.32 (m, 2H); ESI-MS (m/z): calcd for $C_{12}H_{21}N_2O_3$ $[M+H]^+$: 241.1; found: 241.2.

Sample 146: Preparation of Compound 146

In a 250 mL round bottom flask, 3.2 g (40.62 mmol) of compound145 and 1.93 g (23.02 mmol) of $NaHCO$; were dissolved in 60.0 mL of methanol-water (2:1), followed by slow addition of 3.91 g (12.66 mmol) of 6-(N-hydroxysuccinyl lactam) hexanoic acid (N-hydroxysuccinimide) ester, and stirred overnight. Upon completion of the reaction, the reaction mixture was acidified to pH=1.0 with 2.0N HCl, extracted with ethyl acetate three times (300 mL×3), and the organic phases were pooled, dried over $MgSO_4$, filtered, concentrated, and purified on a silica gel column and eluted with methanol in chloroform (2-10%) to give 2.35 g of compound 146. Yield: 47%.

$^1$H NMR (300 MHz, $CD_3OD$, ppm): δ 6.82 (s, 2H), 4.36 (m, 1H), 3.45 (t, J=7.2 Hz, 2H), 3.17 (t, J=7.2 Hz, 2H), 2.35 (t, J=7.2 Hz, 2H), 2.25 (t, J=7.2 Hz, 2H), 2.12 (m, 1H), 1.98 (t, J=2.0 Hz, 1H), 1.75 (m, 4H), 1.62 (m, 2H), 1.52 (m, 6H), 1.31 (m, 2H); ESI-MS (m/z): calcd for $C_{22}H_{32}N_3O_6$ $[M+H]^+$: 434.2; found: 434.3.

Sample 147: Preparation of Functionalized Dextran 147

To a 100 mL round-bottom flask charged with 2.0 g of functionalized dextran 142, 30.0 mL of anhydrous DMSO was added and stirred till completely dissolved. To the above solution, 210 mg (0.48 mmol) of compound 146 (0.73 mmol), 139 mg of (EDC), 98 mg (0.73 mmol) of 1-ethyl-3-(3-dimethylaminopropyl) carbodiimide 1-hydroxybenzotriazole (HOBt), and 138 uL (1.00 mmol) of triethylamine were added and stirred at room temperature for 2 days. Upon completion of the reaction, the reaction mixture was precipitated in methanol, dialyzed against distilled water, and lyophilized to provide 1.83 g of functionalized dextran 147. Yield: 81%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.00-8.60 (m, CONH, CH), 1.35-2.35 (m, $CH_2$), 1.23 (t, $CH_3$).

Synthetic Scheme 33

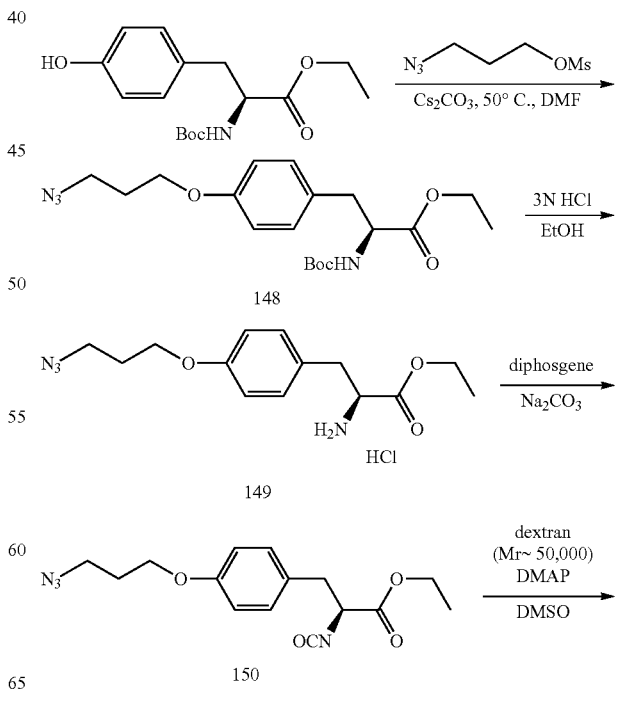

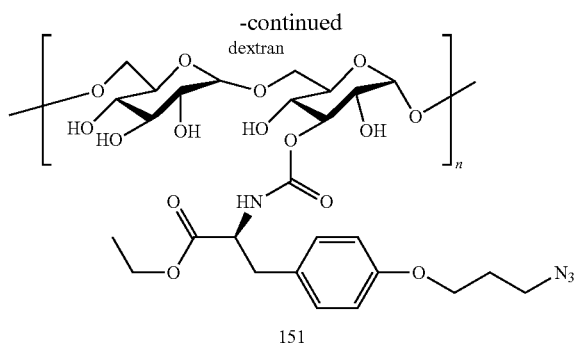

151

Sample 148: Preparation of Compound 148

In a 250 mL round bottom flask, 4.34 g (24.24 mmol) of 3-azidopropanyl methylsulfonate and 5.0 g (16.16 mmol) of L-tyrosine ethyl ester were dissolved in 30.0 mL of anhydrous dimethylformamide, followed by addition of 10.53 g (32.32 mmol) of cesium carbonate, and heated at 50° C. overnight. Upon completion of the reaction, the reaction mixture was partitioned between ethyl acetate (150 mL) and brine (150 mL). The organic phase was further washed with brine (60 mL×2), dried over anhydrous MgSO$_4$, filtered, concentrated, and purified on a silica gel column and eluted with ethyl acetate in petroleum ether (10-70%) to gave 4.31 g of compound 148. Yield: 68%.

$^1$H NMR (300 MHz, CDCl$_3$, ppm): δ 7.06 (d, J=7.3 Hz, 2H), 6.82 (d, J=7.3 Hz, 2H), 4.98 (s, 1H), 4.51 (m, 1H), 4.19 (m, 2H), 4.07 (t, J=7.2 Hz, 2H), 3.52 (t, J=7.2 Hz, 2H), 3.03 (m, 2H), 2.05 (m, 2H), 1.43 (s, 9H), 1.25 (t, J=7.2 Hz, 2H); ESI-MS (m/z): calcd for C$_{19}$H$_{29}$N$_4$O$_5$ [M+H]$^+$: 393.2; found: 393.3.

Sample 149: Preparation of Compound 149

To a 200 mL round-bottom flask charged with 3.8 g (9.69 mmol) of compound 148, 30 mL of hydrochloride ethanol solution (3.0N) was added and stirred at room temperature overnight. After removal of volatiles, the residue was purified on a reverse phase C-18 column and eluted with acetonitrile in water (10-70%) to provide 2.41 g of compound 149. Yield: 85%.

$^1$H NMR (300 MHz, CDCl$_3$, ppm): δ 8.74 (s, 3H), 7.24 (d, J=7.2 Hz, 2H), 6.83 (d, J=7.2 Hz, 2H), 4.33 (s, 1H), 4.17 (m, 2H), 4.13 (t, J=7.2 Hz, 2H), 3.50 (t, J=7.2 Hz, 2H), 3.42 (m, 2H), 2.03 (m, 2H), 1.19 (t, J=7.2 Hz, 3H); ESI-MS (m/z): calcd for C$_{14}$H$_{21}$N$_4$O$_3$ [M+H]$^+$: 293.2; found: 293.2.

Sample 150: Preparation of Compound 150

In a 250 mL round bottom flask, 1.49 g (7.52 mmol) of diphosgene was dissolved in 30.0 mL of dichloromethane and cooled to 0° C., followed by addition of 50 mL of saturated sodium carbonate solution and 2.2 g (7.52 mmol) of compound 149 in dichloromethane, and stirred for 5 h. Upon completion of the reaction, the organic phase was separated, dried over anhydrous MgSO$_4$, filtered, concentrated, and purified on a silica gel column and eluted with ethyl acetate in petroleum ether (10-80%) to provide 1.27 g of compound 150. Yield: 53%.

$^1$H NMR (300 MHz, CDCl$_3$, ppm): δ 7.13 (d, J=7.2 Hz, 2H), 6.87 (d, J=7.2 Hz, 2H), 4.25 (m, 2H), 4.21 (m, 2H), 4.01 (t, J=7.2 Hz, 2H), 3.53 (m, 1H), 3.51 (m, 1H), 2.05 (m, 2H), 1.31 (t, J=7.2 Hz, 3H); ESI-MS (m/z): calcd for C$_{15}$H$_{19}$N$_4$O$_4$ [M+H]$^+$: 319.1; found: 319.3.

Sample 151: Preparation of Functionalized Dextran 151

In a 100 mL round bottom flask, 20.0 mL of anhydrous DMSO was added and heated to 60° C., and followed by addition of 3.0 g of dextran (average molecular weight ~100,000) and stirred until completely dissolved. After the solution was cooled down to 38° C., 200 mg (0.63 mmol) of compound 150 and 77 mg (0.63 mmol) of 4-dimethylaminopyridine (DMAP) were added and stirred for 12 hours. Upon completion of the reaction, the reaction mixture was precipitated in methanol, dialyzed against distilled water, and lyophilized to provide 2.78 g of functionalized dextran 151. Yield: 92%.

$^1$H NMR (selected characteristic signals, 500 MHz, DMSO-d$_6$, ppm): major signals: 4.50-5.00 (m, CHOH, CHOH, CH$_2$OH), 3.30-4.20 (m, CHOH, CH$_2$OH, CH$_2$O); minor signals: 6.70-7.30 (m, ArH), 1.96 (m, CH$_2$), 1.23 (t, CH$_3$).

Part 3. Preparation of Lipid-Polysaccharide Conjugates
Synthetic Scheme 34

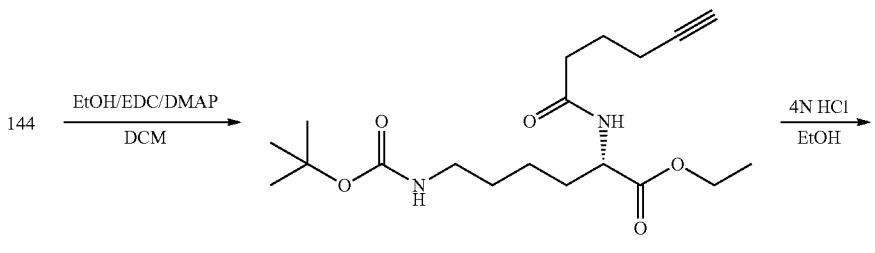

152

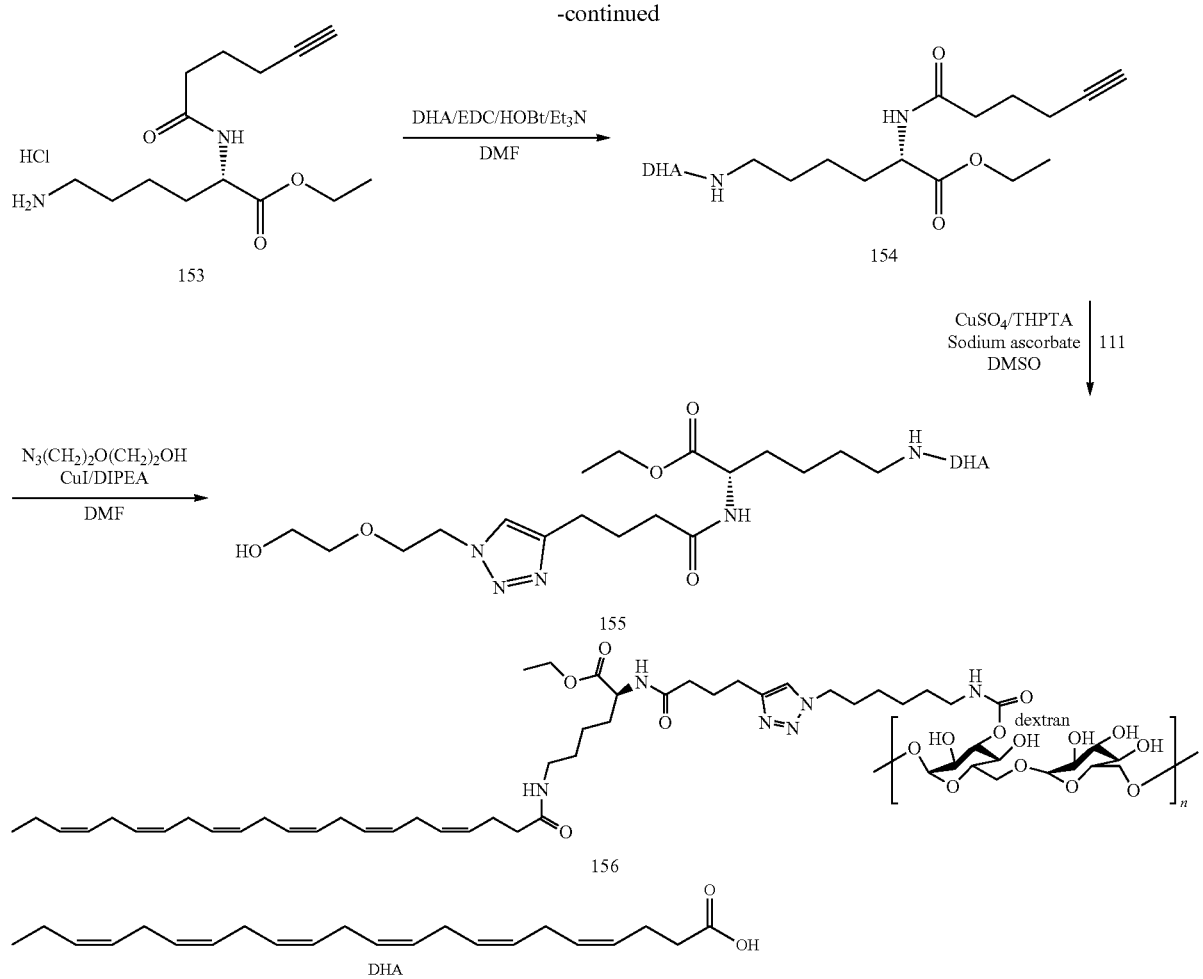

Sample 152: Preparation of Compound 152

To a 250 mL round-bottom flask charged with 3.0 g (8.82 mmol) of compound 144, 2.53 g (13.23 mmol) of 1-ethyl-3-(3-dimethylaminopropyl) carbodiimide (EDC) and 50 mL of anhydrous dichloromethane were added and stirred at room temperature for 30 min; and then 2.0 mL of absolute ethanol and 1.62 g (13.23 mmol) of DMAP were added. The reaction was continuously stirred overnight. The reaction mixture was washed with brine twice (50 mL×2), dried over anhydrous MgSO$_4$, filtered, concentrated, and purified on a silica gel column and eluted with ethyl acetate in petroleum ether (10-80%) to provide 2.63 g of compound 152. Yield: 81%.

$^1$H NMR (300 MHz, CDCl$_3$, ppm): δ 4.51 (m, 1H), 4.15 (q, J=7.2 Hz, 2H), 3.17 (t, J=7.2 Hz, 2H), 2.35 (q, J=7.2 Hz, 2H), 2.21 (m, 2H), 1.95 (t, J=2.1 Hz, 1H), 1.83 (m, 3H), 1.61 (m, 1H), 1.39 (m, 2H), 1.37 (s, 9H), 1.25 (m, 2H), 1.23 (t, J=7.2 Hz, 3H); ESI-MS (m/z): calcd for C$_{19}$H$_{33}$N$_2$O$_5$ [M+H]$^+$: 369.2; found: 369.2.

Sample 153: Preparation of Compound 153

To a 100 mL round-bottom flask charged with 2.5 g (6.79 mmol) of compound 152, 30 mL of hydrochloride ethanol solution (4.0N) was added, and stirred at room temperature overnight. After removal of volatiles, the residue was purified on a reverse phase C-18 column and eluted with acetonitrile in water (10-70%) to provide 1.75 g of compound 153. Yield: 96%.

$^1$H NMR (300 MHz, DMSO-d$_6$, ppm): δ 4.11 (m, 3H), 2.70 (m, 2H), 2.25 (t, J=7.2 Hz, 2H), 2.15 (m, 2H), 2.05 (s, 1H), 1.50-1.75 (m, 6H), 1.31 (m, 2H), 1.17 (t, J=7.2 Hz, 3H); ESI-MS (m/z): calcd for C$_{14}$H$_{25}$N$_2$O$_3$ [M+H]$^+$: 269.2; found: 269.2.

Sample 154: Preparation of Compound 154

To a 250 mL round bottom flask charged with 2.03 g (6.16 mmol) of docosahexaenoic acid (DHA), 1.18 g (6.16 mmol) of 1-ethyl-3-(3-dimethylaminopropyl) carbodiimide (EDC) and 832 mg (6.16 mmol) 1-hydroxybenzotriazole (HOBt), 15.0 mL of anhydrous dimethylformamide were added, and flowed by 1.5 g (5.60 mmol) of compound 153 and 1.5 mL (11.2 mmol) triethylamine, and stirred for 5 hours. Upon completion of the reaction, the reaction mixture was partitioned from ethyl acetate (100 mL) and brine (100 mL). The organic phase was further washed with brine twice (100 mL×2), dried over MgSO$_4$, concentrated, and purified on a silica gel column and eluted with ethyl acetate in petroleum ether to give 2.69 g of compound 154. Yield: 83%.

$^1$H NMR (300 MHz, CDCl$_3$, ppm): δ 5.25-5.00 (m, 12H), 4.51 (m, 1H), 4.21 (t, J=7.2 Hz, 2H), 3.23 (t, J=7.2 Hz, 2H), 2.76 (m, 10H), 2.30-2.50 (m, 4H), 2.23 (t, J=7.2 Hz, 2H), 2.25 (m, 2H), 2.16 (t, J=7.2 Hz, 2H), 2.03 (m, 3H), 1.73 (m, 2H), 1.55 (m, 2H), 1.35 (m, 2H), 1.23 (t, J=7.2 Hz, 3H), 0.95 (t, J=7.2 Hz, 3H); ESI-MS: calcd for C$_{36}$H$_{55}$N$_2$O$_4$ [M+H]$^+$: 579.4; found: 579.6.

Sample 155: Preparation of Compound 155

In a 100 mL round bottom flask, 1.0 g (1.73 mmol) of compound 154 and 339 mg (2.59 mmol) of 2-(2-azidoethoxy) ethanol were dissolved in 10 mL of acetonitrile, and followed by addition of 32 mg (0.17 mmol) of CuI and 50 uL (0.35 mmol) of triethylamine were stirred at room temperature overnight. After removal of volatiles, the residue was purified on a silica gel column and eluted with methanol in chloroform (0-10%) to provide 1.05 g of compound 155. Yield: 85%.

$^1$H NMR (300 MHz, CDCl$_3$, ppm): δ 7.61 (s, 1H), 5.25-5.00 (m, 12H), 4.52 (m, 1H), 4.16 (t, J=7.2 Hz, 2H), 3.83 (t, J=7.2 Hz, 2H), 3.71 (m, 2H), 3.57 (t, J=7.2 Hz, 2H), 3.25 (m, 4H), 2.73 (m, 10H), 2.35-2.50 (m, 4H), 2.23 (t, J=7.2 Hz, 2H), 2.12 (t, J=7.2 Hz, 2H), 2.05 (m, 5H), 1.72 (m, 2H), 1.53 (m, 2H), 1.35 (m, 2H), 1.23 (t, J=7.2 Hz, 3H), 0.93 (t, J=7.2 Hz, 3H); ESI-MS: calcd for $C_{40}H_{64}N_5O_6$ [M+H]$^+$: 710.4; found: 710.6.

Sample 156: Preparation of Conjugate 156

In a 25 mL round bottom flask, 500 mg of functionalized polysaccharide 111 and 80 mg (0.11 mmol) of compound 154 were dissolved in 3.0 mL of DMSO, and followed by addition of copper sulfate solution (30 uL×1.0 M), THPTA (30 uL×1.0 M), and sodium (60 uL×1.0 M), and stirred at room temperature for 2 days. Upon completion of the reaction, the reaction mixture was precipitated in methanol, filtered, and washed three times with methanol. The precipitate was then dissolved in 2.0 mL of distilled water, dialyzed against distilled water, and lyophilized to provide 462 mg of conjugate 156. Yield: 93%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.20-8.50 (m, ArH, CONH), 5.32 (m, CH), 1.24 (t, CH$_3$), 1.01 (t, CH$_3$).

Synthetic Scheme 35

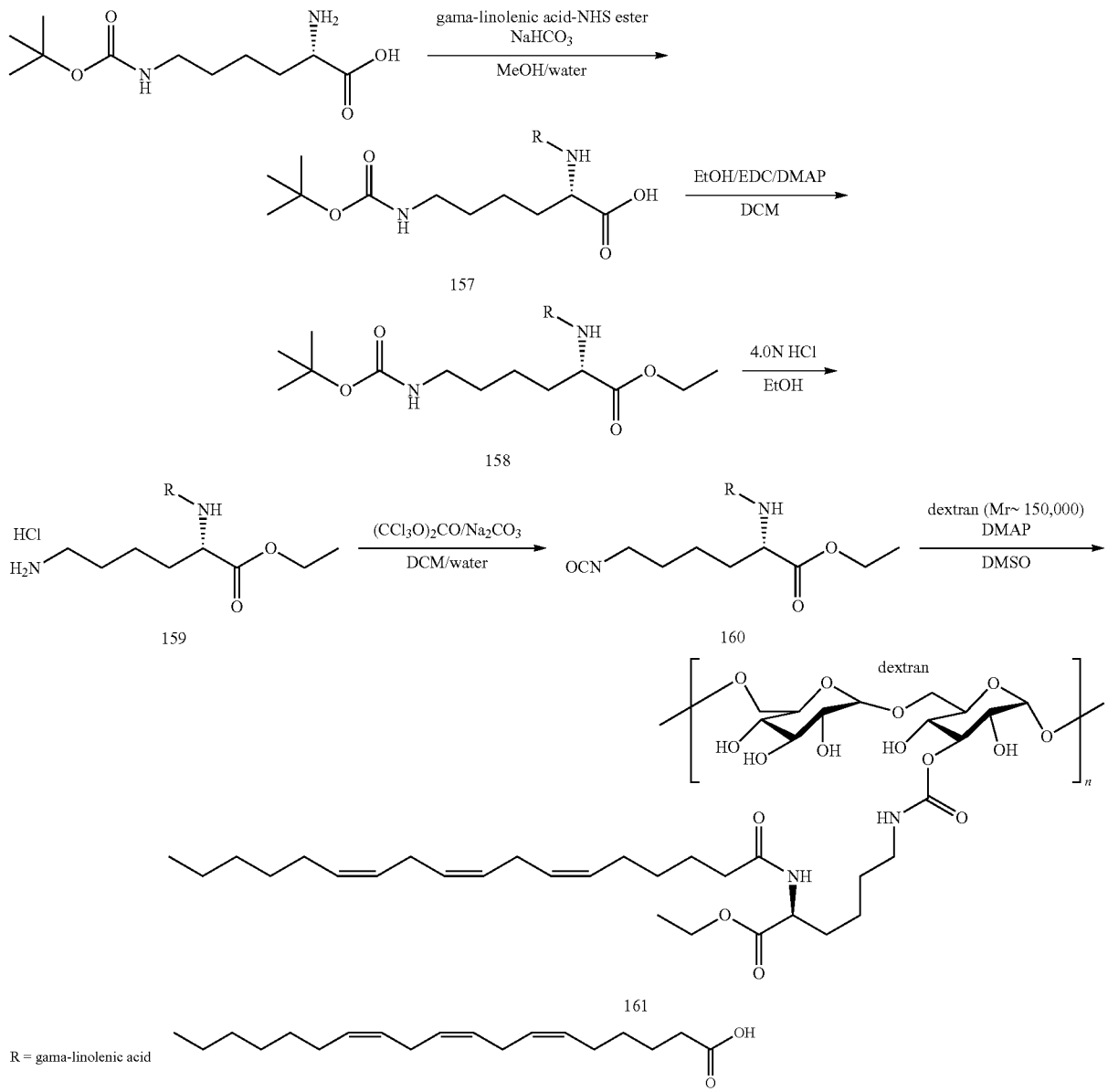

Sample 157: Preparation of Compound 157

In a 250 mL round bottom flask, 9.0 g (36.55 mmol) of compound Boc-L-lysine and 6.25 g (73.11 mmol) of sodium bicarbonate were dissolved in 200.0 mL of methanol-water (2:1), followed by addition of 12.8 g (32.90 mmol) of gama-linoleic acid-(N-hydroxysuccinyl lactam) ester and stirred overnight. Upon completion of the reaction, the reaction mixture was acidified with 2.0N HCl to pH=1.0, extracted with ethyl acetate (100 mL×3); the organic phases were combined together, dried over MgSO$_4$, filtered, concentrated, and purified on a silica gel column and eluted with methanol in chloroform (0-12%) to provide 11.7 g of compound 157. Yield: 67%.

$^1$H NMR (300 MHz, CDCl$_3$, ppm): δ 6.07 (s, 1H), 5.35 (m, 6H), 4.51 (m, 1H), 3.21 (t, J=7.2 Hz, 2H), 2.76 (m, 4H), 2.25 (t, J=7.2 Hz, 2H), 2.17 (m, 4H), 1.82 (m, 2H), 1.51-1.75 (m, 4H), 1.42 (s, 9H), 1.25-1.41 (m, 13H); ESI-MS (m/z): ESI-MS: calcd for C$_{29}$H$_{51}$N$_2$O$_5$ [M+H]$^+$: 507.3; found: 507.4.

Sample 158: Preparation of Compound 158

To a 250 mL round-bottom flask charged with 10.0 g (19.75 mmol) of compound 157 and 5.66 g (29.62 mmol) of 1-ethyl-3-(3-dimethylaminopropyl) carbodiimide (EDC), 100 mL of anhydrous dichloromethane were added and stirred at room temperature for 30 min; and then 3.0 mL of absolute ethanol and 3.62 g (29.62 mmol) of DMAP were added. The reaction was continuously stirred overnight. Upon completion of the reaction, the reaction mixture was washed with brine (100 mL×2), dried over anhydrous MgSO$_4$, filtered, concentrated, and purified on a silica gel column and eluted with ethyl acetate in petroleum ether (10-80%) to provide 8.55 g of compound 158. Yield: 75%.

$^1$H NMR (300 MHz, CDCl$_3$, ppm): δ 6.12 (s, 1H), 5.48 (m, 6H), 4.53 (m, 1H), 4.12 (q, J=7.2 Hz, 2H), 3.21 (t, J=7.2 Hz, 2H), 2.76 (m, 4H), 2.25 (t, J=7.2 Hz, 2H), 2.17 (m, 4H), 1.82 (m, 2H), 1.51-1.75 (m, 4H), 1.42 (s, 9H), 1.25-1.41 (m, 13H), 0.96 (t, J=7.2 Hz, 3H); ESI-MS (m/z): calcd for C$_{31}$H$_{55}$N$_2$O$_5$ [M+H]$^+$: 535.4; found: 535.5.

Sample 159: Preparation of Compound 159

To a 250 mL round-bottom flask charged with 8.5 g (15.90 mmol) of compound 158, 100 mL of hydrochloride ethanol solution (4.0N) was added and stirred at room temperature overnight. After removal of volatiles, the residue was purified on a reverse phase C-18 column and eluted with acetonitrile in water (10-70%) to provide 7.17 g of compound 159. Yield: 96%.

$^1$H NMR (300 MHz, CDCl$_3$, ppm): δ 8.18 (brs, 3H), 5.37 (m, 6H), 4.52 (m, 1H), 4.18 (q, J=7.2 Hz, 2H), 3.05 (t, J=7.2 Hz, 2H), 2.79 (m, 4H), 2.42 (t, J=7.2 Hz, 2H), 2.09 (m, 4H), 1.45-1.95 (m, 6H), 1.25-1.43 (m, 13H), 0.97 (t, J=7.2 Hz, 3H); ESI-MS (m/z): calcd for C$_{26}$H$_{47}$N$_2$O$_3$ [M+H]$^+$: 435.3; found: 435.3.

Sample 160: Preparation of Compound 160

In a 250 mL round bottom flask, 1.71 g (5.75 mmol) of diphosgene was dissolved in 30.0 ml of dichloromethane and cooled to 0° C., followed by addition of 30 mL of saturated sodium carbonate solution and 2.7 g (5.75 mmol) of compound 159 in dichloromethane, and stirred for 3 h. Upon completion of the reaction, the organic phase was separated, dried over anhydrous MgSO$_4$, filtered, concentrated, and purified on a silica gel column and eluted with ethyl acetate in petroleum (5-60%) to provide 1.88 g of compound 160. Yield: 71%.

$^1$H NMR (300 MHz, CDCl$_3$, ppm): δ 6.21 (m, 1H), 5.36 (m, 6H), 4.54 (m, 1H), 4.23 (q, J-7.2 Hz, 2H), 3.20 (t, J=7.2 Hz, 2H), 2.80 (m, 4H), 2.23 (t, J=7.2 Hz, 2H), 2.05 (m, 4H), 1.45-1.95 (m, 6H), 1.25-1.43 (m, 13H), 0.97 (t, J=7.2 Hz, 3H); ESI-MS (m/z): calcd for C$_{27}$H$_{45}$N$_2$O$_4$ [M+H]$^+$: 461.3; found: 461.3.

Sample 161: Preparation of Conjugate 161

In a 100 mL round bottom flask, 20 mL of anhydrous DMSO was added and heated to 60° C., followed by addition of 2.0 g of dextran (average molecular weight ~150,000) and stirred until completely dissolved. After the solution was cooled down to 38° C., 300 mg (0.65 mmol) of compound 160 and 79 mg (0.65 mmol) of 4-dimethylaminopyridine (DMAP) were added and stirred for 12 hours. Upon completion of the reaction, the reaction mixture was precipitated in methanol, dialyzed against distilled water, and lyophilized to provide 1.63 g of functionalized dextran 161. Yield: 86%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 5.33 (m, CH), 1.23 (t, CH$_3$), 0.82 (t, CH$_3$).

Synthetic Scheme 36

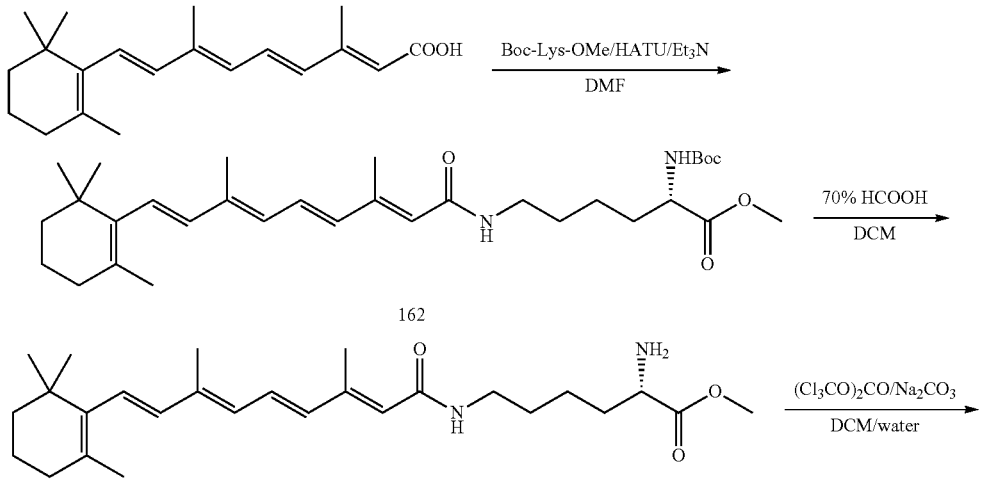

-continued

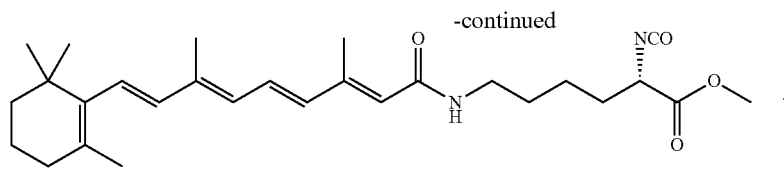

164

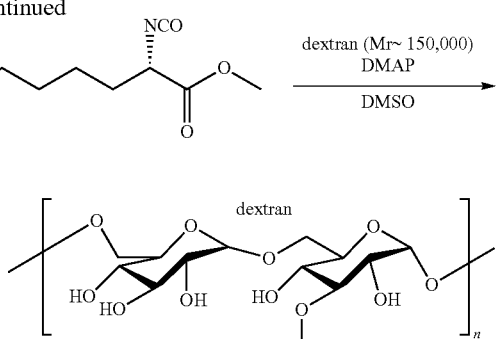

165

Sample 162: Preparation of Compound 162

In a 250 mL round bottom flask, 10.1 g (33.7 mmol) of retinoic acid was dissolved in 50.0 mL of anhydrous dimethylformamide, followed by addition of 15.4 g (40.5 mmol) of 2-(7-azobenzotriazole)-N,N,N',N'-tetramethyluronium hexafluorophosphate (HATU), and stirred for 30 minutes. To the above solution, 10.0 g (33.7 mmol) of Boc-L-lysine methyl ester hydrochloride and 5.6 mL triethylamine (40.5 mmol) were added and stirred for 3 hours. Upon completion of the reaction, the reaction mixture was partitioned from ethyl acetate (150 mL) and brine (150 mL). The organic phase was further washed with brine twice (100 mL×2), and dried over anhydrous MgSO$_4$, filtered, concentrated, and purified on a silica gel column and eluted with ethyl acetate in petroleum ether to give 15.1 g of compound 162. Yield: 83%.

$^1$H NMR (300 MHz, CDCl$_3$, ppm): δ 5.70-7.00 (m, 6H), 4.25 (m, 1H), 3.68 (s, 3H), 3.25 (t, J=7.2 Hz, 2H), 2.35 (s, 3H), 2.02 (m, 5H), 1.76 (m, 2H), 1.72 (s, 3H), 1.63 (s, 3H), 1.36-1.62 (m, 4H), 1.45 (m, 11H), 1.25-1.40 (m, 2H), 1.03 (s, 3H), 1.01 (s, 3H); ESI-MS (m/z): calcd for C$_{32}$H$_{51}$N$_2$O$_5$ [M+H]$^+$: 543.3; found: 543.5.

Sample 163: Preparation of Compound 163

In a 250 mL round bottom flask, 10.0 g (18.30 mmol) of compound 162 was dissolved in 50 mL of formic acid (70%) in dichloromethane, stirred overnight. After removal of volatiles, the residue was purified on a silica gel column and eluted with methanol in chloroform (3-20%) to give 2.56 g of compound 163. Yield: 25%.

$^1$H NMR (300 MHz, CDCl$_3$, ppm): δ 5.70-7.00 (m, 6H), 3.97 (m, 1H), 3.67 (s, 3H), 3.27 (t, J=7.2 Hz, 2H), 2.37 (s, 3H), 2.05 (m, 5H), 1.77 (m, 2H), 1.71 (s, 3H), 1.65 (s, 3H), 1.36-1.62 (m, 4H), 1.45 (m, 2H), 1.25-1.40 (m, 2H), 1.04 (s, 3H), 1.02 (s, 3H); ESI-MS (m/z): calcd for C$_{27}$H$_{43}$N$_2$O$_3$ [M+H]$^+$: 443.3; found: 443.3.

Sample 164: Preparation of Compound 164

In a 250 mL round bottom flask, 1.0 g (3.38 mmol) of diphosgene was dissolved in 30.0 mL of dichloromethane and cooled to 0° C., followed by addition of 30 mL of saturated sodium carbonate solution and 2.7 g (3.38 mmol) of compound 163 in dichloromethane and stirred for 5 h. Upon completion of the reaction, the organic phase was separated, dried over anhydrous MgSO$_4$, filtered, concentrated, and purified on a silica gel column and eluted with ethyl acetate in petroleum (5-60%) to provide 1.88 g of compound 164. Yield: 50%.

$^1$H NMR (300 MHz, CDCl$_3$, ppm): δ 5.70-7.00 (m, 6H), 4.10 (m, 1H), 3.66 (s, 3H), 3.25 (t, J=7.2 Hz, 2H), 2.35 (s, 3H), 2.03 (m, 5H), 1.75 (m, 2H), 1.70 (s, 3H), 1.63 (s, 3H), 1.36-1.62 (m, 4H), 1.45 (m, 2H), 1.25-1.40 (m, 2H), 1.05 (s, 3H), 1.02 (s, 3H); ESI-MS (m/z): calcd for C$_{28}$H$_{41}$N$_2$O$_4$ [M+H]$^+$: 469.3; found: 469.4.

Sample 165: Preparation of Conjugate 165

In a 100 mL round bottom flask, 20 mL of anhydrous DMSO was added and heated to 60° C., followed by addition of 2.0 g of dextran (average molecular weight ~150,000) and stirred until completely dissolved. After the solution was cooled down to 38° C., 250 mg (0.53 mmol) of compound 164 and 65 mg (0.53 mmol) of 4-dimethylaminopyridine (DMAP) were added and stirred for 24 hours. Upon completion of the reaction, the reaction mixture was precipitated in methanol, dialyzed against distilled water, and lyophilized to provide 1.75 g of conjugate 165. Yield: 87%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 6.5 0-7.00 (m, CH), 1.02 (m, CH$_3$).

Synthetic Scheme 37

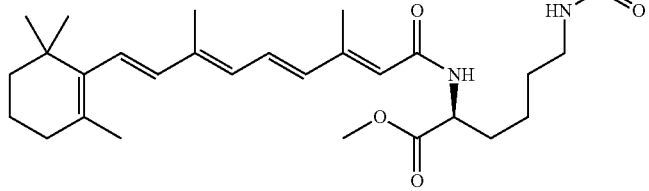

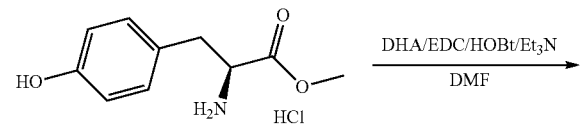

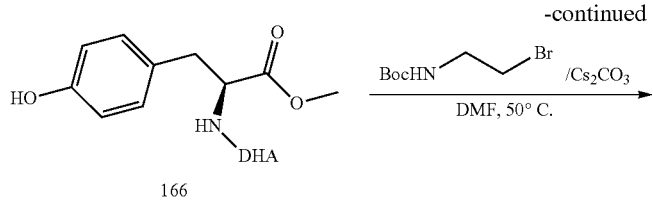

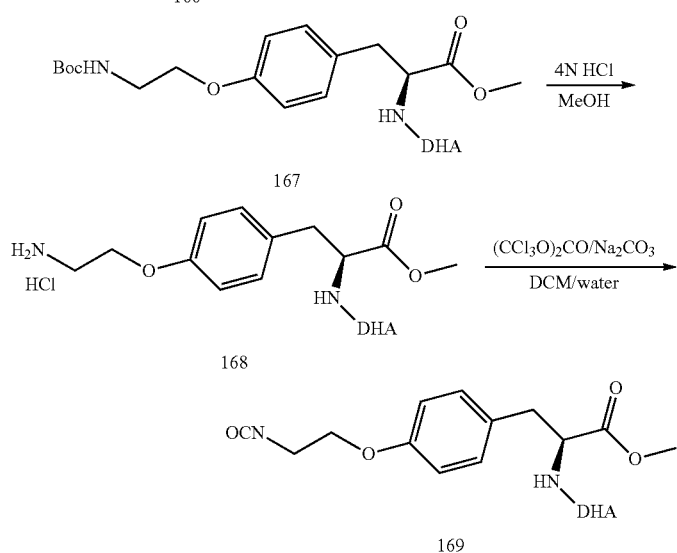

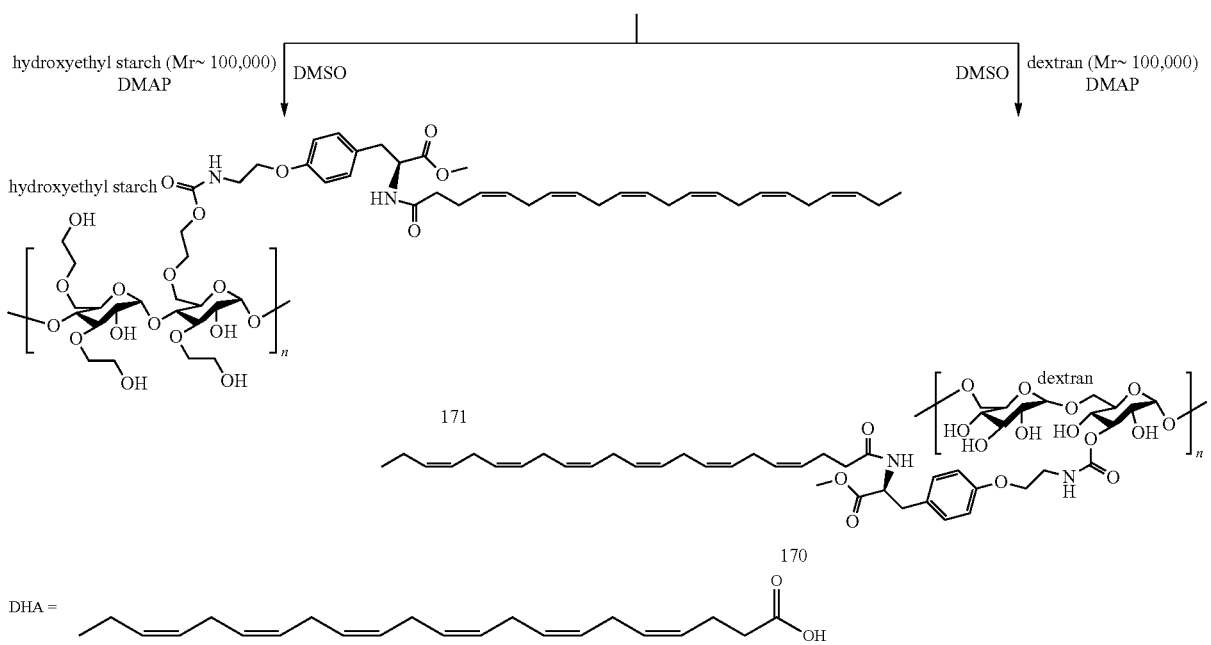

Sample 166: Preparation of Compound 166

To a 250 mL round-bottom flask charged with 2.0 g (6.09 mmol) of docosahexaenoic (DHA), 1.39 g (7.31 mmol) of 1-ethyl-3-(3-dimethylaminopropyl) carbodiimide (EDC), and 987 mg (7.31 mmol) of 1-hydroxybenzotriazole (HOBt), 30.0 mL of dry DMF were added and stirred for 30 min, followed by addition of 1.41 g (6.09 mmol) of L-tyrosine methyl ester and 1.78 mL (12.78 mmol) of triethylamine, and stirred at room temperature for another 5 h. Upon completion of the reaction, the reaction mixture was partitioned between ethyl acetate (100 mL) and brine (100 mL), the organic phase was further washed with brine twice (100 mL×2), dried over anhydrous $MgSO_4$, filtered, concentrated, and purified on a silica gel column and eluted with ethyl acetate in petroleum ether (20-80%) to provide 2.72 g of compound 166. Yield: 95%.

$^1$H NMR (300 MHz, $CDCl_3$, ppm): δ 6.98 (d, J=7.8 Hz, 2H), 6.77 (d, J=7.8 Hz, 2H), 5.37 (m, 12H), 4.87 (m, 1H), 3.73 (s, 3H), 3.06 (m, 2H), 2.85 (m, 10H), 2.37 (m, 2H), 2.25 (m, 2H), 2.05 (m, 2H), 0.97 (t, J=7.2H, 3H); ESI-MS (m/z): calcd for $C_{32}H_{44}NO_4$ $[M+H]^+$: 506.3; found: 506.4.

Sample 167: Preparation of Compound 167

In a 250 mL round bottom flask, 1.33 g (5.95 mmol) of Boc-2-bromoethylamine and 2.5 g (4.95 mmol) of compound 166 were dissolved in 15.0 mL of anhydrous dimethylformamide, and followed by addition of 3.22 g (9.9 mmol) of cesium carbonate, and heated at 50° C. overnight. Upon completion of the reaction, the reaction mixture was partitioned between ethyl acetate (100 mL) and brine (100 mL). The organic phase was further washed with brine (60 mL×2), dried over anhydrous MgSO$_4$, filtered, concentrated, and purified on a silica gel column and eluted with ethyl acetate in petroleum ether (10-60%) to give 2.3 g of compound 167. Yield: 71%.

$^1$H NMR (300 MHz, CDCl$_3$, ppm): δ 6.97 (d, J=7.8 Hz, 2H), 6.75 (d, J=7.8 Hz, 2H), 5.35 (m, 12H), 4.83 (m, 1H), 3.99 (t, J=7.2 Hz, 2H), 3.75 (s, 3H), 3.51 (t, J=7.2 Hz, 2H), 3.07 (m, 2H), 2.83 (m, 10H), 2.35 (m, 2H), 2.27 (m, 2H), 2.03 (m, 2H), 1.45 (s, 3H), 0.97 (t, J=7.2H, 3H); ESI-MS (m/z): calcd for C$_{39}$H$_{56}$N$_2$O$_6$ [M+H]$^+$: 649.4; found: 649.6.

Sample 168: Preparation of Compound 168

To a 200 mL round-bottom flask charged with 2.0 g (3.09 mmol) of compound 167, 30 mL of hydrochloride ethanol solution (4.0N) was added, and stirred at room temperature overnight. After removal of volatiles, the residue was purified on a reverse phase C-18 column and eluted with acetonitrile in water (10-70%) to provide 1.64 g of compound 168. Yield: 91%.

$^1$H NMR (300 MHz, CDCl$_3$, ppm): δ 6.98 (d, J=7.8 Hz, 2H), 6.78 (d, J=7.8 Hz, 2H), 5.33 (m, 12H), 4.81 (m, 1H), 4.10 (t, J=7.2 Hz, 2H), 3.71 (s, 3H), 3.25 (t, J=7.2 Hz, 2H), 3.06 (m, 2H), 2.87 (m, 10H), 2.36 (m, 2H), 2.24 (m, 2H), 2.07 (m, 2H), 0.96 (t, J=7.2H, 3H); ESI-MS (m/z): calcd for C$_{34}$H$_{49}$N$_2$O$_4$ [M+H]$^+$: 549.3; found: 549.3.

Sample 169: Preparation of Compound 169

In a 250 mL round bottom flask, 703 mg (2.37 mmol) of diphosgene was dissolved in 20.0 mL of dichloromethane and cooled to 0° C., followed by addition of 20 mL of saturated sodium carbonate solution and 1.3 g (2.37 mmol) of compound 168 in dichloromethane, and stirred for 5 h. Upon completion of the reaction, the organic phase was separated, dried over anhydrous MgSO$_4$, filtered, concentrated, and purified on a silica gel column and eluted with ethyl acetate in chloroform (5-50%) to provide 982 mg of compound 169. Yield: 72%.

$^1$H NMR (300 MHz, CDCl$_3$, ppm): δ 7.02 (d, J=7.8 Hz, 2H), 6.79 (d, J=7.8 Hz, 2H), 5.35 (m, 12H), 4.85 (m, 1H), 4.06 (t, J=7.2 Hz, 2H), 3.72 (s, 3H), 3.62 (t, J=7.2 Hz, 2H), 3.05 (m, 2H), 2.83 (m, 10H), 2.35 (m, 2H), 2.25 (m, 2H), 2.06 (m, 2H), 0.97 (t, J=7.2H, 3H); ESI-MS (m/z): calcd for C$_{35}$H$_{47}$N$_2$O$_5$ [M+H]$^+$: 575.3; found: 575.5.

Sample 170: Preparation of Conjugate 170

In a 100 mL round bottom flask, 20.0 mL of anhydrous DMSO was added and heated to 60° C., followed by addition of 2.0 g of dextran (average molecular weight ~100,000) and stirred until completely dissolved. After the solution was cooled down to room temperature, 360 mg (0 62 mmol) of compound 169 and 77 mg (0.63 mmol) of 4-dimethylaminopyridine (DMAP) were added and stirred for 24 hours. Upon completion of the reaction, the reaction mixture was precipitated in methanol, dialyzed against distilled water, and lyophilized to provide 1.68 g of conjugate 170. Yield: 84%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 6.75-7.20 (m, ArH), 5.32 (m, CH), 1.01 (t, CH$_3$).

Sample 170: Preparation of Conjugate 171

In a 100 mL round bottom flask, 20.0 mL of anhydrous DMSO was added and heated to 60° C., and followed by addition of 2.0 g of hydroxyethyl starch (average molecular weight ~100,000) and stirred until completely dissolved. After the solution was cooled down to room temperature, 250 mg (0.43 mmol) of compound 169 and 52 mg (0.63 mmol) of 4-dimethylaminopyridine (DMAP) were added and stirred for 24 hours. Upon completion of the reaction, the reaction mixture was precipitated in methanol, dialyzed against distilled water, and lyophilized to provide 1.72 g of conjugate 171. Yield: 86%.

$^1$H NMR (selected characteristic signals, 500 MHz, DMSO-d$_6$, ppm): major signals: 4.50-5.00 (m, CHOH, CHOH, CH$_2$OH), 3.30-4.20 (m, CHOH, CH$_2$OH, CH$_2$O); minor signals: 6.75-7.20 (m, ArH), 5.33 (m, CH), 1.02 (t, CH$_3$).

Synthetic Scheme 38

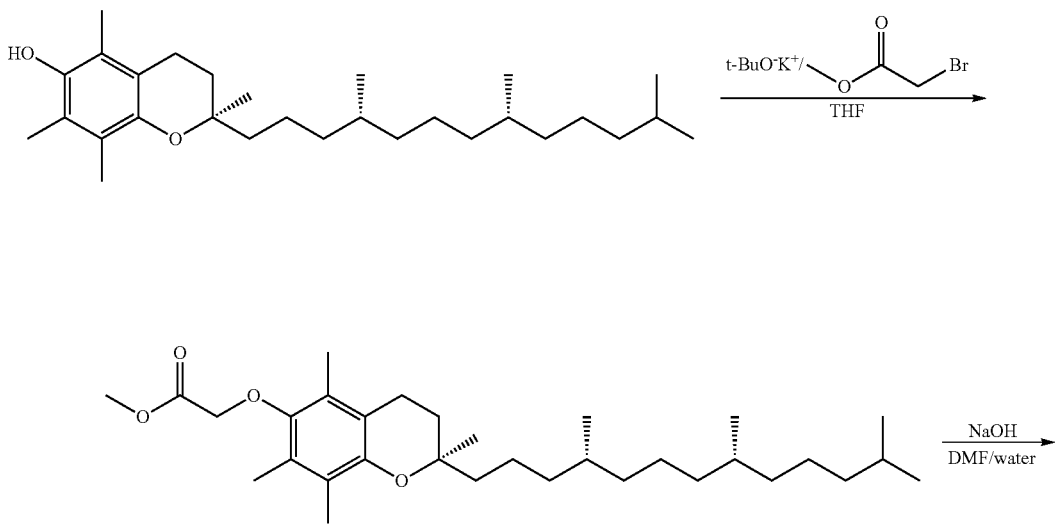

-continued
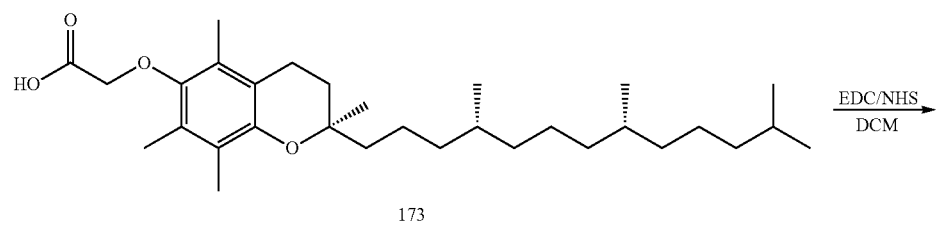
173
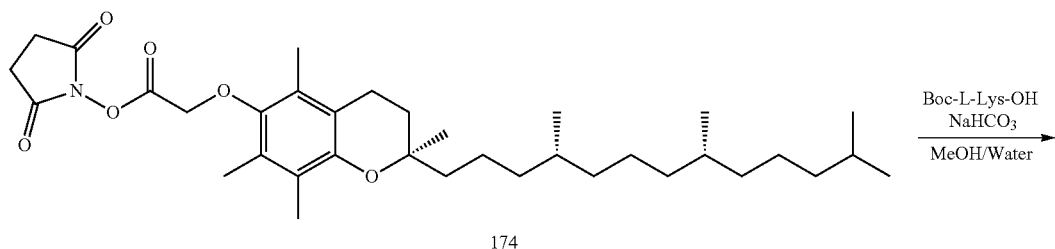
174
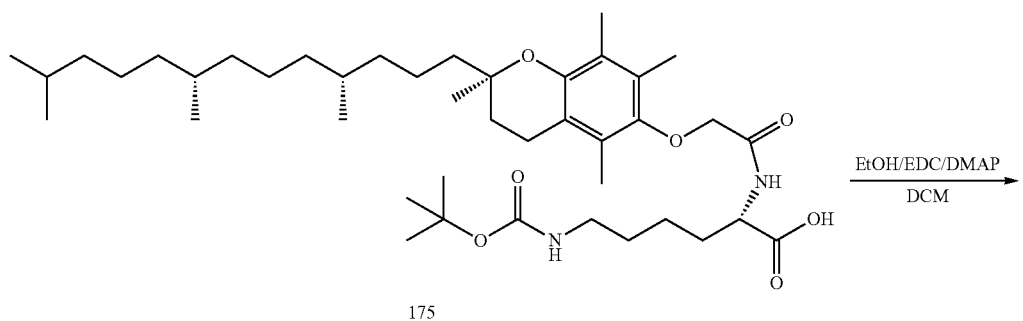
175
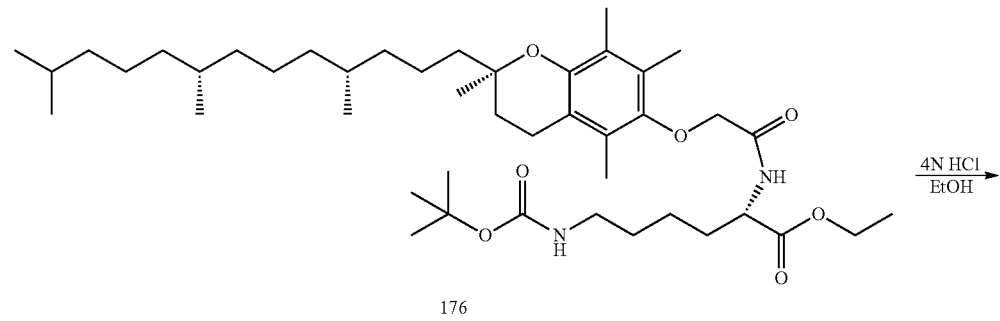
176
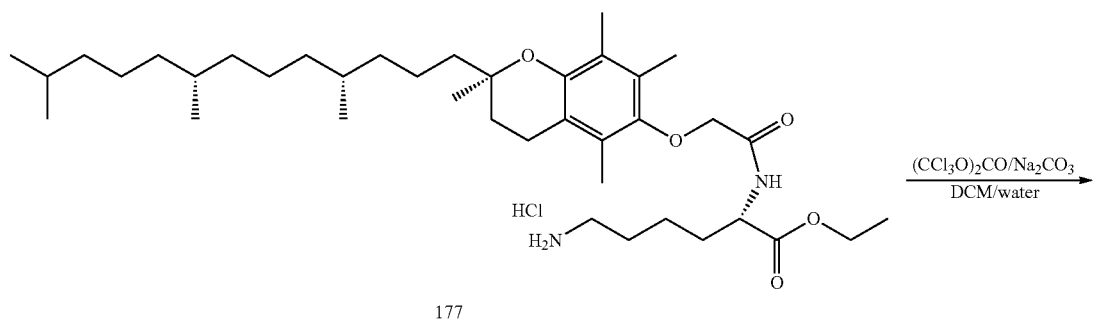
177

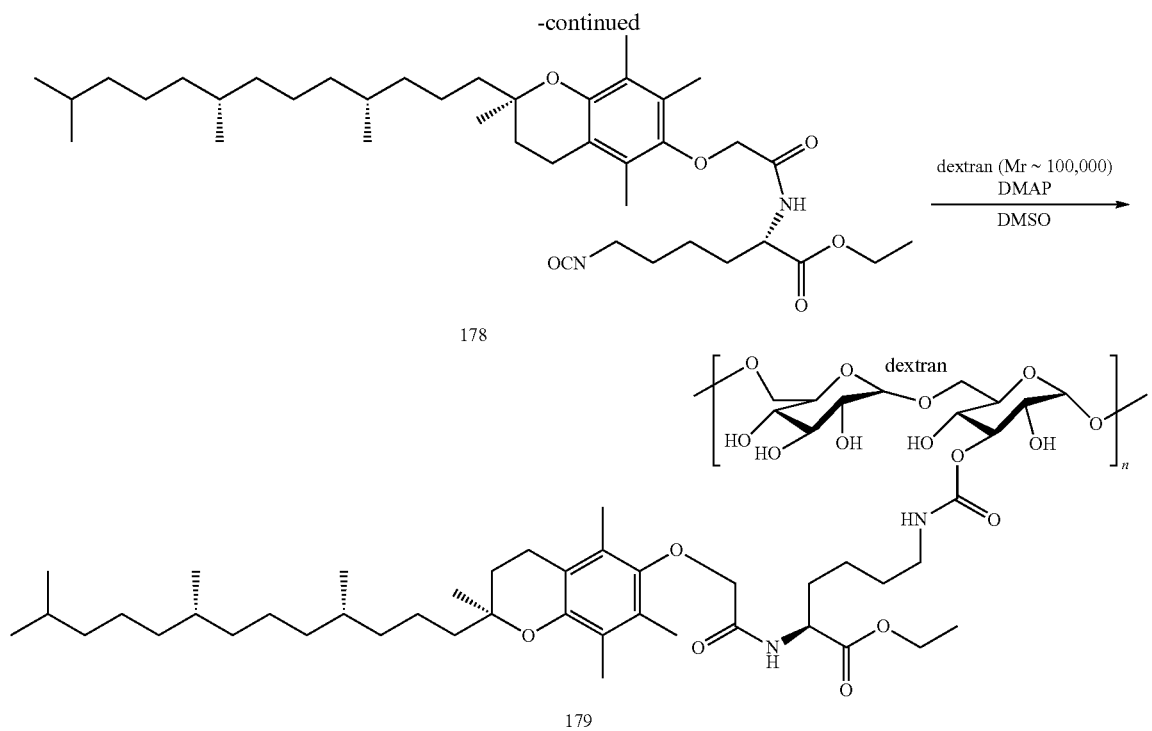

178

179

Sample 172: Preparation of Compound 172

Under the protection of nitrogen, 10.0 g (23.20 mmol) of alpha-tocopherol was dissolved in 100 mL of anhydrous tetrahydrofuran and cooled to −10° C., and then potassium t-butoxide solution (1.0 M×35.0 mL) was added and stirred for 30 minutes. To the above solution, 2.8 mL (30.16 mmol) of methyl bromoacetate was added and stirred overnight. After warming up to room temperature, the reaction mixture was evaporated and the residue was partitioned between ethyl acetate (200 mL) and brine (200 mL); the organic phase was further washed with brine (100 mL×2), dried over anhydrous MgSO$_4$, filtered, concentrated, and purified on a silica gel column and eluted with ethyl acetate in petroleum ether (0-20%) to give 10.3 g of compound 172. Yield: 88%.

$^1$H NMR (300 MHz, CDCl$_3$, ppm): δ 4.30 (s, 2H), 3.84 (s, 3H), 2.59 (t, J=7.0 Hz, 2H), 2.07-2.25 (m, 9H), 1.82 (m, 2H), 1.00-1.70 (m, 24H), 0.85 (m, 12H); ESI-MS (m/z): calcd for C$_{32}$H$_{55}$O$_4$ [M+H]$^+$: 503.4; found: 503.5.

Sample 173: Preparation of Compound 173

In a 250 mL round bottom flask charged with 6.0 g (11.94 mmol) of compound 172 and 1.53 g (38.25 mmol) of sodium hydroxide, 30 mL of dimethylformamide-water (7:3) was added and stirred at room temperature for 2 days. After the completion of the reaction, the mixture was acidified with 2.0N HCl to pH=1.0, and extracted with ethyl acetate (100 mL×3); the organic phases were pooled, dried over MgSO$_4$, filtered, concentrated, and purified on a silica gel column and eluted with ethyl acetate in petroleum ether (0-50%) to give 4.32 g of compound 173. Yield: 74%.

$^1$H NMR (300 MHz, CDCl$_3$, ppm): δ 4.37 (s, 2H), 2.52 (t, J=7.0 Hz, 2H), 2.07-2.25 (m, 9H), 1.82 (m, 2H), 1.00-1.70 (m, 24H), 0.85 (m, 12H); ESI-MS (m/z): calcd for C$_{31}$H$_{53}$O$_4$ [M+H]$^+$: 489.3; found: 489.3.

Sample 174: Preparation of Compound 174

In a 250 mL round bottom flask, 6.5 g (13.31 mmol) of compound 173, 3.82 g (19.96 mmol) of N-(3-dimethylaminopropyl)-N'-ethyl-carbodiimide hydrochloride (EDC) and 2.30 g (19.96 mmol) of N-hydroxysuccinic acid lactam (NHS) were dissolved in 100 mL of chloroform and stirred at room temperature overnight. After the completion of the reaction, the reaction mixture was washed with brine, dried over MgSO$_4$, filtered, and evaporated to dryness to provide 7.63 g of compound 174. Yield: 98%.

$^1$H NMR (300 MHz, CDCl$_3$, ppm): δ 4.33 (s, 2H), 2.75 (m, 4H), 2.53 (t, J=7.0 Hz, 2H), 2.07-2.25 (m, 9H), 1.82 (m, 2H), 1.00-1.70 (m, 24H), 0.85 (m, 12H); ESI-MS (m/z): calcd for C$_{35}$H$_{56}$NO$_6$ [M+H]$^+$: 586.4, found: 586.5.

Sample 175: Preparation of Compound 175

In a 250 mL round bottom flask, 2.78 g (11.27 mmol) of compound Nε-Boc-L-lysine and 3.74 g (45.54 mmol) of sodium bicarbonate were dissolved in 100.0 mL of methanol-water (2:1), followed by addition of 6.0 g (10 25 mmol) of compound 174, and stirred overnight. Upon completion of the reaction, the reaction mixture was acidified with 2.0N HCl to pH=1.0, and extracted with ethyl acetate (100 mL×3); the organic phases were combined together, dried over MgSO$_4$, concentrated, and purified on a silica gel eluted with methanol in chloroform (0-10%) to provide 5.21 g of compound 175. Yield: 71%.

$^1$H NMR (300 MHz, CDCl$_3$, ppm): δ 4.57 (m, 1H), 4.23 (s, 2H), 3.27 (t, J=7.0 Hz, 2H), 2.52 (t, J=7.0 Hz, 2H), 2.07-2.25 (m, 9H), 1.82 (m, 2H), 1.00-1.70 (m, 39H), 0.83 (m, 12H); ESI-MS (m/z): calcd for C$_{42}$H$_{73}$N$_2$O$_7$ [M+H]$^+$: 717.5; found: 717.7.

Sample 176: Preparation of Compound 176

To a 250 mL round-bottom flask charged with 5.0 g (6.98 mmol) of compound 175 and 2.0 g (38.93 mmol) of 1-ethyl-3-(3-dimethylaminopropyl) carbodiimide (EDC), 100 mL of anhydrous dichloromethane were added and stirred at room temperature for 30 min; and then 2.0 mL of absolute ethanol and 1.28 g (10.47 mmol) of DMAP were added. The reaction mixture was continuously stirred overnight. Upon completion of the reaction, the reaction mixture was washed with brine (100 mL×2), dried over anhydrous MgSO$_4$, filtered, concentrated, and purified on a silica gel column and eluted with methanol in chloroform (0-10%) to provide 4.31 g of compound 176. Yield: 83%.

$^1$H NMR (300 MHz, CDCl$_3$, ppm): δ 4.58 (m, 1H), 4.33 (s, 2H), 4.21 (q, J=7.0 Hz, 2H), 3.19 (t, J=7.0 Hz, 2H), 2.52 (t, J=7.0 Hz, 2H), 2.07-2.25 (m, 9H), 1.82 (m, 2H), 1.00-1.70 (m, 42H), 0.83 (m, 12H); ESI-MS (m/z): calcd for C$_{44}$H$_{77}$N$_2$O$_7$ [M+H]$^+$: 745.5; found: 745.6.

Sample 177: Preparation of Compound 177

To a 250 mL round-bottom flask charged with 5.0 g (6.72 mmol) of compound 176, 50 mL of hydrochloride ethanol solution (4.0N) was added and stirred at room temperature overnight. After removal of volatiles, the residue was purified on a silica gel column and eluted with methanol in chloroform (0-12%) to provide 4.53 g of compound 177. Yield: 99%.

$^1$H NMR (300 MHz, CDCl$_3$, ppm): δ 4.70 (m, 1H), 4.11-4.30 (m, 4H), 3.16 (t, J=7.0 Hz, 2H), 2.52 (t, J=7.0 Hz, 2H), 2.07-2.25 (m, 9H), 1.82 (m, 2H), 1.00-1.70 (m, 33H), 0.85 (m, 12H); ESI-MS (m/z): calcd for C$_{39}$H$_{69}$N$_2$O$_5$ [M+H]$^+$: 645.5; found: 645.7.

Sample 178: Preparation of Compound 178

In a 250 mL round bottom flask, 1.31 g (4.40 mmol) of diphosgene was dissolved in 30.0 mL of dichloromethane and cooled to 0° C., followed by addition of 30 mL of saturated sodium carbonate solution and 3.0 g (4.40 mmol) of compound 177 in dichloromethane, and stirred for 5 h. Upon completion of the reaction, the organic phase was separated, dried over anhydrous MgSO$_4$, filtered, concentrated, and purified on a silica gel column and eluted with ethyl acetate in chloroform (5-60%) to provide 1.83 g of compound 178. Yield: 62%.

$^1$H NMR (300 MHz, CDCl$_3$, ppm): δ 4.64 (m, 1H), 4.11-4.30 (m, 4H), 3.23 (t, J=7.0 Hz, 2H), 2.52 (t, J=7.0 Hz, 2H), 2.07-2.25 (m, 9H), 1.82 (m, 2H), 1.00-1.70 (m, 33H), 0.83 (m, 12H); ESI-MS (m/z): calcd for C$_{40}$H$_{67}$N$_2$O$_6$ [M+H]$^+$: 671.5; found: 671.6.

Sample 179: Preparation of Conjugate 179

In a 100 mL round bottom flask, 20 mL of anhydrous DMSO was added and heated to 60° C., and followed by addition of 2.0 g of dextran (average molecular weight ~100,000) and stirred until completely dissolved. After the solution was cooled down to room temperature, 450 mg (0.67 mmol) of compound 178 and 82 mg (0.67 mmol) of 4-dimethylaminopyridine (DMAP) were added and stirred for 24 hours. Upon completion of the reaction, the reaction mixture was precipitated in methanol, dialyzed against distilled water, and lyophilized to provide 1.87 g of conjugate 179. Yield: 93%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 2.00-2.30 (m, CH$_3$), 0.83 (m, CH$_3$).

Synthetic Scheme 39

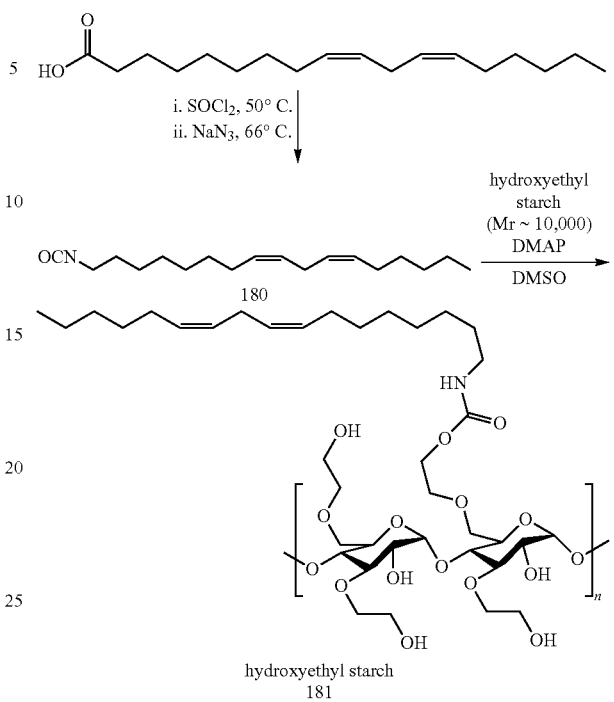

Sample 180: Preparation of Compound 180

In a 250 mL round bottom flask, 20.0 g (71.32 mmol) of linoleic acid was dissolved in 15.5 mL (213.96 mmol) of sulfonyl chloride, and heated to 50° C. for 5 hours After removal of then volatiles, 100 mL of anhydrous tetrahydrofuran and 23.2 g (356.6 mmol) of sodium azide were added, and the mixture was refluxed for 3 hours, filtered, and filtrate was subjected to fractional distillation to give 10.5 g of compound 180. Yield: 51%.

$^1$H NMR (300 MHz, CDCl$_3$, ppm): δ 5.33 (m, 4H), 3.21 (t, J=7.0 Hz, 2H), 2.75 (m, 2H), 2.03 (m, 4H), 1.25-1.70 (m, 16H), 0.85 (t, J=7.0 Hz, 3H); ESI-MS (m/z): calcd for C$_{18}$H$_{32}$NO [M+H]$^+$: 278.2; found: 278.2.

Sample 181: Preparation of Conjugate 181

In a 100 mL round bottom flask, 20 mL of anhydrous DMSO was added and heated to 60° C., and followed by addition of 3.0 g of hydroxyethyl starch (average molecular weight ~10,000) and stirred until completely dissolved. After the solution was cooled down to room temperature, 500 mg (1.81 mmol) of compound 180 and 122 mg (1.81 mmol) of 4-dimethylaminopyridine (DMAP) were added and stirred for 24 hours. Upon completion of the reaction, the reaction mixture was precipitated in methanol, dialyzed against distilled water, and lyophilized to provide 2.21 g of conjugate 181. Yield: 73%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 5.31 (m, CH), 1.25-2.20 (m, CH$_2$), 0.81 (t, CH$_3$).

Synthetic Scheme 40

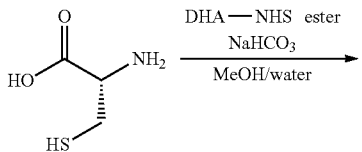

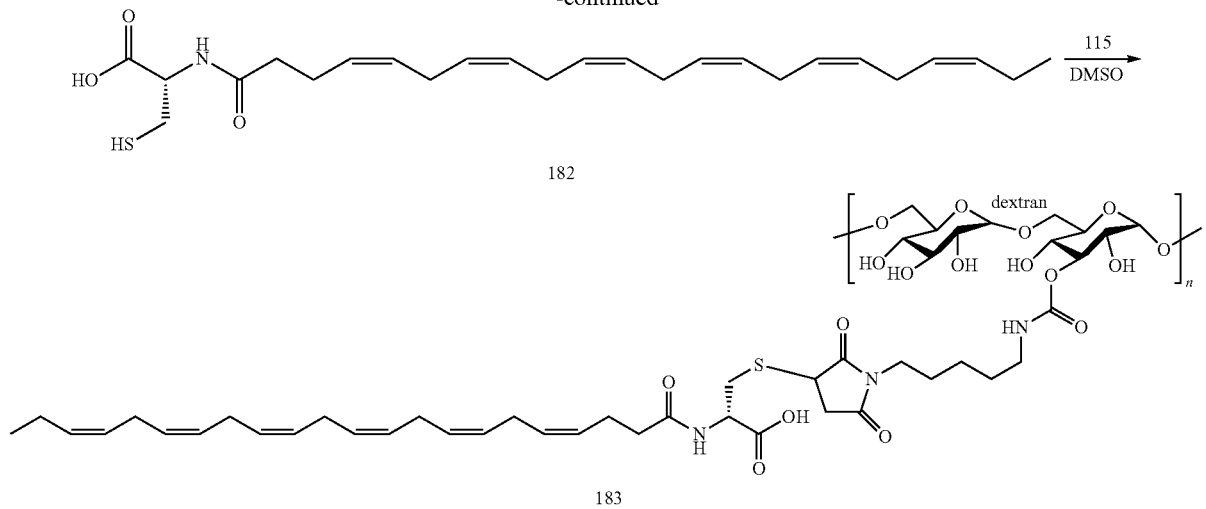

Sample 182: Preparation of Compound 182

In a 250 mL round bottom flask, 1.6 g (13.21 mmol) of cysteine and 2.22 g (26.42 mmol) of NaHCO$_3$ were dissolved in 100.0 mL of methanol-water (2:1), followed by slow addition of 5.06 g (11.89 mmol) of docosahexaenoic acid N-hydroxysuccinimide ester in dry THF, and stirred overnight. Upon completion of the reaction, the reaction mixture was acidified with 2.0N HCl to pH=1.0 and extracted with ethyl acetate three times (100 mL×3); the organic phases were pooled, dried over MgSO$_4$, concentrated, and purified on a silica gel column and eluted with methanol in chloroform (0-12%) to give 2.87 g of compound 182. Yield: 56%.

$^1$H NMR (300 MHz, DMSO-d$_6$, ppm): δ 8.02 (d, J=6.0 Hz, 1H), 5.39 (m, 12H), 4.43 (m, 1H), 2.60-2.80 (m, 14H), 2.32-2.52 (m, 4H), 2.15 (t, J=7.0 Hz, 2H), 0.91 (t, J=7.0 Hz, 3H); ESI-MS (m/z): calcd for C$_{25}$H$_{38}$NO$_3$S [M+H]$^+$: 432.3; found: 432.5.

Sample 183: Preparation of Conjugate 183

In a 100 mL round bottom flask, 2.0 g of functionalized dextran 115 was dissolved in 20.0 mL of anhydrous DMSO, followed by addition of 380 mg (0.89 mmol) of compound 182 in methanol, and stirred for 24 hours. The reaction mixture was precipitated in methanol, dialyzed against distilled water, and lyophilized to provide 1.83 g of conjugate 183. Yield: 91%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 5.35 (m, CH), 1.01 (t, CH$_3$).

Synthetic Scheme 41

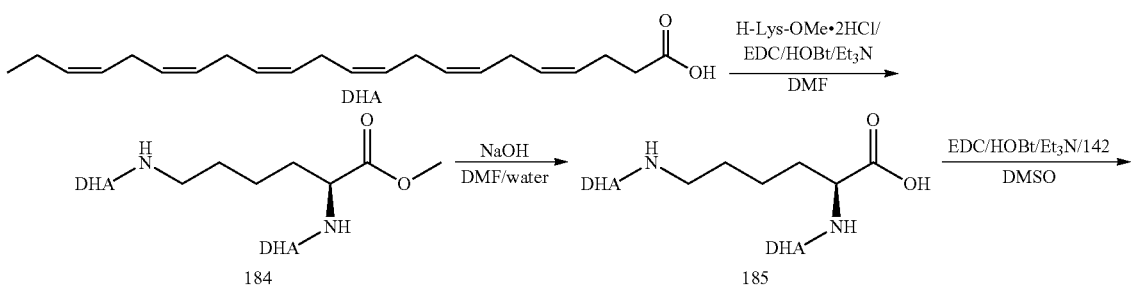

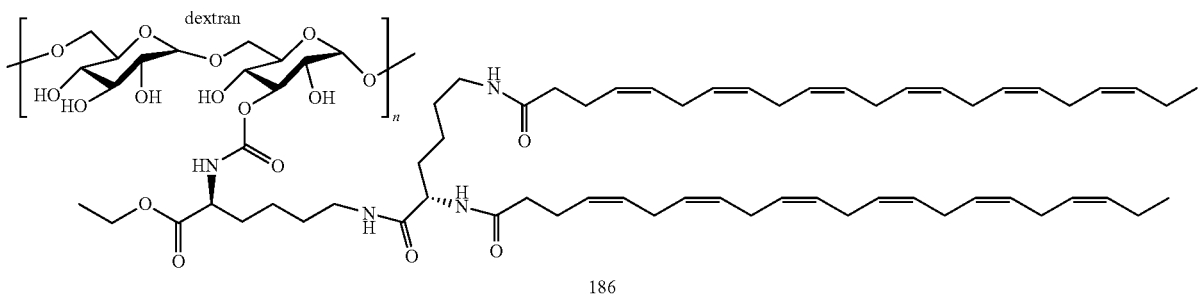

Sample 184: Preparation of Compound 184

To a 250 mL round-bottom flask charged with 2.0 g (6.09 mmol) of docosahexaenoic (DHA), 1.39 g (7.31 mmol) of 1-ethyl-3-(3-dimethylaminopropyl) carbodiimide (EDC), and 987 mg (7.31 mmol) of 1-hydroxybenzotriazole (HOBt), 30.0 mL of dry DMF were added and stirred for 30 min, followed by addition of 706 mg (3.03 mmol) of L-tyrosine methyl ester hydrochloride, and 1.78 mL (12.18 mmol) of triethylamine, and stirred at room temperature for another 5 h. Upon completion of the reaction, the reaction mixture was partitioned between ethyl acetate (100 mL) and brine (100 mL), and the organic phase was further washed with brine twice (100 mL×2), dried over anhydrous MgSO$_4$, filtered, concentrated, and purified on a silica gel column and eluted with ethyl acetate in petroleum ether (20-80%) to provide 1.73 g of compound 184. Yield: 73%.

$^1$H NMR (300 MHz, CDCl$_3$, ppm): δ 5.35-5.45 (m, 24H), 4.42 (m, 1H), 3.65 (s, 3H), 3.21 (t, J=7.2 Hz, 2H), 2.50-3.00 (m, 20H), 2.10-2.40 (m, 8H), 2.01 (m, 4H), 1.75 (m, 2H), 1.47 (m, 2H), 1.32 (m, 2H), 0.92 (t, J=7.0 Hz, 6H); ESI-MS (m/z): calcd for C$_{51}$H$_{77}$N$_2$O$_4$ [M+H]$^+$: 781.6; found: 781.7.

Sample 185: Preparation of Compound 185

In a 100 mL round bottom flask, 1.5 g (1.92 mmol) of compound 180 and 307 mg (7.69 mmol) of sodium hydroxide were dissolved in 30 mL of dimethylformamide-water (7:3), and stirred at room temperature 2 day. After the completion of the reaction, the mixture was acidified with 2.0 N HCl, and extracted with ethyl acetate three times (100 mL×3), the organic phases were pooled, dried over MgSO$_4$, concentrated, and purified on a silica gel column and eluted with methanol in chloroform (0-10%) to give 1.13 g of compound 185. Yield: 77%.

$^1$H NMR (300 MHz, CDCl$_3$, ppm): δ 5.35-5.45 (m, 24H), 4.51 (m, 1H), 3.25 (t, J=7.2 Hz, 2H), 2.50-3.00 (m, 20H), 2.10-2.40 (m, 8H), 2.01 (m, 4H), 1.77 (m, 2H6), 1.49 (m, 2H), 1.32 (m, 2H), 0.94 (t, J=7.0 Hz, 6H); ESI-MS (m/z): calcd for C$_{50}$H$_{75}$N$_2$O$_4$ [M+H]$^+$: 767.6; found: 767.9.

Sample 186: Preparation of Conjugate 186

In a 100 mL round-bottom flask, 3.0 g of functionalized dextran 142 was dissolved in 20.0 mL of anhydrous DMSO, and followed by addition of 131 mg (0.68 mmol) of 1-ethyl-3-(3-dimethylaminopropyl) carbodiimide (EDC), 92 mg (0.68 mmol) of 1-hydroxybenzotriazole (HOBt), and 200 uL (1.36 mmol) of triethylamine were added and stirred for 48 hours. Upon completion of the reaction, the reaction mixture was precipitated in methanol, dialyzed against distilled water, and lyophilized to provide 2 31 g of conjugate 186. Yield: 77%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.20-8.50 (m, CONH), 5.32 (m, CH), 1.01 (m, CH$_3$).

Synthetic Scheme 42

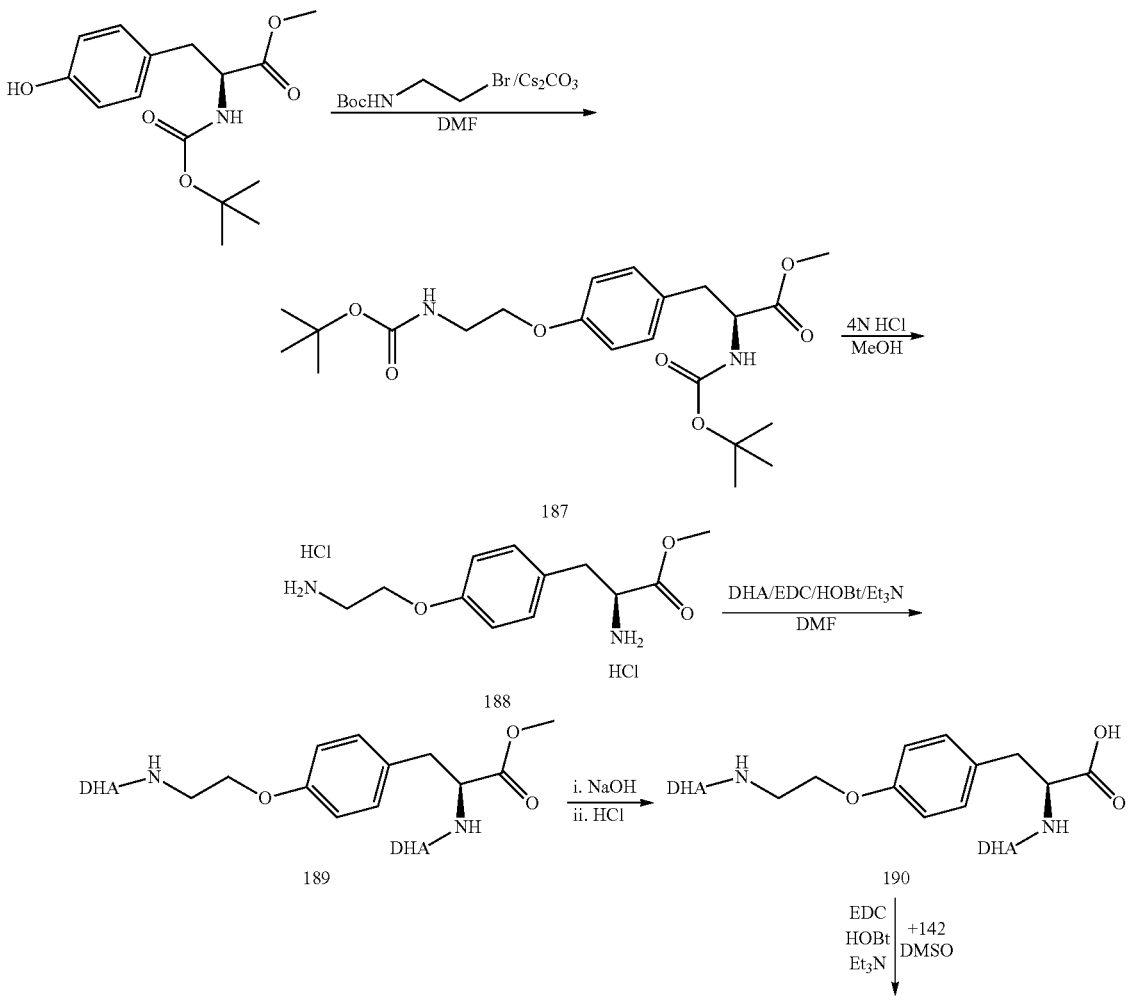

-continued

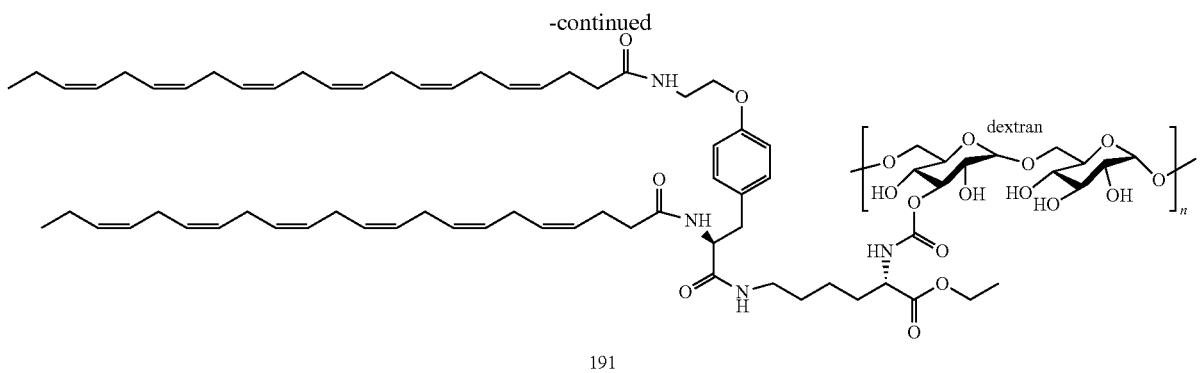

191

DHA = 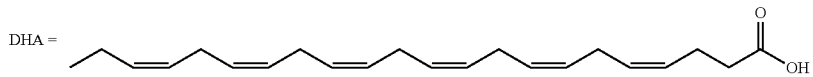

Sample 187: Preparation of Compound 187

In a 250 mL round bottom flask, 4.55 g (20.32 mmol) of Boc-2-bromoethylamine and 5.0 g (16.93 mmol) of Boc-L-tyrosine methyl ester were dissolved in 15.0 mL of anhydrous dimethylformamide, and followed by addition of 11.0 g (9.9 mmol) of cesium carbonate, and heated at 50° C. and stirred overnight. Upon completion of the reaction, the reaction mixture was partitioned between ethyl acetate (200 mL) and brine (200 mL). The organic phase was further washed with brine twice (100 mL×2), dried over anhydrous MgSO$_4$, filtered, concentrated, and purified on a silica gel column and eluted with ethyl acetate in petroleum ether (20-80%) to give 4.82 g of compound 187. Yield: 65%.

$^1$H NMR (300 MHz, CDCl$_3$, ppm): δ 7.03 (d, J=7.8 Hz, 2H), 6.81 (d, J=7.8 Hz, 2H), 5.01 (d, J=6.0 Hz, 1H), 4.51 (m, 1H), 3.95 (t, J=7.2 Hz, 2H), 3.70 (s, 3H), 3.52 (m, 2H), 3.08 (m, 2H), 1.44 (s, 9H), 1.42 (s, 9H); ESI-MS (m/z): calcd for C$_{22}$H$_{35}$N$_2$O$_7$ [M+H]$^+$: 439.2; found: 439.1.

Sample 188: Preparation of Compound 188

To a 250 mL round-bottom flask charged with 4.5 g (10.27 mmol) of compound 187, 50 mL of hydrochloride ethanol solution (4.0 N) was added and stirred at room temperature overnight. After removal of volatiles, the residue was purified on a reverse phase C-18 column and eluted with acetonitrile in water (5-50%) to provide 3.01 g of compound 188. Yield: 95%.

$^1$H NMR (300 MHz, D$_2$O, ppm): δ 7.28 (d, J=7.8 Hz, 2H), 7.06 (d, J=7.8 Hz, 2H), 4.42 (m, 1H), 4.31 (t, J=7.2 Hz, 2H), 3.85 (s, 3H), 3.43 (m, 2H), 3.28 (m, 2H); ESI-MS (m/z): calcd for C$_{12}$H$_{19}$N$_2$O$_3$ [M+H]$^+$: 239.1; found: 239.1.

Sample 189: Preparation of Compound 189

To a 250 mL round-bottom flask charged with 2.0 g (6.09 mmol) of docosahexaenoic (DHA), 1.39 g (7.31 mmol) of 1-ethyl-3-(3-dimethylaminopropyl) carbodiimide (EDC), and 987 mg (7.31 mmol) of 1-hydroxybenzotriazole (HOBt), 30.0 mL of dry DMF was added and stirred for 30 min, and followed by addition of 942 mg (3.03 mmol) of compound 188 and 1.78 mL (12.18 mmol) of triethylamine and stirred at room temperature for another 6 hours. Upon completion of the reaction, the reaction mixture was partitioned between ethyl acetate (100 mL) and brine (100 mL), the organic phase was further washed with brine twice (100 mL×2), dried over anhydrous MgSO$_4$, filtered, concentrated, and purified on a silica gel column and eluted with ethyl acetate in petroleum ether (10-70%) to provide 1.69 g of compound 189. Yield: 65%.

$^1$H NMR (300 MHz, CDCl$_3$, ppm): δ 7.00 (d, J=7.8 Hz, 2H), 6.80 (d, J=7.8 Hz, 2H), 5.92 (m, 2H), 5.35-5.45 (m, 24H), 4.82 (m, 1H), 3.99 (t, J=7.2 Hz, 2H), 3.71 (s, 3H), 3.64 (m, 2H), 3.10 (m, 2H), 2.70-2.90 (m, 20H), 2.41 (m, 4H), 2.23 (m, 4H), 2.06 (m, 4H), 0.96 (t, J=7.2 Hz, 6H); ESI-MS (m/z): calcd for C$_{56}$H$_{79}$N$_2$O$_5$ [M+H]$^+$: 859.6; found: 859.8.

Sample 190: Preparation of Compound 190

In a 100 mL round bottom flask, 1.6 g (1.86 mmol) of compound 189 and 298 mg (7.56 mmol) of sodium hydroxide were dissolved in 30 mL of dimethylformamide-water (7:3), and stirred at room temperature 2 day. After the completion of the reaction, the mixture was acidified with 2.0 N HCl, and extracted with ethyl acetate three times (100 mL×3); the organic phases were pooled, dried over MgSO$_4$, concentrated, and purified on a silica gel column and eluted with methanol in chloroform (0-10%) to give 1.27 g of compound 190. Yield: 81%.

$^1$H NMR (300 MHz, CDCl$_3$, ppm): δ 7.07 (d, J=7.8 Hz, 2H), 6.78 (d, J=7.8 Hz, 2H), 6.15 (m, 2H), 5.30-5.45 (m, 24H), 4.82 (m, 1H), 3.97 (t, J=7.2 Hz, 2H), 3.63 (m, 2H), 3.13 (m, 2H), 2.70-2.90 (m, 20H), 2.39 (m, 4H), 2.25 (m, 4H), 2.02 (m, 4H), 0.95 (t, J=7.2 Hz, 6H); ESI-MS (m/z): calcd for C$_{55}$H$_{77}$N$_2$O$_5$ [M+H]$^+$: 845.6; found: 845.7.

Sample 191: Preparation of Conjugate 191

In a 100 mL round-bottom flask, 3.6 g of functionalized dextran 142 was dissolved in 20.0 mL of anhydrous DMSO, and followed by addition of 450 mg (0.53 mmol) of compound 190, 153 mg (0.79 mmol) of 1-ethyl-3-(3-dimethylaminopropyl) carbodiimide (EDC), 106 mg (0.79 mmol) of 1-hydroxybenzotriazole (HOBt), and 200 uL (1.36 mmol) of triethylamine and stirred for 48 hours. Upon completion of the reaction, the reaction mixture was precipitated in methanol, dialyzed against distilled water, and lyophilized to provide 2.98 g of conjugate 191. Yield: 82%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.25-8.50 (m, CONH), 6.75-7.20 (m, ArH), 5.32 (m, CH), 0.99 (m, CH$_3$).

Synthetic Scheme 43

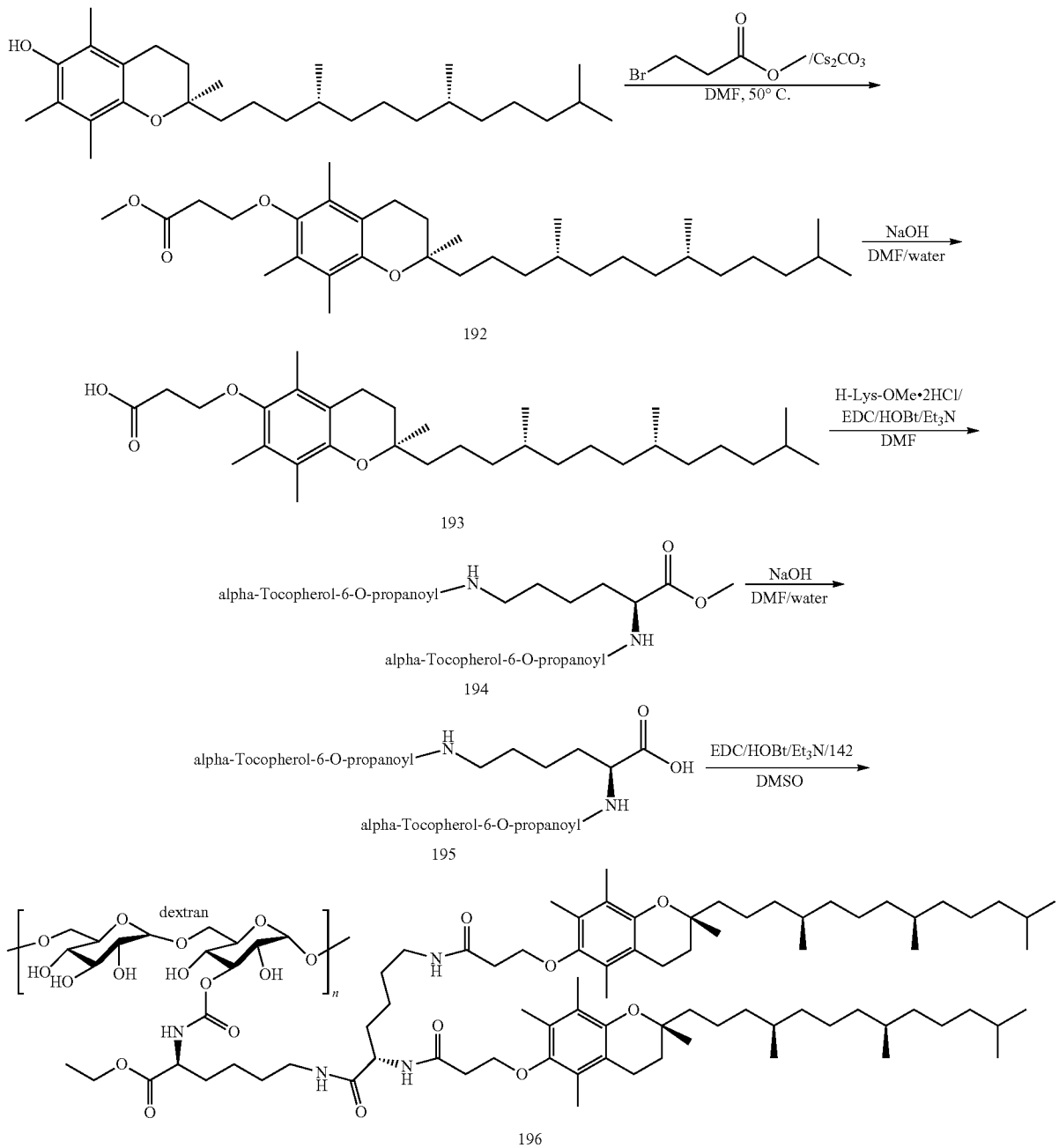

Sample 192: Preparation of Compound 192

In a 500 mL round bottom flask, 9.30 g (55.71 mmol) of methyl 3-bromopropionate and 20.0 g (46.43 mmol) of alpha-tocopherol were dissolved in 50.0 mL of anhydrous dimethylformamide, and followed by addition of 30.3 g (92.86 mmol) of cesium carbonate, heated at 50° C. and stirred for 12 hours. Upon completion of the reaction, the reaction mixture was partitioned between ethyl acetate (200 mL) and brine (200 mL). The organic phase was further washed with brine twice (100 mL×2), dried over anhydrous MgSO$_4$, filtered, concentrated, and purified on a silica gel column and eluted with ethyl acetate in petroleum ether (20-80%) to give 14.6 g of compound 192. Yield: 61%.

$^1$H NMR (300 MHz, CDCl$_3$, ppm): δ 3.95 (t, J=7.0 Hz, 2H), 3.68 (s, 3H), 2.79 (t, J=7.0 Hz, 2H), 2.59 (t, J=7.0 Hz, 2H), 2.07-2.25 (m, 9H), 1.82 (m, 2H), 1.00-1.70 (m, 24H), 0.85 (m, 12H); ESI-MS: calcd for C$_{33}$H$_{57}$O$_4$ [M+H]$^+$: 517.4; found: 517.6.

Sample 193: Preparation of Compound 193

In a 250 mL round bottom flask, 12.0 g (23.23 mmol) of compound 192 and 3 72 g (92.95 mmol) of sodium hydroxide were dissolved in 80 mL of dimethylformamide-water (7:3), and stirred at room temperature 2 day. After the completion of the reaction, the mixture was acidified with 2.0 N HCl to pH=1.0 and extracted with ethyl acetate three times (100 mL×3); the organic phases were pooled, dried over MgSO$_4$, concentrated, and purified on a silica gel column and eluted with ethyl acetate in petroleum ether (0-50%) to give 10.1 g of compound 193. Yield: 86%.

$^1$H NMR (300 MHz, CDCl$_3$, ppm): δ 3.98 (t, J=7.0 Hz, 2H), 2.83 (t, J=7.0 Hz, 2H), 2.59 (t, J=7.0 Hz, 2H), 2.07-2.25 (m, 9H), 1.82 (m, 2H), 1.00-1.70 (m, 24H), 0.85 (m, 12H); ESI-MS: calcd for C32H5504 [M+H]$^+$: 503.4; found: 503.3.

Sample 194: Preparation of Compound 194

To a 250 mL round-bottom flask charged with 9.5 g (18.91 mmol) of compound 193, 5.42 g (28.36 mmol) of 1-ethyl-3-(3-dimethylaminopropyl) carbodiimide (EDC), and 3.83 g (28.36 mmol) of 1-hydroxybenzotriazole (HOBt), 50.0 mL of dry DMF was added and stirred for 30 min, followed by addition of 4.41 g (18.91 mmol) of L-lysine methyl ester hydrochloride and 5.2 mL (37.82 mmol) of triethylamine and stirred at room temperature for another 6 hours. Upon completion of the reaction, the reaction mixture was partitioned between ethyl acetate (200 mL) and brine (200 mL), the organic phase was further washed with brine twice (100 mL×2), dried over anhydrous MgSO$_4$, filtered, concentrated, and purified on a silica gel column and eluted with ethyl acetate in petroleum ether (10-70%) to provide 12.6 g of compound 194. Yield: 59%.

$^1$H NMR (300 MHz, CDCl$_3$, ppm): δ 4.77 (m, 1H), 3.70-4.10 (m, 7H), 3.41 (t, J=7.0 Hz, 2H), 2.70-2.90 (m, 4H), 2.55 (m, 4H), 2.07-2.25 (m, 18H), 1.00-1.83 (m, 56H), 0.85 (m, 24H); ESI-MS: calcd for C71H121N208 [M+H]$^+$: 1129.9; found: 1130.1.

Sample 195: Preparation of Compound 195

In a 250 mL round bottom flask, 11.0 g (9.74 mmol) of compound 194 and 1.56 g (38.98 mmol) of sodium hydroxide were dissolved in 100 mL of dimethylformamide-water (7:3), and stirred at room temperature 2 day. After the completion of the reaction, the mixture was acidified with 2.0 N HCl to pH=1.0 and extracted with ethyl acetate three times (150 mL×3); the organic phases were pooled, dried over MgSO$_4$, concentrated, and purified on a silica gel column and eluted with methanol in chloroform (0-10%) to give 8.79 g of compound 195. Yield: 81%.

$^1$H NMR (300 MHz, CDCl$_3$, ppm): δ 4.73 (m, 1H), 3.70-4.10 (m, 4H), 3.42 (t, J=7.0 Hz, 2H), 2.70-2.90 (m, 4H), 2.55 (m, 4H), 2.07-2.25 (m, 18H), 1.00-1.83 (m, 56H), 0.85 (m, 24H); ESI-MS: calcd for C$_{70}$H$_{119}$N$_2$O$_8$ [M+H]$^+$: 1115.9; found: 1115.8.

Sample 196: Preparation of Conjugate

In a 100 mL round-bottom flask, 3.0 g of functionalized dextran 142 was dissolved in 20.0 mL of anhydrous DMSO, and followed by addition of 500 mg (0.53 mmol) of compound 195, 129 mg (0.68 mmol) of 1-ethyl-3-(3-dimethylaminopropyl) carbodiimide (EDC), 92 mg (0.68 mmol) of 1-hydroxybenzotriazole (HOBt), and 139 uL (1.00 mmol) of triethylamine were added and stirred for 48 hours. Upon completion of the reaction, the reaction mixture was precipitated in methanol, dialyzed against distilled water, and lyophilized to provide 2.16 g of conjugate 196. Yield: 72%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.25-8.50 (m, CONH), 2.00 (m, CH$_3$), 0.82 (m, CH$_3$).

Synthetic Scheme 44

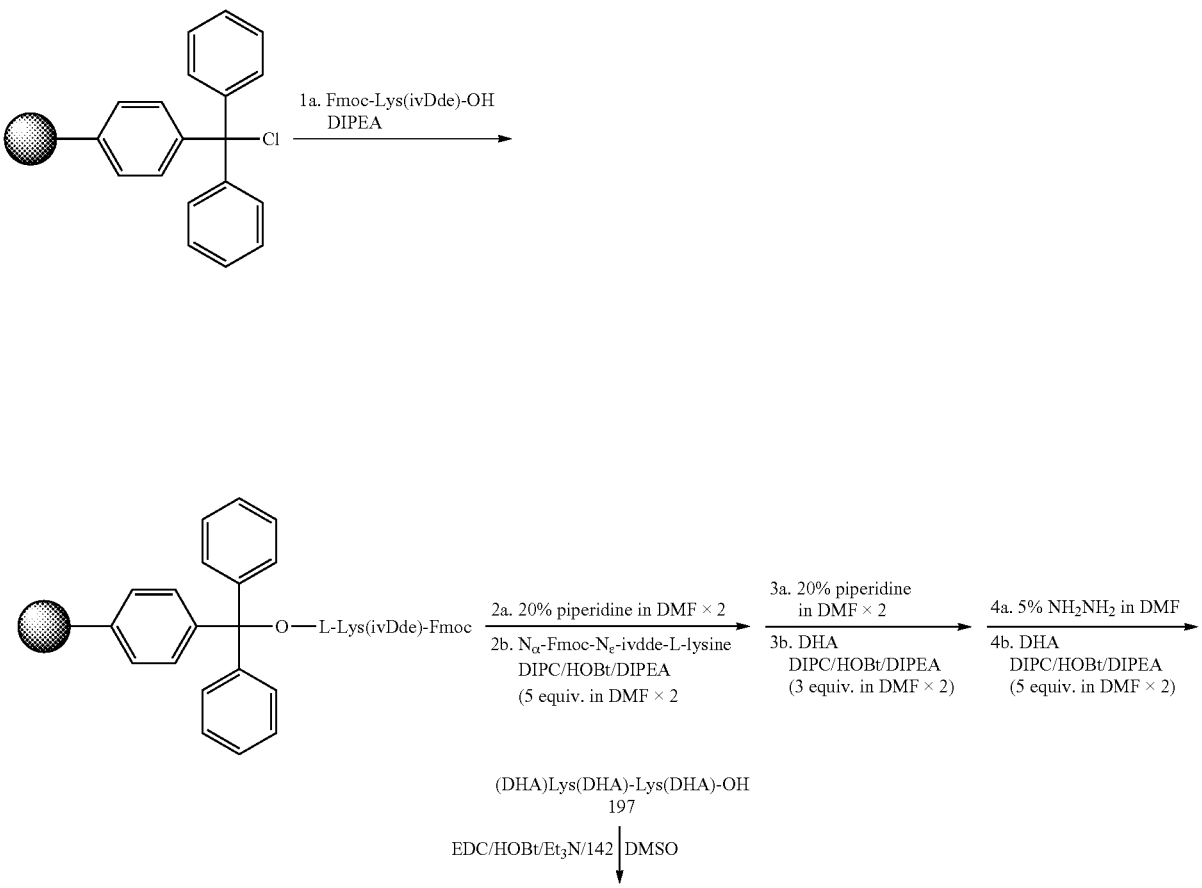

-continued

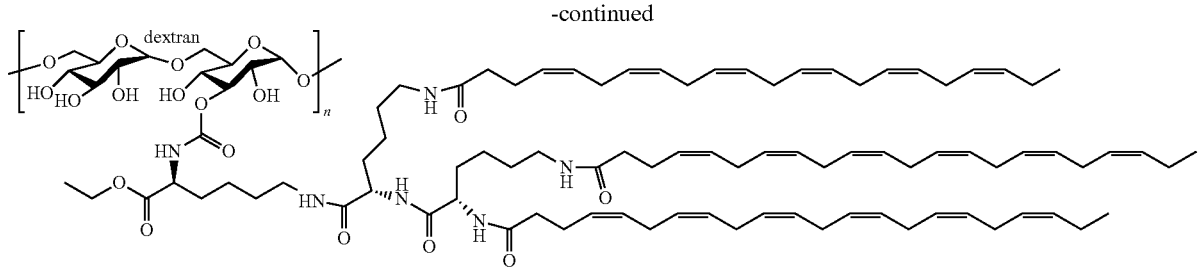

Sample 197: Preparation of Compound 197

Fmoc-L-Lys (ivDde)-OH was bonded to 3.0 g of trityl chloride resin (substitution: 0.61 mmol/g) and loaded onto a peptide synthesizer using standard protocols for Fmoc solid-phase peptide synthesis: Fmoc protecting group was deprotected with 20% piperidine in DMF, and ivdde protecting group deprocted with 5% hydrazine in DMF; 5 equivalents of protected amino acid or docosahexaenoic acid (DHA), 5 equivalents of coupling agent: DIPC and hydroxybenzotriazole (HOBt) and 5 equivalent diisopropylethylamine (DIPEA) were used in coupling steps. After completion of the synthesis, the peptide derivative was cleaved from the resin using the cocktail: a dichloromethane/trifluoroethanol/acetic acid (8:1:1) and purified through a silica gel column and eluted with methanol in chloroform to give 1.21 g of compound 197. Yield: 55%.

$^1$H NMR (300 MHz, CDCl$_3$, ppm): δ 5.35-5.50 (m, 24H), 4.51 (m, 2H), 3.23 (m, 4H), 2.70-2.85 (m, 20H), 2.25-2.50 (m, 8H), 2.17 (m, 4H), 1.75 (m, 4H), 1.56 (m, 4H), 1.31 (m, 4H), 0.96 (t, J=7.2 Hz, 9H); ESI-MS: calcd for C$_{78}$H$_{118}$N$_4$O$_6$ [M+2H]$^+$+: 1206.9; found: 1207.3.

Sample 198: Preparation of Conjugate 198

In a 100 mL round-bottom flask, 2.0 g of functionalized dextran 142 was dissolved in 30.0 mL of anhydrous DMSO, and followed by addition of 200 mg (0.17 mmol) of compound 197, 48 mg (0.25 mmol) of 1-ethyl-3-(3-dimethylaminopropyl) carbodiimide (EDC), 33 mg (0.25 mmol) of 1-hydroxybenzotriazole (HOBt), and 69 uL (0.5 mmol) of triethylamine were added and stirred for 48 hours. Upon completion of the reaction, the reaction mixture was precipitated in methanol, dialyzed against distilled water, and lyophilized to provide 1.73 g of conjugate 198. Yield: 87%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.25-8.50 (m, CONH), 5.33 (m, CH), 1.02 (m, CH$_3$).

Part 4. Preparation of Functionalized Lipid-Polysaccharide Conjugates

Synthetic Scheme 45

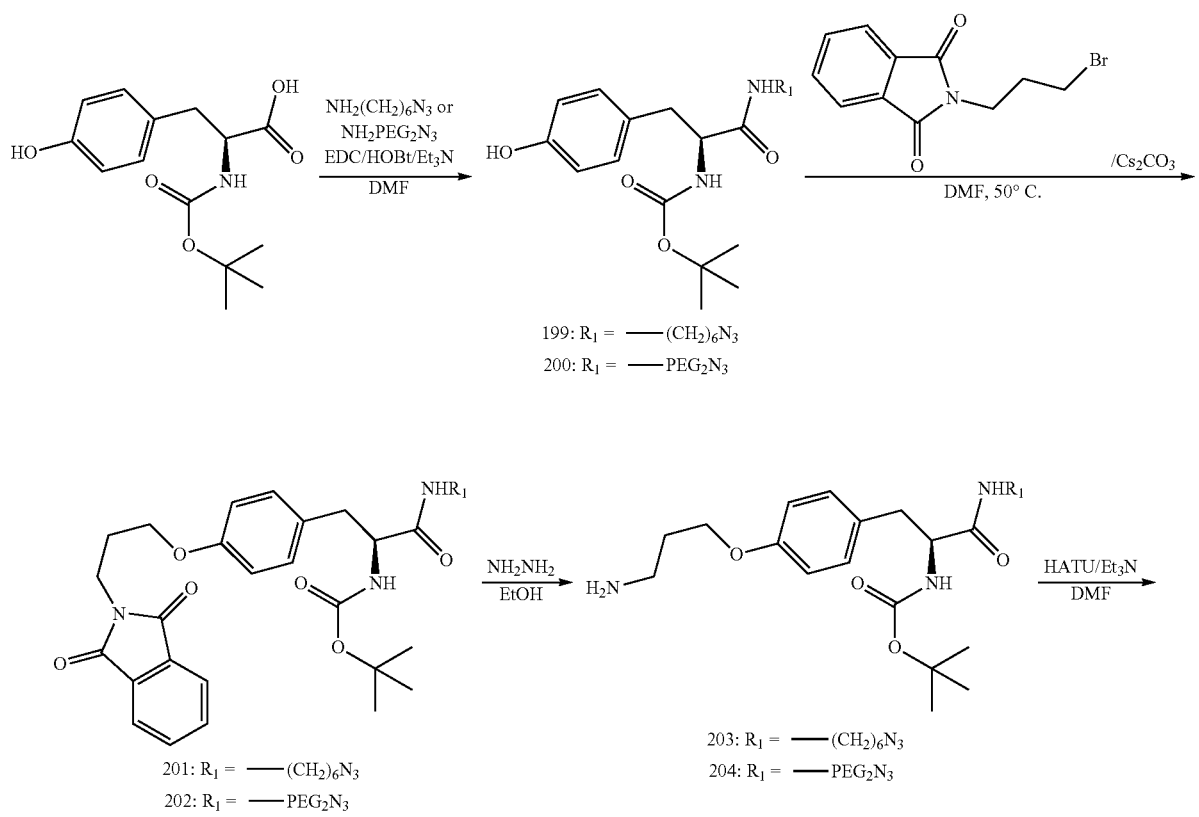

-continued

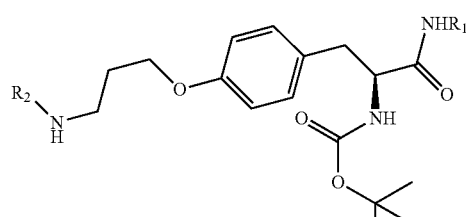
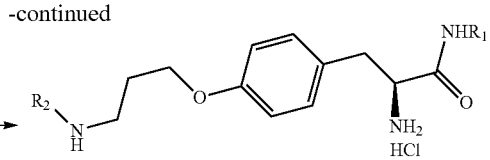

205: $R_1 =$ ——$(CH_2)_6N_3$, $R_2 =$ DHA
206: $R_1 =$ ——$PEG_2N_3$, $R_2 =$ DHA

207: $R_1 =$ ——$(CH_2)_6N_3$, $R_2 =$ DHA
208: $R_1 =$ ——$PEG_2N_3$, $R_2 =$ DHA

130
EDC/HOBt/Et$_3$N | DMSO

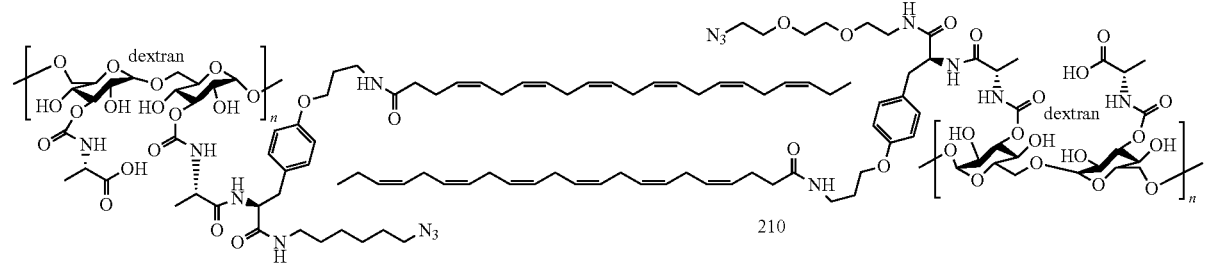

209

210

Sample 199: Preparation of Compound 199

To a 250 mL round-bottom flask charged with 10.0 g (35.55 mmol) of Boc-L-tyrosine methyl ester, 8.15 g (42.66 mmol) of 1-ethyl-3-(3-dimethylaminopropyl) carbodiimide (EDC), and 5.76 g (42.66 mmol) of 1-hydroxybenzotriazole (HOBt), 50.0 mL of dry DMF was added and stirred for 30 min, followed by addition of 6.37 mg (35.66 mmol) of 6-azido-hexanylamine hydrochloride and 9.8 mL (71.1 mmol) of triethylamine and stirred at room temperature overnight. Upon completion of the reaction, the reaction mixture was partitioned between ethyl acetate (200 mL) and brine (200 mL), the organic phase was further washed with brine twice (100 mL×2), dried over anhydrous MgSO$_4$, filtered, concentrated, and purified on a silica gel column and eluted with ethyl acetate in petroleum ether (10-70%) to provide 11.9 g of compound 199. Yield: 83%.

$^1$H NMR (300 MHz, CDCl$_3$, ppm): δ 6.99 (d, J=7.8 Hz, 2H), 6.67 (d, J=7.8 Hz, 2H), 4.15 (m, 1H), 3.25 (t, J=7.2 Hz, 2H), 3.19 (m, 2H), 3.09 (m, 1H), 2.97 (m, 1H), 1.59 (m, 2H), 1.35 (s, 9H), 1.33 (m, 4H), 1.17 (m, 2H); ESI-MS: calcd for C$_{20}$H$_{32}$N$_5$O$_4$ [M+H]$^+$: 406.2; found: 406.3.

Sample 200: Preparation of Compound 200

The preparation of compound 200 was similar to that of compound 199.

$^1$H NMR (300 MHz, Acetone-d$_6$, ppm): δ 7.05 (d, J=7.8 Hz, 2H), 6.72 (d, J=7.8 Hz, 2H), 4.25 (m, 1H), 3.25-3.70 (m, 10H), 2.95 (m, 1H), 2.87 (m, 1H), 1.33 (s, 9H); ESI-MS: calcd for C$_{20}$H$_{32}$N$_5$O$_6$ [M+H]$^+$: 438.2; found: 438.3.

Sample 201: Preparation of Compound 201

In a 250 mL round bottom flask, 10.0 g (20.32 mmol) of compound 199 and 7.93 g (29.58 mmol) 2-(3-bromopropyl) isoindoline-1,3-dione were dissolved in 60.0 ml of anhydrous dimethylformamide, followed by addition of 16.1 g (49.3 mmol) of cesium carbonate, and heated at 50° C. and stirred overnight. Upon completion of the reaction, the reaction mixture was partitioned between ethyl acetate (200 mL) and brine (200 mL). The organic phase was further washed with brine twice (100 mL×2), dried over anhydrous MgSO$_4$, filtered, concentrated, and purified on a silica gel column and eluted with ethyl acetate in petroleum ether (20-80%) to give 9.2 g of compound 201. Yield: 65%

$^1$H NMR (300 MHz, CDCl$_3$, ppm): δ 7.78 (d, J=7.8 Hz, 2H), 7.65 (d, J=7.8 Hz, 2H), 7.00 (d, J=7.8 Hz, 2H), 6.67 (d, J=7.8 Hz, 2H), 4.13 (m, 1H), 3.95 (t, J=7.2 Hz, 2H), 3.83 (t, J=7.2 Hz, 2H), 3.25 (t, J=7.2 Hz, 2H), 3.18 (m, 2H), 2.98 (m, 1H), 2.85 (m, 1H), 2.12 (m, 2H), 1.50 (m, 2H), 1.37 (s, 9H), 1.35 (m, 4H), 1.19 (m, 2H); ESI-MS: calcd for C$_{31}$H$_{41}$N$_6$O$_6$ [M+H]$^+$: 593.3; found: 593.3.

Sample 202: Preparation of Compound 202

The preparation of compound 202 is similar to that of compound 201.

$^1$H NMR (300 MHz, CDCl$_3$, ppm): δ 7.84 (m, 2H), 7.73 (m, 2H), 7.05 (d, J=7.8 Hz, 2H), 6.70 (d, J=7.8 Hz, 2H), 4.25 (m, 1H), 3.96 (t, J=7.2 Hz, 2H), 3.88 (t, J=7.2 Hz, 2H), 3.25-3.70 (m, 10H), 2.96 (m, 2H), 2.20 (m, 2H), 1.43 (s, 9H); ESI-MS: calcd for C$_{31}$H$_{41}$N$_6$O$_8$ [M+H]$^+$: 625.3; found: 625.3.

Sample 203: Preparation of Compound 203

In a 250 mL round bottom flask, 9.0 g (15.17 mmol) of compound 201 was dissolved in 100 mL of ethanol, followed by addition of 1.0 mL of anhydrous hydrazine. Upon completion of the reaction, the white precipitate was filtered off, and the filtrate was concentrated and purified on a reversed phase C-18 column and eluted with acetonitrile in water (10-70%) to provide 5.68 g of compound 203. Yield: 81%.

$^1$H NMR (300 MHz, CDCl$_3$, ppm): δ 7.01 (d, J=7.8 Hz, 2H), 6.72 (d, J=7.8 Hz, 2H), 4.15 (m, 1H), 3.96 (t, J=7.2 Hz, 2H), 3.26 (t, J=7.2 Hz, 2H), 3.18 (m, 2H), 2.97 (m, 1H), 2.87 (m, 1H), 2.67 (m, 2H), 1.96 (m, 2H), 1.53 (m, 2H), 1.35 (m, 4H), 1.19 (m, 2H); ESI-MS: calcd for C$_{23}$H$_{39}$N$_6$O$_4$ [M+H]$^+$: 463.3; found: 463.5.

Sample 204: Preparation of Compound 204

The preparation of compound 204 was similar to that of 203.

¹H NMR (300 MHz, CD₃OD, ppm): δ 7.13 (d, J=7.8 Hz, 2H), 6.85 (d, J=7.8 Hz, 2H), 4.25 (m, 1H), 4.02 (t, J=7.2 Hz, 2H), 3.25-3.70 (m, 10H), 2.96 (m, 1H), 2.86 (d, J=7.8 Hz, 2H), 2.76 (m, 1H), 1.92 (m, 2H), 1.38 (s, 9H); ESI-MS: calcd for $C_{23}H_{39}N_6O_6$ [M+H]⁺: 495.3; found: 495.3.

Sample 205: Preparation of Compound 205

In a 250 mL round bottom flask, 3.56 g (10.82 mmol) of docosahexaenoic acid (DHA) and (12.98 mmol) of 2-(7-azobenzotriazole)-N,N,N',N'-tetramethyluronium hexafluorophosphate (HATU) were combined in 50.0 mL of anhydrous dimethylformamide, followed by addition of 5.0 g (10.82 mmol) of compound 203 and 1.8 mL triethylamine (12.98 mmol) and stirred overnight. Upon completion of the reaction, the reaction mixture was partitioned from ethyl acetate (100 mL) and brine (100 mL); the organic phase was further washed with brine twice (50 mL×2), and dried over anhydrous MgSO₄, filtered, concentrated, and purified on a silica gel column and eluted with ethyl acetate in petroleum ether (10-80%) to give 6.6 g of compound 205. Yield: 79%.

¹H NMR (300 MHz, CDCl₃, ppm): δ 7.05 (d, J=7.8 Hz, 2H), 6.75 (d, J=7.8 Hz, 2H), 5.35-5.50 (m, 12H), 4.15 (m, 1H), 3.95 (t, J=7.2 Hz, 2H), 3.37 (t, J=7.2 Hz, 2H), 3.21 (t, J=7.2 Hz, 2H), 3.18 (m, 2H), 2.95 (m, 2H), 2.89 (m, 10H), 2.35 (m, 2H), 2.17 (m, 2H), 2.12 (m, 2H), 1.98 (m, 2H), 1.51 (m, 2H), 1.37 (s, 9H), 1.34 (m, 4H), 1.18 (m, 2H), 0.95 (t, J=7.2 Hz, 3H); ESI-MS: calcd for $C_{45}H_{69}N_6O_5$ [M+H]⁺: 773.5; found: 773.7.

Sample 206: Preparation of Compound 206

The preparation of compound 206 was similar to that of compound 205.

¹H NMR (300 MHz, CDCl₃, ppm): δ 7.11 (d, J=7.8 Hz, 2H), 6.80 (d, J=7.8 Hz, 2H), 5.35-5.50 (m, 12H), 4.25 (m, 1H), 3.98 (t, J=7.2 Hz, 2H), 3.25-3.70 (m, 10H), 2.96 (m, 3H), 2.87 (m, 10H), 2.40 (m, 2H), 2.25 (d, J=7.2 Hz, 2H), 2.06 (m, 2H), 1.96 (m, 2H), 1.40 (s, 9H), 0.95 (t, J=7.2 Hz, 3H); ESI-MS: calcd for $C_{45}H_{69}N_6O_7$ [M+H]⁺: 805.5, found: 805.6.

Sample 207: Preparation of Compound 207

To a 250 mL round-bottom flask charged with 5.0 g (6.48 mmol) of compound 205, 50 mL of hydrochloride ethanol solution (4.0N) was added, and stirred at room temperature overnight. After removal of volatiles, the residue was purified on a reverse phase column and eluted with acetonitrile in water (10-80%) to provide 3.7 g of compound 207. Yield: 85%.

¹H NMR (300 MHz, CD₃OD, ppm): δ 7.07 (d, J=7.8 Hz, 2H), 6.82 (d, J=7.8 Hz, 2H), 5.28 (m, 12H), 3.89 (t, J=7.2 Hz, 2H), 3.81 (m, 1H), 3.21 (m, 4H), 2.97 (m, 2H), 2.76 (m, 10H), 2.30 (m, 2H), 2.12 (t, J=7.2 Hz, 2H), 1.98 (m, 2H), 1.86 (m, 2H), 1.45 (m, 2H), 1.25 (m, 4H), 1.16 (m, 2H), 0.88 (t, J=7.2 Hz, 2H); ESI-MS: calcd for $C_{40}H_{61}N_6O_3$ [M+H]⁺: 673.5; found: 673.5.

Sample 208: Preparation of Compound 208

The preparation of compound 208 is similar to that of compound 207.

¹H NMR (300 MHz, DMSO-d₆, ppm): δ 8.51 (s, 1H), 8.25 (m, 2H), 7.85 (s, 1H), 7.16 (d, J=7.8 Hz, 2H), 6.82 (d, J=7.8 Hz, 2H), 5.35-5.50 (m, 12H), 4.01 (m, 1H), 3.98 (t, J=7.2 Hz, 2H), 3.15-3.70 (m, 10H), 2.97 (m, 3H), 2.86 (m, 1H), 2.25 (m, 2H), 2.13 (m, 2H), 1.81 (m, 2H), 0.89 (t, J=7.2 Hz, 2H); ESI-MS: calcd for $C_{40}H_{61}N_6O_5$ [M+H]⁺: 705.5; found: 705.7.

Sample 209: Preparation of Conjugate 209

In a 100 mL round-bottom flask, 2.5 g of functionalized dextran 130 was dissolved in 30.0 mL of anhydrous DMSO, followed by addition of 300 mg (0.45 mmol) of compound 206, 129 mg (0.68 mmol) of 1-ethyl-3-(3-dimethylaminopropyl) carbodiimide (EDC), 92 mg (0.68 mmol) of 1-hydroxybenzotriazole (HOBt), and 139 uL (1.0 mmol) of triethylamine, and stirred at room temperature for 48 hours. Upon completion of the reaction, the reaction mixture was precipitated in methanol, dialyzed against distilled water, and lyophilized to provide 1.93 g of conjugate 209. Yield: 77%.

¹H NMR (selected characteristic signals, 500 MHz, DMSO-d₆, ppm): major signals: 4.50-5.00 (m, CHOH, CHOH, CH₂OH), 3.30-4.00 (m, CHOH, CH₂OH); minor signals: 6.75-7.20 (m, ArH), 5.32 (CH), 1.23 (d, CH₃), 1.01 (t, CH₃).

Sample 210: Preparation of Conjugate 210

In a 100 mL round-bottom flask, 3.0 g of functionalized dextran 130 was dissolved in 30.0 mL of anhydrous DMSO, followed by addition of 500 mg (0.71 mmol) of compound 207, 203 mg (1.06 mmol) of 1-ethyl-3-(3-dimethylaminopropyl) carbodiimide (EDC), 143 mg (1.06 mmol) of 1-hydroxybenzotriazole (HOBt), and 276 uL (2.0 mmol) of triethylamine, and stirred for 48 hours. Upon completion of the reaction, the reaction mixture was precipitated in methanol, dialyzed against distilled water, and lyophilized to provide 2.23 g of conjugate 210. Yield: 73%.

¹H NMR (selected characteristic signals, 500 MHz, DMSO-d₆, ppm): major signals: 4.50-5.00 (m, CHOH, CHOH, CH₂OH), 3.30-4.00 (m, CHOH, CH₂OH); minor signals: 6.75-7.20 (m, ArH), 5.33 (CH), 1.22 (d, CH₃), 0.99 (t, CH₃).

Synthetic Scheme 46

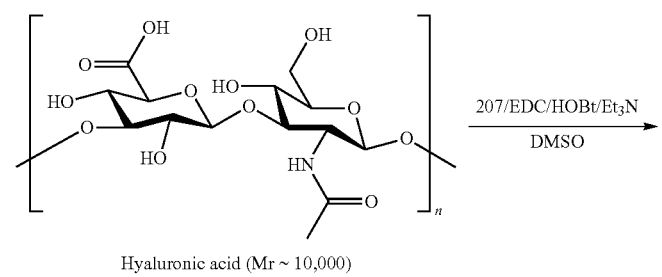

Hyaluronic acid (Mr ~ 10,000)

-continued

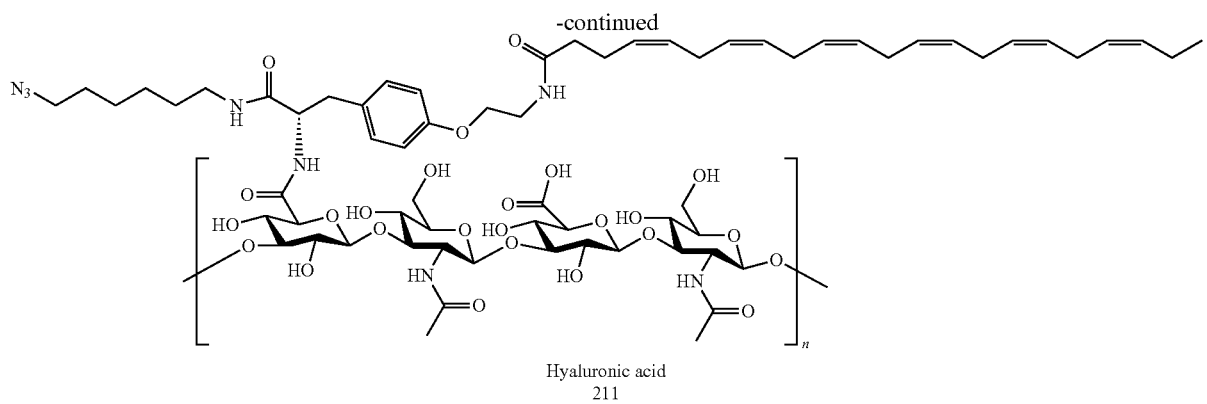

Hyaluronic acid
211

Sample 211: Preparation of Conjugate 211

In a 100 mL round-bottom flask, 500 mg of hyaluronic acid (average molecular weight ~ 10,000) was dissolved in 10.0 mL of anhydrous DMSO at 60° C. and cooled down to room temperature, followed by addition of 60 mg (0.09 mmol) of compound 207, 26 mg (0.14 mmol) of 1-ethyl-3-(3-dimethylaminopropyl) carbodiimide (EDC), 19 mg (0.14 mmol) of 1-hydroxybenzotriazole (HOBt), and 200 µL of triethylamine, and stirred for 48 hours. Upon completion of the reaction, the reaction mixture was precipitated in methanol, dialyzed against distilled water, and lyophilized to provide 353 mg of conjugate 211. Yield: 71%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.70 (m, CONH), 6.75-7.20 (m, ArH), 5.35 (m, CH), 2.06 (s, CH$_3$CO), 0.99 (t, CH$_3$).

Synthetic Scheme 47

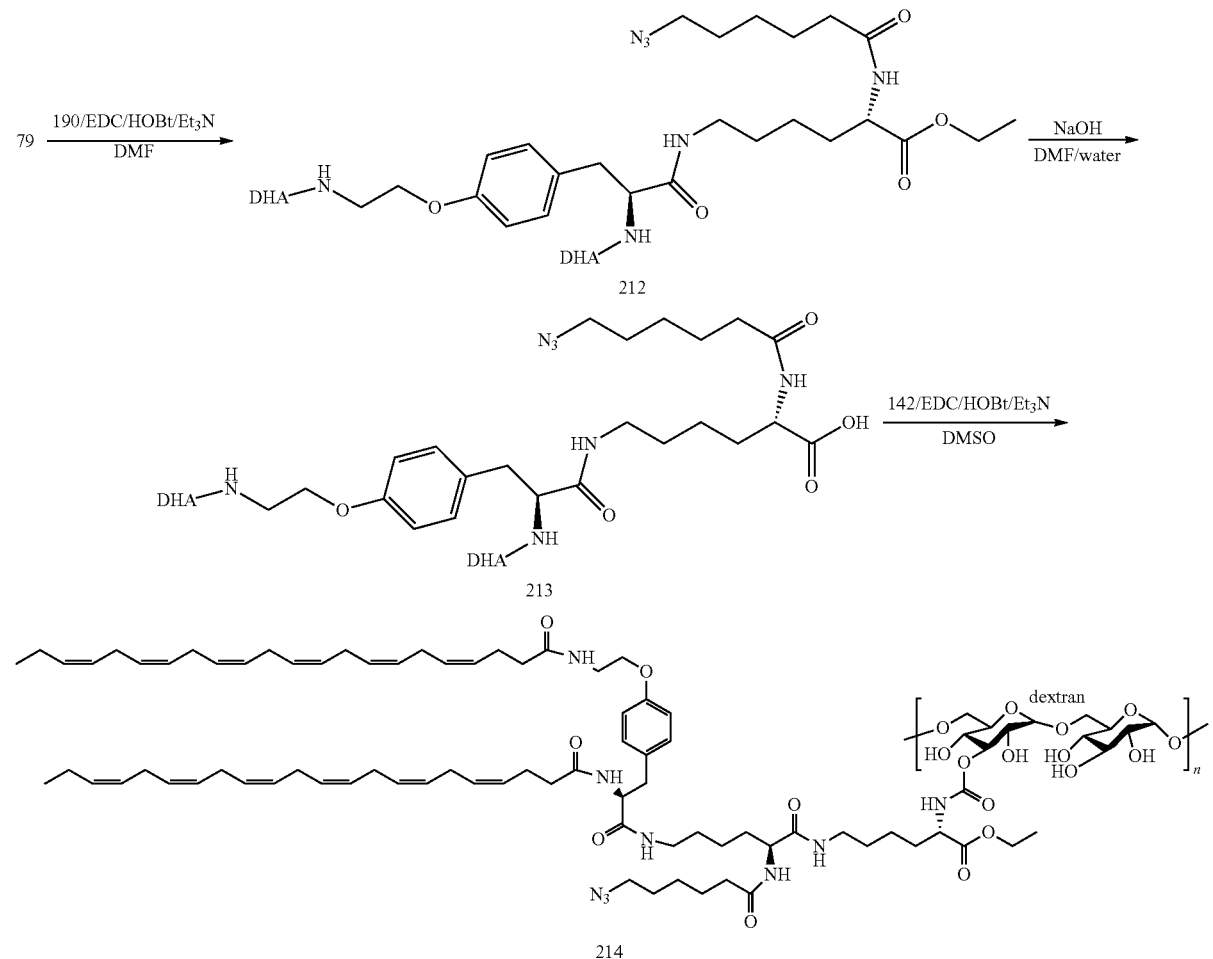

Sample 212: Preparation of Compound 212

To a 250 mL round bottom flask charged with 500 mg (0.59 mmol) of compound 190, 136 mg (0.71 mmol) of 1-ethyl-3-(3-dimethylaminopropyl) carbodiimide (EDC) and 96 mg (0.71 mmol) 1-hydroxybenzotriazole (HOBt), 6.0 mL of anhydrous dimethylformamide was added, flowed by 227 mg (0.65 mmol) of compound 79 and 235 uL (1.70 mmol) triethylamine and stirred for 12 hours Upon completion of the reaction, the reaction mixture was partitioned from ethyl acetate (60 mL) and brine (60 mL), and the organic phase was further washed with brine twice (30 mL×2), dried over $MgSO_4$, concentrated, and purified on a silica gel column and eluted with methanol in chloroform to give 572 mg of compound 212. Yield: 85%.

$^1$H NMR (300 MHz, $CDCl_3$, ppm): δ 7.01 (d, J=7.8 Hz, 2H), 6.75 (d, J=7.8 Hz, 2H), 5.30-5.50 (m, 24H), 4.83 (m, 1H), 4.45 (m, 1H), 4.21 (q, J=7.2 Hz, 2H), 3.95 (t, J=7.2 Hz, 2H), 3.65 (m, 2H), 3.10-3.30 (m, 4H), 2.70-2.90 (m, 20H), 2.39 (m, 4H), 2.25 (m, 6H), 2.02 (m, 4H), 1.82 (m, 2H), 1.50-1.75 (m, 4H), 1.46 (m, 2H), 1.26-1.43 (m, 4H), 1.25 (t, J=7.2 Hz, 3H), 0.95 (t, J=7.2 Hz, 6H); ESI-MS: calcd for $C_{69}H_{102}N_7O_7$ $[M+H]^+$: 1140.7; found: 1141.1.

Sample 213: Preparation of Compound 213

In a 50 mL round bottom flask, 500 mg (0.43 mmol) of compound 212 and 88 mg (2.20 mmol) of sodium hydroxide were dissolved in 10 mL of dimethylformamide-water (7.3), and stirred at room temperature for 2 days. Upon the completion of the reaction, the mixture was acidified with 2.0 N HCl to pH=1 0, and extracted with ethyl acetate three times (20 mL×3); the organic phases were pooled, dried over $MgSO_4$, concentrated, and purified on a silica gel column and eluted with methanol in chloroform (0-10%) to give 435 mg of compound 213. Yield: 91%.

$^1$H NMR (300 MHz, $CDCl_3$, ppm): δ 7.03 (d, J=7.8 Hz, 2H), 6.77 (d, J=7.8 Hz, 2H), 5.30-5.50 (m, 24H), 4.85 (m, 1H), 4.52 (m, 1H), 3.97 (t, J=7.2 Hz, 2H), 3.63 (m, 2H), 3.10-3.30 (m, 4H), 2.70-2.90 (m, 20H), 2.37 (m, 4H), 2.25 (m, 6H), 2.03 (m, 4H), 1.83 (m, 2H), 1.50-1.75 (m, 4H), 1.46 (m, 2H), 1.26-1.43 (m, 4H), 0.97 (t, J=7.2 Hz, 6H); ESI-MS: calcd for $C_{67}H_{98}N_7O_7$ $[M+H]^+$: 1112.7; found: 1112.9.

Sample 214: Preparation of Conjugate 214

In a 100 mL round-bottom flask, 2.0 g of functionalized dextran 142 was dissolved in 10.0 mL of anhydrous DMSO at 60° C. and cooled down to room temperature, followed by addition of 200 mg (0.18 mmol) of compound 213, 69 mg (0.36 mmol) of 1-ethyl-3-(3-dimethylaminopropyl) carbodiimide (EDC), 49 mg (0.36 mmol) of 1-hydroxybenzotriazole (HOBt), and 50 uL (0.36 mmol) of triethylamine and stirred for 48 hours. Upon completion of the reaction, the reaction mixture was precipitated in methanol, dialyzed against distilled water, and lyophilized to provide 1.51 g of conjugate 214. Yield: 76%.

$^1$H NMR (selected characteristic signals, 500 MHz, DMSO-$d_6$, ppm): major signals: 4.50-5.00 (m, CHOH, CHOH, $CH_2OH$), 3.30-4.00 (m, CHOH, $CH_2OH$); minor signals: 7.20-8.70 (m, CONH), 6.75-7.20 (m, ArH), 5.33 (m, CH), 1.02 (m, $CH_3$).

Synthetic Scheme 48

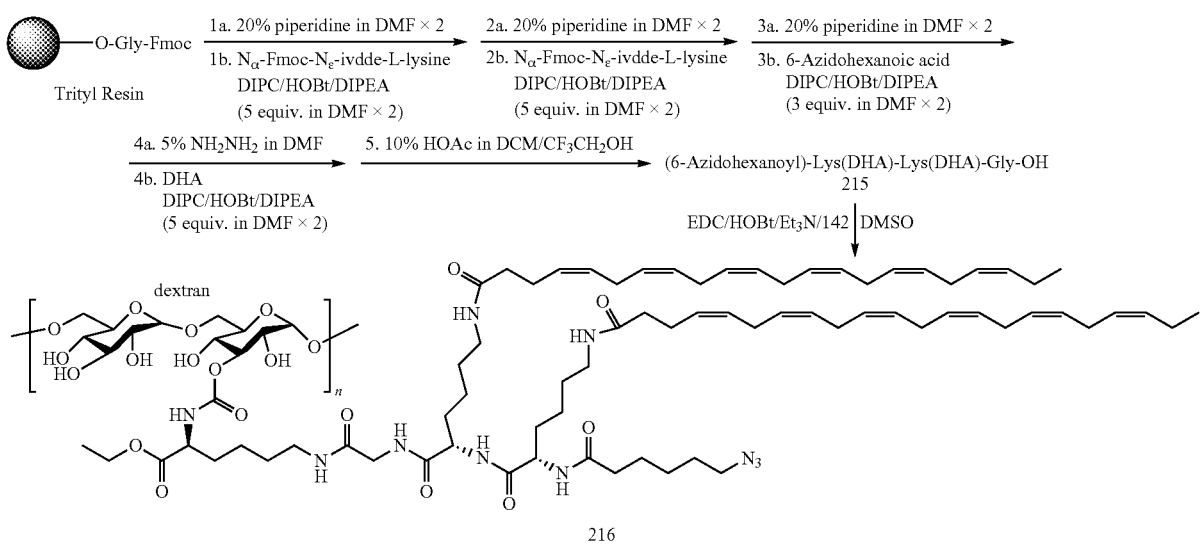

216

Sample 215: Preparation of Compound 215

Fmoc-Gly-OH was covalently attached to 10.0 g of trityl chloride resin (substitution. 0.39 mmol/g) and loaded on to a peptide synthesizer using standard protocols for Fmoc solid-phase peptide synthesis: Fmoc protecting group was deprotected with 20% piperidine in DMF, and ivdde proctecting group deprocted with 5% hydrazine in DMF; 5 equivalents of protected amino acid or 6-azidohexanioc acid, 5 equivalents of coupling agent: DIPC and hydroxybenzotriazole (HOBt) and 5 equivalent diisopropylethylamine (DIPEA), were used in coupling steps. After completion of the synthesis, the peptide derivative was cleaved from the resin using the cocktail: dichloromethane/trifluoroethanol/acetic acid (8:1:1), and purified on a reverse phase column and eluted with acetonitrile in water (10-80%) to give 1.32 g of compound 215. Yield: 31%.

$^1$H NMR (300 MHz, DMSO-$D_6$, ppm): δ 7.00-7.50 (m, 5H), 5.35-5.50 (m, 24H), 4.47 (m, 2H), 4.11 (m, 2H), 3.10-3.30 (m, 6H), 2.75 (m, 20H), 2.15-2.40 (m, 14H), 1.00-2.00 (m, 18H), 0.97 (t, J=7.2 Hz, 6H); ESI-MS: calcd for $C_{64}H_{99}N_8O_7$ $[M+H]^+$: 1091.7; found: 1091.9.

Sample 216: preparation of conjugate 216

In a 100 mL round-bottom flask, 2.0 g of functionalized dextran 142 was dissolved in 30.0 mL of anhydrous DMSO, followed by addition of 200 mg (0.18 mmol) of compound 215, 52 mg (0.28 mmol) of 1-ethyl-3-(3-dimethylaminopropyl) carbodiimide (EDC), 38 mg (0.28 mmol) of 1-hydroxybenzotriazole (HOBt), and 69 uL (0.5 mmol) of triethylamine and stirred for 48 hours. Upon completion of the reaction, the reaction mixture was precipitated in methanol, dialyzed against distilled water, and lyophilized to provide 1.67 g of conjugate 216. Yield: 83%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.70 (m, CONH), 5.32 (m, CH), 1.01 (m, CH$_3$).

Synthetic Scheme 49 acetic acid (8:1:1), and repeatedly crystalized in chloroform-methanol to give 669 mg of compound 217. Yield: 23%.

$^1$H NMR (600 MHz, DMSO-$d_6$, ppm): δ 7.00-7.50 (m, 9H), 5.35-5.50 (m, 18H), 4.43-4.55 (m, 3H), 3.90-4.20 (m, 6H), 3.10-3.30 (m, 8H), 2.78 (m, 12H), 2.37 (m, 12H), 2.15 (m, 8H), 1.00-2.00 (m, 54H), 0.97 (m, 9H); TOF-MS: calcd for $C_{84}H_{142}N_{12}O_{11}$ [M+2H]$^+$: 1495.1; found: 1495.6.

Sample 218: Preparation of Conjugate 218

In a 100 mL round-bottom flask, 1.6 g of functionalized dextran 142 was dissolved in 30.0 mL of anhydrous DMSO, followed by addition of 160 mg (0.11 mmol) of compound 217, 31 mg (0.16 mmol) of 1-ethyl-3-(3-dimethylaminopro-

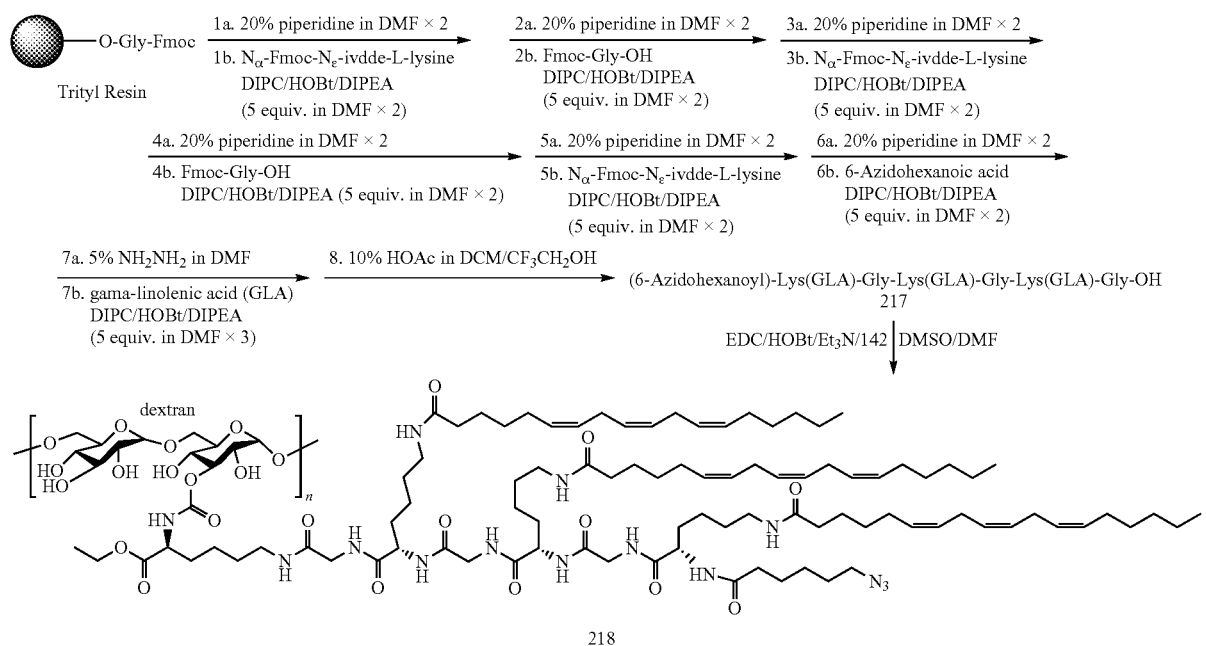

Sample 217: Preparation of Compound 217

Fmoc-Gly-OH was covalently attached to 5.0 g of trityl chloride resin (substitution: 0.39 mmol/g) and loaded on to a peptide synthesizer using standard protocols for Fmoc solid-phase peptide synthesis: Fmoc protecting group was deprotected with 20% piperidine in DMF, and ivdde protecting group deprocted with 5% hydrazine in DMF; 5 equivalents of protected amino acid or gama-linolenic acid (GLA), S equivalents of coupling agent: DIPC, hydroxybenzotriazole (HOBt), and 5 equivalent diisopropylethylamine (DIPEA) were used in coupling steps. After completion of the synthesis, the peptide derivative was cleaved from the resin using the cocktail: dichloromethane/trifluoroethanol/ pyl) carbodiimide (EDC), 22 mg (0.16 mmol) of 1-hydroxybenzotriazole (HOBt), and 69 uL (0.5 mmol) of triethylamine were added and stirred for 48 hours. Upon completion of the reaction, the reaction mixture was precipitated in methanol, dialyzed against distilled water, and lyophilized to provide 1.12 g of conjugate 218. Yield: 70%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.70 (m, CONH), 5.32 (m, CH), 0.81 (m, CH$_3$).

Synthetic Scheme 50

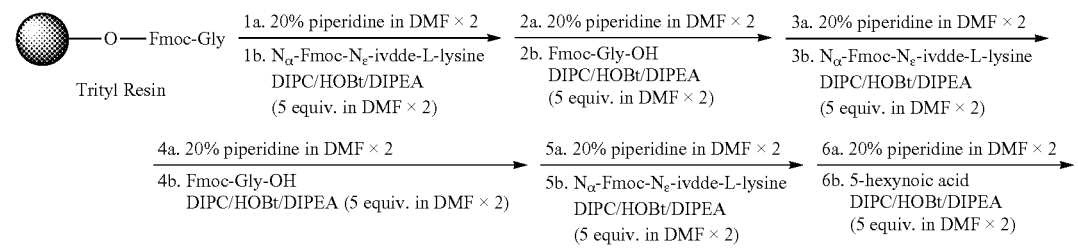

-continued 7a. 5% NH$_2$NH$_2$ in DMF × 2    8. 10% HOAc in DCM/CF$_3$CH$_2$OH 7b. stearoic acid acid
DIPC/HOBt/DIPEA
(6 equiv. in DMF × 3)

(5-hexynoyl)-Lys(GLA)-Gly-Lys(GLA)-Gly-Lys(GLA)-Gly-OH
219

EDC/HOBt/Et$_3$N/142 | DMSO/DMF

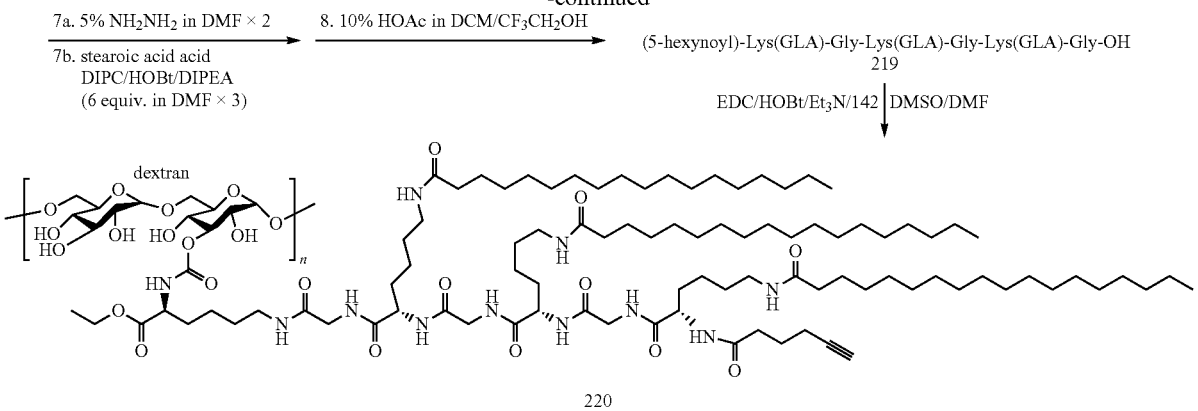

220

Sample 219: Preparation of Compound 219

Fmoc-Gly-OH was covalently attached to 5.0 g of trityl chloride resin (substitution: 0.39 mmol/g) and loaded on to a peptide synthesizer using standard protocols for Fmoc solid-phase peptide synthesis: Fmoc protecting group was deprotected with 20% piperidine in DMF, and ivdde protecting group deprocted with 5% hydrazine in DMF; 5 equivalents of protected amino acid or 5-hexynoic acid and 5 equivalents of stearic acid, 5 equivalents of coupling agent: DIPC and hydroxybenzotriazole (HOBt) and 5 equivalent diisopropylethylamine (DIPEA), were used in coupling steps. After completion of the synthesis, the peptide derivative was cleaved from the resin using the cocktail: dichloromethane/trifluoroethanol/acetic acid (8:1:1), and repeatedly crystalized in chloroform-methanol to give 743 mg of compound 219. Yield: 26%.

$^1$H NMR (600 MHz, DMSO-d$_6$, ppm): δ 7.00-7.50 (m, 9H), 4.43-4.55 (m, 3H), 3.90-4.20 (m, 6H), 3.10-3.30 (m, 6H), 2.15 (m, 8H), 1.00-2.00 (m, 54H), 0.97 (m, 9H); TOF-MS: calcd for C$_{84}$H$_{157}$N$_9$O$_{11}$ [M+2H]$^+$: 1468.2; found: 1468.5.

Sample 220: Preparation of Conjugate 220

In a 100 mL round-bottom flask, 2.0 g of functionalized dextran 142 was dissolved in 30.0 mL of anhydrous DMSO, followed by addition of 200 mg (0.13 mmol) of compound 219, 39 mg (0.20 mmol) of 1-ethyl-3-(3-dimethylaminopropyl) carbodiimide (EDC), 27 mg (0.20 mmol) of 1-hydroxybenzotriazole (HOBt), and 69 uL (0.5 mmol) of triethylamine were added and stirred for 48 hours. Upon completion of the reaction, the reaction mixture was precipitated in methanol, dialyzed against distilled water, and lyophilized to provide 1.53 g of conjugate 220. Yield: 76%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.20-8.70 (m, CONH), 0.83 (m, CH$_3$).

Synthetic Scheme 51

Retinoic acid
6-Azidohexanoic acid
HATU/Et$_3$N

142 $\xrightarrow{\text{DMCO}}$

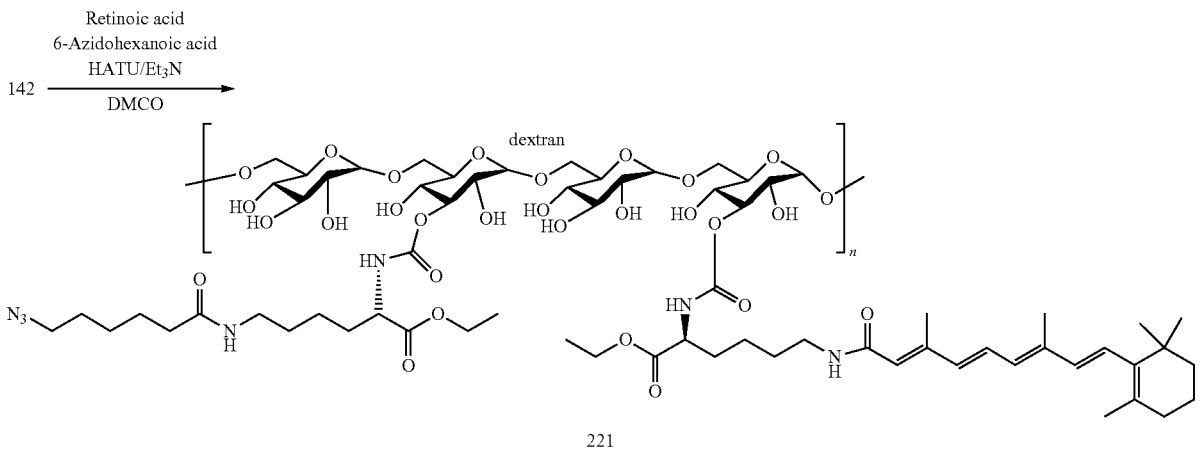

221

Sample 221: Preparation of Conjugate 221

In a 100 mL round-bottom flask, 2.0 g of functionalized dextran 142 was dissolved in 30.0 mL of anhydrous DMSO, followed by addition of 91 mg (0.3 mmol) of retinoic acid, 47 mg (0.3 mmol) of 6-azidohexanoic acid, 380 mg (1.0 mmol) of 2-(7-aza-1H-Benzotriazole-1-yl)-1,1,3,3-Tetramethyluronium hexafluorophosphate (HATU), and 138 uL (1.0 mmol) of triethylamine were added and stirred for 48 hours. Upon completion of the reaction, the reaction mixture was precipitated in methanol, dialyzed against distilled water, and lyophilized to provide 1.62 g of conjugate 221. Yield: 81%.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.10-8.70 (m, CONH), 6.50-7.00 (m, CH), 1.25 (m, CH$_3$), 1.02 (m, CH$_3$).

Synthetic Scheme 52

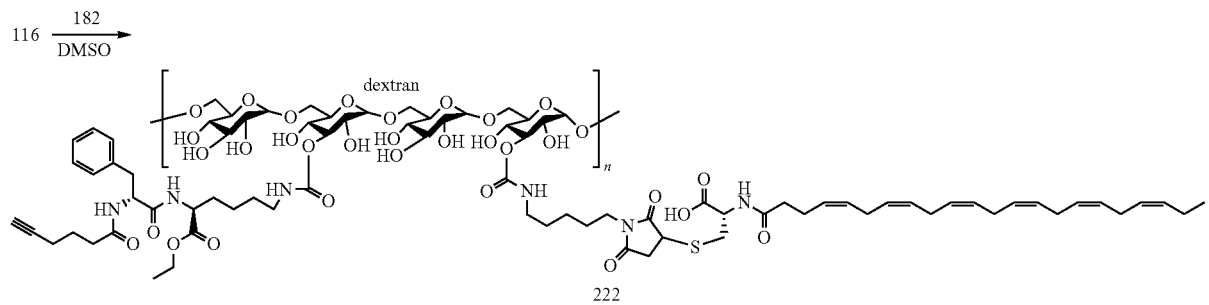

Sample 222: Preparation of Conjugate 222

In a 25 mL round bottom flask, 1.0 g of functionalized polysaccharide 116 was dissolved in 6.0 mL of DMSO-phosphate buffer solution (7:3, pH=8.0), then 86 mg (0.20 mmol) of compound 182 was added and stirred for 12 hours. Upon completion of the reaction, the reaction mixture was precipitated in methanol, dialyzed against distilled water, and lyophilized to provide 732 mg of conjugate 222. Yield: 73%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.70 (m, CONH, ArH), 5.35 (m, CH), 1.23 (t, CH$_3$), 1.01 (m, CH$_3$).

Synthetic Scheme 53

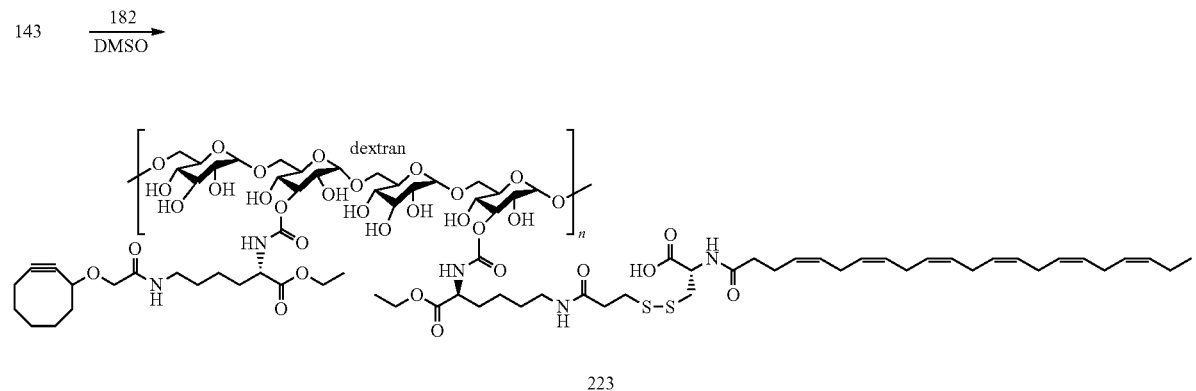

Sample 223: preparation of conjugate 223

In a 25 mL round bottom flask, 1.5 g of functionalized polysaccharide 143 was dissolved in 7.0 mL of DMSO, then 129 mg (0.30 mmol) of compound 182 was added, and stirred for 12 hours. Upon completion of the reaction, the reaction mixture was precipitated in methanol, dialyzed against distilled water, and lyophilized to provide 1.21 g of conjugate 223. Yield: 81%.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.50 (m, CONH), 5.35 (m, CH), 1.23 (m, CH$_3$), 1.00 (m, CH$_3$).

Synthetic Scheme 54

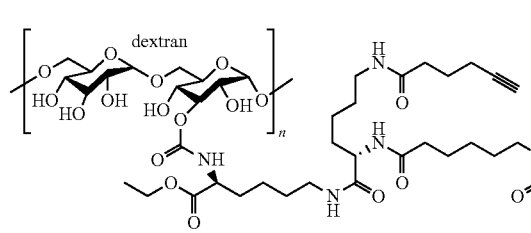

224

Sample 224: Preparation of Conjugate 224

The preparation of conjugate 224 is similar to that of conjugate 223.

¹H NMR (selected characteristic signals, 500 MHz, DMSO-d₆, ppm): major signals: 4.50-5.00 (m, CHOH, CHOH, CH₂OH), 3.30-4.00 (m, CHOH, CH₂OH); minor signals: 7.10-8.60 (m, CONH), 5.32 (m, CH), 1.25 (t, CH₃), 0.99 (t, CH₃).

Synthetic Scheme 55

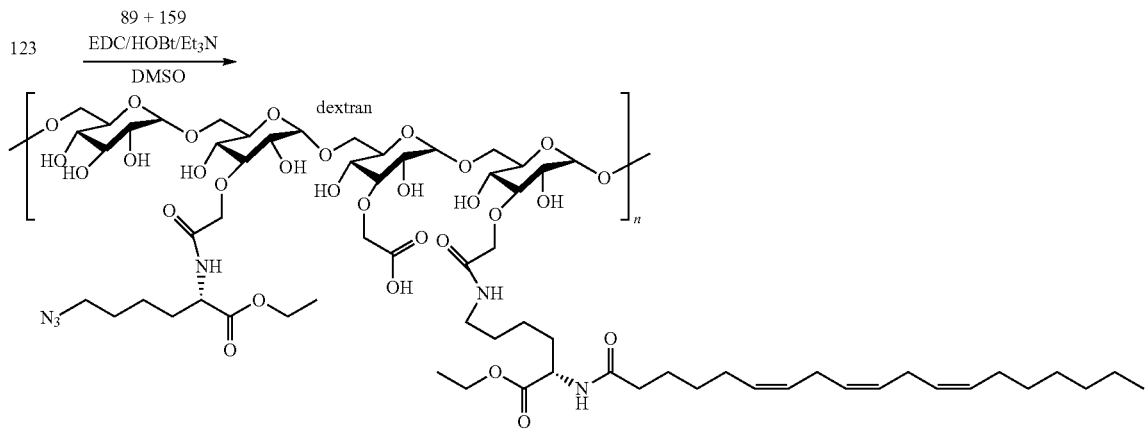

225

Sample 225: Preparation of Conjugate 225

In a 100 mL round-bottom flask, 3.0 g of functionalized dextran 123 was dissolved in 30.0 mL of anhydrous DMSO, followed by addition of 71 mg (0.3 mmol) of compound 89 and 141 mg (0.3 mmol) of compound 159, 191 mg (1.0 mmol) of 1-ethyl-3-(3-dimethylaminopropyl) carbodiimide (EDC), 135 mg (1.0 mmol) of 1-hydroxybenzotriazole (HOBt), and 138 uL (1.0 mmol) of triethylamine were added and stirred for 48 hours. Upon completion of the reaction, the reaction mixture was precipitated in methanol, dialyzed against distilled water, and lyophilized to provide 2.21 g of conjugate 225. Yield: 73%.

¹H NMR (selected characteristic signals, 500 MHz, DMSO-d₆, ppm): major signals: 4.50-5.00 (m, CHOH, CHOH, CH₂OH), 3.30-4.00 (m, CHOH, CH₂OH); minor signals: 7.20-8.50 (m, CONH), 5.35 (m, CH), 1.24 (m, CH₃), 0.83 (t, CH₃).

Synthetic Scheme 56

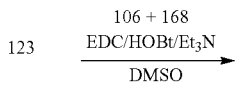

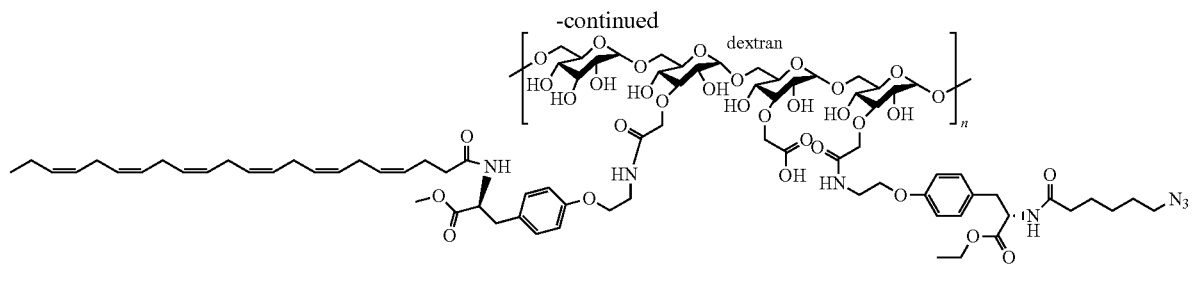

226

Sample 226: Preparation of Conjugate 226

The preparation of conjugate 226 is similar to that of conjugate 225.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.60 (m, CONH), 6.75-7.10 (m, ArH), 5.32 (m, CH), 1.23 (t, CH$_3$), 1.01 (t, CH$_3$).

Synthetic Scheme 57

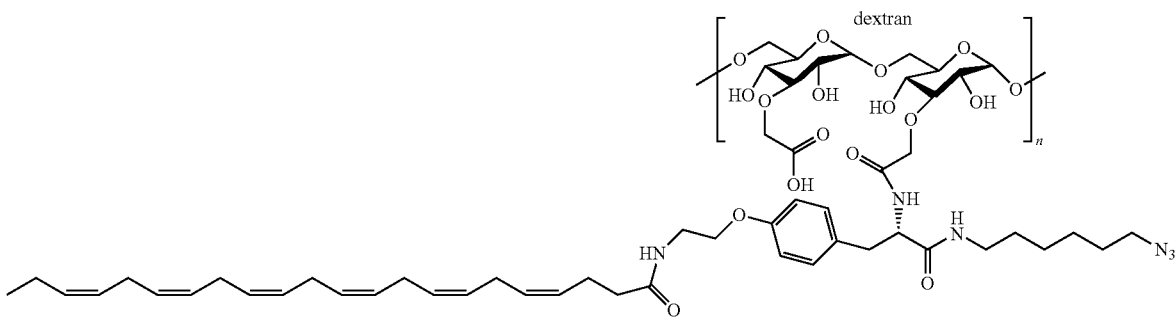

227

Sample 227: Preparation of Conjugate 227

The preparation of conjugate 227 is similar to that of conjugate 225.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.60 (m, CONH), 6.75-7.10 (m, ArH), 5.33 (m, CH), 1.01 (t, CH$_3$).

Synthetic Scheme 58

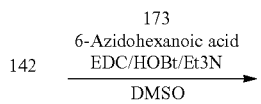

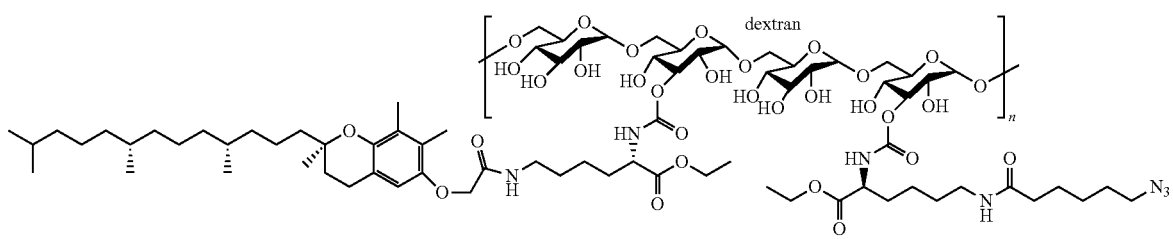

228

Sample 228: Preparation of Conjugate 228

The preparation of conjugate 228 is similar to that of conjugate 225.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.20-8.60 (m, CONH), 2.00 (m, CH$_3$), 0.83 (m, CH$_3$).

Part. 5. Preparation of Taxane-Polysaccharide Conjugates
Synthetic Scheme 59

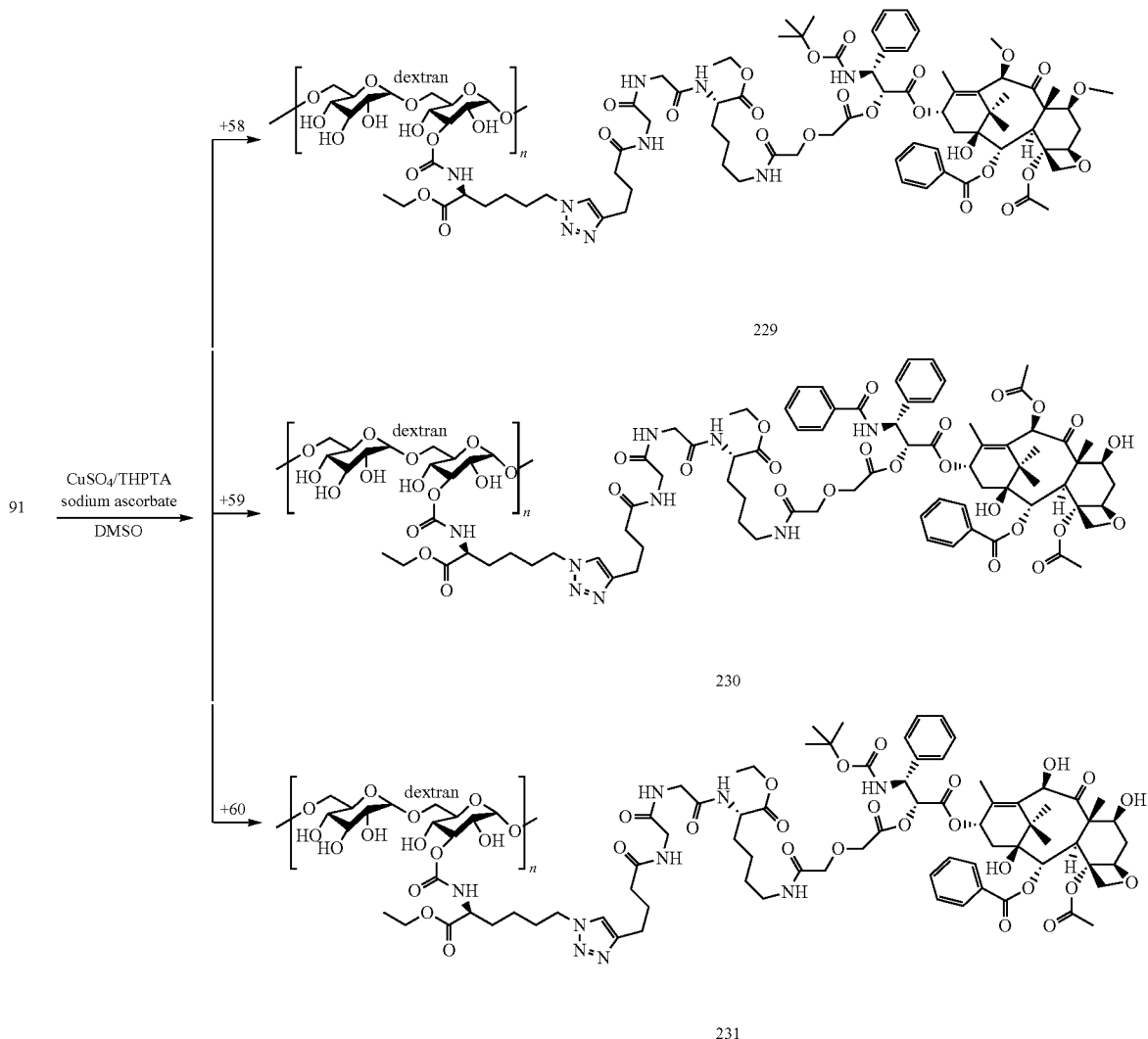

Sample 229: Preparation of Conjugate 229

In a 25 mL round bottom flask, 300 mg of functionalized dextran 91 and 36 mg (0.025 mmol) of compound 58 were dissolved in 2.0 mL of DMSO, followed by addition of copper sulfate solution (30 uL×1.0 M), THPTA (Tris (3-hydroxypropyltriazolylmethyl) amine, 30 uL×1.0 M) and sodium ascorbate solution (30 uL×1.0 M) were stirred at room temperature for 2 days. Upon completion of the reaction, the reaction mixture was precipitated with methanol, filtered, and washed with methanol three times. The precipitate was then dissolved in 2.0 mL of distilled water, dialyzed against distilled water, and lyophilized to offer 203 mg of conjugate 229. By comparing its UV absorption with that of compound 63 at wavelength of 280 nm, 7% (w/w) cabazitaxel content was determined in conjugate 229.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.45 (m, CONH, ArH), 1.35 (s, OC (CH$_3$) 3), 1.23 (m, CH$_3$), 1.01 (m, CH$_3$).

Sample 230: Preparation of Conjugate 230

The preparation of conjugate 230 is similar to that of conjugate 229.

By comparing its UV absorption with that of compound 61 at wavelength of 280 nm, 10% (w/w) paclitaxel content was determined in conjugate 230.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.23 (m, CH$_3$), 0.99 (m, CH$_3$).

Sample 231: Preparation of Conjugate 231

The preparation of conjugate 231 is similar to that of conjugate 229.

By comparing its UV absorption with that of compound 62 at wavelength of 280 nm, 9% (w/w) docetaxel content was determined in conjugate 231.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.35 (s, OC (CH$_3$) 3), 1.23 (m, CH$_3$), 1.00 (m, CH$_3$).

Synthetic Scheme 60

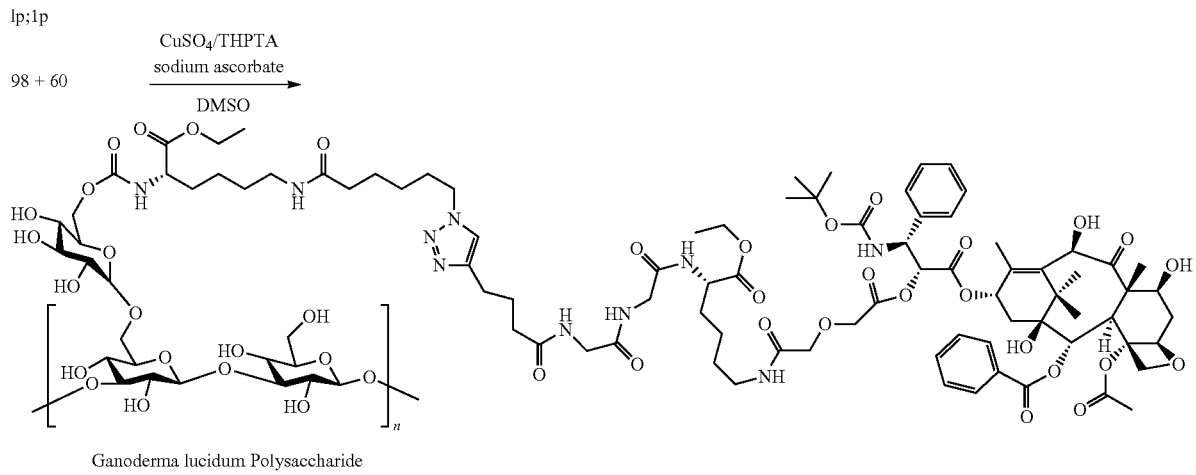

232

Sample 232: Preparation of Conjugate 232

The preparation of conjugate 232 is similar to that of conjugate 229.

By comparing its UV absorption with that of compound 62 at wavelength of 280 nm, 8% (w/w) docetaxel content was determined in conjugate 232.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.34 (s, OC (CH$_3$) 3), 1.24 (m, CH$_3$), 1.01 (m, CH$_3$).

Synthetic Scheme 61

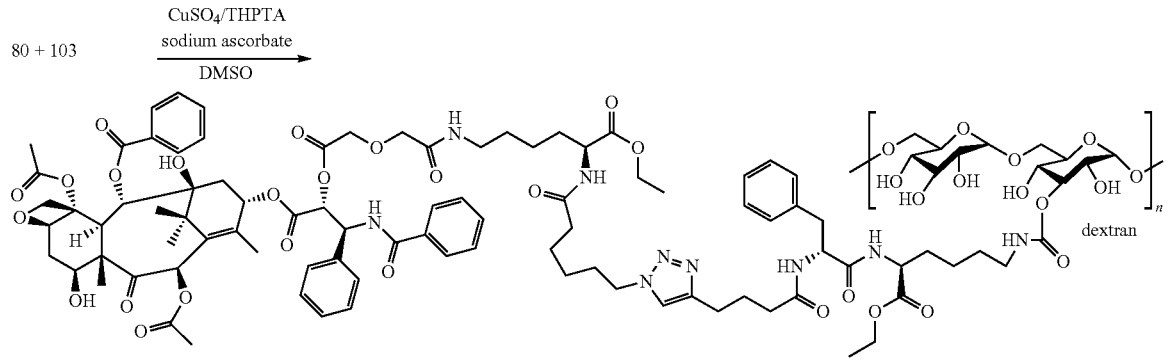

233

Sample 233: Preparation of Conjugate 233

The preparation of conjugate 233 is similar to that of conjugate 229.

By comparing its UV absorption with that of compound 7 and functionalized dextran 103 at wavelength of 280 nm, 6% (w/w) paclitaxel content was determined in conjugate 233.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.23 (m, CH$_3$), 0.99 (m, CH$_3$).

Synthetic Scheme 62

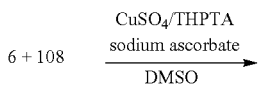

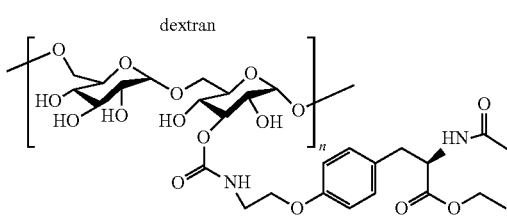

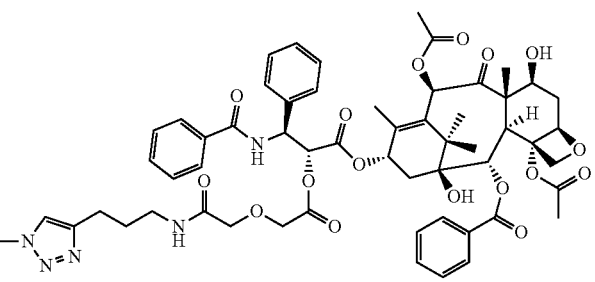

234

Sample 234: Preparation of Conjugate 234

The preparation of conjugate 234 is similar to that of conjugate 229.

By comparing its UV absorption with that of compound 7 and functionalized dextran 108 at wavelength of 280 nm, 11% (w/w) paclitaxel content was determined in conjugate 234.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 6.80-8.50 (m, CONH, ArH), 1.24 (m, CH$_3$), 1.02 (m, CH$_3$).

Synthetic Scheme 63

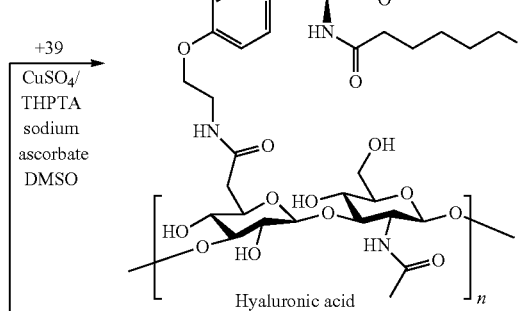

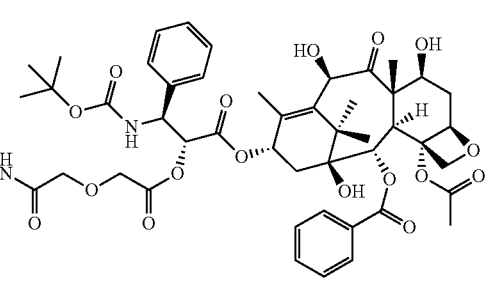

235

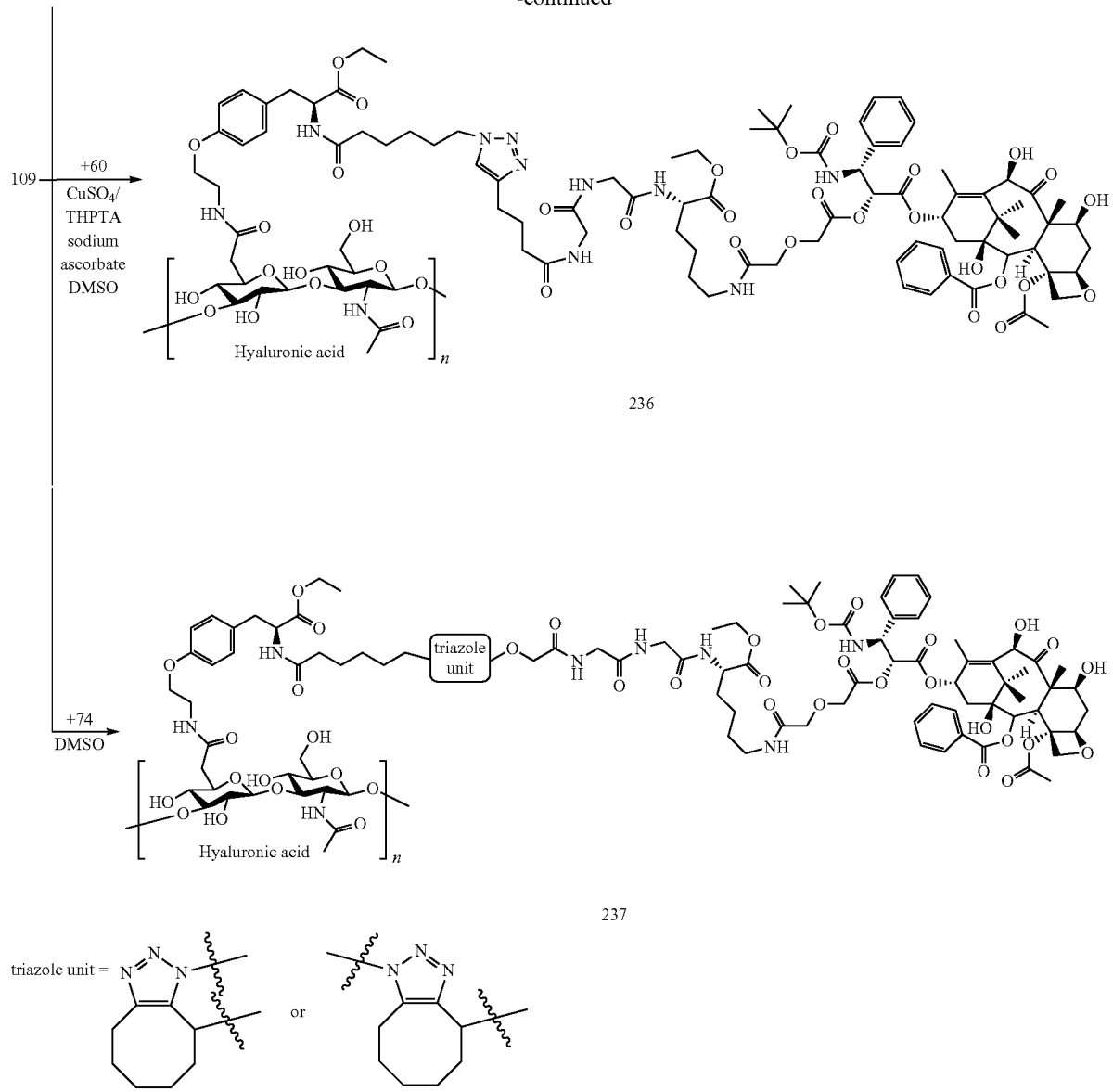

Sample 235: Preparation of Conjugate 235

The preparation of conjugate 231 is similar to that of conjugate 235.

By comparing its UV absorption with that of compound 62 and functionalized hyaluronic acid 109 at wavelength of 280 nm, 11% (w/w) docetaxel content was determined in conjugate 235.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 6.75-8.45 (m, CONH, ArH), 2.05 (s, CH$_3$CO), 1.35 (s, OC (CH$_3$) 3), 1.23 (m, CH$_3$), 1.01 (m, CH$_3$).

Sample 236: Preparation of Conjugate 236

The preparation of conjugate 236 is similar to that of conjugate 229.

By comparing its UV absorption with that of compound 40 and functionalized hyaluronic acid 109 at wavelength of 280 nm, 9% (w/w) docetaxel content was determined in conjugate 236.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 6.75-8.45 (m, CONH, ArH), 2.06 (s, CH$_3$CO), 1.34 (s, OC(CH$_3$)$_3$), 1.24 (m, CH$_3$), 1.00 (m, CH$_3$).

Sample 237: Preparation of Conjugate 237

In a 25 mL round bottom flask, 500 mg of functionalized hyaluronic acid 109 and 100 mg (0.07 mmol) of compound 74 were dissolved in 5.0 mL of DMSO, and stirred at room temperature for 3 days. Upon completion of the reaction, the reaction mixture was precipitated with methanol, filtered, and washed with methanol three times. The precipitate was then dissolved in 2.0 mL of distilled water, dialyzed against distilled water, and lyophilized to give 321 mg of conjugate 237. By comparing its UV absorption with that of compound 76a (76b) at wavelength of 280 nm, 6% (w/w) docetaxel content was determined in conjugate 237.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 6.75-8.50 (m, CONH, ArH), 2.04 (s, CH$_3$CO), 1.35 (s, OC(CH$_3$)$_3$), 1.22 (m, CH$_3$), 0.99 (m, CH$_3$).

Synthetic Scheme 64

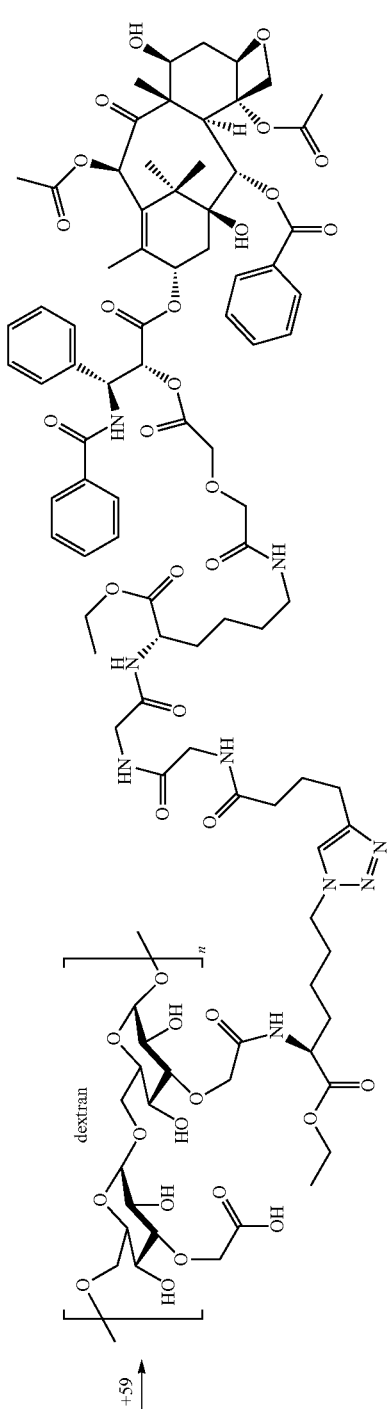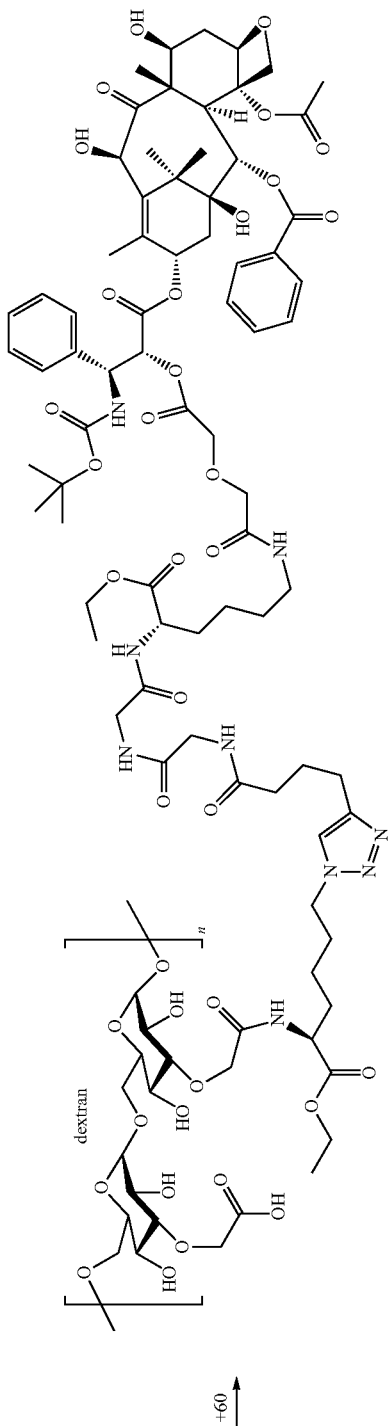

Sample 238: Preparation of Conjugate 238

The preparation of conjugate 238 is similar to that of conjugate 229.

By comparing its UV absorption with that of compound 61 at wavelength of 280 nm, 5% (w/w) paclitaxel content was determined in conjugate 238.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.23 (m, CH$_3$), 0.99 (m, CH$_3$).

Sample 239: Preparation of Conjugate 239

The preparation of conjugate 239 is similar to that of conjugate 229.

By comparing its UV absorption with that of compound 62 at wavelength of 280 nm, 12% (w/w) docetaxel content was determined in conjugate 239.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.34 (s, OC (CH$_3$) 3), 1.24 (m, CH$_3$), 1.01 (m, CH$_3$).

Synthetic Scheme 65

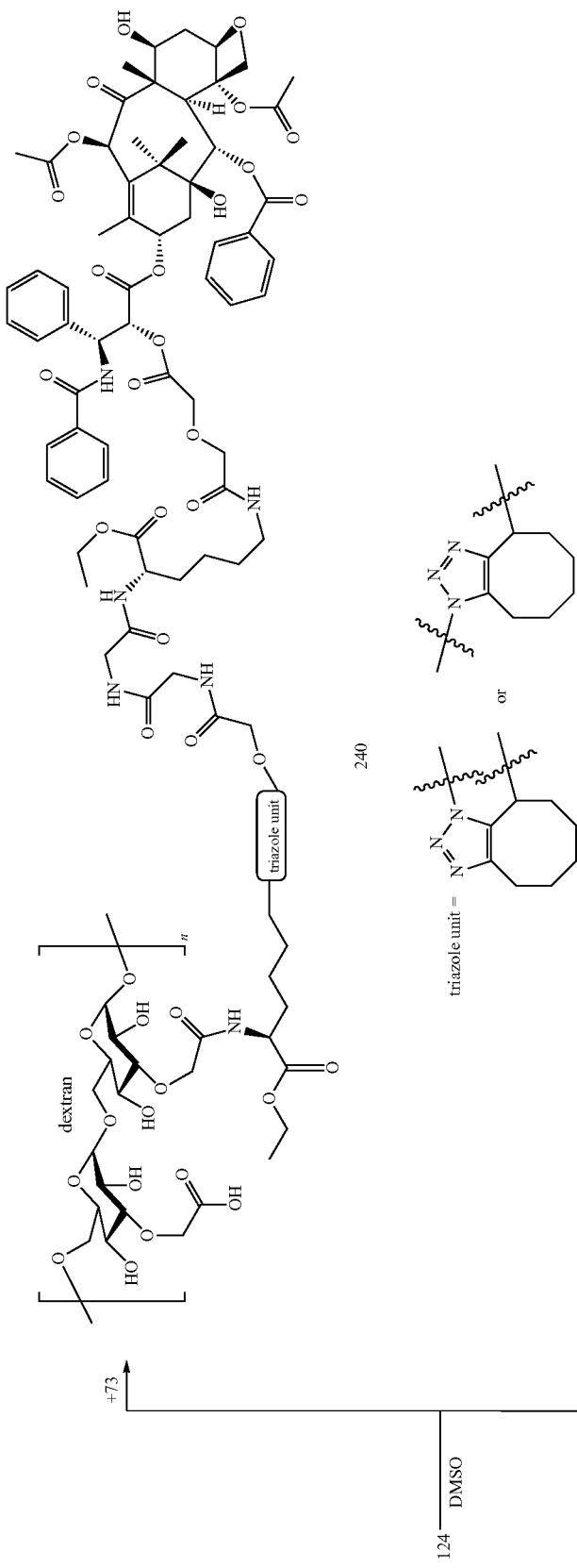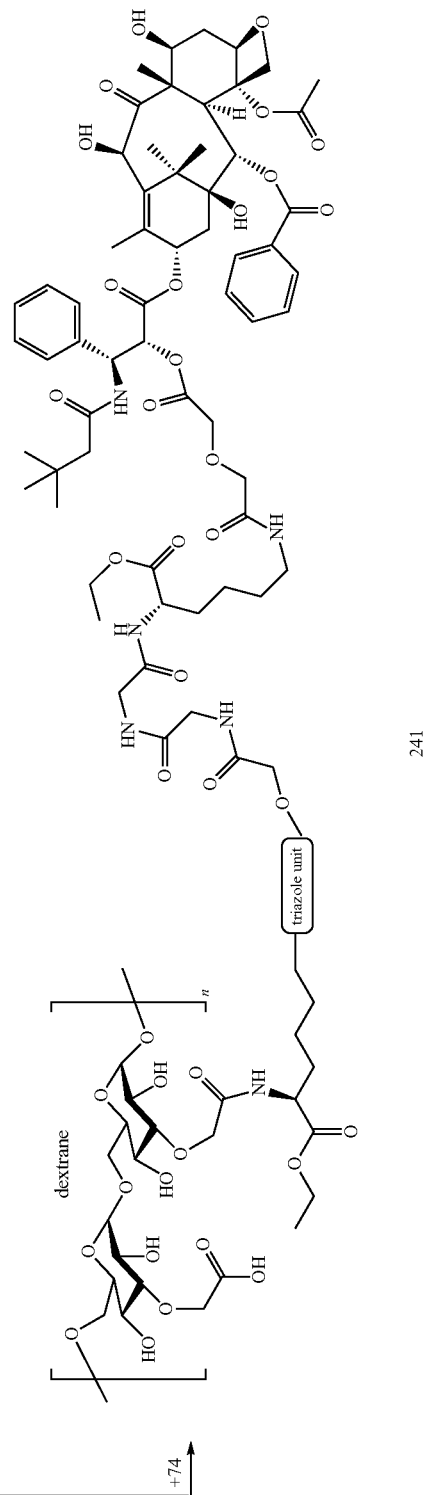

Sample 240: Preparation of Conjugate 240

The preparation of conjugate 240 is similar to that of conjugate 237.

By comparing its UV absorption with that of compound 75a (75b) at wavelength of 280 nm, 12% (w/w) paclitaxel content was determined in conjugate 240.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.24 (m, CH$_3$), 0.99 (m, CH$_3$).

Sample 241: Preparation of Conjugate 241

The preparation of conjugate 241 is similar to that of conjugate 237.

By comparing its UV absorption with that of compound 76a (76b) at wavelength of 280 nm, 11% (w/w) docetaxel content was determined in conjugate 241.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.34 (s, OC (CH$_3$) 3), 1.23 (m, CH$_3$), 1.00 (m, CH$_3$).

Synthetic Scheme 66

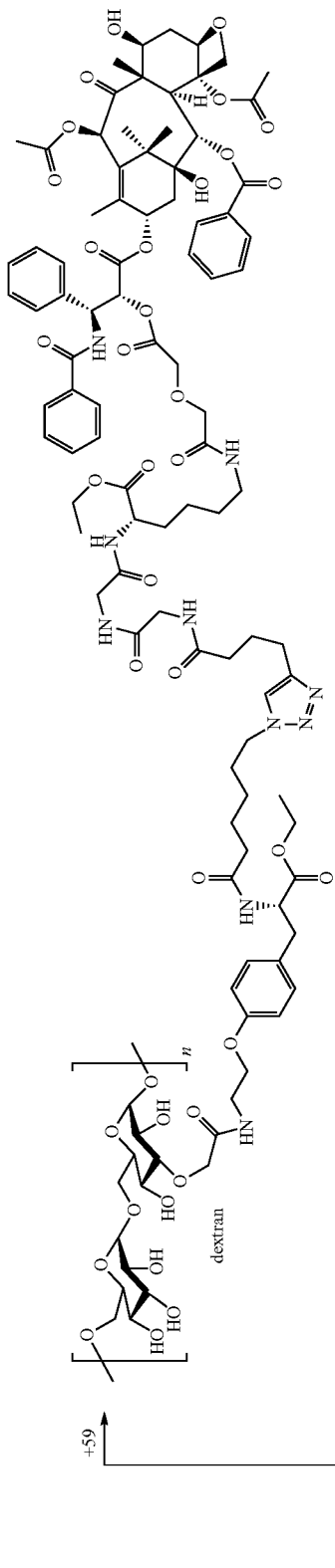
343
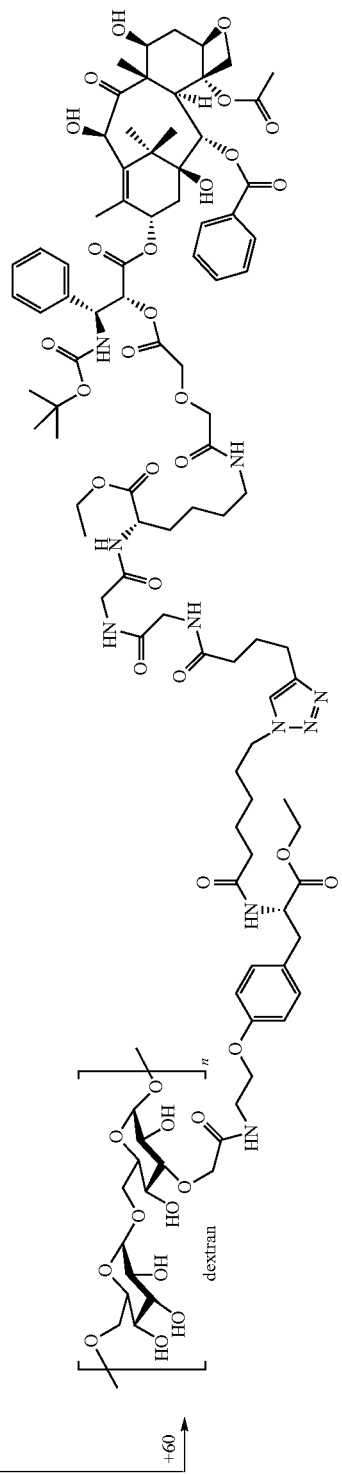
344
CuSO₄/THPTA
sodium ascorbate
DMSO

Sample 242: Preparation of Conjugate 242

The preparation of conjugate 242 is similar to that of conjugate 229.

By comparing its UV absorption with that of compound 61 and functionalized dextran 125 at wavelength of 280 nm, 9% (w/w) paclitaxel content was determined in conjugate 242.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 1.24 (m, CH$_3$), 0.99 (m, CH$_3$).

Sample 243: Preparation of Conjugate 243

The preparation of conjugate 243 is similar to that of conjugate 229.

By comparing its UV absorption with that of compound 62 and functionalized dextran 125 at wavelength of 280 nm, 12% (w/w) docetaxel content was determined in conjugate 243.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 1.34 (s, OC(CH$_3$)$_3$), 1.25 (m, CH$_3$), 1.01 (m, CH$_3$).

Synthetic Scheme 67

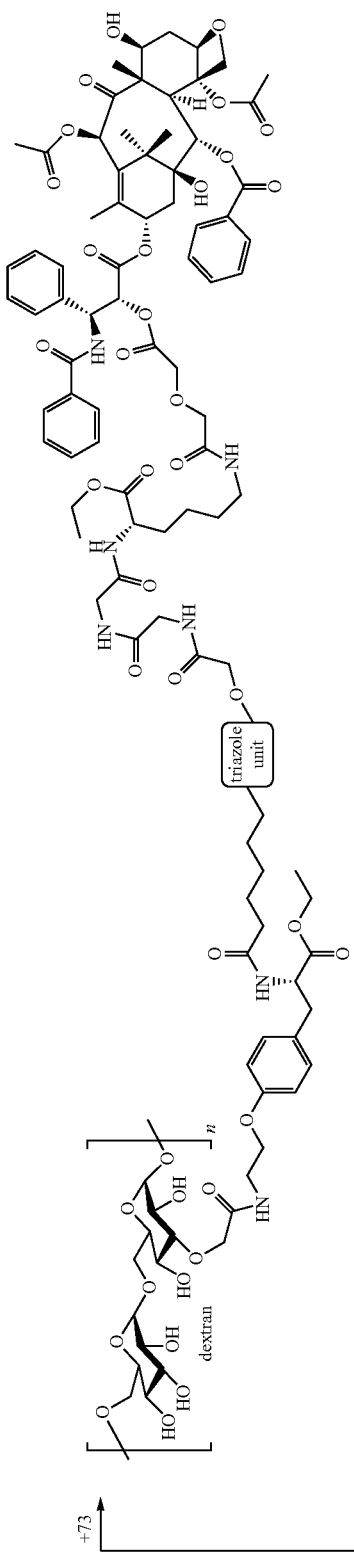
347
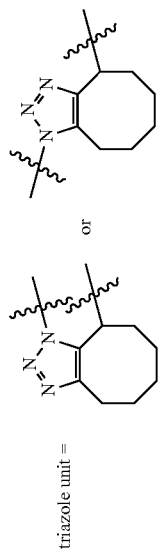
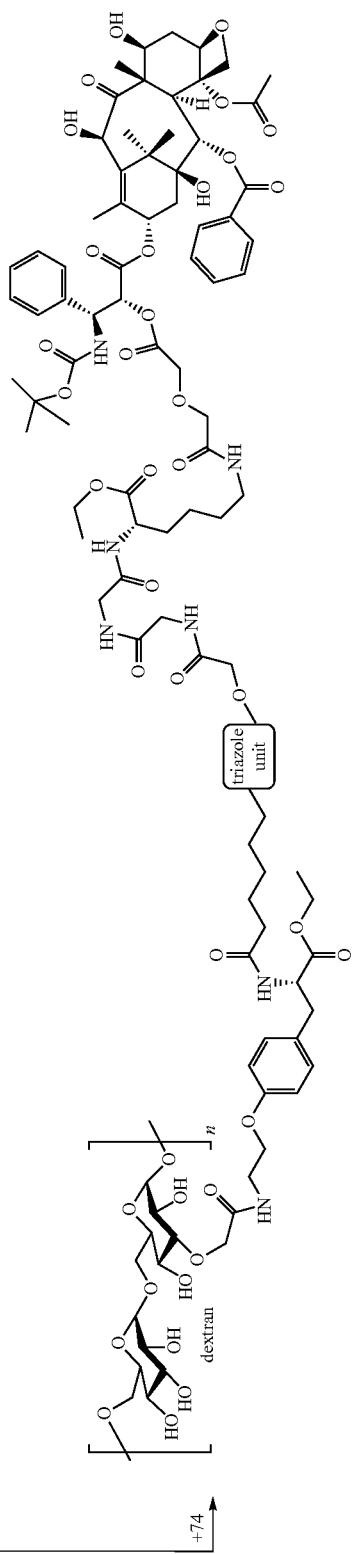
348

Sample 244: Preparation of Conjugate 244

The preparation of conjugate 244 is similar to that of conjugate 237.

By comparing its UV absorption with that of compound 75a (75b) and functionalized dextran 125 at wavelength of 280 nm, 11% (w/w) paclitaxel content was determined in conjugate 244.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 1.23 (m, CH$_3$), 0.98 (m, CH$_3$).

Sample 245: Preparation of Conjugate 245

The preparation of conjugate 245 is similar to that of conjugate 237.

By comparing its UV absorption with that of compound 76a (76b) and functionalized dextran 125 at wavelength of 280 nm, 9% (w/w) docetaxel content was determined in conjugate 245.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 1.35 (s, OC(CH$_3$) 3), 1.24 (m, CH$_3$), 1.00 (m, CH$_3$).

Synthetic Scheme 68

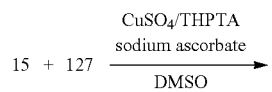

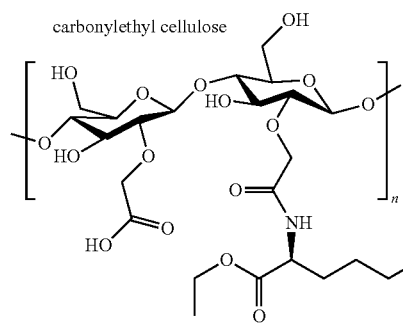

246

Sample 246: Preparation of Conjugate 246

The preparation of conjugate 246 is similar to that of conjugate 229.

By comparing its UV absorption with that of compound 16 at wavelength of 280 nm, 7% (w/w) paclitaxel content was determined in conjugate 246.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 1.95-2.30 (m, CH$_3$CO), 1.23 (t, CH$_3$), 0.99 (m, CH$_3$).

Synthetic Scheme 69

247

Sample 247: Preparation of Conjugate 247

The preparation of conjugate 247 is similar to that of conjugate 229.

By comparing its UV absorption with that of compound 7 and functionalized dextran 132 at wavelength of 280 nm, 7% (w/w) paclitaxel content was determined in conjugate 247.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.23-1.26 (m, CH$_3$), 0.98 (m, CH$_3$).

Synthetic Scheme 70

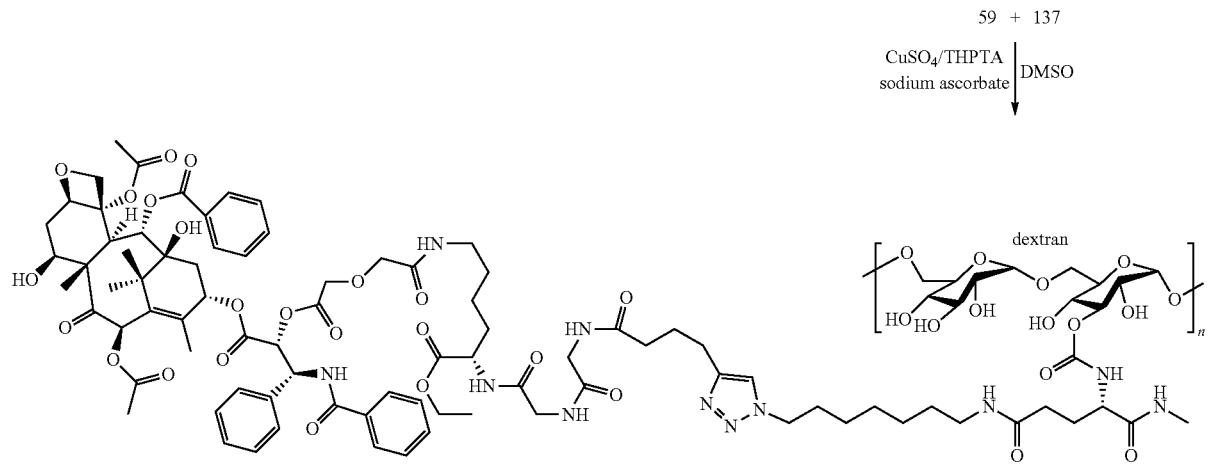

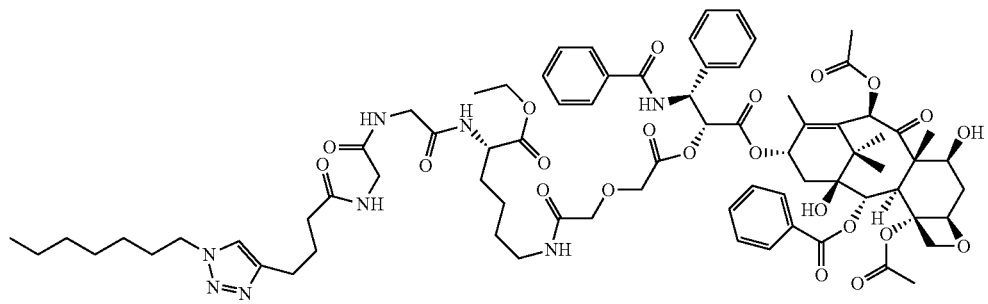

248

Sample 248: Preparation of Conjugate 248

The preparation of conjugate 248 is similar to that of conjugate 229.

By comparing its UV absorption with that of compound 61 at wavelength of 280 nm, 17% (w/w) paclitaxel content was determined in conjugate 248.

$^1$H NMR (selected characteristic signals, 500 MHz, DMSO-d$_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.24 (m, CH$_3$), 1.01 (m, CH$_3$).

Synthetic Scheme 71

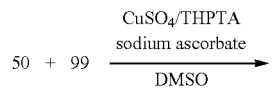

-continued

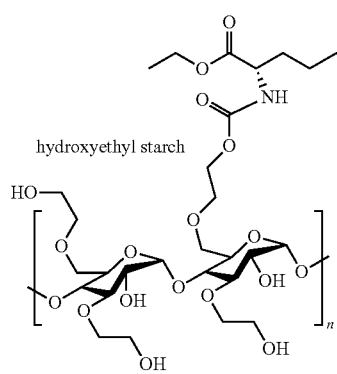
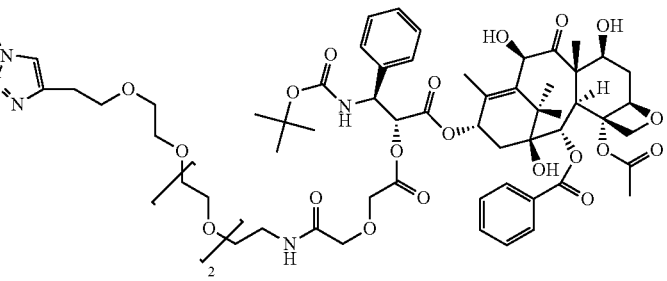

249

Sample 249: Preparation of Conjugate 249

The preparation of conjugate 249 is similar to that of conjugate 229.

By comparing its UV absorption with that of compound 40 at wavelength of 280 nm, 6% (w/w) paclitaxel content was determined in conjugate 249.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.10-8.50 (m, CONH, ArH), 1.34 (s, OC(CH$_3$) 3), 1.23 (t, CH$_3$), 1.01 (m, CH$_3$).

Synthetic Scheme 72

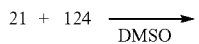

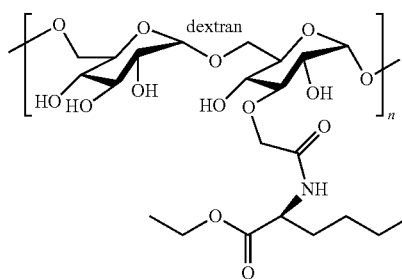

250

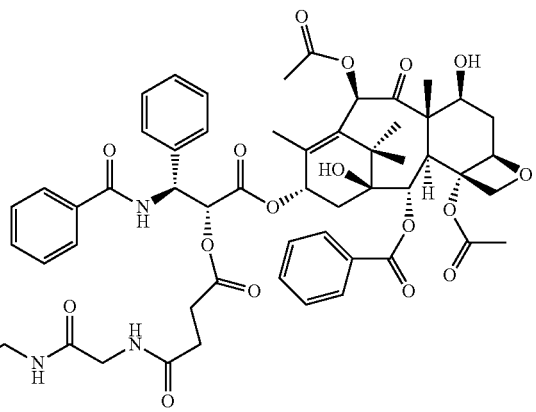

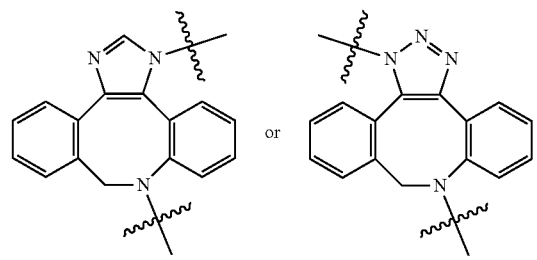

triazole unit

Sample 250: Preparation of Conjugate 250

The preparation of conjugate 250 is similar to that of conjugate 237.

By comparing its UV absorption with that of compound 22a (22b) at wavelength of 280 nm, 9% (w/w) paclitaxel content was determined in conjugate 250.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH); minor signals: 7.10-8.50 (m, CONH, ArH), 1.23 (t, CH$_3$), 0.99 (m, CH$_3$).

Synthetic Scheme 73

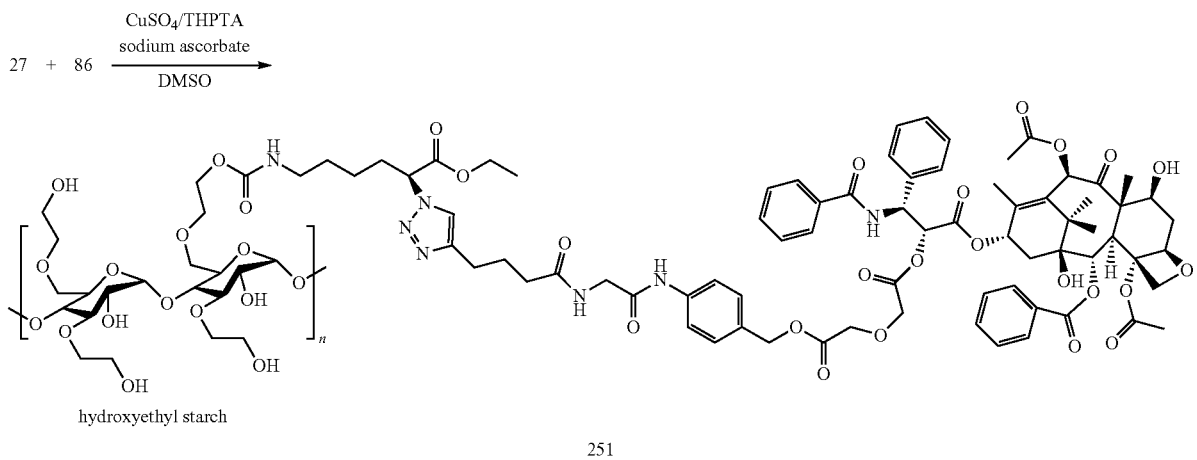

251

Sample 251: Preparation of Conjugate 251

The preparation of conjugate 251 is similar to that of conjugate 229.

By comparing its UV absorption with that of compound 28 at wavelength of 280 nm, 12% (w/w) paclitaxel content was determined in conjugate 251.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 1.23 (t, CH$_3$), 0.99 (m, CH$_3$).

Part 6. Preparation of Functionalized Lipid-Taxane Conjugates

Synthetic Scheme 74

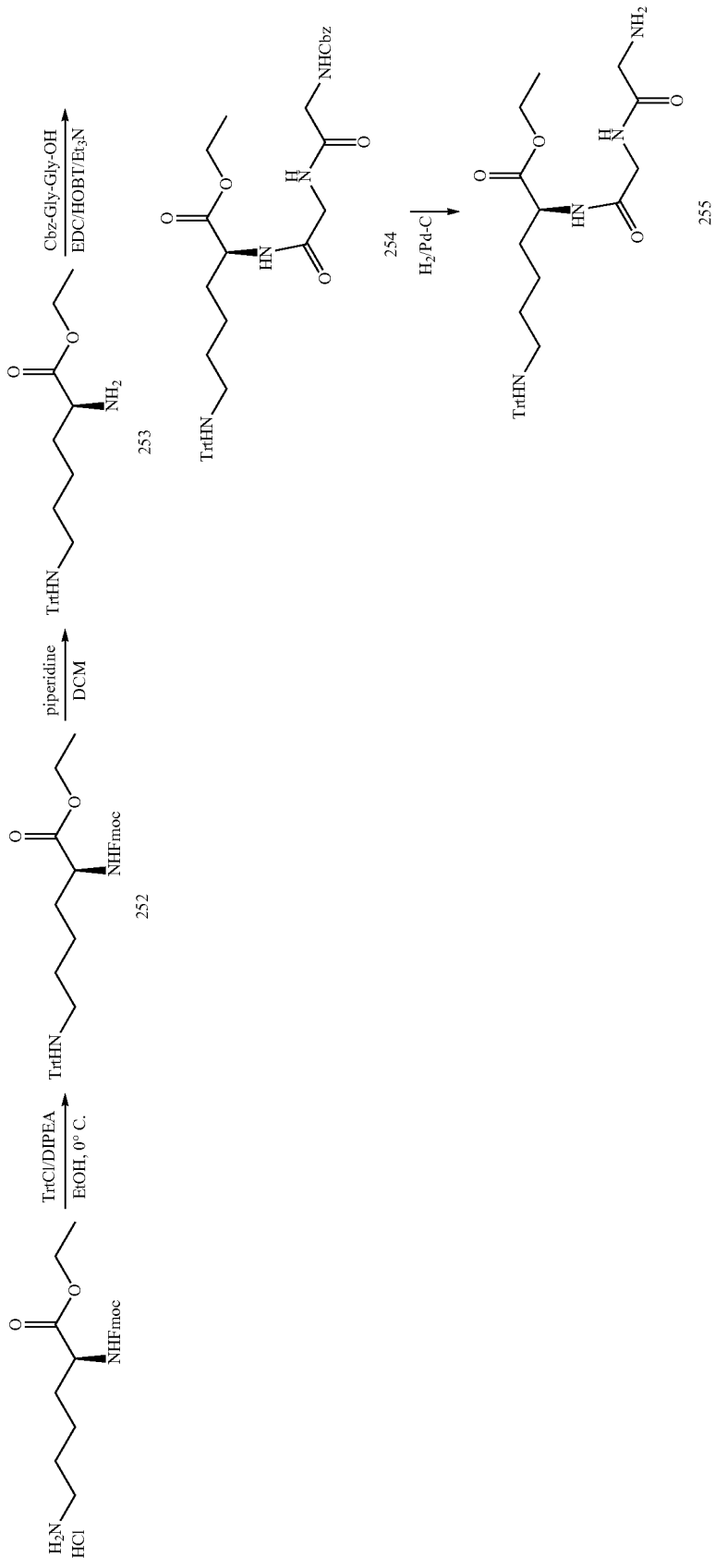

-continued
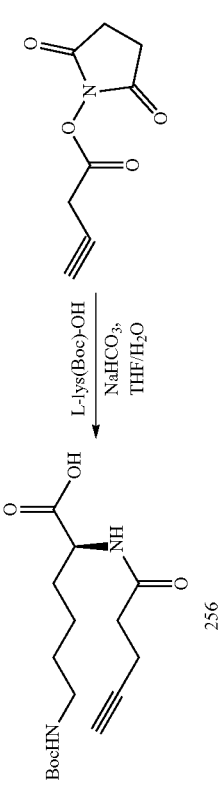
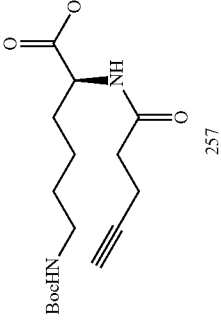
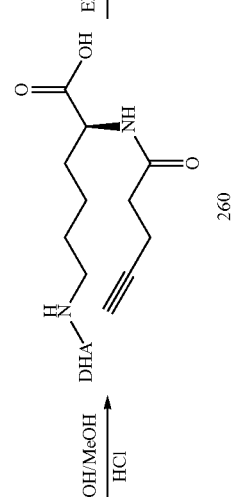
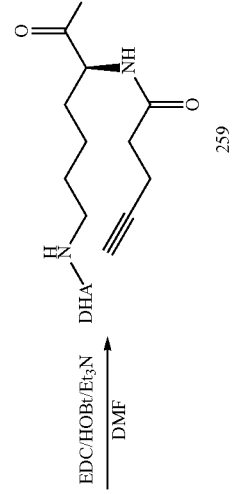
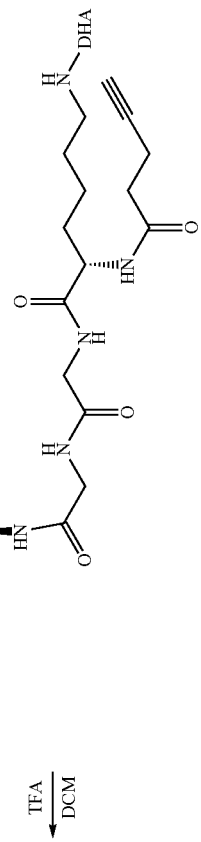

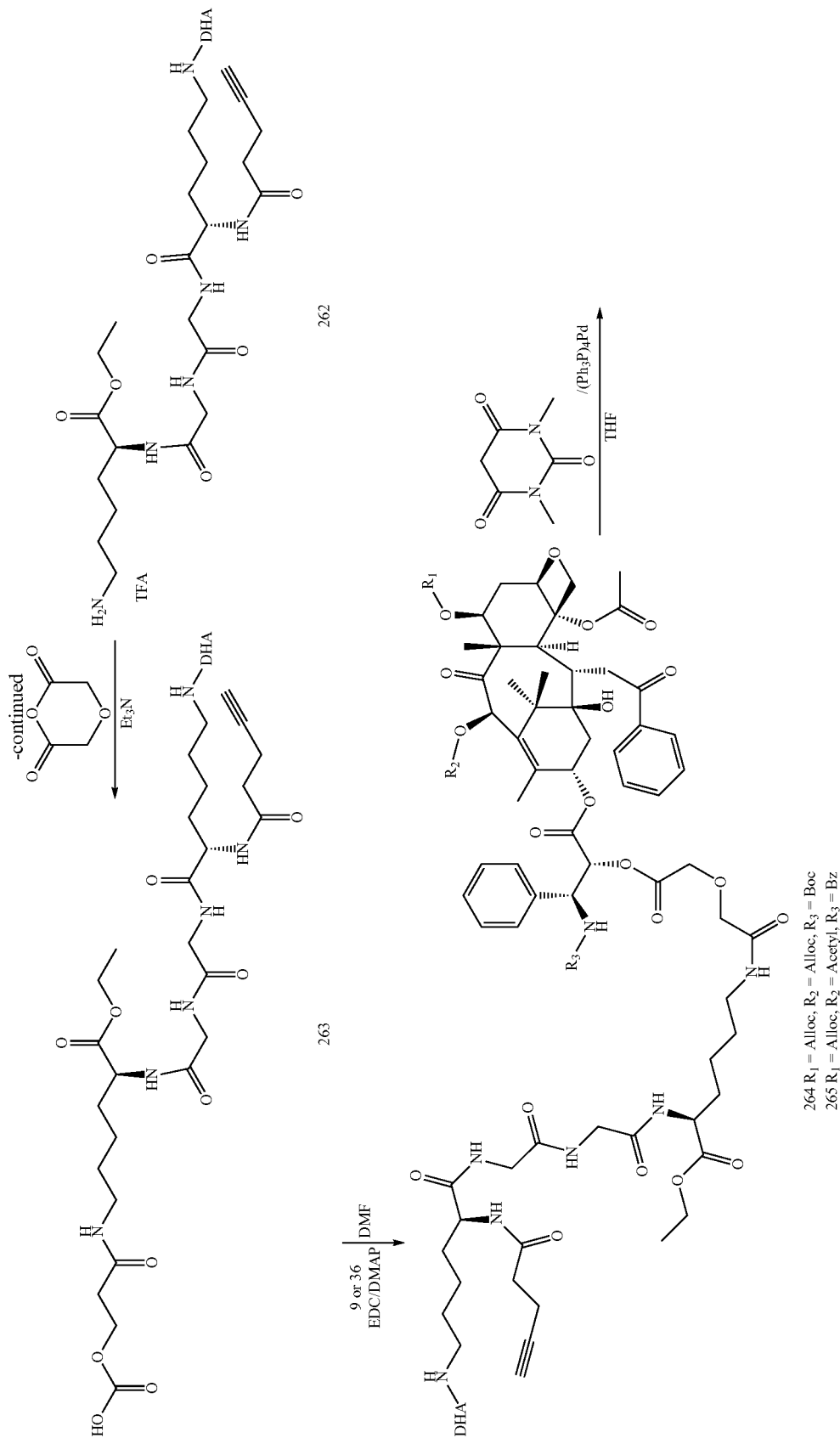

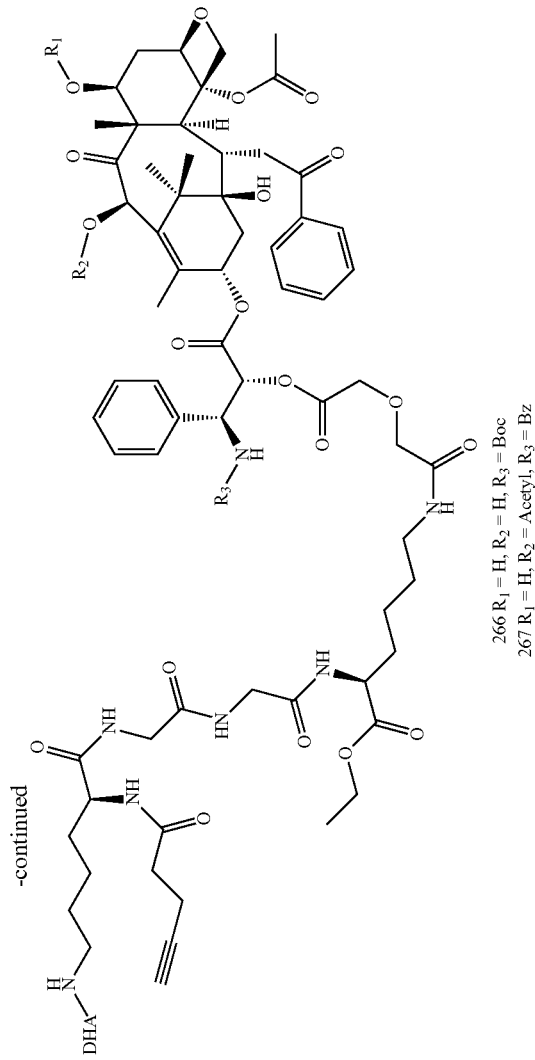

Sample 252: Preparation of Compound 252

To a 1000 mL round-bottom flask charged with 62.0 g (143.2 mmol) of Fmoc L-lysine ethyl ester, 70 mL (716 mmol) of diisopropyl ethylamine, 500 mL of anhydrous ethanol was added and cooled down to 0° C. and stirred for 30 mins, followed by addition of 48.0 g (171.8 mmol) of triphenyl methyl chloride and stirred overnight. Upon completion of the reaction, the reaction mixture was evaporated and the residue was partitioned between ethyl acetate (600 mL) and brine (600 mL), the organic phase was further washed with brine twice (600 mL×2), dried over anhydrous $MgSO_4$, filtered, concentrated, and purified on a silica gel column and eluted with ethyl acetate in petroleum ether (10-70%) to provide 57.0 g of compound 252. Yield: 62%.

$^1$H NMR (400 MHZ, DMSO-$d_6$, ppm): δ 7.83 (d, J=6.8 Hz, 1H), 7.72 (d, J=6.8 Hz, 1H), 7.45 (m, 6H), 7.26 (m, 6H), 7.21 (m, 3H), 4.32 (d, J=7.2 Hz, 2H), 4.21 (m, 1H), 4.17 (m, 2H), 1.95 (m, 2H), 1.61 (m, 2H), 1.47 (m, 2H), 1.26 (m, 2H), 1.13 (t, J=7.2 Hz, 3H); ESI-MS (m/z): calcd for $C_{42}H_{43}N_2O_4$ [M+H]$^+$: 639.3; found: 639.4.

Sample 253: Preparation of Compound 253

To a 1000 mL round-bottom flask was loaded with 57.0 g (89.3 mmol) of compound 252 in 500 mL of dichloromethane, 38.0 g (446.5 mmol) of piperidine was added and stirred at room temperature for 2 hours. Upon completion of the reaction, the reaction mixture was evaporated, and the residue was purified on a silica gel column and eluted with ethyl acetate in petroleum ether (10-70%) to provide 33.0 g of compound 253. Yield: 89%.

$^1$H NMR (400 MHZ, DMSO-$d_6$, ppm): δ 7.47 (m, 6H), 7.32 (m, 6H), 7.21 (m, 3H), 4.17 (m, 2H), 3.25 (m, 1H), 1.89 (m, 2H), 1.25-1.50 (m, 6H), 1.14 (t, J=7.2 Hz, 3H); ESI-MS (m/z): calcd for $C_{27}H_{33}N_2O_2$ [M+H]$^+$: 417.2; found: 417.3.

Sample 254: Preparation of Compound 254

In a 500 mL round-bottom flask, 25.2 g (94.4 mmol) of Cbz-Gly-Gly-OH, 19.6 g (102.2 mmol) of 1-ethyl-3-(3-dimethylaminopropyl) carbodiimide (EDC), 13.5 g (102.2 mmol) of 1-hydroxybenzotriazole (HOBt) was dissolved in 150 mL of dry DMF, and followed by addition of 33 g (79.1 mmol) of compound 253 and 14 mL (102 mmol) of triethylamine and stirred at room temperature overnight. Upon completion of the reaction, the reaction mixture was partitioned between ethyl acetate (600 mL) and brine (600 mL), the organic phase was further washed with brine twice (600 mL×2), dried over anhydrous $MgSO_4$, filtered, concentrated, and purified on a silica gel column and eluted with methanol in chloroform (0-10%) to provide 34.0 g of compound 254. Yield: 65%.

$^1$H NMR (400 MHz, DMSO-$d_6$, ppm): δ 8.23 (d, J=6.8 Hz, 1H), 8.21 (t, J=6.8 Hz, 1H), 7.49 (t, J=6.8 Hz, 1H), 7.21-7.48 (m, 20H), 4.19 (m, 1H), 4.08 (m, 2H), 3.75 (t, J=7.2 Hz, 2H), 3.62 (t, J=7.2 Hz, 2H), 1.95 (m, 2H), 1.25-1.68 (m, 6H), 1.15 (t, J=7.2 Hz, 3H); ESI-MS (m/z): calcd for $C_{39}H_{45}N_4O_6$[M+H]$^+$: 665.3; found: 665.4.

Sample 255: Preparation of Compound 255

In a 500 mL round-bottom flask, 34 g (51.1 mmol) of compound 254 was dissolved in 250 mL of ethanol, and bubbled with hydrogen gas in the presence of 3.4 g of 10% Pd—C for 4 hours. Upon completion of the reaction, Pd-carbon was filtered off, and the filtrate was concentrated and purified on a reverse phase C-18 column and eluted with acetonitrile in water (10-80%) to give 6.2 g of compound 255. Yield: 23%.

$^1$H NMR (400 MHz, DMSO-$d_6$, ppm): δ 8.24 (d, J=6.8 Hz, 1H), 8.22 (t, J=6.8 Hz, 1H), 7.20-7.50 (m, 15H), 4.20 (m, 1H), 4.07 (m, 2H), 3.76 (s, 2H), 3.09 (s, 2H), 1.95 (m, 2H), 1.25-1.70 (m, 2H), 1.14 (t, J=7.2 Hz, 3H); ESI-MS (m/z): calcd for $C_{31}H_{39}N_4O_6$ [M+H]$^+$: 531.3; found: 531.3.

Sample 256: Preparation of Compound 256

In a 500 mL round-bottom flask, 12.6 g (51.2 mmol) of $N_6$-Boc-L-lysine and 9.5 g (113 mmol) of sodium bicarbonate were dissolved in 100 mL of distilled water, followed by addition of 10.0 g (51.2 mmol) of 4-alkynoic acid-(N-hydroxysuccinyl lactam) ester in tetrahydrofuran, and stirred at room temperature overnight. After removal of volatiles, the residue was acidified with 2.0 N hydrochloride solution to pH=1.0, and extracted with dichloromethane three times (200 mL×3); the organic phases were pooled, dried over anhydrous $MgSO_4$, filtered, concentrated, and purified on a silica gel column and eluted with methanol in chloroform (0-10%) to provide 14.0 g of compound 256. Yield: 83%.

$^1$H NMR (400 MHz, DMSO-$d_6$, ppm): δ 8.01 (d, J=7.2 Hz, 1H), 6.71 (d, J=7.2 Hz, 1H), 4.21 (m, 1H), 2.93 (m, 2H), 2.82 (s, 1H), 2.75 (m, 4H), 1.71 (m, 1H), 1.51 (m, 1H), 1.27 (s, 9H), 1.23-1.25 (m, 4H); ESI-MS (m/z): calcd for $C_{16}H_{27}N_2O_5$ [M+H]$^+$: 327.2; found: 327.3.

Sample 257: Preparation of Compound 257

To a 500 mL round-bottom flask was loaded with 14.0 g (42.9 mmol) of compound 252, 12 g (86.6 mmol) potassium carbonate, 200 mL of acetonitrile, 15 g (105.6 mmol) of methyl iodide was added, and heated at 40° C. and stirred overnight. After removal of volatiles, the residue was partitioned between ethyl acetate (200 mL) and brine (200 mL), the organic phase was further washed with brine twice (200 mL×2), dried over anhydrous $MgSO_4$, filtered, concentrated, and purified on a silica gel column and eluted with ethyl acetate in petroleum ether (20-90%) to provide 10.6 g of compound 257. Yield: 72%.

$^1$H NMR (400 MHZ, DMSO-$d_6$, ppm): δ 8.25 (d, J=6.8 Hz, 1H), 8.75 (t, J=6.8 Hz, 1H), 4.25 (m, 1H), 3.63 (s, 3H), 2.83 (m, 2H), 2.75 (s, 1H), 2.35 (m, 2H), 1.72 (m, 1H), 1.53 (m, 1H), 1.27 (s, 9H), 1.20-1.25 (m, 4H); ESI-MS (m/z): calcd for $C_{17}H_{29}N_2O_5$ [M+H]$^+$: 341.2; found: 341.1.

Sample 258: Preparation of Compound 258

To a 250 mL round-bottom flask charged with 10.6 g (31.1 mmol) of compound 257, 50 mL of hydrochloride ethanol solution (3.0N) was added and stirred at room temperature overnight. After removal of volatiles, the residue was purified on a reverse phase C-18 column and eluted with acetonitrile in water (10-70%) to provide 8.6 g of compound 258. Yield: 99%.

$^1$H NMR (400 MHz, DMSO-$d_6$, ppm): δ 8.05 (d, J=6.8 Hz, 1H), 8.01 (brs, 3H), 4.23 (m, 1H), 3.53 (s, 3H), 2.71 (m, 3H), 2.35 (m, 4H), 1.50-1.72 (m, 4H), 1.27 (m, 2H); ESI-MS (m/z): calcd for $C_{12}H_{21}N_2O_3$ [M+H]$^+$: 241.1; found: 241.1.

Sample 259: Preparation of Compound 259

To a 250 mL round-bottom flask charged with 4.0 g (12.2 mmol) of docosahexaenoic acid (DHA), 3.0 g (15.6 mmol) of 1-ethyl-3-(3-dimethylaminopropyl) carbodiimide (EDC), 2.2 g (16.2 mmol) of 1-hydroxybenzotriazole (HOBt) in 30 mL of dry DMF, 3.4 g (12.2 mmol) of compound 258 and 3.5 mL (24.5 mmol) of triethylamine were added and stirred at room temperature overnight. Upon completion of the reaction, the reaction mixture was partitioned between ethyl acetate (200 mL) and brine (200 mL), the organic phase was further washed with brine twice (100 mL×2), dried over anhydrous $MgSO_4$, filtered, concentrated, and purified on a silica gel column and eluted with methanol in chloroform (0-10%) to provide 4.8 g of compound 259. Yield: 72%.

$^1$H NMR (400 MHZ, $CD_3OD$, ppm): δ 5.41 (m, 12H), 4.41 (m, 1H), 3.75 (s, 3H), 2.89 (m, 10H), 2.49 (m, 4H), 2.46 (m, 2H), 2.27 (t, J=3.0 Hz, 1H), 2.25 (t, J=7.2 Hz, 2H), 2.10 (m, 2H), 1.81 (m, 2H), 1.72 (m, 2H), 1.53 (m, 2H), 1.47 (m, 2H), 1.02 (t, J=7.2 Hz, 3H); ESI-MS (m/z): calcd for $C_{34}H_{51}N_2O_4$ [M+H]$^+$: 551.3; found: 551.4.

Sample 260: Preparation of Compound 260

To a 250 mL round bottom flask charged with 4.8 g (8.72 mmol) of compound 259 in 50 mL of dimethylformamide-water (7:3), 1.05 g (26.2 mmol) of sodium hydroxide was added, and stirred at room temperature for 1 day. Upon completion of the reaction, the mixture was acidified with 2.0N HCl to pH=1.0, and extracted with ethyl acetate (100 mL×3); the organic phases were pooled, dried over MgSO$_4$, filtered, concentrated, and purified on a silica gel column and eluted with methanol in dichloromethane (0-10%) to give 4.5 g of compound 260. Yield: 96%.

$^1$H NMR (400 MHZ, DMSO-d$_6$, ppm): δ 8.21 (d, J=6.8 Hz, 1H), 7.80 (t, J=6.8 Hz, 1H), 5.31 (m, 12H), 4.21 (m, 1H), 3.01 (m, 2H), 2.81 (m, 10H), 2.21-2.70 (m, 6H), 2.05 (m, 4H), 1.71 (m, 1H), 1.57 (m, 1H), 1.25-1.45 (m, 4H), 0.92 (t, J=7.2 Hz, 3H); ESI-MS (m/z): calcd for $C_{33}H_{49}N_2O_4$ [M+H]$^+$: 537.4; found: 537.4.

Sample 261: Preparation of Compound 261

To a 250 mL round-bottom flask charged with 4.5 g (8.39 mmol) of compound 260, 2.0 g (10.4 mmol) of 1-ethyl-3-(3-dimethylaminopropyl) carbodiimide (EDC), 1.4 g (10.4 mmol) of 1-hydroxybenzotriazole (HOBt) in 30 mL of dry DMF, 5.0 g (9.42 mmol) of compound 255 and 3.5 mL (24.5 mmol) of triethylamine were added and stirred at room temperature overnight. Upon completion of the reaction, the reaction mixture was partitioned between ethyl acetate (200 mL) and brine (200 mL), the organic phase was further washed with brine twice (100 mL×2), dried over anhydrous MgSO$_4$, filtered, concentrated, and purified on a silica gel column and eluted with methanol in chloroform (0-10%) to provide 5.5 g of compound 261. Yield: 63%.

$^1$H NMR (400 MHZ, CD$_3$OD, ppm): 8; 7.20-7.50 (m, 15H), 5.38 (m, 12H), 4.37 (m, 1H), 4.17 (m, 3H), 3.89 (t, J=7.2 Hz, 2H), 3.81 (t, J=7.2 Hz, 2H), 3.16 (t, J=7.2 Hz, 2H), 2.86 (m, 10H), 2.49 (m, 4H), 2.45 (m, 2H), 2.27 (t, J=2.9 Hz, 1H), 2.25 (t, J=7.2 Hz, 2H), 2.10 (m, 4H), 1.60-1.75 (m, 4H), 1.25-1.55 (m, 8H), 1.22 (t, J=7.2 Hz, 2H), 0.97 (t, J=7.2 Hz, 2H); ESI-MS (m/z): calcd for $C_{64}H_{85}N_6O_7$ [M+H]$^+$: 1049.6; found: 1049.7.

Sample 262: Preparation of Compound 262

To a 250 mL round-bottom flask charged with 5.5 g (5.25 mmol) of compound 261 in 50 mL of dichloromethane, 5.0 mL of trifluoroacetic acid was added, and stirred at 0° C. for 1 hour. After removal of volatiles, the residue was purified on a reverse phase C-18 column and eluted with acetonitrile in water (10-80%) to provide 4.8 g of compound 262. Yield: 98%.

$^1$H NMR (400 MHz, CD$_3$OD, ppm): 8; 5.37 (m, 12H), 4.45 (m, 1H), 4.21 (m, 1H), 3.89 (d, J=7.2 Hz, 2H), 3.85 (d, J=7.2 Hz, 2H), 3.18 (t, J=7.2 Hz, 2H), 2.94 (t, J=7.2 Hz, 2H), 2.88 (m, 10H), 2.51 (m, 4H), 2.47 (m, 2H), 2.27 (t, J=3.0 Hz, 1H), 2.23 (t, J=7.2 Hz, 2H), 2.06 (m, 2H), 1.55-1.90 (m, 6H), 1.27-1.55 (m, 6H), 1.26 (t, J=7.2 Hz, 2H), 0.97 (t, J=7.2 Hz, 2H); ESI-MS (m/z): calcd for $C_{45}H_{71}N_6O_7$ [M+H]$^+$: 807.5; found: 807.5.

Sample 263: Preparation of Compound 263

To a 250 mL round-bottom flask charged with 4.8 g (5.95 mmol) of compound 262 in 50 mL of anhydrous acetonitrile, 2.0 g (17.9 mmol) of DMAP and 1.45 g (11.9 mmol) of diglycolic acid anhydride were added and stirred at room temperature overnight. After removal of volatiles, the residue was partitioned between ethyl acetate (200 mL) and 3.0 N hydrochloride (200 mL), and the aqueous solution was further with 3.0 N hydrochloride twice (100 mL×2), dried over anhydrous MgSO$_4$, filtered, concentrated, and purified on a silica gel column and eluted with methanol in chloroform (0-30%) to provide 3.26 g of compound 263. Yield: 59%.

$^1$H NMR (400 MHZ, DMSO-d$_6$, ppm): δ 9.61 (s, 1H), 9.05 (s, 1H), 8.22 (m, 2H), 8.51 (d, J=6.8 Hz, 1H), 8.22 (m, 2H), 7.76 (t, J=7.2 Hz, 2H), 5.37 (m, 12H), 4.21 (m, 1H), 4.19 (m, 1H), 3.91 (s, 2H), 3.85 (d, J=6.8 Hz, 2H), 3.81 (s, 2H), 3.76 (t, J=6.8 Hz, 2H), 3.19 (m, 2H), 3.17 (m, 2H), 2.81 (m, 10H), 2.75 (m, 4H), 2.25 (m, 2H), 2.01-2.30 (m, 6H), 1.55-1.75 (m, 3H), 1.20-1.55 (m, 9H), 1.18 (t, J=7.2 Hz, 2H), 0.92 (t, J=7.2 Hz, 2H); ESI-MS (m/z): calcd for $C_{45}H_{71}N_6O_7$ [M+H]$^+$: 923.5; found: 923.6.

Sample 264: Preparation of Compound 264

To a 100 mL round-bottom flask charged with 300 mg (0.325 mmol) of compound 263 and 125 mg (0.65 mmol) of 1-ethyl-3-(3-dimethylaminopropyl) carbodiimide (EDC) in 5.0 mL of dry DMF, 708 mg (0.65 mmol) of compound 36 and 79 mg (0.65 mmol) of DMAP were added, and the reaction mixture was stirred at room temperature for 24 hours. Upon completion of the reaction, the reaction mixture was partitioned between ethyl acetate (100 mL) and brine (100 mL); the aqueous phase was extracted with ethyl acetate (50 mL×2), and the organic phases were pooled, dried over anhydrous MgSO$_4$, filtered, concentrated, and purified on a silica gel column and eluted with methanol in chloroform (0-10%) to provide 237 mg of compound 264. Yield: 39%.

$^1$H NMR (500 MHz, CDCl$_3$, ppm): δ 8.02 (d, J=7.2 Hz, 2H), 6.80-7.85 (m, 12H), 6.12 (s, 1H), 5.93 (m, 4H), 5.61 (t, J=7.2 Hz, 1H), 5.15-5.50 (m, 17H), 4.92 (m, 1H), 4.40-4.70 (m, 5H), 3.70-4.30 (m, 14H), 3.25 (m, 4H), 2.91 (m, 10H), 2.10-2.60 (m, 13H), 1.85-2.05 (m, 10H), 1.60-2.05 (m, 19H), 1.00-1.55 (m, 30H), 0.89 (t, J=7.2 Hz, 3H); ESI-MS (m/z): calcd for $C_{100}H_{134}N_7O_{28}$ [M+H]$^+$: 1880.9; found: 1882.3.

Sample 265: Preparation of Compound 265

The preparation of compound 265 is similar to that of compound 264.

$^1$H NMR (500 MHz, CDCl$_3$, ppm): δ 8.05 (d, J=7.2 Hz, 2H), 6.80-7.85 (m, 15H), 6.15 (s, 1H), 5.95 (m, 2H), 5.65 (t, J=7.2 Hz, 1H), 5.15-5.50 (m, 15H), 4.96 (m, 1H), 4.40-4.70 (m, 3H), 3.70-4.30 (m, 14H), 3.25 (m, 4H), 2.93 (m, 10H), 2.10-2.60 (m, 16H), 1.85-2.05 (m, 10H), 1.60-2.05 (m, 19H), 1.00-1.55 (m, 21H), 0.91 (t, J=7.2 Hz, 3H); ESI-MS (m/z): calcd for $C_{100}H_{128}N_7O_{26}$ [M+H]$^+$: 1843.9; found: 1844.5.

Sample 266: Preparation of Compound 266

To a 50 mL round-bottom flask charged with 200 mg (0.11 mmol) of compound 264, and 39 mg (0.25 mmol) of 1,3-dimethylbarbituric acid in 10.0 mL of anhydrous THF, 39 mg (0.011 mmol) of tetrakis (triphenylphosphine) palladium (0) was added under nitrogen protection; the reaction mixture was stirred at room temperature for 5 h. After removal of volatiles and the residue was purified on a silica gel column and eluted with methanol in chloroform (0-15%) to give 133 mg of compound 266. Yield: 71%.

$^1$H NMR (500 MHz, CDCl$_3$, ppm): δ 8.03 (d, J=7.2 Hz, 2H), 6.90-7.60 (m, 12H), 6.12 (s, 1H), 5.98 (m, 2H), 5.61 (t, J=7.2 Hz, 1H), 5.20-5.45 (m, 13H), 4.91 (m, 1H), 4.46 (m, 2H), 3.70-4.30 (m, 16H), 3.23 (m, 4H), 2.87 (m, 10H), 2.10-2.60 (m, 13H), 1.60-2.05 (m, 19H), 1.00-1.55 (m, 30H), 1.00 (t, J=7.2 Hz, 3H), 0.91 (m, 3H); ESI-MS (m/z): calcd for $C_{92}H_{126}N_7O_{24}$ [M+H]$^+$: 1712.9; found: 1714.5.

Sample 267: Preparation of Compound 267

The preparation of compound 267 is similar to that of compound 266.

¹H NMR (500 MHz, CDCl₃, ppm): δ 8.03 (d, J=7.2 Hz, 2H), 6.80-7.85 (m, 15H), 6.15 (s, 1H), 5.95 (m, 1H), 5.63 (t, J=7.2 Hz, 1H), 5.15-5.50 (m, 13H), 4.96 (m, 1H), 4.30 (m, 3H), 3.70-4.20 (m, 14H), 3.26 (m, 4H), 2.91 (m, 10H), 2.10-2.60 (m, 16H), 1.85-2.05 (m, 10H), 1.60-2.05 (m, 19H), 1.00-1.55 (m, 21H), 0.90 (t, J=7.2 Hz, 3H); ESI-MS (m/z): calcd for $C_{96}H_{124}N_7O_{24}$ [M+H]⁺: 1758.9; found: 1759.6.
Synthetic Scheme 75
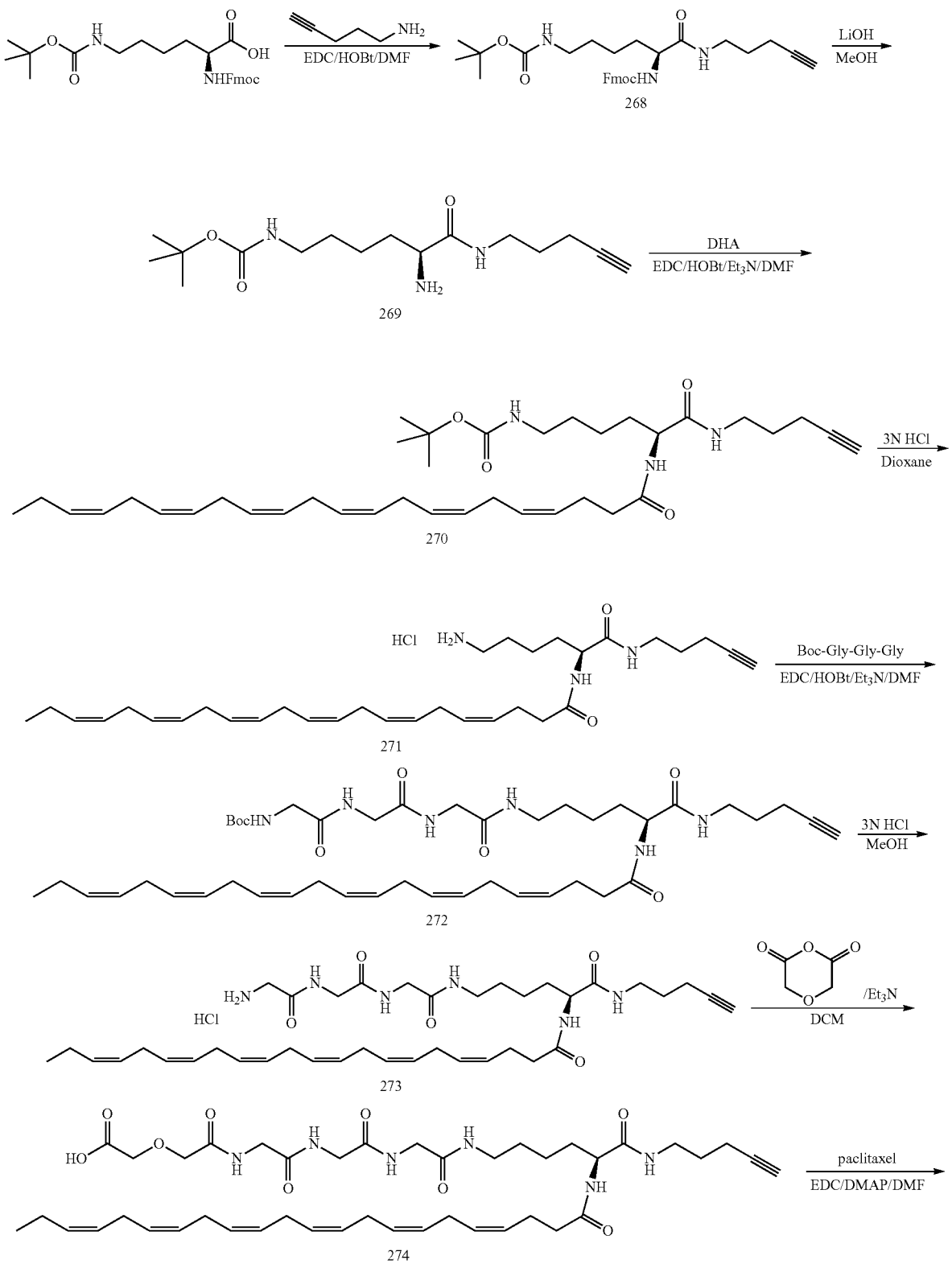

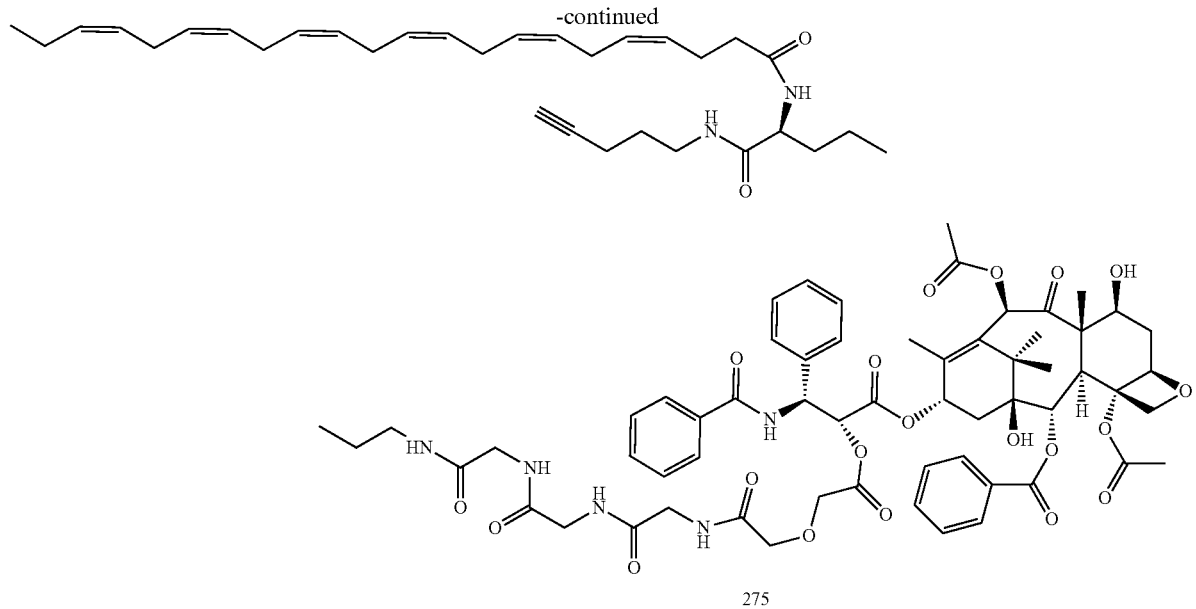
275

Sample 268: Preparation of Compound 268

To a 500 mL round-bottom flask charged with 30 g (64.0 mmol) of Nε-Boc-Nα-Fmoc-L-lysine, 13.5 g (70.4 mmol) of 1-ethyl-3-(3-dimethylaminopropyl) carbodiimide (EDC), 9.5 g (70.4 mmol) of 1-hydroxybenzotriazole (HOBt) in 100 mL of dry DMF, 5.1 g (64.0 mmol) of 4-alkyn-1-amine was added and stirred at room temperature overnight. Upon completion of reaction, the reaction mixture was partitioned between ethyl acetate (200 mL) and brine (200 mL), the organic phase was further washed with brine twice (200 mL×2), dried over anhydrous MgSO$_4$, filtered, concentrated, and purified on a silica gel column and eluted with methanol in chloroform (0-10%) to provide 22.2 g of compound 268. Yield: 65%.

$^1$H NMR (300 MHz, DMSO-d$_6$, ppm): δ 7.89 (d, J=7.3 Hz, 3H), 7.76 (q, J=2.5 Hz, 2H), 7.42 (t, J=7.2 Hz, 3H), 7.33 (t, J=7.6 Hz, 2H), 6.78 (m, 1H), 4.22 (m, 3H), 3.91 (m, 1H), 3.12 (m, 2H), 2.89 (d, J=6.4 Hz, 2H), 2.77 (t, J=2.8 Hz, 1H), 2.15 (m, 2H), 1.57 (m, 4H), 1.36 (s, 9H), 1.21 (m, 4H); ESI-MS (m/z): calcd for $C_{31}H_{40}N_3O_5$ [M+H]$^+$: 534.3; found: 534.5.

Sample 269: Preparation of Compound 269

To a 500 mL round-bottom flask charged with 20 g (37.5 mmol) of compound 268 in 200 mL of methanol-water (9:1), 3.6 g (150.0 mmol) of lithium hydroxide were added and stirred at room temperature overnight. Upon completion of the reaction, the reaction mixture was extracted with dichloromethane three times (200 mL×3), the organic phases were pooled, dried over anhydrous MgSO$_4$, filtered, concentrated, and purified on a silica gel column and eluted with methanol in chloroform (0-10%) to provide 7.2 g of compound 269. Yield: 61%.

$^1$H NMR (300 MHz, CDCl$_3$, ppm): δ 7.49 (s, 1H), 4.62 (s, 1H), 3.36 (q, J=6.8 Hz, 2H), 3.13 (t, J=7.0 Hz, 2H), 2.23 (m, 2H), 1.99 (t, J=2.4 Hz, 1H), 1.70-1.85 (m, 5H), 1.25-1.60 (m, 13H); ESI-MS (m/z): calcd for $C_{16}H_{30}N_3O_3$ [M+H]$^+$: 312.2; found: 312.3.

Sample 270: Preparation of Compound 270

To a 250 mL round-bottom flask charged with 6.33 g (19.3 mmol) of docosahexaenoic acid (DHA), 4.43 g (23.1 mmol) of 1-ethyl-3-(3-dimethylaminopropyl) carbodiimide (EDC), 3.12 g (4.43 mmol) of 1-hydroxybenzotriazole (HOBt) in 50 mL of dry DMF, 3.4 g (12.2 mmol) of compound 269 and 4.0 mL (28.95 mmol) of triethylamine were added and stirred at room temperature overnight. Upon completion of the reaction, the reaction mixture was partitioned between ethyl acetate (150 mL) and brine (150 mL), the organic phase was further washed with brine twice (100 mL×2), dried over anhydrous MgSO$_4$, filtered, concentrated, and purified on a silica gel column and eluted with methanol in chloroform (0-10%) to provide 10.3 g of compound 270. Yield: 86%.

$^1$H NMR (300 MHz, CDCl$_3$, ppm): δ 6.32 (d, J=7.6 Hz, 1H), 5.35 (m, 12H), 4.67 (m, 1H), 4.38 (m, 3H), 3.37 (m, 2H), 3.23 (m, 2H), 2.89 (m, 10H), 2.379-2.433 (m, 2H), 2.25 (m, 4H), 2.076 (m, 1H), 1.99 (t, J=2.8 Hz, 1H), 1.70-1.87 (m, 6H), 1.30-1.70 (m, 14H), 0.97 (t, J=7.2 Hz, 3H). ESI-MS (m/z): calcd for $C_{38}H_{60}N_3O_4$ [M+H]$^+$: 622.4; found: 622.6.

Sample 271: Preparation of Compound 271

To a 250 mL round-bottom flask charged with 10.0 g (16.1 mmol) of compound 270, 50 mL of hydrochloride ethanol solution (3.0N) was added and stirred at room temperature overnight. After removal of volatiles, the residue was purified on a reverse phase C-18 column and eluted with acetonitrile in water (10-80%) to provide 7.47 g of compound 271. Yield: 89%.

$^1$H NMR (300 MHz, DMSO-d$_6$, ppm): δ 7.95 (m, 5H), 5.35 (m, 12H), 4.17 (m, 1H), 3.12 (m, 2H), 2.60-2.93 (m, 12H), 2.00-2.40 (m, 8H), 1.20-1.70 (m, 9H), 0.91 (t, J=7.2 Hz, 3H); ESI-MS (m/z): calcd for $C_{33}H_{52}N_3O_2$ [M+H]$^+$: 522.4; found: 522.7.

Sample 272: Preparation of Compound 272

To a 500 mL round-bottom flask charged with 7.76 g (26.82 mmol) of Boc-Gly-Gly-Gly, 6.69 g (34.88 mmol) of 1-ethyl-3-(3-dimethylaminopropyl) carbodiimide (EDC), 4.72 g (34.88 mmol) of 1-hydroxybenzotriazole (HOBt) in 100 mL of dry DMF, 15.0 g (26.82 mmol) of compound 271 and 9.6 mL (53.64 mmol) of triethylamine were added and stirred at room temperature overnight. Upon completion of the reaction, the reaction mixture was partitioned between ethyl acetate (200 mL) and brine (200 mL), the organic phase was further washed with brine twice (150 mL×2), dried over anhydrous MgSO$_4$, filtered, concentrated, and purified on a silica gel column and eluted with methanol in chloroform (0-15%) to provide 15.9 g of compound 272. Yield: 75%.

$^1$H NMR (300 MHz, CDCl$_3$+CD$_3$OD, ppm): 8; 5.35 (m, 12H), 4.23 (m, 1H), 3.75-4.10 (m, 6H), 3.31 (m, 2H), 3.23 (m, 2H), 2.89 (m, 10H), 2.20-2.45 (m, 6H), 2.15 (m, 4H), 1.98 (s, 1H), 1.71 (m, 3H), 1.20-1.60 (m, 16H), 0.97 (t, J=7.6 Hz, 3H); ESI-MS (m/z): calcd for C$_{44}$H$_{69}$N$_6$O$_7$ [M+H]$^+$: 793.5; found: 793.8.

Sample 273: Preparation of Compound 273

To a 250 mL round-bottom flask charged with 9.0 g (11.35 mmol) of compound 272, 60 mL of hydrochloride ethanol solution (3.0 N) was added and stirred at room temperature overnight. After removal of volatiles, the residue was purified on a reverse phase C-18 column and eluted with acetonitrile in water (10-80%) to provide 7.86 g of compound 273. Yield: 71%.

$^1$H NMR (300 MHz, CD$_3$OD, ppm): δ 5.37 (m, 12H), 4.25 (m, 1H), 4.03 (s, 2H), 3.85 (s, 2H), 3.80 (s, 2H), 3.22 (m, 4H), 2.85 (m, 10H), 2.00-2.50 (m, 9H), 1.76 (m, 4H), 1.63 (m, 2H), 1.47 (m, 2H), 0.98 (t, J=7.2 Hz, 3H); ESI-MS (m/z): calcd for C$_{39}$H$_{61}$N$_6$O$_5$ [M+H]$^+$: 693.5; found: 693.7.

Sample 274: Preparation of Compound 274

To a 250 mL round-bottom flask charged with 5.0 g (7.22 mmol) of compound 273 in 50 mL of anhydrous DMF, 3.5 mL (25.0 mmol) of triethylamine and 2.43 g (21.66 mmol) of diglycolic acid anhydride were added and stirred at room temperature overnight. After removal of volatiles, the residue was partitioned between ethyl acetate (200 mL) and 3.0 N hydrochloride (200 mL), and the aqueous solution was further with 3.0 N hydrochloride twice (100 mL×2), dried over anhydrous MgSO$_4$, filtered, concentrated, and purified on a silica gel column and eluted with methanol in chloroform (0-30%) to provide 3.05 g of compound 274. Yield: 52%.

$^1$H NMR (300 MHz, DMSO-d$_6$, ppm): δ 7.50-8.20 (m, 6H), 5.33 (m, 12H), 4.00-4.20 (m, 5H), 3.50-4.00 (m, 6H), 3.32 (m, 4H), 2.82 (m, 10H), 2.00-2.45 (m, 8H), 1.10-1.70 (m, 8H), 0.93 (t, J=7.2 Hz, 3H); ESI-MS (m/z): calcd for C$_{43}$H$_{65}$N$_6$O$_9$ [M+H]$^+$: 809.5; found: 809.9.

Sample 275: Preparation of Compound 275

To a 100 mL round-bottom flask charged with 100 mg (0.13 mmol) of compound 274 and 60 mg (0.13 mmol) of 1-ethyl-3-(3-dimethylaminopropyl) carbodiimide (EDC) in 5.0 mL of dry DMF, 263 mg (0.31 mmol) of paclitaxel and 38 mg (0.31 mmol) of DMAP were added, and the reaction mixture was stirred at room temperature for 24 hours. Upon completion of the reaction, the reaction mixture was partitioned between ethyl acetate (100 mL) and brine (100 mL); the aqueous phase was extracted with ethyl acetate (50 mL×2), and the organic phases were pooled, dried over anhydrous MgSO$_4$, filtered, concentrated, and purified on a reverse phase C-18 column and eluted with acetonitrile in water (30-100%) to provide 112 mg of compound 275. Yield: 53%.

$^1$H NMR (500 MHz, CDCl$_3$+CD$_3$OD, ppm): δ 8.12 (d, J=7.2 Hz, 2H), 7.00-8.00 (m, 14H), 6.21 (s, 1H), 6.14 (m, 1H), 5.93 (m, 1H), 5.63 (d, J=9.6 Hz, 1H), 5.51 (d, J=7.1 Hz, 1H), 5.35 (m, 12H), 4.98 (d, J=9.6 Hz), 4.00-5.00 (m, 5H), 3.50-4.00 (m, 8H), 3.20-3.40 (m, 4H), 2.83 (m, 10H), 2.00-2.50 (m, 17H), 1.00-2.00 (m, 22H), 0.93 (t, J=7.2 Hz, 3H); ESI-MS (m/z): calcd for C$_{90}$H$_{114}$N$_7$O$_{22}$ [M+H]$^+$: 1644.8; found: 1645.1.

Synthetic Scheme 76

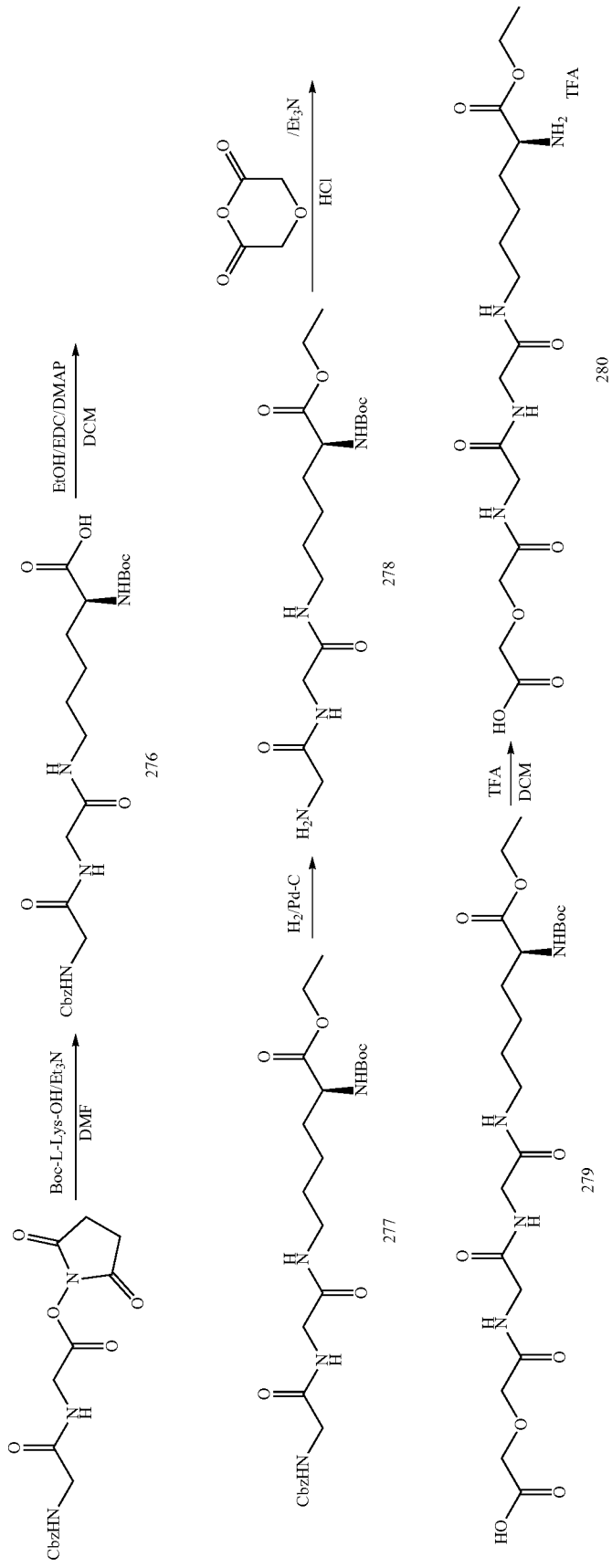

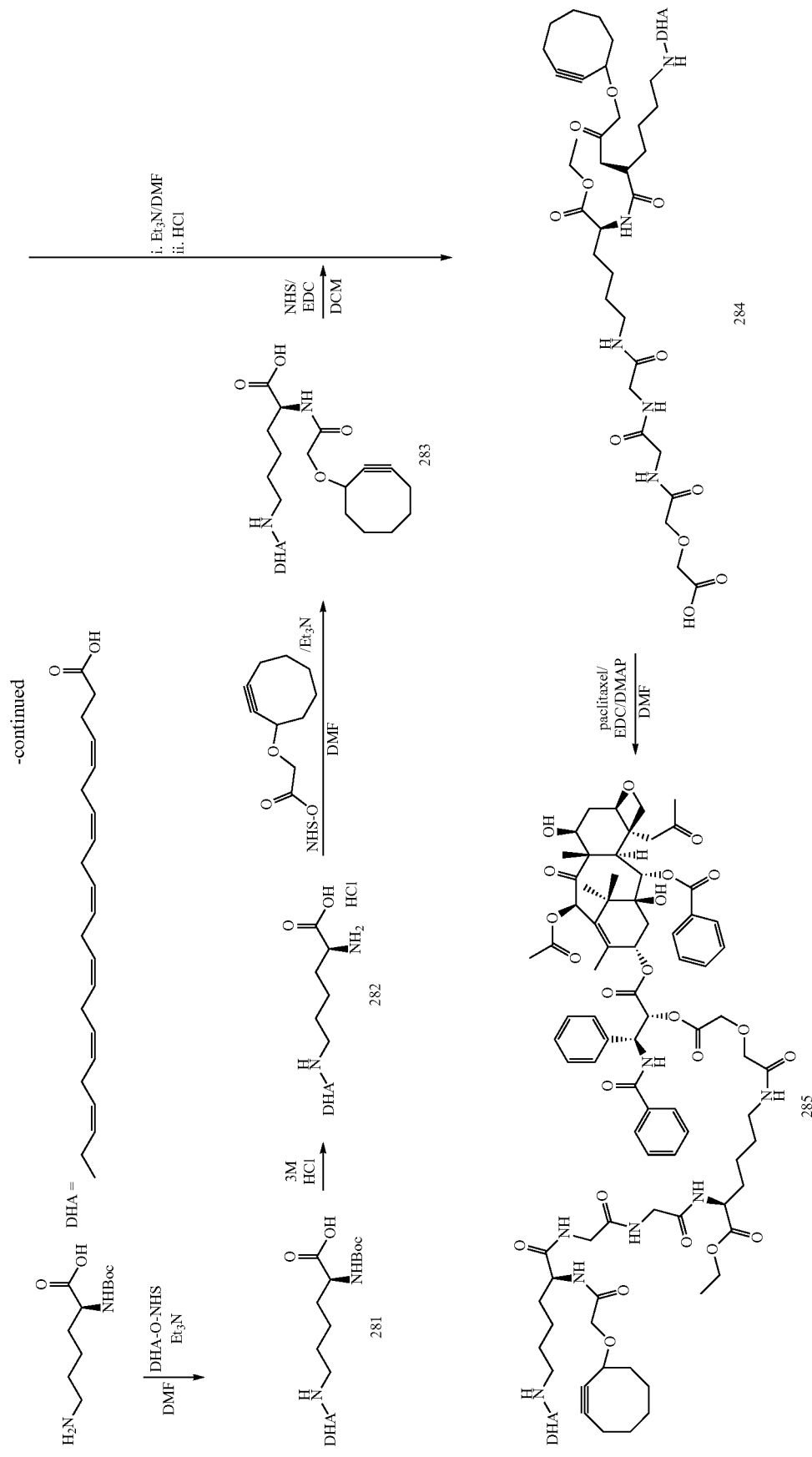

Sample 276: Preparation of Compound 276

To a 1000 mL round-bottom flask charged with 30.0 g (121.9 mmol) of $N_6$-Boc-L-lysine and 33 mL (143 mmol) of triethylamine in 100 mL of DMF, 44.2 g (121.9 mmol) of Cbz-Gly-Gly N-hydroxy-succinimide ester in DMF was dropwise added and stirred at room temperature overnight; After removal of volatiles, the residue was partitioned between ethyl acetate (300 mL) and 3N HCl solution (300 mL); and the organic phases were further washed with 3N HCl solution twice (150 mL×2), dried over anhydrous $MgSO_4$, filtered, concentrated, and purified on a silica gel column and eluted with methanol in chloroform (0-20%) to provide 33.8 g of compound 276. Yield: 56%.

$^1$H NMR (300 MHz, DMSO-$d_6$, ppm): δ 8.12 (s, 1H), 7.75 (s, 1H), 7.36 (t, J=5.2 Hz, 1H), 7.32 (m, 5H), 7.02 (d, J=7.6 Hz, 1H), 5.04 (s, 2H), 3.83 (m, 1H), 3.67 (m, 4H), 3.05 (m, 2H), 1.50-1.70 (m, 2H), 1.20-1.40 (m, 13H); ESI-MS (m/z): calcd for $C_{23}H_{35}N_4O_8$ [M+H]$^+$: 495.3; found: 495.5.

Sample 277: Preparation of Compound 277

To a 250 mL round-bottom flask charged with 25.0 g (50.6 mmol) of compound 276 and 14.6 g (75.9 mmol) of 1-ethyl-3-(3-dimethylaminopropyl) carbodiimide (EDC) in 300 ml of anhydrous dichloromethane, 10.0 mL of absolute ethanol and 9.3 g (75.9 mmol) of DMAP were added, and stirred at room temperature overnight. After removal of volatiles, the residue was partitioned between ethyl acetate (200 mL) and brine (200 mL), and the organic phase was washed with brine (100 mL×2), dried over anhydrous $MgSO_4$, filtered, concentrated, and purified on a silica gel column and eluted with methanol in dichloromethane (0-10%) to provide 19.1 g of compound 277. Yield: 72%.

$^1$H NMR (300 MHz, DMSO-$d_6$, ppm): δ 8.12 (t, J=5.2 Hz, 1H), 7.75 (t, J=5.2 Hz, 1H), 7.51 (t, J=5.2 Hz, 1H), 7.37 (m, 5H), 7.17 (d, J=7.6 Hz, 1H), 5.04 (s, 2H), 4.10 (m, 2H), 3.88 (m, 1H), 3.68 (m, 4H), 3.07 (m, 2H), 1.50-1.70 (m, 2H), 1.20-1.40 (m, 13H), 1.14 (t, J=7.2 Hz, 3H); ESI-MS (m/z): calcd for $C_{25}H_{39}N_4O_8$ [M+H]$^+$: 523.3; found: 523.6.

Sample 278: Preparation of Compound 278

In a 500 mL round-bottom flask, 26.0 g (49.8 mmol) of compound 277 was dissolved in 250 mL of anhydrous ethanol, followed by addition of 3.0 g of Pd—C and bubbled with hydrogen gas for 5 hours. Upon completion of the reaction, Pd—C was filtered off, and the filtrate was concentrated, purified on a reverse phase C-18 column and eluted with acetonitrile in water (10-70%) to provide 15.7 g of compound 278. Yield: 81%.

$^1$H NMR (300 MHz, DMSO-$d_6$, ppm): δ 8.10 (s, 1H), 7.86 (t, J=5.2 Hz, 1H), 7.19 (t, J=5.2 Hz, 1H), 4.11 (m, 2H), 4.05 (s, 2H), 3.88 (m, 1H), 3.69 (m, 4H), 3.05 (m, 2H), 1.50-1.70 (m, 2H), 1.20-1.40 (m, 13H), 1.16 (t, J=7.2 Hz, 3H); ESI-MS (m/z): calcd for $C_{17}H_{33}N_4O_6$ [M+H]$^+$: 389.2; found: 389.3.

Sample 279: Preparation of Compound 279

To a 500 mL round-bottom flask charged with 10.0 g (5.95 mmol) of compound 278 in 50 mL of anhydrous acetonitrile, 11.0 mL (77.26 mmol) of triethylamine and 8.67 g (77.26 mmol) of diglycolic acid anhydride were added and stirred at room temperature overnight. After removal of volatiles, the residue was partitioned between ethyl acetate (200 mL) and 3.0 N hydrochloride (200 mL), and the organic phase was further with 3.0 N hydrochloride twice (100 mL×2), dried over anhydrous $MgSO_4$, filtered, concentrated, and purified on a reverse phase C-18 column and eluted with acetonitrile in water (5-70%) to provide 8.05 g of compound 279. Yield: 62%.

$^1$H NMR (300 MHz, $D_2O$, ppm): δ 4.24 (m, 3H), 4.21 (s, 2H), 4.04 (m, 1H), 3.98 (s, 2H), 3.81 (s, 1H), 3.16 (m, 2H), 1.85 (m, 1H), 1.75 (m, 1H), 1.45 (m, 2H), 1.28 (m, 11H), 1.17 (t, J=7.2 Hz, 3H); ESI-MS (m/z): calcd for $C_{21}H_{37}N_4O_{10}$ [M+H]$^+$: 505.2; found: 505.3.

Sample 280: Preparation of Compound 280

In a 500 mL round-bottom flask, 17.0 g (33.71 mmol) of compound 279 was dissolved in 100 mL of 30% trifluoro-acetic acid in dichloromethane and stirred overnight. After removal of volatiles, the residue was purified on a reverse phase C-18 column and eluted with acetonitrile in water (5-60%) to provide 11.7 g of compound 280. Yield: 86%.

$^1$H NMR (300 MHz, DMSO-$d_6$, ppm): δ 8.45 (s, 3H), 8.21 (t, J=5.2 Hz, 1H), 8.10 (t, J=5.2 Hz, 1H), 7.77 (t, J=5.2 Hz, 1H), 4.25 (m, 2H), 4.19 (s, 2H), 4.05 (s, 2H), 4.02 (m, 1H), 3.78 (d, J=5.2 Hz, 2H), 3.65 (d, J=5.2 Hz, 2H), 3.06 (m, 2H), 1.78 (m, 2H), 1.43 (m, 4H), 1.21 (t, J=7.2 Hz, 3H); ESI-MS (m/z): calcd for $C_{16}H_{29}N_4O_8$ [M+H]$^+$: 405.2; found: 405.3.

Sample 281: Preparation of Compound 281

To a 1000 mL round-bottom flask charged with 25.0 g (101.5 mmol) of $N_6$-Boc-lysine and 28.1 mL (203 mmol) of triethylamine in 100 mL of DMF, 43.2 g (101.5 mmol) of docosahexaenoic acid (DHA) N-hydroxy-succinimide ester in DMF was dropwise added and stirred at room temperature overnight; After removal of volatiles, the residue was partitioned between ethyl acetate (300 mL) and 3.0N HCl solution (300 mL); and the organic phase was further washed with 3.0 N HCl solution twice (150 mL×2), dried over anhydrous $MgSO_4$, filtered, concentrated, and purified on a silica gel column and eluted with methanol in chlorform (0-10%) to provide 27.7 g of compound 281. Yield: 49%.

$^1$H NMR (300 MHz, DMSO-$d_6$, ppm): δ 7.80 (t, J=5.2 Hz, 1H), 6.32 (d, J=7.6 Hz, 1H), 5.32 (m, 12H), 4.05 (m, 1H), 3.05 (m, 2H), 2.85 (m, 10H), 2.25 (m, 2H), 2.10 (m, 4H), 1.40-1.70 (m, 4H), 1.37 (s, 9H), 1.32 (m, 2H), 0.97 (t, J=7.2 Hz, 3H); ESI-MS (m/z): calcd for $C_{33}H_{53}N_2O_5$ [M+H]$^+$: 557.4; found: 557.7.

Sample 282: Preparation of Compound 282

To a 500 mL round-bottom flask charged with 15.0 g (26.94 mmol) of compound 281, 100 mL of hydrochloride tetrahydrofurane solution (3.0N) was added and stirred at room temperature overnight. After removal of volatiles, the residue was purified on a reverse phase C-18 column and eluted with acetonitrile in water (10-80%) to provide 8.01 g of compound 282. Yield: 65%.

$^1$H NMR (300 MHz, DMSO-$d_6$, ppm): δ 8.29 (s, 3H), 7.82 (t, J=5.2 Hz, 1H), 5.35 (m, 12H), 3.87 (m, 1H), 3.03 (m, 2H), 2.83 (m, 10H), 2.27 (m, 2H), 2.10 (m, 4H), 1.79 (m, 2H), 1.37 (m, 4H), 0.92 (t, J=7.2 Hz, 3H); ESI-MS (m/z): calcd for $C_{28}H_{45}N_2O_3$ [M+H]$^+$: 457.3; found: 457.5.

Sample 283: Preparation of Compound 283

To a 250 mL round-bottom flask charged with 7.0 g (14.16 mmol) of compound 282 and 4.9 mL (35.4 mmol) of triethylamine in 35 mL of DMF, 4.18 g (15.0 mmol) of 2-(cyclooct-2-ynyloxy) acetic acid N-hydroxy-succinimide ester in DMF was dropwise added and stirred at room temperature overnight; After removal of volatiles, the residue was partitioned between ethyl acetate (300 mL) and 3N HCl solution (300 mL); and the organic phase was further washed with 3.0N HCl solution twice (150 mL×2), dried over anhydrous $MgSO_4$, filtered, concentrated, and purified on a silica gel column and eluted with methanol in chlorform (0-10%) to provide 3.7 g of compound 283. Yield: 43%.

$^1$H NMR (300 MHz, DMSO-$d_6$, ppm): δ 7.92 (t, J=5.2 Hz, 1H), 7.57 (s, 1H), 5.36 (m, 12H), 4.30 (m, 2H), 4.06 (m, 2H), 3.88 (m, 1H), 3.03 (m, 2H), 2.87 (m, 10H), 2.15 (m, 2H), 2.05 (m, 4H), 1.45-2.00 (m, 10H), 1.27 (m, 4H), 1.22 (m, 3H), 0.95 (t, J=7.2 Hz, 3H); ESI-MS (m/z): calcd for $C_{38}H_{57}N_2O_5$ [M+H]$^+$: 621.4; found: 621.5.

Sample 284: Preparation of Compound 284

To a 250 mL round-bottom flask charged with 3.0 g (4.83 mmol) of compound 283, 1.2 g (6.28 mmol) of 1-ethyl-3-(3-dimethylaminopropyl) carbodiimide (EDC), and 723 mg (6.28 mmol) N-hydroxy-succinimide ester, 15.0 mL of anhydrous DMF was added and stirred at room temperature for 5 hours. To a stirred solution of compound 280 and 1.8 mL (12.56 mmol) of triethylamine in DMF, the above reaction mixture was dropwise added, and the final reaction mixture was stirred at room temperature overnight. After removal of volatiles, the residue the residue was partitioned between ethyl acetate (100 mL) and 3.0N HCl solution (100 mL); and the organic phases were further washed with 3.0N HCl solution twice (100 mL×2), dried over anhydrous MgSO$_4$, filtered, concentrated, and purified on a silica gel column and eluted with methanol in chlorform (0-30%) to provide 1.61 g of compound 284. Yield: 33%.

$^1$H NMR (300 MHz, CD$_3$OD, ppm): δ 5.39 (m, 12H), 4.33 (m, 1H), 4.31 (m, 2H), 4.24 (s, 2H), 4.17 (m, 2H), 4.06 (m, 4H), 3.86 (s, 2H), 3.21 (m, 4H), 2.87 (m, 10H), 2.00-2.45 (m, 7H), 1.60-2.00 (m, 10H), 1.35-1.60 (m, 9H), 1.25 (t, J=7.2 Hz, 3H), 0.98 (t, J=7.2 Hz, 3H); ESI-MS (m/z): calcd for $C_{54}H_{83}N_6O_{12}$ [M+H]$^+$: 1007.6; found: 1008.0.

Sample 285: Preparation of Compound 285

To a 100 mL round-bottom flask charged with 150 mg (0.15 mmol) of compound 284 and 71 mg (0.37 mmol) of 1-ethyl-3-(3-dimethylaminopropyl) carbodiimide (EDC) in 5.0 mL of dry DMF, 316 mg (0.37 mmol) of paclitaxel, and 45 mg (0.37 mmol) of DMAP were added, and the reaction mixture was stirred at room temperature for 24 hours. Upon completion of the reaction, the reaction mixture was partitioned between ethyl acetate (50 mL) and brine (50 mL); the aqueous phase was extracted with ethyl acetate (50 mL×2), and the organic phases were pooled, dried over anhydrous MgSO$_4$, filtered, concentrated, and purified on a reverse phase C-18 column and eluted with methanol in water (30-100%) to provide 86 mg of compound 285. Yield: 31%.

$^1$H NMR (500 MHz, CDCl$_3$+CD$_3$OD, ppm): δ 8.07 (d, J=7.2 Hz, 2H), 7.00-8.00 (m, 14H), 6.26 (s, 1H), 6.07 (m, 1H), 5.61 (m, 1H), 5.49 (d, J=7.1 Hz, 1H), 5.33 (m, 12H), 4.92 (d, J=9.6 Hz, 1H), 4.00-4.60 (m, 15H), 3.50-4.00 (m, 4H), 3.19 (m, 4H), 2.78 (m, 10H), 2.00-2.50 (m, 17H), 1.50-2.00 (m, 15H), 1.10-1.50 (m, 12H), 0.70-1.00 (m, 9H); ESI-MS (m/z): calcd for $C_{101}H_{132}N_7O_{25}$ [M+H]$^+$: 1842.9; found: 1843.2.

Part 7. Preparative of Taxane-Lipid-Polysaccharide Drual Conjugates

Synthetic Scheme 77

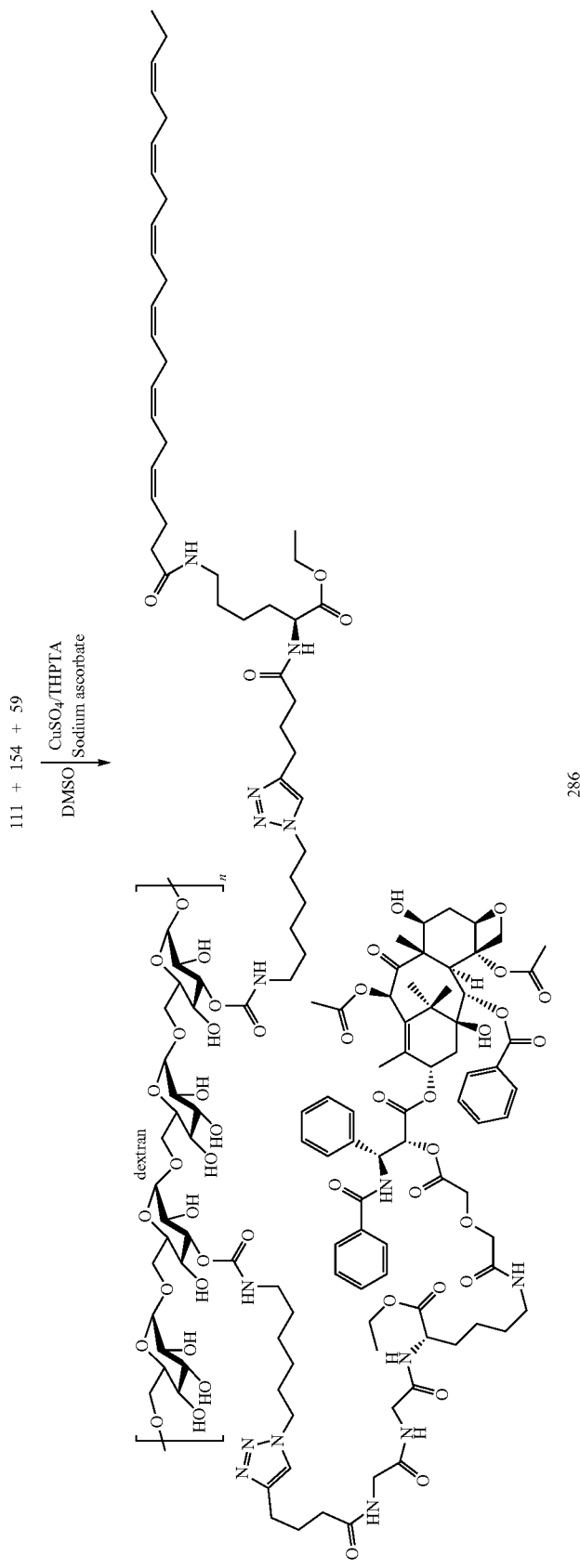

Sample 286: Preparation of Dual Conjugate 286

In a 25 mL round bottom flask, 600 mg of functionalized dextran 111, 120 mg (0.08 mmol) of compound 59 and 46 mg (0.08 mmol) of compound 154 were dissolved in 2.0 mL of DMSO, and followed by addition of copper sulfate solution (100 uL×1.0 M), THPTA (Tris (3-hydroxypropyl-triazolylmethyl) amine, 100 uL×1.0 M) and sodium ascorbate solution (30 uL×1.0 M), and were stirred at room temperature for 2 days. Upon completion of the reaction, the reaction mixture was precipitated with methanol, filtered, and washed with methanol three times. The precipitate was then dissolved in 2.0 mL of distilled water, dialyzed against distilled water, and lyophilized to offer 379 mg of conjugate 286. By comparing its UV absorption with that of compound 61 and compound 151 at wavelength of 280 nm, 11% (w/w) paclitaxel content was determined in conjugate 286.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.10-8.50 (m, CONH, ArH), 5.32 (m, CH), 1.23 (m, CH$_3$), 1.00 (m, CH$_3$).

Synthetic Scheme 78

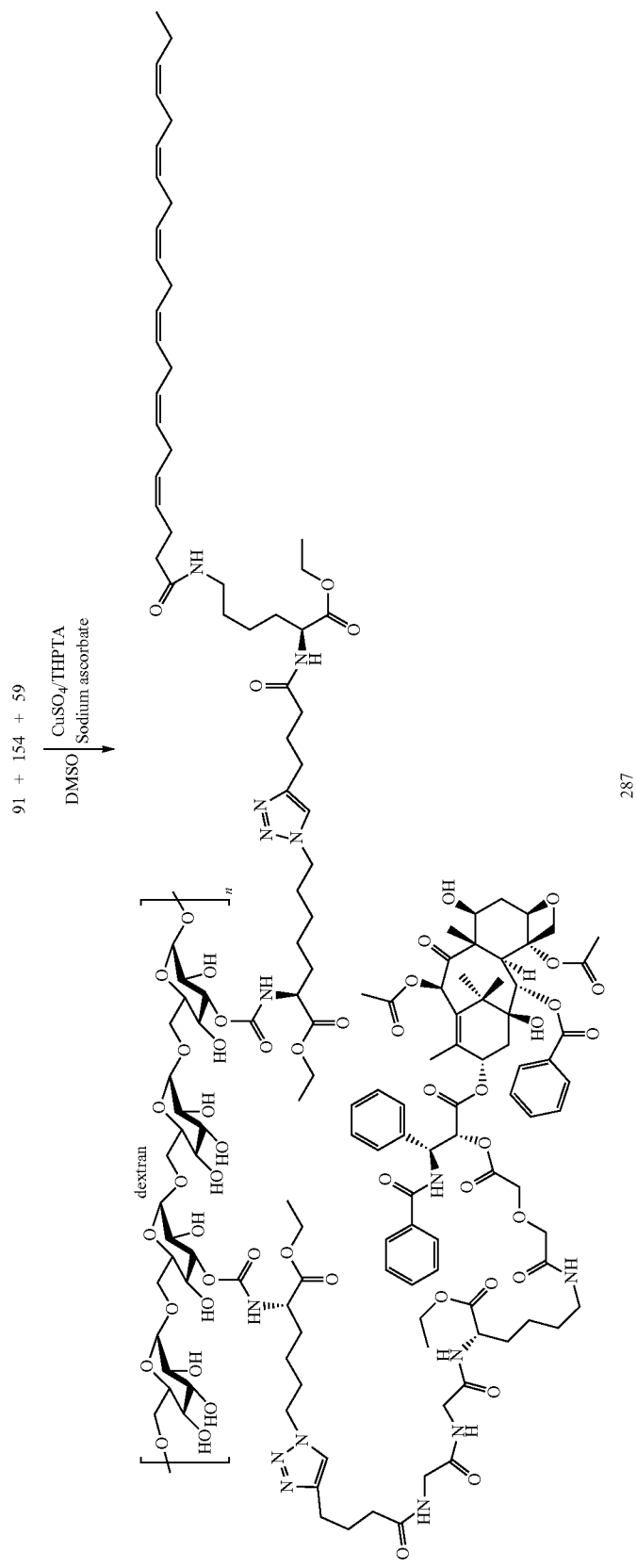

Sample 287: Preparation of Dual Conjugate 287

The preparation of conjugate 287 is similar to that of conjugate 286.

By comparing its UV absorption with that of compound 61 and compound 155 at wavelength of 280 nm, 6% (w/w) paclitaxel content was determined in conjugate 287.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.10-8.50 (m, CONH, ArH), 5.32 (m, CH), 1.23 (m, CH$_3$), 0.99 (m, CH$_3$).

Synthetic Scheme 79

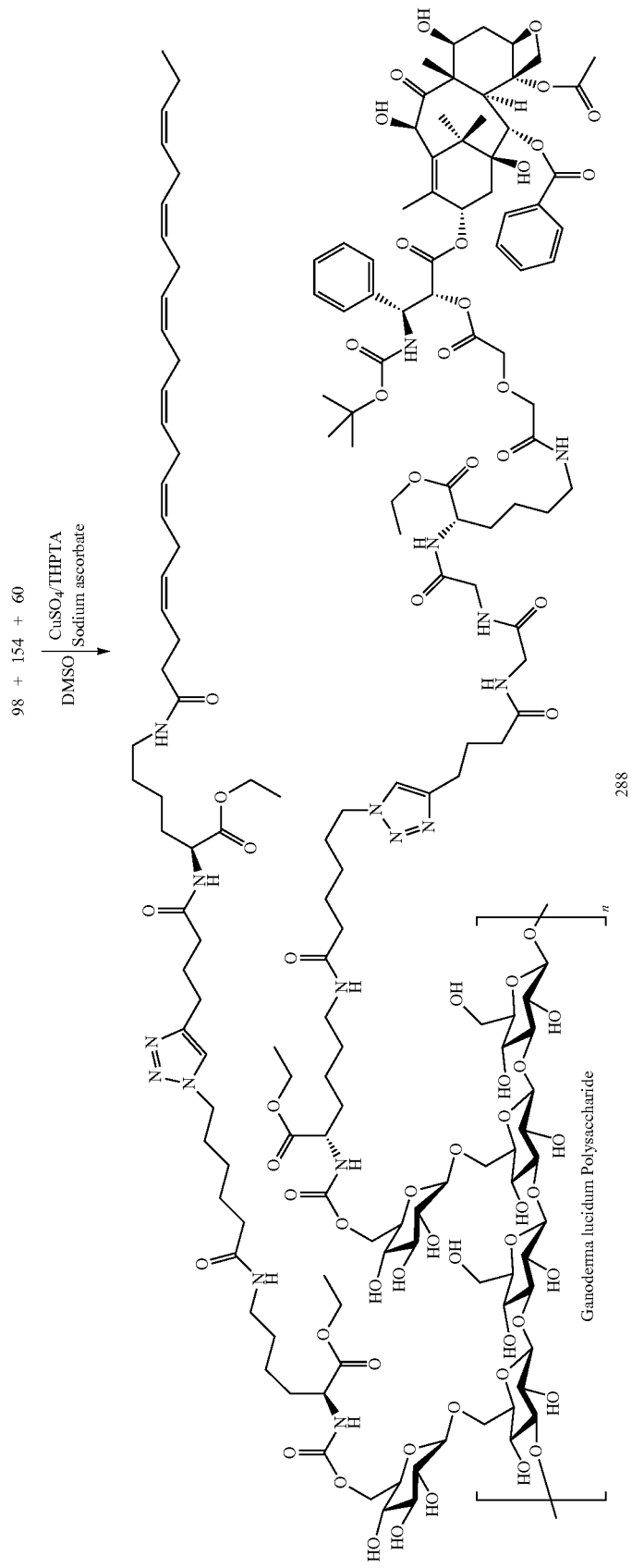

Sample 288: Preparation of Dual Conjugate 288

The preparation of conjugate 288 is similar to that of conjugate 286.

By comparing its UV absorption with that of compound 62 and compound 154 at wavelength of 280 nm, 9% (w/w) docetaxel content was determined in conjugate 288.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.10-8.50 (m, CONH, ArH), 5.32 (m, CH), 1.23 (m, CH$_3$), 1.00 (m, CH$_3$).

Synthetic Scheme 80

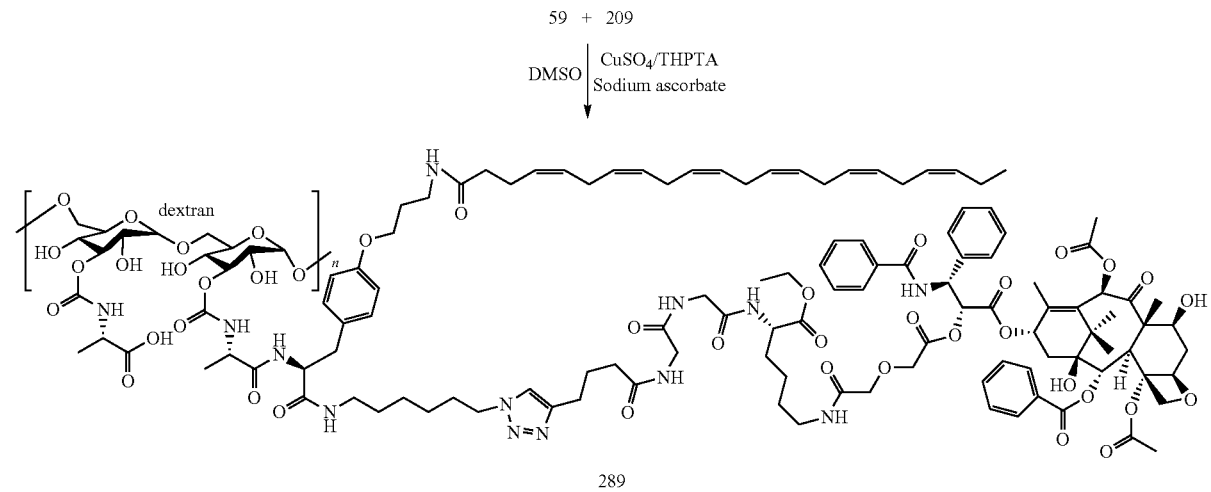

Sample 289: Preparation of Dual Conjugate 289

The preparation of conjugate 289 is similar to that of conjugate 286.

By comparing its UV absorption with that of compound 61 and compound 209 at wavelength of 280 nm, 6% (w/w) paclitaxel content was determined in conjugate 289.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.75-8.50 (m, CONH, ArH), 5.32 (m, CH), 1.23 (m, CH$_3$), 0.99 (m, CH$_3$).

Synthetic Scheme 81

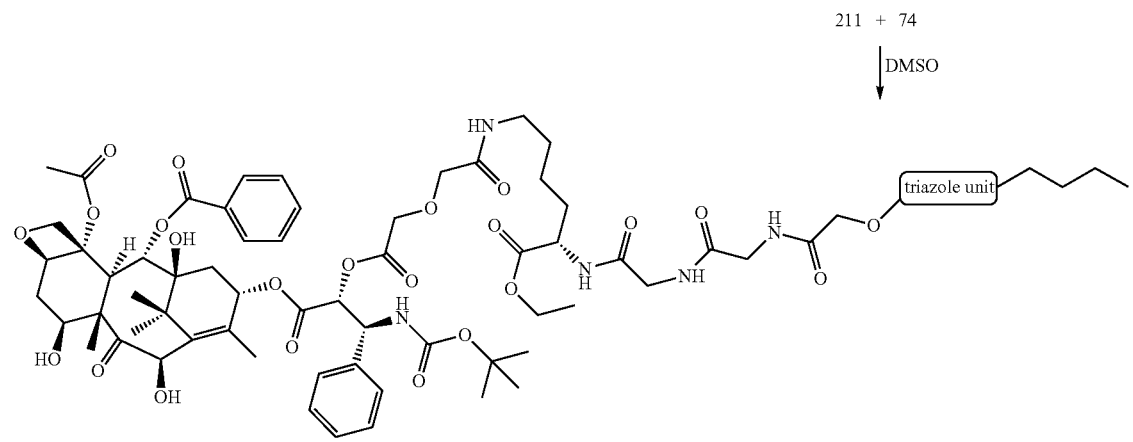

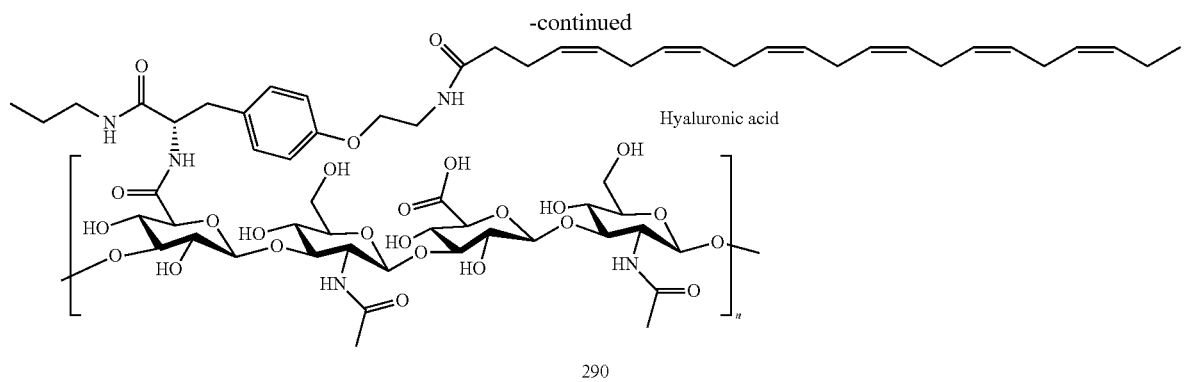

290

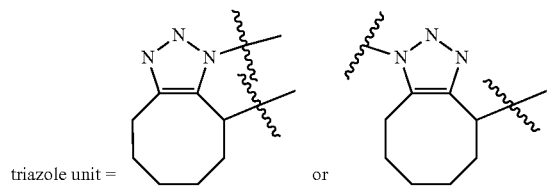

triazole unit =

Sample 290: Preparation of Dual Conjugate 290

In a 25 mL round bottom flask, 300 mg of conjugate 211 and 50 mg (0.07 mmol) of compound 74 were dissolved in 5.0 mL of DMSO, and stirred at room temperature for 3 days. Upon completion of the reaction, the reaction mixture was precipitated with methanol, filtered, and washed with methanol three times. The precipitate was then dissolved in 3.0 mL of distilled water, dialyzed against distilled water, and lyophilized to give 271 mg of conjugate 290. By comparing its UV absorption with that of compound 76a (76b) and functionalized hyaluronic acid 211 at wavelength of 280 nm, 9% (w/w) docetaxel content was determined in conjugate 290.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.10-8.50 (m, CONH, ArH), 5.32 (m, CH), 2.03 (m, CH$_3$CO), 1.35 (s, OC (CH$_3$) 3), 1.23 (m, CH$_3$), 1.00 (m, CH$_3$).

Synthetic Scheme 82

59 + 214

DMSO | CuSO$_4$/THPTA
Sodium ascorbate

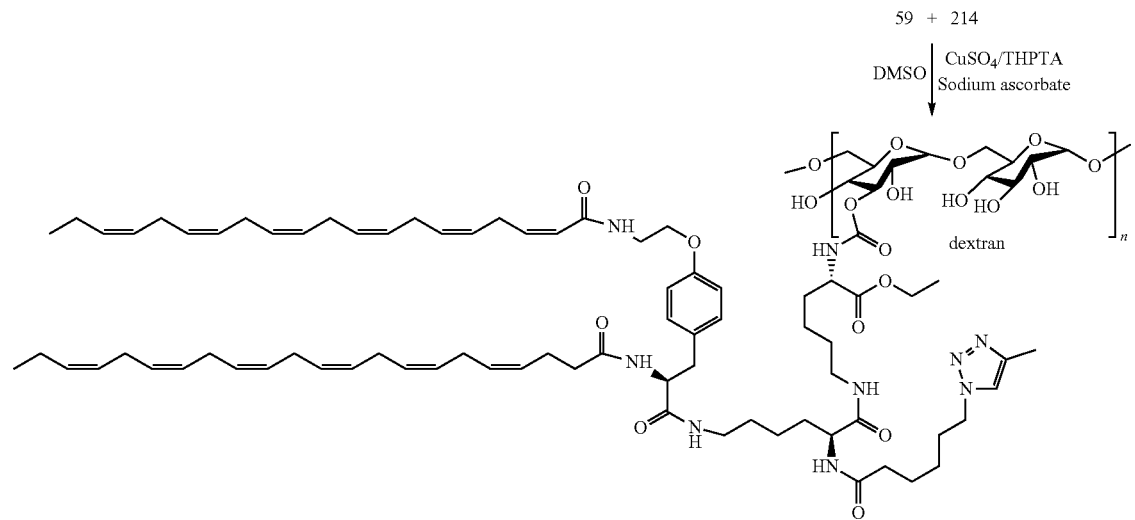

-continued

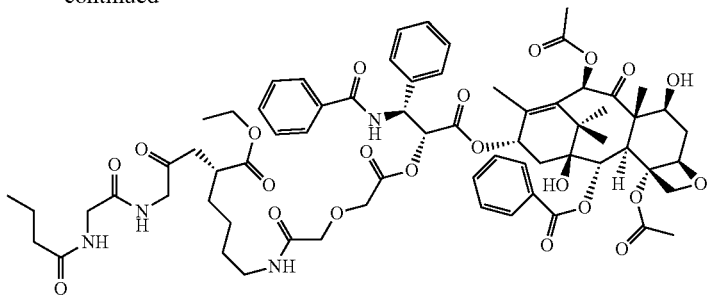

291

Sample 291: Preparation of Dual Conjugate 291

The preparation of conjugate 291 is similar to that of conjugate 286.

By comparing its UV absorption with that of compound 61 and conjugate 214 at wavelength of 280 nm, 7% (w/w) paclitaxel content was determined in conjugate 291.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.50 (m, CONH, ArH), 5.32 (m, CH), 2.03 (m, CH$_3$CO), 1.35 (s, OC (CH$_3$) 3), 1.23 (m, CH$_3$), 1.00 (m, CH$_3$).

Synthetic Scheme 83

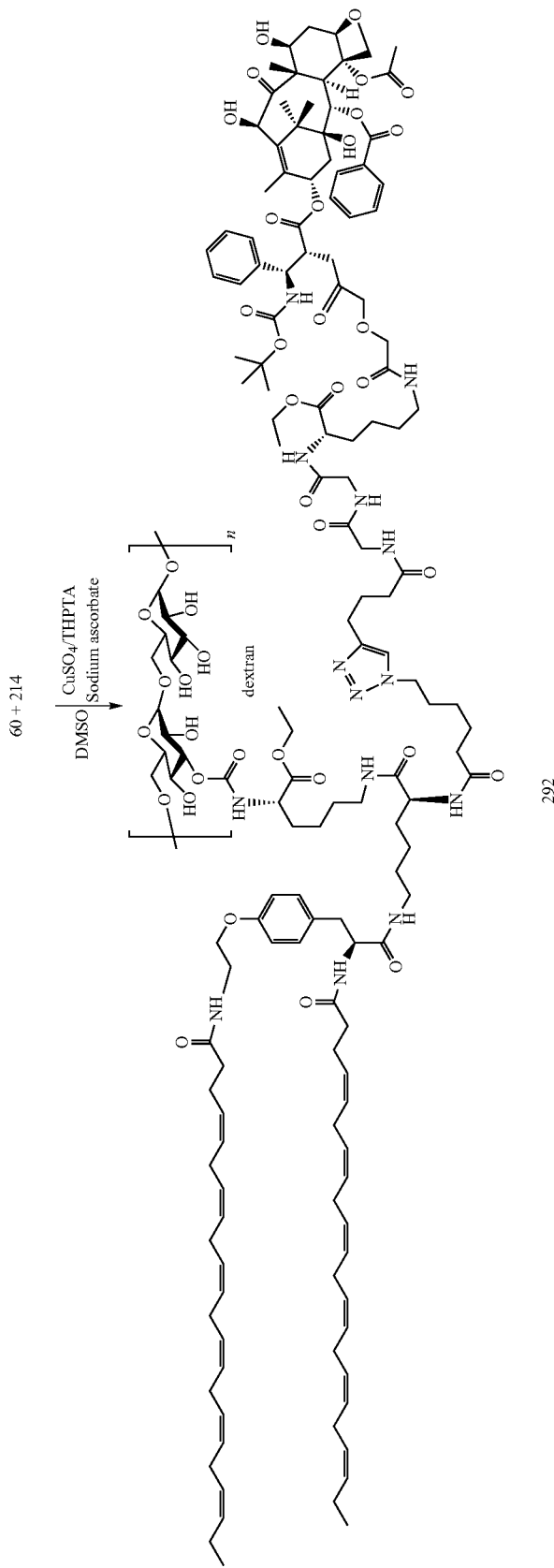

Sample 292: Preparation of Dual Conjugate 292

The preparation of conjugate 292 is similar to that of conjugate 286.

By comparing its UV absorption with that of compound 62 and conjugate 214 at wavelength of 280 nm, 11% (w/w) docetaxel content was determined in conjugate 292.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 5.32 (m, CH), 1.33 (s, OC (CH$_3$) 3), 1.22 (m, CH$_3$), 0.99 (m, CH$_3$).

Synthetic Scheme 84

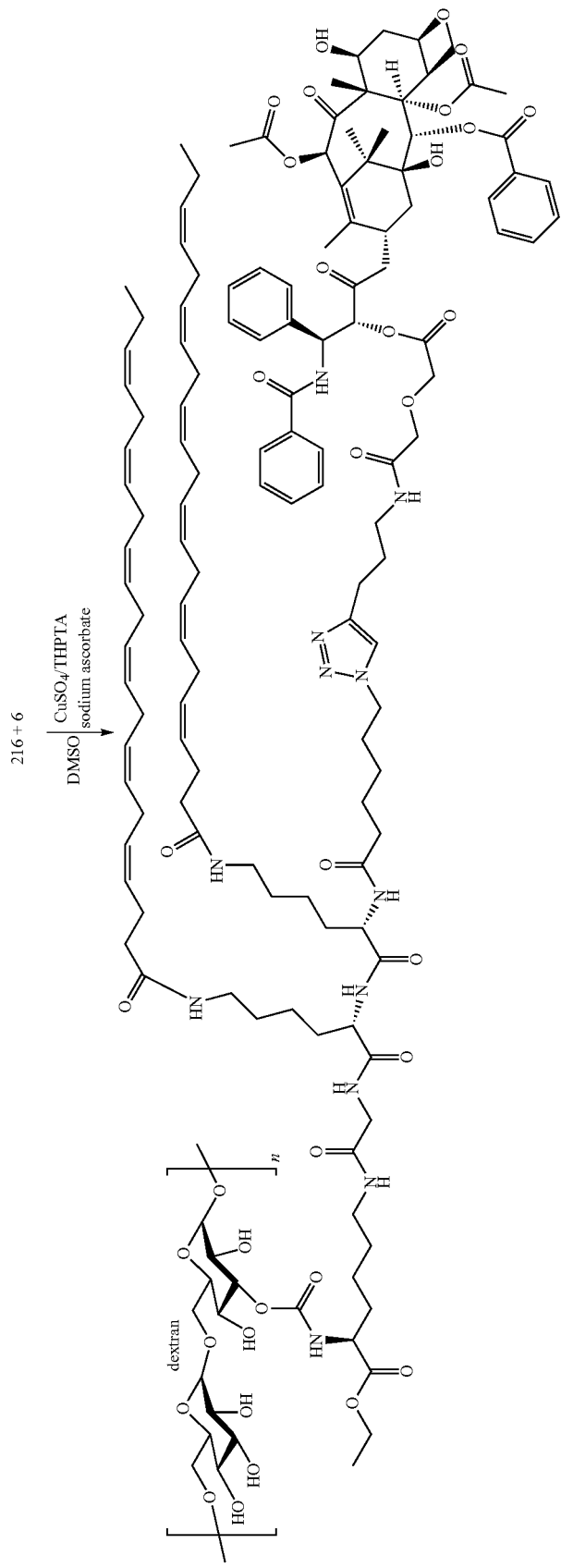

Sample 293: Preparation of Dual Conjugate 293

The preparation of conjugate 293 is similar to that of conjugate 286.

By comparing its UV absorption with that of compound 7 and conjugate 216 at wavelength of 280 nm, 9% (w/w) paclitaxel content was determined in conjugate 293.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 5.35 (m, CH), 0.99 (m, CH$_3$).

Synthetic Scheme 85

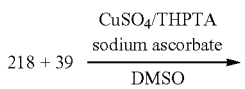

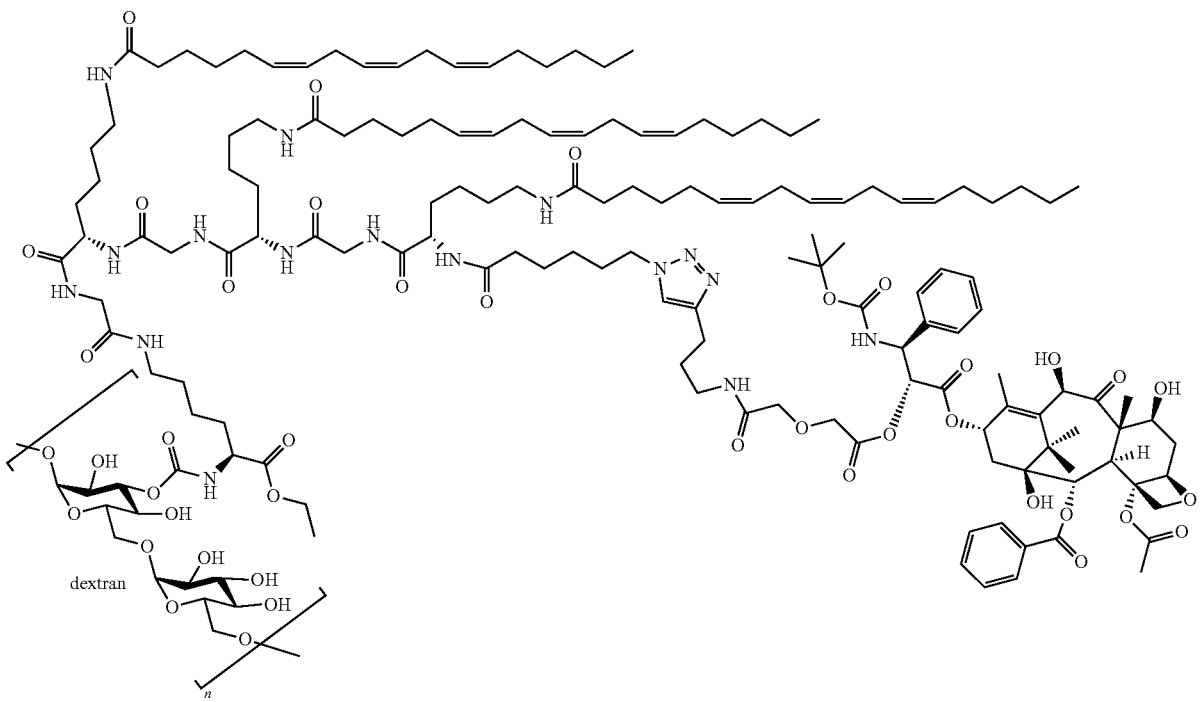

294

Sample 294: Preparation of Dual Conjugate 294

The preparation of conjugate 294 is similar to that of conjugate 286.

By comparing its UV absorption with that of compound 40 and conjugate 218 at wavelength of 280 nm, 5% (w/w) docetaxel content was determined in conjugate 294.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 5.33 (m, CH), 1.34 (s, OC (CH$_3$) 3), 1.00 (m, CH$_3$), 0.83 (m, CH$_3$).

Synthetic Scheme 86

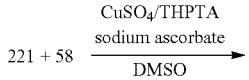

-continued

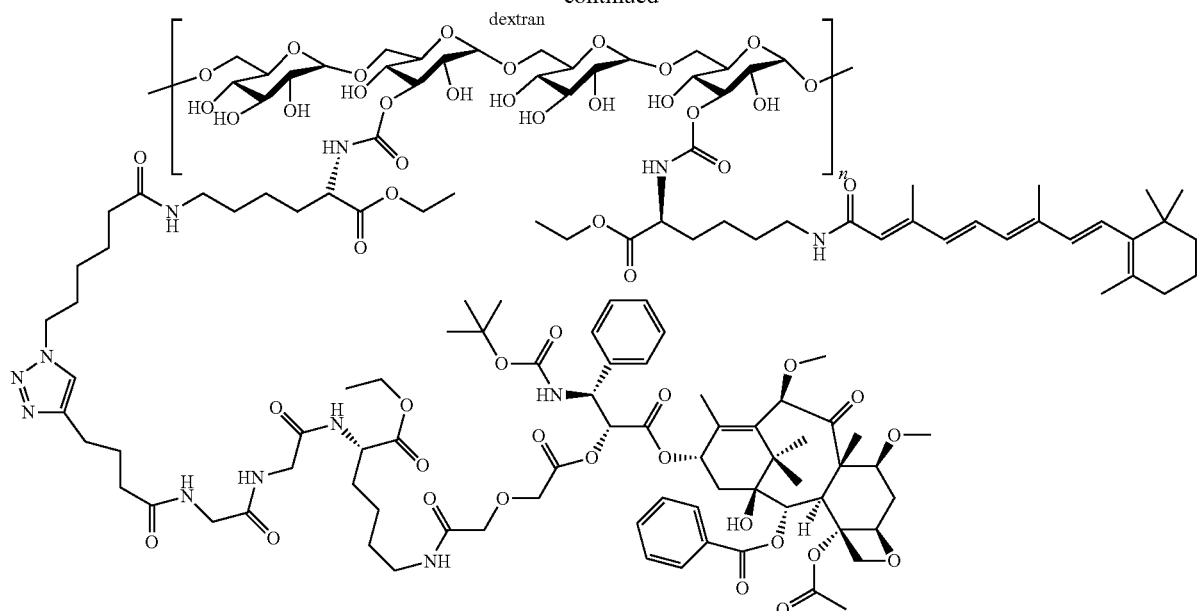

295

Sample 295: Preparation of Dual Conjugate 295

The preparation of conjugate 295 is similar to that of conjugate 286.

By comparing its UV absorption with that of compound 63 and conjugate 221 at wavelength of 280 nm, 6% (w/w) carbazitaxel content was determined in conjugate 295.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 6.25 (m, CH), 1.34 (s, OC (CH$_3$) 3), 1.00 (m, CH$_3$).

Synthetic Scheme 87

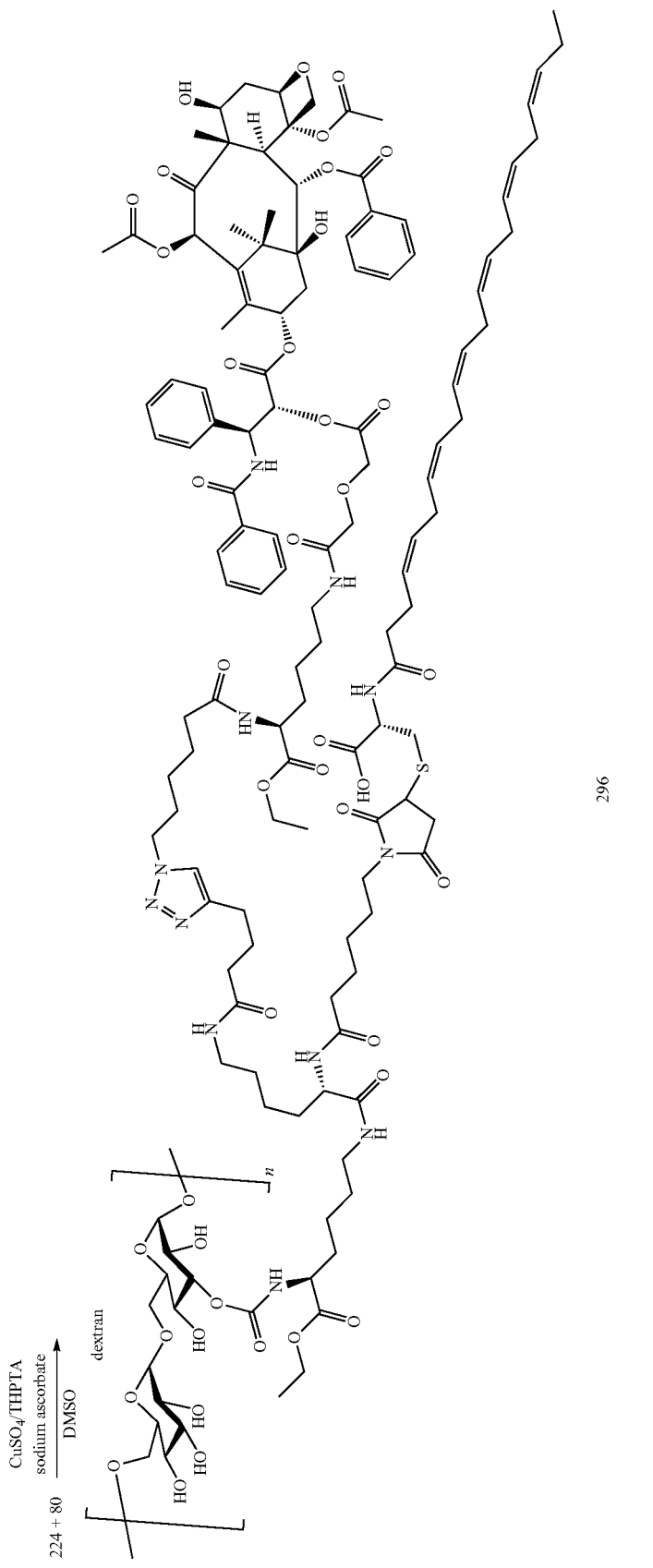

Sample 296: Preparation of Dual Conjugate 296

The preparation of conjugate 296 is similar to that of conjugate 286.

By comparing its UV absorption with that of compound 7 and conjugate 224 at wavelength of 280 nm, 7% (w/w) paclitaxel content was determined in conjugate 296.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 5.35 (m, CH), 1.25 (m, CH$_3$), 1.00 (m, CH$_3$).

Synthetic Scheme 88

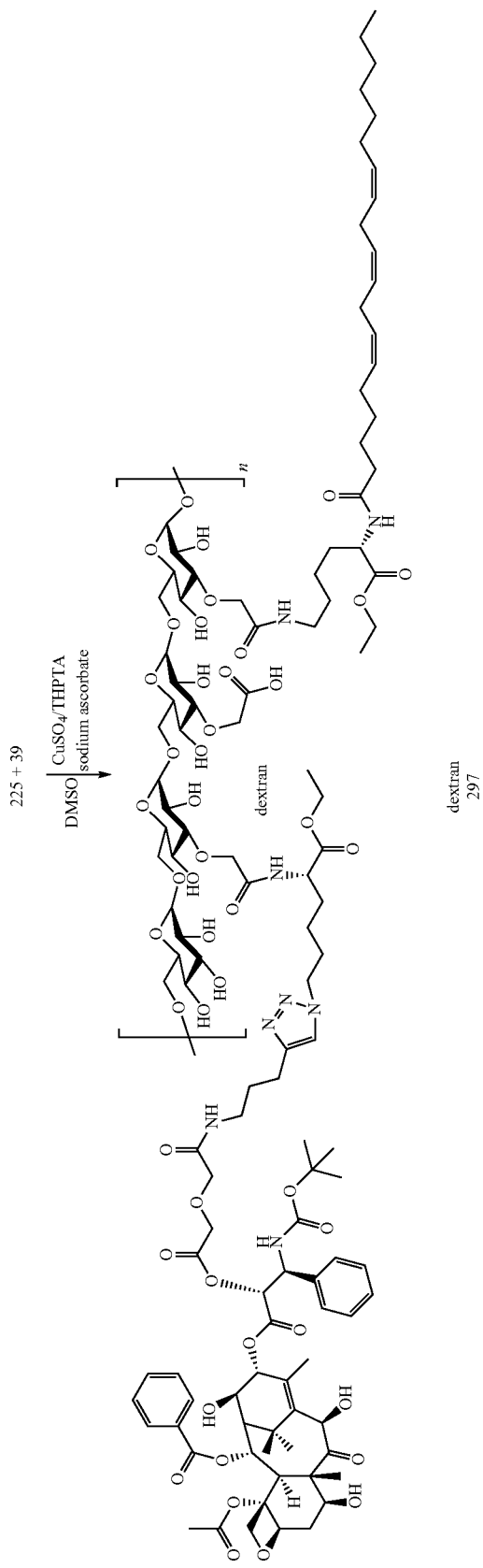

Sample 297: Preparation of Dual Conjugate 297

The preparation of conjugate 297 is similar to that of conjugate 286.

By comparing its UV absorption with that of compound 40 and conjugate 225 at wavelength of 280 nm, 10% (w/w) docetaxel content was determined in conjugate 297.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.10-8.50 (m, CONH, ArH), 5.35 (m, CH), 1.35 (s, OC (CH$_3$) 3), 1.00 (m, CH$_3$), 0.83 (t, CH$_3$).

Synthetic Scheme 89

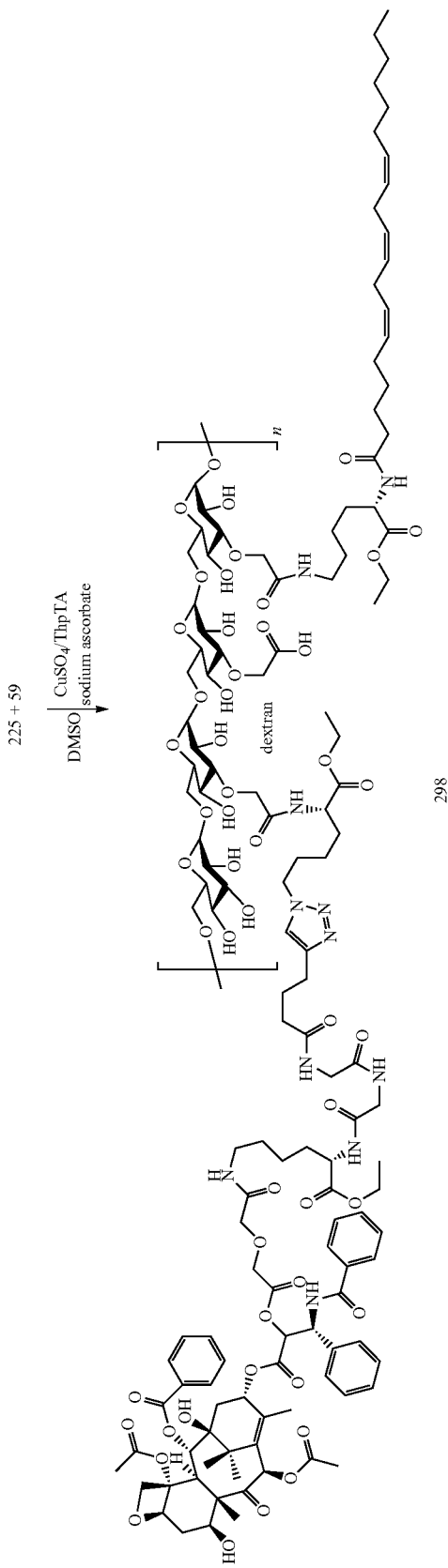

Sample 298: Preparation of Dual Conjugate 298

The preparation of conjugate 298 is similar to that of conjugate 286.

By comparing its UV absorption with that of compound 61 and conjugate 225 at wavelength of 280 nm, 9% (w/w) paclitaxel content was determined in conjugate 298.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 8.50 (m, CONH, ArH), 5.33 (m, CH), 1.23 (m, CH$_3$), 1.00 (m, CH$_3$), 0.85 (t, CH$_3$).

Synthetic Scheme 90

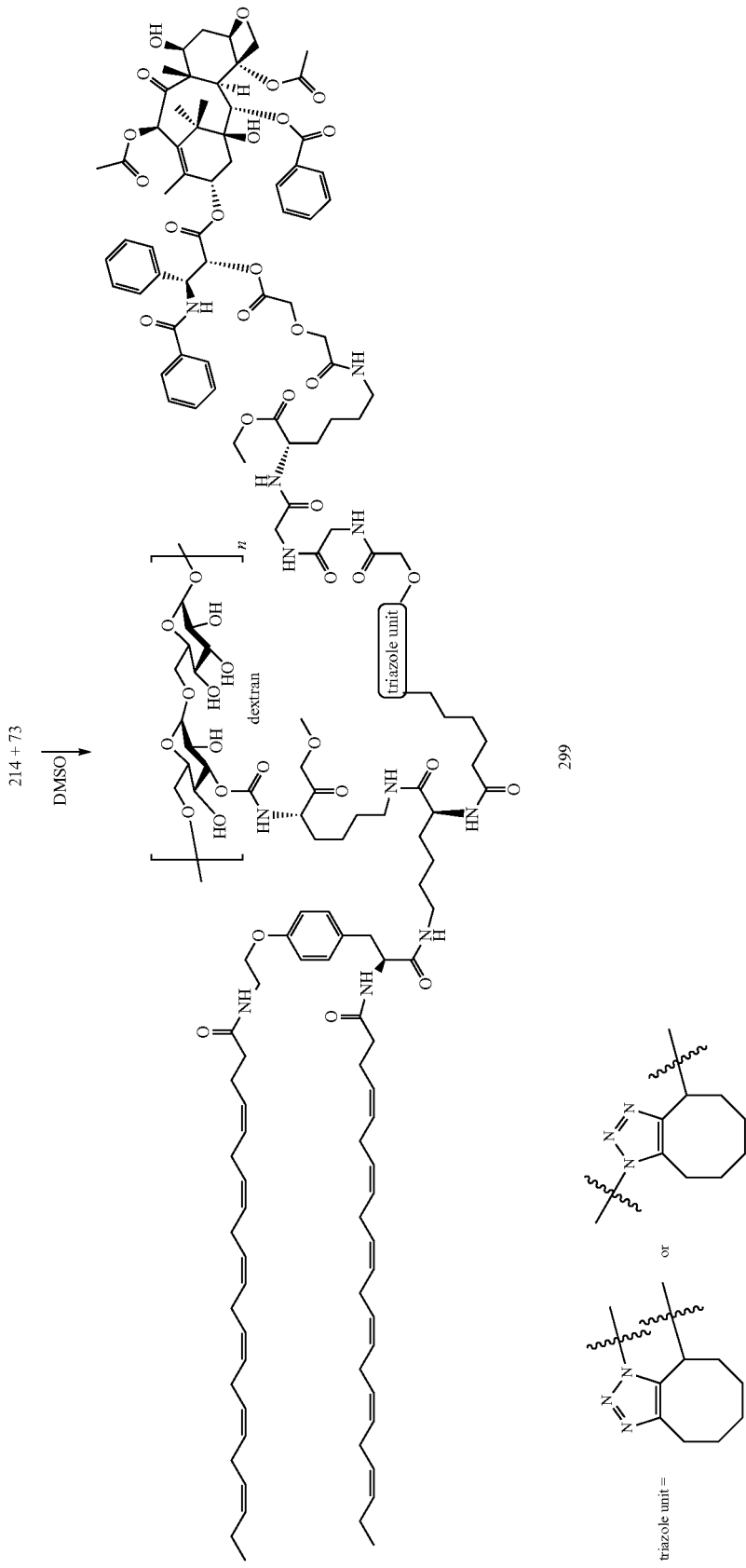

Sample 299: Preparation of Dual Conjugate 299

The preparation of conjugate 299 is similar to that of conjugate 290.

By comparing its UV absorption with that of compound 75a (75b) and conjugate 214 at wavelength of 280 nm, 7% (w/w) paclitaxel content was determined in conjugate 299.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 7.00-8.60 (m, CONH, ArH), 5.32 (m, CH), 1.23 (m, CH$_3$), 1.00 (m, CH$_3$).

Synthetic Scheme 91

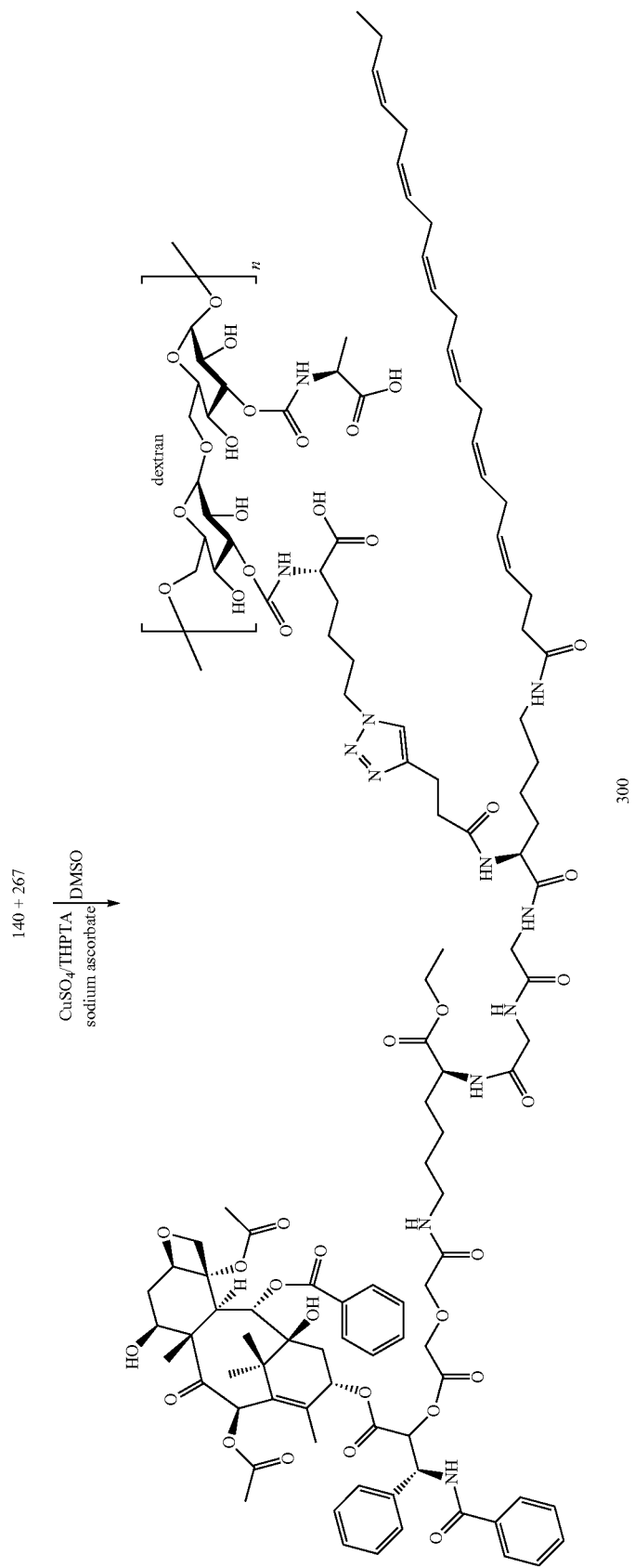

Sample 300: Preparation of Dual Conjugate 300

The preparation of conjugate 300 is similar to that of conjugate 286.

By comparing its UV absorption with that of compounds 61 and functionalized dextran 140 at wavelength of 280 nm, 13% (w/w) paclitaxel content was determined in conjugate 300.

$^1$H NMR (selected characteristic signals, 500 MHz, DMSO-$d_6$, ppm): major signals: 4.50-5.00 (m, CHOH, CHOH, CH$_2$OH), 3.30-4.00 (m, CHOH, CH$_2$OH, CH$_2$O); minor signals: 6.70-8.50 (m, CONH, ArH), 5.33 (m, CH), 0.90-1.23 (m, CH$_3$).

Synthetic Scheme 92

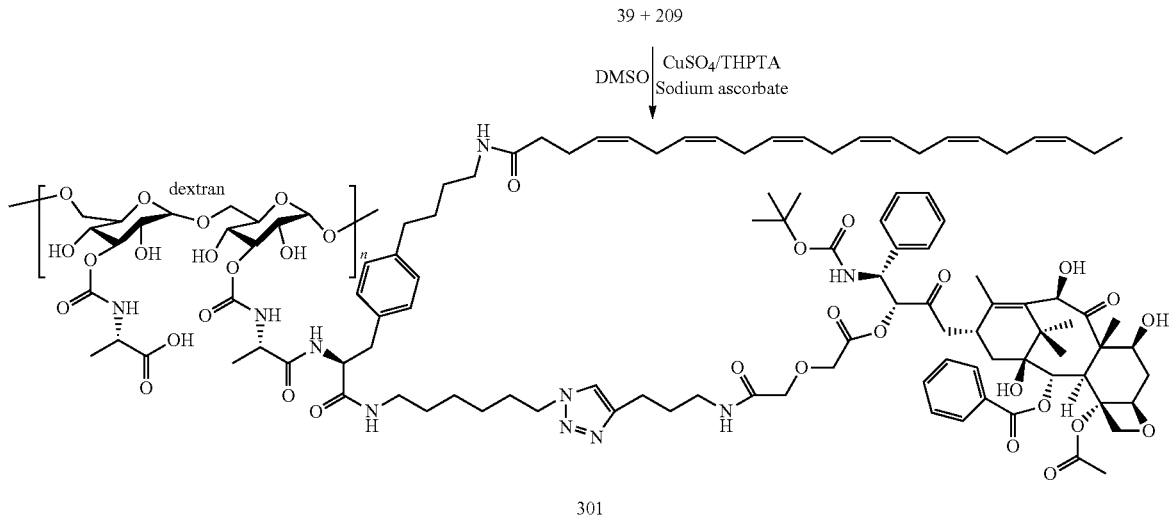

301

Sample 301: Preparation of Dual Conjugate 301

The preparation of conjugate 301 is similar to that of conjugate 286.

By comparing its UV absorption with that of compounds 40 and functionalized dextran 209 at wavelength of 280 nm, 11% (w/w) docetaxel content was determined in conjugate 301.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.50-8.50 (m, CONH, ArH), 5.33 (m, CH), 0.90-1.23 (m, CH$_3$).

Synthetic Scheme 93

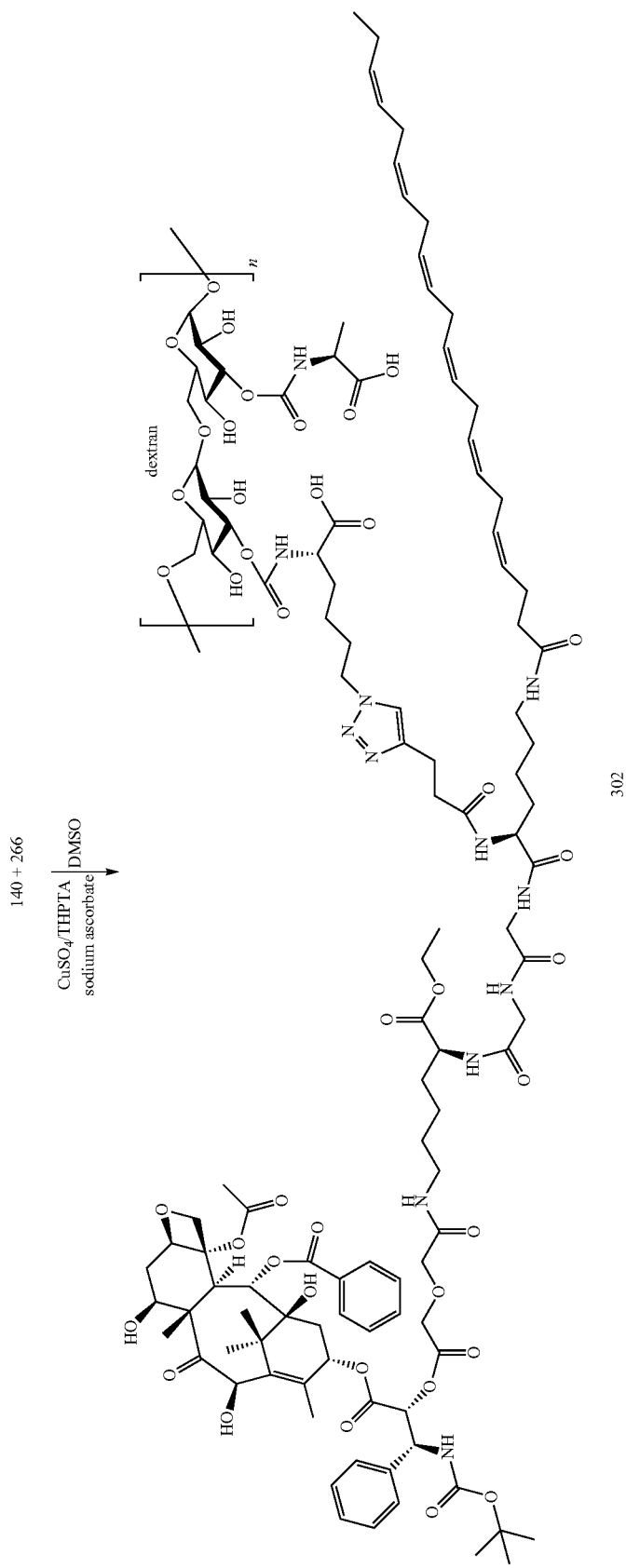

Sample 302: Preparation of Dual Conjugate 302

The preparation of conjugate 302 is similar to that of conjugate 286.

By comparing its UV absorption with that of compound 62 and functionalized dextran 140 at wavelength of 280 nm, 12% (w/w) docetaxel content was determined in conjugate 302.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.50-8.50 (m, CONH, ArH), 5.33 (m, CH), 0.90-1.23 (m, CH$_3$).

Synthetic Scheme 94

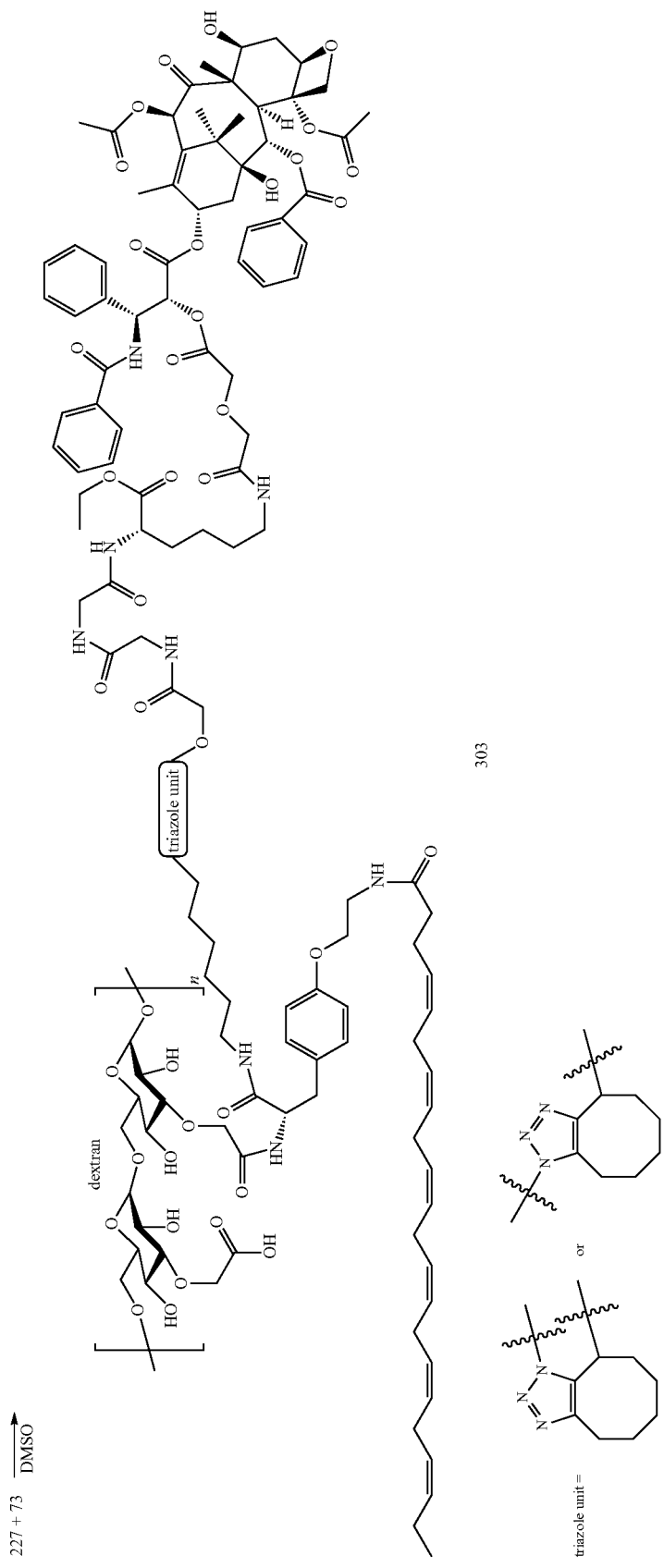

Sample 303: Preparation of Dual Conjugate 303

The preparation of conjugate 303 is similar to that of conjugate 290.

By comparing its UV absorption with that of compound 75a (75b) and conjugate 227 at wavelength of 280 nm, 9% (w/w) paclitaxel content was determined in conjugate 303.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.60 (m, CONH, ArH), 5.33 (m, CH), 0.99 (m, CH$_3$).

Synthetic Scheme 95

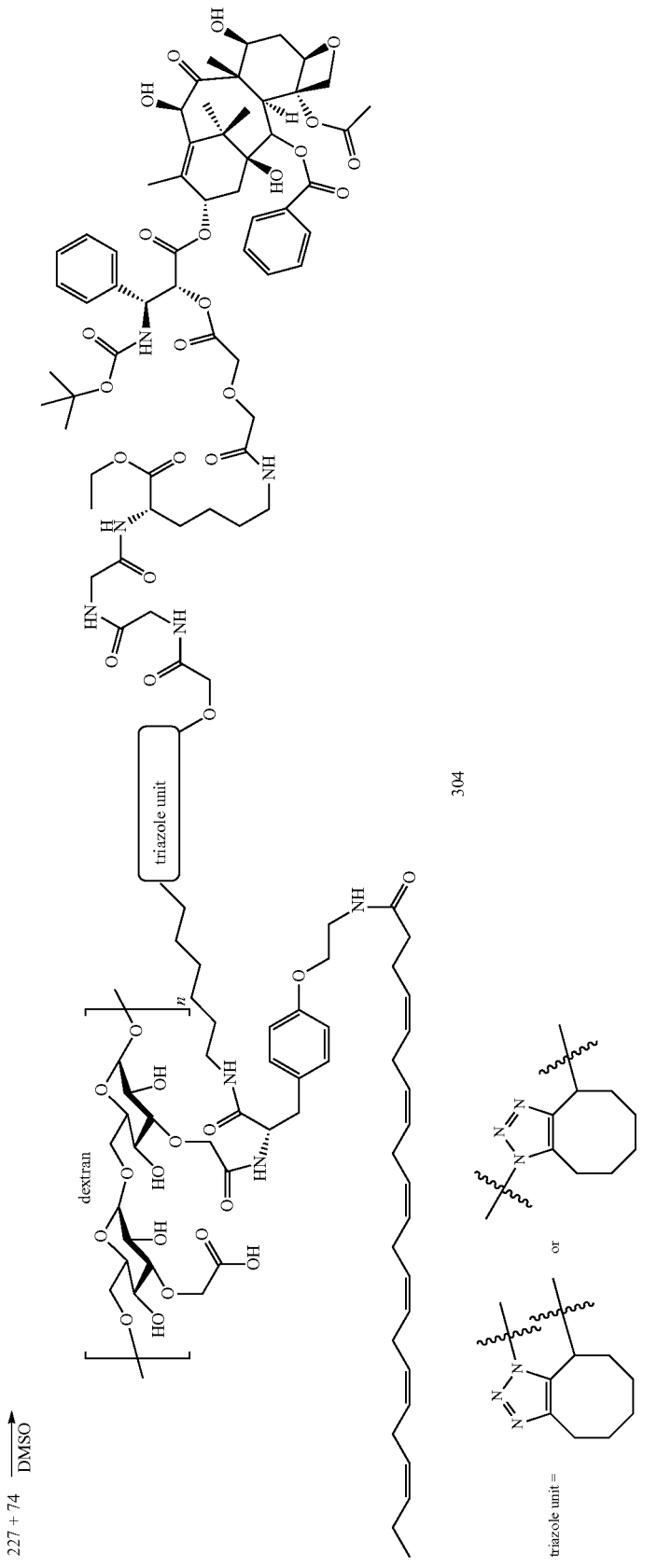

Sample 304: Preparation of Dual Conjugate 304

The preparation of conjugate 304 is similar to that of conjugate 290.

By comparing its UV absorption with that of compound 76a (76b) and conjugate 227 at wavelength of 280 nm, 11% (w/w) docetaxel content was determined in conjugate 304.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.50-8.50 (m, CONH, ArH), 5.33 (m, CH), 1.22 (m, CH$_3$), 1.01 (m, CH$_3$). 0.83 (m, CH$_3$). 7.00-8.60 (m, CONH, ArH), 5.33 (m, CH), 1.34 (s, OC (CH$_3$) 3), 1.00 (m, CH$_3$).

Synthetic Scheme 96

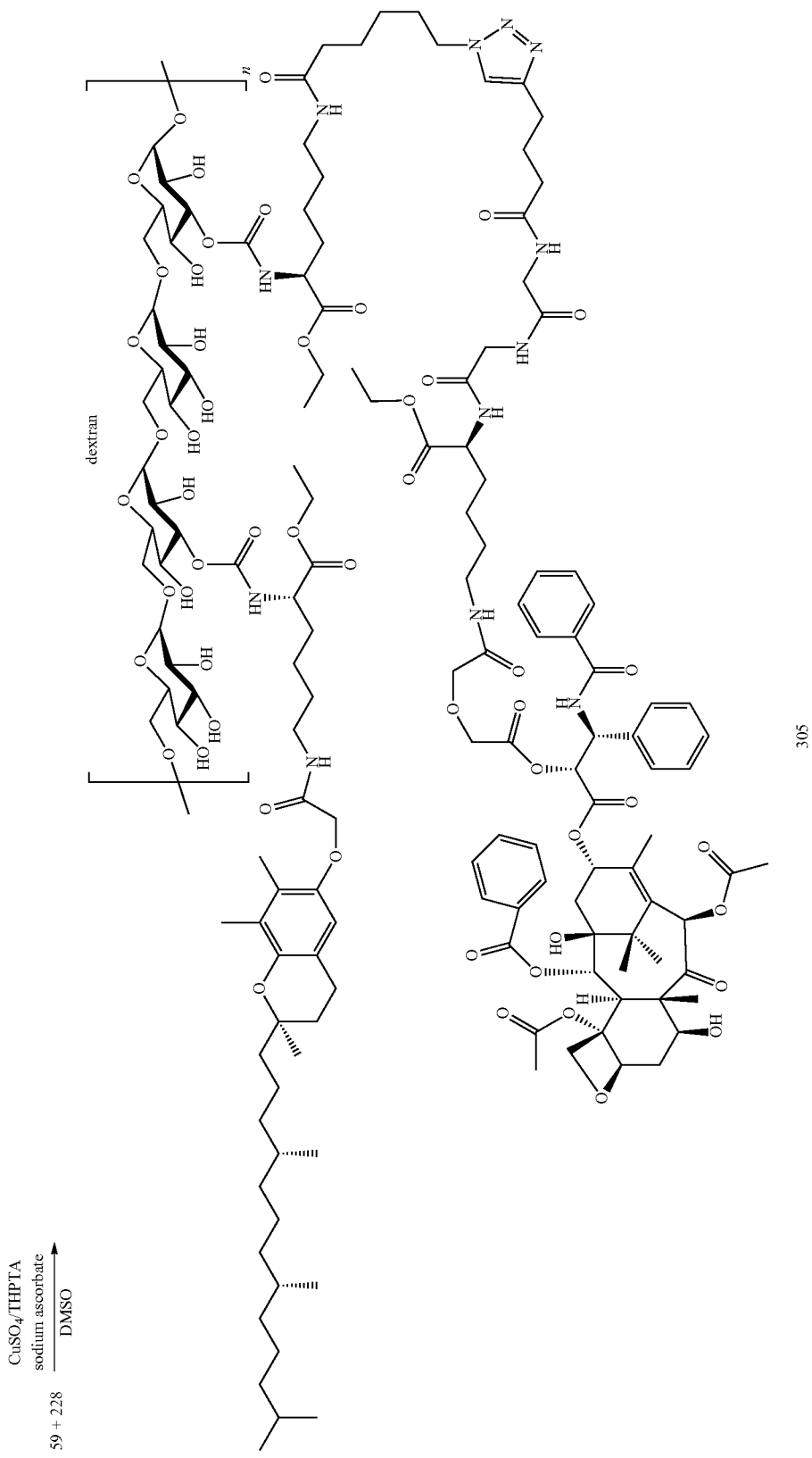

Sample 305: Preparation of Dual Conjugate 305

The preparation of conjugate 305 is similar to that of conjugate 286.

By comparing its UV absorption with that of compound 61 and conjugate 228 at wavelength of 280 nm, 9% (w/w) paclitaxel content was determined in conjugate 305.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.50-8.50 (m, CONH, ArH), 5.33 (m, CH), 1.22 (m, CH$_3$), 1.01 (m, CH$_3$). 0.83 (m, CH$_3$).

Synthetic Scheme 97

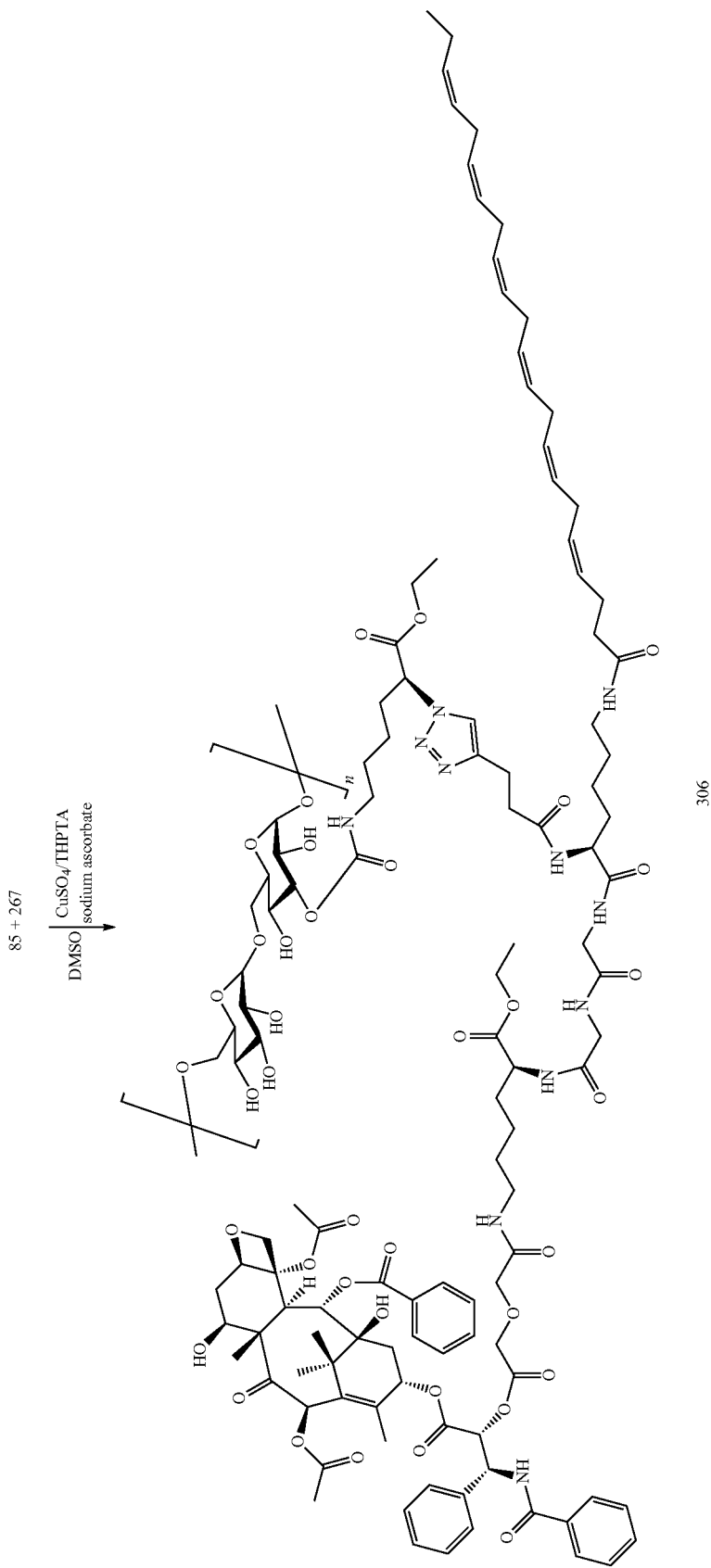

Sample 306: Preparation of Dual Conjugate 306

The preparation of conjugate 306 is similar to that of conjugate 286.

By comparing its UV absorption with that of compound 61 and conjugate 85 at wavelength of 280 nm, 7% (w/w) paclitaxel content was determined in conjugate 306.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.50 (m, CONH, ArH), 5.33 (m, CH), 0.90-1.23 (m, CH$_3$).

Synthetic Scheme 98

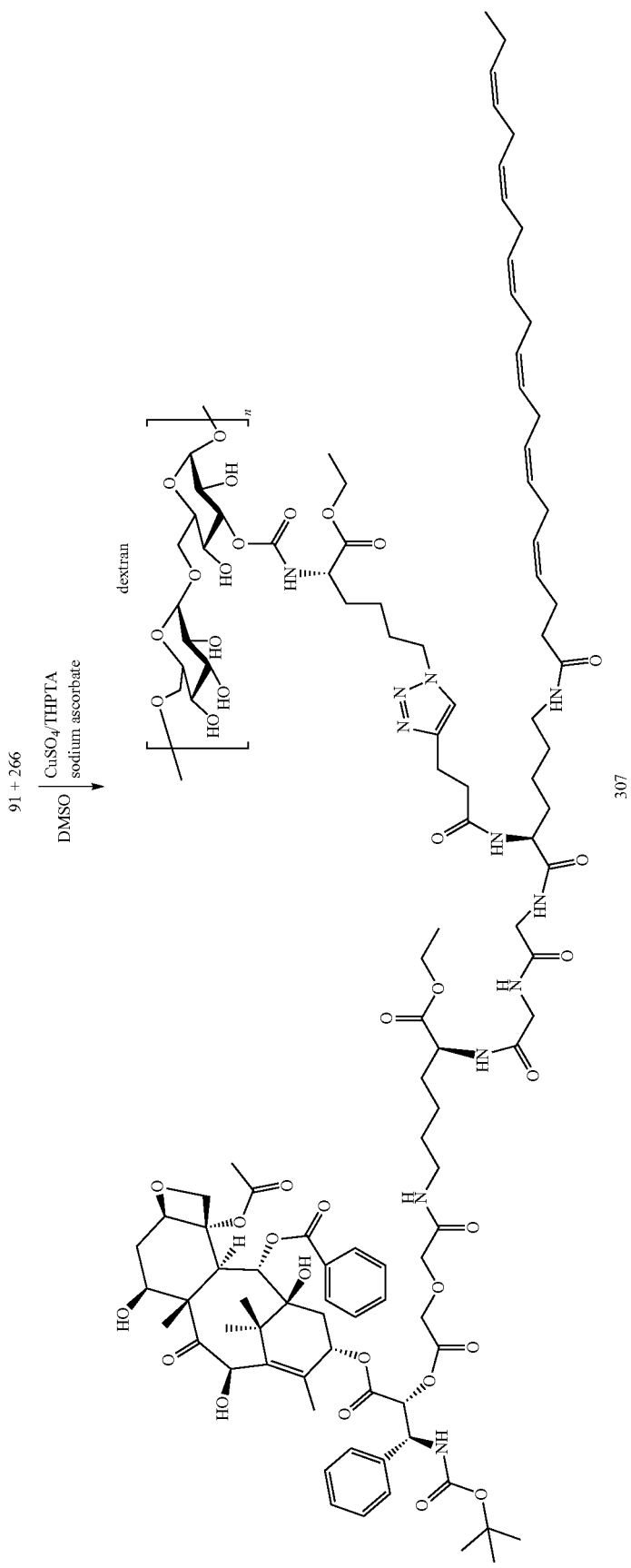

Sample 307: Preparation of Dual Conjugate 307

The preparation of conjugate 307 is similar to that of conjugate 286.

By comparing its UV absorption with that of compound 62 and conjugate 91 at wavelength of 280 nm, 9% (w/w) docetaxel content was determined in conjugate 307.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.50 (m, CONH, ArH), 5.33 (m, CH), 0.90-1.23 (m, CH$_3$).

Synthetic Scheme 99

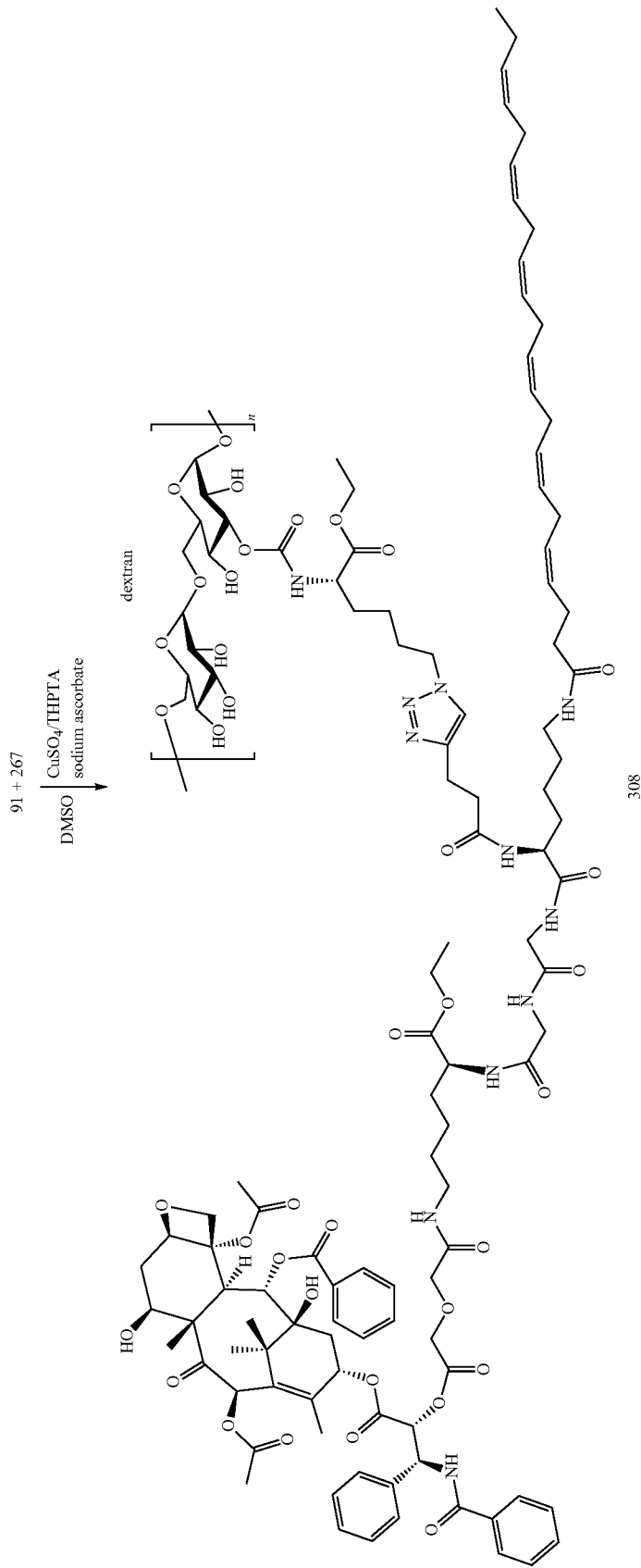

Sample 308: Preparation of Dual Conjugate 308

The preparation of conjugate 308 is similar to that of conjugate 286.

By comparing its UV absorption with that of compound 61 and conjugate 91 at wavelength of 280 nm, 7% (w/w) paclitaxel content was determined in conjugate 308.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.50 (m, CONH, ArH), 5.33 (m, CH), 0.90-1.23 (m, CH$_3$).

Synthetic Scheme 100

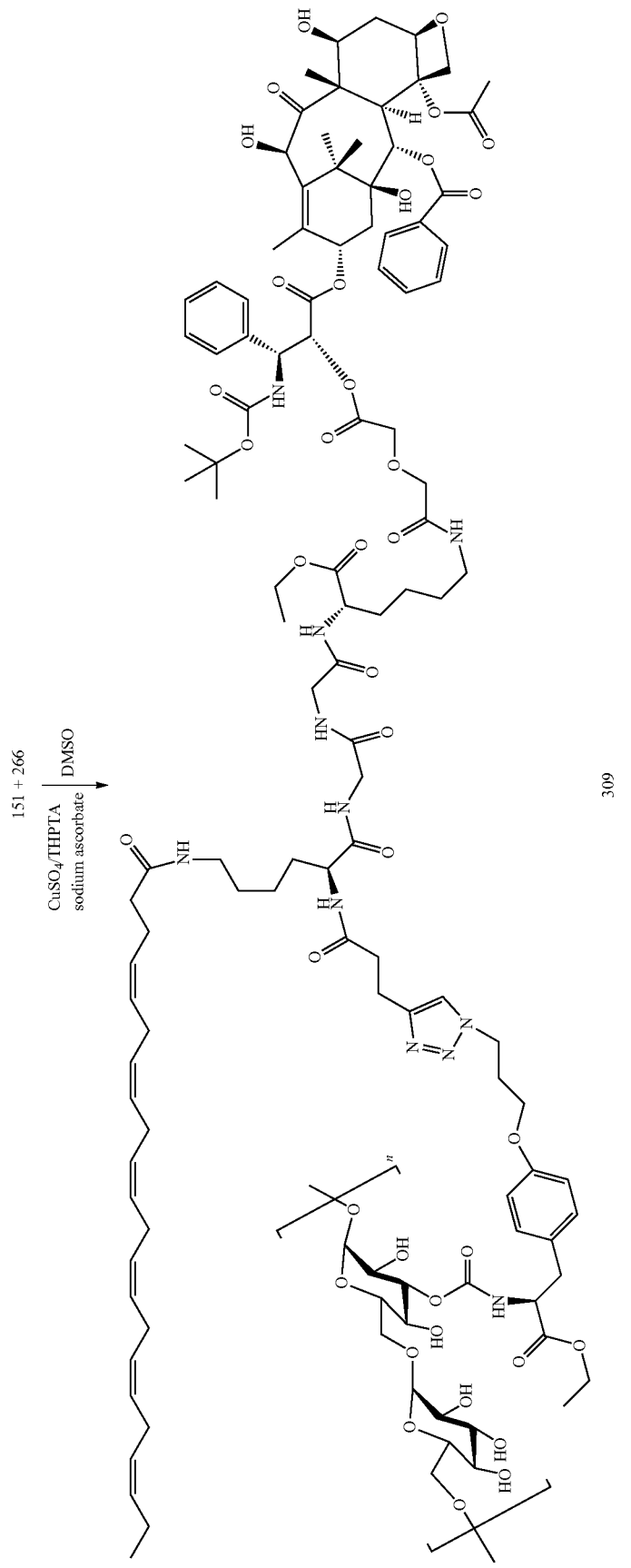

Sample 309: Preparation of Dual Conjugate 309

The preparation of conjugate 309 is similar to that of conjugate 286.

By comparing its UV absorption with that of functionalized dextran 151 and conjugate 266 at wavelength of 280 nm, 7% (w/w) docetaxel content was determined in conjugate 309.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.70-8.50 (m, CONH, ArH), 5.33 (m, CH), 0.90-1.23 (m, CH$_3$).

Synthetic Scheme 101

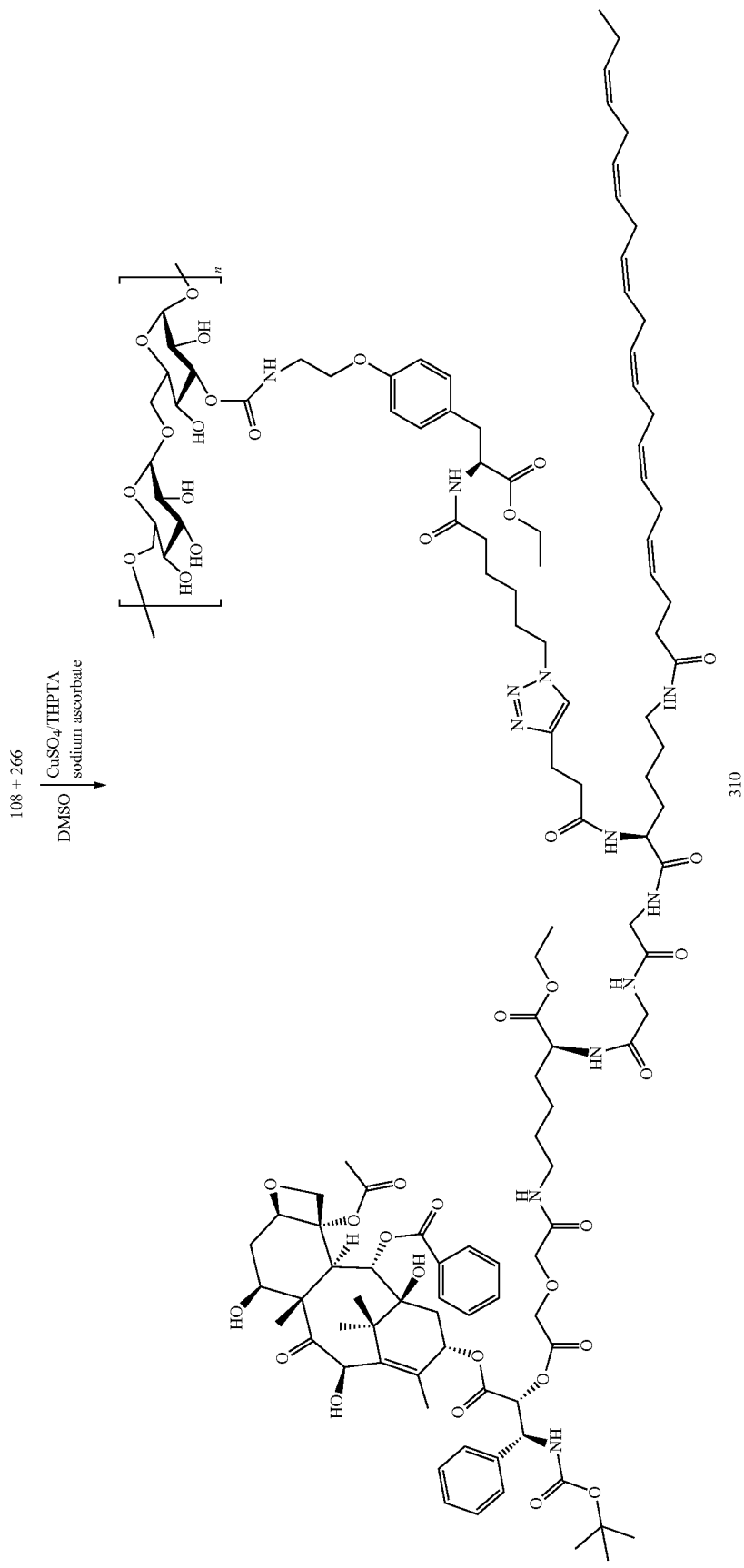

Sample 310: Preparation of Dual Conjugate 310

The preparation of conjugate 310 is similar to that of conjugate 286.

By comparing its UV absorption with that of compound 62 and conjugate 108 at wavelength of 280 nm, 6% (w/w) docetaxel content was determined in conjugate 310.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.70-8.50 (m, CONH, ArH), 5.33 (m, CH), 0.90-1.23 (m, CH$_3$).

Synthetic Scheme 102

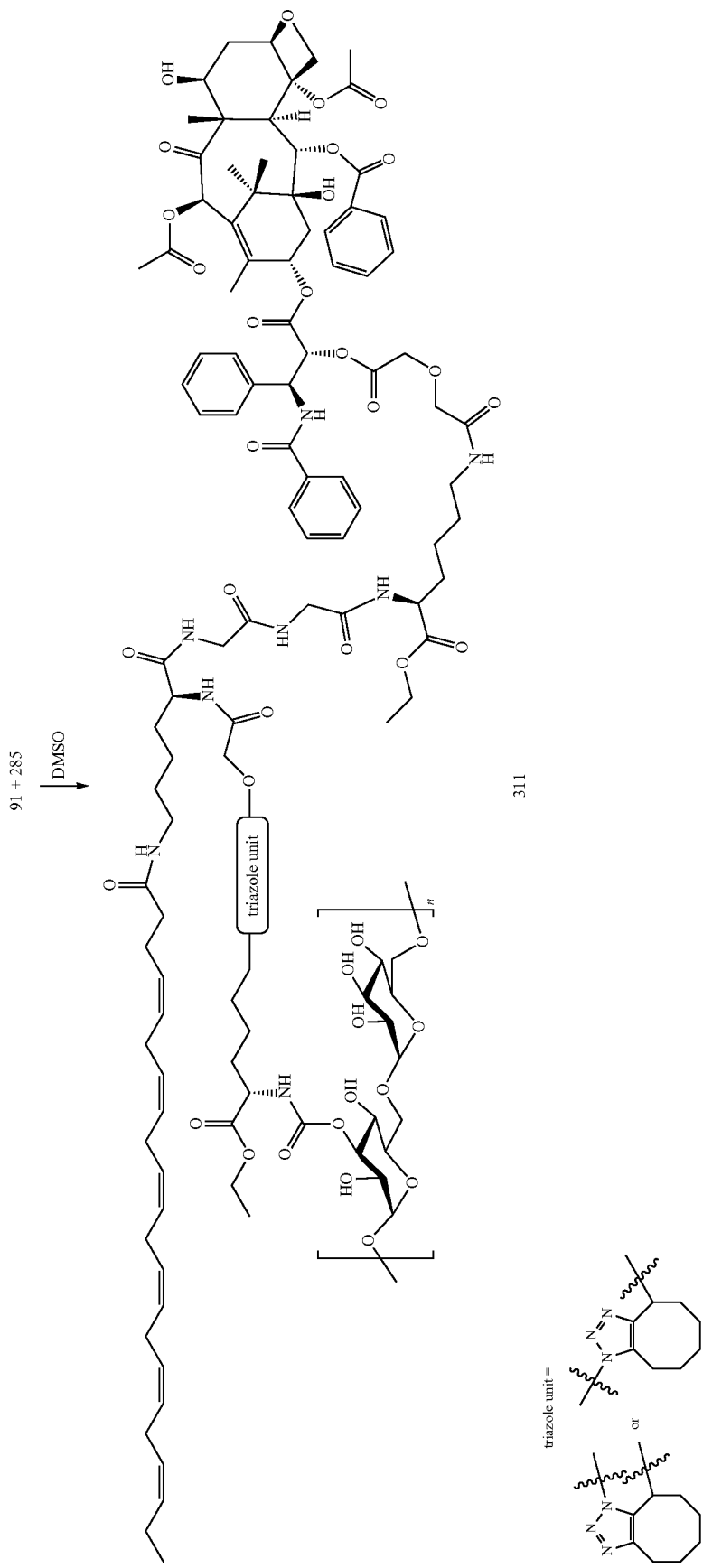

Sample 311: Preparation of Dual Conjugate 311

The preparation of conjugate 311 is similar to that of conjugate 290.

By comparing its UV absorption with that of compound 75a (75b) and conjugate 91 at wavelength of 280 nm, 8% (w/w) paclitaxel content was determined in conjugate 311.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 7.00-8.50 (m, CONH, ArH), 5.33 (m, CH), 0.90-1.23 (m, CH$_3$).

Synthetic Scheme 103

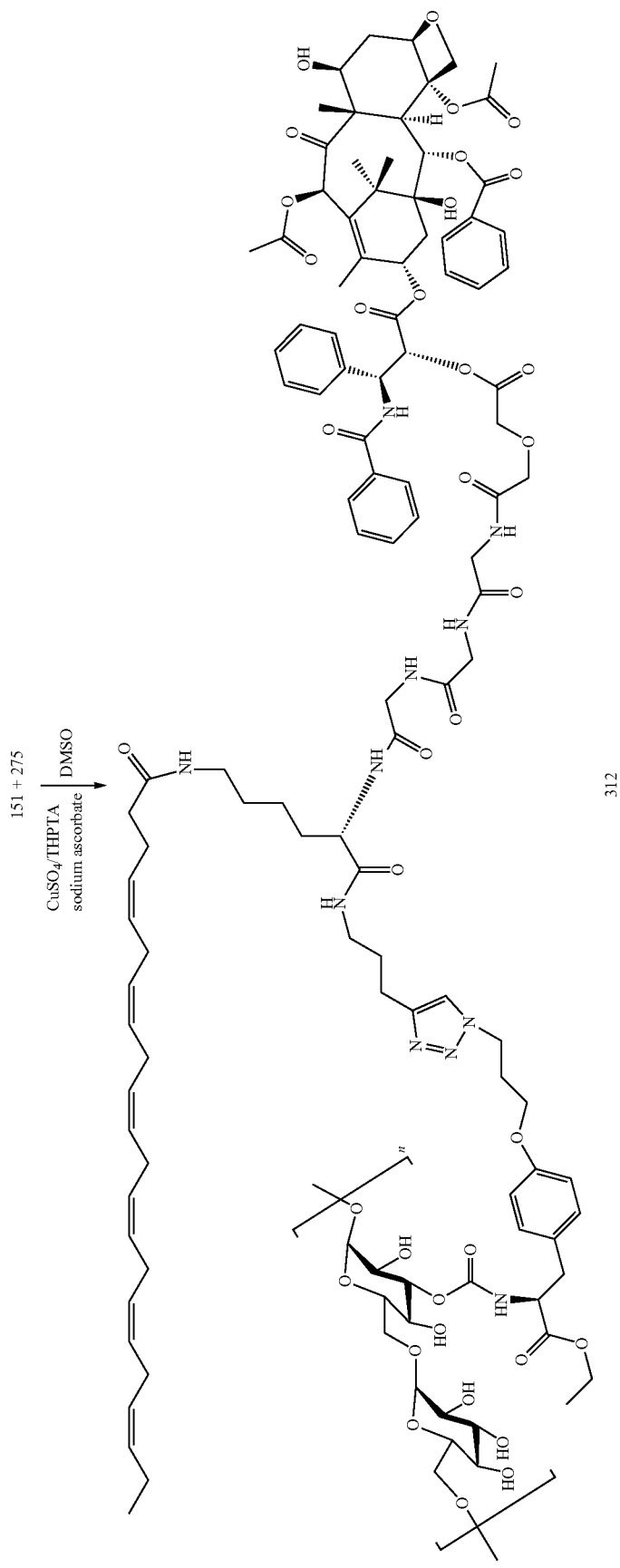

Sample 312: Preparation of Dual Conjugate 312

The preparation of conjugate 312 is similar to that of conjugate 286.

By comparing its UV absorption with that of compound 61 and conjugate 151 at wavelength of 280 nm, 9% (w/w) paclitaxel content was determined in conjugate 312.

$^1$H NMR (selected characteristic signals, 500 MHz, DMSO-$d_6$, ppm): major signals: 4.50-5.00 (m, CHOH, CHOH, CH$_2$OH), 3.30-4.20 (m, CHOH, CH$_2$OH, CH$_2$O); minor signals: 6.70-8.50 (m, CONH, ArH), 5.33 (m, CH), 0.90-1.23 (m, CH$_3$).

Enhanced Solubility Test for Poorly Water-Soluble Compounds

In a 5.0 mL glass vial, 300 mg of conjugate 196 was dissolved in 3.0 mL of distilled water and followed by addition of a solution of 1.0 mg of docetaxel in 100 µL of tetrahydrofuran, sonicated for 1 minute, and the resulting mixture was lyophilized to obtain white powder. The powder was then added to a glass vial with 2.0 mL of distilled water and sonicated for 1 minute to obtain a translucent misty solution. No precipitation was observed at the bottom of the bottle, and no floating powder was observed on the liquid surface, as a result the enhanced docetaxel solubility is 0.5 mg/mL in water. In contrast, 1.0 mg of docetaxel was weighed into a 5.0 mL glass vial, then 2.0 ml of distilled water was added to the glass vial, the vial was sonicated for 1 minute, and the undissolved powder floated over water surface was clearly observed.

The literature reports that the solubility of docetaxel in water is 0.00127 mg/ml (https://www.drugbank.ca/drugs/DB01248).

In a 5.0 mL glass vial, 300 mg of conjugate 198 was dissolved in 3.0 mL of distilled water and followed by addition of a solution of 1.0 mg of stearic acid in 100 µL of tetrahydrofuran, sonicated for 1 minute, and the resulting mixture was lyophilized to obtain white powder. The powder was then added to a glass vial with 2.0 mL of distilled water and sonicated for 1 minute to obtain a translucent misty solution. No precipitation was observed at the bottom of the bottle, and no floating powder was observed on the liquid surface, as a result the enhanced stearic acid solubility is 0.5 mg/mL in water. In contrast, 1.0 mg of stearic acid was weighed into a 5.0 mL glass vial, then 2.0 ml of distilled water was added to the glass vial, the vial was sonicated for 1 minute, and the undissolved powder floated over water surface was clearly observed.

The literature reports that the solubility of stearic acid in water is 0.000597 mg/mL (https://www.drugbank.ca/drugs/DB03193).

In a 5.0 mL glass vial, 250 mg of conjugate 291 was dissolved in 3.0 mL of distilled water and followed by addition of a solution of 1.0 mg of paclitaxel in 100 µL of tetrahydrofuran, sonicated for 1 minute, and the resulting mixture was lyophilized to obtain white powder. The powder was then added to a glass vial with 2.0 mL of distilled water and sonicated for 1 minute to obtain a milk-like solution. No precipitation was observed at the bottom of the bottle, and no floating powder was observed on the liquid surface, as a result the enhanced paclitaxel solubility is 0.5 mg/mL in water. In contrast, 1.0 mg of paclitaxel was weighed into a 5.0 mL glass vial, then 2.0 ml of distilled water was added to the glass vial, the vial was sonicated for 1 minute, and the undissolved powder floated over water surface was clearly observed.

The literature reports that the solubility of paclitaxel in water is 0.00556 mg/ml (https://www.drugbank.ca/drugs/DB01229).

In summary, theses four types of substances: polysaccharide-lipid conjugates, functionalized polysaccharide-lipid conjugates, polysaccharide-taxane conjugates, and taxane-polysaccharide-lipid dual conjugates, contain a hydrophilic component and a lipophilic component, and enhance solubility of poorly water-soluble compounds.

In Vitro Antitumor Activity Assay

In order to determine if the activity of the prepared intermediates and prepared conjugates, we evaluated their antitumor activities by using MTT assay.

All cell lines were maintained in a humidified atmosphere containing 5% CO2 at 37° C. in different media supplemented with 10% FBS, 100 U/ml penicillin, and 100 µg/ml streptomycin. MCF-7, NCI-H460 or OVCAR-3 tumor cells were seeded into a 96-well cell culture plate and incubated overnight. The 96-well culture plate was taken out from the incubator, and the conjugates or mixture of different compounds or polysaccharides were added into it. The concentration of each compound or conjugate were set to 500 nM, 200 nM, 100 nM, 50 nM, 25 nM, 12.5 nM, 6 nM, 3 nM and 1 nM. Three wells were set at each concentration. Blank control contained tumor cells in normal medium without any sample. After treatment for 72 h, 20 µL of 3-(4, 5-dimethylthiazole-2)-2,5-diphenyltetrazolium bromide (MTT) were added to each well and incubated for 4 hours at 37° C. After the removal of the supernatant, MTT formazan was dissolved in 150 µl dimethyl sulfoxide (DMSO) and monitored using a microplate reader at a wavelength of 570 nM. The half-inhibitory concentration (IC$_{50}$ value) of each compound or conjugate was calculated. The growth inhibition rate (%) of each drug concentration group=(1-average OD value of the experimental well/average OD value of the control well)×100%; MTT assay were repeated for 3 times and the average IC$_{50}$ value was repeated for each sample.

TABLE 1

The antitumor activity of some samples (IC$_{50}$ value: nM)

| Substance | MCF-7 | NCI-H460 | Compounds | MCF-7 | NCI-H460 |
|---|---|---|---|---|---|
| Cabazitaxel | 8.3 ± 0.5 | 7.1 ± 0.3 | Dual conjugate 288 | 27.7 ± 5.1 | 38.4 ± 6.3 |
| Docetaxel | 9.5 ± 0.2 | 6.7 ± 0.6 | Dual conjugate 289 | 36.2 ± 7.3 | 25.9 ± 3.8 |
| Paclitaxel | 21.9 ± 1.1 | 17.9 ± 1.3 | Dual conjugate 290 | 39.1 ± 5.2 | 45.6 ± 4.7 |
| Conjugate 165 | >500 | >500 | Dual conjugate 291 | 32.6 ± 6.3 | 23.6 ± 3.9 |
| Conjugate 179 | >500 | >500 | Dual conjugate 292 | 15.3 ± 4.7 | 21.8 ± 3.2 |
| Conjugate 191 | >500 | >500 | Dual conjugate 293 | 47.3 ± 7.1 | 53.9 ± 6.2 |
| Conjugate 218 | >500 | >500 | Dual conjugate 294 | 33.3 ± 5.6 | 29.3 ± 5.5 |
| Conjugate 229 | 39.1 ± 3.7 | 27.3 ± 5.2 | Dual conjugate 295 | 43.9 ± 3.7 | 33.6 ± 5.6 |
| Conjugate 230 | 56.5 ± 2.5 | 67.5 ± 3.3 | Dual conjugate 296 | 33.2 ± 4.5 | 41.9 ± 5.2 |
| Conjugate 231 | 45.6 ± 5.1 | 33.9 ± 4.7 | Dual conjugate 297 | 25.6 ± 3.6 | 15.9 ± 3.2 |
| Conjugate 232 | 36.7 ± 3.2 | 54.6 ± 7.1 | Dual conjugate 298 | 38.6 ± 6.1 | 26.9 ± 3.5 |

TABLE 1-continued

The antitumor activity of some samples (IC$_{50}$ value: nM)

| Substance | MCF-7 | NCI-H460 | Compounds | MCF-7 | NCI-H460 |
|---|---|---|---|---|---|
| Conjugate 236 | 58.9 ± 2.1 | 36.3 ± 5.3 | Dual conjugate 299 | 32.1 ± 5.4 | 29.1 ± 3.8 |
| Conjugate 237 | 47.3 ± 4.9 | 65.5 ± 3.6 | Dual conjugate 300 | 35.7 ± 4.5 | 28.7 ± 4.6 |
| Conjugate 239 | 39.7 ± 5.6 | 45.3 ± 5.2 | Dual conjugate 301 | 31.5 ± 5.3 | 23.6 ± 7.2 |
| Conjugate 243 | 53.8 ± 7.2 | 37.3 ± 3.5 | Dual conjugate 302 | 27.7 ± 3.9 | 15.3 ± 5.6 |
| Conjugate 244 | 67.6 ± 6.5 | 41.5 ± 6.3 | Dual conjugate 303 | 36.8 ± 5.7 | 29.9 ± 4.5 |
| Conjugate 245 | 48.2 ± 3.9 | 31.3 ± 5.7 | Dual conjugate 304 | 21.3 ± 2.6 | 17.7 ± 3.1 |
| Conjugate 249 | 128.6 ± 9.5 | 97.3 ± 8.6 | Dual conjugate 305 | 37.8 ± 3.3 | 31.9 ± 5.6 |
| Dual conjugate 286 | 32.3 ± 4.5 | 42.5 ± 5.6 | | | |
| Dual conjugate 287 | 41.7 ± 6.3 | 30.9 ± 6.3 | | | |

IC$_{50}$ values of conjugates were calculated in terms of taxane molar equivalents.

In summary, 1 both the taxane-polysaccharide conjugates and the taxane-lipid-polysaccharide dual conjugates well keep their antitumor activities; 2) introduction of lipid compounds, particularly unsaturated fatty acids, can enhance the antitumor activities of the taxane-lipid-polysaccharide dual conjugates.

TABLE 2

The antitumor activity of some compounds (IC$_{50}$ value: nM)

| Substance or mixture | Molar ratio of taxane to lipid | OVCAR-3 (drug resistance) |
|---|---|---|
| Paclitaxel | Paclitaxel: DHA/1:0 | 57.6 ± 6.3 |
| Paclitaxel + DHA | Paclitaxel: DHA/1:1 | 45.6 ± 5.1 |
| Paclitaxel + Conjugate 191 | Paclitaxel: DHA/1:2 | 51.6 ± 3.9 |
| Dual conjugate 291 + Conjugate191 | Paclitaxel: DHA/1:4 | 39.2 ± 4.3 |

IC$_{50}$ values of conjugates were calculated in terms of taxane molar equivalents.

In summary, unsaturated fatty acids can enhance the antitumor activity of taxanes in both free form and conjugated form.

In Vitro Drug Release Test

In order to confirm if free taxane drug or its derivatives can be effectively released from the polysaccharide-taxane-lipid dual conjugates, in vitro plasma drug release tests were performed. LC-MS analysis technology was used to quantify free taxane drug.

Normally, the retention time (RT) and molecular weight of standard sample of paclitaxel, docetaxel, or cabazitaxel were acquired by the optimized test condition of LC-MS, and then polysaccharide-taxane-lipid dual conjugate was added in the incubation solution with rat plasma. At the same time, standard taxane drug was separately added into rat plasma incubation solution as compared to the control sample. At different time points during drug release incubation test, a certain volume of incubation solution was sampled, processed, and subjected to LC-MS analysis. For an example, to test free paclitaxel release from conjugate 298, the experiments were simultaneously carried out in two incubation solution consisting of tested substance, rat plasma, PBS; one incubated with standard taxane drug and another incubated with conjugate 298. The drug release test procedure was performed as following details: 200 µL of the measured substance (100 uM standard taxane drug or conjugate 298 containing with equivalent taxane drug in PBS buffer, pH 7.4), 200 µL of rat plasma, and 600 µL of PBS buffer (pH=7.4) were added to make a final solution of 1.0 mL of the reaction mixture. Prior to incubation, 100 µL of the reaction mixture was transferred into 1.5 ml Eppendorf vial, and two volumes of cold 90% acetonitrile was added to precipitate proteins, then sample was centrifuged at 15,000 rpm for 15 min, the supernatant was subjected to LC-MS analysis as 0 min time point, the free paclitaxel reaction mixture was processed the same way and used as a standard for calculating the relative release drug concentration. Subsequently, the remaining 900 uL of the reaction mixture was incubated at 37° C. with shaking moderately at 500 rpm, and 100 uL of the incubation solution mixture was taken at different time points at 0.5, 1, 3, 5, 12, and 20 hours, and processed as the same procedure as above mentioned; The supernatant was obtained and subjected to LC-MS analysis, the amounts of released paclitaxel in the conjugate at the time points were calculated;

The results of dual conjugate 298 drug release experiments are as follows:

TABLE 3

The percentage of paclitaxel released from conjugate 298 at different time points determined by LC-MS analysis

| Incubation (hrs) | 0 | 0.5 | 1 | 3 | 5 | 12 | 20 |
|---|---|---|---|---|---|---|---|
| Paclitaxel | 100% | 87% | 77% | 77% | 67% | 58% | 58% |
| Dual conjugate 298 | 0% | 16% | 25% | 32% | 48% | 74% | 99% |

In conclusion, the in vitro drug release test of dual conjugate 298 showed: 1) the paclitaxel can be released effectively from dual conjugate 298; 2) up to 20 hrs incubation in rat plasma, the paclitaxel can be almost fully released from conjugate 298 (see FIG. 1).

In Vivo Safety Assay

BALB/c (nu/nu) mice (20±2 g, 4-6 weeks old) were housed under pathogen-free conditions. Cancer cells such MCF-7 and NCI-H460 5.0×10$^6$, suspended in 100 µl PBS, were subcutaneously inoculated into the lower right rank of the nude mice. When the tumor size reached 100-150 mm$^3$, the mice were divided randomly into different groups (n=6 in each group). The control group received the solvent only. The treatment groups received docexal (8.0 mg/kg), or dual conjugate 307 (average molecular weight: 11K Dalton, an equimolar dose of docetaxol, 8.0 mg/kg) intravenously through mice tails once a week. The mice were treated for 4 weeks. After the administration, the mice are raised normally. The tumor volume and mouse body weight were measured on every 3 days.

During the whole experiment period, there was no death of nude mice, and their diet and activities were normal. The mice in the dual conjugate 307 group and the docetaxel group showed similar tumor inhibition rates. However, the weight loss rate of dual conjugate 307 group was significantly lower than that of the docetaxel group (see FIG. 2), which confirmed that the dual conjugate is highly safe and well tolerated; it also indicates that the dual conjugate conjugate can bring high survival rate and has a long survival time.

On the other hand, the studies showed that as the molecular weight of polysaccharides increases (for example, average molecular weight is above 25 k Dalton), it is expected that the tumor targeting of these dual conjugates will be further improved, and the dual conjugates in the present invention may exhibit their in vivo enhanced anti-tumor effects and safety than their original drugs.

The invention claimed is:
1. A taxane-lipid-polysaccharide dual conjugate depicted by formula Ia or Formula Ib as shown below, or a pharmaceutically acceptable salt or solvate thereof,

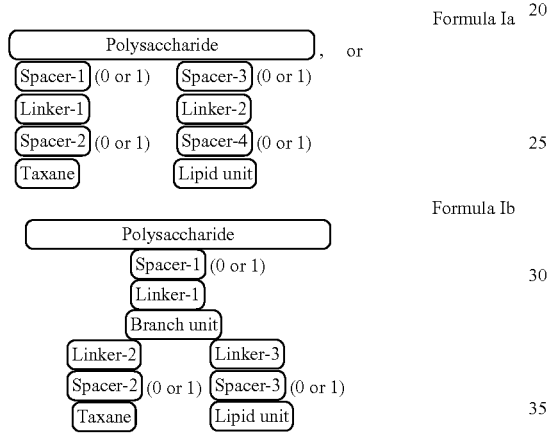

Formula Ia

Formula Ib wherein the taxane or the lipid unit is covalently linked to the polysaccharide via spacers, linkers, or a combination thereof, wherein the spacers and the linkers are covalently linked;

wherein the linkers comprising linker-1, linker-2 and linker-3 are same or different from each other, and wherein a branch unit in formula Ib is covalently linked to the linkers;

wherein the spacers comprising spacer-1, spacer-2, spacer-3 and spacer-4 are same or different from each other, and the number of any one of the spacers is 0 or 1;

wherein the polysaccharide is covalently linked to spacers, linkers, or a combination thereof through two conjugation sites thereof;

wherein the conjugation site to polysaccharide refers to a hydroxyl group, a carboxyl group, an amino group, or a sulfonic acid group inherent to the polysaccharide;

wherein the polysaccharide is selected from dextran, hydroxyethyl starch, *Ganoderma lucidum* polysaccharide, or alginate, optionally carrying groups of COOH or $SO_3H$;

wherein the polysaccharide has a molecular weight ranging from 300 to 1,000,000; wherein the taxane consists of paclitaxel, docetaxel, cabazitaxel, milataxel, tesetaxel, ortataxel, or larotaxel;

wherein the lipid unit comprises one or more of a single molecular lipid compound, and when the lipid unit comprises more than one single molecular lipid compounds, the single molecular lipid compounds are the same or different; wherein the single molecular lipid compound is selected from alpha-linolenic acid (ALA), gamma-linoleic acid (GLA), arachidonic acid, eicosapentaic acid (EPA), docosahexaenoic acid (DHA), or vitamin A;

wherein linker-1, linker-2, and linker-3 are independently selected from the following structures: a di-substituted $C_{5-20}$alkyl, $C_{5-20}$ cycloalkyl, $C_{5-20}$ heterocycloalkyl, $C_{5-20}$ alkenyl, $C_{5-20}$alkynyl, $C_{6-20}$ aryl, or $C_{5-20}$ heteroaryl; a di-substituted peptide containing 3 to 10 natural or unnatural amino acids; poly (ethylene glycol) chain with a molecular weight of 300 to 5,000; or a combination thereof; wherein the natural amino acid is selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or a derivative thereof; wherein the unnatural amino acid is selected from D-alanine, D-arginine, D-asparagine, D-aspartic acid, D-cysteine, D-glutamic acid, D-glutamine, D-histidine, D-isoleucine, D-leucine, D-lysine, D-methionine, D-phenylalanine, D-proline, D-serine, D-threonine, D-tryptophan, D-tyrosine, D-valine, $NH_2(CH_2)_{2-10}COOH$ or a derivative thereof; wherein the spacer-1, spacer-2, spacer-3, and spacer-4 are independently selected from the following structures: a di-substituted $C_{1-10}$ alkyl, $C_{3-t}o$ cycloalkyl, $C_{3-t}o$ heterocycloalkyl, $C_{3-10}$3alkenyl, $C_{3-t}o$ alkynyl, $C_{6-t}o$ aryl, or $C_{5-10}$ heteroaryl; a natural amino acid, or an unnatural amino acid; a di-substituted peptide containing 2 to 3 natural or unnatural amino acids; poly (ethylene glycol) chain with a molecularweight of 100 to 500, or a combination thereof; wherein the natural amino acid is selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or a derivative thereof; wherein the unnatural amino acid is selected from D-alanine, D-arginine, D-asparagine, D-aspartic acid, D-cysteine, D-glutamic acid, D-glutamine, D-histidine, D-isoleucine, D-leucine, D-lysine, D-methionine, D-phenylalanine, D-proline, D-serine, D-threonine, D-tryptophan, D-tyrosine, D-valine, $NH_2(CH_2)_{2-t}oCOOH$, or a derivative thereof;

wherein the branch unit is a tri-substituted structure with 6 to 100 atoms in length and selected from an alkyl, cycloalkyl, heterocycloalkyl, alkenyl, alkynyl, aryl, heteroaryl, or a derivative thereof; and wherein the taxane-lipid-polysaccharide dual conjugate is selected from the group consisting of the following compounds:

477  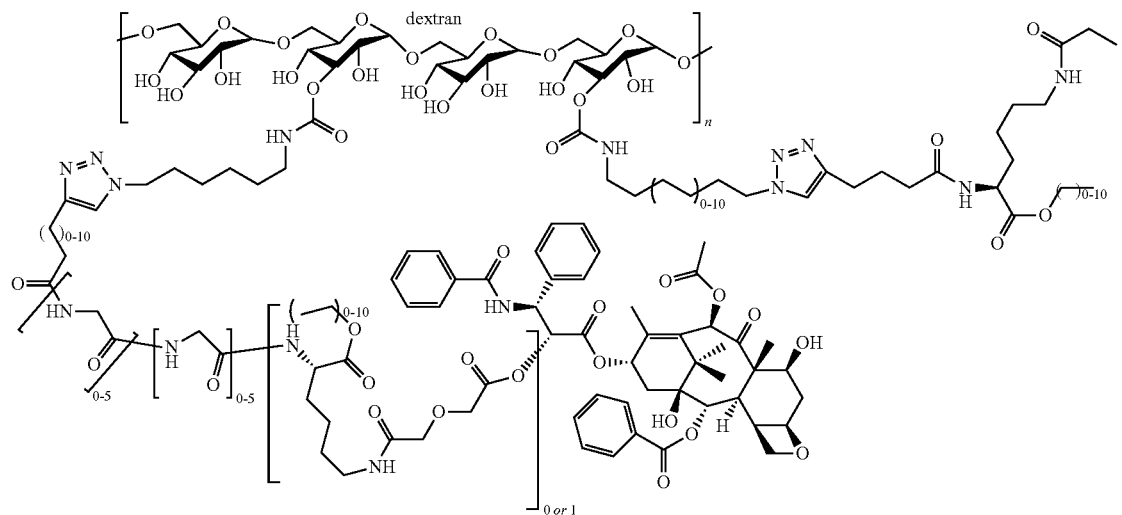
478  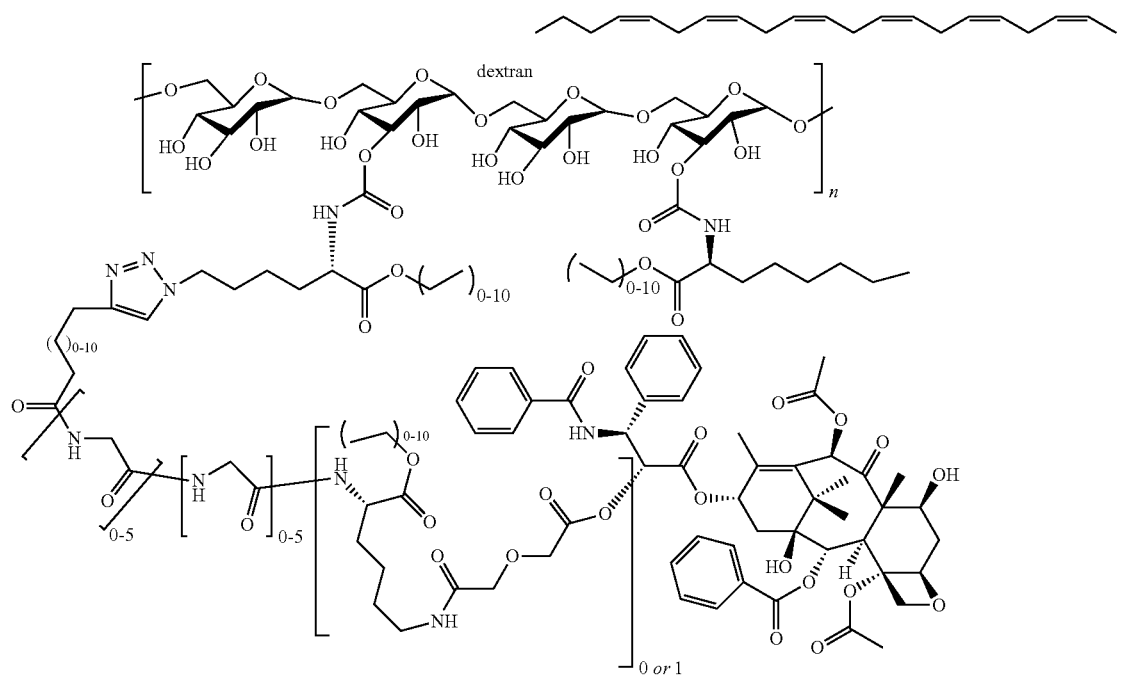
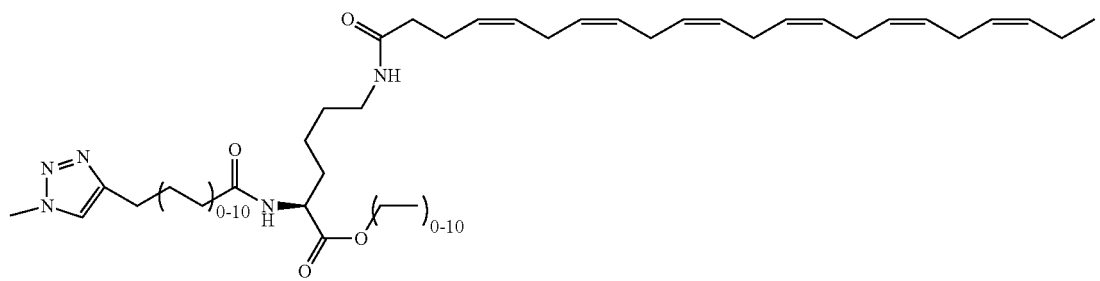

-continued
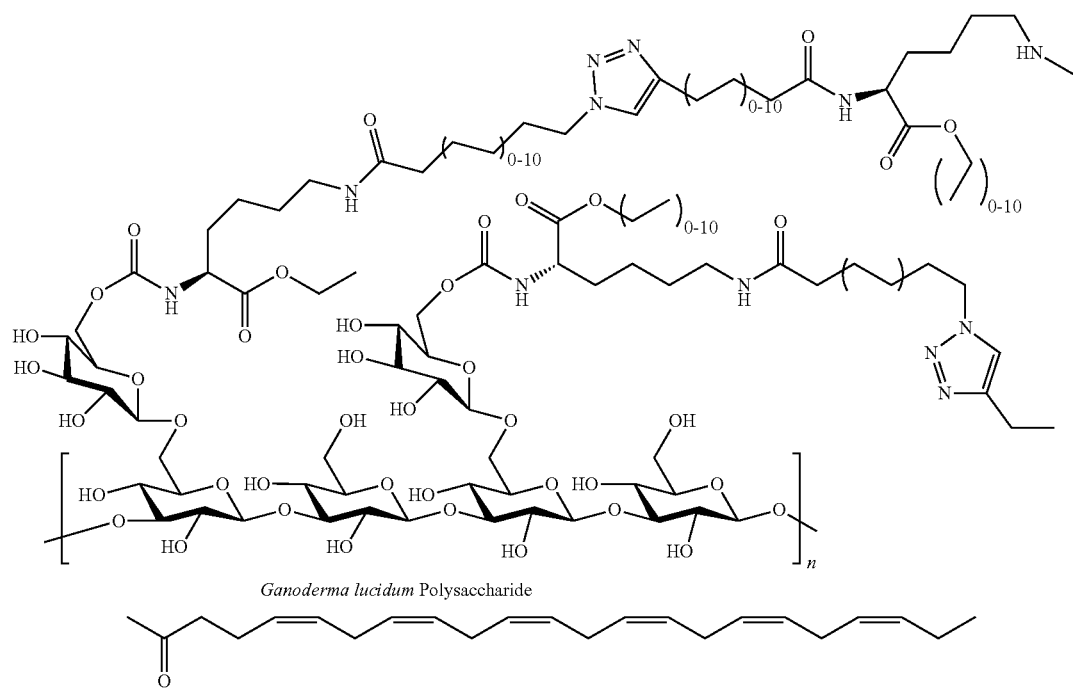
*Ganoderma lucidum* Polysaccharide
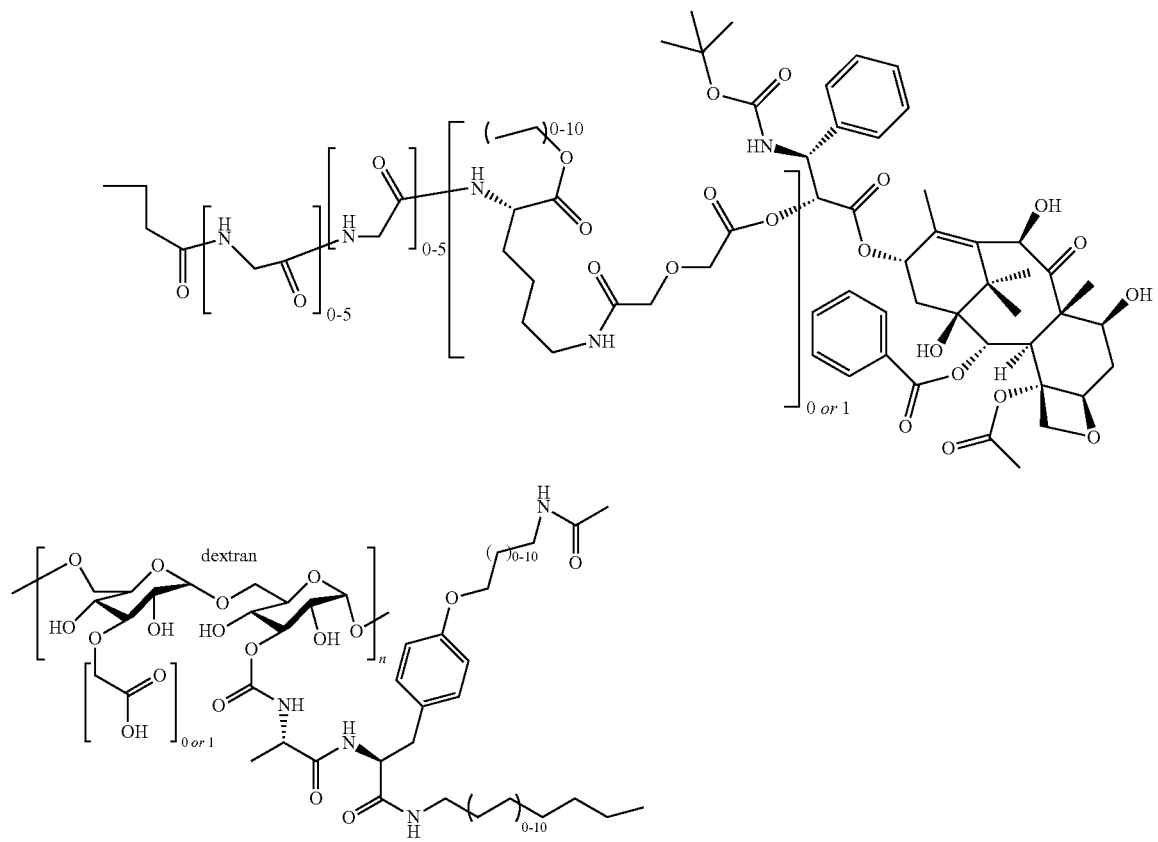

481 482
-continued
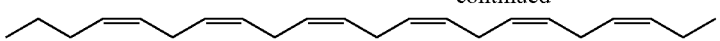
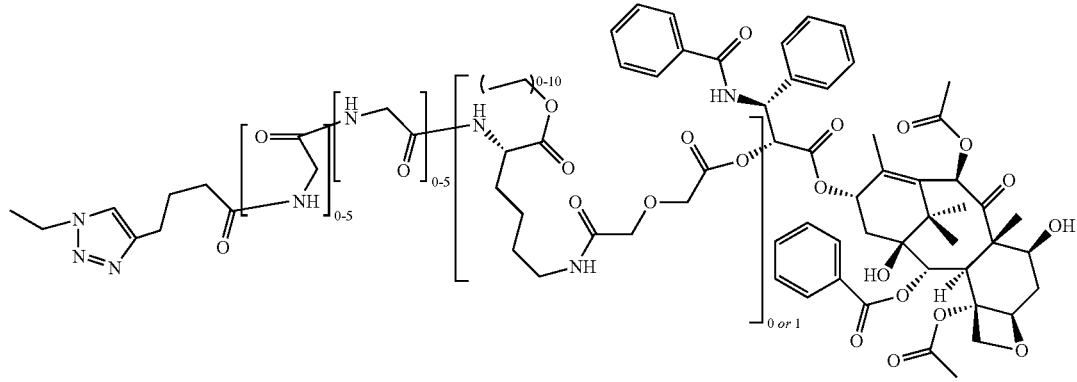
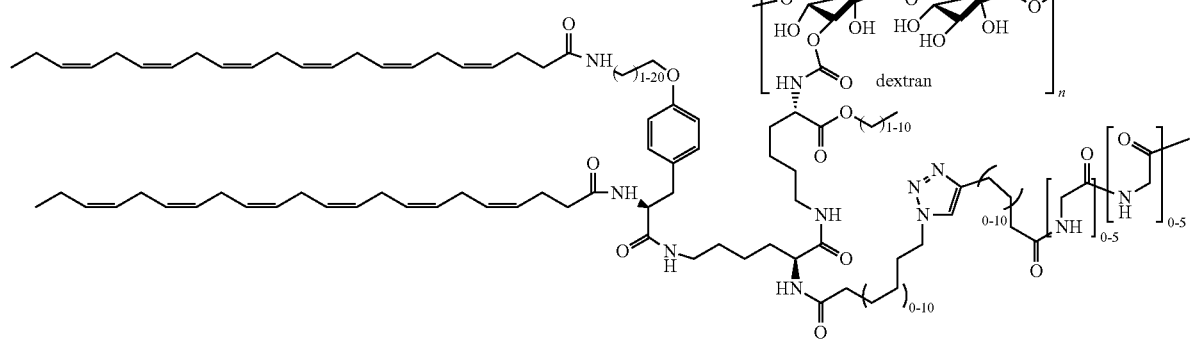
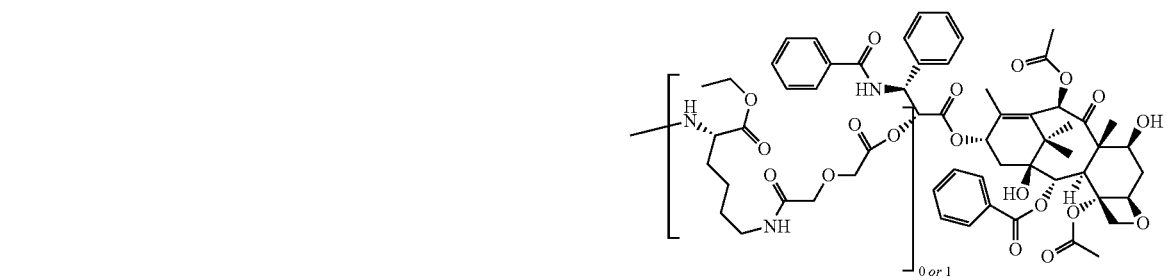
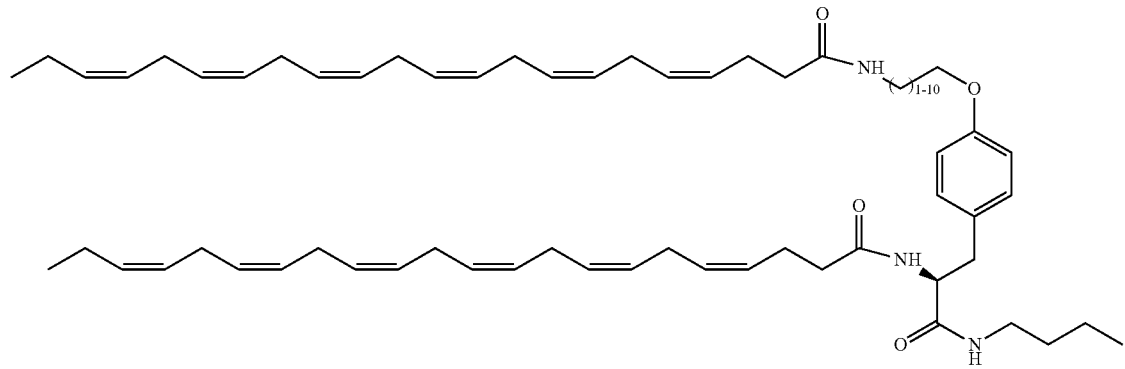

483 484
-continued
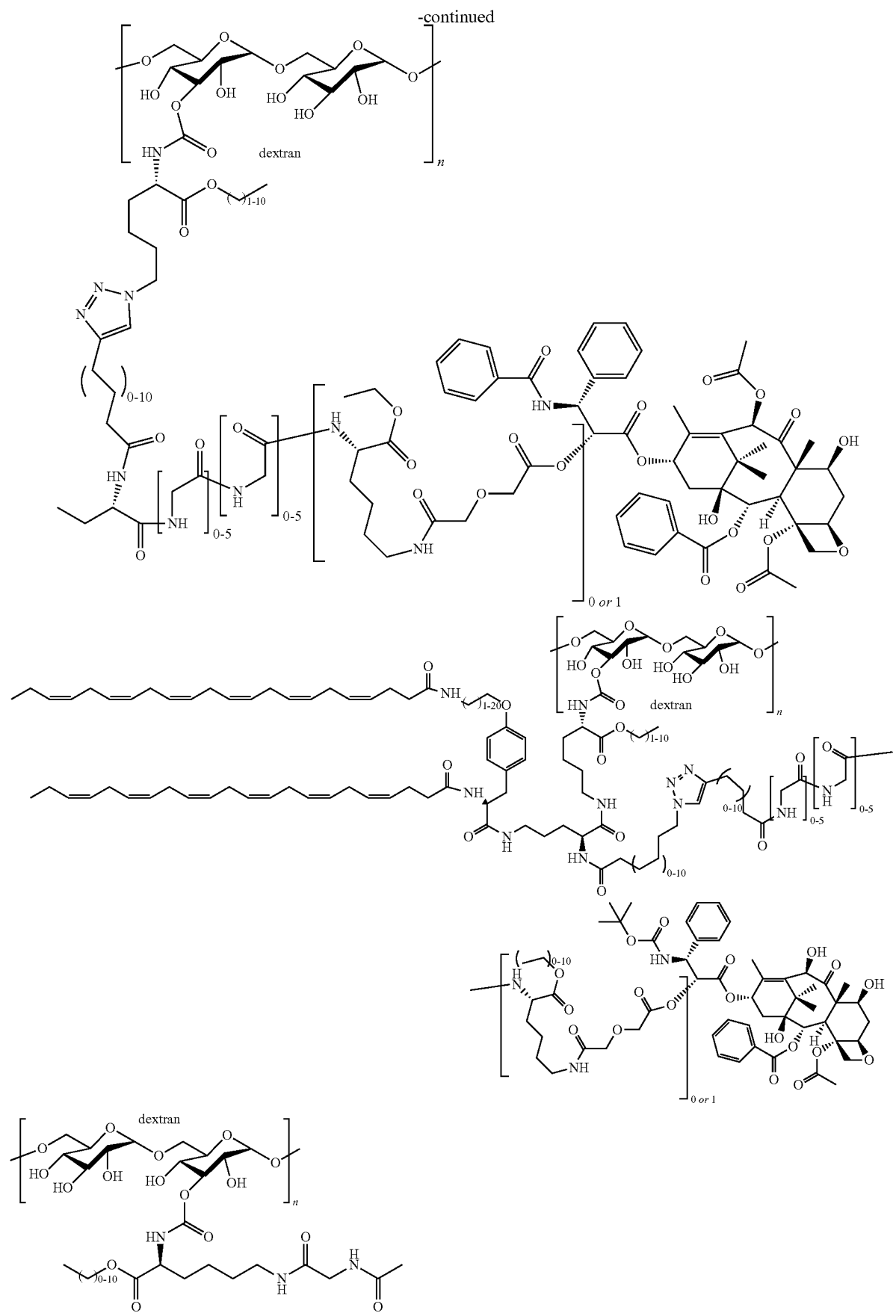

485
486
-continued
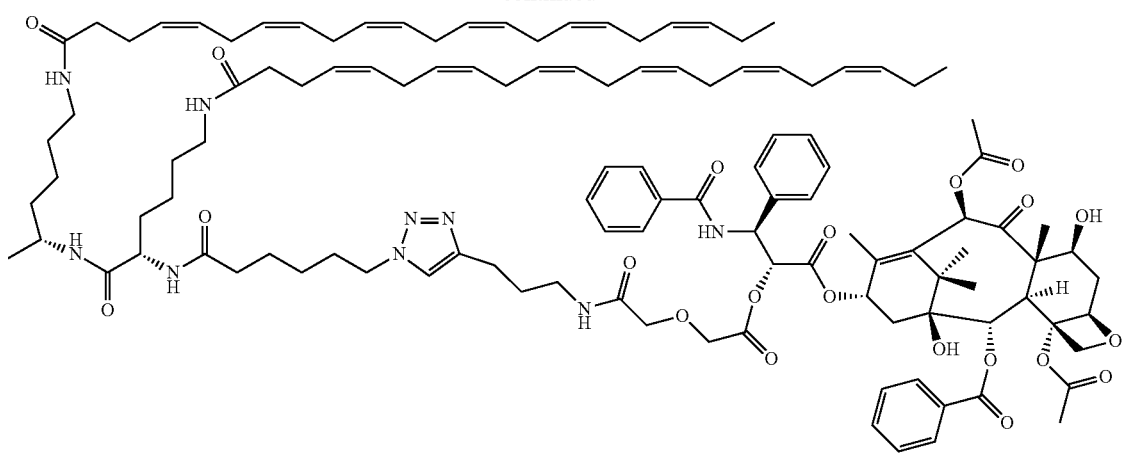
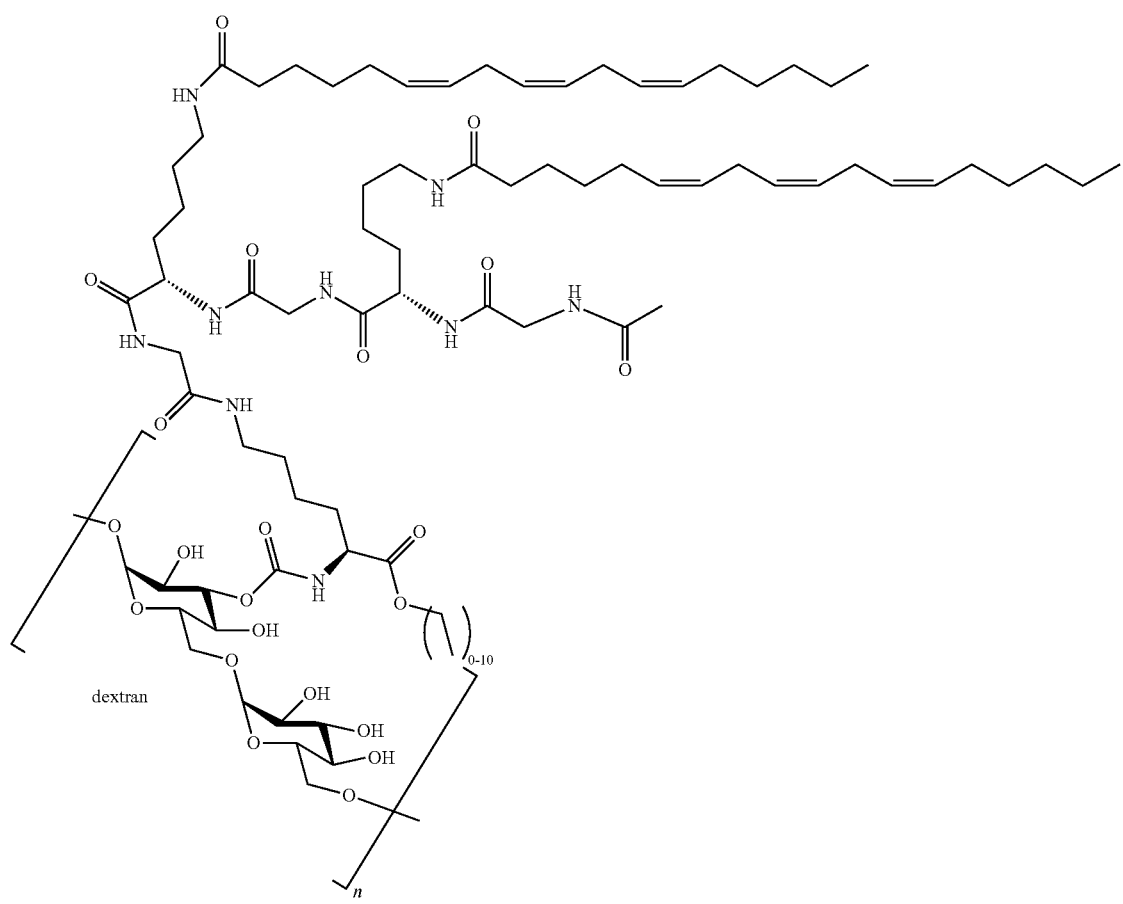

487 488
-continued
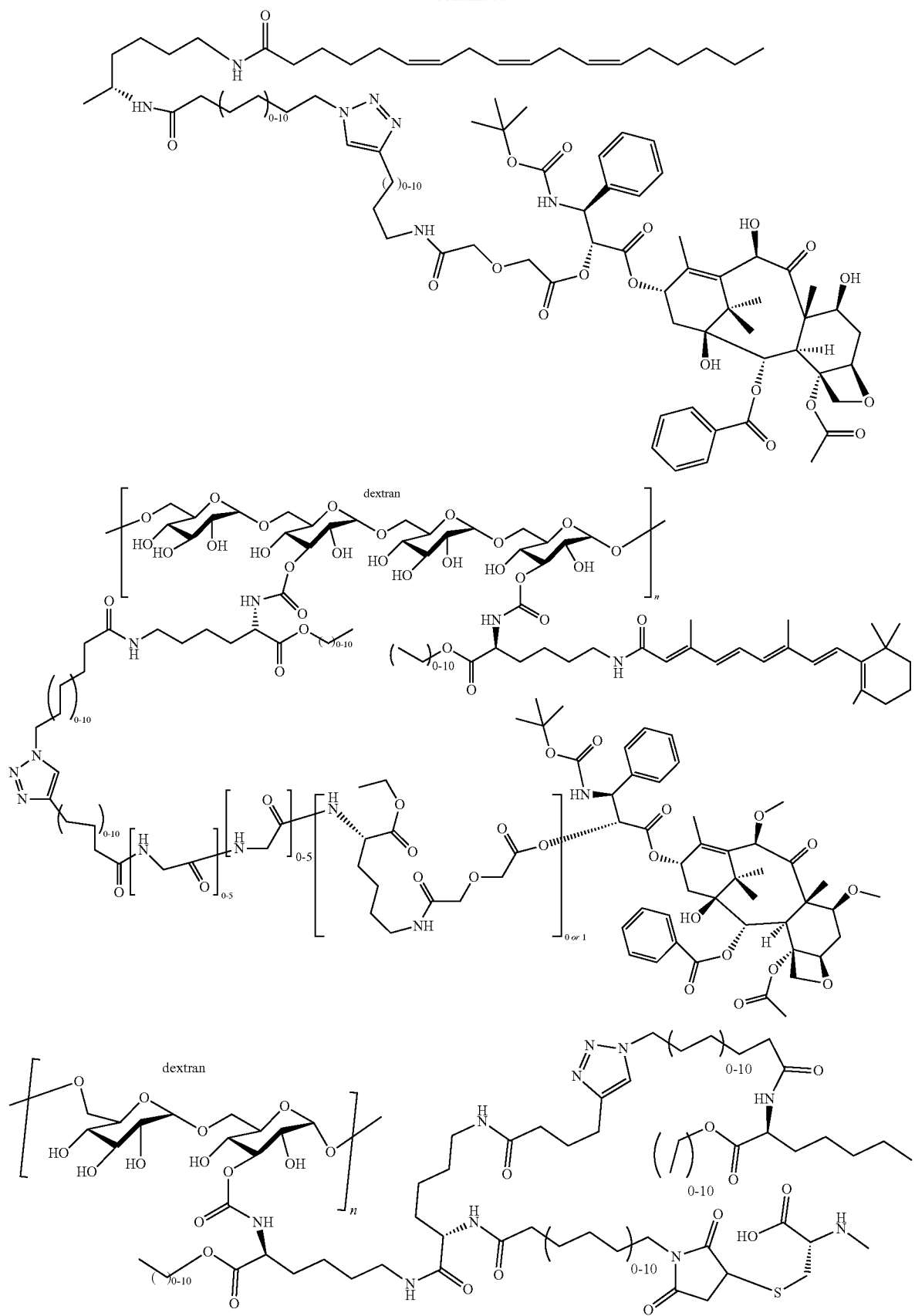

489 490
-continued
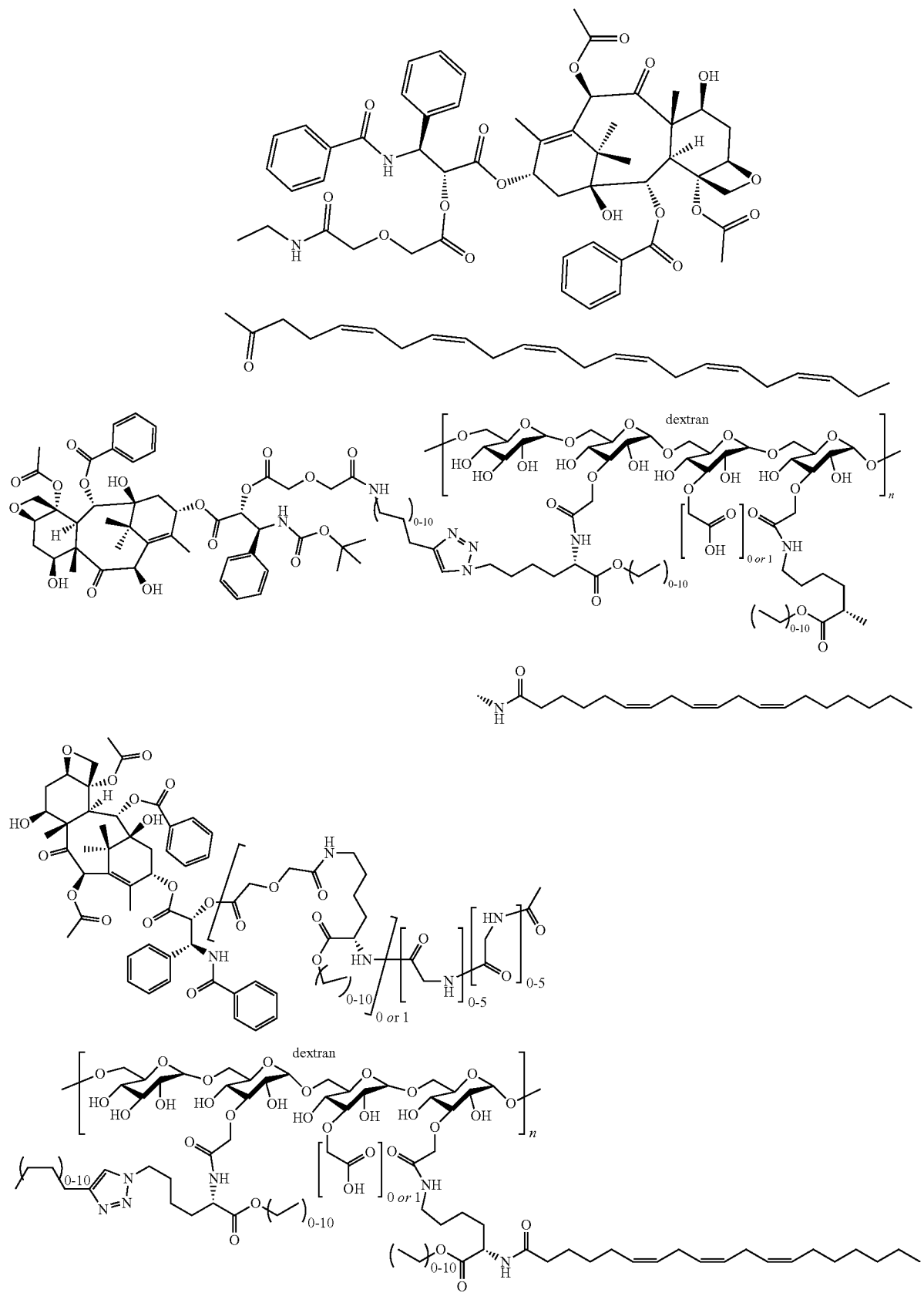

491
-continued
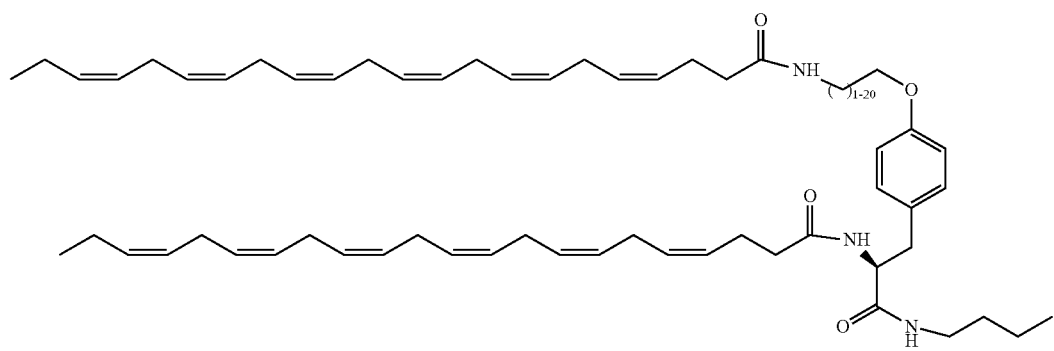
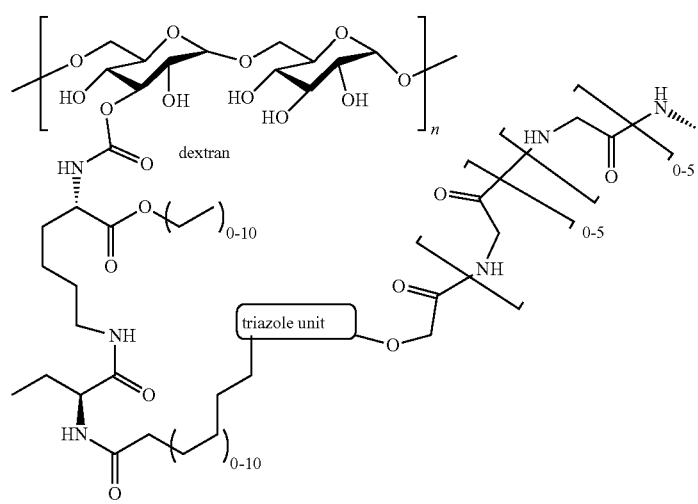
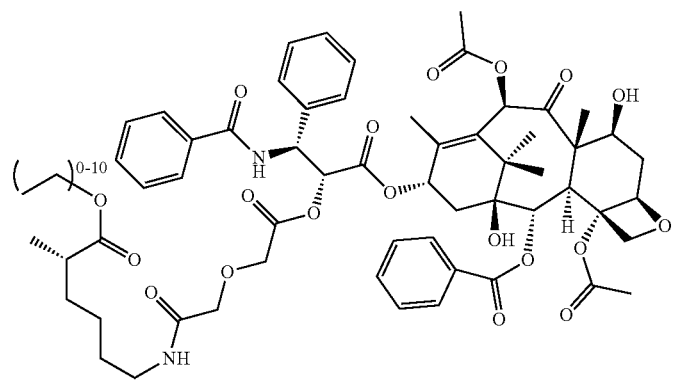
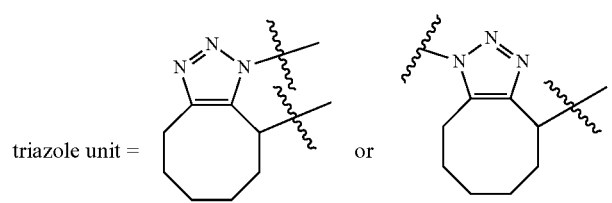
triazole unit =                    or 493 494
-continued
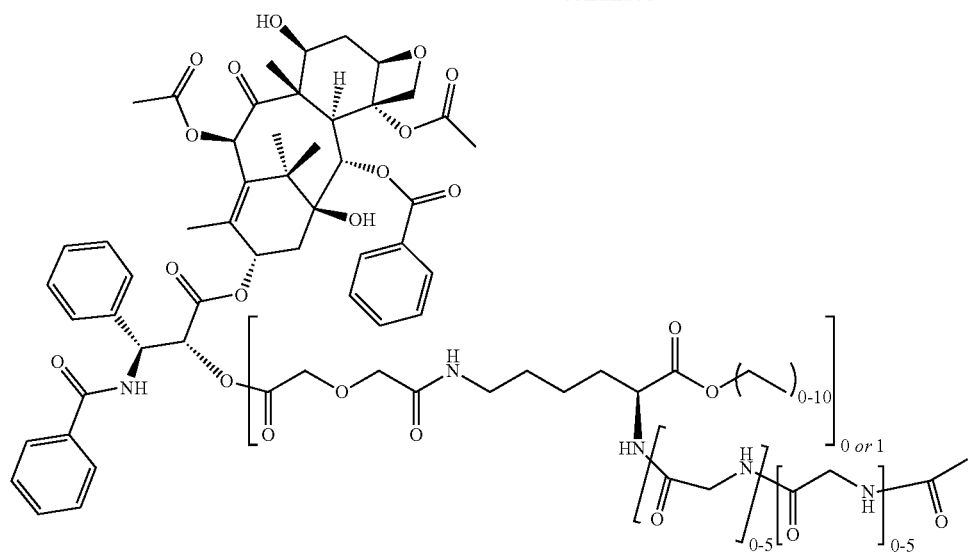
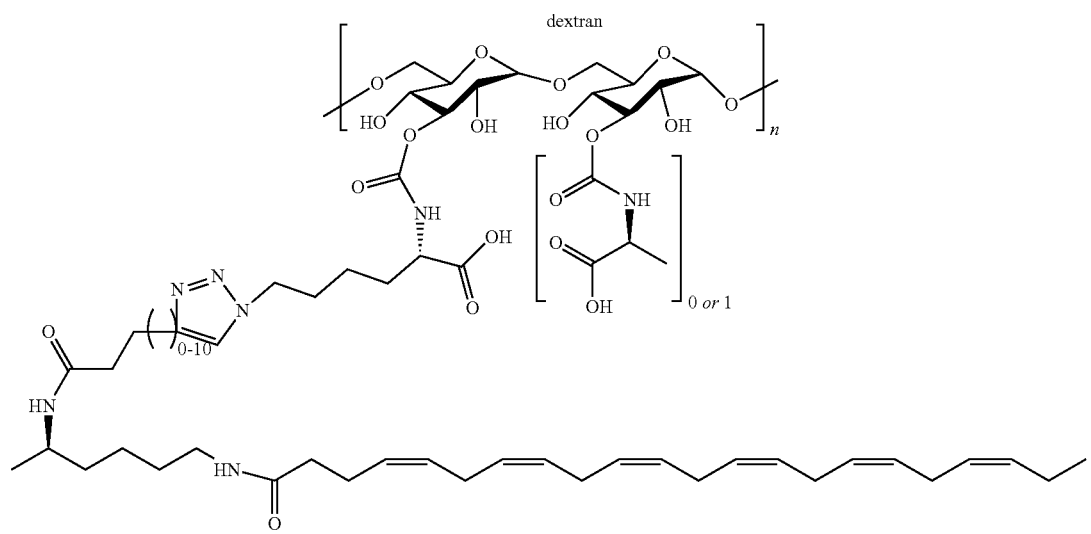
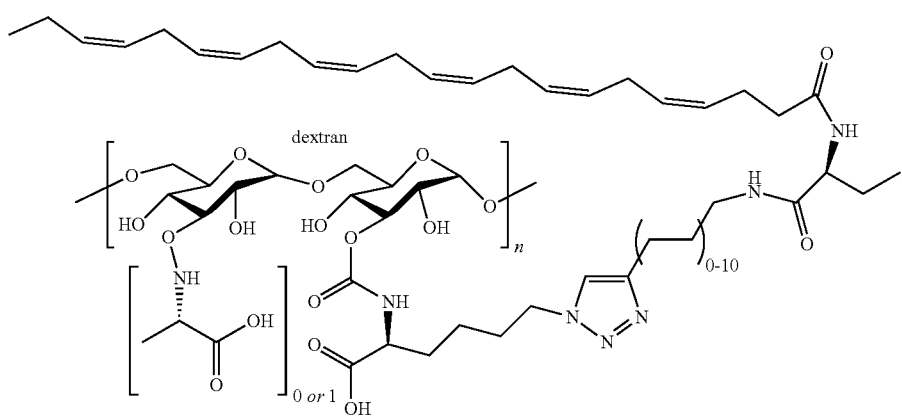

495
496
-continued
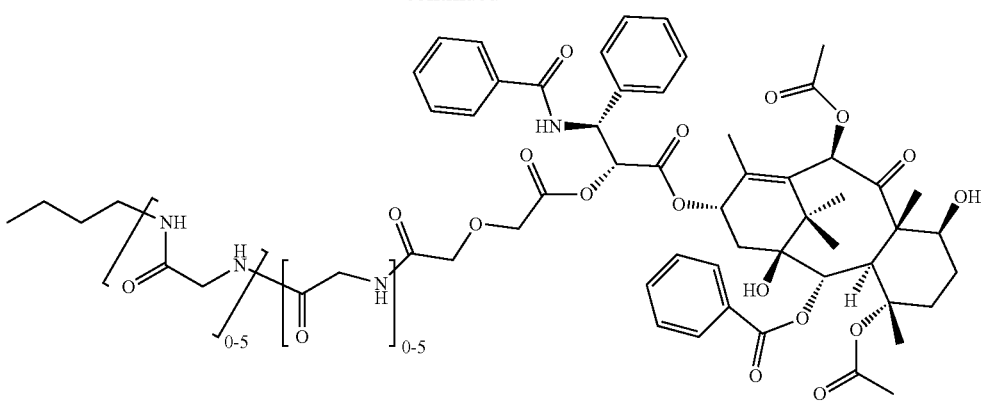
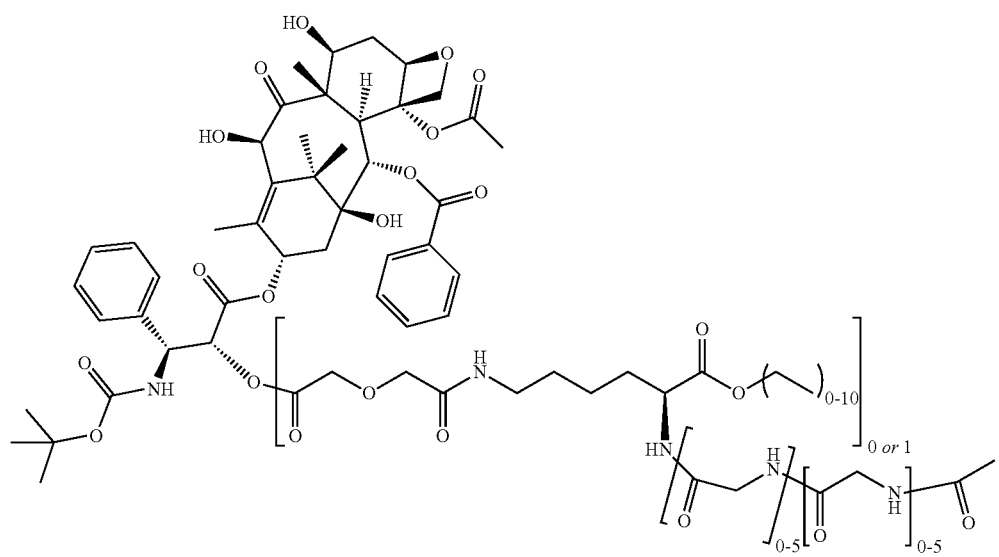
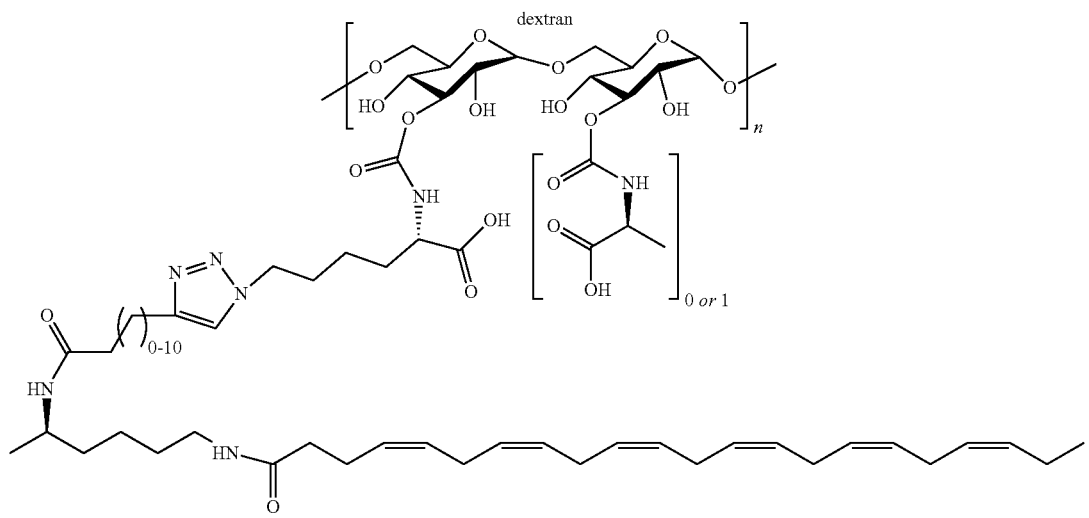

-continued
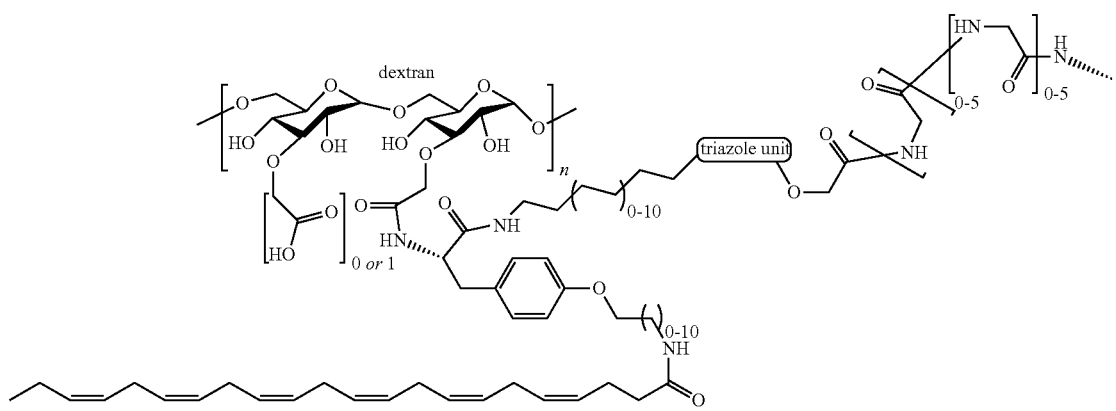
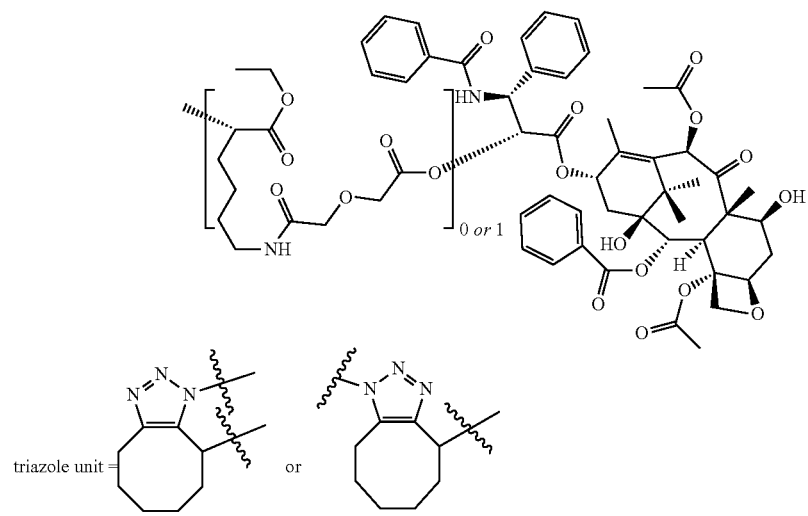
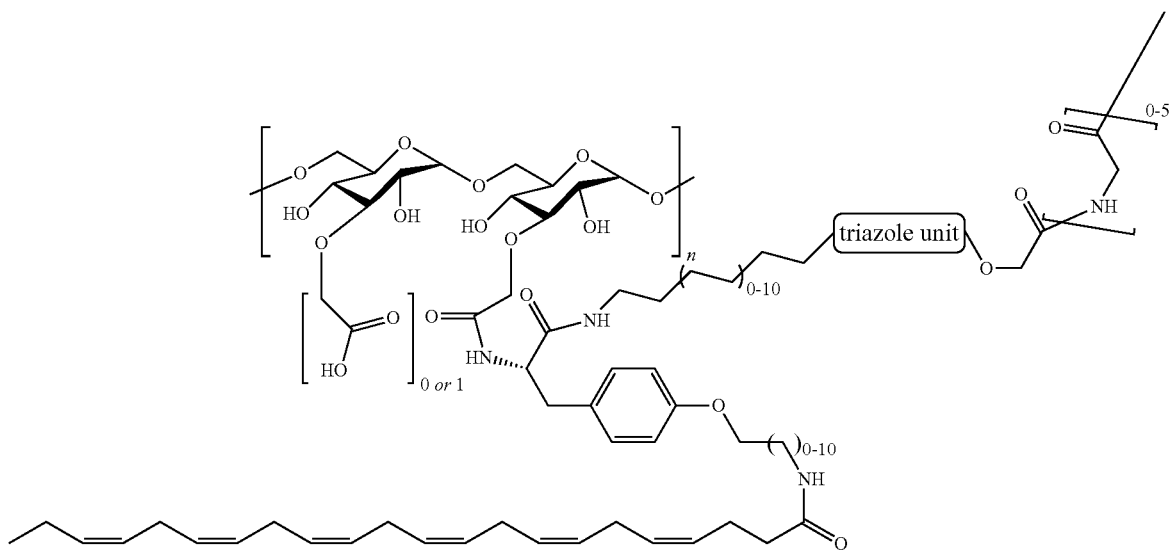

-continued
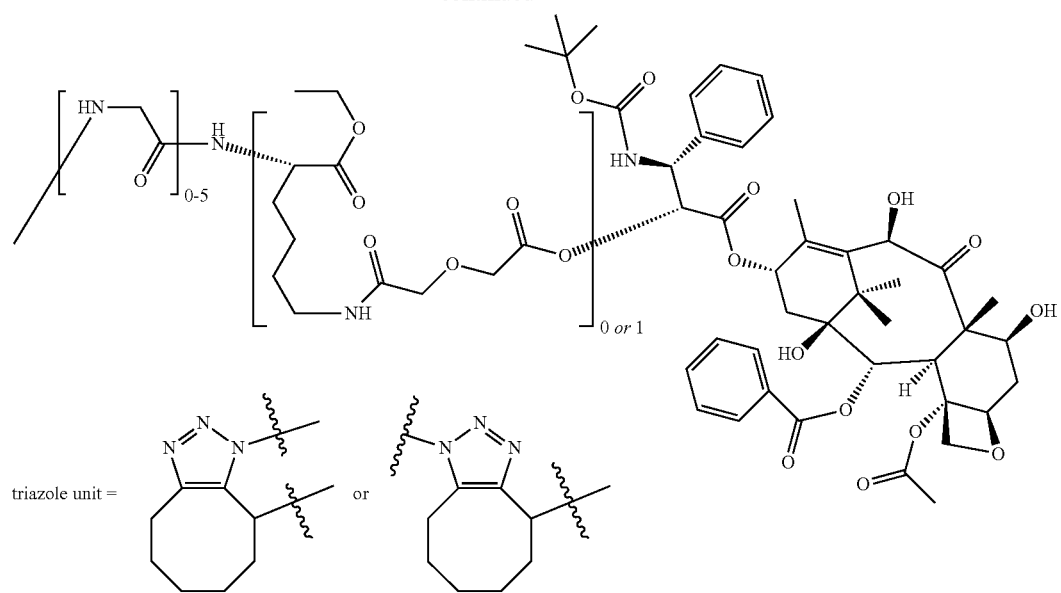
triazole unit =
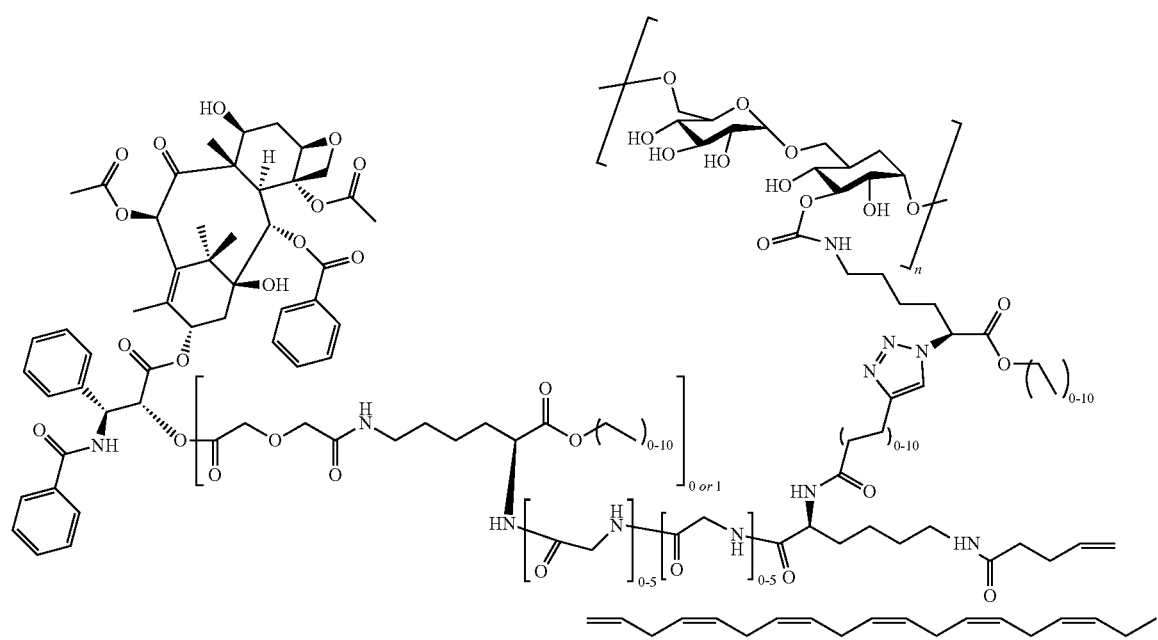

501
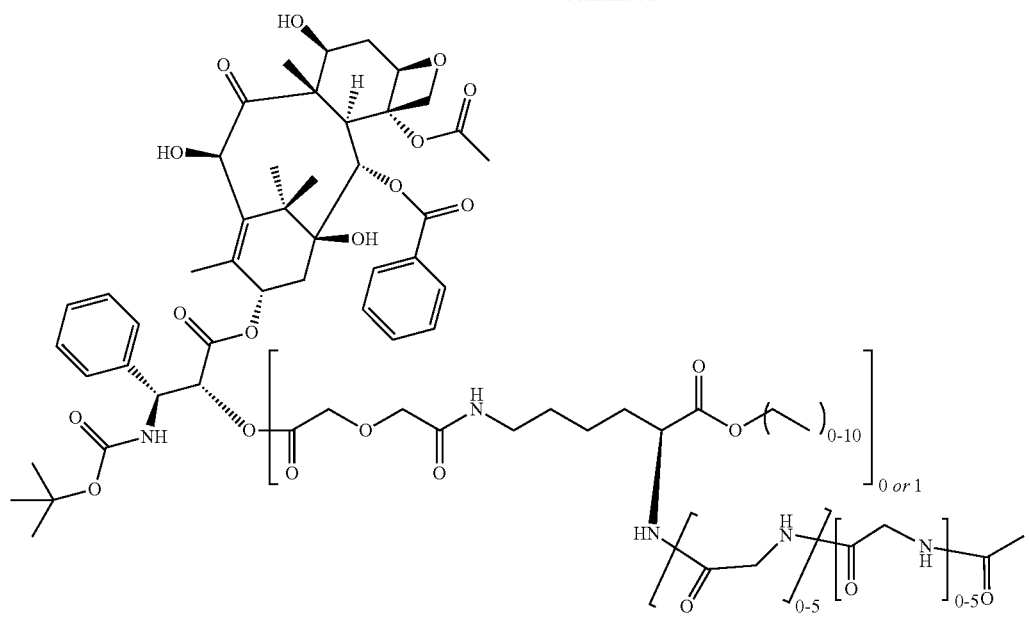
502
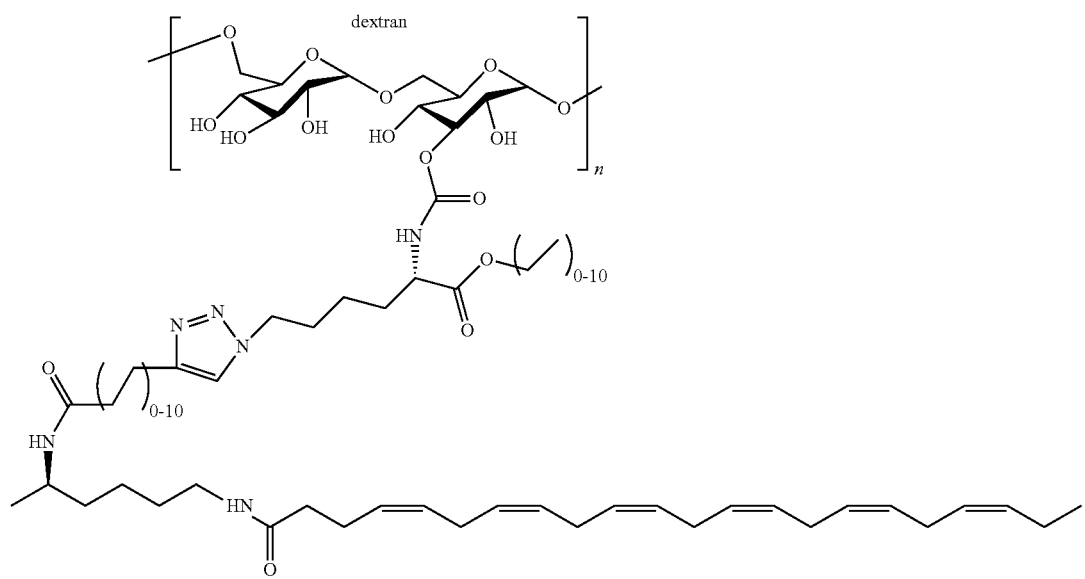

-continued
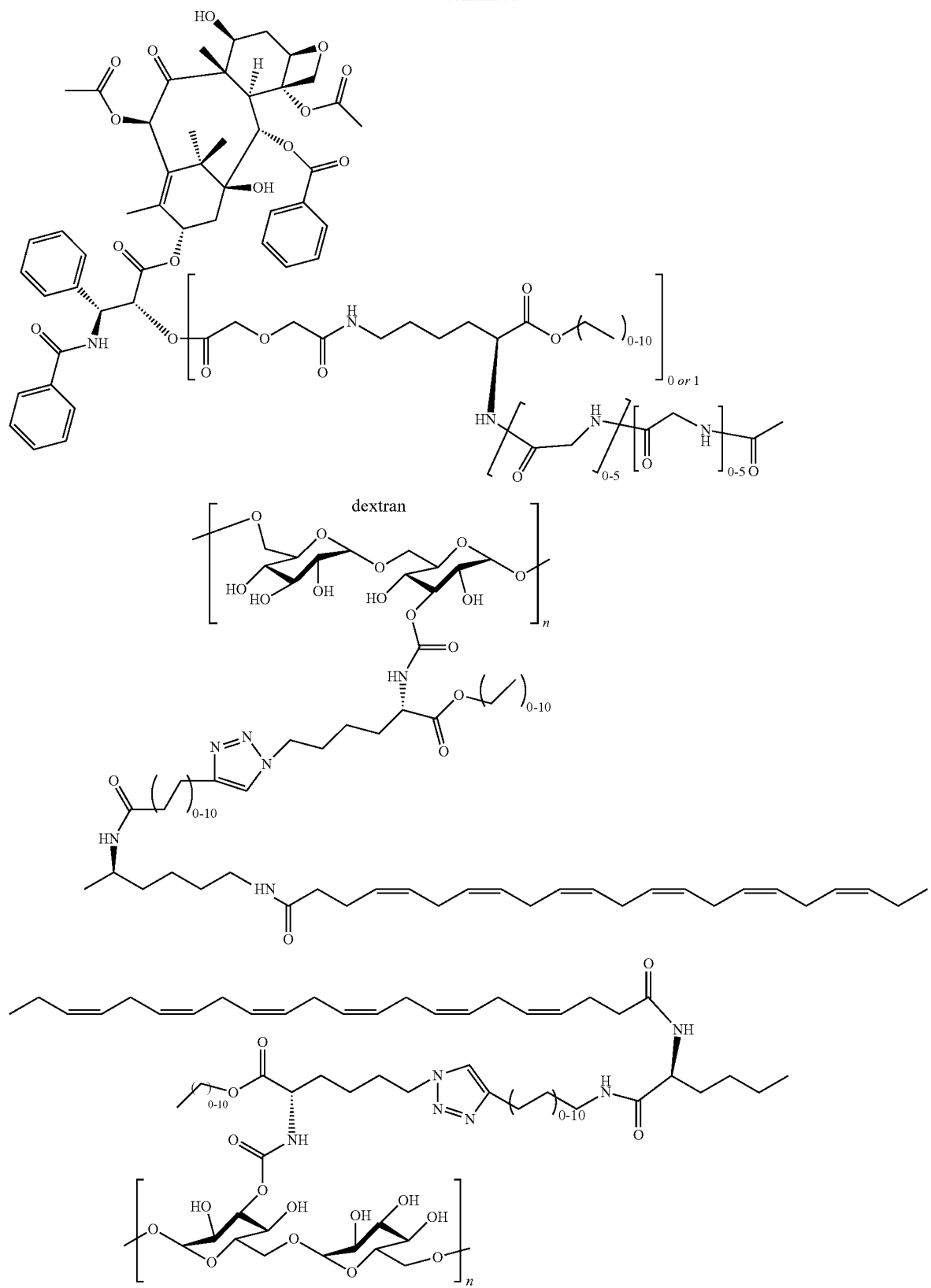

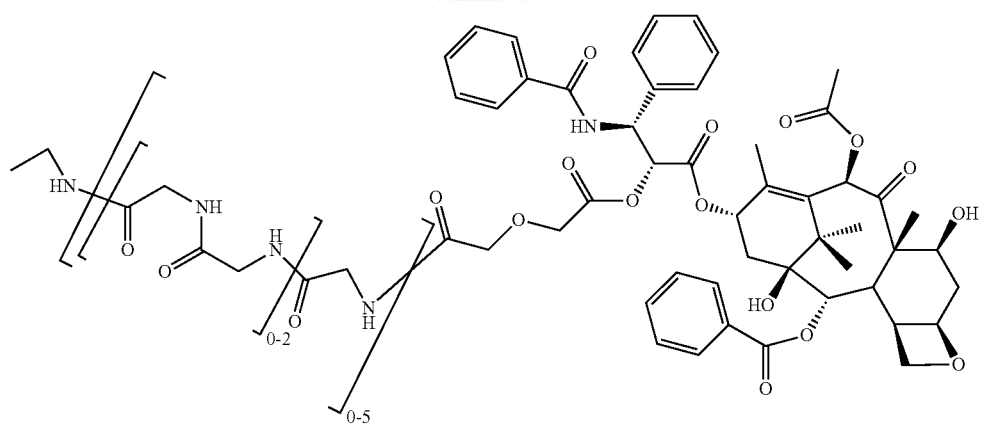
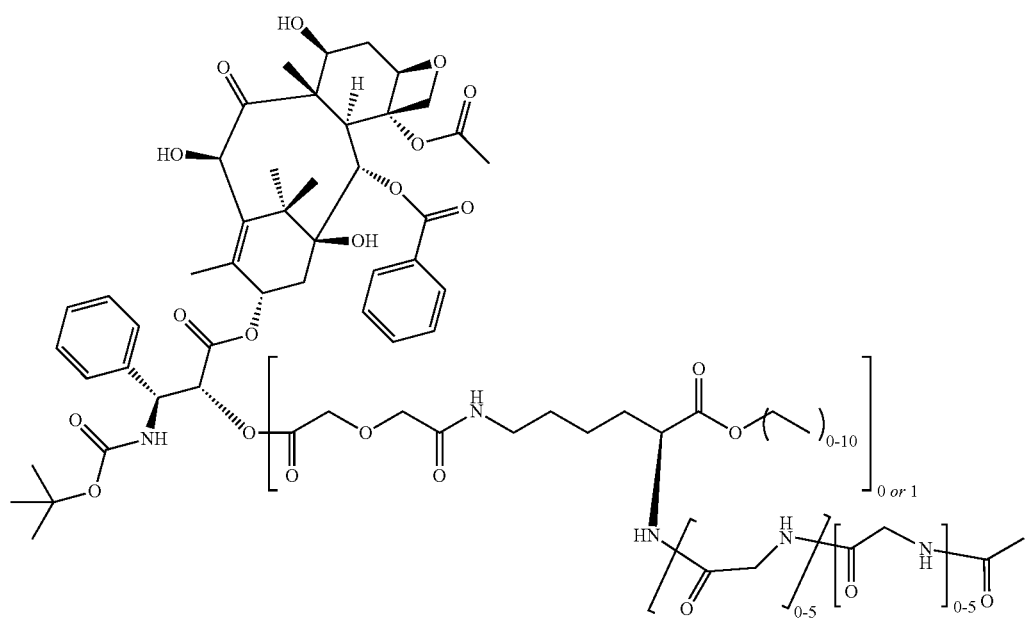

-continued
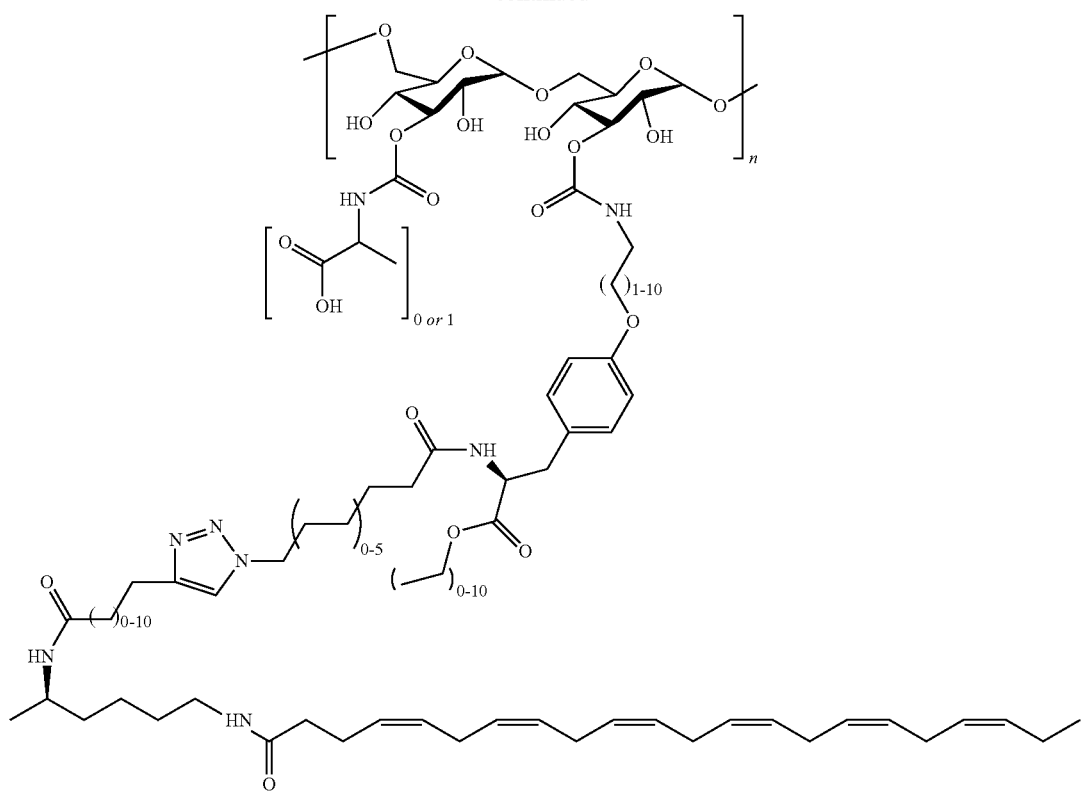
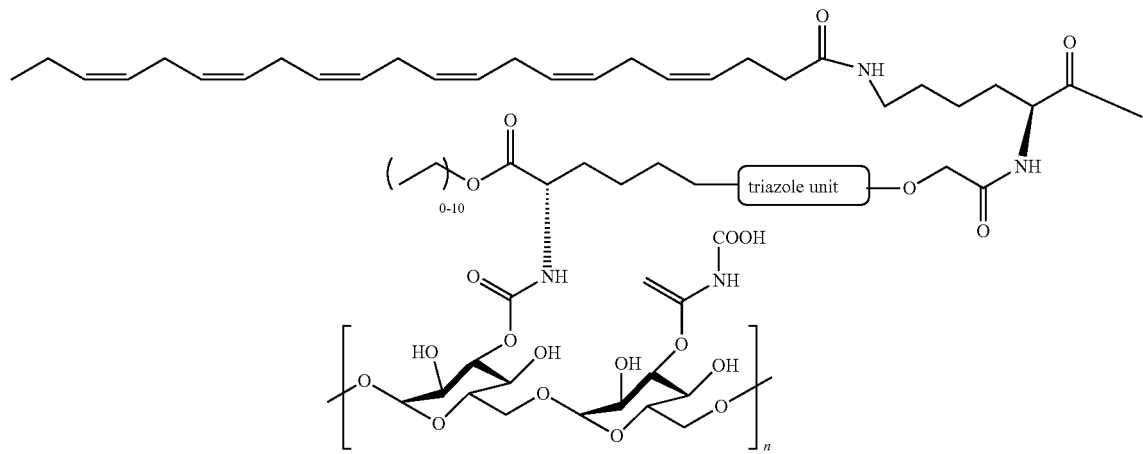
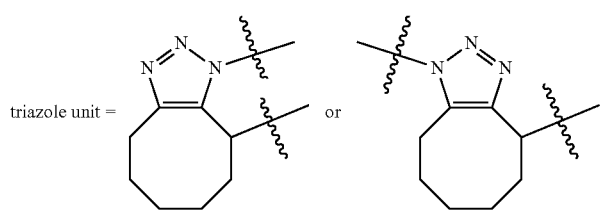

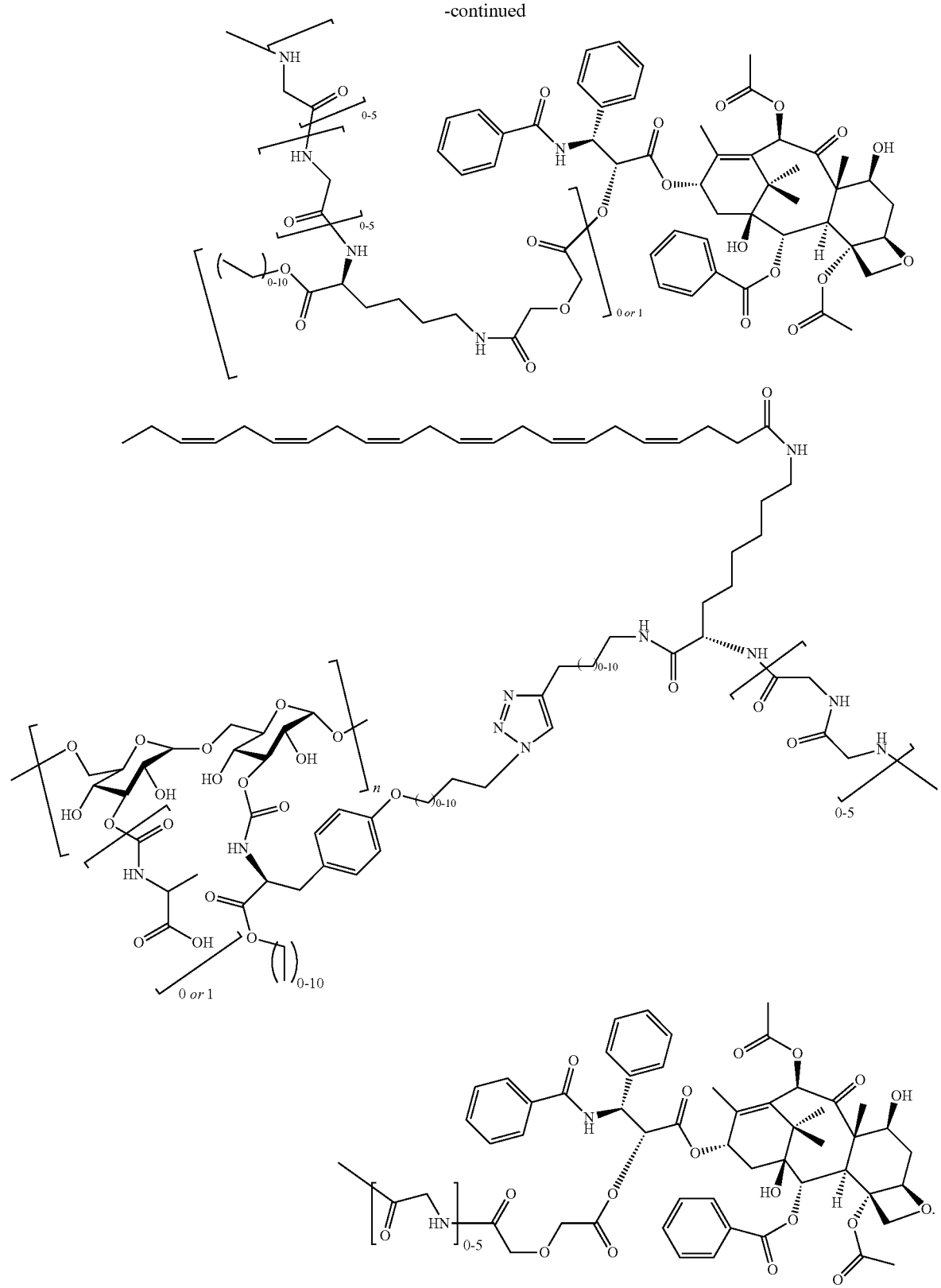
* * * * *